United States Patent
Zhang et al.

(10) Patent No.: US 9,303,061 B2
(45) Date of Patent: Apr. 5, 2016

(54) SPIRO COMPOUNDS AS HEPATITIS C VIRUS INHIBITORS

(75) Inventors: Jiancun Zhang, San Mateo, CA (US); Yingjun Zhang, Dongguan (CN); Hongming Xie, Dongguan (CN); Qingyun Ren, Dongguan (CN); Huichao Luo, Dongguan (CN); Tianzhu Yu, Dongguan (CN); Yumei Tan, Dongguan (CN)

(73) Assignee: Sunshine Luke Pharma Co., Ltd., Dongguan, Guangdong (CN)

( * ) Notice: Subject to any disclaimer, the term of this patent is extended or adjusted under 35 U.S.C. 154(b) by 183 days.

(21) Appl. No.: 14/130,320

(22) PCT Filed: Jul. 9, 2012

(86) PCT No.: PCT/CN2012/000945
§ 371 (c)(1),
(2), (4) Date: Feb. 11, 2014

(87) PCT Pub. No.: WO2013/007106
PCT Pub. Date: Jan. 17, 2013

(65) Prior Publication Data
US 2014/0147412 A1    May 29, 2014

(30) Foreign Application Priority Data
Jul. 9, 2011    (CN) .......................... 2011 1 0195113

(51) Int. Cl.
*A61K 39/00* (2006.01)
*C07D 235/02* (2006.01)
*A61K 31/5377* (2006.01)
*A61K 31/438* (2006.01)
*A61K 38/00* (2006.01)
*C07D 277/00* (2006.01)
*C07D 491/00* (2006.01)
*A61K 38/21* (2006.01)
*C07K 5/062* (2006.01)
*C07D 401/14* (2006.01)
*C07D 405/14* (2006.01)
*C07D 403/14* (2006.01)
*C07D 409/14* (2006.01)
*C07D 471/04* (2006.01)
*A61K 45/06* (2006.01)
*A61K 38/05* (2006.01)

(52) U.S. Cl.
CPC ............ *C07K 5/06052* (2013.01); *A61K 38/05* (2013.01); *A61K 45/06* (2013.01); *C07D 401/14* (2013.01); *C07D 403/14* (2013.01); *C07D 405/14* (2013.01); *C07D 409/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 5,464,859 A * | 11/1995 | Cordi | .................. C07D 235/02 514/401 |
| 7,704,992 B2 | 4/2010 | Bachand et al. | |
| 8,143,414 B2 | 3/2012 | Lavoie et al. | |
| 8,221,737 B2 | 7/2012 | Or et al. | |
| 8,314,135 B2 | 11/2012 | Qiu et al. | |
| 8,354,419 B2 | 1/2013 | Henderson et al. | |
| 8,362,068 B2 | 1/2013 | Dousson et al. | |
| 8,426,458 B2 | 4/2013 | Or et al. | |
| 8,574,563 B2 | 11/2013 | Bachand et al. | |
| 8,575,118 B2 | 11/2013 | Guo et al. | |
| 8,575,135 B2 | 11/2013 | Bacon et al. | |
| 2011/0112100 A1 | 5/2011 | Milbank et al. | |

(Continued)

FOREIGN PATENT DOCUMENTS

| | | |
|---|---|---|
| WO | WO2010134014 | 11/2010 |
| WO | WO2011079327 | 6/2011 |

(Continued)

OTHER PUBLICATIONS

Schill, Gottfried et al, Chemische Berichte (1971), 104(11), 3587-93 CODEN: CHBEAM; ISSN: 0009-2940 Document Type: Journal Language: German IT 34729-10-7P 34729-11-8P (Abstract English; Complete Article, German).*

(Continued)

*Primary Examiner* — Alicia L Otton
*Assistant Examiner* — Jeanmarie Calvillo
(74) *Attorney, Agent, or Firm* — Kam W. Law; Squire Patton Boggs (US) LLP

(57) ABSTRACT

Disclosed are spiro compounds of formula (I), or stereomers, geometric isomers, tautomers, nitrogen oxides, hydrates, solvates, metabolites, pharmaceutically acceptable salts or prodrugs thereof. The compounds can be used to treat hepatitis C virus (HCV) infection or hepatitis C disease. Furthermore disclosed are pharmaceutical compositions containing the compounds and the method of using the compounds or pharmaceutical compositions in the treatment of HCV infection or hepatitis C disease.

(I)

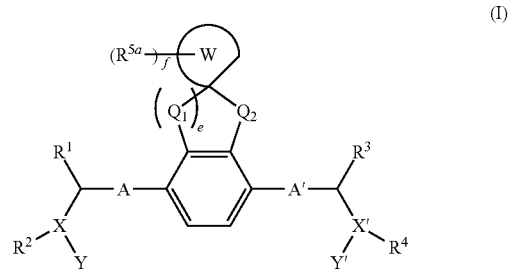

32 Claims, No Drawings

(56) References Cited

U.S. PATENT DOCUMENTS

| | | |
|---|---|---|
| 2011/0312996 A1 | 12/2011 | Buckman et al. |
| 2012/0028978 A1 | 2/2012 | Zhong et al. |
| 2012/0039847 A1 | 2/2012 | Zhao |
| 2012/0040962 A1 | 2/2012 | Li et al. |
| 2012/0083483 A1 | 4/2012 | Coburn et al. |
| 2012/0115918 A1 | 5/2012 | DeGoey et al. |
| 2012/0195857 A1 | 8/2012 | Belema et al. |
| 2012/0251491 A1 | 10/2012 | Rosenblum et al. |
| 2012/0258909 A1 | 10/2012 | Liepold et al. |
| 2012/0264780 A1 | 10/2012 | Kullmann et al. |
| 2012/0276047 A1 | 11/2012 | Rosenblum et al. |
| 2013/0072523 A1 | 3/2013 | Liu et al. |
| 2013/0090351 A1 | 4/2013 | Das et al. |
| 2013/0090364 A1 | 4/2013 | Chan Chun Kong et al. |
| 2013/0096101 A1 | 4/2013 | Li et al. |
| 2013/0115193 A1 | 5/2013 | Lavoie et al. |
| 2013/0123244 A1 | 5/2013 | Vandyck et al. |
| 2013/0156731 A1 | 6/2013 | Chen et al. |
| 2013/0164258 A1 | 6/2013 | Chen et al. |
| 2013/0203656 A1 | 8/2013 | Zhong et al. |
| 2013/0296304 A1 | 11/2013 | Li et al. |

FOREIGN PATENT DOCUMENTS

| | | | | |
|---|---|---|---|---|
| WO | WO2011156543 | 12/2011 | | |
| WO | WO2012003642 | 1/2012 | | |
| WO | WO2012018534 | 2/2012 | | |
| WO | WO2012040923 | 4/2012 | | |
| WO | WO2012040924 | 4/2012 | | |
| WO | WO2012041014 | 4/2012 | | |
| WO | WO2012041227 | 4/2012 | | |
| WO | WO2012050848 | 4/2012 | | |
| WO | WO2012075140 | * | 6/2012 | ............ C07H 19/06 |
| WO | WO2012083048 | 6/2012 | | |
| WO | WO2012083053 | 6/2012 | | |
| WO | WO2012122716 | 9/2012 | | |
| WO | WO2012125926 | 9/2012 | | |
| WO | WO2013021337 | 2/2013 | | |
| WO | WO2013022810 | 2/2013 | | |
| WO | WO2013098313 | 7/2013 | | |
| WO | WO2013118097 | 8/2013 | | |
| WO | WO2013118102 | 8/2013 | | |

OTHER PUBLICATIONS

ISR.
Written Opinion.
IPRP.

* cited by examiner

SPIRO COMPOUNDS AS HEPATITIS C VIRUS INHIBITORS

CROSS-REFERENCE TO RELATED APPLICATIONS

This is a U.S. national stage application of the International Patent Application No. PCT/CN2012/000945, filed Jul. 9, 2012, which claims priority to Chinese Patent Application No. 201110195113.8, filed Jul. 9, 2011, both of which are incorporated herein by reference in their entirety.

FIELD OF THE INVENTION

The present invention is in the field of medicine. The invention relates to spiro compounds for treating Hepatitis C virus (HCV) infection, compositions comprising such compounds, the use and the methods thereof. In particular, the invention relates to use of heterocyclic compounds as NS5A protein inhibitors. More specifically, the invention relates to compounds which can inhibit the function of the NS5A protein encoded by Hepatitis C virus (HCV), pharmaceutical compositions comprising such compounds, and methods for inhibiting the function of the NS5A protein by the compounds and pharmaceutical compositions disclosed herein.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. Chronic HCV infection is thus a major worldwide cause of liver-related premature mortality.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. The treatment has side effects in many patients, so they do not durably respond to treatment. Thus, new and effective methods of treating HCV infection are urgently needed.

HCV is a positive-stranded RNA virus. Based on a comparison of the deduced amino acid sequence and the extensive similarity in the 5'untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame (ORF).

Considerable heterogeneity is found within nucleotide and encoded amino acid sequence throughout the HCV genome. At least seven major genotypes have been characterized, and more than 50 subtypes have been described. In HCV infected cells, viral RNA is translated into a polyprotein that is cleaved into ten individual proteins. At the amino terminus are structural proteins, follows E1 and E2. Additionally, there are six non-structural proteins, NS2, NS3, NS4A, NS4B, NS5A and NS5B, which play a function role in the HCV lifecycle (see, for example, Lindenbach et al., *Nature*, 2005, 436, 933-938).

The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A and NS5B) is effected by two viral proteases. The first one is believed to be a metalloprotease and cleaves at the NS2-NS3 junction; the second one is a serine protease within the N-terminal region of NS3 (also referred herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Compounds useful for treating HCV-infected patients are desired which selectively inhibit HCV viral replication. In particular, compounds which are effective to inhibit the function of the NS5A protein are desired. The HCV NS5A protein is described, for example, in Tan et al., *Virology*, 2001, 284, 1-12; and in Park et al., *J. Biol. Chem.*, 2003, 278, 30711-30718.

SUMMARY OF THE INVENTION

Provided herein are novel spiro ring compounds and methods of their use to treat HCV infection. Specifically, it has been found that the spiro ring compounds disclosed herein, and pharmaceutical compositions thereof, are effective as inhibitors of HCV infection, especially the non-structural 5A (NS5A) protein of HCV.

In one aspect, provided herein are compounds having formula (I) as shown below:

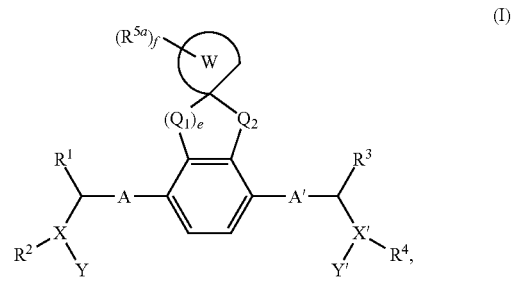

or a stereoisomer, a geometric isomer, a tautomer, an N-oxide, a hydrate, a solvate, a metabolite, a pharmaceutically acceptable salt or a prodrug thereof, wherein:

each of A and A' is independently a bond, alkylene, alkenylene, cycloalkylene, heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N$ $(R^5)$—$(CR^8R^{8a})_p$—, —$(CR^8R^{8a})_n$—C(=O)—N$(R^5)$—$(CR^8R^{8a})_p$—, —$(CR^8R^{8a})_n$—N$(R^5)$—C(=O)—N$(R^5)$—$(CR^8R^{8a})_p$—, —$(CR^8R^{8a})_n$—C(=O)—O—$(CR^8R^{8a})_p$—, —$(CR^8R^{8a})_n$—N$(R^5)$—S(=O)$_r$—N$(R^5)$—$(CR^8R^{8a})_p$—, or —$(CR^8R^{8a})_n$—N$(R^5)$—C(=O)—O—$(CR^8R^{8a})_p$—, or each of A and A' is independently one of the following groups:
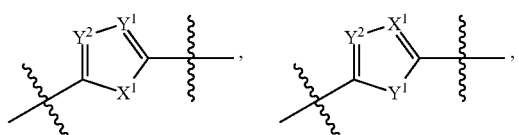

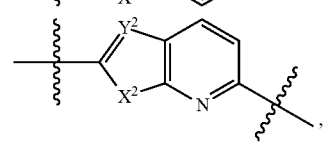
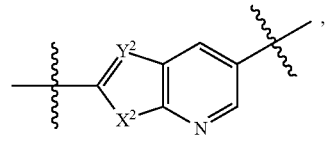
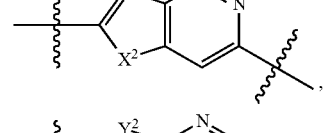
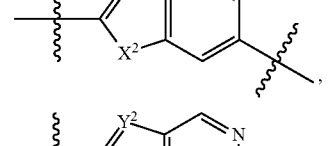
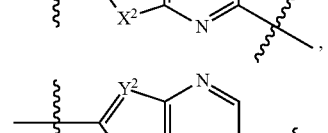
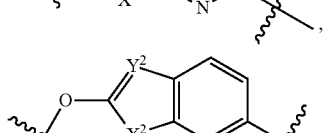
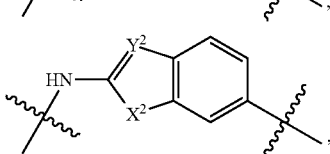
-continued
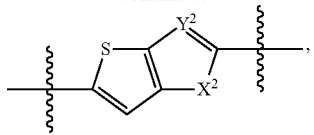
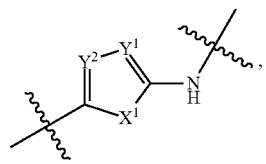
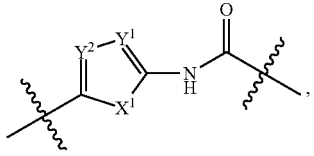
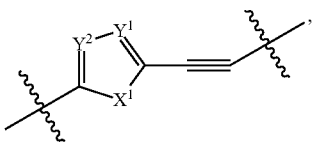
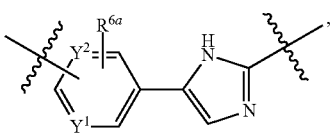
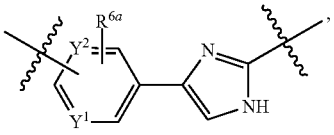
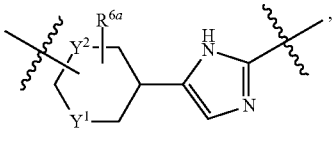
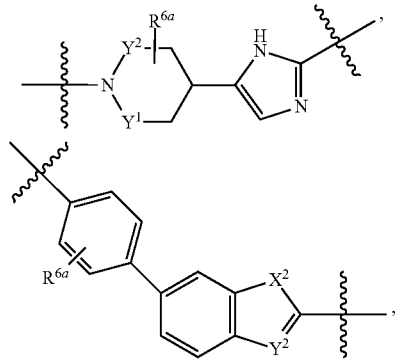
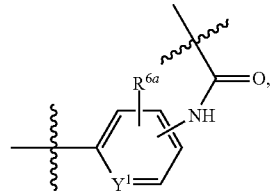

-continued

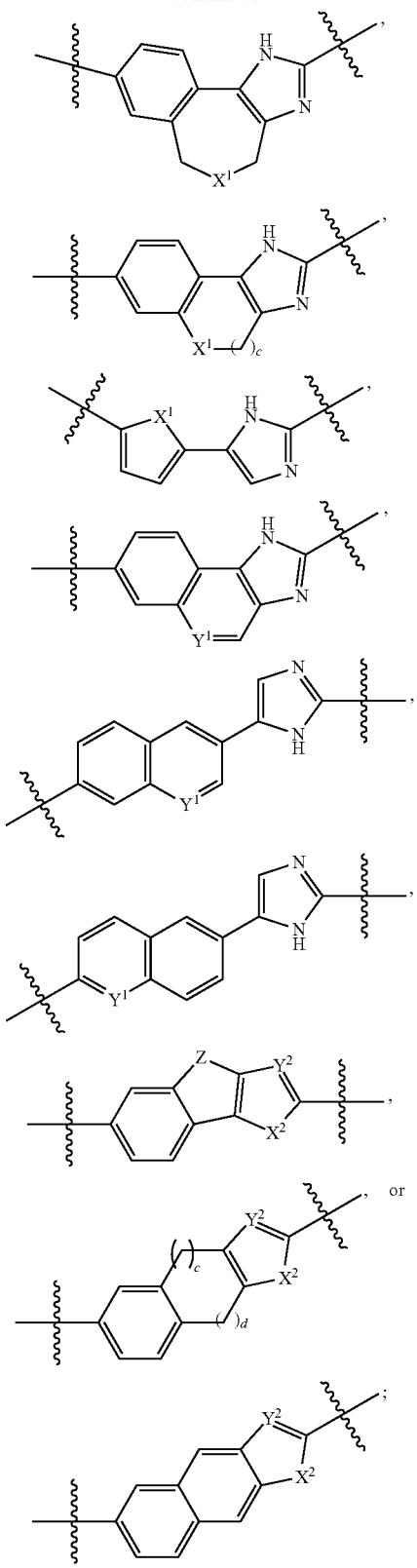

wherein $X^1$ is O, S, $NR^6$ or $CR^7R^{7a}$;
each $Y^1$ and $Y^2$ is independently N or $CR^7$;
$X^2$ is $NR^6$, O or S;

Z is $-(CH_2)_a-$, $-CH=CH-$, $-N=CH-$, $-(CH_2)_a-N(R^5)-(CH_2)_b-$, or $-(CH_2)_a-O-(CH_2)_b-$, wherein each a and b is independently 0, 1, 2 or 3;

each c is independently 1 or 2;
d is 1 or 2;
each n is independently 0, 1, 2 or 3;
each p is independently 0, 1, 2 or 3;
each r is independently 0, 1 or 2;
e is 1, 2, 3 or 4;
f is 0, 1, 2, 3 or 4;
each $Q_1$ and $Q_2$ is independently $NR^6$, O, S, C(=O) or $CR^7R^{7a}$, with the proviso that when $Q_1$ is $NR^6$, O, S or C(=O), e is 1;
W is carbocyclyl or heterocyclyl;
each of X and X' is independently N or $CR^7$;
each of Y and Y' is independently H, alkyl, heteroalkyl, cycloalkyl, heterocyclyl, aryl, heteroaryl, aralkyl, a group derived from a naturally occurring or commercially available α-amino acid or an optically isomer thereof, or each of Y and Y' is independently $-[U-(CR^9R^{9a})_t-N(R^{10})-(CR^9R^{9a})_t]_k-U-(CR^9R^{9a})_t-N(R^{11})-(CR^9R^{9a})_t-R^{12}$, $-U-(CR^9R^{9a})_t-R^{12}$ or $-[U-(CR^9R^{9a})_t-N(R^{10})-(CR^9R^{9a})_t]_k-U-(CR^9R^{9a})_t-O-(CR^9R^{9a})_t-R^{12}$;
each U is independently $-C(=O)-$, $-C(=S)-$, $-S(=O)-$ or $-S(=O)_2-$;
each t is independently 0, 1, 2, 3 or 4;
each k is independently 0, 1 or 2;
each of $R^1$, $R^2$, $R^3$ and $R^4$ is independently H, alkyl, heteroalkyl, aralkyl, cycloalkyl, heterocyclyl, heteroaryl or aryl; or $R^1$ and $R^2$, together with X—CH, form a 3-8 membered heterocycle or carbocycle, $C_{5-12}$ fused bicycle, $C_{5-12}$ fused heterobicycle, $C_{5-12}$ spiro bicycle or $C_{5-12}$ Spiro heterobicycle; or $R^3$ and $R^4$, together with X'—CH, form a 3-8 membered heterocycle or carbocycle, $C_{5-12}$ fused bicycle, $C_{5-12}$ fused heterobicycle, $C_{5-12}$ Spiro bicycle or $C_{5-12}$ Spiro heterobicycle;
each $R^5$ is independently H, hydroxy, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$— or aminosulfonyl;
each $R^{5a}$ is independently H, oxo (=O), hydroxy, amino, F, Cl, Br, I, cyano, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, $R^{7a}R^7N$-alkyl, $R^7S(=O)$-alkyl, $R^7R^{7a}N-C(=O)$-alkyl, $R^{7a}R^7N$-alkoxy, $R^7S(=O)$-alkoxy, $R^7R^{7a}N-C(=O)$-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy;
$R^6$ is independently H, $R^7R^{7a}NC(=O)-$, $R^7OC(=O)-$, $R^7C(=O)-$, $R^7R^{7a}NS(=O)-$, $R^7OS(=O)-$, $R^7S(=O)-$, $R^7R^{7a}NS(=O)_2-$, $R^7OS(=O)_2-$, $R^7S(=O)_2-$, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;

$R^{6a}$ is independently H, oxo, hydroxy, amino, F, Cl, Br, I, cyano, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, $R^7R^{7a}N$—S(=O)$_2$—, $R^7$S(=O)$_2$—, $R^7$S(=O)$_2$N(R$^{7a}$)—, $R^{7a}R^7N$-alkyl, $R^7$S(=O)-alkyl, $R^7R^{7a}N$—C(=O)-alkyl, $R^{7a}R^7N$-alkoxy, $R^7$S(=O)-alkoxy, $R^7R^{7a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino, or aryloxy;

each $R^7$ and $R^{7a}$ is independently H, F, Cl, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring including spiro bicycle and fused bicycle;

each $R^8$ and $R^{8a}$ is independently H, hydroxy, cyano, nitro, F, Cl, Br, I, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$—, or aminosulfonyl;

each $R^9$, $R^{9a}$, $R^{10}$ and $R^{11}$ is independently H, alkyl, heteroalkyl, cycloalkyl, heterocyclyl, aryl, heteroaryl, aralkyl, haloalkyl, hydroxyalkyl, heteroarylalkyl, heterocyclylalkyl, or cycloalkylalkyl;

$R^{12}$ is independently $R^{13a}R^{13}N$—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, $R^{13}R^{13a}N$—S(=O)$_2$—, $R^{13}$S(=O)$_2$—, $R^{13}$S(=O)$_2$N(R$^{13a}$)—, $R^{13}$OS(=O)$_2$—, alkyl, heteroalkyl, cycloalkyl, heterocyclyl, aryl, heteroaryl or aralkyl;

or $R^{11}$ and $R^{12}$, together with the nitrogen atom they are attached to, form a 4-7 membered ring; and each $R^{13}$ and $R^{13a}$ is independently H, alkyl, heteroalkyl, cycloalkyl, heterocyclyl, aryl, heteroaryl, or aralkyl;

wherein each of the following groups —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=O)—N(R$^5$)—(CR$^8$R$^{8a}$)$_p$—, —(CR$^8$R$^{8a}$)$_n$—N(R$^5$)—C(=O)—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, —(CR$^8$R$^{8a}$)$_n$—N(R$^5$)—C(=O)—O—(CR$^8$R$^{8a}$)$_p$—, —[U—(CR$^9$R$^{9a}$)$_t$—N(R$^{10}$)—(CR$^9$R$^{9a}$)$_t$]$_k$—U—(CR$^9$R$^{9a}$)$_t$—N(R$^{11}$)—(CR$^9$R$^{9a}$)$_t$—R$^{12}$, —U—(CR$^9$R$^{9a}$)$_t$—R$^{12}$, —[U—(CR$^9$R$^{9a}$)$_t$—N(R$^{10}$)—(CR$^9$R$^{9a}$)$_t$]$_k$—U—(CR$^9$R$^{9a}$)$_t$—O—(CR$^9$R$^{9a}$)$_t$—R$^{12}$, NR$^6$, CR$^7$R$^{7a}$, CR$^7$—, —(CH$_2$)$_a$—, —CH=CH—, —N=CH—, —(CH$_2$)$_a$—N(R$^5$)—(CH$_2$)$_b$—, —(CH$_2$)$_a$—O—(CH$_2$)$_b$—, $R^{13a}R^{13}N$—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, $R^{13}R^{13a}N$—S(=O)$_2$—, $R^{13}$S(=O)$_2$—, $R^{13}$S(=O)$_2$N(R$^{13a}$)—, $R^{13}$OS(=O)$_2$—, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, $R^7R^{7a}N$—S(=O)$_2$—, $R^7$S(=O)$_2$—, $R^7$S(=O)$_2$N(R$^{7a}$)—, alkyl-OC(=O)—, alkyl-C(=O)—, alkyl-OS(=O)$_r$—, alkyl-S(=O)$_r$O—, alkyl-S(=O)$_r$—, $R^{7a}R^7NC(=O)$—, $R^7OC(=O)$—, $R^7C(=O)$—, $R^{7a}R^7NS(=O)$—, $R^7OS(=O)$—, $R^7S(=O)$—, $R^{7a}R^7NS(=O)_2$—, $R^7OS(=O)_2$—, $R^7S(=O)_2$—, $R^{7a}R^7N$-alkyl, $R^7$S(=O)-alkyl, $R^7R^{7a}N$—C(=O)-alkyl, $R^{7a}R^7N$-alkoxy, $R^7$S(=O)-alkoxy, $R^7R^{7a}N$—C(=O)-alkylamino, alkyl, heteroalkyl, carbocyclyl, cycloalkyl, heterocyclyl, aryl, heteroaryl, aralkyl, α-amino acid, $C_{5-12}$ fused bicycle, $C_{5-12}$ fused heterobicycle, $C_{5-12}$ spiro bicycle, $C_{5-12}$ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted or unsubstituted.

In some embodiments, W is $C_{3-8}$ carbocyclyl or $C_{2-10}$ heterocyclyl.

In some embodiments, the structural unit of

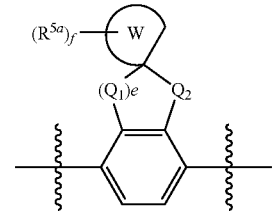

has one of the following structures:

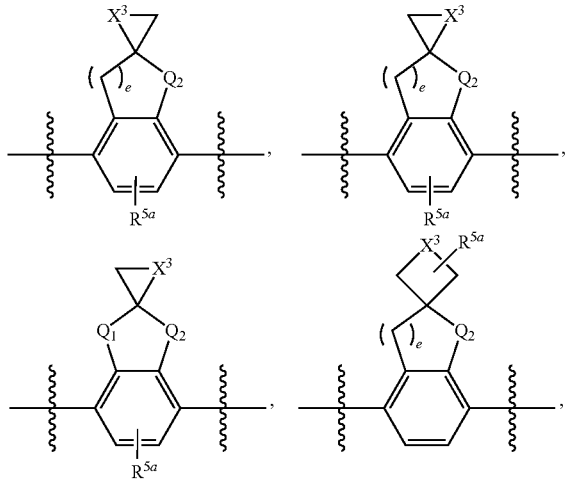

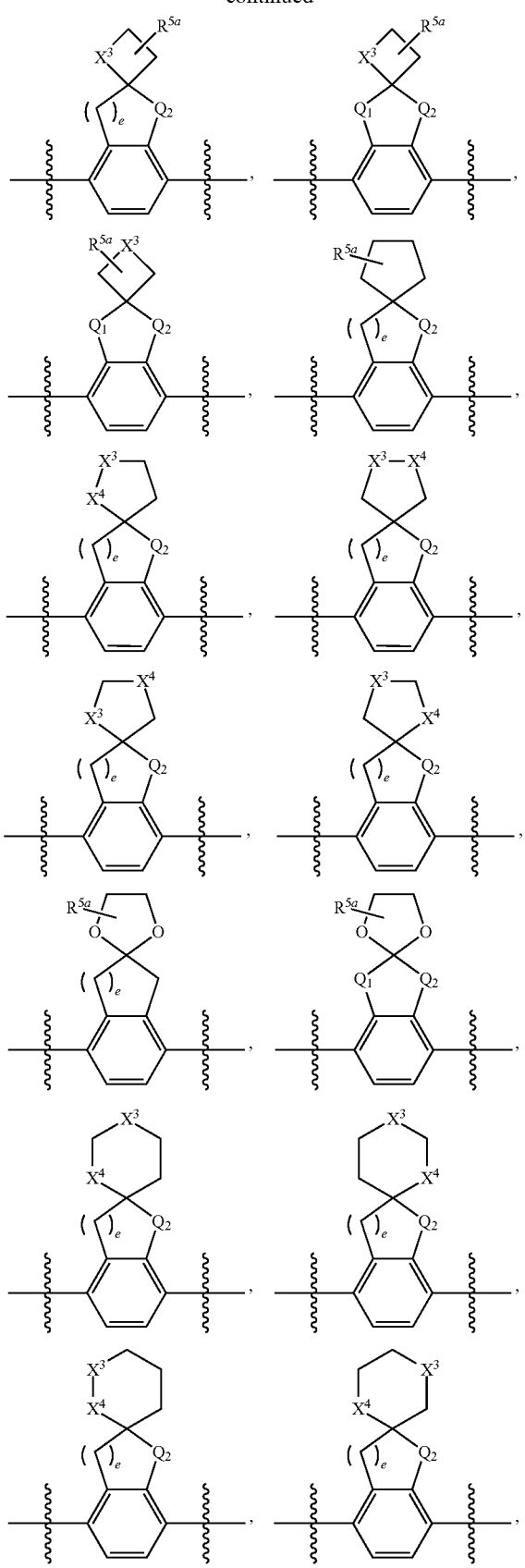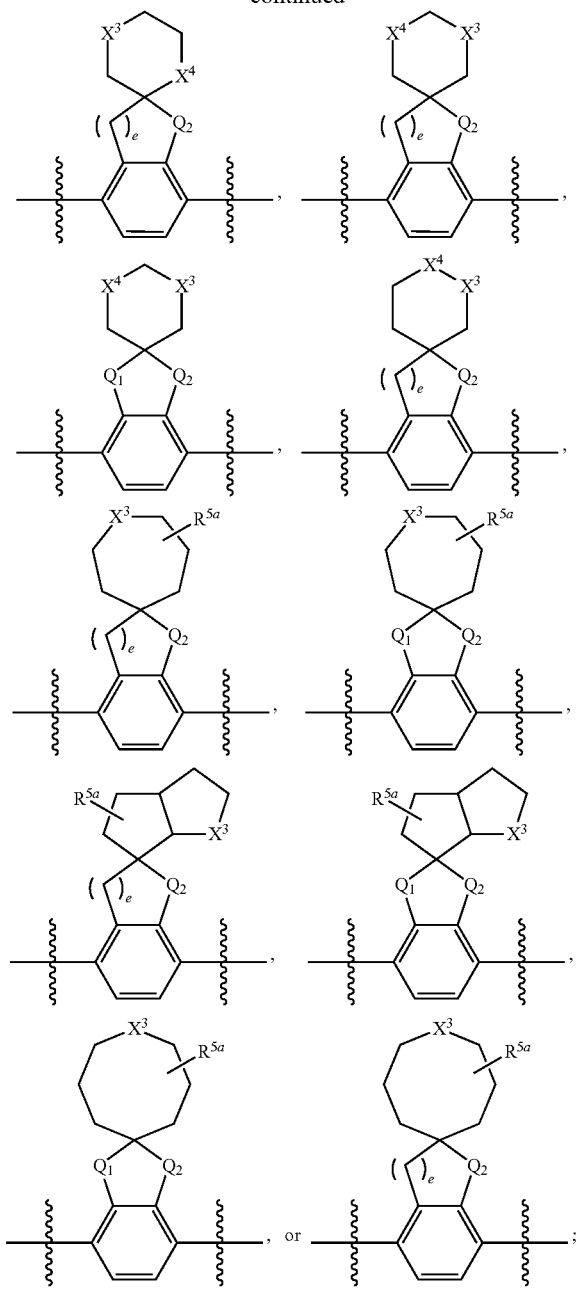

wherein each $X^3$ and $X^4$ is independently O, S, $NR^6$, or $CR^7R^{7a}$;

each e is 1, 2, 3 or 4;

f is 0, 1, 2, 3 or 4;

each $Q_1$ and $Q_2$ is independently $NR^6$, O, S, C(=O), or $CR^7R^{7a}$, with the proviso that when $Q_1$ is $NR^6$, O, S or C(=O), e is 1; and each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy.

In some embodiments, the structural unit of
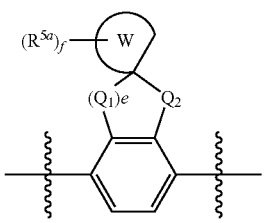
has one of the following structures:
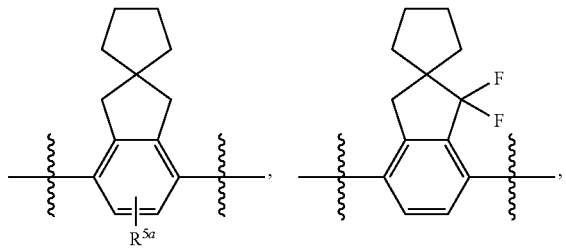
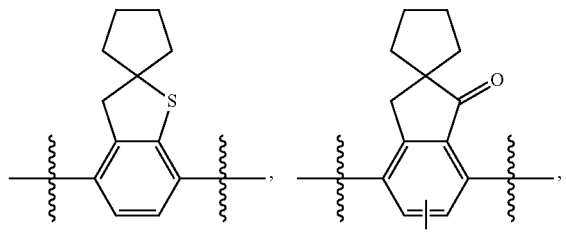
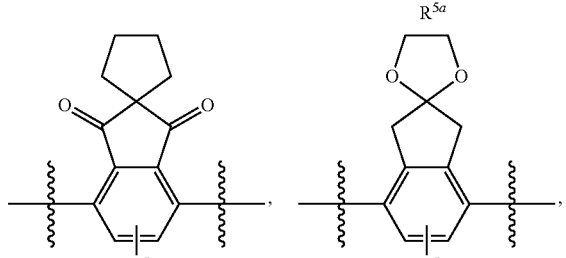
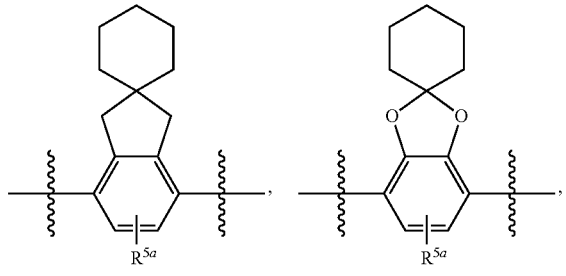
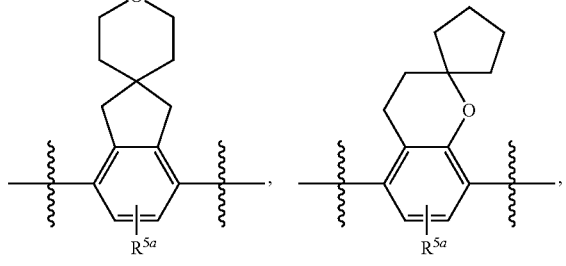
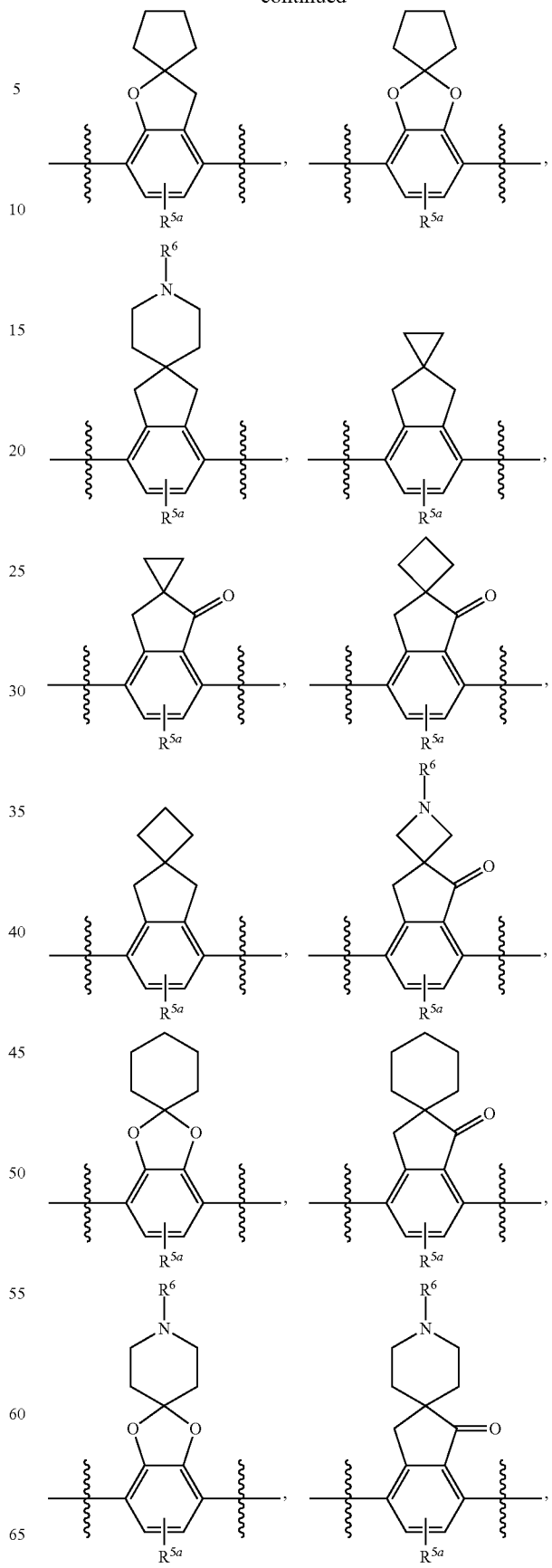

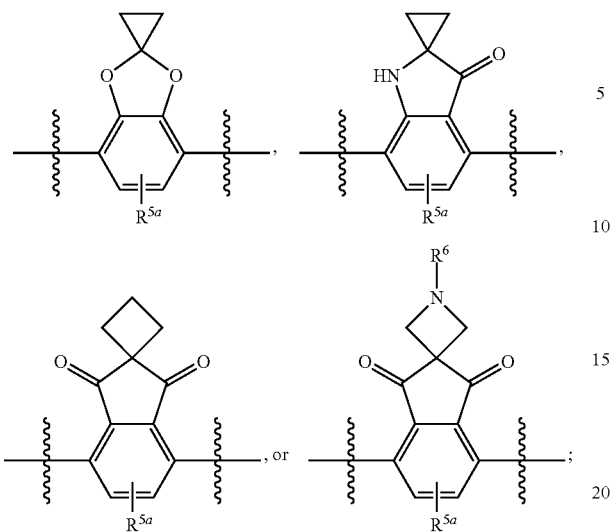

wherein $R^{5a}$ is H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, or $C_{1-6}$ alkylamino; and $R^6$ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic or $C_{3-8}$ cycloalkyl-$C_{1-6}$-aliphatic.

In some embodiments, each of A and A' is independently a bond, $C_{1-6}$ alkylene, $C_{2-6}$ alkenylene, $C_{3-8}$ cycloalkylene, $C_{2-10}$ heterocycloalkylene, —$(CR^8R^{8a})_n$—O—$(CR^8R^{8a})_p$—, —$(CR^8R^{8a})_n$—N($R^5$)—$(CR^8R^{8a})_p$—, —$(CR^8R^{8a})_n$—S(=O)$_r$—N($R^5$)—$(CR^8R^{8a})_p$—, —$(CR^8R^{8a})_n$—C(=O)—N($R^5$)—$(CR^8R^{8a})_p$—, —$(CR^8R^{8a})_n$—N($R^5$)—C(=O)—N($R^5$)—$(CR^8R^{8a})_p$—, —$(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, —$(CR^8R^{8a})_n$—N($R^5$)—C(=O)—O—$(CR^8R^{8a})_p$—, or each of A and A' is independently one of the following groups:

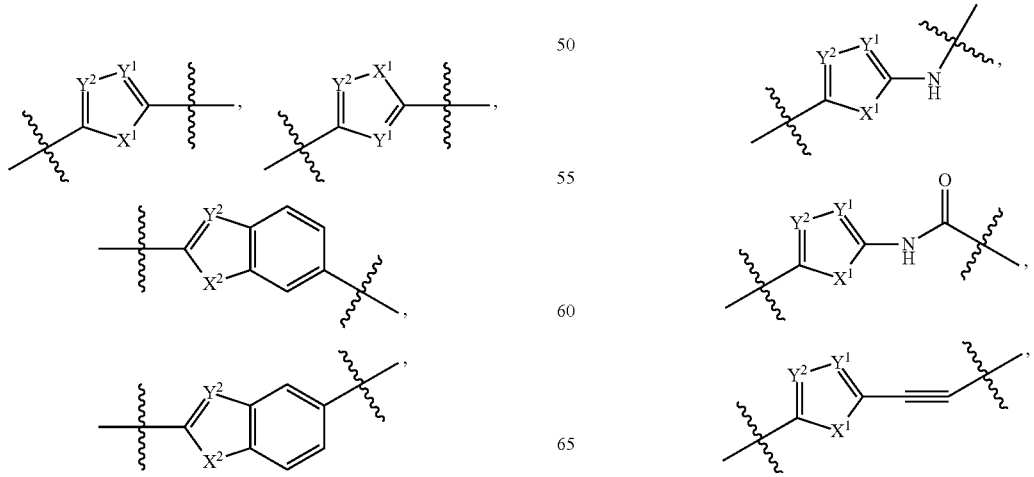

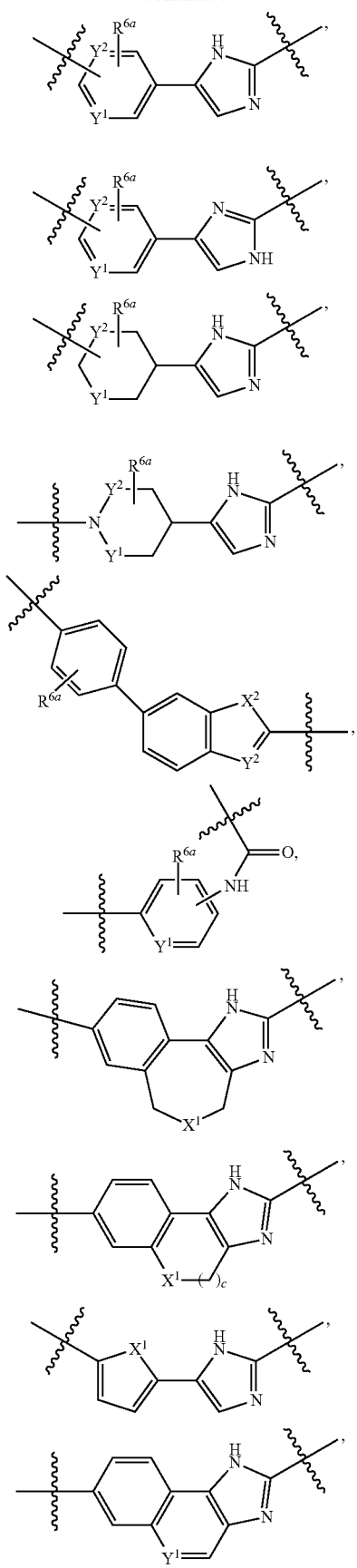

wherein R⁵ is independently H, hydroxy, $C_{1-6}$ alkyl, $C_{1-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

$R^{6a}$ is H, oxo, hydroxy, amino, F, Cl, Br, I, cyano, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2$N($R^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-9}$ heteroarylamino, or $C_{6-10}$ aryloxy;

each $R^7$ and $R^{7a}$ is independently H, F, Cl, $C_{1-6}$ aliphatic, $C_{1-6}$ heteroalkyl, $C_{1-6}$ haloaliphatic, hydroxy $C_{1-6}$ aliphatic, amino $C_{1-6}$ aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heterocyclyl-$C_{1-6}$-aliphatic, $C_{3-8}$ cycloalkyl-$C_{1-6}$-aliphatic, $C_{6-10}$ aryloxy-$C_{1-6}$-aliphatic, $C_{2-10}$ heterocycloxy-$C_{1-6}$-aliphatic, $C_{3-8}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-8}$ cycloalkylamino-$C_{1-6}$-aliphatic, $C_{6-10}$ aryl, $C_{1-9}$ heteroaryl, $C_{2-10}$ heterocyclyl or $C_{3-8}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring including $C_{5-12}$ spiro bicycle and $C_{5-12}$ fused bicycle; and each $R^8$ and $R^{8a}$ is independently H, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl.

In some embodiments, each of A and A' is independently a bond, —CH$_2$—, —(CH$_2$)$_2$—, —CH=CH—, —CH=CH—CH$_2$—, —N(R$^6$)—, —C(=O)—, —C(=S)—, —C(=O)—O—, —C(=O)N(R$^6$)—, —OC(=O)N(R$^6$)—, —OC(=O)O—, —N(R$^6$)C(=O)N(R$^6$)—, —(R$^6$)N—S(=O)$_2$—, —S(=O)$_2$—, —OS(=O)$_2$—, —(R$^6$)N—S(=O)—, —S(=O)—, —OS(=O)—, or each of A and A' is independently one of the following groups:

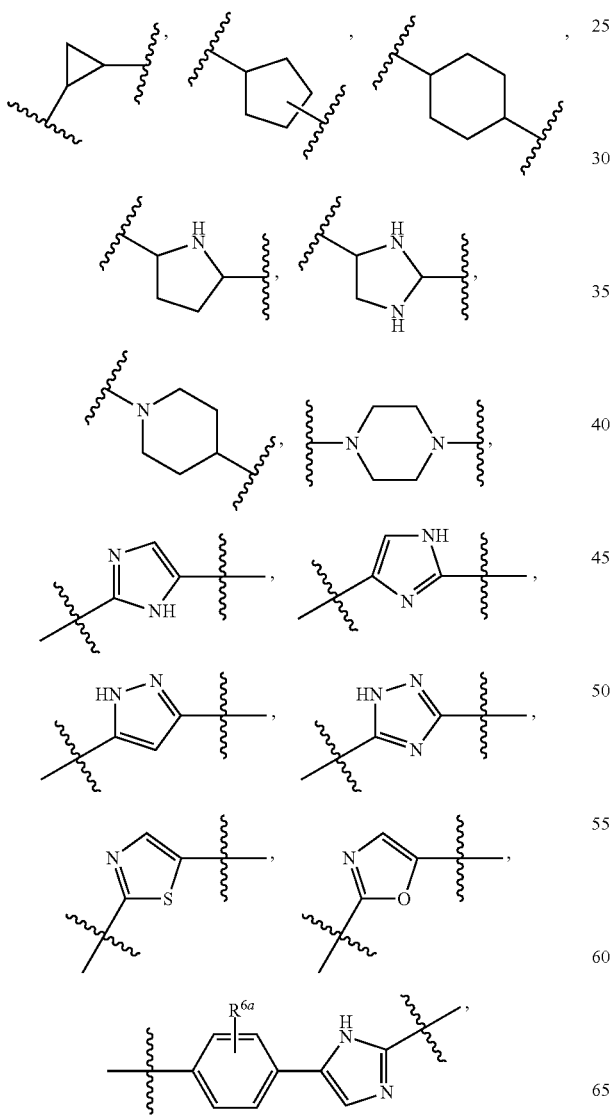

-continued

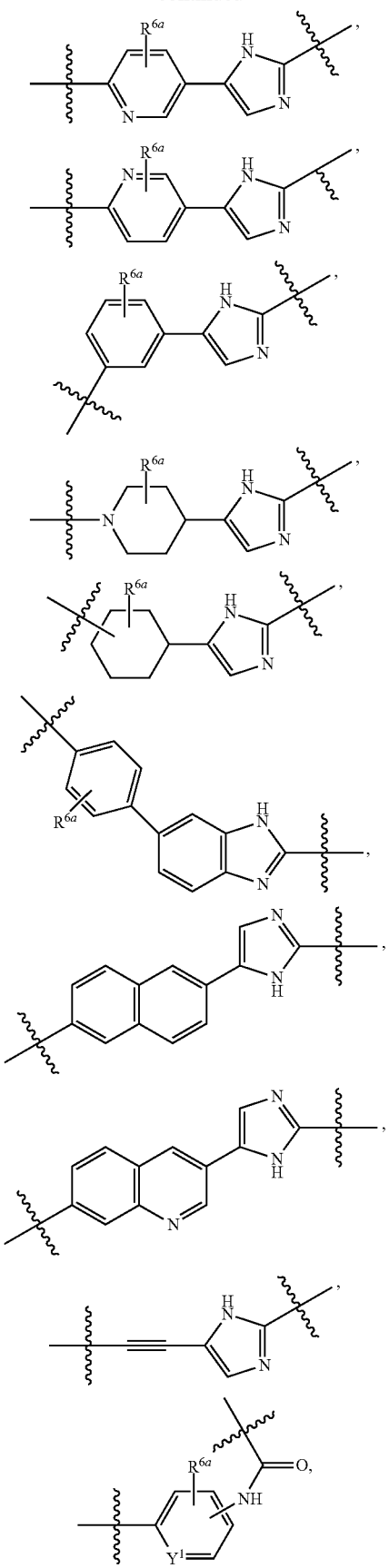

-continued

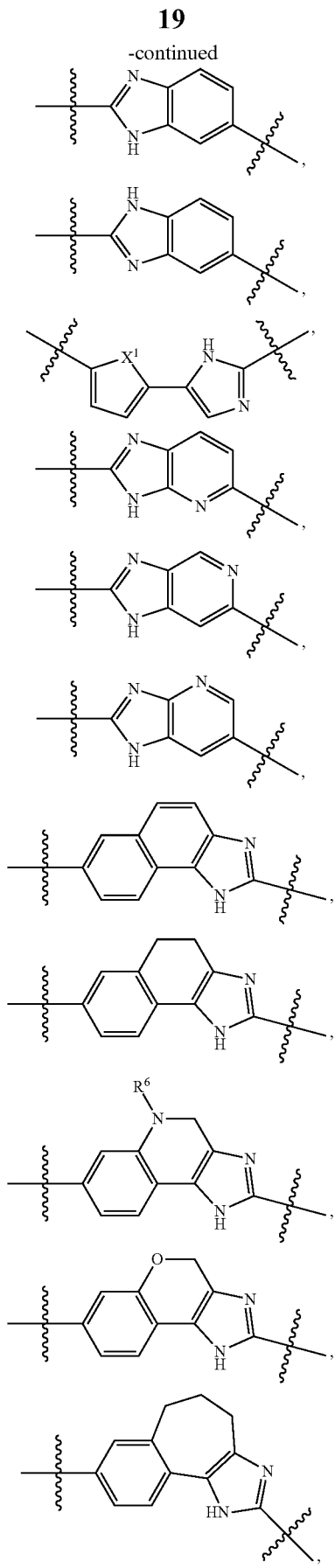

-continued

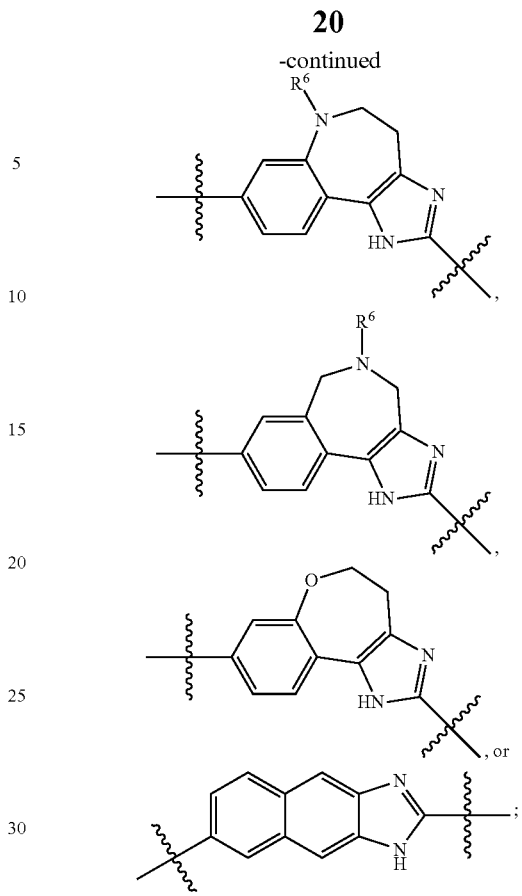

wherein $X^1$ is O or S;

$R^6$ is independently H, $C_{1-6}$ aliphatic, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic or $C_{3-8}$ cycloalkyl-$C_{1-6}$-aliphatic;

$R^{6a}$ is H, hydroxy, amino, F, Cl, Br, I, cyano, oxo, $R^{7a}R^7N-$, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, mercapto or nitro; and each of $R^7$ and $R^{7a}$ is independently H, F, Cl, $C_{1-6}$ aliphatic, $C_{1-6}$ heteroalkyl, $C_{1-6}$ haloaliphatic, hydroxy $C_{1-6}$ aliphatic, amino $C_{1-6}$ aliphatic, $C_{1-6}$ alkoxy-$C_{1-6}$-aliphatic, $C_{1-6}$ alkylamino-$C_{1-6}$-aliphatic or $C_{1-6}$ alkylthio-$C_{1-6}$-aliphatic.

In some embodiments, each of $R^1$, $R^2$, $R^3$ and $R^4$ is independently H, $C_{1-8}$ alkyl, $C_{1-8}$ heteroalkyl, $C_{6-10}$ aryl-$C_{1-6}$-alkyl, $C_{3-10}$ cycloalkyl, $C_{2-10}$ heterocyclyl, $C_{1-9}$ heteroaryl or $C_{6-10}$ aryl; or $R^1$ and $R^2$, together with X—CH, form a 3-8 membered heterocycle or carbocycle, $C_{5-12}$ fused bicycle, $C_{5-12}$ fused heterobicycle, $C_{5-12}$ Spiro bicycle or $C_{5-12}$ Spiro heterobicycle; or $R^3$ and $R^4$, together with X'—CH, form a 3-8 membered heterocycle or carbocycle, $C_{5-12}$ fused bicycle, $C_{5-12}$ fused heterobicycle, $C_{5-12}$ Spiro bicycle or $C_{5-12}$ Spiro heterobicycle.

In other embodiments, $R^1$ and $R^2$, together with X—CH, or $R^3$ and $R^4$, together with X'—CH, form a 3-8 membered heterocycle, $C_{5-12}$ fused bicycle, $C_{5-12}$ fused heterobicycle, $C_{5-12}$ Spiro bicycle or $C_{5-12}$ Spiro heterobicycle.

In other embodiments, $R^1$, $R^2$ and X—CH together form a heterocycle or fused ring or Spiro ring system having one of the following structures:

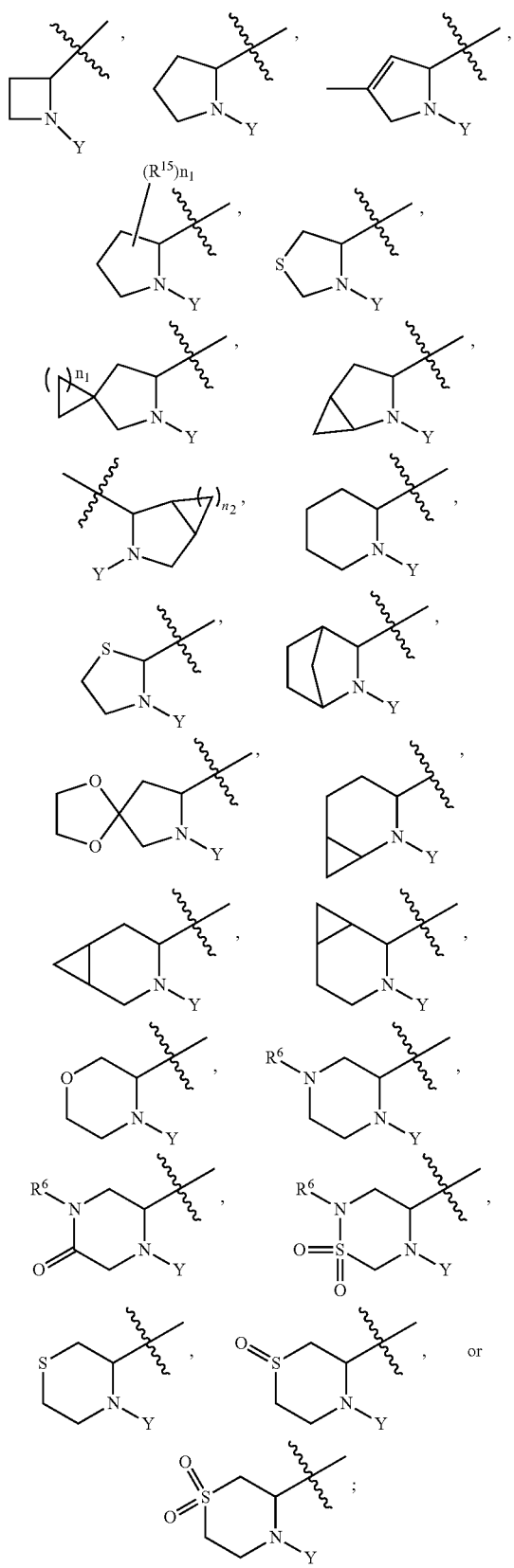

wherein R[15] is H, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl; and each $n_1$ and $n_2$ is independently 1, 2, 3 or 4.

In other embodiments, R[3], R[4] and X'—CH together form a heterocycle or fused ring or Spiro ring system having one of the following structures:

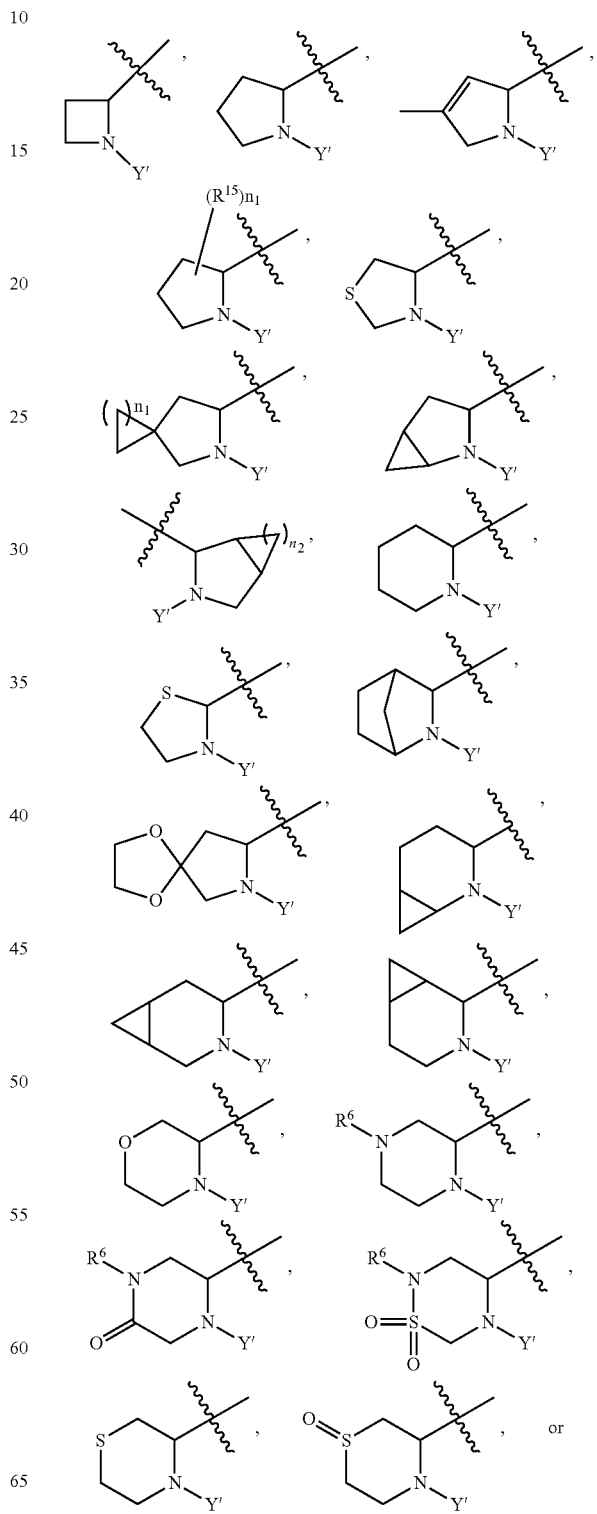

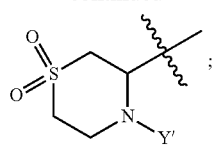

wherein $R^{15}$ is H, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl; and each $n_1$ and $n_2$ is independently 1, 2, 3 or 4.

In some embodiments, the compound having formula (I) of the present invention is the compound having formula (II):

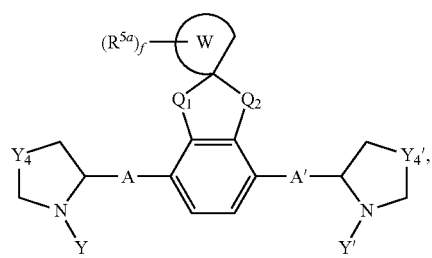
(II)

wherein the structural unit of

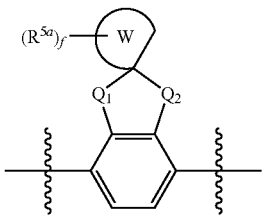

has one of the following structures:

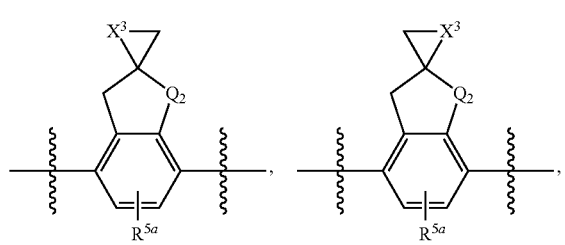

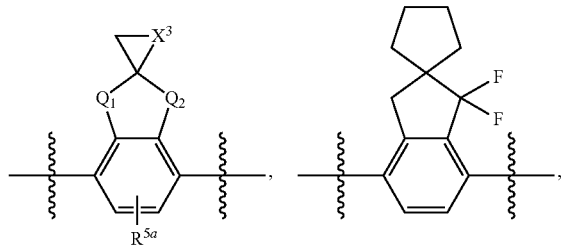

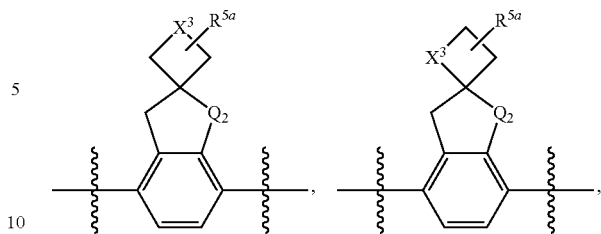

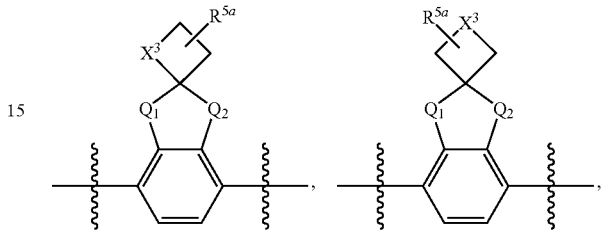

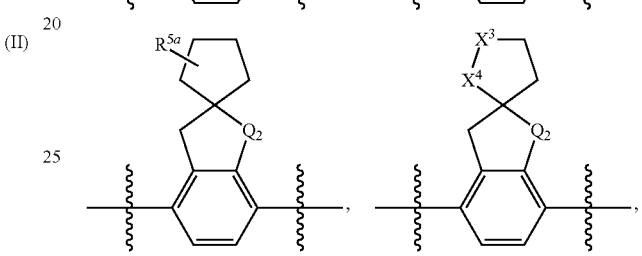

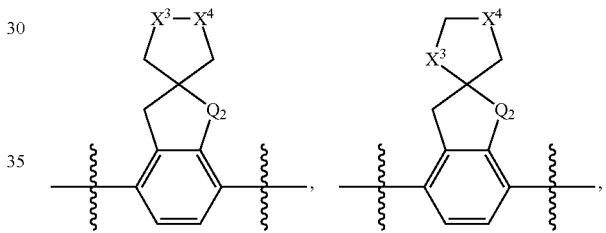

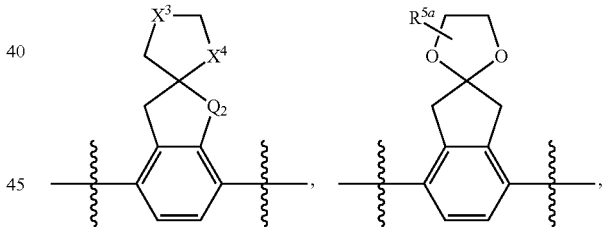

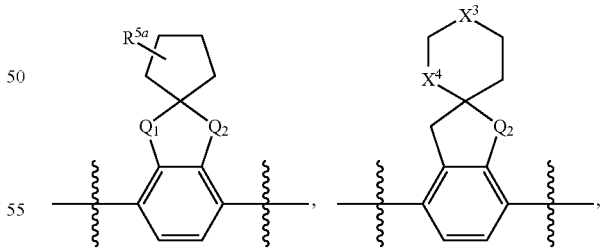

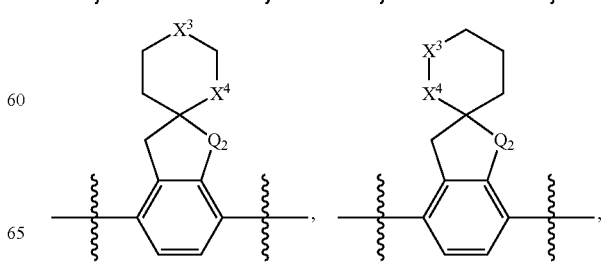

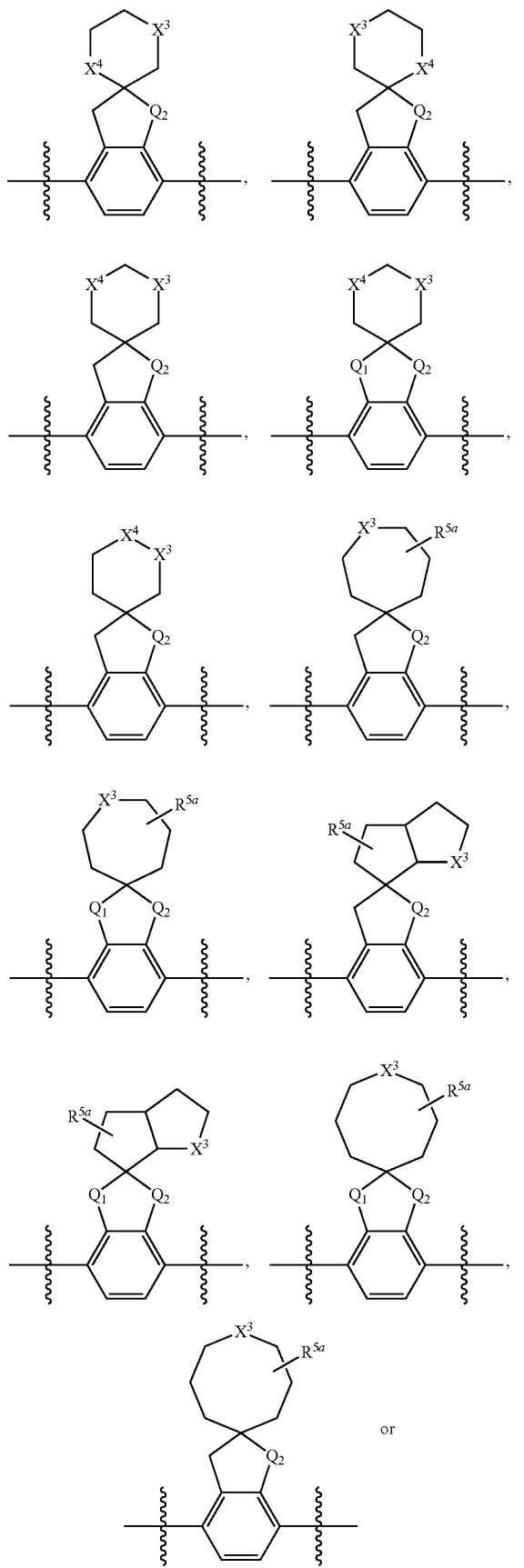

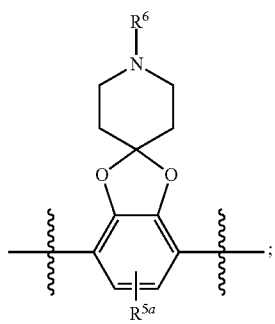

wherein each $Q_1$ and $Q_2$ is independently $NR^6$, O, S, C(=O) or $CH_2$;

each $X^3$ and $X^4$ is independently O, S, $NR^6$ or $CR^7R^{7a}$;

each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, or each of A and A' is independently one of the following groups:

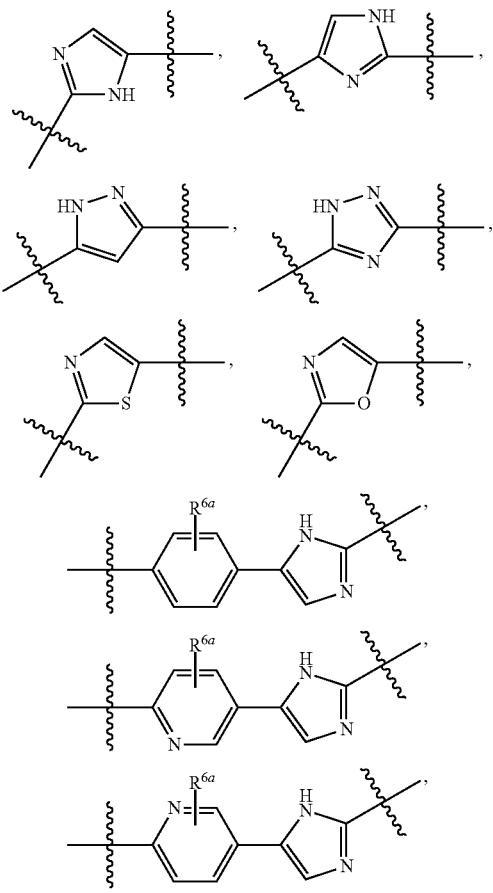

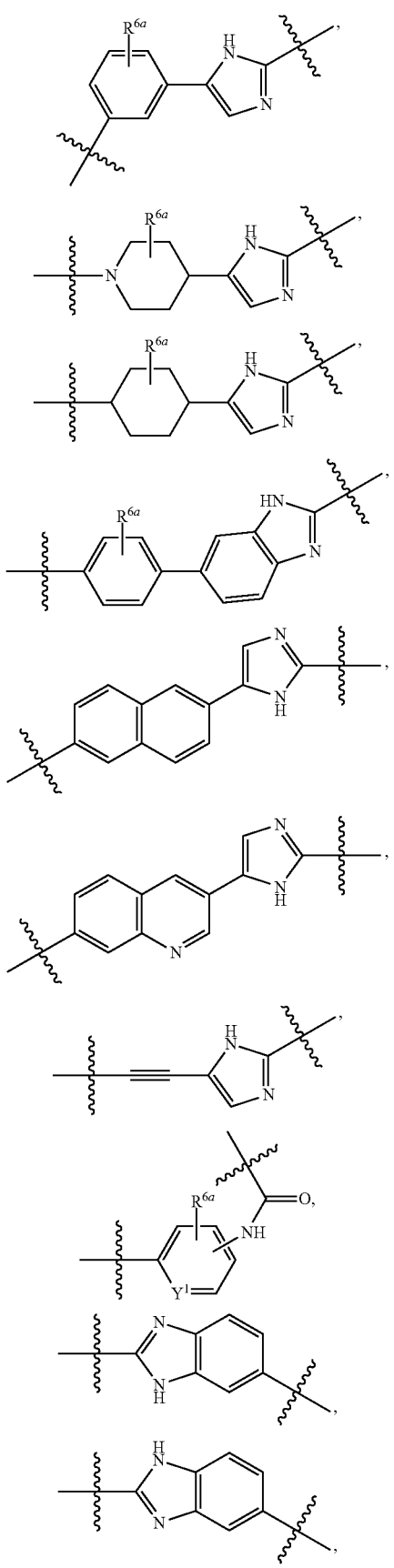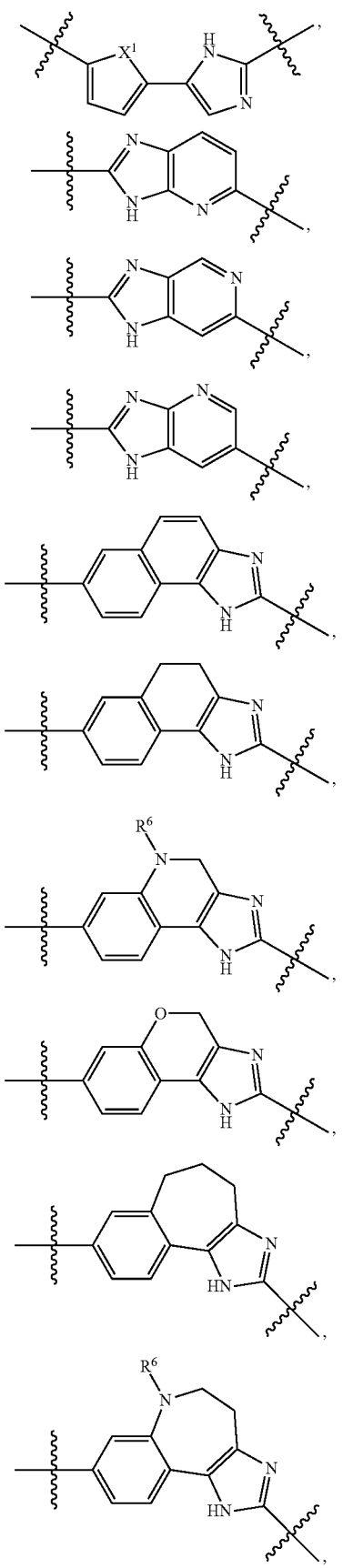

-continued

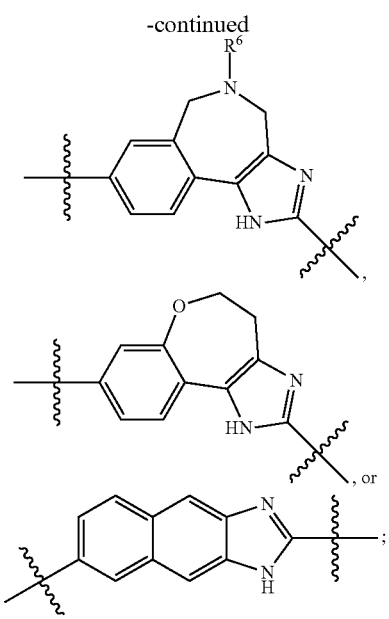

R⁵ is independently H, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, alkyl-S(=O)$_r$— or aminosulfonyl;

each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF₃, —OCF₃, mercapto, nitro, $C_{1-6}$ alkylamino, $C_{3-10}$ cycloalkyl or $C_{6-10}$ aryloxy;

$R^6$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{6a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF₃, —OCF₃, mercapto, nitro, $C_{1-6}$ alkylamino, $C_{3-10}$ cycloalkyl or $C_{6-10}$ aryloxy;

each $R^7$ and $R^{7a}$ is independently H, $C_{1-6}$ aliphatic, $C_{1-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring including spiro bicycle and fused bicycle;

each $R^8$ and $R^{8a}$ is independently H, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each n is independently 0, 1, 2 or 3;

each p is independently 0, 1, 2 or 3;

each k is independently 0, 1 or 2;

each r is independently 0, 1 or 2; and each of $Y_4$ and $Y_4'$ is independently a bond, O, S, —(CH₂)$_n$—, —CH=CH—, —S(=O)$_r$—, —CH₂O—, —CH₂S—, —CH₂S(=O)$_r$—, or —CH₂N($R^6$)—.

In some embodiments, the compound having formula (I) of the present invention is the compound having formula (III):

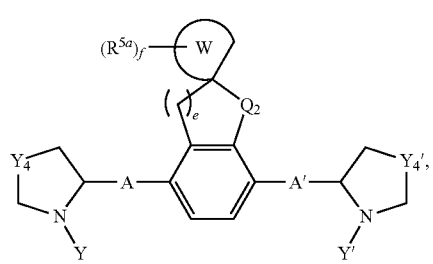

(III)

wherein the structural unit of

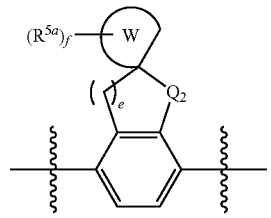

has one of the following structures:

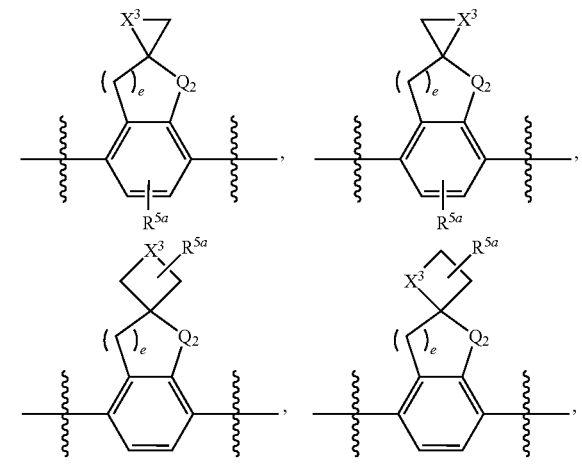

-continued

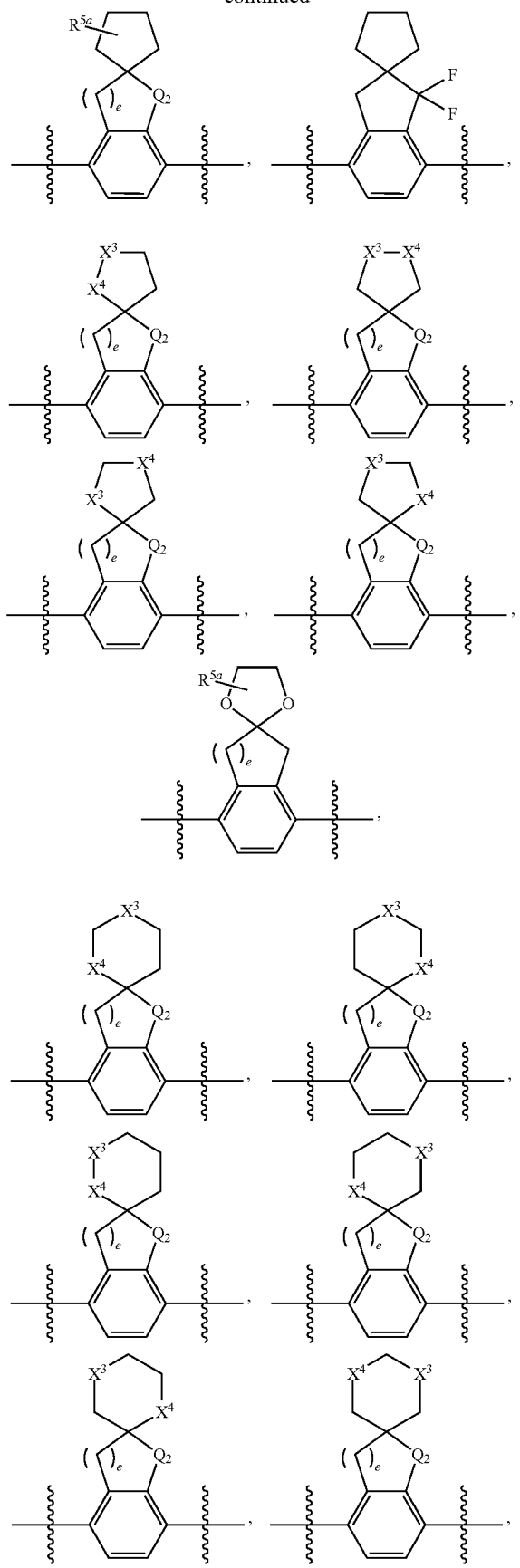

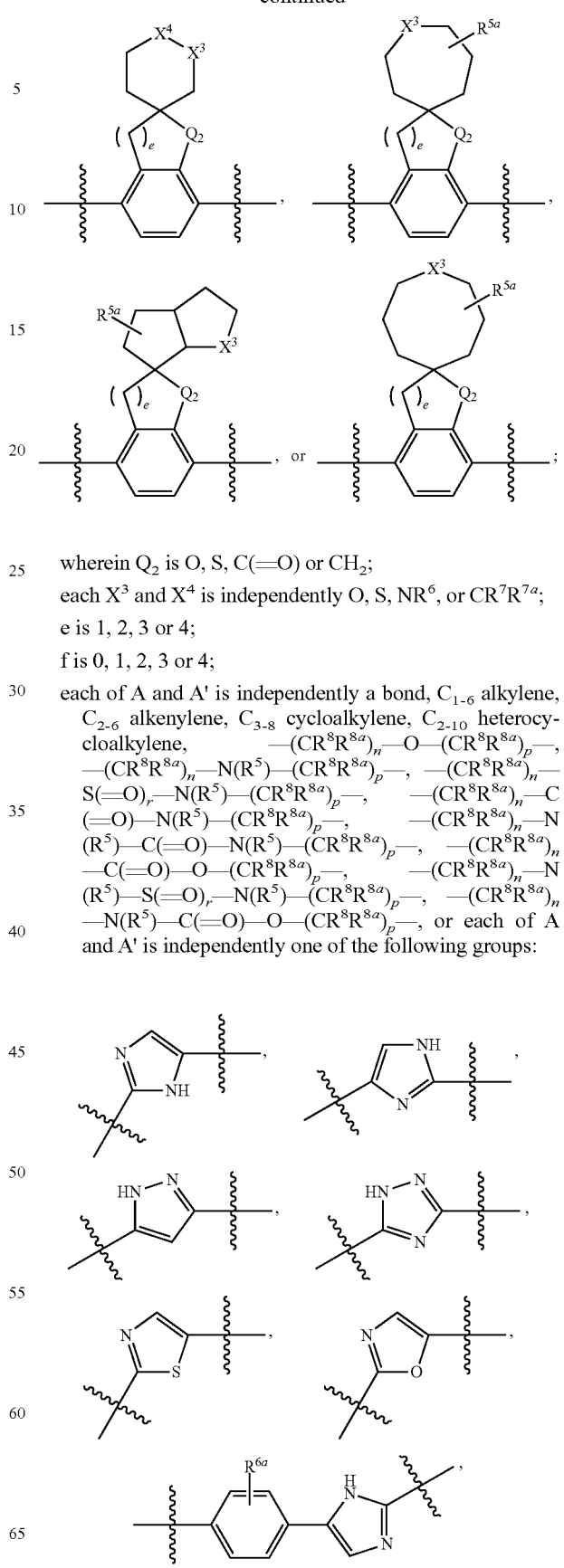

wherein $Q_2$ is O, S, C(=O) or $CH_2$;

each $X^3$ and $X^4$ is independently O, S, $NR^6$, or $CR^7R^{7a}$;

e is 1, 2, 3 or 4;

f is 0, 1, 2, 3 or 4;

each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, or each of A and A' is independently one of the following groups:

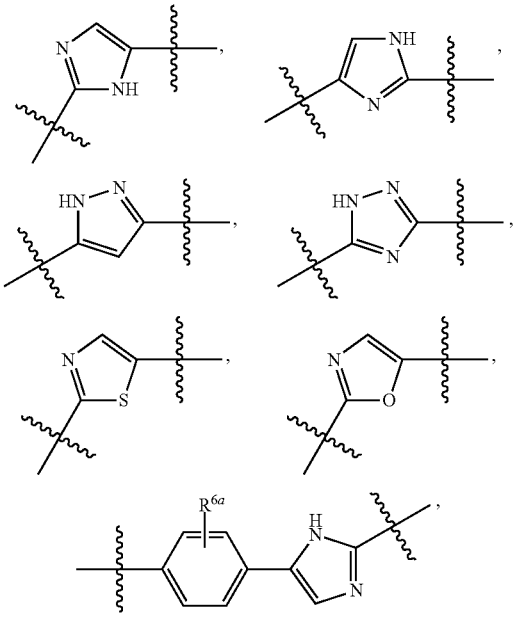

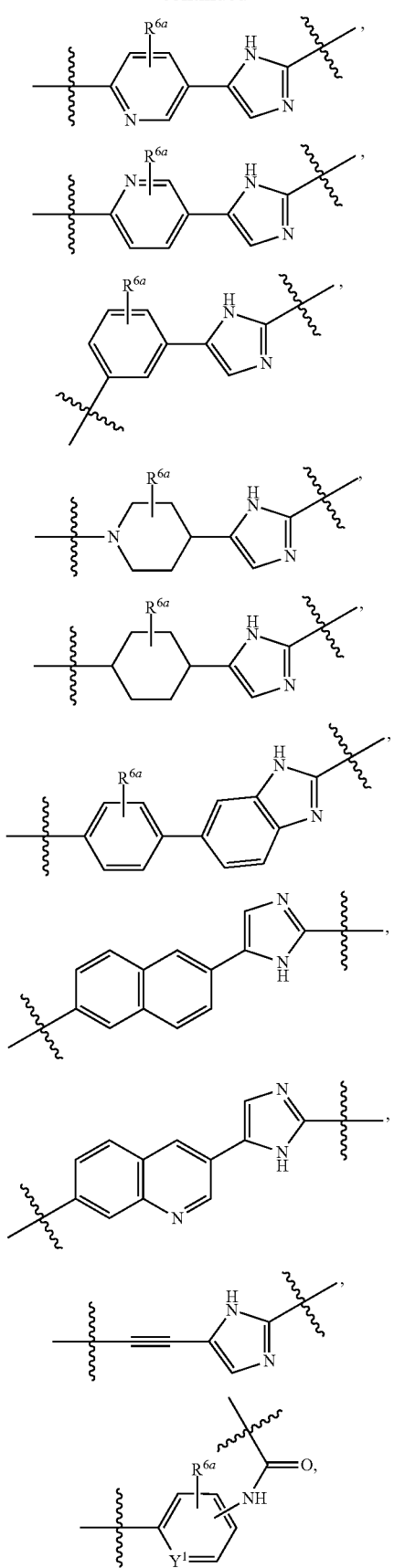
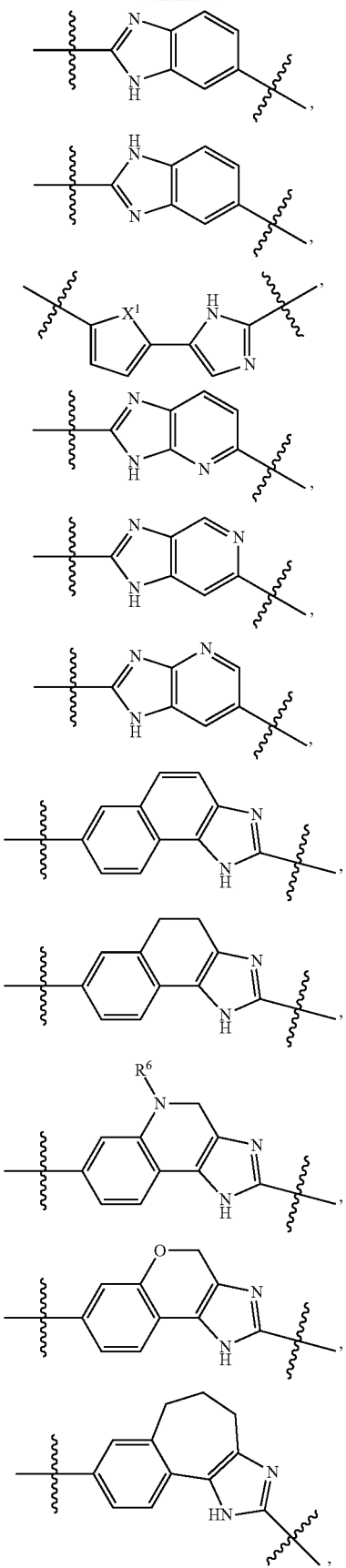

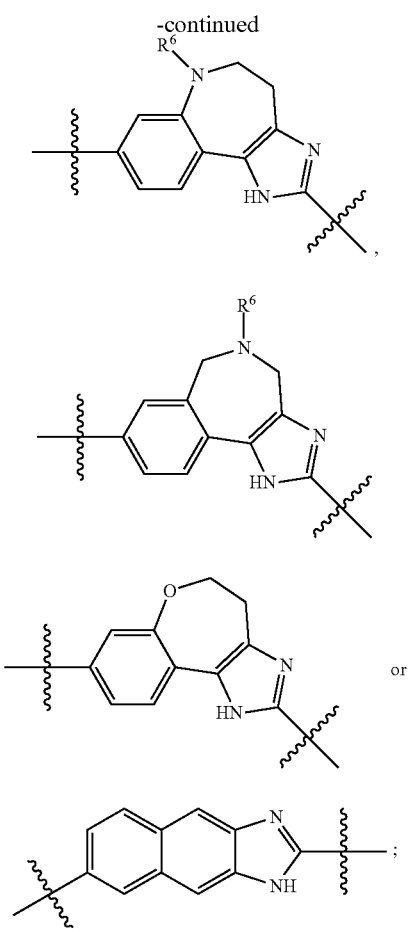

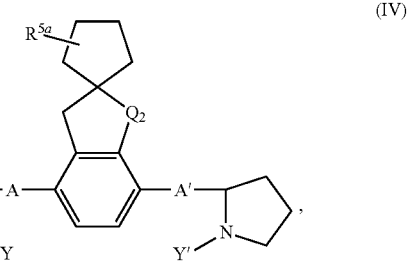

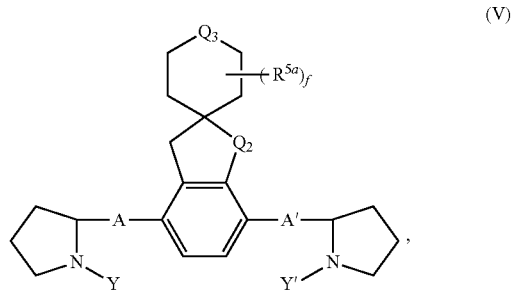

R[5] is independently H, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, alkyl-S(=O)$_r$— or aminosulfonyl;

each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

$R^6$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{6a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^7$ and $R^{7a}$ is independently H, $C_{1-6}$ aliphatic, $C_{1-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring including spiro bicycle and fused bicycle;

each $R^8$ and $R^{8a}$ is independently H, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each n is independently 0, 1, 2 or 3;

each p is independently 0, 1, 2 or 3;

each k is independently 0, 1 or 2;

each r is independently 0, 1 or 2; and each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, or —CH$_2$N(R$^6$)—.

In other embodiments, the compound having formula (I) of the present invention is the compound having formula (IV):

(IV)

wherein each of A, A', Y, Y', $Q_2$ and $R^{5a}$ is as defined in formula (I).

In other embodiments, the compound having formula (I) of the present invention is the compound having formula (V):

(V)

wherein each of A, A', Y, Y', $R^{5a}$ and f is as defined in formula (I); and each of $Q_2$ and $Q_3$ is independently O, S, C(=O), NR$^6$, or CH$_2$.

In other embodiments, the compound having formula (I) of the present invention is the compound having formula (VI):

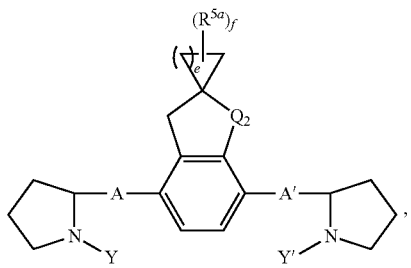

(VI)

wherein each of A, A', Y, Y', $Q_2$, $R^{5a}$ and f is as defined in formula (I); and e is 1, 2, 3 or 4.

In some embodiments, each of Y and Y' is independently a group derived from an α-amino acid.

In other embodiments, the naturally occurring or commercially available α-amino acid is isoleucine, leucine, lysine, methionine, phenylalanine, threonine, tryptophane, valine, alanine, asparagine, aspartic acid, glutamic acid, glutamine, proline, serine, p-tyrosine, arginine, histidine, cysteine, glycine, sarcosine, N,N-dimethylglycine, homoserine, norvaline, norleucine, ornithine, homocysteine, homophenylalanine, phenylglycine, o-tyrosine, m-tyrosine or hydroxyproline.

In other embodiments, the α-amino acid is in the D configuration.

In other embodiments, each of Y and Y' is independently —[U—$(CR^9R^{9a})_t$—$N(R^{10})$—$(CR^9R^{9a})_t]_k$—U—$(CR^9R^{9a})_t$—$N(R^{11})$—$(CR^9R^{9a})_t$—$R^{12}$, —U—$(CR^9R^{9a})_t$—$R^{12}$ or —[U—$(CR^9R^{9a})_t$—$N(R^{10})$—$(CR^9R^{9a})_t]_k$—U—$(CR^9R^{9a})_t$—O—$(CR^9R^{9a})_t$—$R^{12}$.

In other embodiments, each of Y and Y' is independently —[U—$(CR^9R^{9a})_t$N$(R^{10})$—$(CR^9R^{9a})_t]_k$—U—$(CR^9R^{9a})_t$—N$(R^{11})$—$(CR^9R^{9a})_t$—$R^{12}$.

In other embodiments, each of Y and Y' is independently —U—$(CR^9R^{9a})_t$—N$(R^{10})$—$(CR^9R^{9a})_t$—U—$(CR^9R^{9a})_t$—N$(R^{11})$—$(CR^9R^{9a})_t$—$R^{12}$.

In other embodiments, each of Y and Y' is independently —U—$(CR^9R^{9a})_t$—N$(R^{11})$—$(CR^9R^{9a})_t$—$R^{12}$.

In other embodiments, each of Y and Y' is independently —[C(=O)—$(CR^9R^{9a})_t$—N$(R^{10})$—$(CR^9R^{9a})_t]_k$—U—$(CR^9R^{9a})_t$—N$(R^{11})$—$(CR^9R^{9a})_t$—$R^{12}$.

In other embodiments, each of Y and Y' is independently —C(=O)—$(CR^9R^{9a})_t$—N$(R^{10})$—$(CR^9R^{9a})_t$—U—$(CR^9R^{9a})_t$—N$(R^{11})$—$(CR^9R^{9a})_t$—$R^{12}$.

In other embodiments, each of Y and Y' is independently —[C(=O)—$(CR^9R^{9a})_t$—N$(R^{10})$—$(CR^9R^{9a})_t]_k$—C(=O)—$(CR^9R^{9a})_t$—N$(R^{11})$—$(CR^9R^{9a})_t$—$R^{12}$.

In other embodiments, each of Y and Y' is independently —C(=O)—$(CR^9R^{9a})_t$—N$(R^{10})$—$(CR^9R^{9a})_t$—C(=O)—$(CR^9R^{9a})_t$—N$(R^{11})$—$(CR^9R^{9a})_t$—$R^{12}$.

In other embodiments, each of Y and Y' is independently —C(=O)—$(CR^9R^{9a})_t$—N$(R^{11})$—$(CR^9R^{9a})_t$—$R^{12}$.

In other embodiments, each of Y and Y' is independently —C(=O)—$(CR^9R^{9a})_n$—N$(R^{11})$—$(CR^9R^{9a})_n$—C(=O)—$R^{13}$.

In other embodiments, each of Y and Y' is independently —C(=O)—$(CR^9R^{9a})_n$—N$(R^{11})$—C(=O)—$R^{13}$.

In other embodiments, each of Y and Y' is independently —C(=O)—$(CR^9R^{9a})_n$—N$(R^{11})$—$(CR^9R^{9a})_n$—C(=O)—O—$R^{13}$.

In other embodiments, each of Y and Y' is independently —C(=O)—$(CR^9R^{9a})_n$—N$(R^{11})$—C(=O)—O—$R^{13}$.

In other embodiments, each of Y and Y' is independently —U—$(CR^9R^{9a})_t$—$R^{12}$.

In other embodiments, each of Y and Y' is independently —C(=O)—$(CR^9R^{9a})_t$—$R^{12}$.

In other embodiments, each of Y and Y' is independently —[U—$(CR^9R^{9a})_t$—N$(R^{10})$—$(CR^9R^9)_t]_k$—U—$(CR^9R^{9a})_t$—O—$(CR^9R^{9a})_t$—$R^{12}$.

In other embodiments, each of Y and Y' is independently —U—$(CR^9R^{9a})_t$—N$(R^{10})$—$(CR^9R^{9a})_t$—U—$(CR^9R^{9a})_t$—O—$(CR^9R^{9a})_t$—$R^{12}$.

In other embodiments, each of Y and Y' is independently —C(=O)—$(CR^9R^{9a})_t$—N$(R^{10})$—$(CR^9R^{9a})_t$—C(=O)—$(CR^9R^{9a})_t$—O—$(CR^9R^{9a})_t$—$R^{12}$.

In other embodiments, each of Y and Y' is independently —U—$(CR^9R^{9a})_t$—O—$(CR^9R^{9a})_t$—$R^{12}$.

In other embodiments, each of Y and Y' is independently —C(=O)—$(CR^9R^{9a})_t$—O—$(CR^9R^{9a})_t$—$R^{12}$.

In other embodiments, each of Y and Y' is independently —C(=O)—$(CR^9R^{9a})_n$—$NR^{11}$—$R^{12}$, wherein $R^{11}$ and $R^{12}$, together with the nitrogen atom they are attached to, form a 4-7 membered ring.

In other embodiments, each $R^9$, $R^{9a}$, $R^{10}$ and $R^{11}$ is independently H, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ haloalkyl, $C_{1-6}$ hydroxyalkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

$R^{12}$ is independently $R^{13a}R^{13}N$—, —C(=O)$R^{13}$, —C(=S)$R^{13}$, —C(=O)—O—$R^{13}$, —C(=O)N$R^{13}R^{13a}$, —OC(=O)N$R^{13}R^{13a}$, —OC(=O)O$R^{13}$, —N($R^{13}$)C(=O)N$R^{13}R^{13a}$, —N($R^{13}$)C(=O)O$R^{13a}$, —N($R^{13}$)C(=O)—$R^{13a}$, $R^{13}R^{13a}N$—S(=O)$_2$—, $R^{13}S$(=O)$_2$—, $R^{13}S$(=O)$_2N(R^{13a})$—, $R^{13}OS$(=O)$_2$—, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl;

or $R^{11}$ and $R^{12}$, together with the nitrogen atom they are attached to, form a 4-7 membered ring; and each $R^{13}$ and $R^{13a}$ is independently H, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl.

In other embodiments, each $R^9$, $R^{9a}$, $R^{10}$ and $R^{11}$ is independently H, methyl, ethyl, isopropyl, cyclohexyl, isobutyl or phenyl;

$R^{12}$ is independently —C(=O)$R^{13}$, —C(=O)—O—$R^{13}$, —C(=O)N$R^{13}R^{13a}$, methyl, ethyl, propyl, phenyl, cyclohexyl, morpholinyl or piperidinyl;

or $R^{11}$ and $R^{12}$, together with the nitrogen atom they are attached to, form a 4-7 membered ring; and each $R^{13}$ and $R^{13a}$ is independently H, methyl, ethyl, propyl, phenyl, cyclohexyl, morpholinyl or piperidinyl.

In other embodiments, the compound having formula (I) of the present invention is the compound having formula (VII):

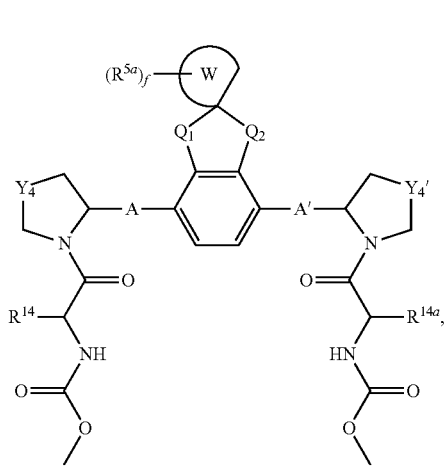

(VII)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl.

In other embodiments, the compound having formula (I) of the present invention is the compound having formula (VIII):

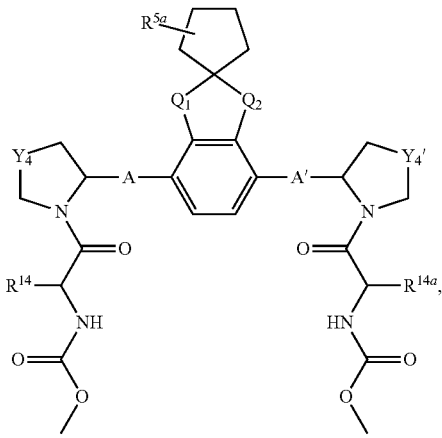

(VIII)

wherein each of $R^{14}$ and $R^{14a}$ is independently H, $C_{1-3}$ hydroxyalkyl, methyl, ethyl, isopropyl, isobutyl, tert-butyl, allyl, propargyl, trifluoroethyl, phenyl, pyranyl, morpholinyl, —$NR^7R^{7a}$, benzyl, piperazinyl, cyclopentyl, cyclopropyl, cyclohexyl, or $C_{1-9}$ heteroaryl.

In some embodiments, the compound having formula (I) of the present invention is the compound having formula (IX):

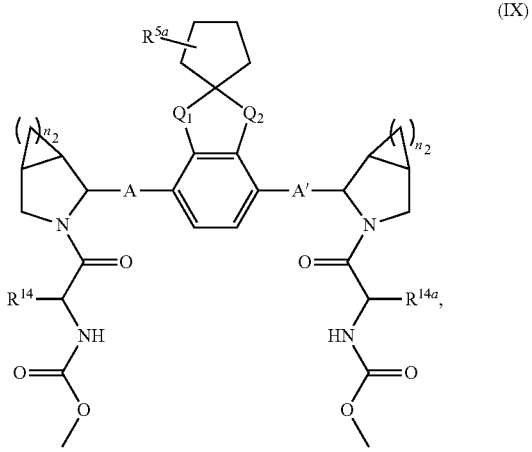

(IX)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_2$ is independently 1, 2, 3 or 4.

In some embodiments, the compound having formula (I) of the present invention is the compound having formula (X):

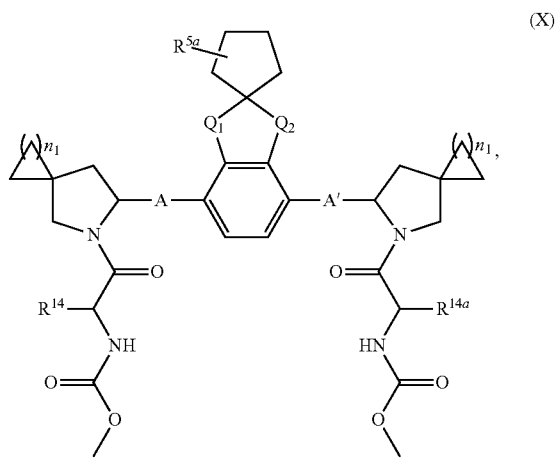

(X)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_1$ is independently 1, 2, 3 or 4.

In some embodiments, the compound having formula (I) of the present invention is the compound having formula (XI):

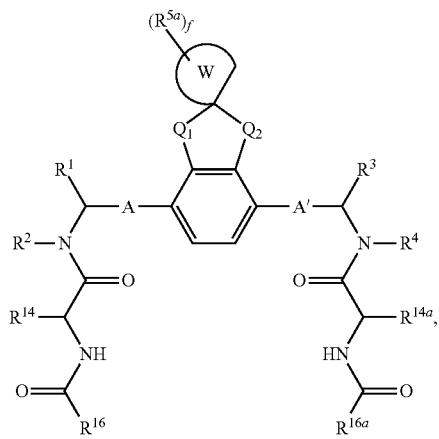

wherein $R^{5a}$ is H, methyl, ethyl, F, Cl, Br or I;
$Q_1$ is $CH_2$, $C(=O)$, O, S, or NH;
$Q_2$ is $CH_2$, $C(=O)$, $CF_2$, O, or S;
each of $R^{14}$ and $R^{14a}$ is independently methyl, ethyl, phenyl, cyclohexyl, 1-methylpropyl, isopropyl or tert-butyl; and
each of $R^{16}$ and $R^{16a}$ is independently hydroxy, methoxy, ethoxy, phenoxy,

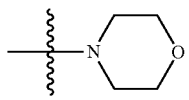

or tert-butoxy;
wherein the structural unit of

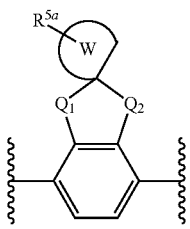

has one of the following structures:

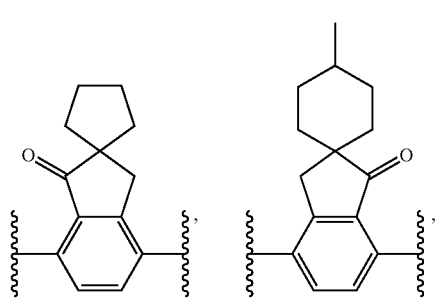

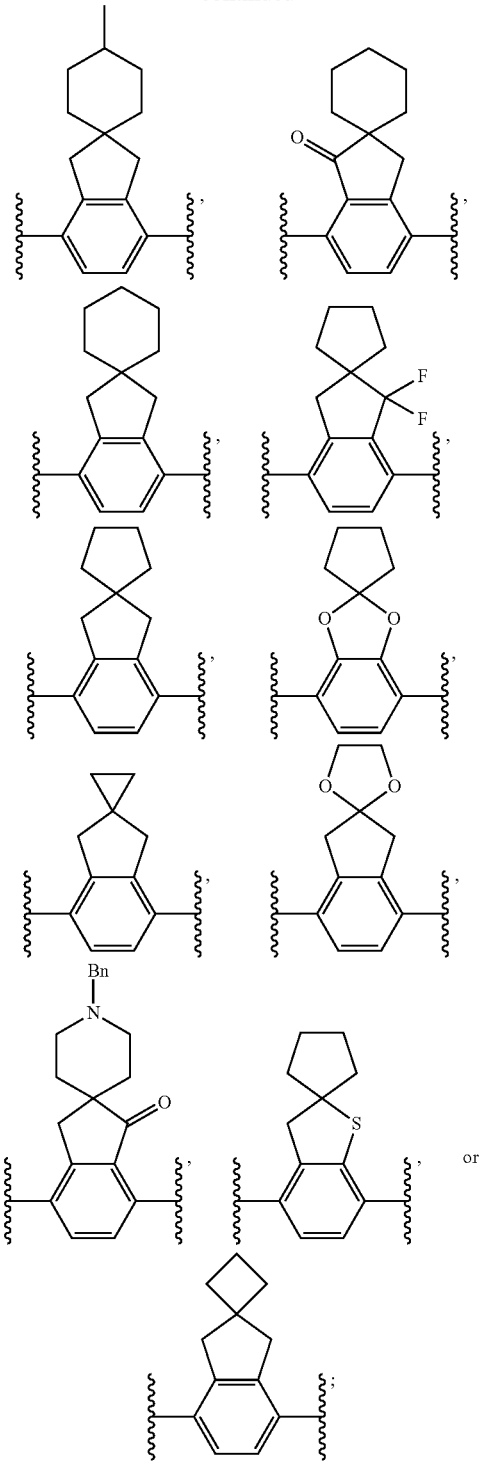

each of A and A' is independently

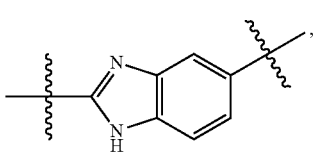

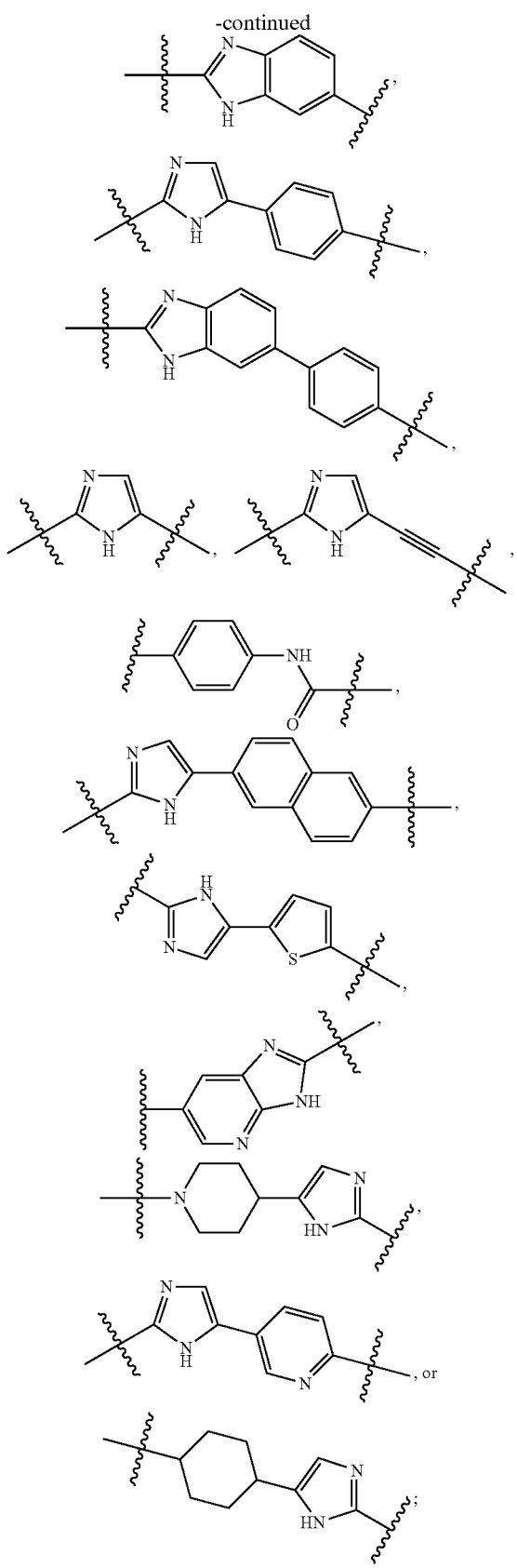
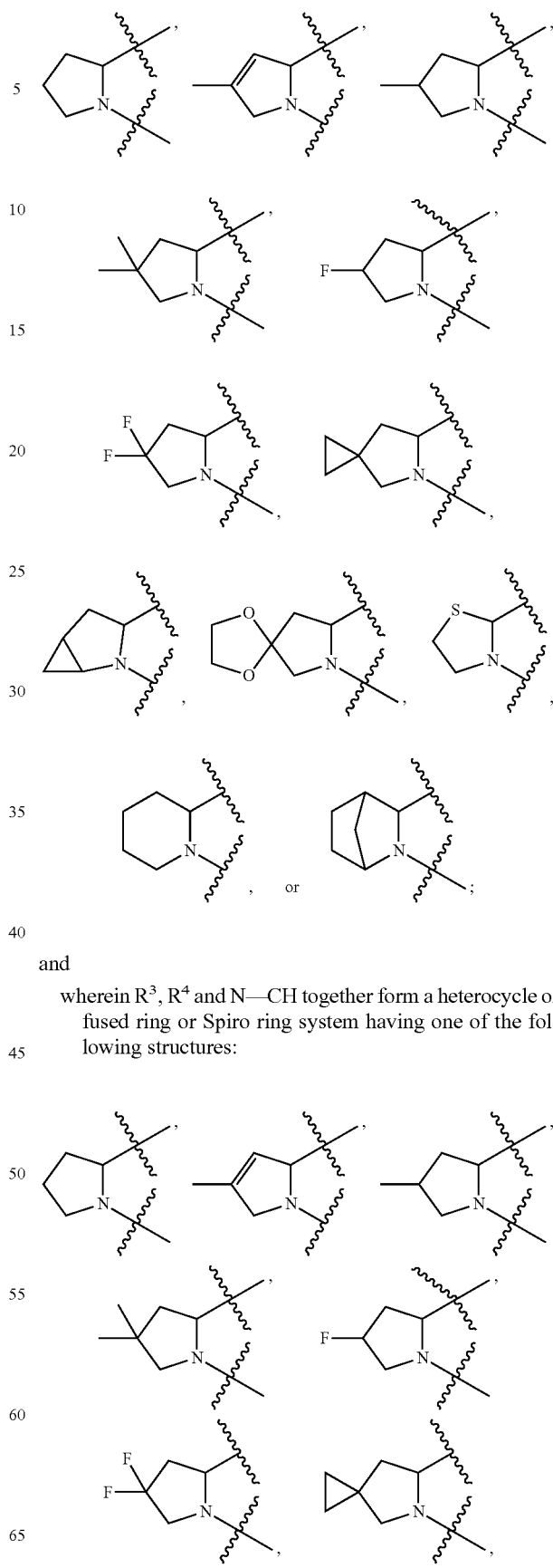
wherein $R^1$, $R^2$ and N—CH together form a heterocycle or fused ring or Spiro ring system having one of the following structures:
and
wherein $R^3$, $R^4$ and N—CH together form a heterocycle or fused ring or Spiro ring system having one of the following structures:

-continued

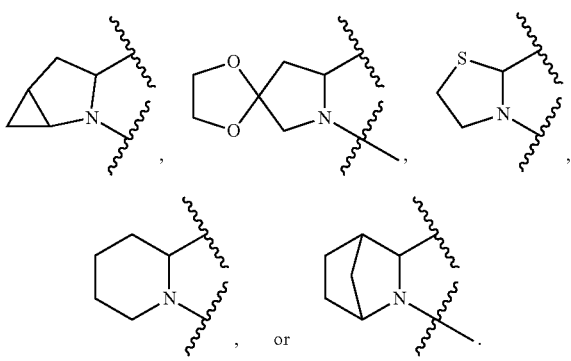

, 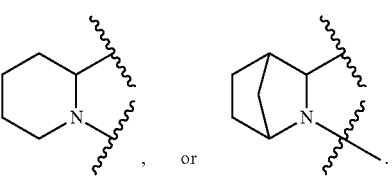 or .

In other embodiments, the compound having formula (I) of the present invention is the compound having formula (XII):

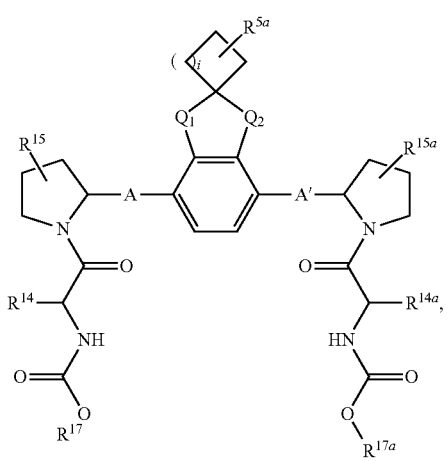

(XII)

wherein i is 1, 2, or 3;

$R^{5a}$ is H or methyl;

each of $Q_1$ and $Q_2$ is independently $CH_2$, $CF_2$, O or C(=O);

each of $R^{14}$ and $R^{14a}$ is independently methyl, ethyl, isobutyl, cyclohexyl, phenyl or isopropyl;

each of $R^{15}$ and $R^{15a}$ is independently H, F, Cl, Br, methyl, ethyl, isopropyl or tert-butyl;

each of $R^{17}$ and $R^{17a}$ is independently methyl, phenyl or ethyl; and each of A and A' is independently

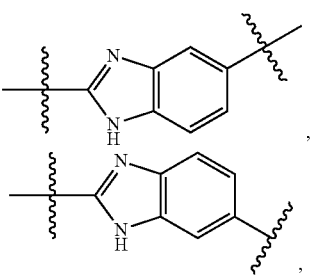

,

-continued

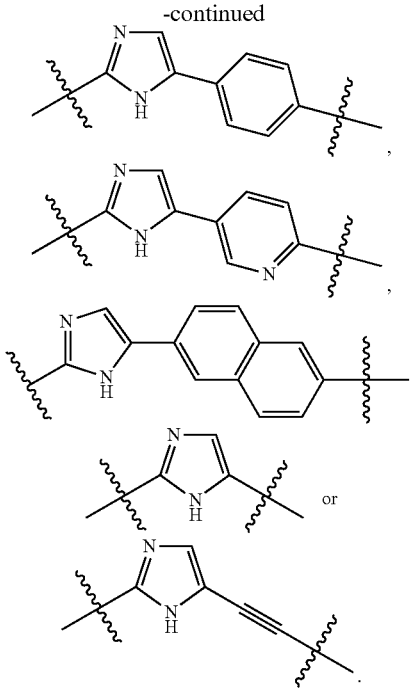

,

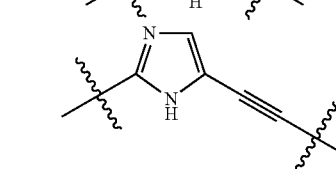 or

,

In one aspect, provided herein are pharmaceutical compositions comprising the compound disclosed herein; and a pharmaceutically acceptable carrier, excipient, diluent, adjuvant, vehicle or a combination thereof.

In certain embodiments, the pharmaceutical composition disclosed herein further comprises an anti-HCV agent.

In other embodiments, the anti-HCV agent is interferon, ribavirin, IL-2, IL-6, IL-12, a compound that enhances the development of a type 1 helper T cell response, interfering RNA, anti-sense RNA, imiquimod, an inosine5'-monophosphate dehydrogenase inhibitor, amantadine, rimantadine, boceprevir, telaprevir, daclatasvir or a combination thereof.

In other embodiments, the interferon is interferon α-2b, pegylated interferon α, interferon α-2a, pegylated interferon α-2a, consensus interferon-α or interferon γ.

In other embodiments, the pharmaceutical composition disclosed herein, further comprises at least one additional compound which is effective to inhibit the function of a target to treat HCV infection, wherein the target is selected from HCV metalloproteinase, HCV serine proteinase, HCV polymerase, HCV helicase, HCV NS4B protein, HCV entry, HCV assembly, HCV egress, HCV NS5A protein and IMPDH.

In another aspect, the compounds disclosed herein, are effective in inhibiting the function of a target to treat HCV infection, wherein the target is selected from HCV metalloproteinase, HCV serine proteinase, HCV polymerase, HCV helicase, HCV NS4B protein, HCV entry, HCV assembly, HCV egress, HCV NS5A protein and IMPDH.

In another aspect, the pharmaceutical composition comprising the compound disclosed herein, further comprises at least one HCV inhibitor, wherein the HCV inhibitor inhibits HCV viral protein, HCV replication or a combination thereof, and wherein the HCV viral protein or HCV replication is selected from helicase, proteinase, polymerase, metalloproteinase, serine proteinase, non-structural protein NS4A, non-structural protein NS5A, non-structural protein NS4B, HCV entry, HCV assembly, HCV egress, internal ribosome entry site (IRES) and inosine-5'-monophosphate dehydrogenase (IMPDH)

In another aspect, provided herein is a compound or a pharmaceutical composition for use in inhibiting HCV viral protein, HCV replication or a combination thereof, and wherein the HCV viral protein or HCV replication is selected from helicase, proteinase, polymerase, metalloproteinase, serine proteinase, non-structural protein NS4A, non-structural protein NS5A, non-structural protein NS4B, HCV entry, HCV assembly, HCV egress, internal ribosome entry site (IRES) and inosine-5'-monophosphate dehydrogenase (IMPDH).

In another aspect, provided herein is use of the compound or the pharmaceutical composition disclosed herein in the manufacture of a medicament for preventing, managing, treating or lessening the severity of a HCV disorder in a patient.

In another aspect, provided herein is a method of the compound or the pharmaceutical composition disclosed herein for preventing, managing, treating or lessening the severity of HCV infection and a HCV disorder in a patient, which comprises administering a therapeutically effective amount of the (a) compound or pharmaceutical composition disclosed herein to the patient.

In another aspect, provided herein include methods of preparing, methods of separating, and methods of purifying compounds of formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the Handbook of Chemistry and Physics, 75$^{th}$ Ed. 1994. Additionally, general principles of organic chemistry are described in Sorrell et al., "Organic Chemistry", University Science Books, Sausalito: 1999, and Smith et al., "March's Advanced Organic Chemistry", John Wiley & Sons, New York: 2007, all of which are incorporated herein by reference in their entireties.

As described herein, compounds may optionally be substituted with one or more substituents, such as those illustrated above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents described herein include, but are not limited to, hydroxy, amino, halo, cyano, aryl, heteroaryl, alkoxy, alkylamino, alkylthio, alkyl, alkenyl, alkynyl, heterocyclyl, mercapto, nitro, aryloxy, heteroaryloxy, oxo (=O), carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. In other embodiments, aliphatic groups contain 1-3 carbon atoms. Some non-limiting examples of aliphatic groups include linear or branched, substituted or unsubstituted alkyl, alkenyl, or alkynyl groups, as methyl, ethyl, propyl, isopropyl, butyl, tert-butyl, hexyl, isobutyl, sec-butyl, vinyl, and the like.

The term "haloaliphatic" refers to an aliphatic group substituted with one or more of the same or different halogen atoms (i.e., F, Cl, Br or I), wherein the aliphatic group is as defined herein. Some non-limiting examples include trifluoromethyl, trifluoroethyl, chloromethyl, 2-chlorovinyl, and the like.

The term "hydroxyaliphatic" refers to an aliphatic group substituted with one or more hydroxy groups, wherein the aliphatic group is as defined herein. Some non-limiting examples include hydroxyethyl, 2-hydroxypropyl, hydroxymethyl, and the like.

The term "aminoaliphatic" refers to an aliphatic group substituted with one or more amino groups, wherein the aliphatic group is as defined herein. Some non-limiting examples include aminomethyl, 2-aminoethyl, 2-amino isopropyl, and the like.

The term "alkyl" refers to a saturated linear or branched chain monovalent hydrocarbon radical of one to twenty carbon atoms, or one to ten carbon atoms, or one to eight carbon atoms, or one to six carbon atoms, or one to four carbon atoms, or one to three carbon atoms, wherein the alkyl radical may be optionally substituted independently with one or more substituents described herein. The examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like. The terms "alkyl" and the prefix "alk-" are inclusive of both straight chain and branched saturated carbon chain. The term "alkylene", as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkenyl" refers to a linear or branched chain monovalent hydrocarbon radical of two to twelve carbon atoms, or two to eight carbon atoms, or two to six carbon atoms, or two to four carbon atoms, with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Some non-limiting examples include ethenyl or vinyl (—CH=CH$_2$), allyl (—CH$_2$CH=CH$_2$), and the like.

The term "alkynyl" refers to a linear or branched chain monovalent hydrocarbon radical of two to twelve carbon atoms, or two to eight carbon atoms, or two to six carbon atoms, or two to four carbon atoms, with at least one site of unsaturation, i.e., a carbon-carbon, sp triple bond, wherein the alkynyl radical may be optionally substituted independently with one or more substituents described herein. Some non-limiting examples include ethynyl (—C≡CH), 2-propynyl or propargyl (—CH$_2$C≡CH), and the like.

The term "hydroxy-substituted alkyl" refers to an alkyl group substituted with one or more hydroxy groups, wherein the alkyl group is as defined herein. Some non-limiting examples include hydroxymethyl, hydroxyethyl, 1,2-dihydroxyethyl, and the like.

The term "haloalkyl" refers to an alkyl group substituted with one or more of the same or different halogen atoms (i.e., F, Cl, Br or I), wherein the alkyl group is as defined herein. Some non-limiting examples include trifluoromethyl, trifluoroethyl, chloromethyl, fluoromethyl, and the like.

The term "hydroxyalkyl" refers to an alkyl group substituted with one or more hydroxy groups, wherein the alkyl group is as defined herein. Some non-limiting examples include hydroxyethyl, 2-hydroxypropyl, hydroxymethyl, and the like.

The term "aminoalkyl" refers to an alkyl group substituted with one or more amino groups, wherein the alkyl group is as defined herein. Some non-limiting examples include aminomethyl, 2-aminoethyl, 2-amino isopropyl, and the like.

The term "heteroalkyl" refers to alkyl chain inserted with one or more heteroatoms, wherein the alkyl and heteroatom are as defined herein. Unless otherwise specified, heteroalkyl groups contain 1-10 carbon atoms. In other embodiments, heteroalkyl groups contain 1-8 carbon atoms. In still other embodiments, heteroalkyl groups contain 1-6 carbon atoms, and in yet other embodiments, heteroalkyl groups contain 1-4 carbon atoms. In other embodiments, heteroalkyl groups contain 1-3 carbon atoms. Some non-limiting examples include CH$_3$OCH$_2$—, CH$_3$CH$_2$OCH$_2$—, CH$_3$SCH$_2$—, (CH$_3$)$_2$NCH$_2$—, (CH$_3$)$_2$CH$_2$OCH$_2$—, CH$_3$OCH$_2$CH$_2$—, CH$_3$CH$_2$OCH$_2$CH$_2$—, and the like.

The term "cycloaliphatic", "cyclic aliphatic", "carbocycle", "carbocyclyl", or "cycloalkyl" refers to a monovalent or multivalent non-aromatic, saturated or partially unsaturated ring exclusive of heteroatoms, having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of cycloaliphatic groups include cycloalkyl, cycloalkenyl, and cycloalkynyl. Further examples of cycloaliphatic groups include cyclopropyl, cyclobutyl, cyclopentyl, 1-cyclopentyl-1-enyl, 1-cyclopentyl-2-enyl, 1-cyclopentyl-3-enyl, cyclohexyl, 1-cyclohexyl-1-enyl, 1-cyclohexyl-2-enyl, 1-cyclohexyl-3-enyl, cyclohexadienyl, cycloheptyl, cyclooctyl, cyclononyl, cyclodecyl, cycloundecyl, cyclododecyl, and the like. The term "cycloaliphatic", "carbocycle", "carbocyclyl", or "cycloalkyl" may be substituted or unsubstituted, wherein the substituent may be, but is not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "cycloalkyloxy" or "carbocyclyloxy" refers to an optionally substituted cycloalkyl or carbocyclyl radical, as defined herein, attached to an oxygen atom, wherein the oxygen atom serves as the attaching point to the rest of the molecule. Some non-limiting examples include cyclopropyloxy, cyclopentyloxy, cyclohexyloxy, hydroxy-substituted cyclopropyloxy, and the like.

The term "cycloalkylamino" refers to an amino group substituted with one or two optionally substituted cycloalkyl radicals, wherein the cycloalkyl group is as defined herein. Some non-limiting examples include cyclopropylamino, cyclopentylamino, cyclohexylamino, hydroxy-substituted cyclopropylamino, dicyclohexylamino, dicyclopropylamino, and the like.

The term "carbocyclyloxyalkoxy" refers to an alkoxy group substituted with one or more carbocyclyloxy groups, wherein the alkoxy group and carbocyclyloxy group are as defined herein. Some non-limiting examples include cyclopropyloxymethoxy, cyclopropyloxyethoxy, cyclopentyloxyethoxy, cyclohexyloxyethoxy, cyclohexenyl-3-oxyethoxy, and the like.

The term "cycloalkyloxyaliphatic" refers to an aliphatic group substituted with one or more optionally substituted cycloalkyloxy groups, wherein the aliphatic group and cycloalkyloxy group are as defined herein. Some non-limiting examples include cyclopropyloxymethyl, cyclopropyloxyethyl, cyclopentyloxymethyl, cyclopentyloxyethyl, cyclohexyloxyethyl, halocyclopropyloxyethyl, and the like.

The term "cycloalkylaminoaliphatic" refers to an aliphatic group substituted with one or more optionally substituted cycloalkylamino groups, wherein the aliphatic group and cycloalkylamino group are as defined herein. Some non-limiting examples include cyclopropylaminomethyl, cyclopropylaminoethyl, cyclopentylaminomethyl, cyclopentylaminoethyl, cyclohexylaminoethyl, halocyclopropylaminoethyl, and the like.

The term "cycloalkylaliphatic" refers to an aliphatic group substituted with one or more cycloalkyl groups, wherein the cycloalkyl group and aliphatic group are as defined herein. Some non-limiting examples include cyclopropylmethyl, cyclopropylethyl, cyclopropylpropyl, cyclopentylmethyl, cyclohexylethyl, and the like.

The term "cycloalkylalkoxy" ("carbocyclylalkoxy") refers to an alkoxy group substituted with one or more cycloalkyl (carbocyclyl) groups, wherein the cycloalkyl (carbocyclyl) group and alkoxy group are as defined herein. Some non-limiting examples include cyclopropylmethoxy, cyclopropylethoxy, cyclopentylethoxy, cyclohexylethoxy, cyclohexylmethoxy, cyclopropylpropoxy, and the like.

The term "heterocycle", "heterocyclyl", "heterocycloaliphatic", or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or $SO_2$, PO or $PO_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or $SO_2$, PO or $PO_2$).

The heterocyclyl may be a carbon radical or heteroatom radical. "Heterocyclyl" also includes radicals where heterocycle radicals are fused with a saturated, partially unsaturated ring, or heterocyclic ring. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, piperidyl, morpholinyl, thiomorpholinyl, thioxanyl, thiazolidinyl, oxazolidinyl, piperazinyl, homopiperazinyl, azetidinyl, oxetanyl, thietanyl, homopiperidinyl, epoxypropyl (oxiranyl), azepanyl, oxepanyl, thiepanyl, 4-methoxy-piperidin-1-yl, 1,2,3,6-tetrahydropyridine-1-yl, oxazepinyl, diazepinyl, thiazepinyl, pyrrolidin-1-yl, 2-pyrrolinyl, 3-pyrrolinyl, 2H-indolinyl, 2H-pyranyl, 4H-pyranyl, dioxolan-2-yl, 1,3-dioxopenyl, pyrazolinyl, dithianyl, ditholanyl, dihydrothienyl, pyrazolidinylimidazolinyl, imidazolidinyl, 1,2,3,4-tetrahydroisoquinolinyl, 1,2,6-dithiazinyl, 1,1-dioxo-2-yl, 4-hydroxy-1,4-azaphosphine-4-oxide-1-yl, 2-hydroxy-1-(piperazin-1-yl)ethanone-4-yl, 2-hydroxy-1-(5,6-dihydro-1,2,4-triazin-1(4H)-yl)ethanone-4-yl, 5,6-dihydro-4H-1,2,4-oxadiazine-4-yl, 2-hydroxy-1-(5,6-diludine-1(2H)-yl)ethanone-4-yl, 3-azabicyclo[3,1,0]hexyl, 3-azabicyclo[4,1,0]heptyl, azabicyclo[2,2,2]hexyl, 2-methyl-5,6,7,8-tetrahydro-[1,2,4]triazole[1,5-c]pyrimidine-6-yl, 4,5,6,7-tetrahydro-isoxazolo[4,3-c]pyridine-5-yl, 3H-indoxyl-2-oxo-5-azabicyclo[2,2,1]heptane-5-yl, 2-oxo-5-azabicyclo[2,2,2]octane-5-yl, quinolizinyl and N-pyridyl urea. Some non-limiting examples of a heterocyclic ring include 1,1-dioxo-thiomorpholinyl and heterocyclic group wherein 2 carbon atoms on the ring are substituted with oxo (=O) moieties are pyrimidindionyl. The heterocyclic groups herein may be substituted or unsubstituted, wherein the substituent may be, but is not limited to, oxo (=O), hydroxy, amino, halo, cyano, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxyl substituted alkyl-S(=O)$_2$—, carboxyalkoxy, and the like.

The term "heterocyclylalkyl" refers to heterocyclic-substituted alkyl radical. The term "heterocyclylalkoxy" refers to heterocyclic-substituted alkoxy radical wherein oxygen atom serves as the attaching point to the rest of the molecule. The term "heterocyclylalkylamino" refers to heterocyclic-substituted alkylamino radical wherein nitrogen atom serves as the attaching point to the rest of the molecule. Wherein the heterocyclyl, alkyl, alkoxy and alkylamino group are as defined herein. Some non-limiting examples include pyrrol-2-ylmethyl, morpholin-4-ylethyl, morpholin-4-ylethoxy, piperazin-4-ylethoxy, piperidin-4-ylethylamino, and the like.

The term "heterocyclylaliphatic" refers to heterocyclic-substituted aliphatic group, wherein the heterocyclic group and aliphatic group are as defined herein. Some non-limiting examples include pyrrol-2-ylmethyl, piperidin-2-ylethyl, piperazin-2-ylethyl, piperidin-2-ylmethyl, and the like.

The term "heterocyclyloxy" refers to optionally substituted heterocyclyl radical, as defined herein, connected to an oxygen atom, and the oxygen atom serves as the attaching point to the rest of the molecule. Some non-limiting examples include pyrrol-2-yloxy, pyrrol-3-yloxy, piperidin-2-yloxy, piperidin-3-yloxy, piperazin-2-yloxy, piperidin-4-yloxy, and the like.

The term "heterocyclylamino" refers to an amino group substituted with one or two heterocyclyl groups, wherein nitrogen atom serves as the attaching point to the rest of the molecule and the heterocyclyl group is as defined herein. Some non-limiting examples include pyrrol-2-ylamino, pyrrol-3-ylamino, piperidin-2-ylamino, piperidin-3-ylamino, piperidin-4-ylamino, piperazin-2-ylamino, dipyrrol-2-ylamino, and the like.

The term "heterocyclyloxyalkoxy" refers to an alkoxy group substituted with one or more heterocyclyloxy groups, wherein the alkoxy group and heterocyclyloxy group are as defined herein. Some non-limiting examples include pyrrol-2-yloxymethoxy, pyrrol-3-yloxyethoxy, piperidin-2-yloxyethoxy, piperidin-3-yloxyethoxy, piperazin-2-yloxymethoxy, piperidin-4-yloxyethoxy, and the like.

The term "heterocyclyloxyaliphatic" refers to an aliphatic group substituted with one or more heterocyclyloxy groups, wherein the aliphatic group and heterocyclyloxy group are as defined herein. Some non-limiting examples include pyrrol-2-yloxymethyl, piperazin-3-yloxyethyl, piperazin-2-yloxyethyl, morpholin-2-yloxymethyl, piperidin-2-yloxyethyl, and the like.

The term "heterocyclylaminoaliphatic" refers to an aliphatic group substituted with one or more heterocyclylamino groups, wherein the aliphatic group and heterocyclylamino group are as defined herein. Some non-limiting examples include pyrrol-2-ylaminomethyl, piperazin-3-ylaminoethyl, piperazin-2-yaminoethyl, piperidin-2-ylaminoethyl, morpholin-2-ylaminomethyl, and the like.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" or "halo" refers to F, Cl, Br or I.

The term "unsaturated" as used herein, refers to a moiety having one or more units of unsaturation.

The term "alkoxy" refers to an alkyl group, as previously defined, attached to the principal carbon chain through an oxygen ("alkoxy") atom. Some non-limiting examples include methoxy, ethoxy, propoxy, butoxy, and the like. And the alkoxy defined above may be substituted or unsubstituted, wherein the substituent may be, but is not limited to, hydroxy, amino, halo, cyano, alkoxy, alkyl, alkenyl, alkynyl, thiol, nitro, and the like.

The term "hydroxy-substituted alkoxy" or "hydroxyalkoxy" refers to an alkoxy group substituted with one or more hydroxy groups, wherein the alkoxy group is as defined herein. Some non-limiting examples include hydroxymethoxy, 2-hydroxyethoxy, 2-hydroxypropoxy, 2-hydroxyisopropoxy, and the like.

The term "aminoalkoxy" refers to an alkoxy group substituted with one or more amino groups, wherein the alkoxy group is as defined herein. Some non-limiting examples include aminomethoxy, 2-aminoethoxy, 2-aminopropoxy, 2-aminoisopropoxy, and the like.

The term "azidoalkoxy" refers to an alkoxy group substituted with one or more azido groups, wherein the alkoxy group is as defined herein. Some non-limiting examples include 2-azidoethoxy, 3-azidopropoxy, 2-azidopropoxy, and the like.

The term "alkoxyalkoxy" refers to an alkoxy group substituted with one or more alkoxy groups, wherein the alkoxy group is as defined herein. Some non-limiting examples include methoxymethoxy, methoxyethoxy, ethoxymethoxy, ethoxyethoxy, ethoxypropoxy, and the like.

The term "alkoxyaliphatic" refers to an aliphatic group substituted with one or more alkoxy groups, wherein the aliphatic group and alkoxy group are as defined herein. Some non-limiting examples include methoxymethyl, ethoxymethyl, ethoxyethyl, ethoxypropenyl, and the like.

The term "alkylaminoaliphatic" refers to an aliphatic group substituted with one or more alkylamino groups, wherein the aliphatic group and alkylamino group are as defined herein. Some non-limiting examples include dimethylaminoethyl, methylaminoethyl, diethylaminomethyl, diethylaminoethyl, and the like.

The term "alkylthioaliphatic" refers to an aliphatic group substituted with one or more alkylthio groups, wherein the aliphatic group and alkylthio group are as defined herein. Some non-limiting examples include methylthioethyl, methylthiopropyl, ethylthioethyl, methylthiopropenyl, and the like.

The term "haloalkyl", "haloalkenyl" or "haloalkoxy" refers to an alkyl group, alkenyl group or alkoxy group substituted with one or more halogen atoms. Some non-limiting examples include trifluoromethyl, 2-chloro-ethenyl, trifluoromethoxy, and the like.

The term "aryl" used alone or as part of a larger moiety as in "aralkyl", "arylalkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthryl. The aryl may be substituted or unsubstituted, wherein the substituents include, but are not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "arylaliphatic" refers to an aliphatic group substituted with one or more optionally substituted aryl groups, wherein the aliphatic group and the aryl group are as defined herein. Some non-limiting examples include phenylethyl, benzyl, (p-tolyl)ethyl, styryl, and the like.

The term "aryloxy" refers to optionally substituted aryl radicals, as defined herein, attached to an oxygen atom, and the oxygen atom serves as the attaching point to the rest of the molecule, wherein the aryl group is as defined herein. Some non-limiting examples include phenyloxy, methylphenyloxy, ethylphenyloxy, and the like.

The term "arylamino" refers to an amino group substituted with one or two optionally substituted aryl groups, wherein the aryl group is as defined herein. Some non-limiting examples include phenylamino, (p-fluorophenyl)amino, diphenylamino, ditolylamino, (di-p-tolyl)amino, and the like.

The term "aryloxyalkoxy" refers to an alkoxy group substituted with one or more optionally substituted aryloxy groups, wherein the alkoxy group and the aryloxy group are as defined herein. Some non-limiting examples include phenyloxymethoxy, phenyloxyethoxy, phenyloxypropoxy, and the like.

The term "aryloxyaliphatic" refers to an aliphatic group substituted with one or more optionally substituted aryloxy groups, wherein the aryloxy group and the aliphatic group are as defined herein. Some non-limiting examples include phenyloxymethyl, phenyloxyethyl, tolyloxyethyl, phenyloxypropyl, and the like.

The term "arylaminoaliphatic" refers to an aliphatic group substituted with one or more optionally substituted arylamino groups, wherein the arylamino group and the aliphatic group are as defined herein. Some non-limiting examples include phenylaminomethyl, phenylaminoethyl, tolylaminoethyl, phenylaminopropyl, phenylaminoallyl, and the like.

The term "arylalkoxy" refers to an alkoxy group substituted with one or more optionally substituted aryl groups, wherein the aryl group and the alkoxy group are as defined herein. Some non-limiting examples include phenylmethoxy, phenylethoxy, (p-tolyl)methoxy, phenylpropoxy, and the like.

The term "arylalkylamino" refers to an alkylamino group substituted with one or more optionally substituted aryl groups, wherein the aryl group and the alkylamino group are as defined herein. Some non-limiting examples include phenylmethylamino, phenylethylamino, phenylpropylamino, (p-tolyl)methylamino, and the like.

The term "heteroaryl" used alone or as part of a larger moiety as in "heteroarylalkyl" or "heteroarylalkoxy" refers to monocyclic, bicyclic, and tricyclic ring systems having a total of five to fourteen ring members, wherein at least one ring in the system is aromatic, and at least one ring in the system is inclusive of one or more heteroatoms, wherein each ring in the system contains 3 to 7 ring members and that has a single point of attachment to the rest of the molecule. The term "heteroaryl" may be used interchangeably with the term "heteroaryl ring" or "heteroaromatic compound". The heteroaryl defined herein may be substituted or unsubstituted, wherein the substituents include, but are not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

Some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazolyl-5-yl, N-pyrrolyl, 2-pyrrolyl, 3-pyrrolyl, 2-pyridyl, 3-pyridyl, 4-pyridyl, 2-pyrimidinyl, 4-pyrimidinyl, pyrimidin-5-yl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, pyrazin-2-yl, 1,3,5-triazinyl, benzo[d]thiazol-2-yl, imidazo[1,5-a]pyridin-6-yl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "heteroaryloxy" refers to an optionally substituted heteroaryl radical, as defined herein, attached to an oxygen atom, wherein the oxygen atom serves as the attaching point to the rest of the molecule. Some non-limiting examples include pyrid-2-yloxy, thiazol-2-yloxy, imidazol-2-yloxy, pyrimidin-2-yloxy, and the like.

The term "heteroaryloxyaliphatic" refers to an aliphatic group substituted with one or more optionally substituted heteroaryloxy groups, wherein the aliphatic group and the heteroaryloxy group are as defined herein. Some non-limiting examples include pyrid-2-yloxyethyl, thiazol-2-yloxymethyl, imidazol-2-yloxyethyl, pyrimidin-2-yloxypropyl, and the like.

The term "sulfonyl", whether used alone or linked to other terms such as "alkylsulfonyl", refers to respectively divalent radicals —SO₂—.

The term "alkylsulfonyl", refers to a sulfonyl radical substituted with an alkyl radical, forming an alkylsulfonyl (—SO₂-alkyl, such as —SO₂CH₃).

The term "sulfamyl", "aminosulfonyl" or "sulfonamidyl" refer to a sulfonyl radical substituted with an amine radical, forming a sulfonamide (—SO₂NH₂).

The term "carboxy" or "carboxyl", whether used alone or with other terms, such as "carboxyalkyl", refers to —CO₂H.

The term "carbonyl", whether used alone or with other terms, such as "aminocarbonyl" or "carbonyloxy", refers to —(C=O)—.

The term "carboxyalkoxy" refers to an alkoxy group substituted with one or more carboxy groups, wherein the alkoxy group and the carboxy group are as defined herein. Some non-limiting examples include carboxymethoxy, carboxyethoxy, and the like.

The term "aralkyl" or "arylalkyl" refers to aryl-substituted alkyl radicals. In some embodiments, aralkyl radicals are "lower aralkyl" radicals having aryl radicals attached to alkyl radicals having one to six carbon atoms. In other embodiments, aralkyl radicals are "phenylalkylenyl" attached to alkyl portions having one to three carbon atoms. Some non-limiting examples of such radicals include benzyl, diphenylmethyl and phenylethyl. The aryl in said aralkyl can be additionally substituted with halo, alkyl, alkoxy, haloalkyl or haloalkoxy.

The term "alkylthio" refers to radicals containing a linear or branched alkyl radical, of one to ten carbon atoms, attached to a divalent sulfur atom. In other embodiments, alkylthio radicals are lower alkylthio radicals having one to three carbon atoms. Some non-limiting examples of "alkylthio" include methylthio (CH₃S—).

The term "haloalkylthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" include trifluoromethylthio.

The term "alkylamino" refers to "N-alkylamino" and "N,N-dialkylamino", wherein amino groups are independently substituted with one alkyl radical or with two alkyl radicals, respectively. In other embodiments, alkylamino radicals are lower alkylamino radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "alkylaminohaloalkoxy" refers to a haloalkoxy group substituted with one or more alkylamino groups, wherein the haloalkoxy group and the alkylamino group are as defined herein. Some non-limiting examples include methylaminodifluoromethoxy, ethylaminotrifluoromethoxy, and the like.

The term "heteroarylamino" refers to amino groups substituted with one or two heteroaryl radicals, wherein the heteroaryl group is as defined herein. Some non-limiting examples of heteroarylamino include N-thienylamino. In other embodiments, the "heteroarylamino" radicals include substituted on the heteroaryl ring portion of the radical.

The term "heteroarylaliphatic" refers to aliphatic groups substituted with one or more heteroaryl radicals, wherein the heteroaryl group and the aliphatic group are as defined herein. Some non-limiting examples of heteroarylaliphatic include thiophen-2-ylpropenyl, pyridin-4-ylethyl, imidazol-2-ylmethyl, furan-2-ylethyl, indol-3-ylmethyl, and the like.

The term "heteroarylalkyl" refers to alkyl groups substituted with one or more heteroaryl radicals, wherein the heteroaryl group and the alkyl group are as defined herein. Some non-limiting examples of heteroarylalkyl include imidazol-2-ylmethyl, furan-2-ylethyl, indol-3-ylmethyl, and the like.

The term "heteroarylalkylamino" refers to nitrogen-containing heteroarylalkyl radicals attached through a nitrogen atom to other radicals, wherein the heteroarylalkyl radical is as defined herein. Some non-limiting examples of heteroarylalkylamino include pyridin-2-ylmethylamino, thiazol-2-ylethylamino, imidazol-2-ylethylamino, pyrimidin-2-ylpropylamino, pyrimidin-2-ylmethylamino, and the like.

The term "aminoalkyl" refers to a linear or branched alkyl radical having one to ten carbon atoms, substituted with one or more amino radicals. In some embodiments, aminoalkyl radicals are "lower aminoalkyl" radicals having one to six carbon atoms and one or more amino radicals. Some non-limiting examples of such radicals include aminomethyl, aminoethyl, aminopropyl, aminobutyl and aminohexyl.

The term "alkylaminoalkyl" refers to alkyl radicals substituted with alkylamino radicals. In some embodiments, alkylaminoalkyl radicals are "lower alkylaminoalkyl" radicals having alkyl radicals of one to six carbon atoms. In other embodiments, alkylaminoalkyl radicals are lower alkylaminoalkyl radicals having alkyl radicals of one to three carbon atoms. Some non-limiting examples of suitable alkylaminoalkyl radicals include mono and dialkyl substituted, such as N-methylaminomethyl, N,N-dimethylaminoethyl, N,N-diethylaminomethyl, and the like.

The term "carboxyalkyl" refers to a linear or branched alkyl radical having one to ten carbon atoms substituted with one or more carboxy radicals. Some non-limiting examples of such radicals include carboxymethyl, carboxypropyl, and the like.

The term "aryloxy" refers to optionally substituted aryl radicals, as defined herein, attached to an oxygen atom, wherein the oxygen atom serves as the attaching point to the rest of the molecule. Some non-limiting examples of such radicals include phenoxy.

The term "heteroarylalkoxy" refers to oxy-containing heteroarylalkyl radicals attached through an oxygen atom to other radicals, wherein the heteroarylalkyl radical is as defined herein. Some non-limiting examples of such radicals include pyridin-2-ylmethoxy, thiazol-2-ylethoxy, imidazol-2-ylethoxy, pyrimidin-2-ylpropoxy, pyrimidin-2-ylmethoxy, and the like.

The term "cycloalkylalkyl" refers to cycloalkyl-substituted alkyl radicals. Some non-limiting examples of such radicals include cyclohexylmethyl. The cycloalkyl in the radicals may be additionally substituted with halo, alkyl, alkoxy or hydroxy.

The term "fused bicyclic", "fused cyclic", "fused bicyclyl" or "fused cyclyl" refers to unsaturated or saturated fused cyclic system and bridged ring system that is not aromatic. For example, as depicted below (Formula (a1)), ring A1 and ring A2 share a bond or share an alkyl chain, wherein j is 0, 1, 2, 3 or 4. Such a system may contain isolated or conjugated unsaturation, but not aromatic or heteroaromatic rings in its core structure (but may have aromatic substitution thereon). Each cyclic ring in a fused bicyclyl can be either a carbocyclic or a heteroalicyclic. Some non-limiting examples of fused bicyclic ring system or bridged ring system include hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, bicyclo[2.2.1]heptane, 2-azabicyclo[2.2.1]heptane, and 1,2,3,4,4a,5,8,8a-octahydro-naphthalene. The fused bicyclyl defined herein may be substituted or unsubstituted, wherein the substituents include, but are not limited to, oxo (=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

(a1)

The term "fused heterobicyclyl" refers to unsaturated or saturated fused cyclic system and bridged ring system that is not aromatic. Such a system may contain isolated or conjugated unsaturation, but not aromatic or heteroaromatic rings in its core structure (but may have aromatic substitution thereon). And at least one ring in the system is inclusive of one or more heteroatoms, wherein each ring in the system contains 3 to 7 ring members, e.g., 1 to 6 carbon atoms and 1 to 3 heteroatoms selected from N, O, P or S, wherein the S or P is optionally substituted with one or more oxo to provide the group SO or SO$_2$, PO or PO$_2$. Some non-limiting examples of fused heterobicyclic ring system include hexahydro-furo[3,2-b]furan, 7-azabicyclo[2.3.0]heptane, 2-azabicyclo[2.2.1]heptane, and the like. The fused heterobicyclyl defined herein may be substituted or unsubstituted, wherein the substituents include, but are not limited to, oxo (=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "spirocyclyl", "spirocyclic", "spiro bicyclyl" or "spiro bicyclic" refers to a ring originating from a particular annular carbon of another ring. For example, as depicted below, ring A and ring B share a carbon atom between the two saturated ring system, which terms as a "spirocyclyl" or "spiro bicyclyl". Each cyclic ring in the spirocyclyl or spiro bicyclyl can be either a carbocyclic or a heteroalicyclic. Some non-limiting examples of such radicals include 2,7-diazaspiro[4.4]non-2-yl, 7-oxo-2-azaspiro[4.5]dec-2-yl, 4-azaspiro[2.4]hept-5-yl, 4-oxaspiro[2.4]hept-5-yl, 5-azaspiro[2.4]hept-5-yl, spiro[2.4]heptyl, spiro[4.4]nonyl, 7-hydroxy-5-azaspiro[2.4]hept-5-yl, and the like. The spirocyclyl or spiro bicyclyl may be substituted or unsubstituted, wherein the substituents include, but are not limited to, oxo (=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

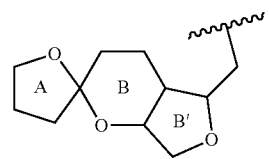

The term "spiro bicyclylene" refers to spiro bicyclyl system having two connection points connected to the rest of the molecule, wherein the spiro bicyclyl radical is as defined herein.

The term "spiro heterobicyclyl" refers to a ring originating from a particular annular carbon of another ring. For example, as depicted above, ring A and ring B share a carbon atom between the two saturated ring system, which terms as a "spirocyclyl". And at least one ring in the system is inclusive of one or more heteroatoms, wherein each ring in the system contains 3 to 7 ring members, e.g., 1 to 6 carbon atoms and 1 to 3 heteroatoms selected from N, O, P or S, wherein the S or P is optionally substituted with one or more oxo to provide the group SO or SO$_2$, PO or PO$_2$. Some non-limiting examples of such radicals include 4-azaspiro[2,4]hept-5-yl, 4-oxaspiro[2,4]hept-5-yl, 5-azaspiro[2,4]hept-5-yl, 7-hydroxy-5-azaspiro[2,4]hept-5-yl, and the like. The spiro heterobicyclyl defined herein may be substituted or unsubstituted, wherein the substituents include, but are not limited to, oxo (=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

As described herein, a bond drawn from a substituent to the center of one ring within a ring system (as shown in Formula (a)) represents substitution of the substituent $R^{5a}$ at any substitutable position on the rings (W1, W2, and W). For example, Formula (a) represents possible substitution in any of the positions on the W1, W2, and W ring.

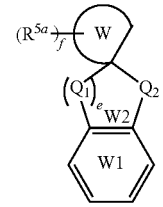

(a)

As described herein, two attaching points either E or E', within a ring system (as shown in Formula (b)), attach to the rest of the molecule, e.g., E and E' may be used interchangeably with each other.

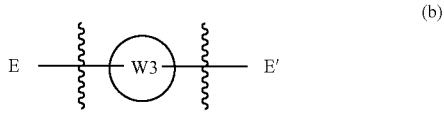

(b)

As described herein, a dot line drawn together with a bond within a ring system (as shown in Formula (c)) represents either a double bond or a single bond. For example, structure in Formula (c) represents any structures selected from Formula (d).

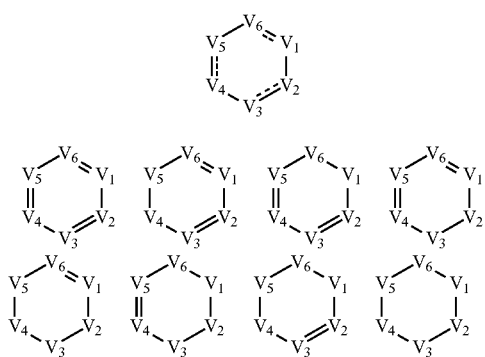

(c)

(d)

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., *Pro-drugs as Novel Delivery Systems*, Vol. 14, A.C.S. Symposium Series; Roche, et al. ed., *Bioreversible Carriers in Drug Design*, American Pharmaceutical Association and Pergamon Press, 1987; Rautio et al., Prodrugs: Design and Clinical Applications, *Nature Reviews Drug Discovery*, 2008, 7, 255-270, and Hecker et al, Prodrugs of Phosphates and Phosphonates, *J. Med. Chem.*, 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof Stereochemical definitions and conventions used herein generally follow Parker et al., McGraw-Hill Dictionary of Chemical Terms (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in *J. Pharmacol Sci*, 1977, 66: 1-19, which is incorporated herein by reference. Some non-limiting examples of pharmaceutically salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and —N$^+$(C$_{1-4}$ alkyl)$_4$ salts. This invention also envisions the quaternization of any basic nitrogen-containing groups of the compounds disclosed herein. Water or oil soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, C$_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)-ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

Description of Compounds of the Invention

Provided herein are spiro ring compounds, and pharmaceutical formulations thereof, that are useful in inhibiting HCV infection, especially inhibiting the activity of the non-structural 5A ("NS5A") protein.

In one aspect, provided herein are compounds having formula (I) as shown below:

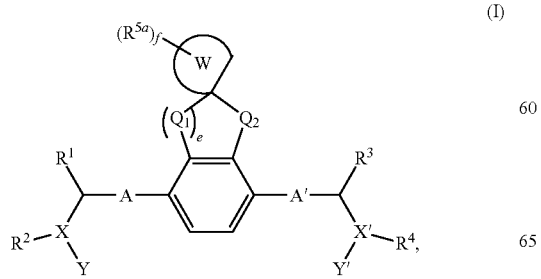

(I)

or a stereoisomer, a geometric isomer, a tautomer, an N-oxide, a hydrate, a solvate, a metabolite, a pharmaceutically acceptable salt or a prodrug thereof, wherein:

each of A and A' is independently a bond, alkylene, alkenylene, cycloalkylene, heterocycloalkylene, —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=O)—N(R$^5$)—(CR$^8$R$^{8a}$)$_p$—, —(CR$^8$R$^{8a}$)$_n$—N(R$^5$)—C(=O)—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, or —(CR$^8$R$^{8a}$)$_n$—N(R$^5$)—C(=O)—O—(CR$^8$R$^{8a}$)$_p$—, or each of A and A' is independently one of the following groups:

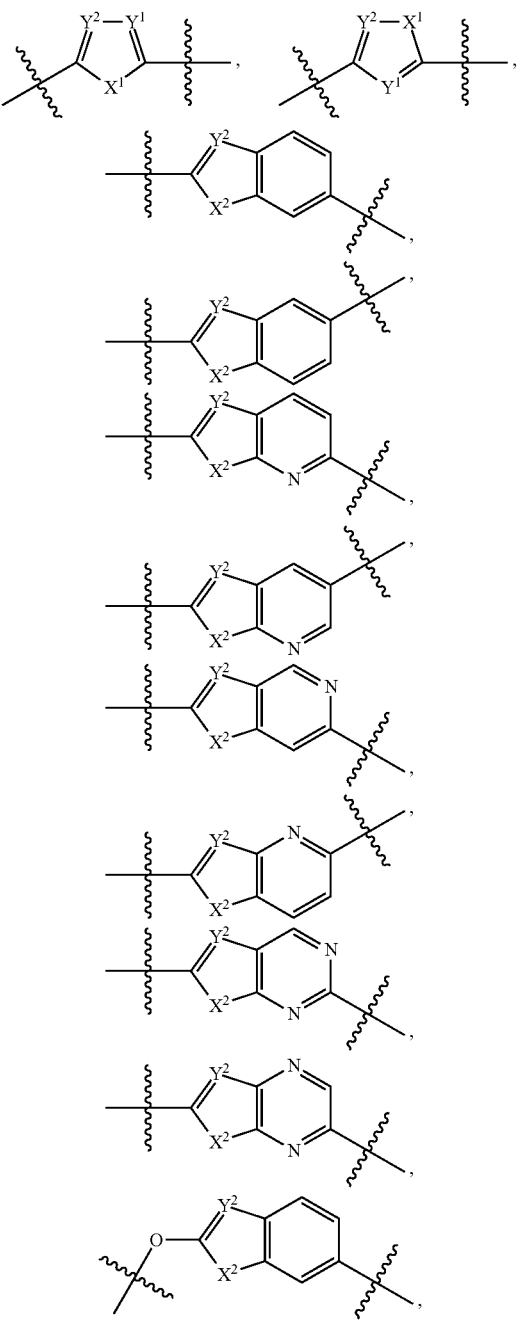

-continued
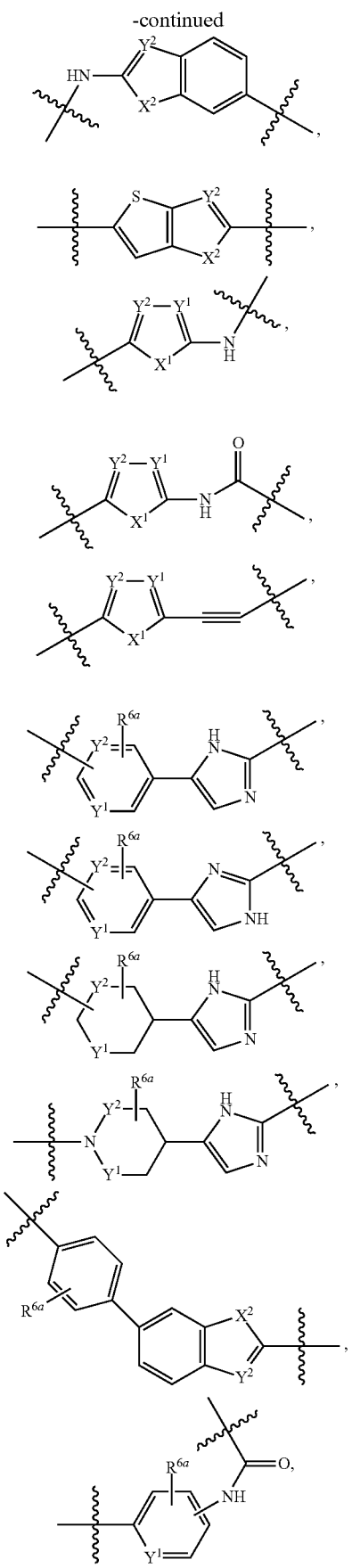
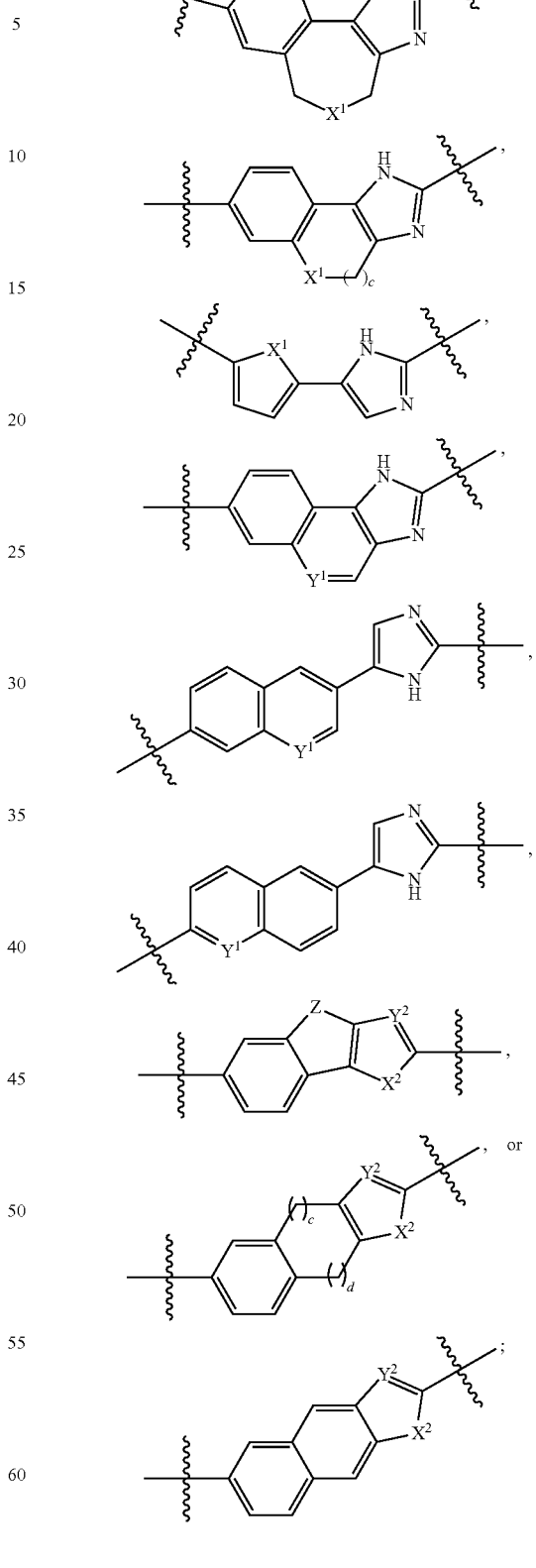
wherein $X^1$ is O, S, $NR^6$ or $CR^7R^{7a}$;
each $Y^1$ and $Y^2$ is independently N or $CR^7$;
$X^2$ is $NR^6$, O or S;

Z is —(CH$_2$)$_a$—, —CH=CH—, —N=CH—, —(CH$_2$)$_a$—N(R$^5$)—(CH$_2$)$_b$—, or —(CH$_2$)$_a$—O—(CH$_2$)$_b$—, wherein each a and b is independently 0, 1, 2 or 3;

each c is independently 1 or 2;

d is 1 or 2;

each n is independently 0, 1, 2 or 3;

each p is independently 0, 1, 2 or 3;

r is 0, 1 or 2;

e is 1, 2, 3 or 4;

f is 0, 1, 2, 3 or 4;

each Q$_1$ and Q$_2$ is independently NR$^6$, O, S, C(=O) or CR$^7$R$^{7a}$, with the proviso that when Q$_1$ is NR$^6$, O, S or C(=O), e is 1;

W is carbocyclyl or heterocyclyl;

each of X and X' is independently N or CR$^7$;

each of Y and Y' is independently H, alkyl, heteroalkyl, cycloalkyl, heterocyclyl, aryl, heteroaryl, aralkyl, a group derived from a naturally occurring or commercially available α-amino acid or an optically isomer thereof, or each of Y and Y' is independently —[U—(CR$^9$R$^{9a}$)$_t$—N(R$^{10}$)—(CR$^9$R$^{9a}$)$_t$]$_k$—U—(CR$^9$R$^{9a}$)$_t$—N(R$^{11}$)—(CR$^9$R$^{9a}$)$_t$—R$^{12}$, —U—(CR$^9$R$^{9a}$)$_t$—R$^{12}$ or —[U—(CR$^9$R$^{9a}$)$_t$—N(R$^{10}$)—(CR$^9$R$^{9a}$)$_t$]$_k$—U—(CR$^9$R$^{9a}$)$_t$—O—(CR$^9$R$^{9a}$)$_t$—R$^{12}$;

each U is independently —C(=O)—, —C(=S)—, —S(=O)— or —S(=O)$_2$—;

each t is independently 0, 1, 2, 3 or 4;

each k is independently 0, 1 or 2;

each of R$^1$, R$^2$, R$^3$ and R$^4$ is independently H, alkyl, heteroalkyl, aralkyl, cycloalkyl, heterocyclyl, heteroaryl or aryl; or R$^1$ and R$^2$, together with X—CH, form a 3-8 membered heterocycle or carbocycle, C$_{5-12}$ fused bicycle, C$_{5-12}$ fused heterobicycle, C$_{5-12}$ spiro bicycle or C$_{5-12}$ spiro heterobicycle; or R$^3$ and R$^4$, together with X'—CH, form a 3-8 membered heterocycle or carbocycle, C$_{5-12}$ fused bicycle, C$_{5-12}$ fused heterobicycle, C$_{5-12}$ spiro bicycle or C$_{5-12}$ spiro heterobicycle;

each R$^5$ is independently H, hydroxy, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$, alkyl-S(=O)$_r$O—, alkyl-S(=O)$_r$— or aminosulfonyl;

each R$^{5a}$ is independently H, oxo (=O), hydroxy, amino, F, Cl, Br, I, cyano, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N-alkyl, R$^7$S(=O)-alkyl, R$^7$R$^{7a}$N—C(=O)-alkyl, R$^7$R$^{7a}$N-alkoxy, R$^7$S(=O)-alkoxy, R$^7$R$^{7a}$N—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy;

R$^6$ is independently H, R$^7$R$^{7a}$NC(=O)—, R$^7$OC(=O)—, R$^7$C(=O)—, R$^7$R$^{7a}$NS(=O)—, R$^7$OS(=O)—, R$^7$S(=O)—, R$^7$R$^{7a}$NS(=O)$_2$—, R$^7$OS(=O)$_2$—, R$^7$S(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;

R$^{6a}$ is H, oxo, hydroxy, amino, F, Cl, Br, I, cyano, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N-alkyl, R$^7$S(=O)-alkyl, R$^7$R$^{7a}$N—C(=O)-alkyl, R$^7$R$^{7a}$N-alkoxy, R$^7$S(=O)-alkoxy, R$^7$R$^{7a}$N—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino, or aryloxy;

each R$^7$ and R$^{7a}$ is independently H, F, Cl, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; with the proviso that where R$^7$ and R$^{7a}$ are bonded to the same nitrogen atom, R$^7$ and R$^{7a}$, together with the nitrogen atom, form a substituted or unsubstituted 3-8 membered ring including spiro bicycle and fused bicycle;

each R$^8$ and R$^{8a}$ is independently H, hydroxy, cyano, nitro, F, Cl, Br, I, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$—, or aminosulfonyl;

each R$^9$, R$^{9a}$, R$^{10}$ and R$^{11}$ is independently H, alkyl, heteroalkyl, cycloalkyl, heterocyclyl, aryl, heteroaryl, aralkyl, haloalkyl, hydroxyalkyl, heteroarylalkyl, heterocyclylalkyl, or cycloalkylalkyl;

R$^{12}$ is independently R$^{13a}$R$^{13}$N—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13}$OS(=O)$_2$—, alkyl, heteroalkyl, cycloalkyl, heterocyclyl, aryl, heteroaryl or aralkyl;

or R$^{11}$ and R$^{12}$, together with the nitrogen atom they are attached to, form a 4-7 membered ring; and each R$^{13}$ and R$^{13a}$ is independently H, alkyl, heteroalkyl, cycloalkyl, heterocyclyl, aryl, heteroaryl, or aralkyl;

wherein each of the following groups —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=O)—N(R$^5$)—(CR$^8$R$^{8a}$)$_p$—, —(CR$^8$R$^{8a}$)$_n$—N(R$^5$)—C(=O)—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, —(CR$^8$R$^{8a}$)$_n$—N(R$^5$)—C(=O)—O—(CR$^8$R$^{8a}$)$_p$—, —[U—(CR$^9$R$^{9a}$)$_t$—N(R$^{10}$)—(CR$^9$R$^{9a}$)$_t$]$_k$—U—(CR$^9$R$^{9a}$)$_t$—N(R$^{11}$)—(CR$^9$R$^{9a}$)$_t$—R$^{12}$, —U—(CR$^9$R$^{9a}$)$_t$—R$^{12}$, —[U—(CR$^9$R$^{9a}$)$_t$—N(R$^{10}$)—(CR$^9$R$^{9a}$)$_t$]$_k$—U—(CR$^9$R$^{9a}$)$_t$—O—(CR$^9$R$^{9a}$)$_t$—R$^{12}$, NR$^6$, CR$^7$R$^{7a}$, CR$^7$, —(CH$_2$)$_a$—, —CH=CH—, —N=CH—, —(CH$_2$)$_a$—N(R$^5$)—(CH$_2$)$_b$—, —(CH$_2$)$_a$—O—(CH$_2$)$_b$—, R$^{13a}$R$^{13}$N—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$,—

N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13}$OS(=O)$_2$—, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, alkyl-OC(=O)—, alkyl-C(=O)—, alkyl-OS(=O)$_r$—, alkyl-S(=O)$_r$O—, alkyl-S(=O)$_r$—, R$^7$R$^{7a}$NC(=O)—, R$^7$OC(=O)—, R$^7$C(=O)—, R$^7$R$^{7a}$NS(=O)—, R$^7$OS(=O)—, R$^7$S(=O)—, R$^7$R$^{7a}$NS(=O)$_2$—, R$^7$OS(=O)$_2$—, R$^7$S(=O)$_2$—, R$^{7a}$R$^7$N-alkyl, R$^7$S(=O)-alkyl, R$^7$R$^{7a}$N—C(=O)-alkyl, R$^{7a}$R$^7$N-alkoxy, R$^7$S(=O)-alkoxy, R$^7$R$^{7a}$N—C(=O)-alkylamino, alkyl, heteroalkyl, carbocyclyl, cycloalkyl, heterocyclyl, aryl, heteroaryl, aralkyl, α-amino acid, C$_{5-12}$ fused bicycle, C$_{5-12}$ fused heterobicycle, C$_{5-12}$ spiro bicycle, C$_{5-12}$ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted or unsubstituted.

In some embodiments, W is C$_{3-8}$ carbocyclyl or C$_{2-10}$ heterocyclyl.

In some embodiments, the structural unit of

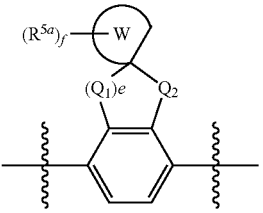

has one of the following structures:

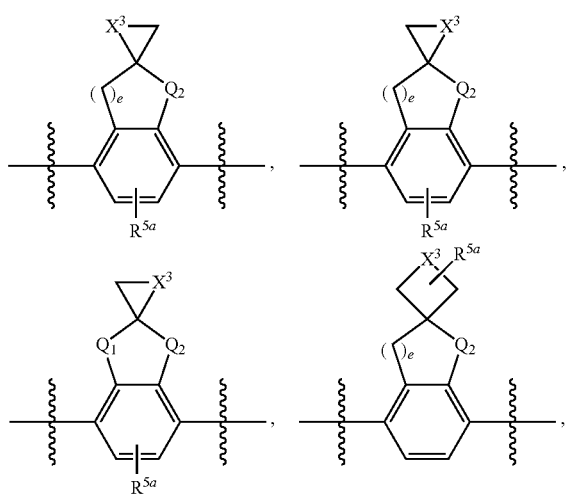

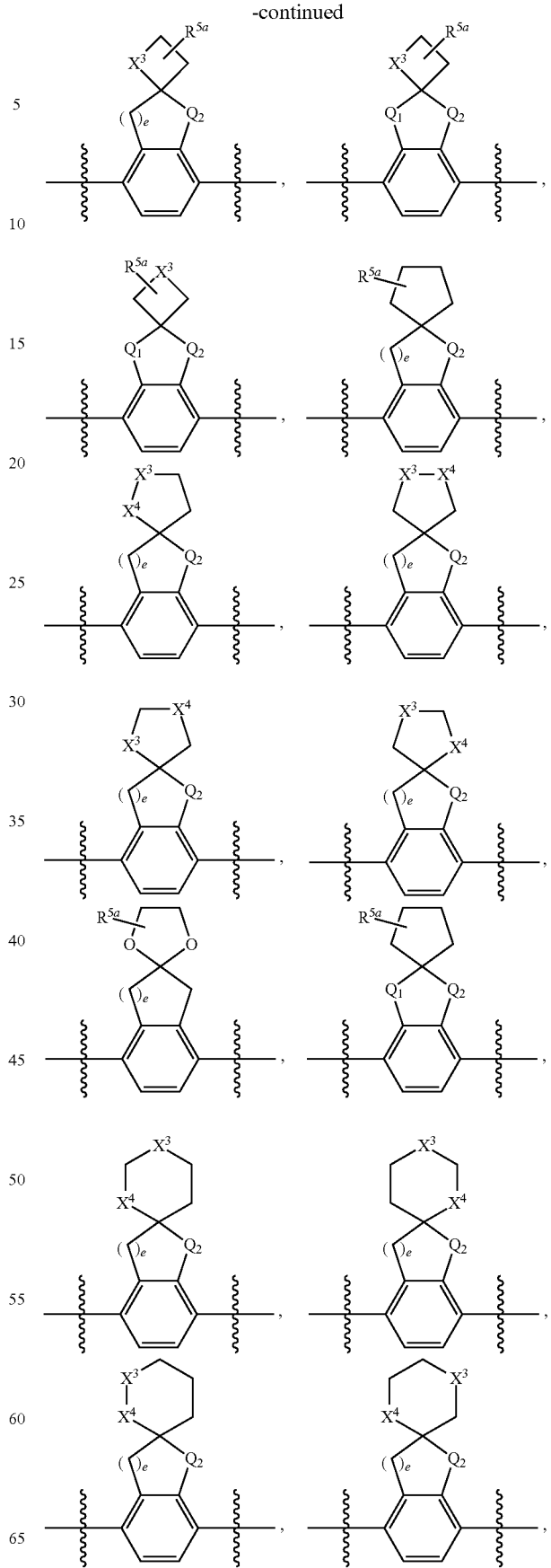

-continued

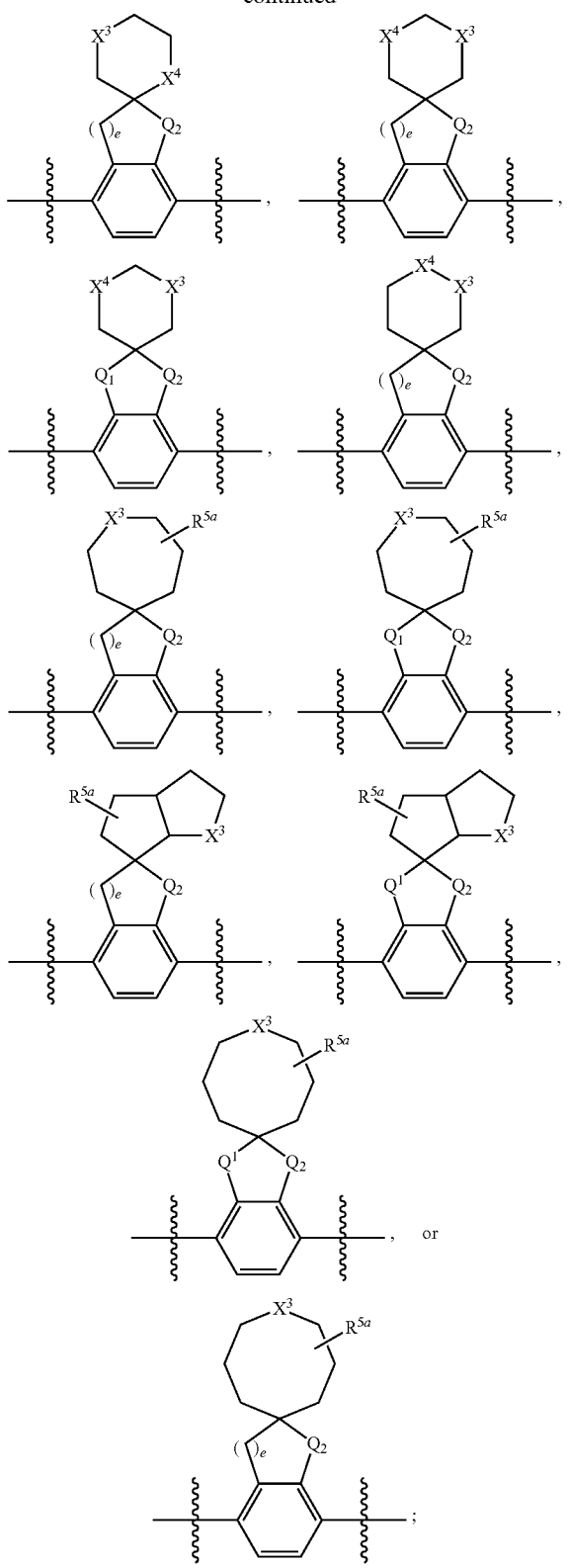

wherein each $X^3$ and $X^4$ is independently O, S, $NR^6$, or $CR^7R^{7a}$;
each e is 1, 2, 3 or 4;
f is 0, 1, 2, 3 or 4;

each $Q_1$ and $Q_2$ is independently $NR^6$, O, S, C(=O), or $CR^7R^{7a}$, with the proviso that when $Q_1$ is $NR^6$, O, S or C(=O), e is 1; and each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy.

In some embodiments, the structural unit of

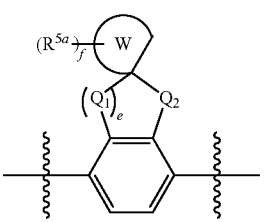

has one of the following structures:

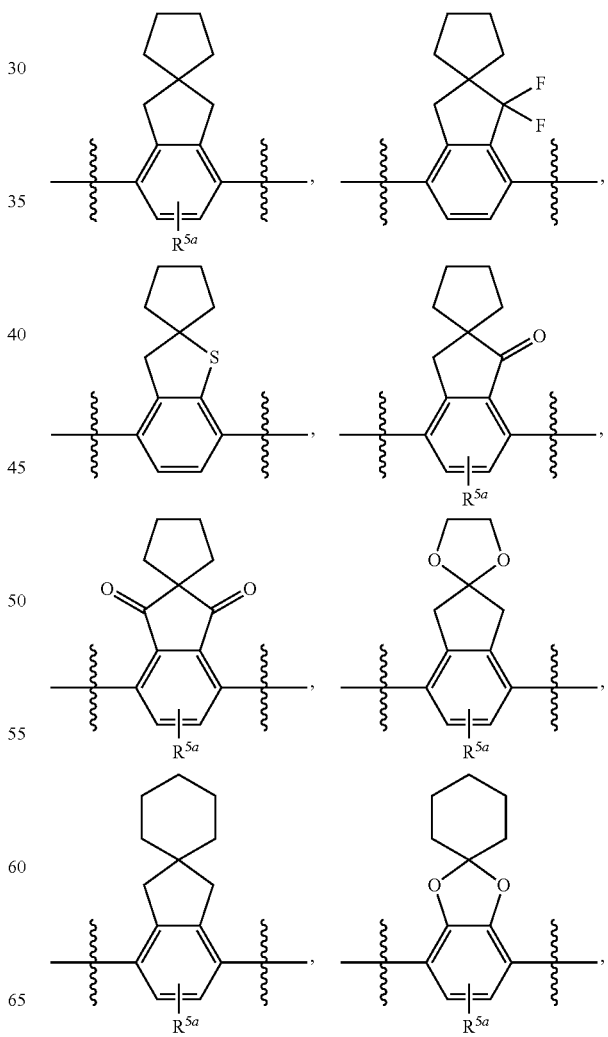

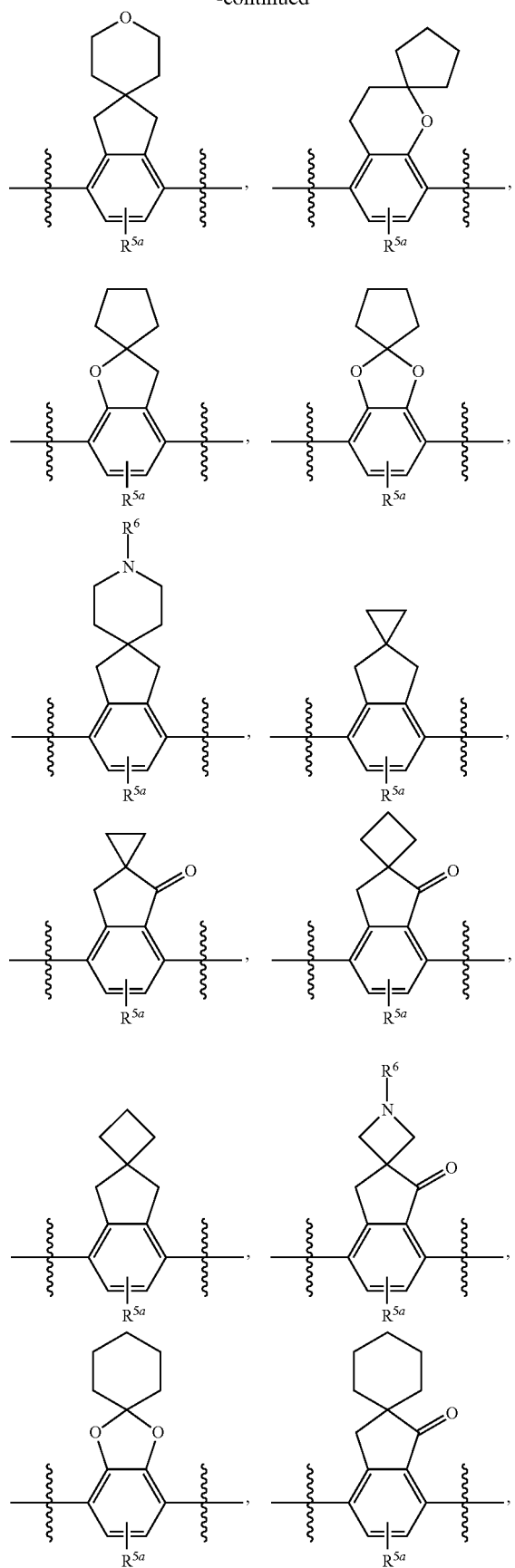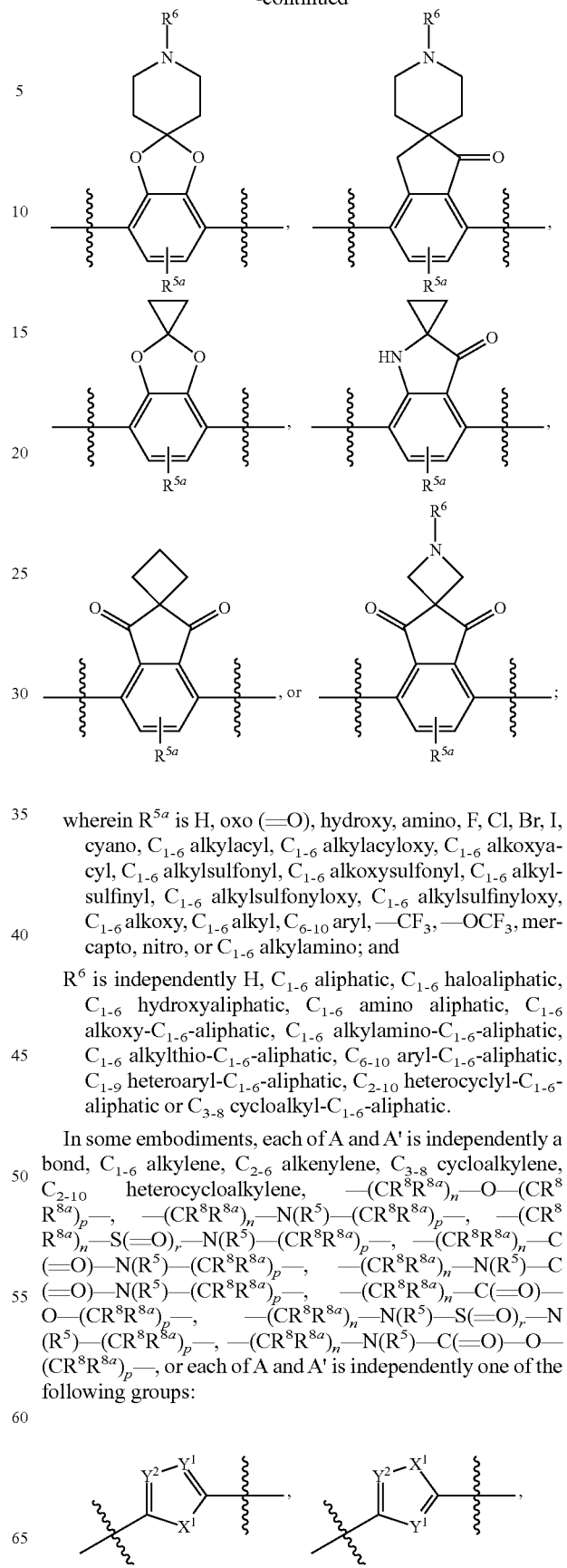

wherein $R^{5a}$ is H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, or $C_{1-6}$ alkylamino; and $R^6$ is independently H, $C_{1-6}$ aliphatic, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic or $C_{3-8}$ cycloalkyl-$C_{1-6}$-aliphatic.

In some embodiments, each of A and A' is independently a bond, $C_{1-6}$ alkylene, $C_{2-6}$ alkenylene, $C_{3-8}$ cycloalkylene, $C_{2-10}$ heterocycloalkylene, —$(CR^8R^{8a})_n$—O—$(CR^8R^{8a})_p$—, —$(CR^8R^{8a})_n$—N($R^5$)—$(CR^8R^{8a})_p$—, —$(CR^8R^{8a})_n$—S(=O)$_r$—N($R^5$)—$(CR^8R^{8a})_p$—, —$(CR^8R^{8a})_n$—C(=O)—N($R^5$)—$(CR^8R^{8a})_p$—, —$(CR^8R^{8a})_n$—N($R^5$)—C(=O)—N($R^5$)—$(CR^8R^{8a})_p$—, —$(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, —$(CR^8R^{8a})_n$—N($R^5$)—C(=O)—O—$(CR^8R^{8a})_p$—, or each of A and A' is independently one of the following groups:

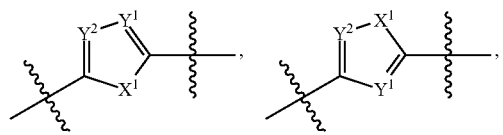

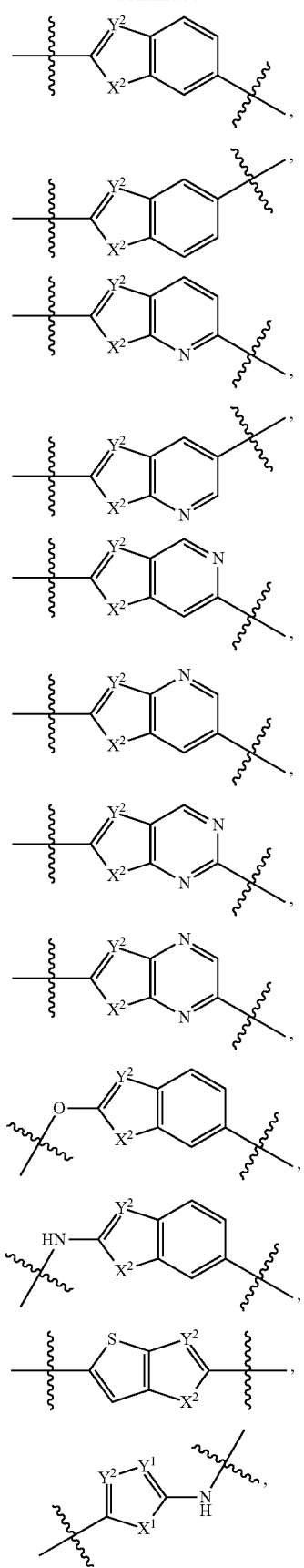
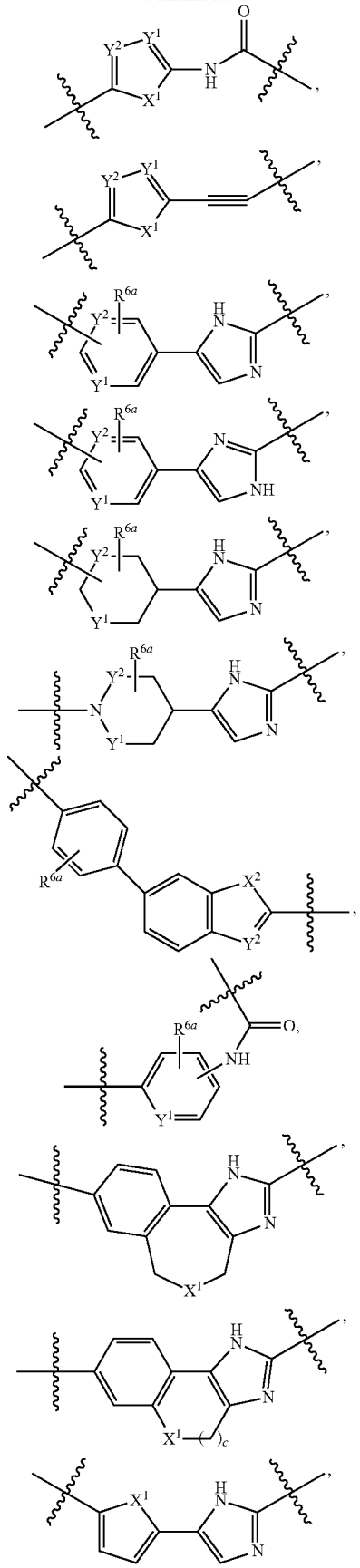

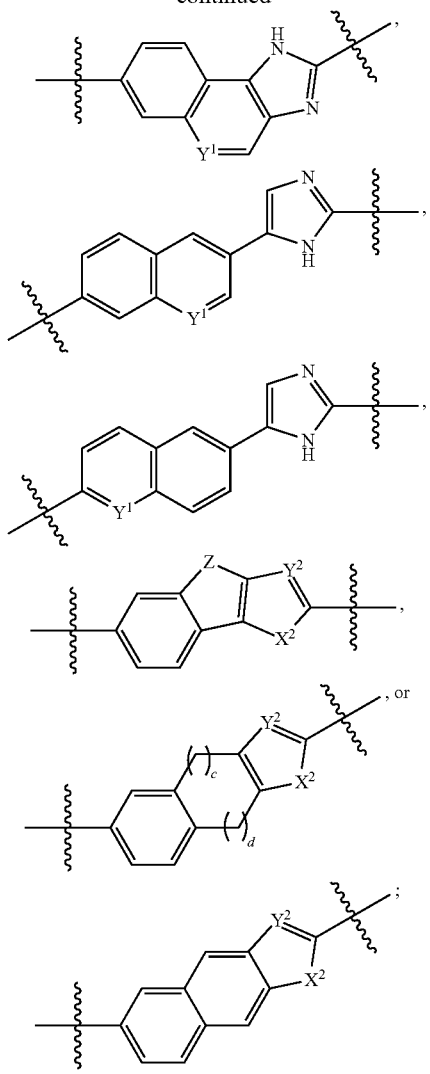

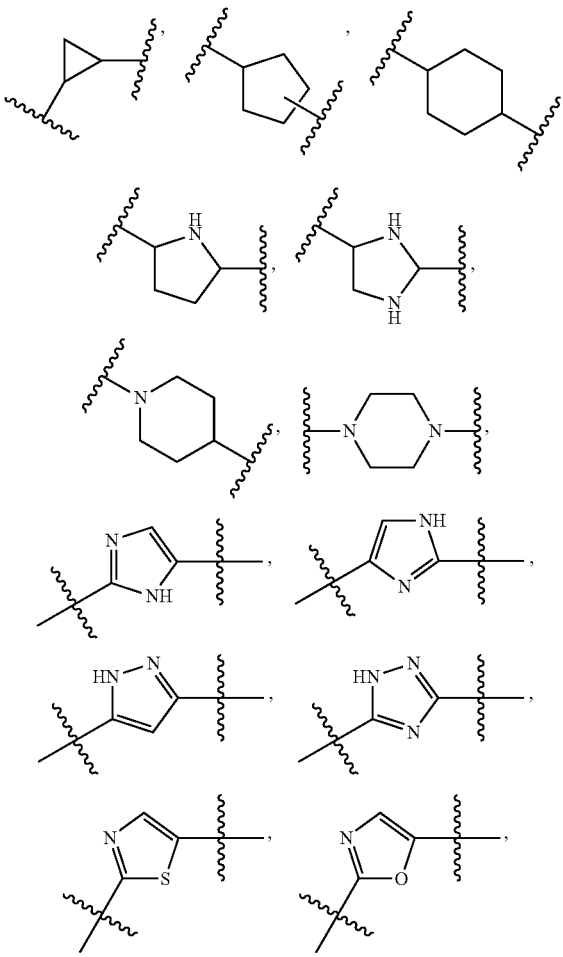

aliphatic, $C_{3-8}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-8}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-8}$ cycloalkylamino-$C_{1-6}$-aliphatic, $C_{6-10}$ aryl, $C_{1-9}$ heteroaryl, $C_{2-10}$ heterocyclyl or $C_{3-8}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring including $C_{5-12}$ spiro bicycle and $C_{5-12}$ fused bicycle; and each $R^8$ and $R^{8a}$ is independently H, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl.

In some embodiments, each of A and A' is independently a bond, —CH$_2$—, —(CH$_2$)$_2$—, —CH=CH—, —CH=CH—CH$_2$—, —N(R$^6$)—, —C(=O)—, —C(=S)—, —C(=O)—O—, —C(=O)N(R$^6$)—, —OC(=O)N(R$^6$)—, —OC(=O)O—, —N(R$^6$)C(=O)N(R$^6$)—, —(R$^6$)N—S(=O)$_2$—, —S(=O)$_2$—, —OS(=O)$_2$—, —(R$^6$)N—S(=O)—, —S(=O)—, —OS(=O)—, or each of A and A' is independently one of the following groups:

wherein $R^5$ is independently H, hydroxy, $C_{1-6}$ alkyl, $C_{1-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

$R^{6a}$ is H, oxo, hydroxy, amino, F, Cl, Br, I, cyano, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N—$C_{1-6}$ alkyl, R$^7$S(=O)—$C_{1-6}$ alkyl, R$^7$R$^{7a}$N—C(=O)—$C_{1-6}$ alkyl, R$^{7a}$R$^7$N—$C_{1-6}$ alkoxy, R$^7$S(=O)—$C_{1-6}$ alkoxy, R$^7$R$^{7a}$N—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-9}$ heteroarylamino, or $C_{6-10}$ aryloxy;

each $R^7$ and $R^{7a}$ is independently H, F, Cl, $C_{1-6}$ aliphatic, $C_{1-6}$ heteroalkyl, $C_{1-6}$ haloaliphatic, hydroxy $C_{1-6}$ aliphatic, amino $C_{1-6}$ aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heterocyclyl-$C_{1-6}$-

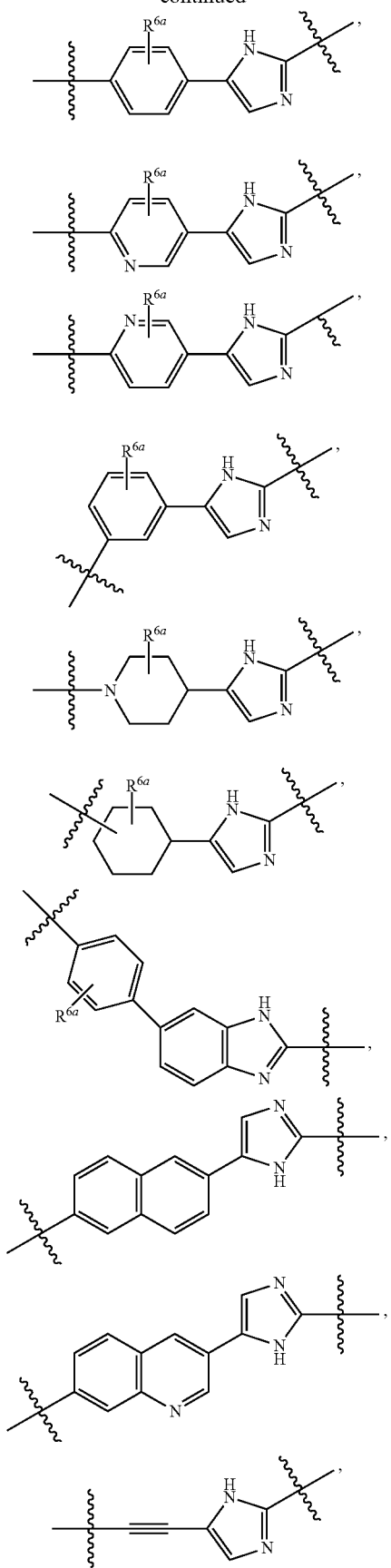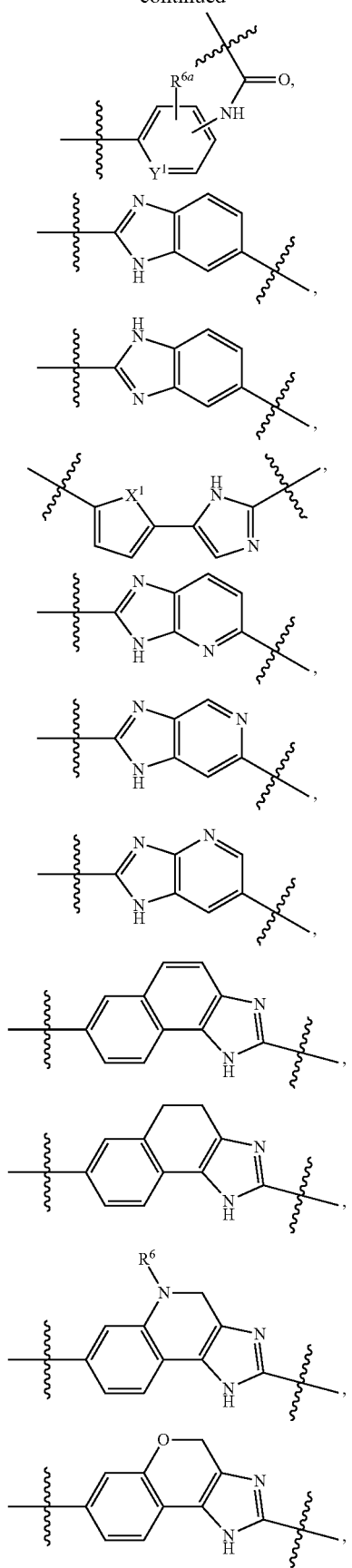

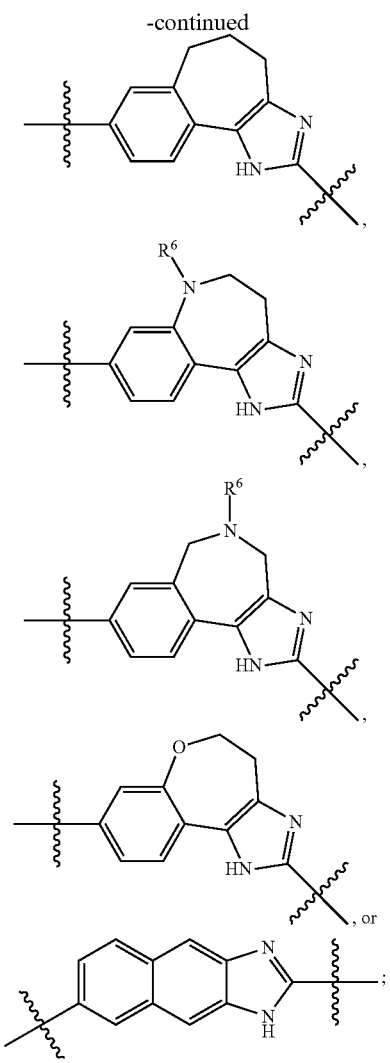

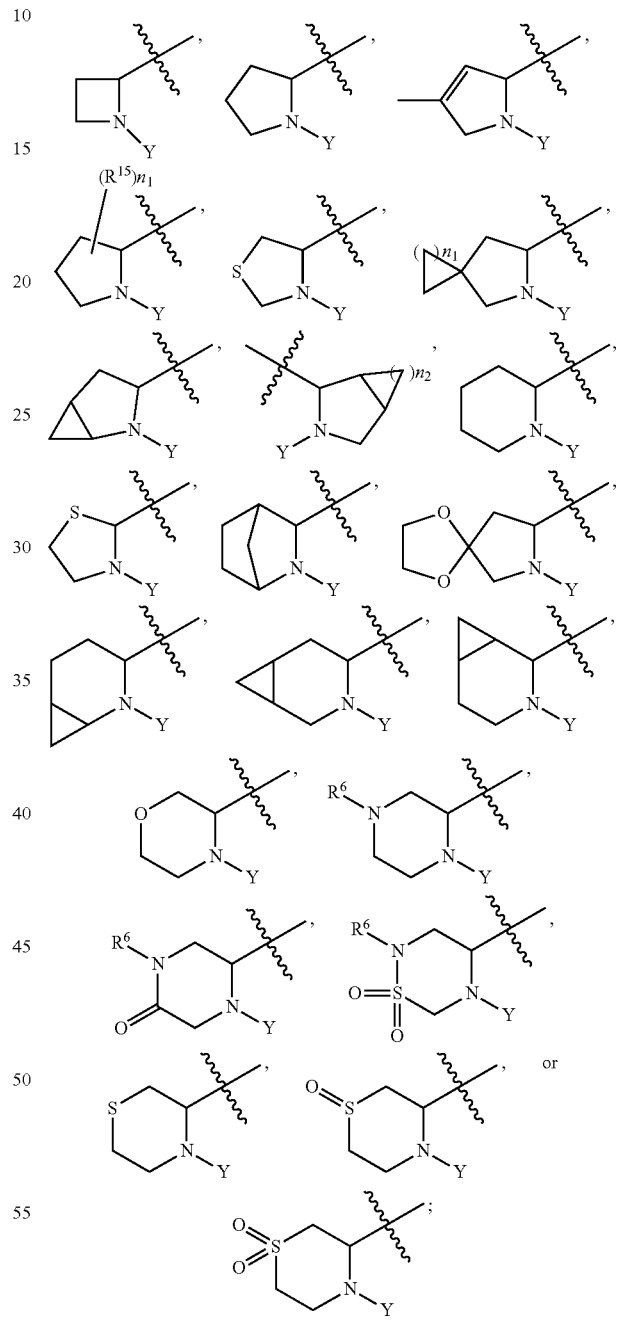

In other embodiments, R$^1$ and R$^2$, together with X—CH, or R$^3$ and R$^4$, together with X'—CH, form a 3-8 membered heterocycle, C$_{5-12}$ fused bicycle, C$_{5-12}$ fused heterobicycle, C$_{5-12}$ spiro bicycle or C$_{5-12}$ spiro heterobicycle.

In other embodiments, R$^1$, R$^2$ and X—CH together form a heterocycle or fused ring or spiro ring system having one of the following structures:

wherein R$^{15}$ is H, F, Cl, Br, I, cyano, hydroxy, C$_{1-3}$ alkyl, C$_{1-3}$ haloalkyl, C$_{1-3}$ alkoxy, C$_{1-3}$ alkylamino, C$_{1-3}$ alkylthio, C$_{6-10}$ arylamino, C$_{6-10}$ aryloxy, C$_{1-9}$ heteroaryl, C$_{1-9}$ heteroaryloxy, C$_{1-9}$ heteroaryl-C$_{1-3}$-alkyl, or C$_{2-10}$ heterocyclyl; and each n$_1$ and n$_2$ is independently 1, 2, 3 or 4.

wherein X$^1$ is O or S;

R$^6$ is independently H, C$_{1-6}$ aliphatic, C$_{1-6}$ haloaliphatic, C$_{1-6}$ hydroxyaliphatic, C$_{1-6}$ amino aliphatic, C$_{1-6}$ alkoxy-C$_{1-6}$-aliphatic, C$_{1-6}$ alkylamino-C$_{1-6}$-aliphatic, C$_{1-6}$ alkylthio-C$_{1-6}$-aliphatic, C$_{6-10}$ aryl-C$_{1-6}$-aliphatic, C$_{1-9}$ heteroaryl-C$_{1-6}$-aliphatic, C$_{2-10}$ heterocyclyl-C$_{1-6}$-aliphatic or C$_{3-8}$ cycloalkyl-C$_{1-6}$-aliphatic;

R$^{6a}$ is H, hydroxy, amino, F, Cl, Br, I, cyano, oxo, R$^{7a}$R$^7$N—, C$_{1-6}$ alkoxy, C$_{1-6}$ alkylamino, C$_{1-6}$ alkyl, C$_{1-6}$ haloalkyl, C$_{2-6}$ alkenyl, C$_{2-6}$ alkynyl, mercapto or nitro; and each of R$^7$ and R$^{7a}$ is independently H, F, Cl, C$_{1-6}$ aliphatic, C$_{1-6}$ heteroalkyl, C$_{1-6}$ haloaliphatic, hydroxy C$_{1-6}$ aliphatic, amino C$_{1-6}$ aliphatic, C$_{1-6}$ alkoxy-C$_{1-6}$-aliphatic, C$_{1-6}$ alkylamino-C$_{1-6}$-aliphatic or C$_{1-6}$ alkylthio-C$_{1-6}$-aliphatic.

In some embodiments, each of R$^1$, R$^2$, R$^3$ and R$^4$ is independently H, C$_{1-8}$ alkyl, C$_{1-8}$ heteroalkyl, C$_{6-10}$ aryl-C$_{1-6}$-alkyl, C$_{3-10}$ cycloalkyl, C$_{2-10}$ heterocyclyl, C$_{1-9}$ heteroaryl or C$_{6-10}$ aryl, or R$^1$ and R$^2$, together with X—CH, form a 3-8 membered heterocycle or carbocycle, C$_{5-12}$ fused bicycle, C$_{5-12}$ fused heterobicycle, C$_{5-12}$ spiro bicycle or C$_{5-12}$ spiro heterobicycle; or R$^3$ and R$^4$, together with X'—CH, form a 3-8 membered heterocycle or carbocycle, C$_{5-12}$ fused bicycle, C$_{5-12}$ fused heterobicycle, C$_{5-12}$ spiro bicycle or C$_{5-12}$ spiro heterobicycle.

In other embodiments, $R^3$, $R^4$ and X'—CH together form a heterocycle or fused ring or spiro ring system having one of the following structures:

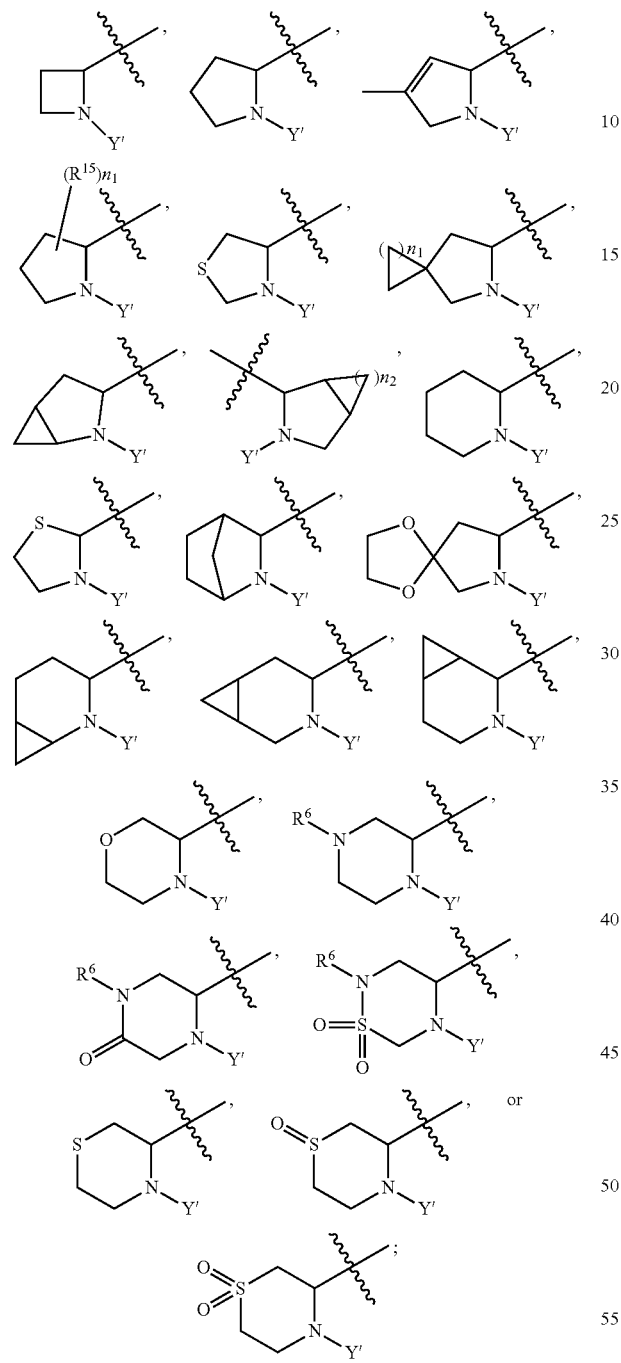

wherein $R^{15}$ is H, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl; and each $n_1$ and $n_2$ is independently 1, 2, 3 or 4.

In some embodiments, the compound having formula (I) of the present invention is the compound having formula (II):

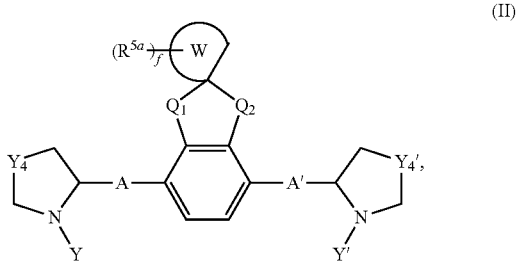

wherein the structural unit of

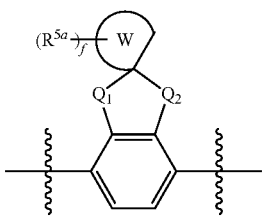

has one of the following structures:

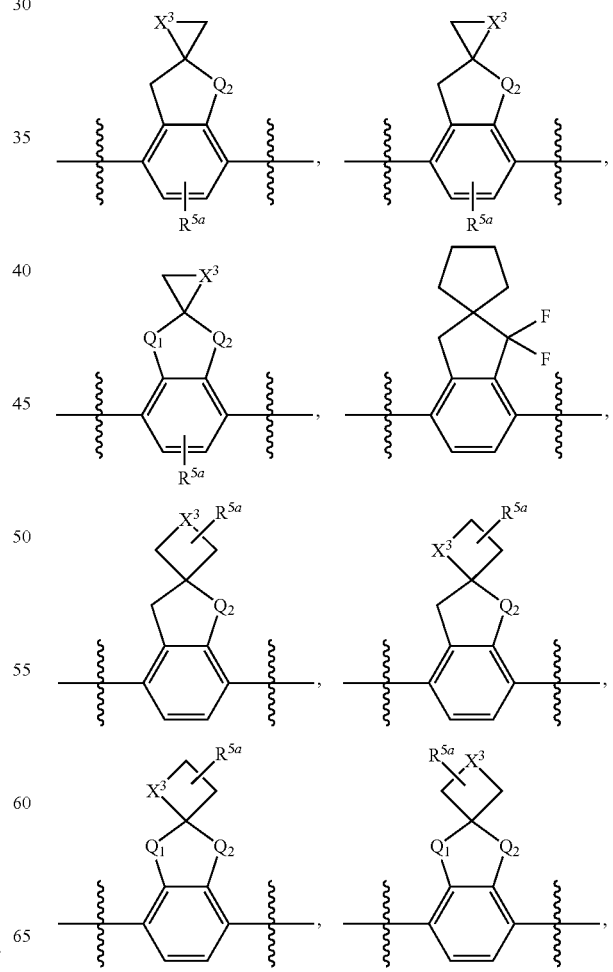

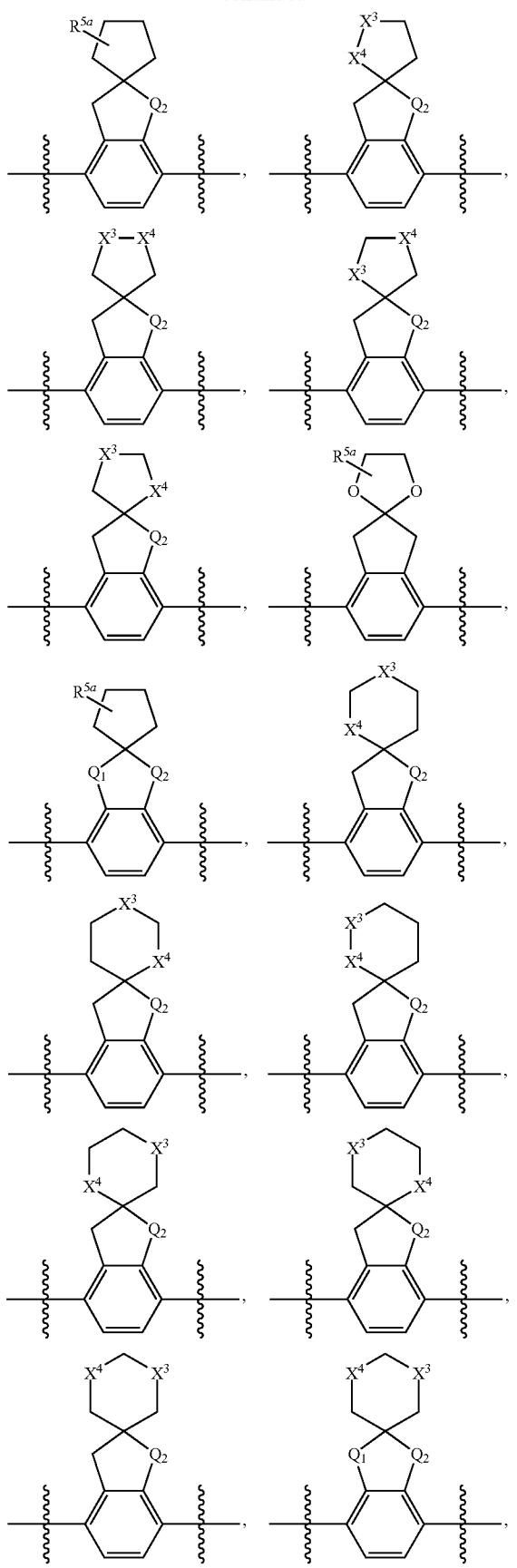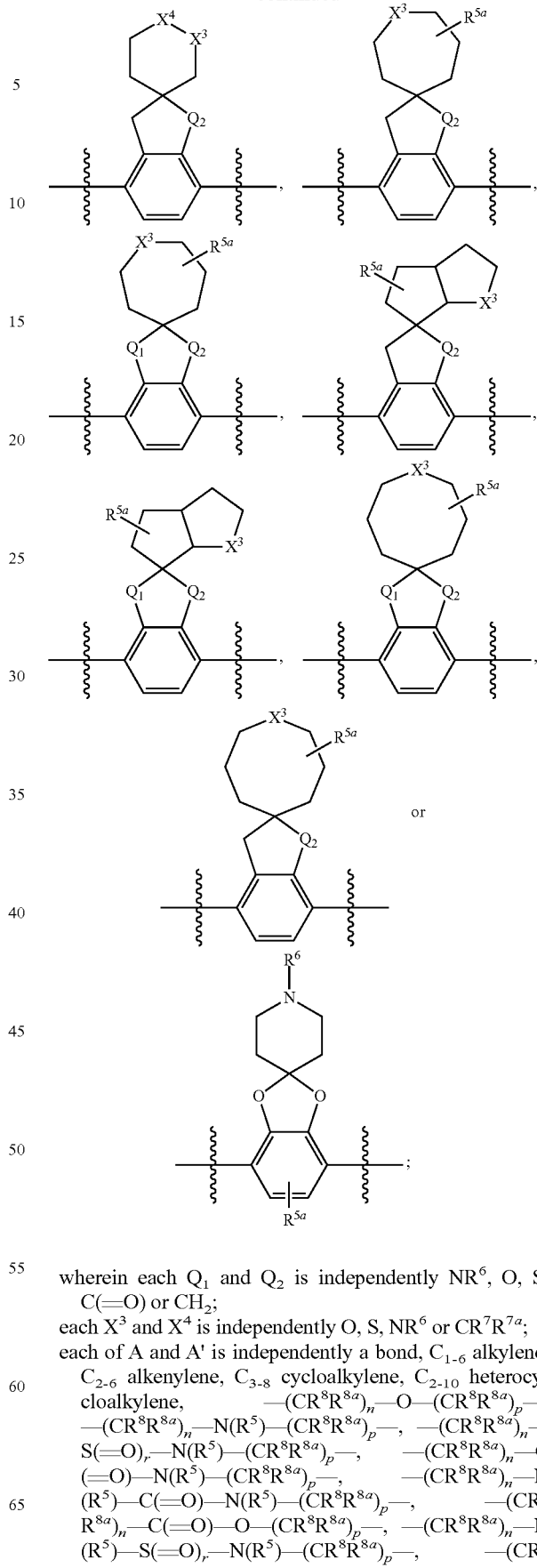

wherein each $Q_1$ and $Q_2$ is independently $NR^6$, O, S, C(=O) or $CH_2$;
each $X^3$ and $X^4$ is independently O, S, $NR^6$ or $CR^7R^{7a}$;
each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8$ $R^{8a})_n$—N($R^5$)—C(=O)—O—(C$R^8R^{8a}$)$_p$—, or each of A and A' is independently one of the following groups:
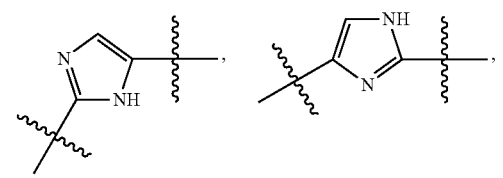
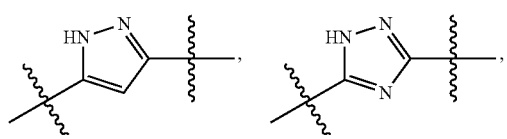
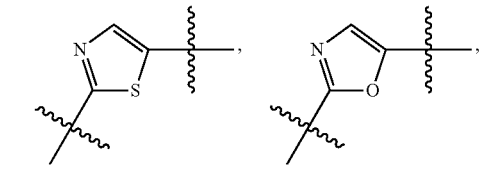
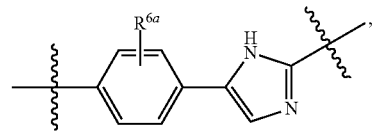

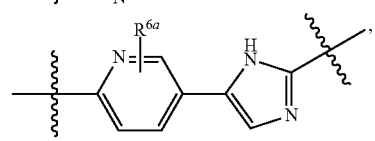
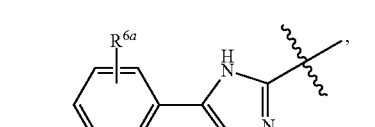
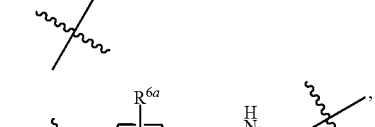
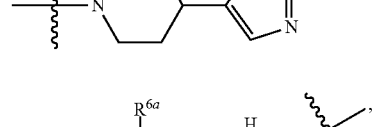
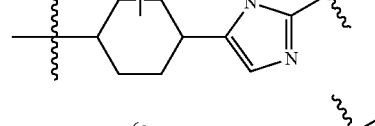
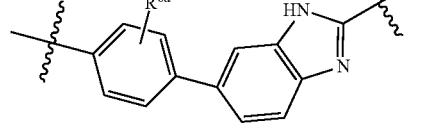
-continued
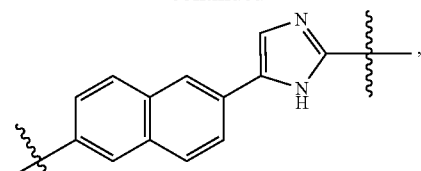
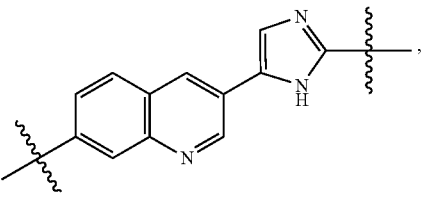
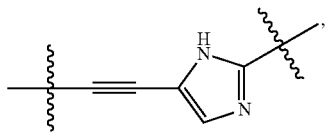
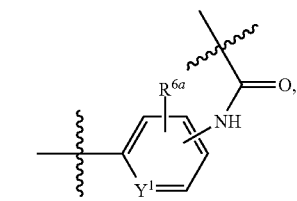
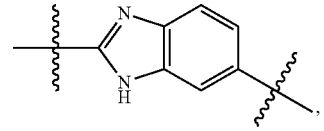
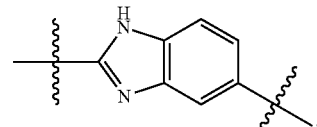
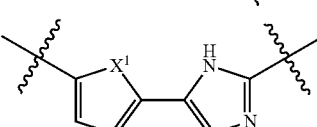
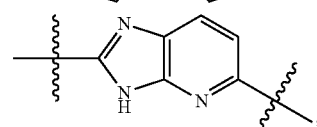
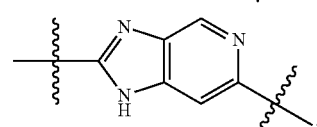
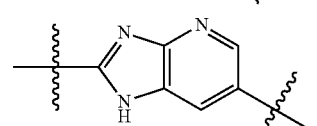
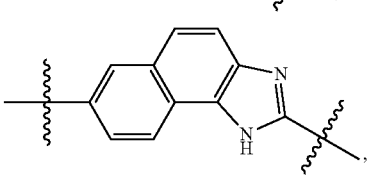

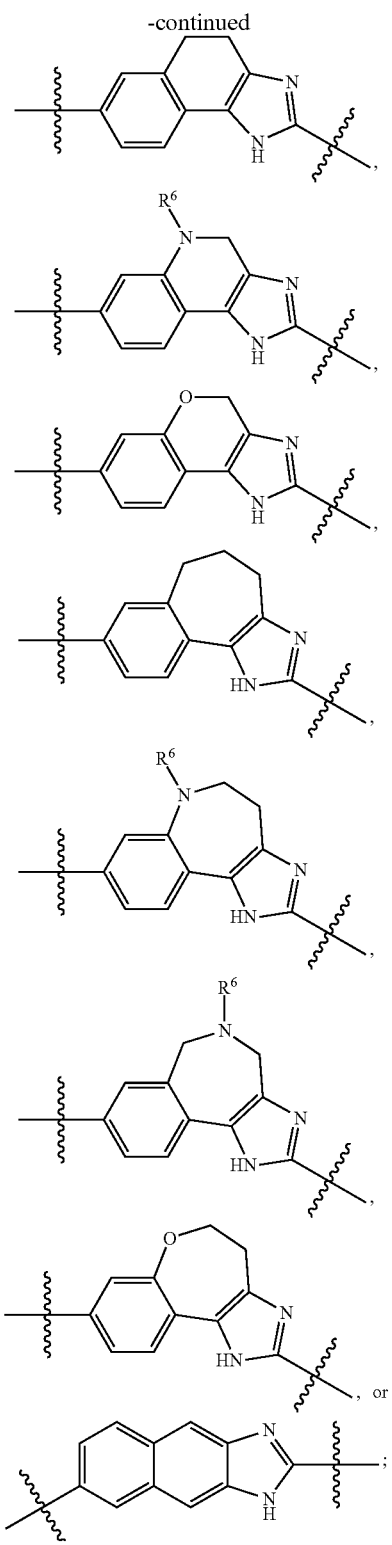

, , , , , or ;

R⁵ is independently H, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, alkyl-S(=O)$_r$— or aminosulfonyl;

each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

$R^6$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{6a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^7$ and $R^{7a}$ is independently H, $C_{1-6}$ aliphatic, $C_{1-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring including spiro bicycle and fused bicycle;

each $R^8$ and $R^{8a}$ is independently H, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each n is independently 0, 1, 2 or 3;
each p is independently 0, 1, 2 or 3;
each k is independently 0, 1 or 2;
each r is independently 0, 1 or 2; and
each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, or —CH$_2$N(R$^6$)—.

In some embodiments, the compound having formula (I) of the present invention is the compound having formula (III):

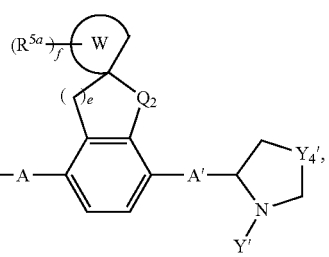

(III)

wherein the structural unit of

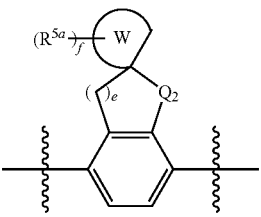

has one of the following structures:

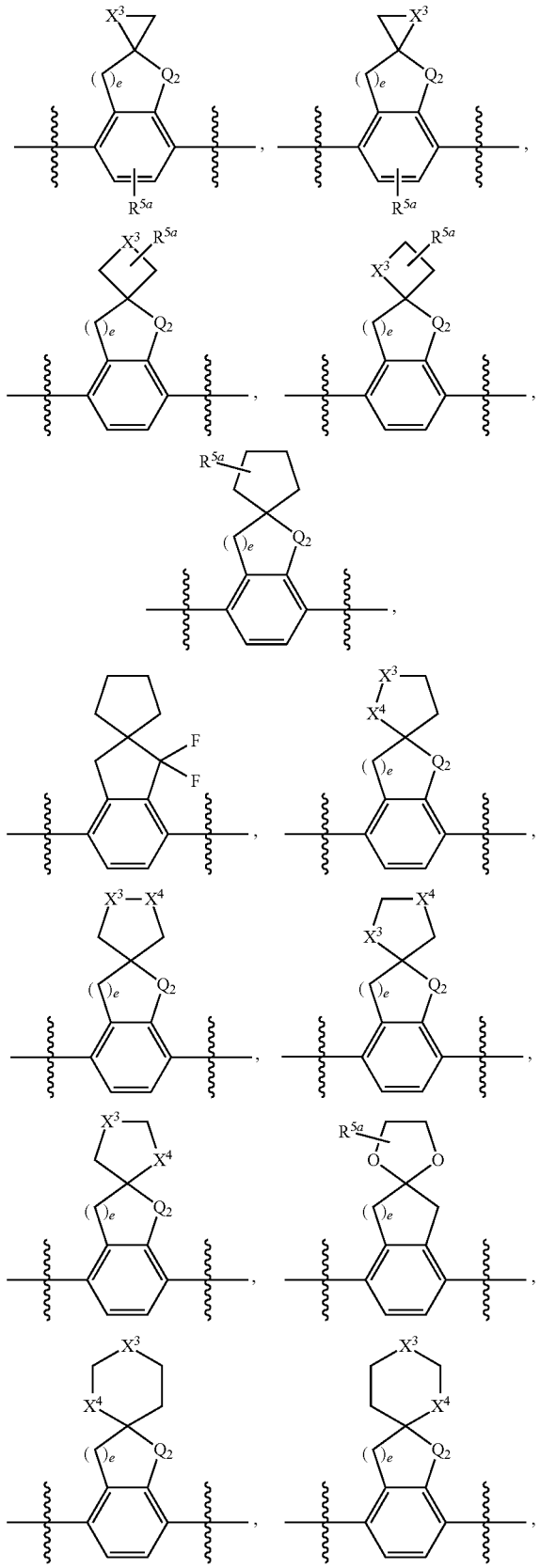

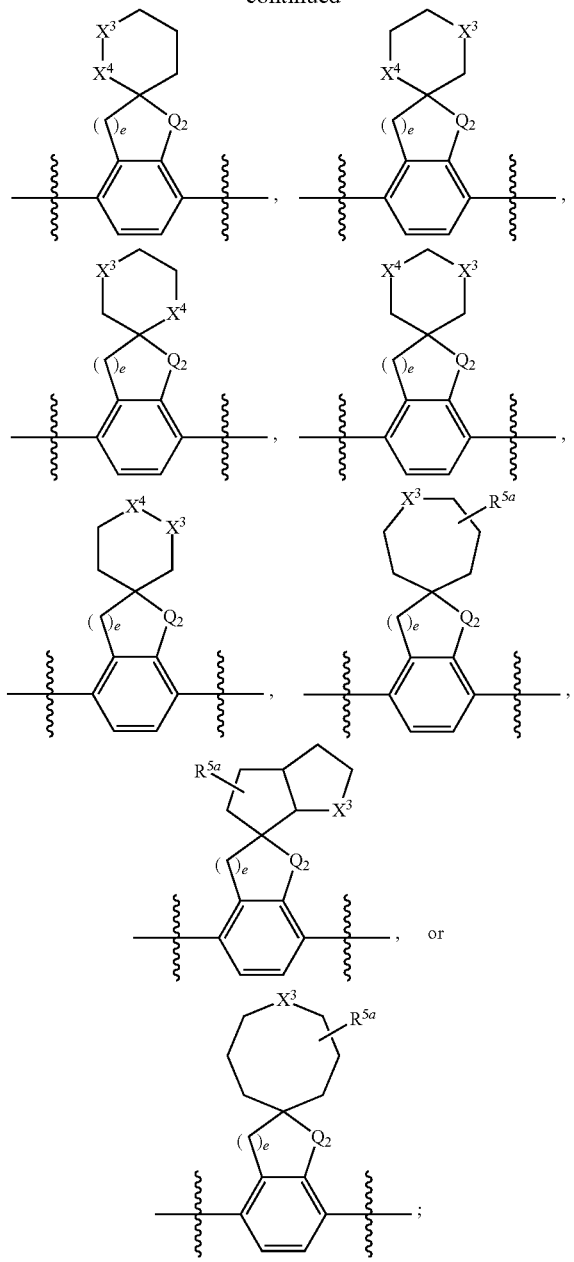

wherein $Q_2$ is O, S, C(=O) or $CH_2$;

each $X^3$ and $X^4$ is independently O, S, $NR^6$, or $CR^7R^{7a}$;

e is 1, 2, 3 or 4;

f is 0, 1, 2, 3 or 4;

each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-N(R^5)-C(=O)-O-(CR^8R^{8a})_p-$, or each of A and A' is independently one of the following groups:

-continued
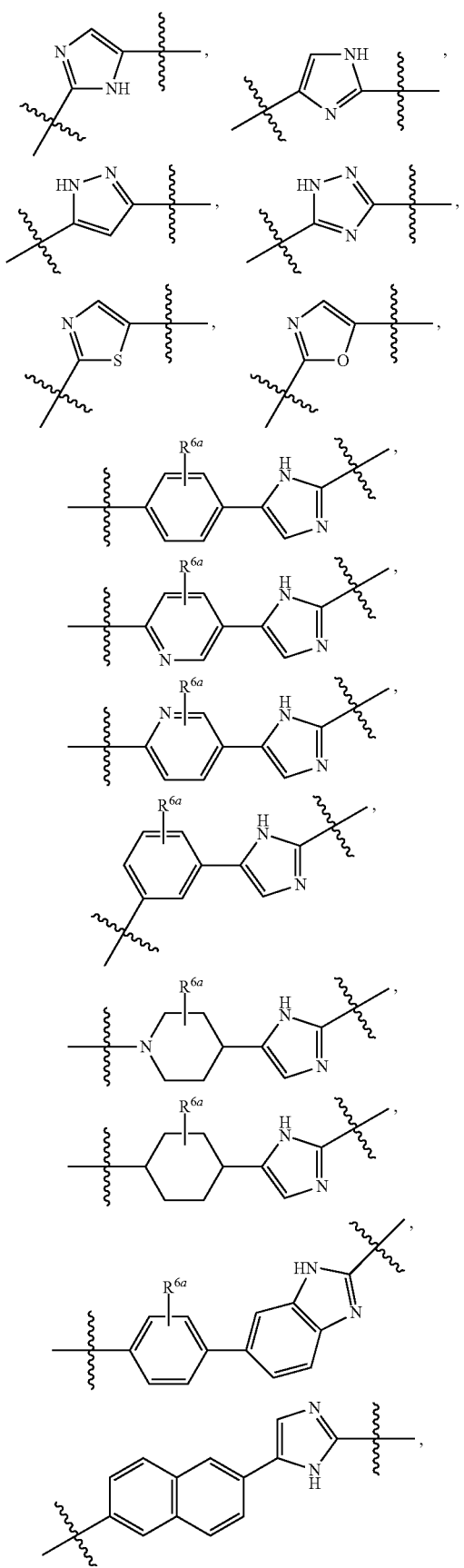
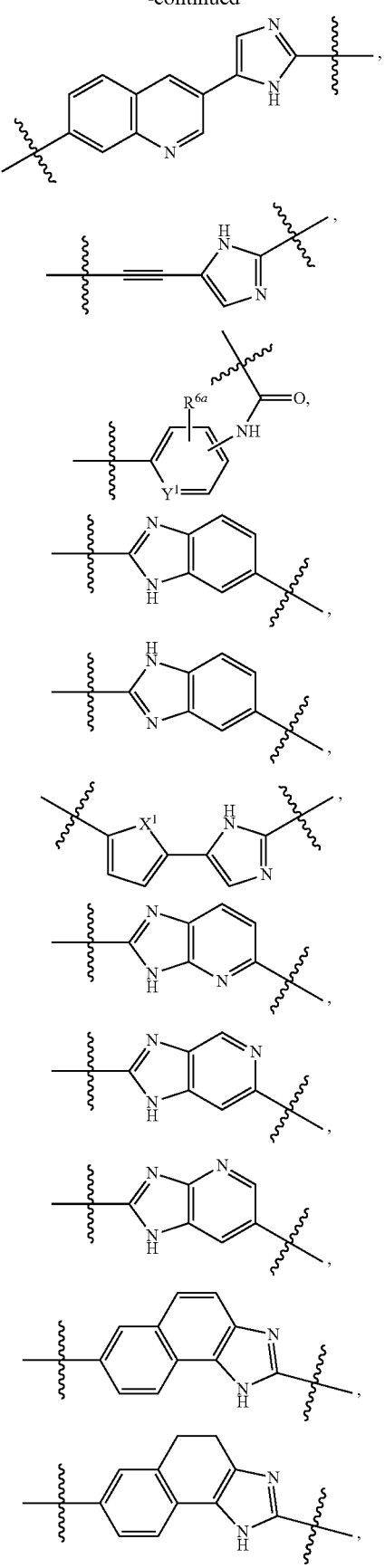

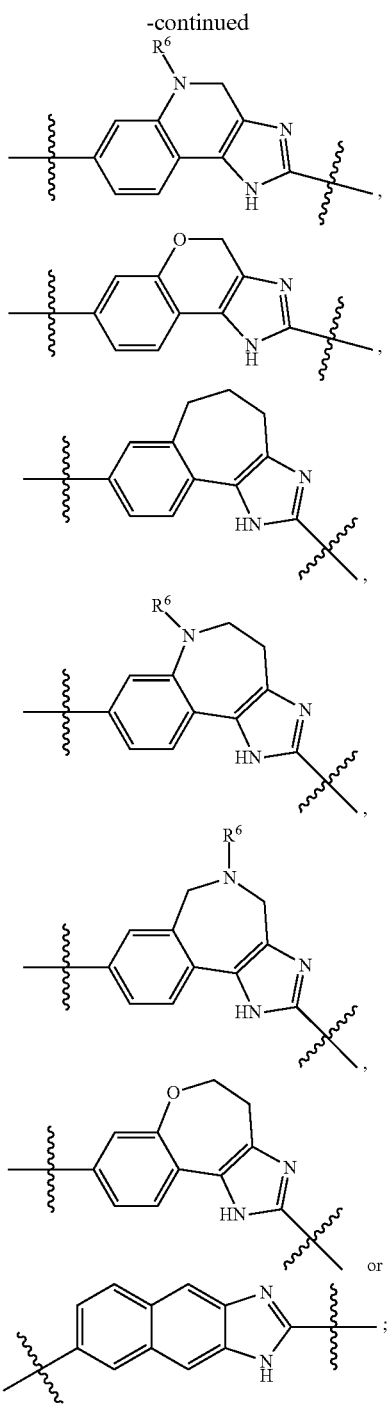

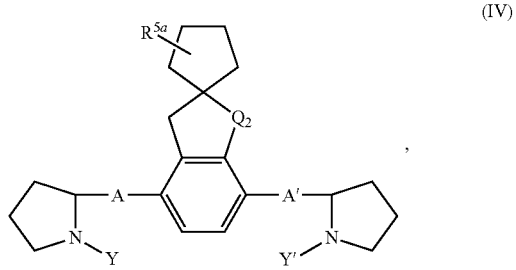

$R^5$ is independently H, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, alkyl-S(=O)$_r$— or aminosulfonyl;

each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

$R^6$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{6a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^7$ and $R^{7a}$ is independently H, $C_{1-6}$ aliphatic, $C_{1-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring including spiro bicycle and fused bicycle;

each $R^8$ and $R^{8a}$ is independently H, hydroxy, cyano, nitro, F, Cl, Br, I, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-10}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$—, or aminosulfonyl;

each n is independently 0, 1, 2 or 3;
each p is independently 0, 1, 2 or 3;
each k is independently 0, 1 or 2;
each r is independently 0, 1 or 2; and
each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, or —CH$_2$N(R$^6$)—.

In other embodiments, the compound having formula (I) of the present invention is the compound having formula (IV):

(IV)

wherein each of A, A', Y, Y', Q$_2$ and R$^{5a}$ is as defined in formula (I).

In other embodiments, the compound having formula (I) of the present invention is the compound having formula (V):

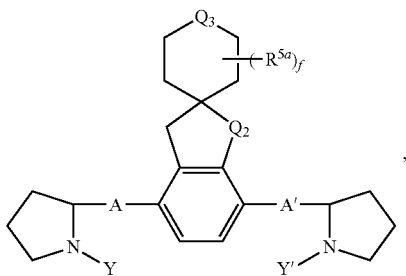

(V)

wherein each of A, A', Y, Y', $R^{5a}$ and f is as defined in formula (I); and each of $Q_2$ and $Q_3$ is independently O, S, C(=O), $NR^6$, or $CH_2$.

In other embodiments, the compound has formula (VI):

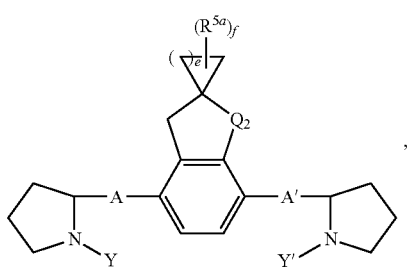

(VI)

wherein each of A, A', Y, Y', $Q_2$, $R^{5a}$ and f is as defined in formula (I); and e is 1, 2, 3 or 4.

In some embodiments, each of Y and Y' is independently a group derived from an α-amino acid.

In other embodiments, the naturally occurring or commercially available α-amino acid is isoleucine, leucine, lysine, methionine, phenylalanine, threonine, tryptophane, valine, alanine, asparagine, aspartic acid, glutamic acid, glutamine, proline, serine, p-tyrosine, arginine, histidine, cysteine, glycine, sarcosine, N,N-dimethylglycine, homoserine, norvaline, norleucine, ornithine, homocysteine, homophenylalanine, phenylglycine, o-tyrosine, m-tyrosine or hydroxyproline.

In other embodiments, the α-amino acid is in the D configuration.

In other embodiments, each of Y and Y' is independently —[U—$(CR^9R^{9a})_t$—$N(R^{10})$—$(CR^9R^{9a})_t]_k$—U—$(CR^9R^{9a})_t$—$N(R^{11})$—$(CR^9R^{9a})_t$—$R^{12}$, —U—$(CR^9R^{9a})_t$—$R^{12}$ or —[U—$(CR^9R^{9a})_t$—$N(R^{10})$—$(CR^9R^{9a})_t]_k$—U—$(CR^9R^{9a})_t$—O—$(CR^9R^{9a})_t$—$R^{12}$.

In other embodiments, each of Y and Y' is independently —[U—$(CR^9R^{9a})_t$—$N(R^{10})$—$(CR^9R^{9a})_t]_k$—U—$(CR^9R^{9a})_t$—$N(R^{11})$—$(CR^9R^{9a})_t$—$R^{12}$.

In other embodiments, each of Y and Y' is independently —U—$(CR^9R^{9a})_t$—$N(R^{10})$—$(CR^9R^{9a})_t$—U—$(CR^9R^{9a})_t$—$N(R^{11})$—$(CR^9R^{9a})_t$—$R^{12}$.

In other embodiments, each of Y and Y' is independently —U—$(CR^9R^{9a})_t$—$N(R^{11})$—$(CR^9R^{9a})_t$—$R^{12}$.

In other embodiments, each of Y and Y' is independently —[C(=O)—$(CR^9R^{9a})_t$—$N(R^{10})$—$(CR^9R^{9a})_t]_k$—U—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_t$—$N(R^{10})$—$(CR^9R^{9a})_t$—U—$(CR^9R^{9a})_t$—$N(R^{11})$—$(CR^9R^{9a})_t$—$R^{12}$.

In other embodiments, each of Y and Y' is independently —[C(=O)—$(CR^9R^{9a})_t$—$N(R^{10})$—$(CR^9R^{9a})_t]_k$—C(=O)—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_t$—$N(R^{10})$—$(CR^9R^{9a})_t$—C(=O)—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_t$—$N(R^{11})$—$(CR^9R^{9a})_t$—$R^{12}$.

In other embodiments, each of Y and Y' is independently —C(=O)—$(CR^9R^{9a})_n$—$N(R^{11})$—$(CR^9R^{9a})_n$—C(=O)—$R^{13}$.

In other embodiments, each of Y and Y' is independently —C(=O)—$(CR^9R^{9a})_n$—$N(R^{11})$—C(=O)—$R^{13}$.

In other embodiments, each of Y and Y' is independently —C(=O)—$(CR^9R^{9a})_n$—$N(R^{11})$—$(CR^9R^{9a})_n$—C(=O)—O—$R^{13}$.

In other embodiments, each of Y and Y' is independently —C(=O)—$(CR^9R^{9a})_n$—$N(R^{11})$—C(=O)—O—$R^{13}$.

In other embodiments, each of Y and Y' is independently —U—$(CR^9R^{9a})_t$—$R^{12}$.

In other embodiments, each of Y and Y' is independently —C(=O)—$(CR^9R^{9a})_t$—$R^{12}$.

In other embodiments, each of Y and Y' is independently —[U—$(CR^9R^{9a})_t$—$N(R^{10})$—$(CR^9R^{9a})_t]_k$—U—$(CR^9R^{9a})_t$—O—$(CR^9R^{9a})_t$—$R^{12}$.

In other embodiments, each of Y and Y' is independently —U—$(CR^9R^{9a})_t$—$N(R^{10})$—$(CR^9R^{9a})_t$—U—$(CR^9R^{9a})_t$—O—$(CR^9R^{9a})_t$—$R^{12}$.

In other embodiments, each of Y and Y' is independently —C(=O)—$(CR^9R^{9a})_t$—$N(R^{10})$—$(CR^9R^{9a})_t$—C(=O)—$(CR^9R^{9a})_t$—O—$(CR^9R^{9a})_t$—$R^{12}$.

In other embodiments, each of Y and Y' is independently —U—$(CR^9R^{9a})_t$—O—$(CR^9R^{9a})_t$—$R^{12}$.

In other embodiments, each of Y and Y' is independently —C(=O)—$(CR^9R^{9a})_t$—O—$(CR^9R^{9a})_t$—$R^{12}$.

In other embodiments, each of Y and Y' is independently —C(=O)—$(CR^9R^{9a})_n$—$NR^{11}$—$R^{12}$, wherein $R^{11}$ and $R^{12}$, together with the nitrogen atom they are attached to, form a 4-7 membered ring.

In other embodiments, each $R^9$, $R^{9a}$, $R^{10}$ and $R^{11}$ is independently H, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ haloalkyl, $C_{1-6}$ hydroxyalkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

$R^{12}$ is independently $R^{13a}R^{13}N$—, —C(=O)$R^{13}$, —C(=S)$R^{13}$, —C(=O)—O—$R^{13}$, —C(=O)$NR^{13}R^{13a}$, —OC(=O)$NR^{13}R^{13a}$, —OC(=O)$OR^{13}$, —N($R^{13}$)C(=O)$NR^{13}R^{13a}$, —N($R^{13}$)C(=O)$OR^{13a}$, —N($R^{13}$)C(=O)—$R^{13a}$, $R^{13}R^{13a}N$—S(=O)$_2$—, $R^{13}S(=O)_2$—, $R^{13}S(=O)_2N(R^{13a})$—, $R^{13}OS(=O)_2$—, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl;

or $R^{11}$ and $R^{12}$, together with the nitrogen atom they are attached to, form a 4-7 membered ring; and each $R^{13}$ and $R^{13a}$ is independently H, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl.

In other embodiments, each $R^9$, $R^{9a}$, $R^{10}$ and $R^{11}$ is independently H, methyl, ethyl, isopropyl, cyclohexyl, isobutyl or phenyl;

$R^{12}$ is independently —C(=O)$R^{13}$, —C(=O)—O—$R^{13}$, —C(=O)N$R^{13}R^{13a}$, methyl, ethyl, propyl, phenyl, cyclohexyl, morpholinyl or piperidinyl;

or $R^{11}$ and $R^{12}$, together with the nitrogen atom they are attached to, form a 4-7 membered ring; and each $R^{13}$ and $R^{13a}$ is independently H, methyl, ethyl, propyl, phenyl, cyclohexyl, morpholinyl or piperidinyl.

In other embodiments, the compound having formula (I) of the present invention is the compound having formula (VII):

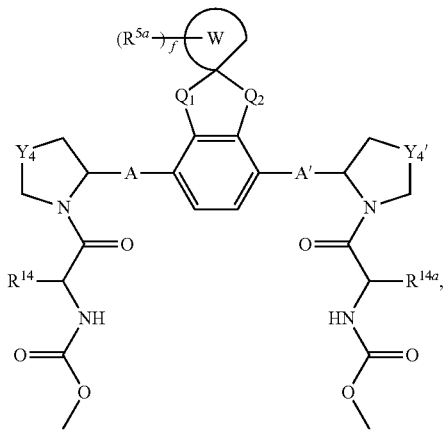

(VII)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl.

In other embodiments, the compound having formula (I) of the present invention is the compound having formula (VIII):

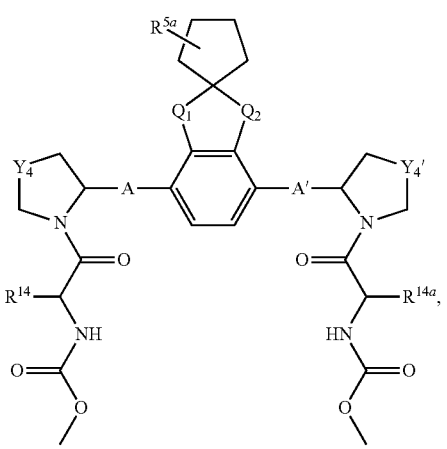

(VIII)

wherein each of $R^{14}$ and $R^{14a}$ is independently H, $C_{1-3}$ hydroxyalkyl, methyl, ethyl, isopropyl, isobutyl, tert-butyl, allyl, propargyl, trifluoroethyl, phenyl, pyranyl, morpholinyl, —N$R^7R^{7a}$, benzyl, piperazinyl, cyclopentyl, cyclopropyl, cyclohexyl, or $C_{1-9}$ heteroaryl.

In other embodiments, the compound having formula (I) of the present invention is the compound having formula (VIII'):

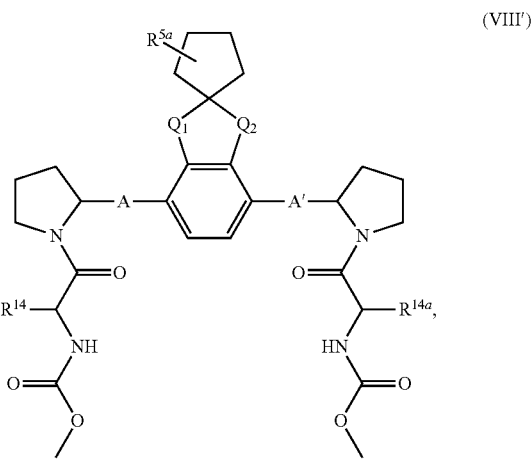

(VIII')

wherein each of $R^{14}$ and $R^{14a}$ is independently H, $C_{1-3}$ hydroxyalkyl, methyl, ethyl, isopropyl, isobutyl, tert-butyl, allyl, propargyl, trifluoroethyl, phenyl, pyranyl, morpholinyl, —N$R^7R^{7a}$, benzyl, piperazinyl, cyclopentyl, cyclopropyl, cyclohexyl, or $C_{1-9}$ heteroaryl.

In some embodiments, the compound having formula (I) of the present invention is the compound having formula (IX'):

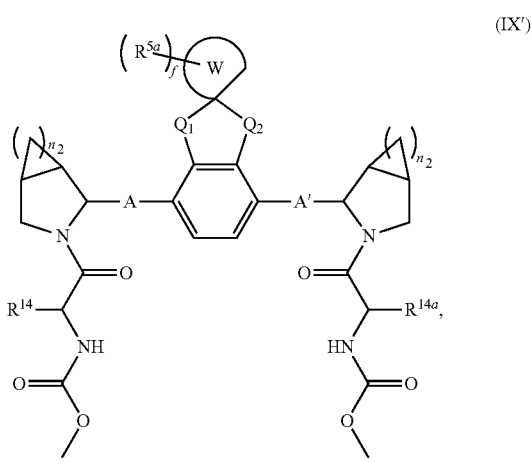

(IX')

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_2$ is independently 1, 2, 3 or 4.

In some embodiments, the compound having formula (I) of the present invention is the compound having formula (IX):

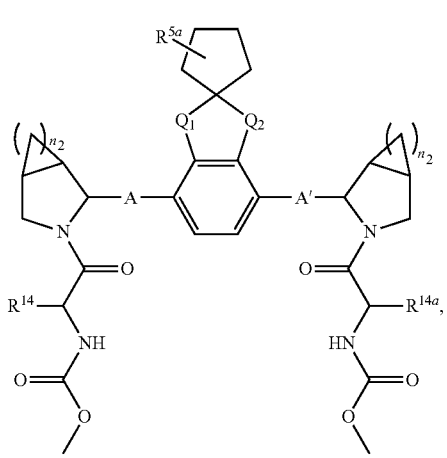

(IX)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_2$ is independently 1, 2, 3 or 4.

In some embodiments, the compound having formula (I) of the present invention is the compound having formula (X'):

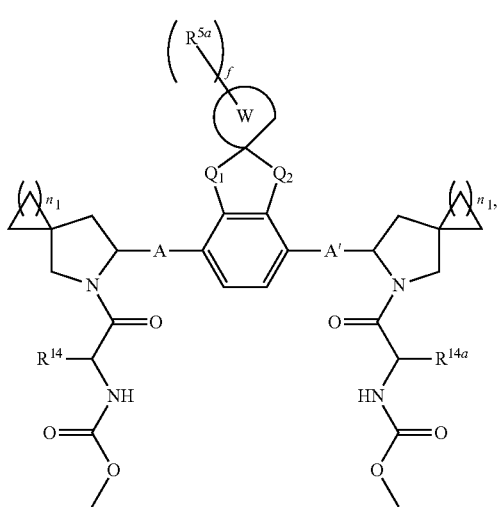

(X')

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_1$ is independently 1, 2, 3 or 4.

In some embodiments, the compound having formula (I) of the present invention is the compound having formula (X):

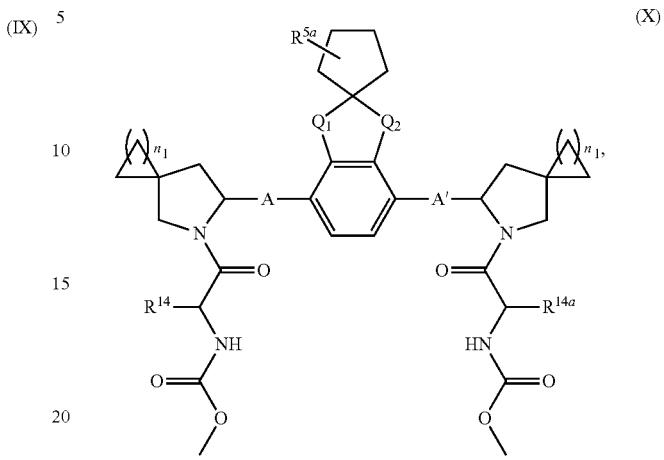

(X)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_1$ is independently 1, 2, 3 or 4.

In some embodiments, the compound having formula (I) of the present invention is the compound having formula (XI):

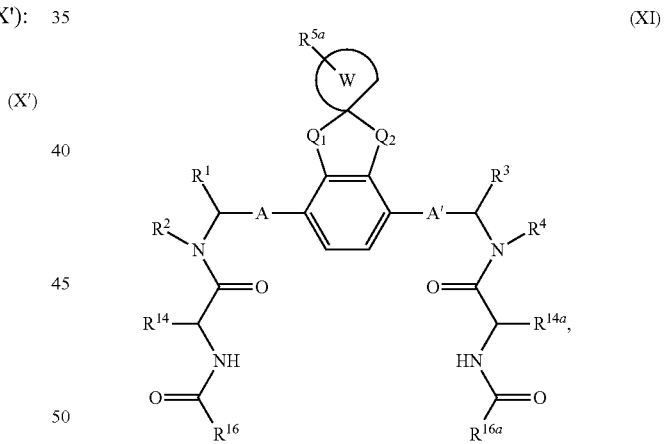

(XI)

wherein $R^{5a}$ is H, methyl, ethyl, F, Cl, Br or I;
$Q_1$ is $CH_2$, C(=O), O, S, or NH;
$Q_2$ is $CH_2$, C(=O), $CF_2$, O, or S;
each of $R^{14}$ and $R^{14a}$ is independently methyl, ethyl, phenyl, cyclohexyl, 1-methylpropyl, isopropyl or tert-butyl;
each of $R^{16}$ and $R^{16a}$ is independently hydroxy, methoxy, ethoxy, phenoxy,

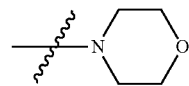

or tert-butoxy;

wherein the structural unit of
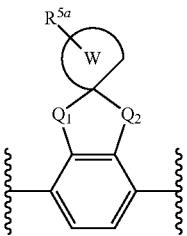
has one of the following structures:
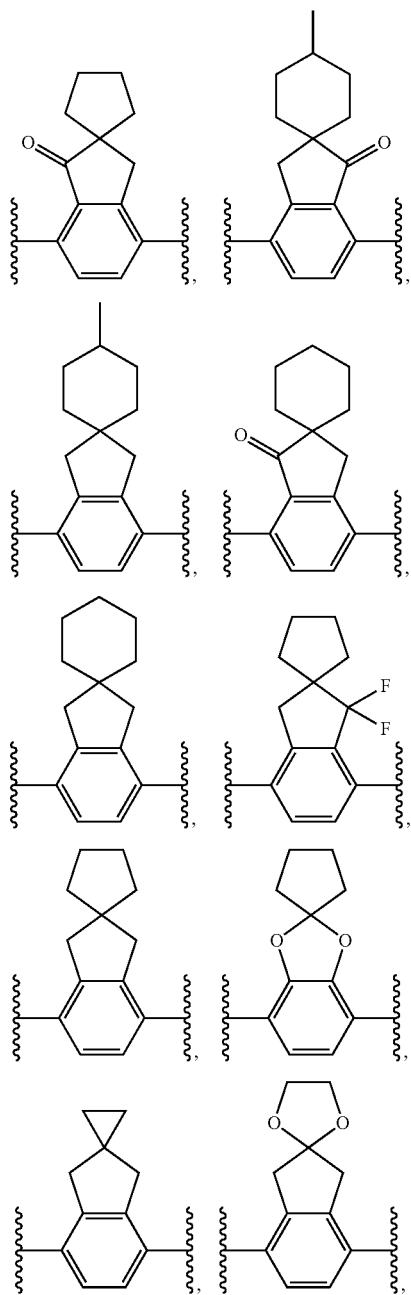
each of A and A' is independently
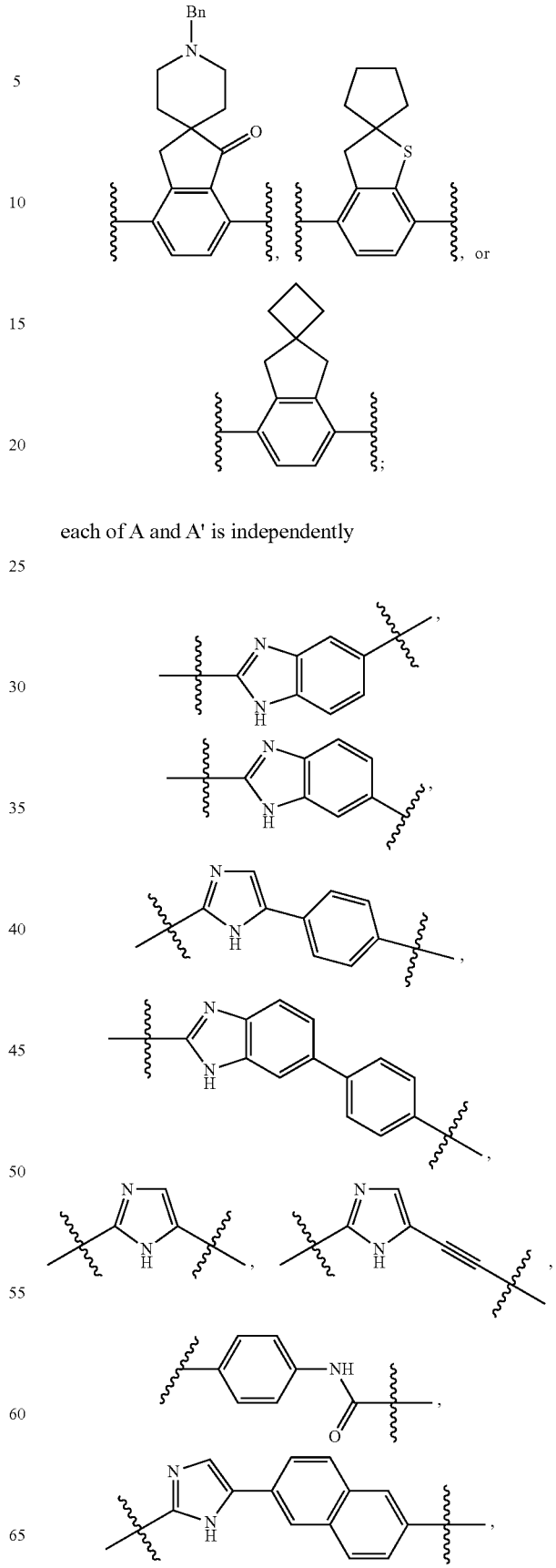

-continued

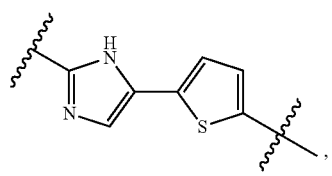,

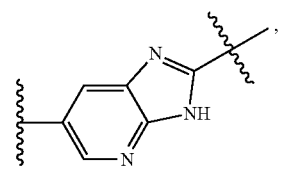,

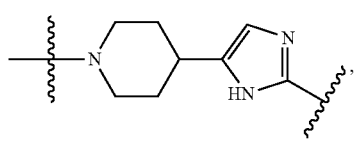,

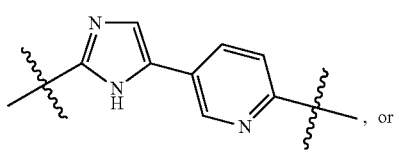, or

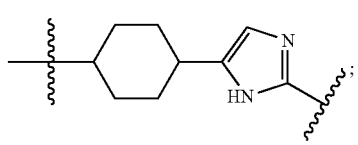;

wherein R¹, R² and N—CH together form a heterocycle or fused ring or spiro ring system having one of the following structures:

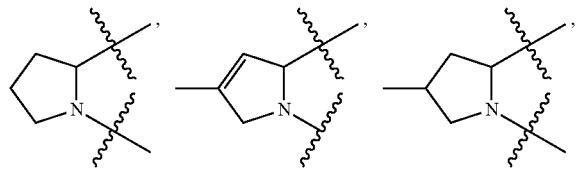,

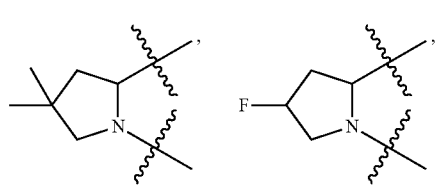,

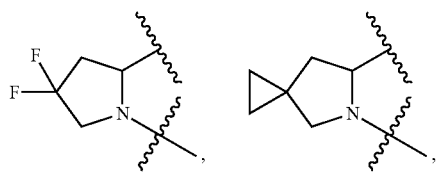,

-continued

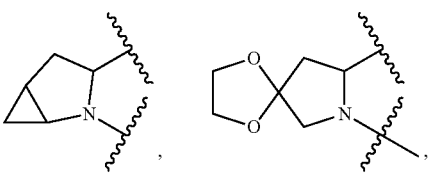,

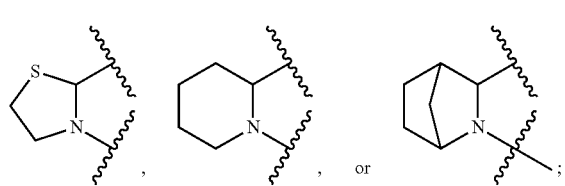, or and
wherein R³, R⁴ and N—CH together form a heterocycle or fused ring or spiro ring system having one of the following structures:

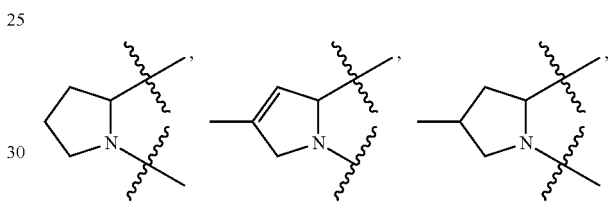,

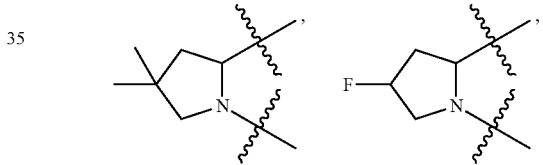,

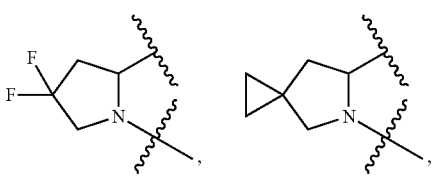,

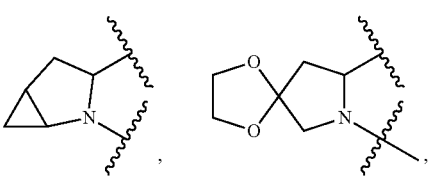,

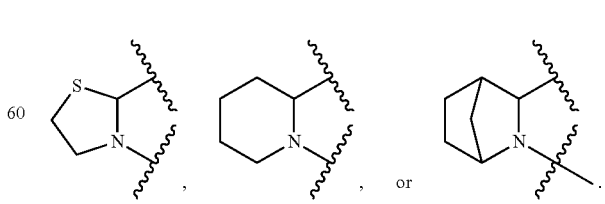, or

In other embodiments, the compound having formula (I) of the present invention is the compound having formula (XII):

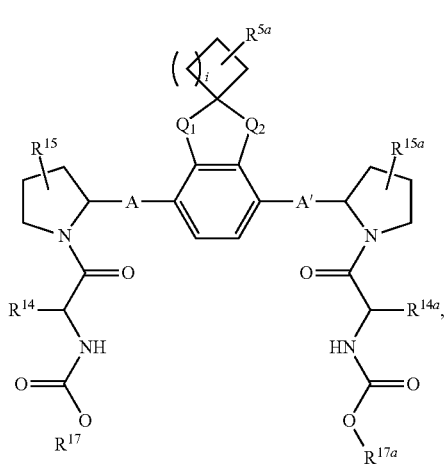

(XII)

wherein i is 1, 2, or 3;
$R^{5a}$ is H or methyl;
each of $Q_1$ and $Q_2$ is independently $CH_2$, $CF_2$, O or C(=O);
each of $R^{14}$ and $R^{14a}$ is independently methyl, ethyl, isobutyl, cyclohexyl, phenyl or isopropyl;
each of $R^{15}$ and $R^{15a}$ is independently H, F, Cl, Br, methyl, ethyl, isopropyl or tert-butyl;
each of $R^{17}$ and $R^{17a}$ is independently methyl, phenyl or ethyl; and
each of A and A' is independently

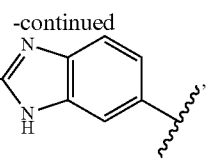

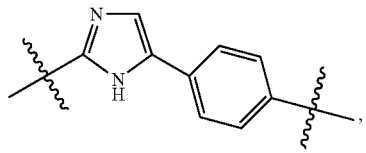

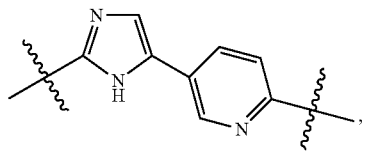

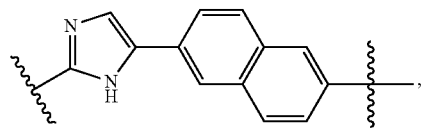

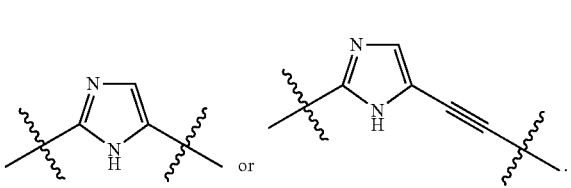

In some embodiments, non-limiting examples of compounds disclosed herein, or a stereoisomer, a geometric isomer, a tautomer, an N-oxide, a hydrate, a solvate, or a pharmaceutically acceptable salt thereof, are shown in the following:

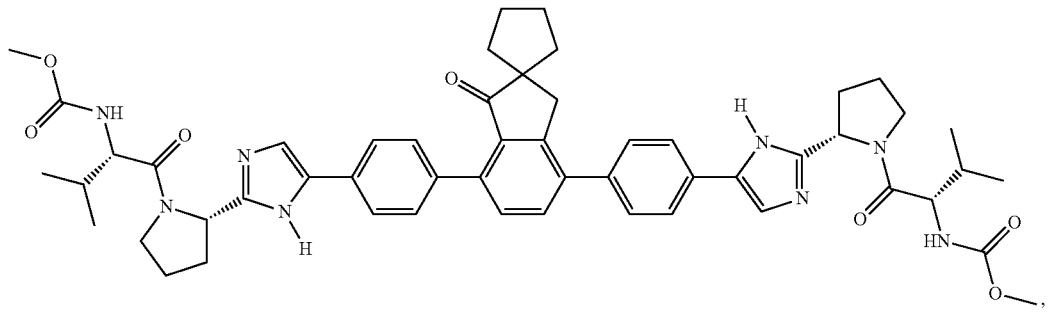

(1)

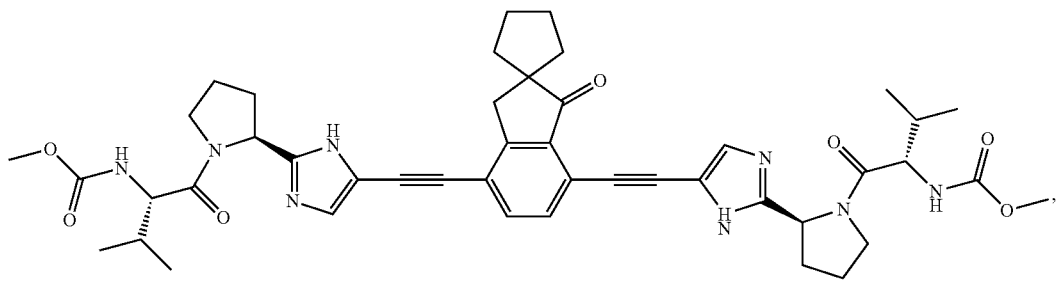

(2)

(3)
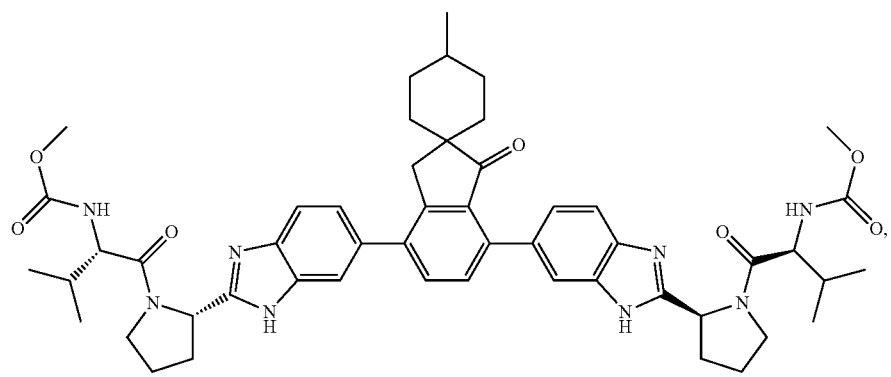
(4)
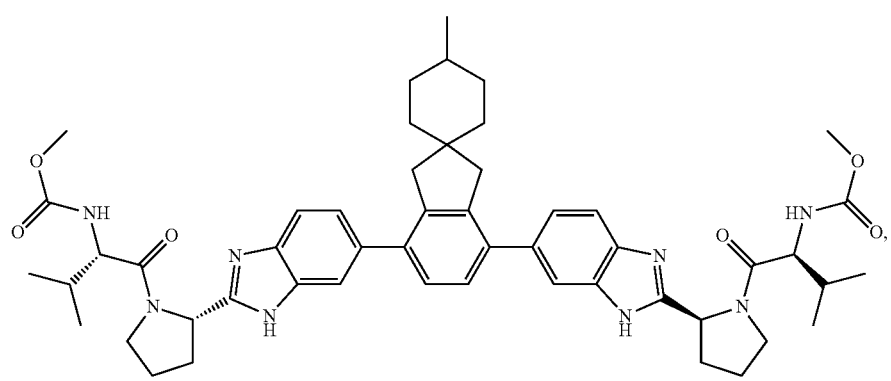
(5)
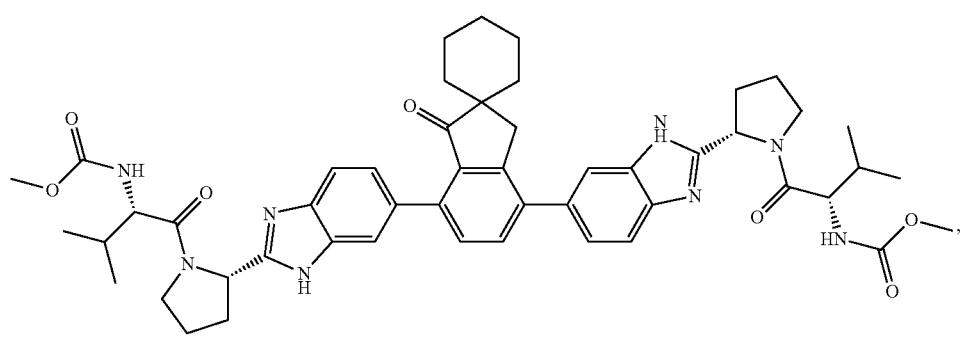
(6)
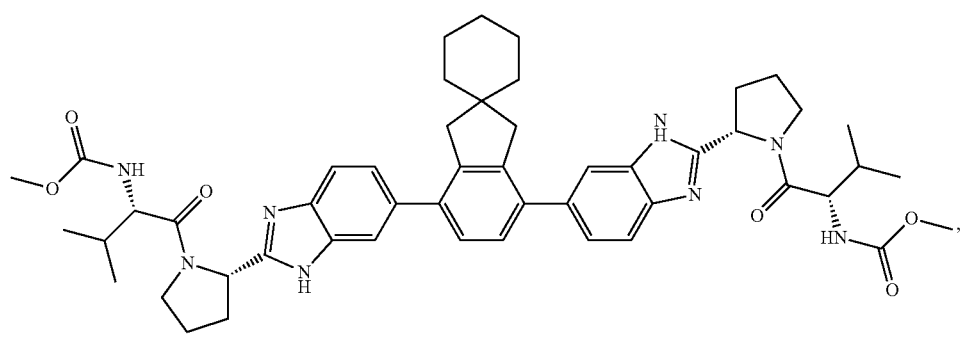

(7)
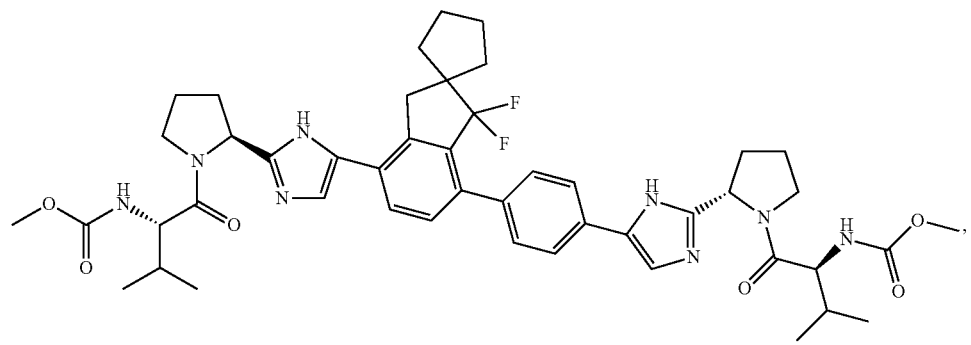
(8)
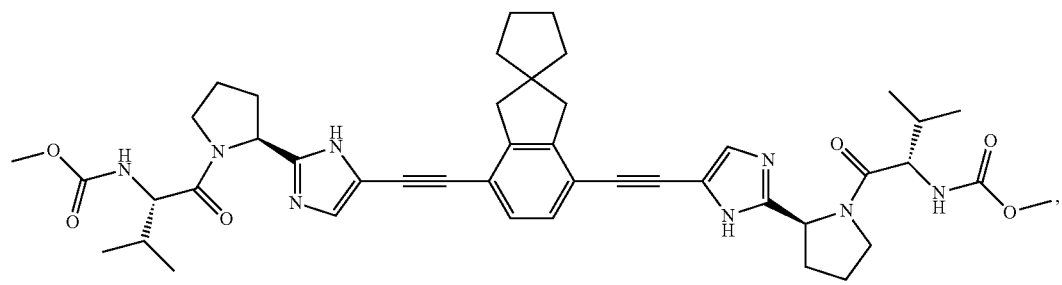
(9)
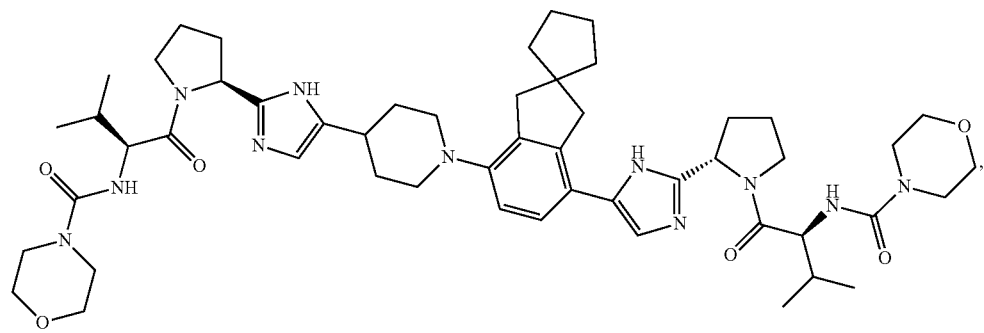
(10)
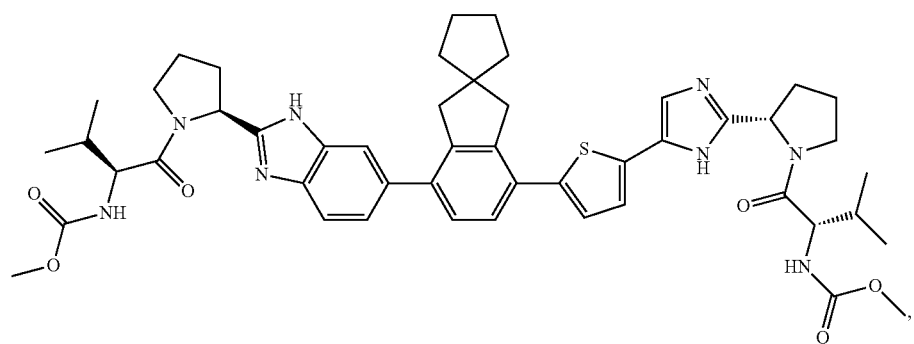
(11)
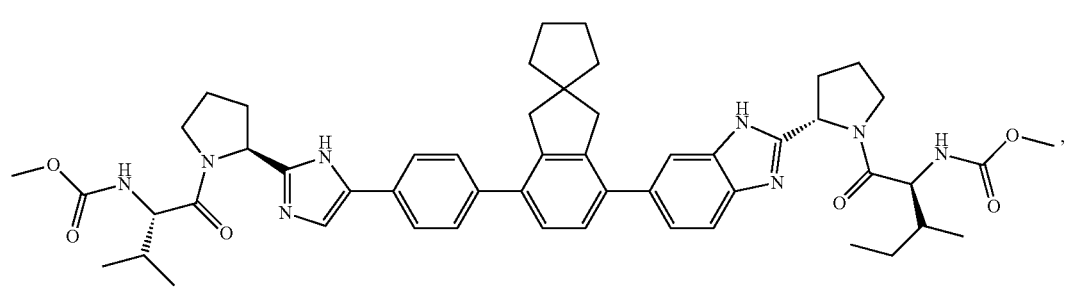

(12)
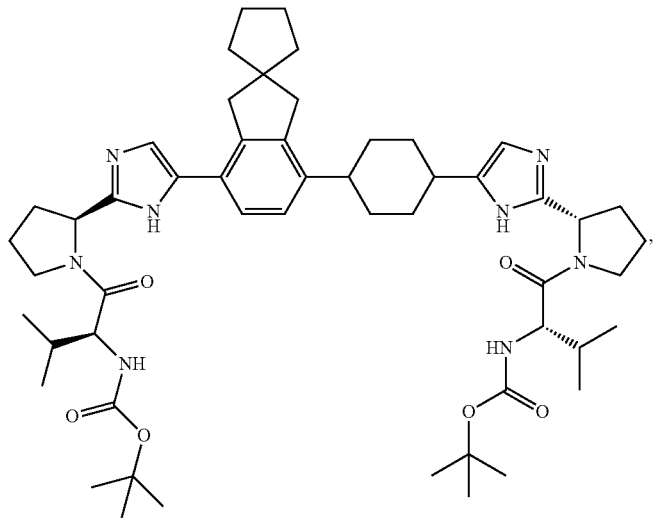
(13)
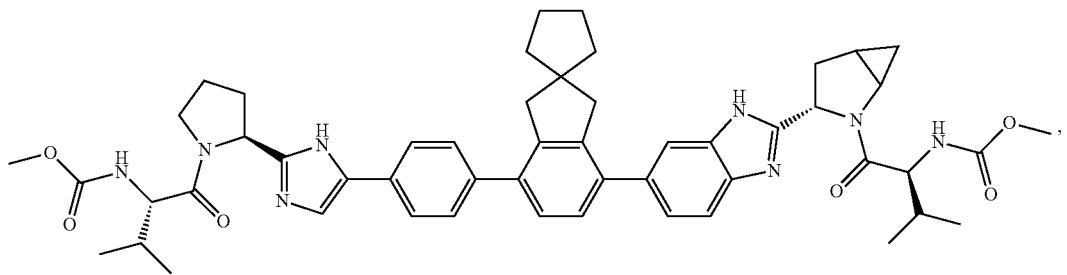
(14)
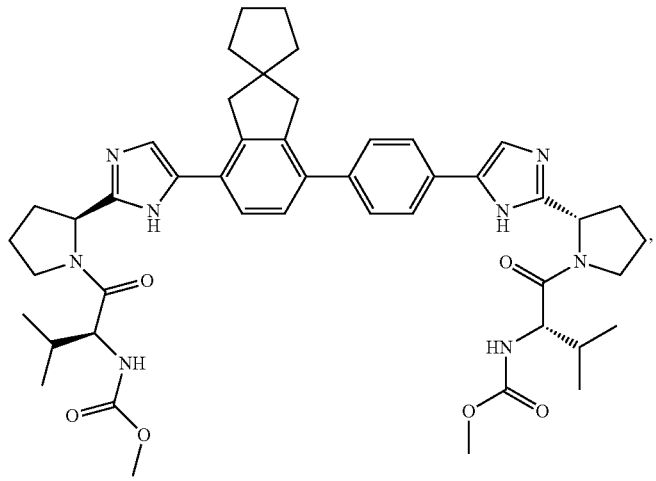
(15)
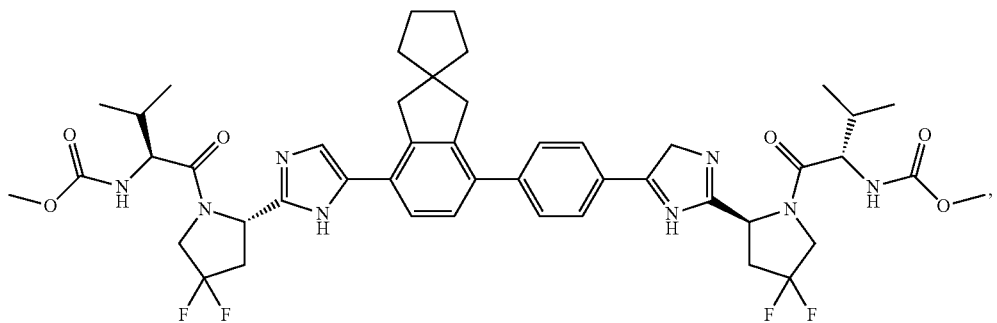

-continued
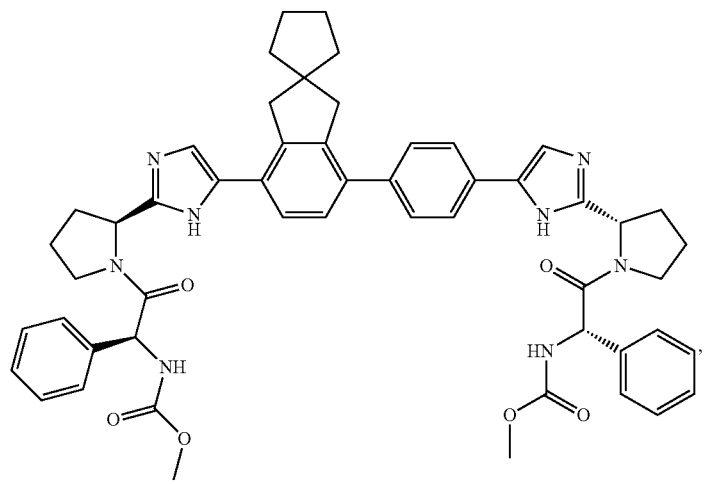
(16)
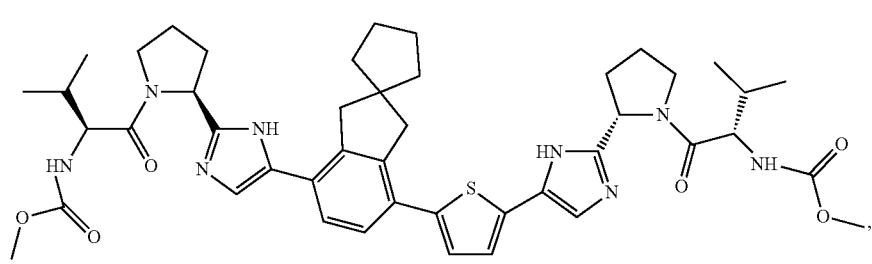
(17)
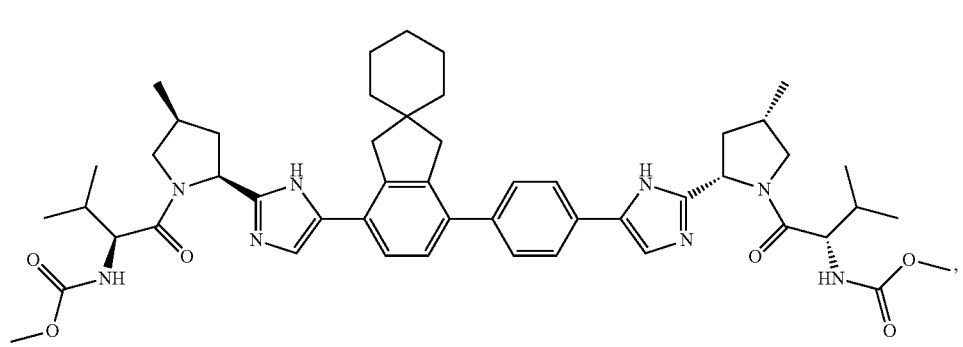
(18)
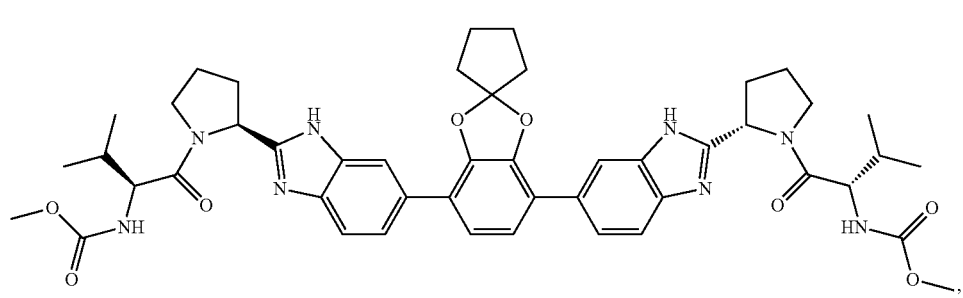
(19)

-continued
(20)
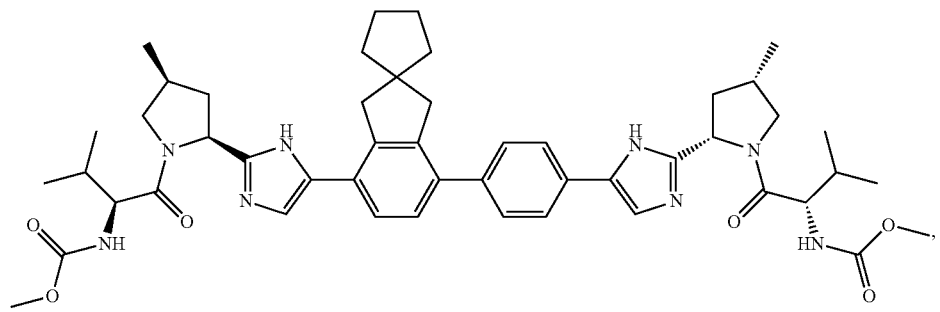
(21)
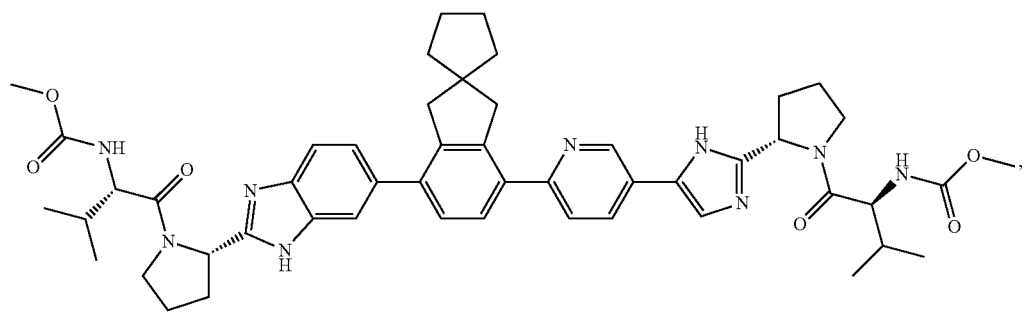
(22)
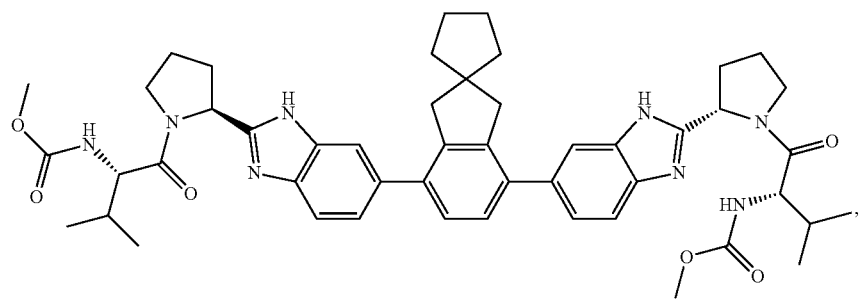
(23)
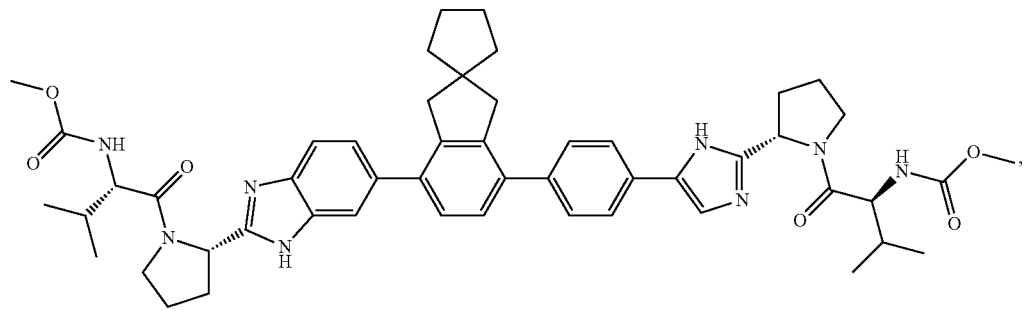

(24)
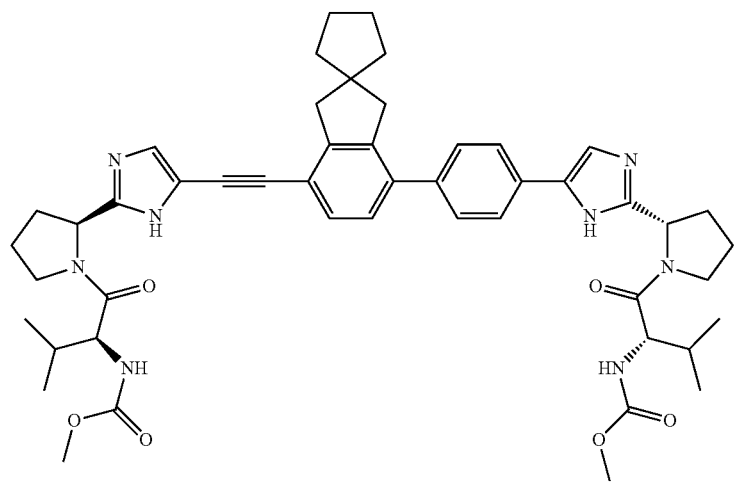
(25)
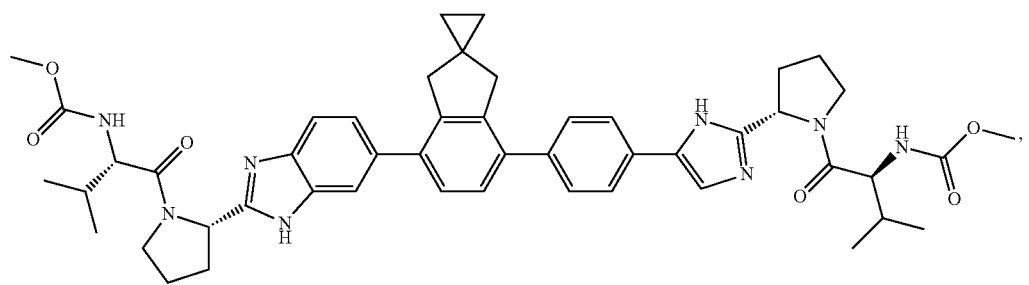
(26)
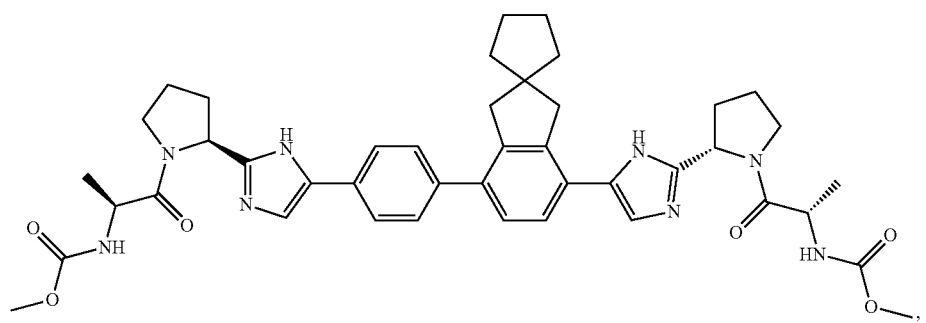
(27)
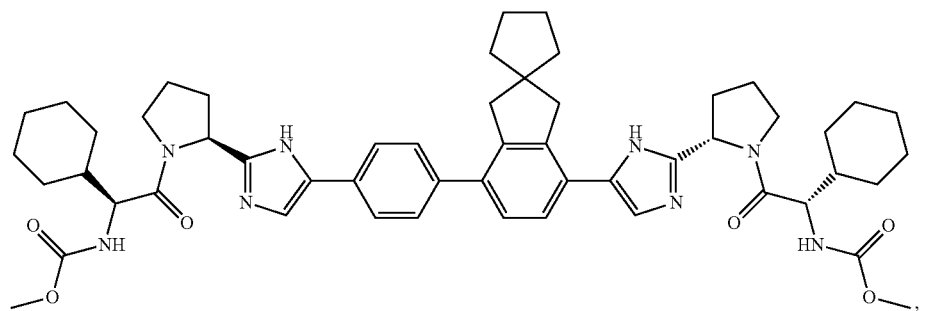

-continued
(28)
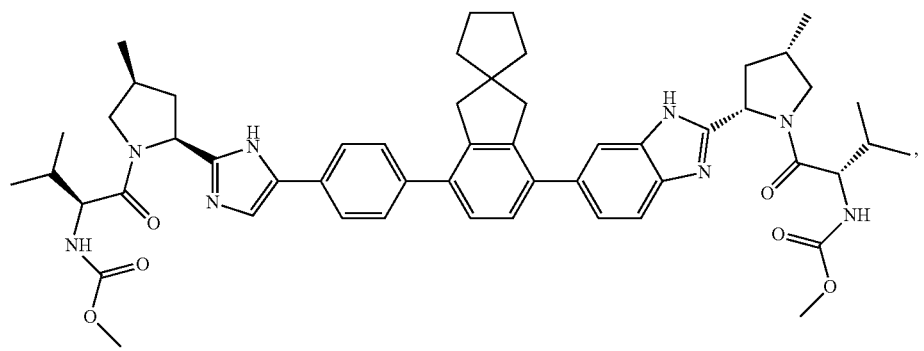
(29)
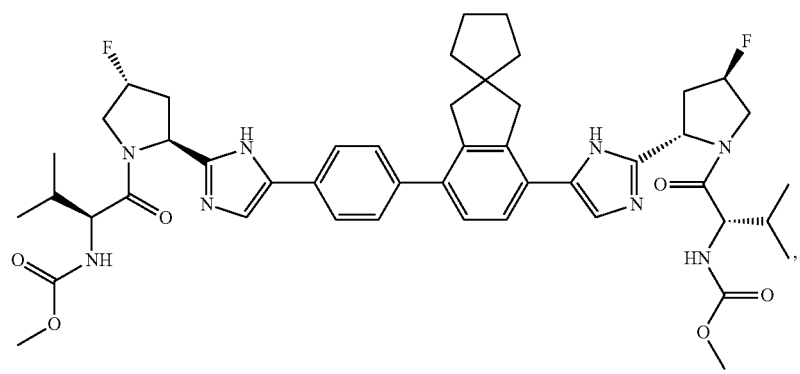
(30)
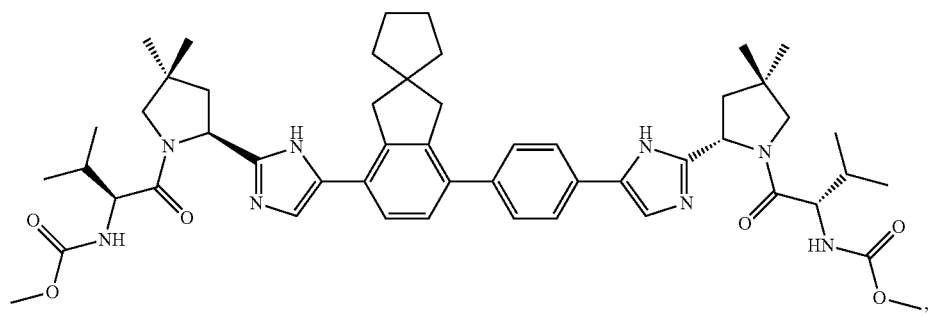
(31)
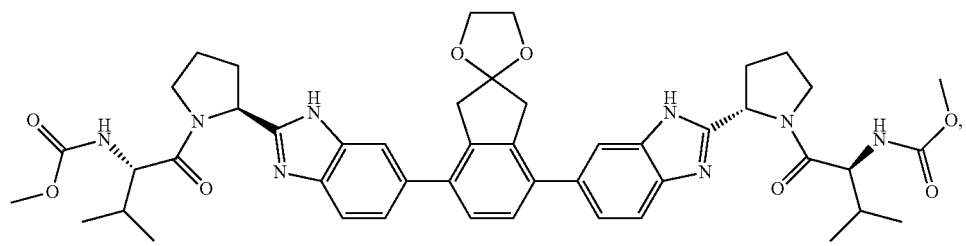
(32)
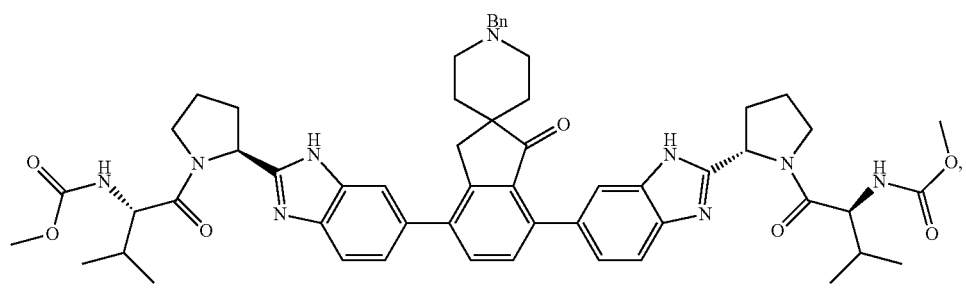

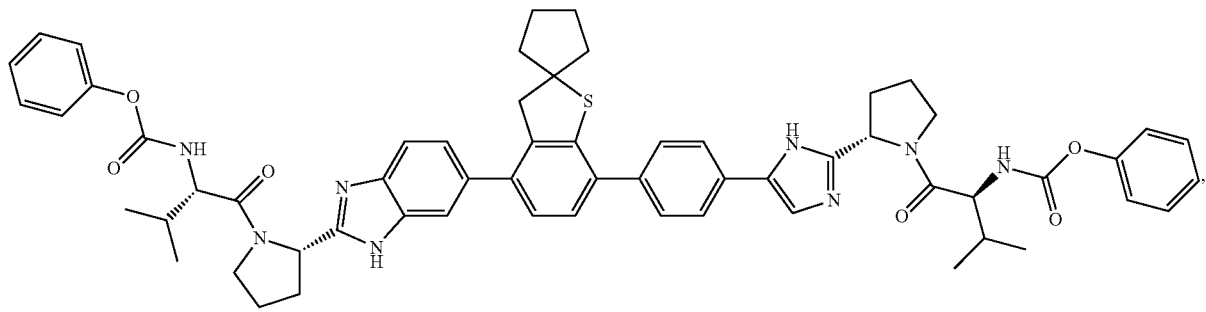
(33)
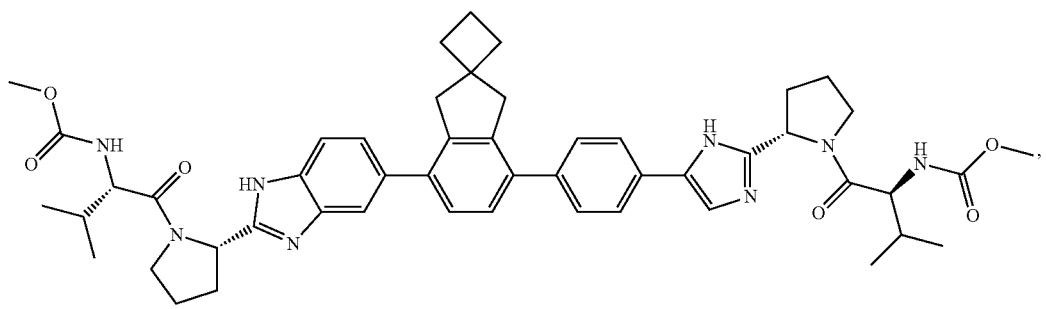
(34)
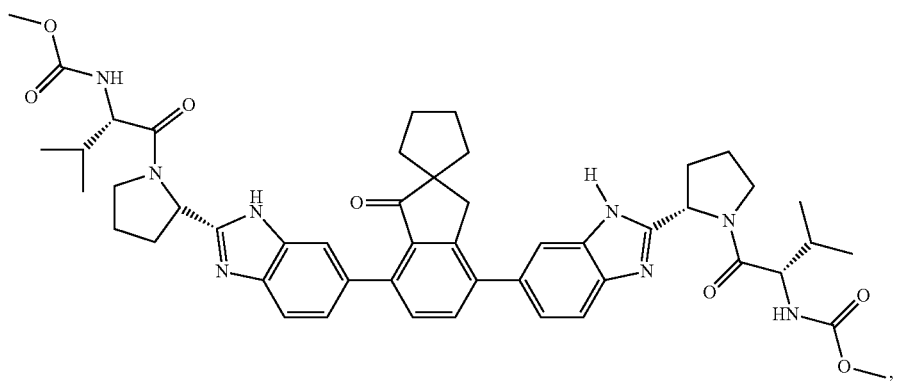
(35)
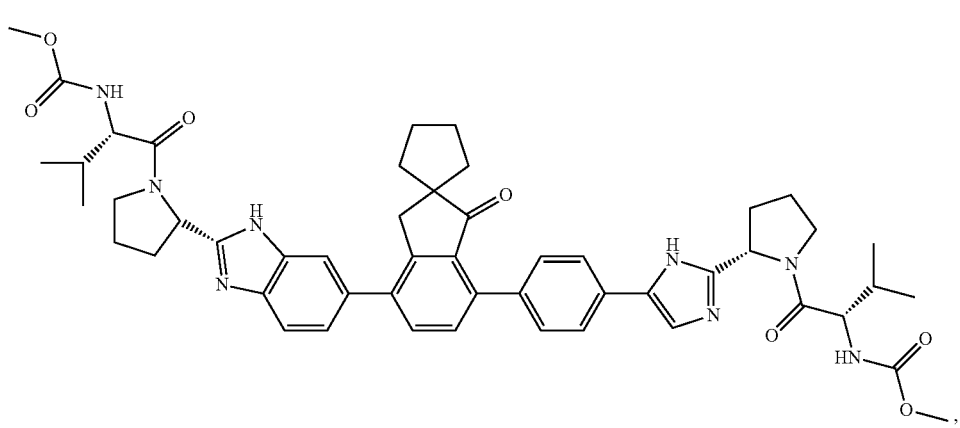
(36)

-continued
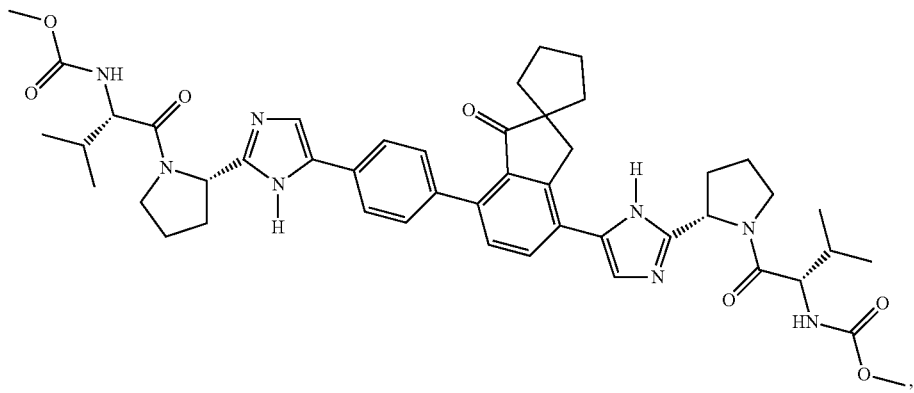
(37)
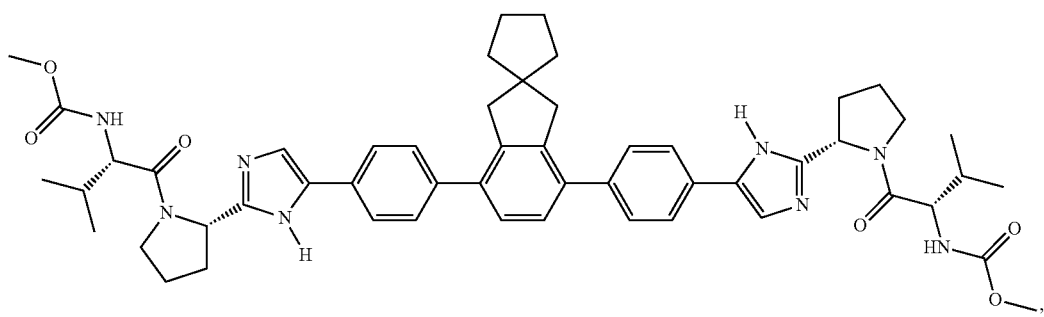
(38)
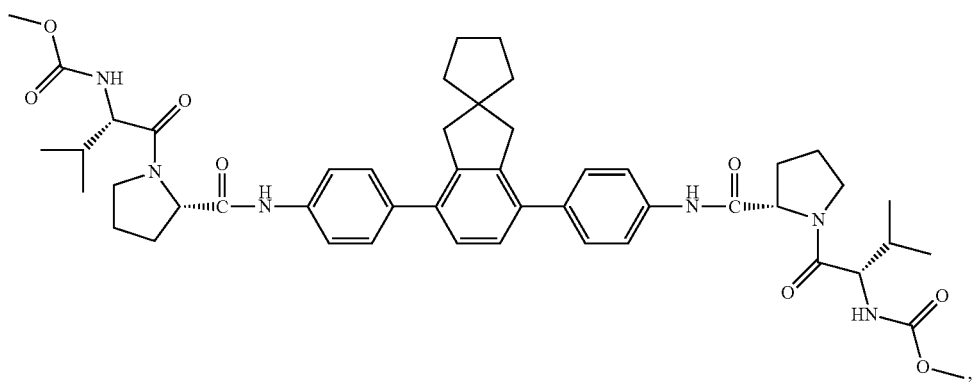
(39)
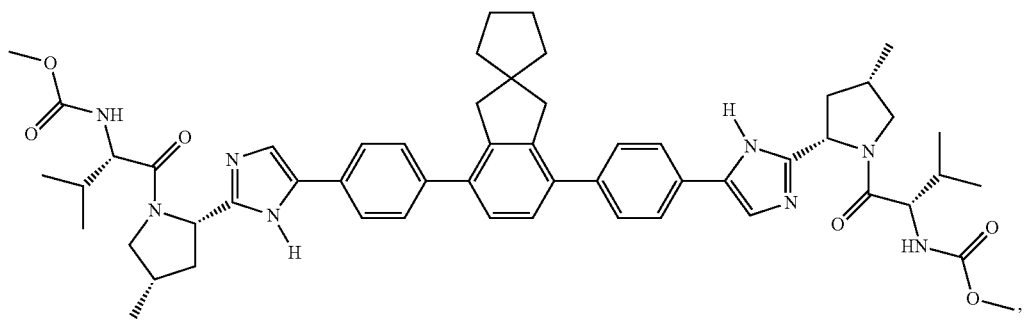
(40)

(41)
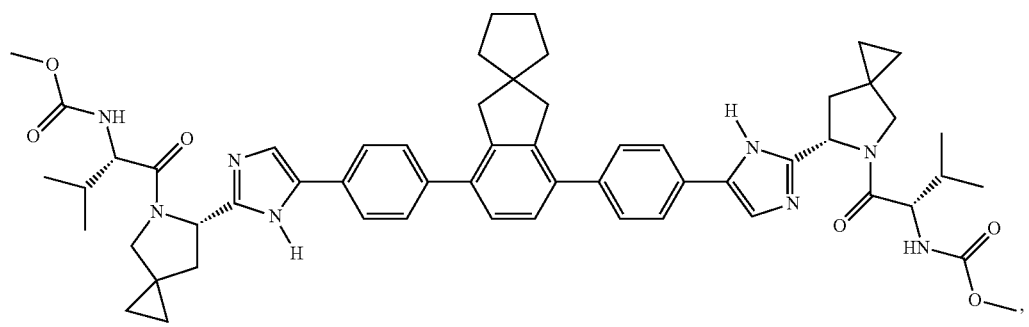
(42)
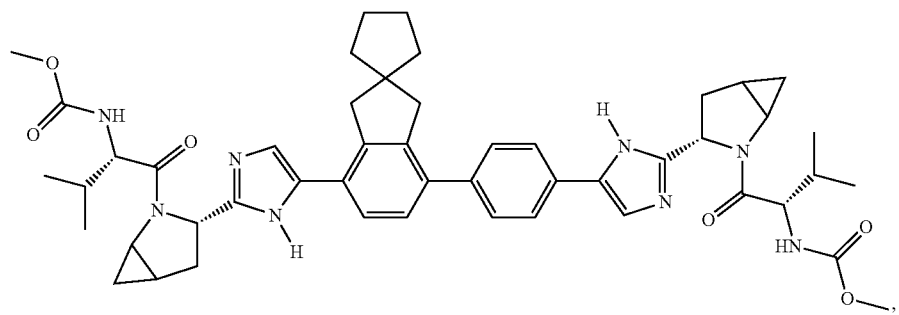
(43)
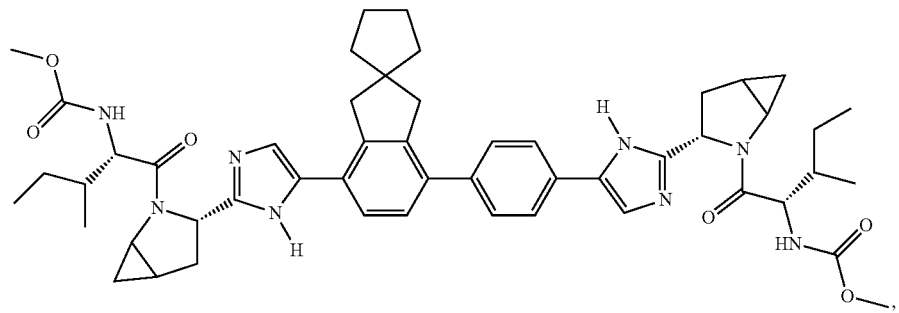
(44)
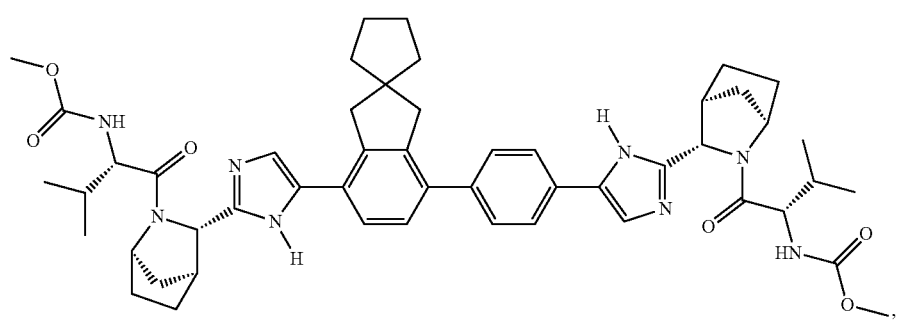
(45)
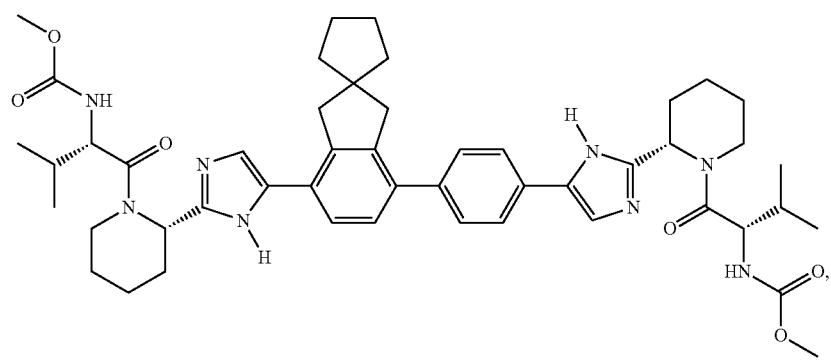

-continued
(46)
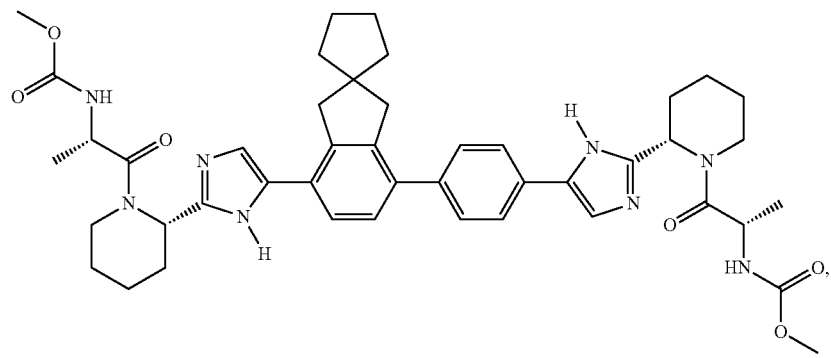
(47)
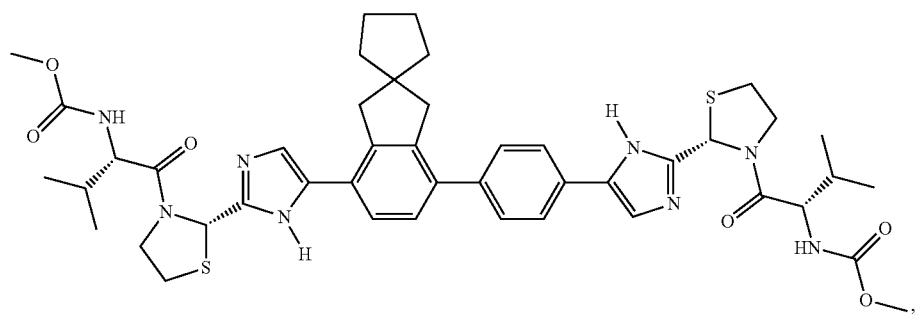
(48)
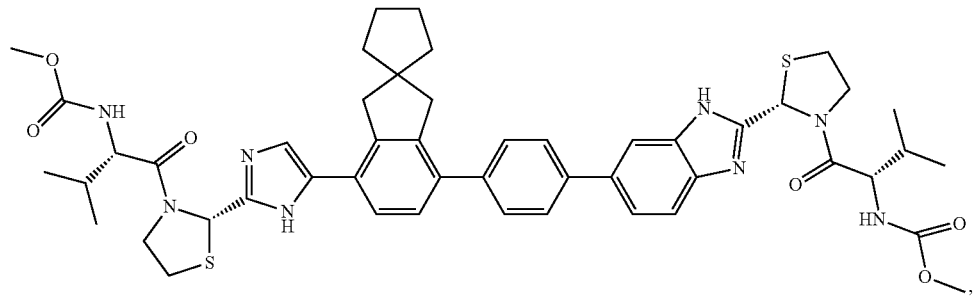
(49)
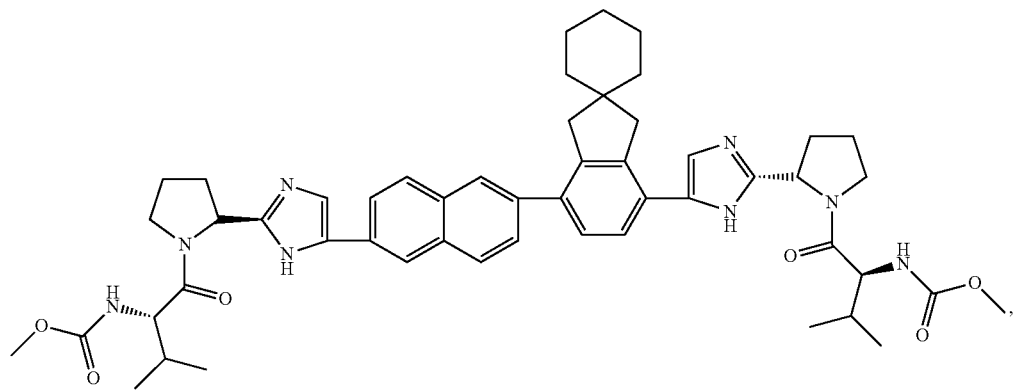

-continued
(50)
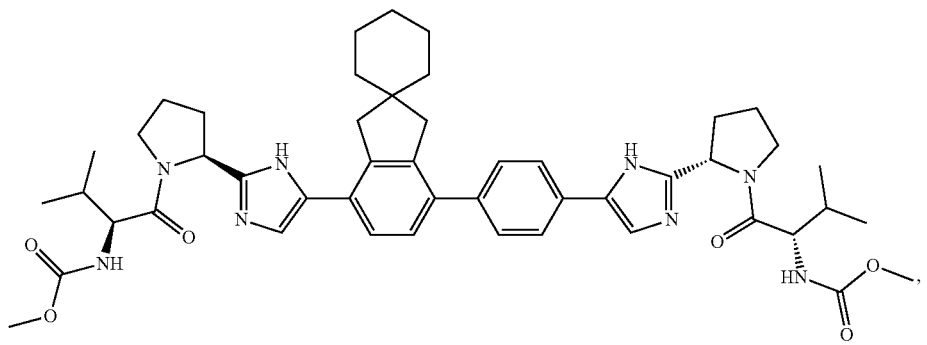
(51)
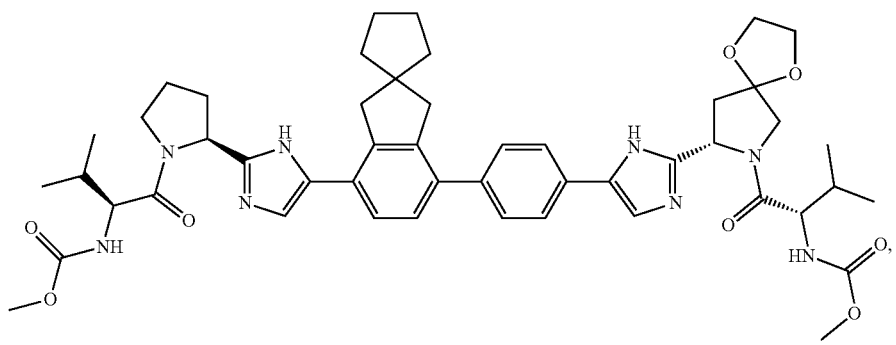
(52)
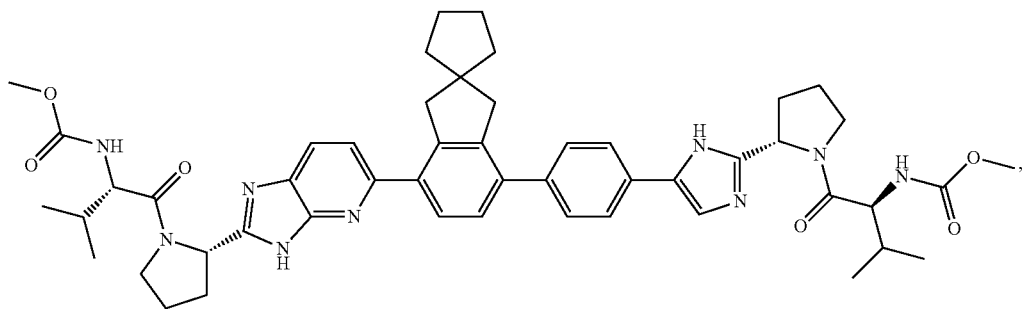
(53)
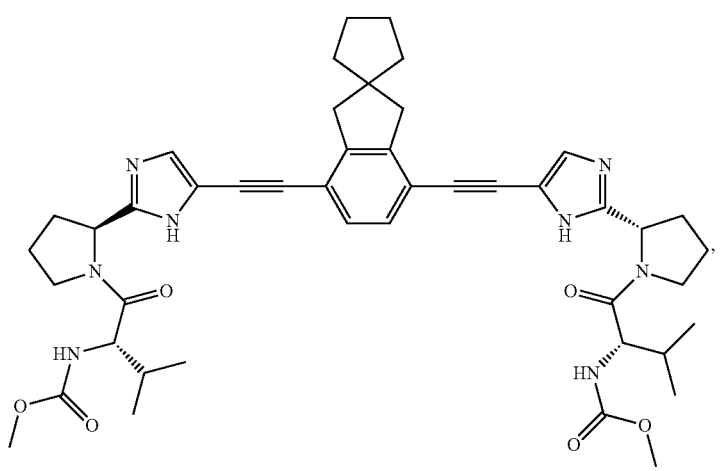

(54)

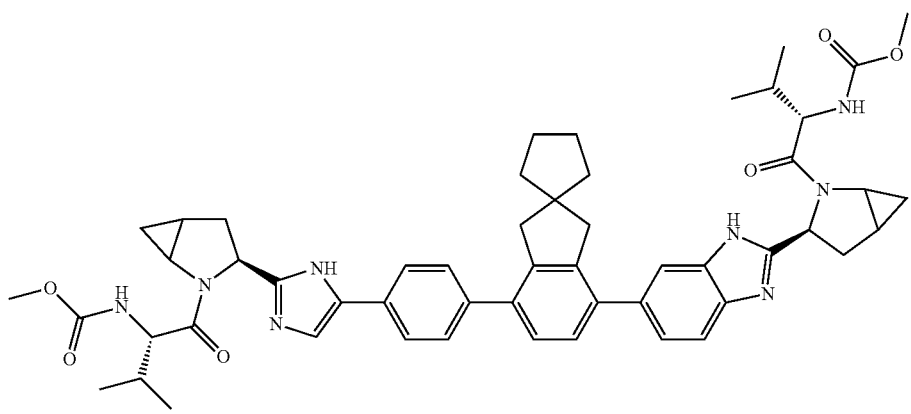

(55)

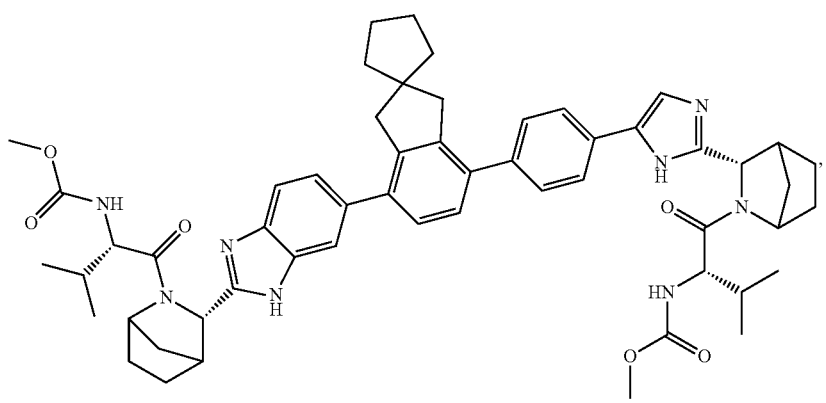

(56)

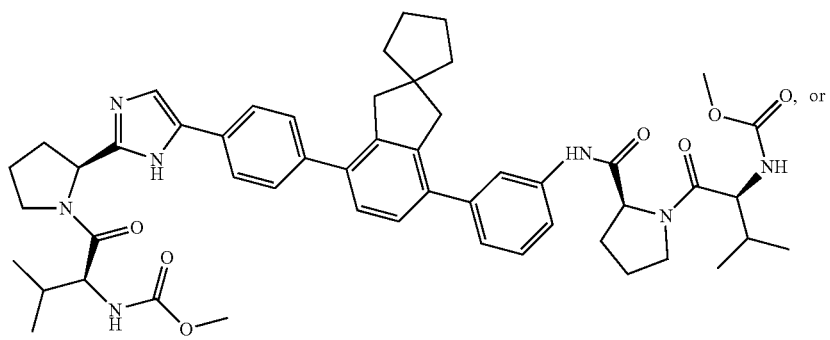

or (57)

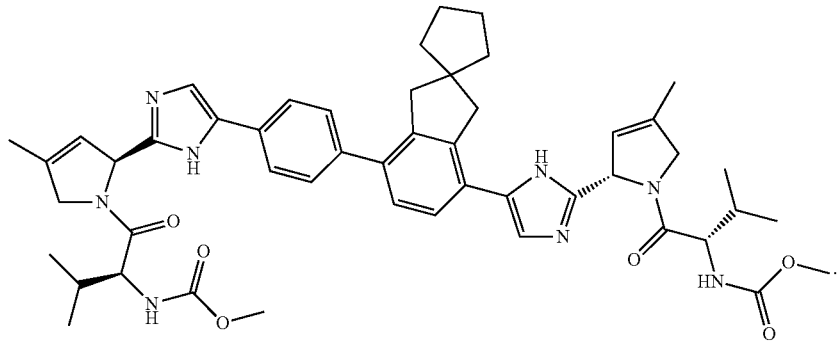

Provided herein includes the use of a compound disclosed herein, or a pharmaceutically acceptable salt thereof, in the manufacture of a medicament for the treatment either acutely or chronically of HCV infection in a patient, including those described herein. Provided herein is use of the compound in the manufacture of an anti-HCV medicament. Provided herein is the use of the compound disclosed herein, in the manufacture of a medicament to attenuate, prevent, manage or treat HCV-mediated disease, especially HCV's NS5A protein. Also provided herein is a pharmaceutical composition comprising a therapeutically effective amount of a compound of formula (I) in association with at least one pharmaceutically acceptable carrier, adjuvant or diluent.

Unless otherwise stated, all stereoisomers, geometric isomers, tautomers, nitrogen oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a Formulation, and/or the mammal being treated therewith.

The compounds disclosed herein also include salts of such compounds which are not necessarily pharmaceutically acceptable salts, and which may be useful as intermediates for preparing and/or purifying compounds of formula (I) and/or for separating enantiomers of compounds of formula (I).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

When it is possible that, for use in therapy, therapeutically effective amounts of a compound of formula (I), as well as pharmaceutically acceptable salts thereof, may be administered as the raw chemical, it is possible to present the active ingredient as a pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount" refers to the total amount of each active component that is sufficient to show a meaningful patient benefit (e.g., a reduction in viral load). When applied to individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluents(s), or excipient(s) must be acceptable in the sense of being compatible with the other ingredients of the formulation and not deleterious to recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable" refers to those compounds, materials, composition, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 to 80% of the dosage normally administered in a monotherapy regimen. Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection is preferred.

Pharmaceutical formulations adapted for oral administration may be presented as discrete units such as capsules or tablets; powders or granules; solution or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose, β-lactose, corn sweetener, natural gum and synthetic resin, such as Arabic gum, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or and absorption agent such as bentonite, kaolin, or dicalcium phosphate. The powder mixture can be granulated by wetting with a binder such as syrup, starch paste, acadiamucilage, or solution of cellulosic or polymeric materials and forcing through a screen. As an alternative to granulation, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additives such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating of embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and pharmaceutically acceptable salts thereof may also be delivered by the use of monoclonal antibodies as individual carrier to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, poly(ε-caprolactone), polyhydroxy butyric acid, polyorthoesters, polyacetals, polydihydropyrans, polycyanoacrylates, and cross-linked or amphipathic block copolymers of hydrogels.

Uses of the Compounds and Compositions of the Invention

According to another aspect, the invention features pharmaceutical compositions that include a compound of formula (I), a compound listed herein, and a pharmaceutically acceptable carrier, adjuvant, or vehicle.

The amount of the compound in the compositions disclosed herein is effective to detectably inhibit the function of a target to treat HCV infection, wherein the target is selected from HCV metalloproteinase, HCV serine proteinase, HCV polymerase, HCV helicase, non-structural protein NS4B, HCV entry, HCV assembly, HCV egress, non-structural protein NS5A and inosine5'-monophosphate dehydrogenase (IMPDH).

Also provided herein is a method, which comprises the compound or the pharmaceutical composition disclosed herein, further comprising administering to the patient additional anti-HCV agents (combination therapy), wherein the anti-HCV agent is interferon, ribavirin, IL-2, IL-6, IL-12, a compound that enhances the development of a type 1 helper T cell response, interfering RNA, anti-sense RNA, imiquimod, an inosine-5'-monophosphate dehydrogenase inhibitor, amantadine, rimantadine, boceprevir, telaprevir, daclatasvir, or a combination thereof and wherein the interferon is interferon α-2b, pegylated interferon α, interferon α-2a, pegylated interferon α-2a, consensus interferon-α, or interferon γ.

The treatment method that includes administering a compound or composition disclosed herein can further include administering to the patient an additional anti-HCV agent, wherein the additional anti-HCV drug is administered together with a compound or composition disclosed herein as a single dosage form or separately from the compound or composition as part of a multiple dosage form. The additional anti-HCV agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

Specific Application Methods

General Synthetic Procedures

Generally, the compounds disclosed herein may be prepared by methods described herein, wherein the substituents are as defined for formula (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Inc., Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were determined on an Agilent 6320 Series LC-MS spectrometer equipped with G1312A binary pumps and a G1316A TCC (Temperature Control of Column, maintained at 30° C.). A G1329A autosampler and G1315B DAD detector were used in the analysis. An ESI source was used on the LC-MS spectrometer.

Low-resolution mass spectral (MS) data were determined on an Agilent 6120 Series LC-MS spectrometer equipped with G1311A Quaternary pump and a G1316A TCC (Temperature Control of Column, maintained at 30° C.). A G1329A autosampler and a G1315D DAD detector were used in the analysis. An ESI source was used on the LC-MS spectrometer.

Both LC-MS spectrometers were equipped with an Agilent Zorbax SB-C18 column (2.1×30 mm, 5 micron). Injection volume was decided by the sample concentration. The flow rate is 0.6 mL/min. The HPLC peaks were recorded by UV-Vis wavelength at 210 nm and 254 nm. The mobile phase was 0.1% formic acid in $CH_3CN$ (phase A) and 0.1% formic acid in ultrapure water (phase B). The gradient condition is shown in Table 1:

TABLE 1

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were also assessed by Agilent 1100 Series high performance liquid chromatography (HPLC) with UV detection at 210 nm and 254 nm (Zorbax SB-C18, 2.1×30 mm, 4 micron, 10 minutes, 0.6 mL/min flow rate, 5 to 95% (0.1% formic acid in $CH_3CN$) in (0.1% formic acid in $H_2O$)). Column was operated at 40° C.

The following abbreviations are used throughout the specification:
HOAc acetic acid
MeCN, $CH_3CN$ acetonitrile
$NH_3$ ammonia
$NH_4Cl$ ammonium chloride
$BBr_3$ boron tribromide
BSA bovine serum albumin
$Br_2$ bromine
BOC, Boc tert-butyloxycarbonyl
$Cs_2CO_3$ cesium carbonate
$CHCl_3$ chloroform
$CDCl_3$ chloroform deuterated
Cu copper
CuI copper (I) iodide
$Et_2O$ diethyl ether
DMF dimethylformamide
DMAP 4-dimethylaminopyridine
DMSO dimethylsulfoxide
EDC, EDCI 1-(3-dimethylaminopropyl)-3-ethylcarbodiimide hydrochloride
Dppa diphenylphosphoryl azide
EtOAc ethyl acetate
EA ethyl acetate
HBr hydrobromic acid HCl hydrochloric acid
HOAt, HOAT 1-hydroxy-7-azabenzotriazole
HOBT 1-hydroxybenzotriazole hydrate
$H_2$ hydrogen
$H_2O_2$ hydrogen peroxide
Fe iron
LDA lithium diisopropylamide
MCPBA meta-chloroperbenzoic acid
$MgSO_4$ magnesium sulfate
MeOH, $CH_3OH$ methanol
MeI methyl iodide
$CH_2Cl_2$, DCM methylene chloride
NMP N-methylpyrrolidinone
mL, m milliliter
$N_2$ nitrogen
Pd/C palladium on carbon
PE petroleum ether (60-90° C.)
PBS phosphate buffered saline
$POCl_3$ phosphorous oxychloride
$Pd(PPh_3)_4$ palladium tetrakis triphenylphosphine
$Pd(dppf)Cl_2$ 1,1-bis(diphenylphosphino)ferrocene palladium chloride
$K_2CO_3$ potassium carbonate
KOH potassium hydroxide
RT, rt room temperature
Rt retention time
$NaHCO_3$ sodium bicarbonate
$NaBH_4$ sodium borohydride
$NaBH_3CN$ sodium cyanoborohydride
NaOtBu sodium tert-butoxide
NaOH sodium hydroxide
$NaClO_2$ sodium chlorite
NaCl sodium chloride
$NaH_2PO_4$ sodium dihydric phosphate
NaH sodium hydride
NaI sodium iodide
$Na_2SO_4$ sodium sulfate
TBTU O-benzotriazol-1-yl-N,N,N',N'-tetramethyluronium tetrafluoroborate
THF tetrahydrofuran
$Et_3N$, TEA triethylamine
TFA trifluoroacetic acid
$P(t-bu)_3$ tri(tert-butyl)phosphine
NBS N-bromosuccinimide
TBAI tetrabutylammonium iodide
$H_2O$ water
TEAF formic acid triethylamine complex 5:2
PPA polyphosphoric acid
$Tf_2O$ Trifluoromethanesulfonic anhydride
HCl.EA a solution of HCl in ethyl acetate
DIPEA N,N-diisopropylethylamine
DME 1,2-dimethoxyethane
HATU 2-(7-aza-1H-benzotriazole-1-yl)-1,1,3,3-tetramethyluronium hexafluorophosphate NIS N-iodosuccinimide
TFAA trifluoroaceticanhydride
SEMCl 2-(Trimethylsilyl)ethoxymethyl chloride
Dess-Martin (1,1,1-triacetoxy)-1,1-dihydro-1,2-benziodoxol-3(1H)-one
TsOH p-toluenesulfonic acid
TMSA Trimethyl silyl acetylene
Meldrum's acid 2,2-Dimethyl-1,3-dioxane-4,6-dione
BAST bis(2-methoxyethyl)aminosulphur trifluoride (DEOXO-FLUOR® Reagent)
$SbCl_3$ antimony trichloride
$SmCl_3$ samarium chloride
LiHMDS lithium hexamethyldisilazide
TMSCl trimethyl chlorosilane
$PhNTf_2$ N,N-bis(trifluoromethylsulfonyl)aniline
TBDMSOTf trifluoromethanesulfonic acid tert-butyldimethylsilyl ester
$Et_2NSF_3$ diethylaminosulfur trifluoride
MTBE methyl tert-butyl ether
$LiN(SiMe_3)_2$ lithium bis(trimethylsilyl)amide
$PPh_3MeBr$ Methyltriphenylphosphonium bromide
Lawesson's Reagent 2,4-bis(4-methoxyphenyl)-1,3-dithia-2,4-diphosphetane-2,4-disulfide
MTBE methyl tert-butyl ether

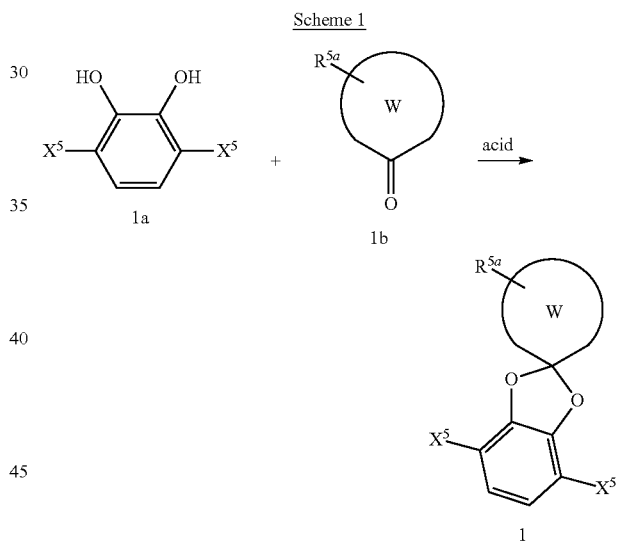

Scheme 1

Compound 1 can be prepared by a general synthetic procedure illustrated in Scheme 1, wherein each of $R^{5a}$ and W is as defined herein, and $X^5$ is a leaving group such as F, Cl, Br or I. Ketone compound 1b can react with catechol derivative 1a in the presence of an acid to afford compound 1.

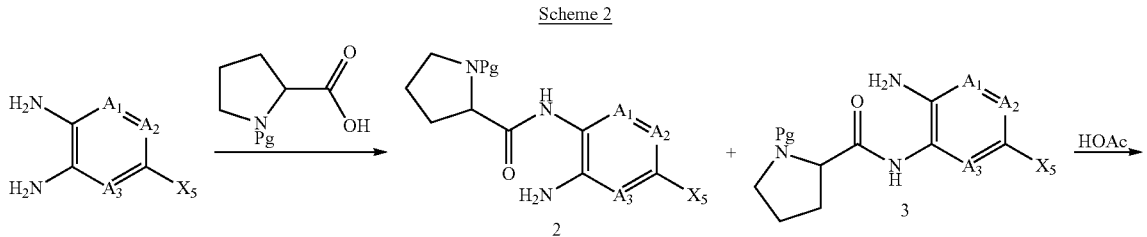

Scheme 2

-continued

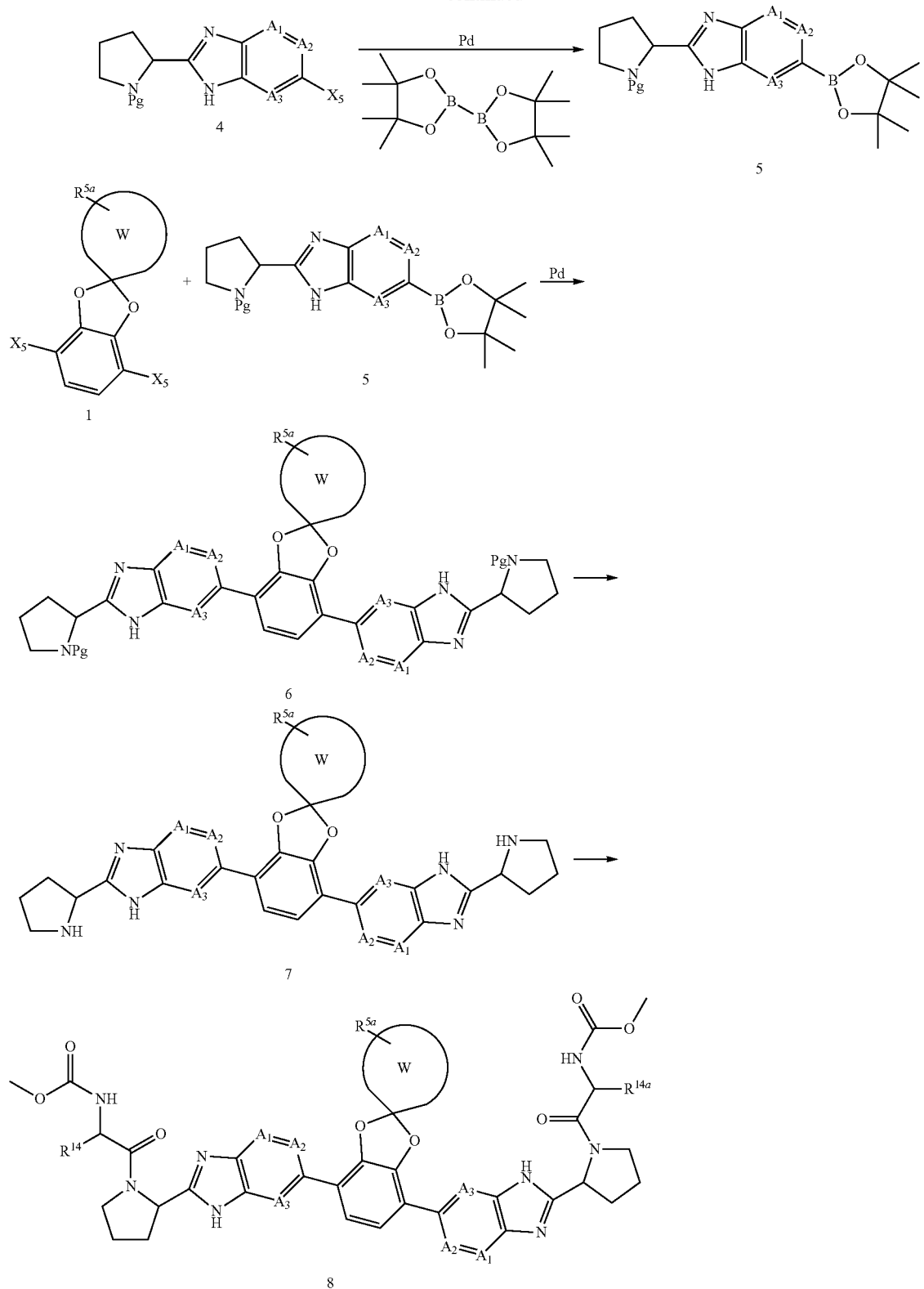

Compound 8 can be prepared by a general synthetic procedure illustrated in Scheme 2, wherein each of $A_1$, $A_2$ and $A_3$ is independently N or $CR^7$, each of $R^{5a}$, $R^7$, $R^{14}$ and $X_5$ is as defined herein, and Pg is an amino-protecting group, such as Boc, Fmoc or CBZ. Condensation of aromatic diamine with protected proline can give a mixture of compound 2 and compound 3. Then compound 2 and compound 3 can be cyclized at elevated temperature in acetic acid system to give compound 4. Compound 4 can further react with bis(pinacolato)diboron in the presence of a Pd catalyst to afford compound 5. Coupling reaction of compound 5 with compound 1 in the presence of a Pd catalyst can give compound 6. The protecting group Pg in compound 6 can be removed to provide compound 7, which in turn can be condensed with amino acid to give compound 8.
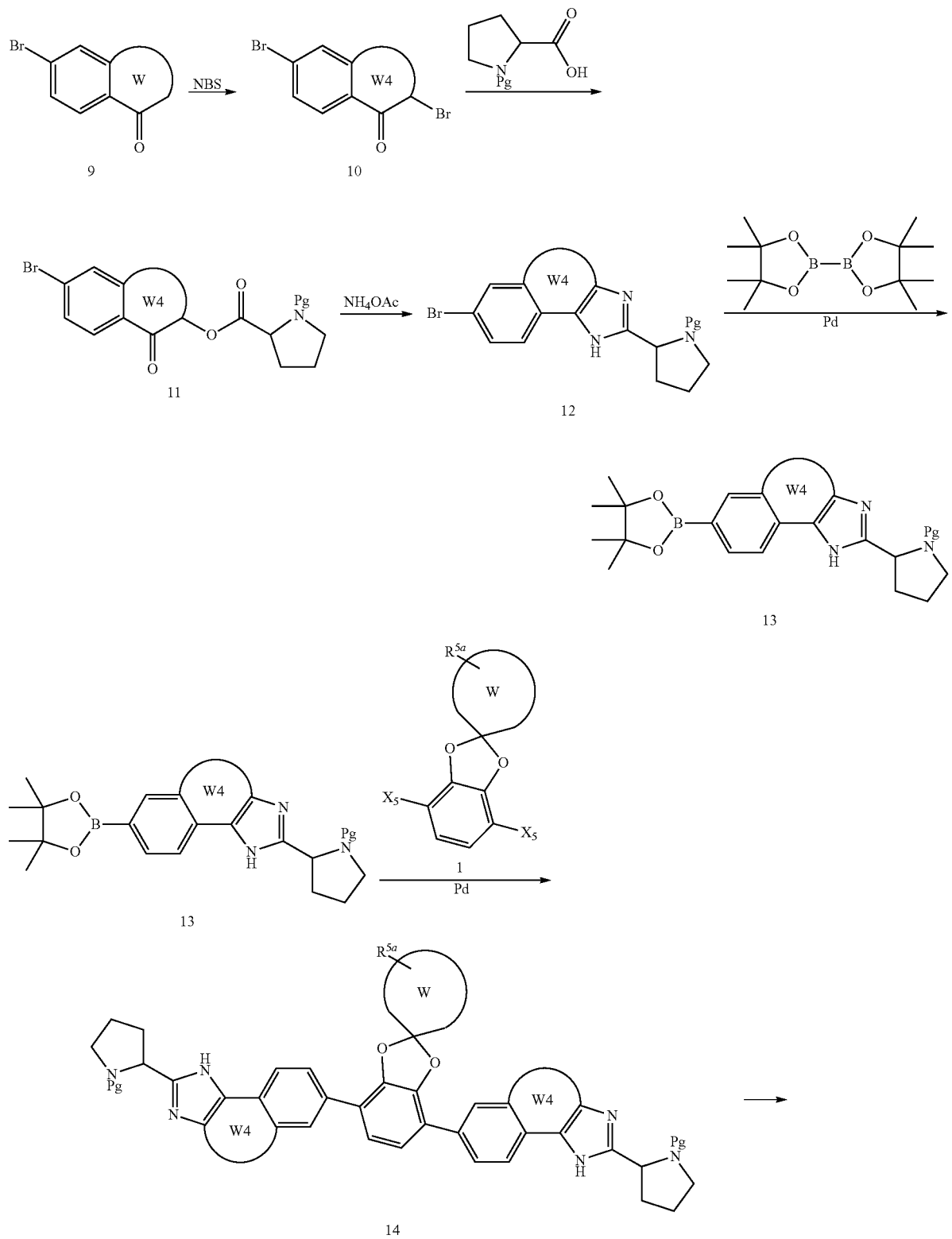
Scheme 3

-continued

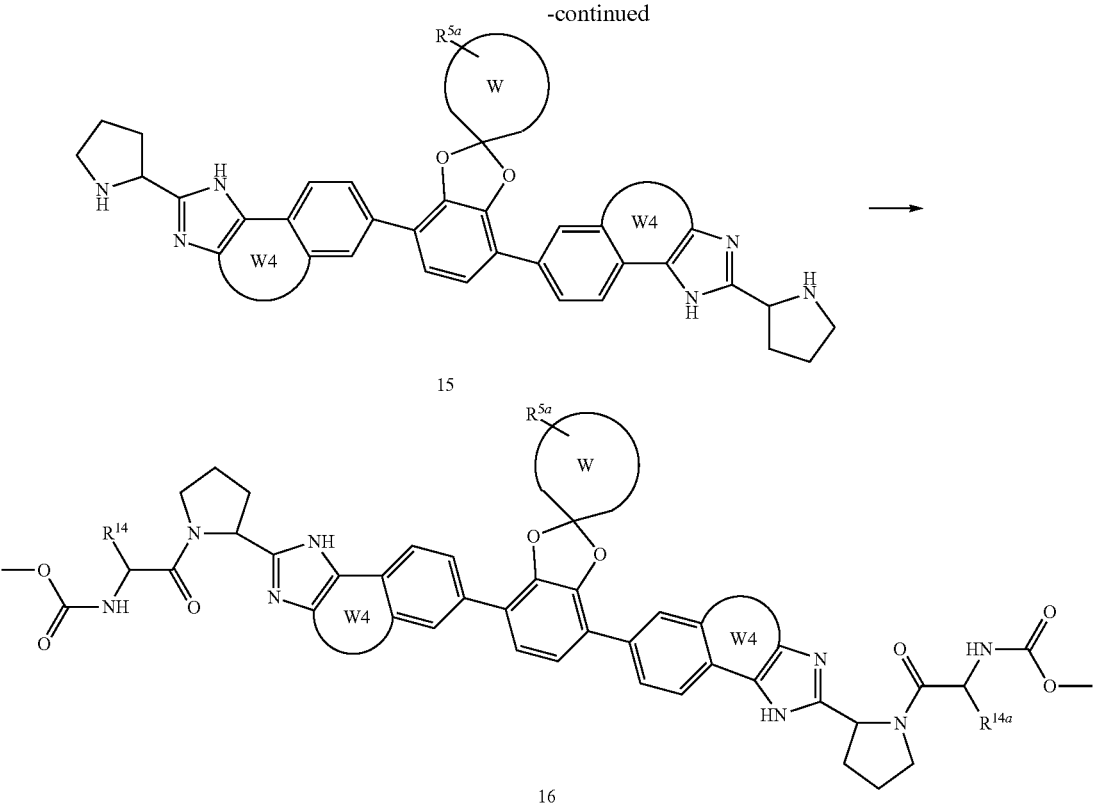

Compound 16 can be prepared by a general synthetic procedure illustrated in Scheme 3, wherein W4 is cycloalkyl or heterocyclyl, each of $R^{5a}$, $R^{14}$, $R^{14a}$ and $X_5$ is as defined herein, and Pg is an amino-protecting group, such as Boc, Fmoc or CBZ. Compound 9 can react with NBS to give compound 10. Compound 10 can further react with protected proline to afford compound 11. Cyclization of compound 11 with ammonium acetate under heating conditions can give compound 12. Then compound 12 can react with bis(pinacolato)diboron in the presence of a Pd catalyst to afford compound 13. Coupling reaction of compound 13 with compound 1 in the presence of a Pd catalyst can give compound 14. The protecting group Pg in compound 14 can be removed to provide compound 15, which in turn can be condensed with amino acid to give compound 16.

Scheme 4

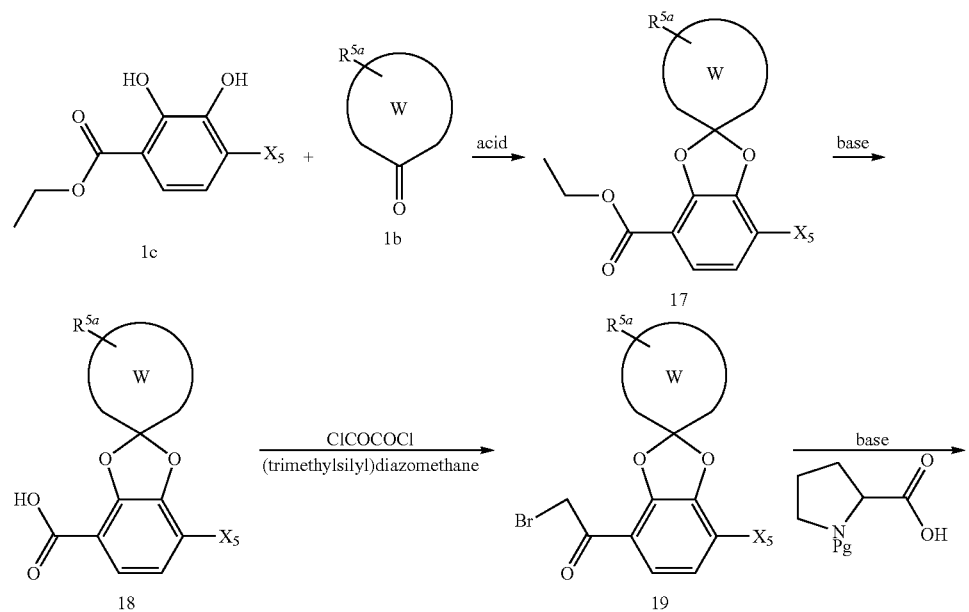

-continued
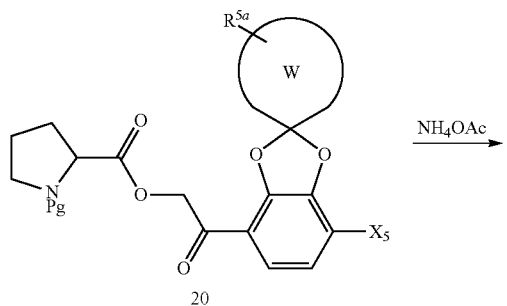
20
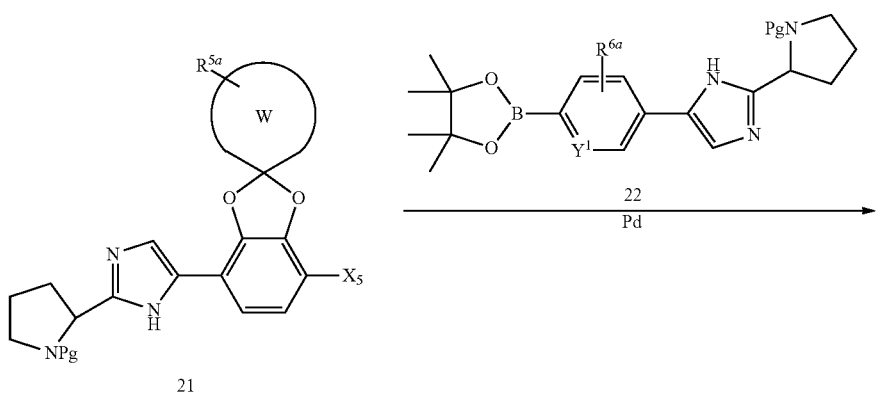
21  22
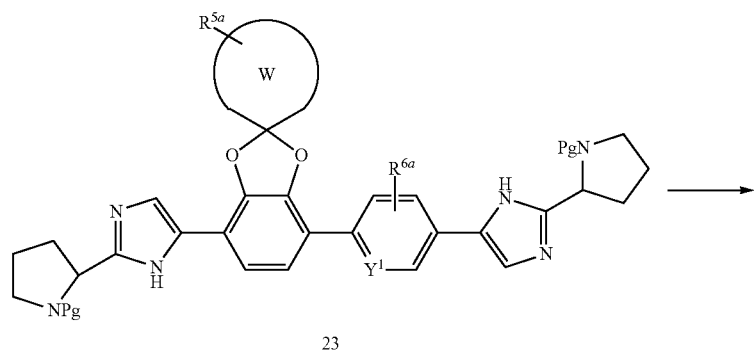
23
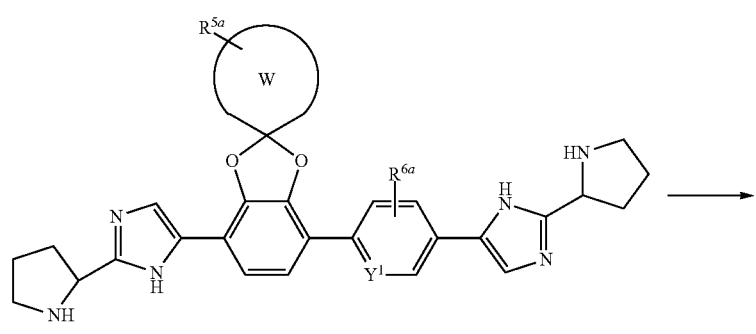
24

-continued

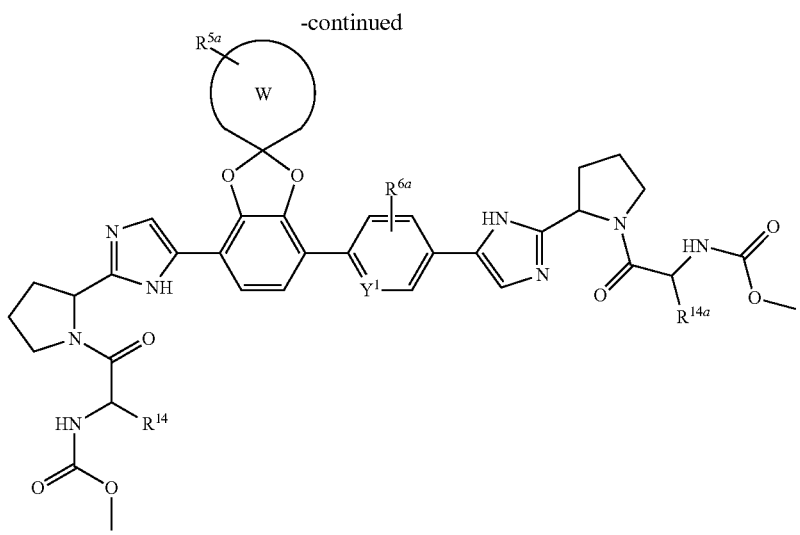

25

Compound 25 can be prepared by a general synthetic procedure illustrated in Scheme 4, wherein each of $R^{5a}$, $R^{6a}$, $X_5$, $Y^1$, W and Pg is as defined herein. Condensation of catechol derivative 1c with ketone 1b in the presence of an acid can give compound 17. Then compound 17 can be converted to compound 18 by hydrolysis under basic condition. Compound 18 can be converted to compound 19 by diazotization and bromination. Compound 19 can react with protected proline to afford compound 20. Cyclization of compound 20 with ammonium acetate under heating conditions can give compound 21. Coupling reaction of compound 21 with compound 22 in the presence of a Pd catalyst can give compound 23. The protecting group Pg in compound 23 can be removed to provide compound 24, which in turn can be condensed with amino acid to give compound 25.

Scheme 5

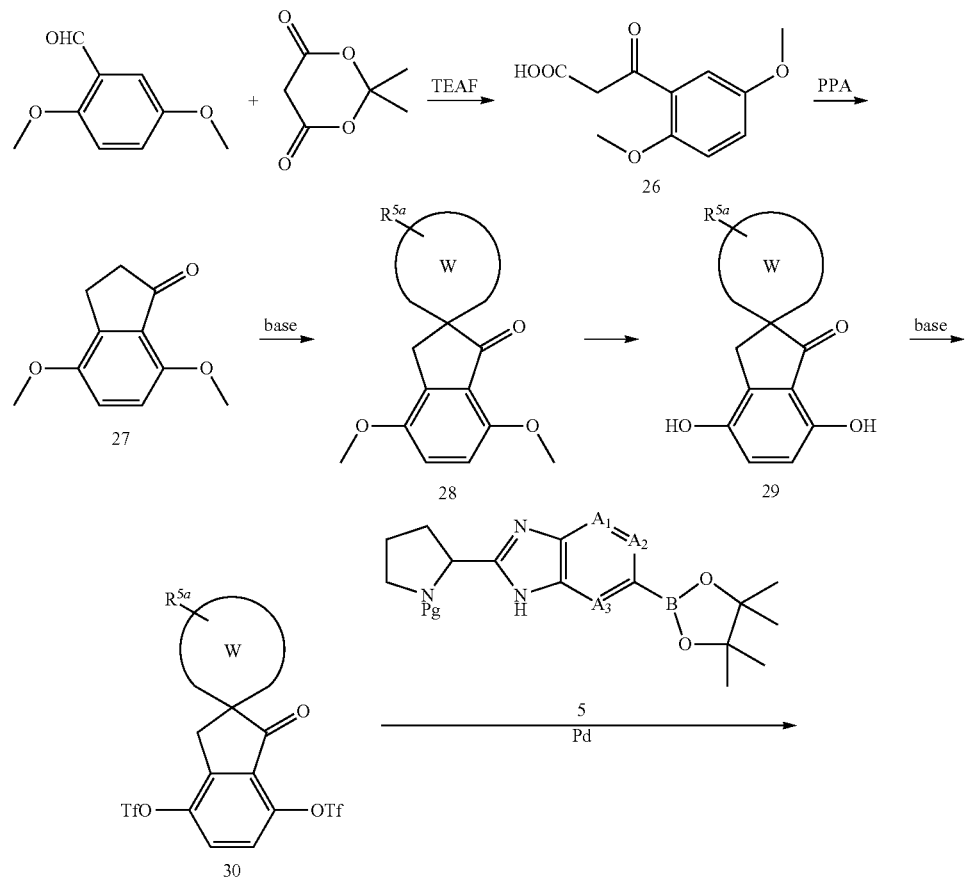

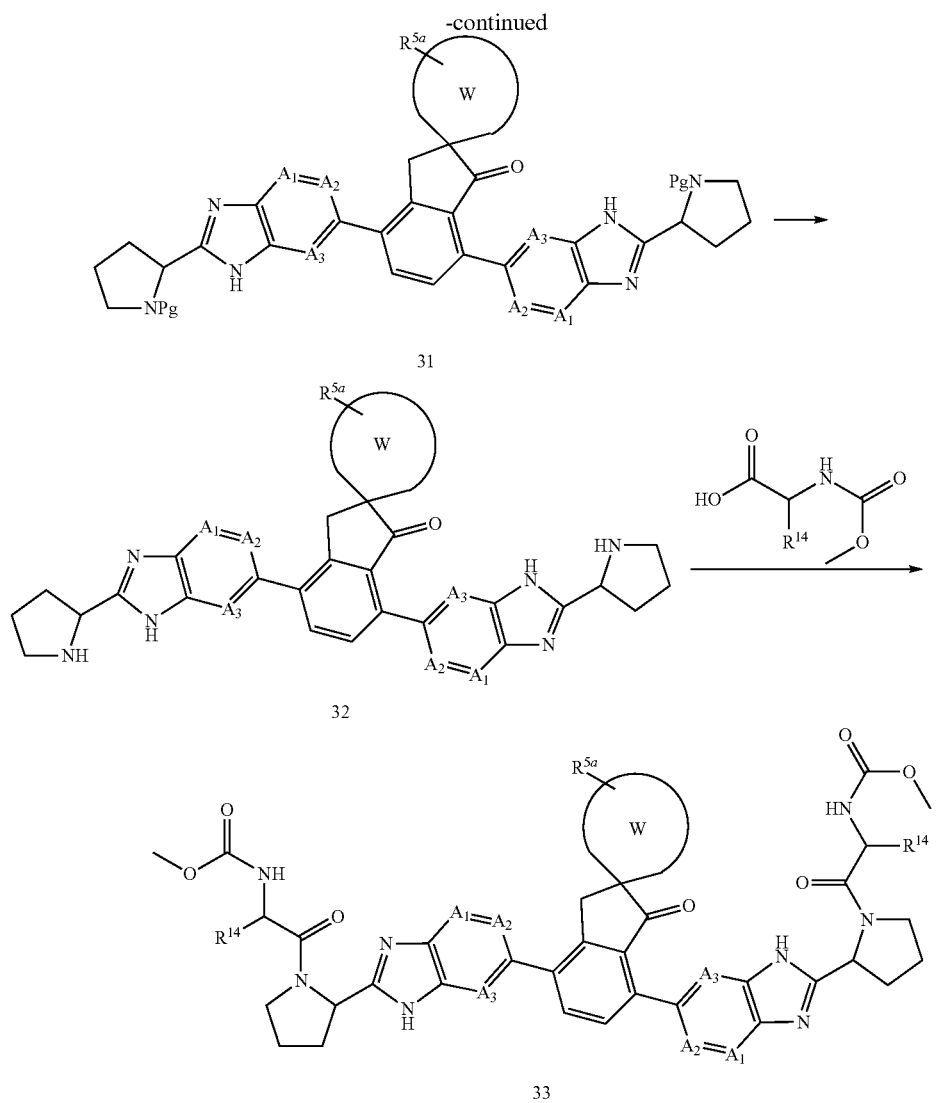

Compound 33 can be prepared by a general synthetic procedure illustrated in Scheme 5, wherein each of $A_1$, $A_2$, $A_3$, $R^{5a}$ and $R^{14}$ is as defined herein. Benzaldehyde can react with Meldrum's acid in the presence of TEAF to afford compound 26. Compound 26 can be converted to compound 27 in PPA under heating conditions by cyclization, and compound 27 can further be converted to compound 28 in alkali conditions by cyclization. The methyl in compound 28 can be removed to give compound 29. Compound 29 can react with trifluoromethanesulfonic anhydride in alkali conditions to afford compound 30. Coupling reaction of compound 30 with compound 5 in the presence of a Pd catalyst can give compound 31. The protecting group Pg in compound 31 can be removed to provide compound 32, which in turn can be condensed with amino acid to give compound 33.

Scheme 6

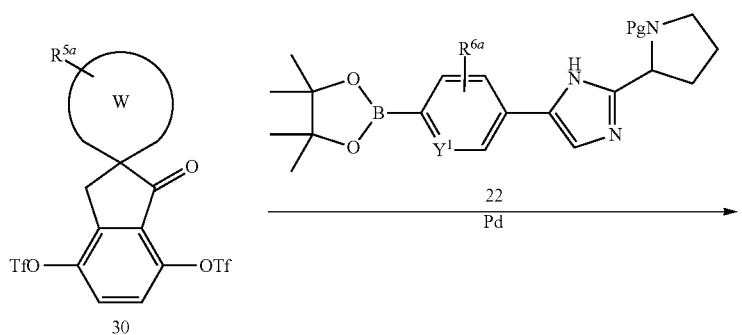

-continued

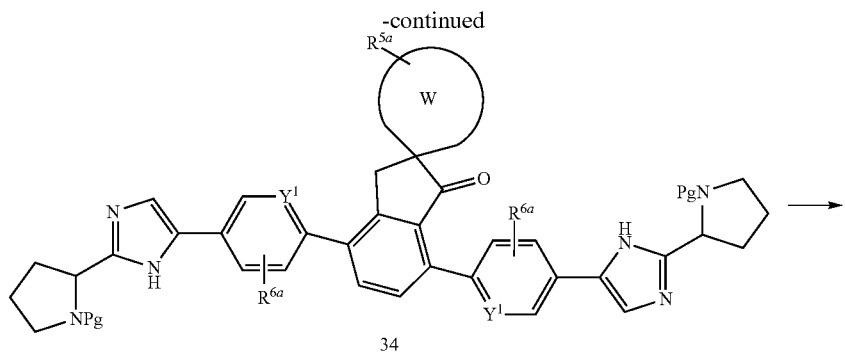

34

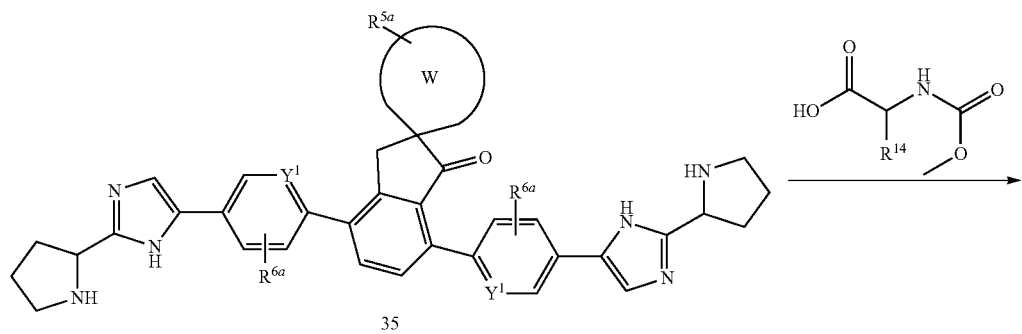

35

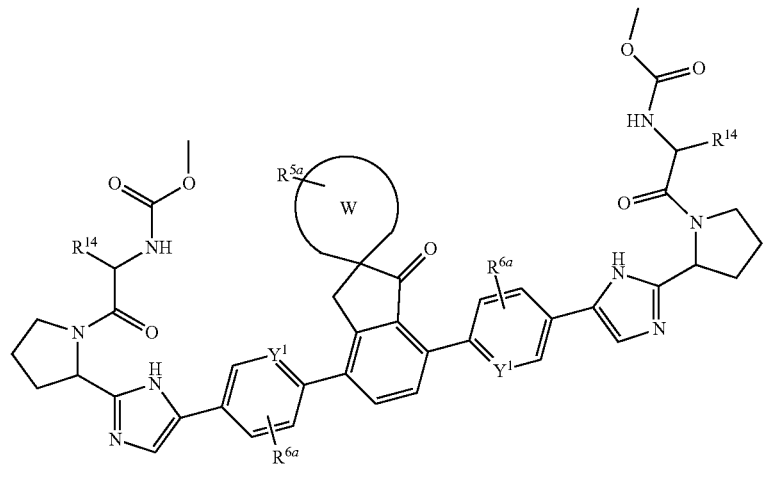

36

Compound 36 can be prepared by a general synthetic procedure illustrated in Scheme 6, wherein each of $R^{5a}$, $R^{6a}$, $Y^1$, W, $R^{14}$ and Pg is as defined herein. Coupling reaction of compound 30 with compound 22 in the presence of a Pd catalyst can give compound 34. The protecting group Pg in compound 34 can be removed to provide compound 35, which in turn can be condensed with amino acid to give compound 36.

Scheme 7

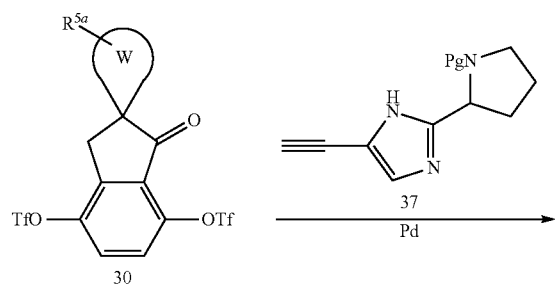

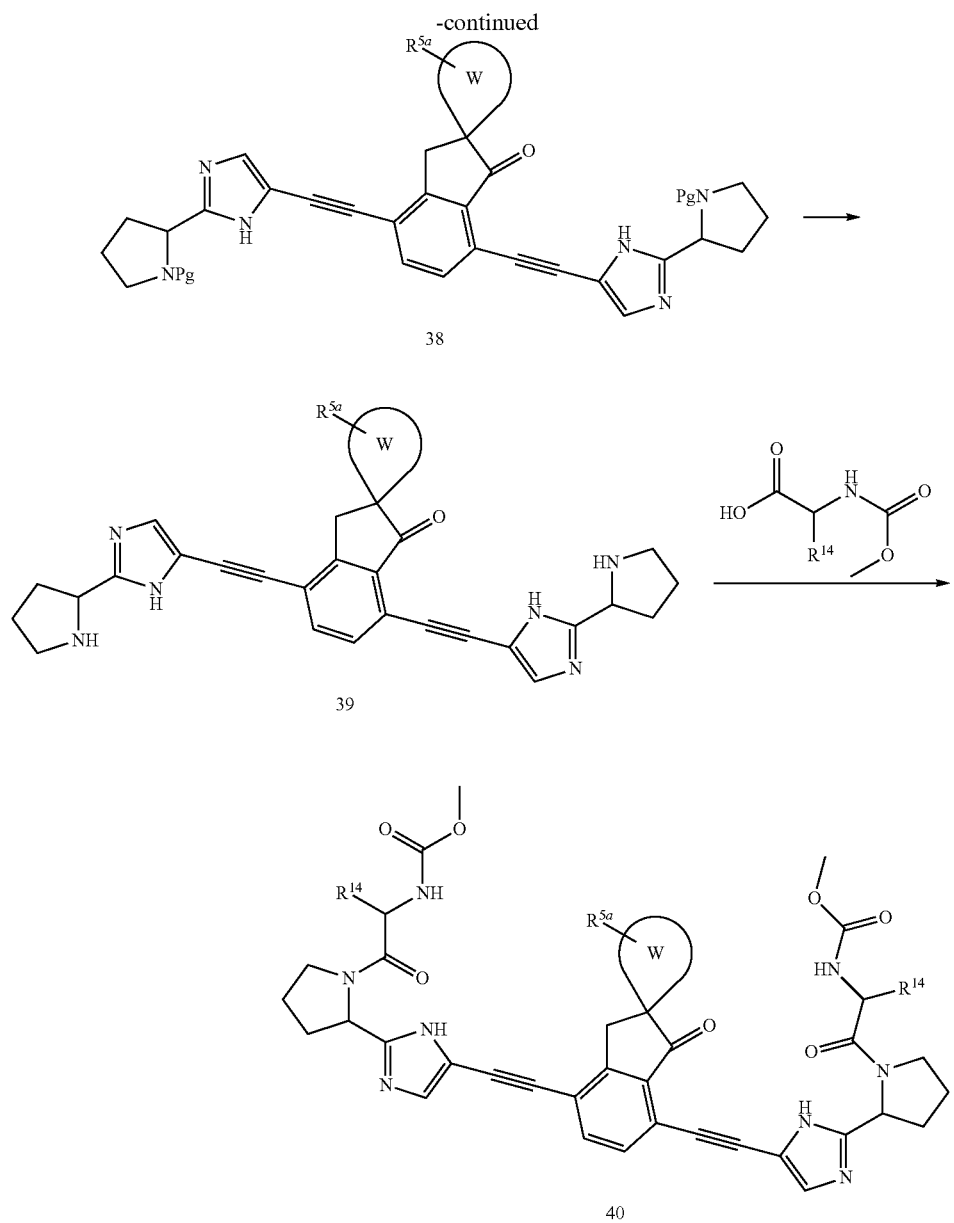

Compound 40 can be prepared by a general synthetic procedure illustrated in Scheme 7, wherein each of $R^{5a}$, W, $R^{14}$ and Pg is as defined herein. Coupling reaction of compound 30 with compound 37 in the presence of a Pd catalyst can give compound 38. The protecting group Pg in compound 38 can be removed to provide compound 39, which in turn can be condensed with amino acid to give compound 40.

Scheme 8

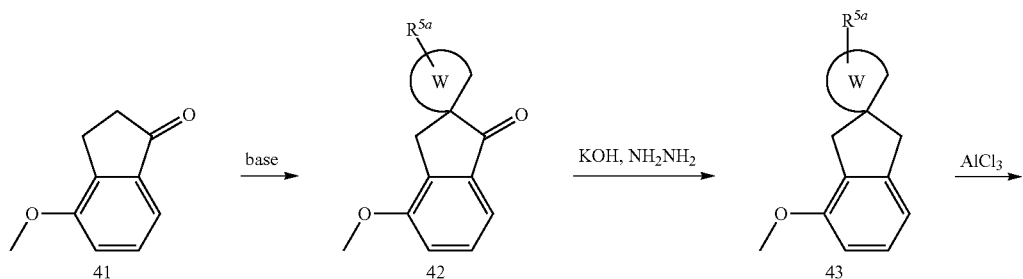

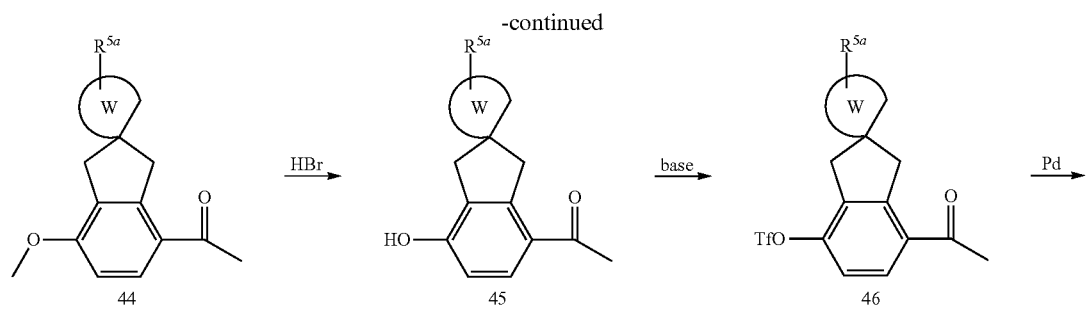
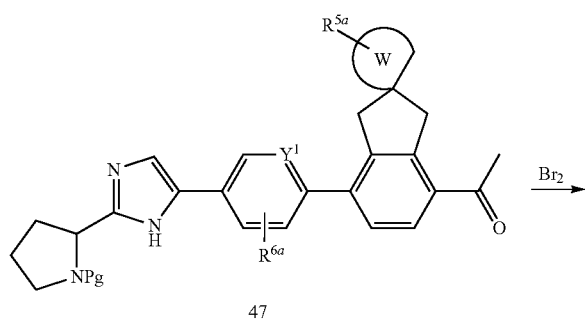
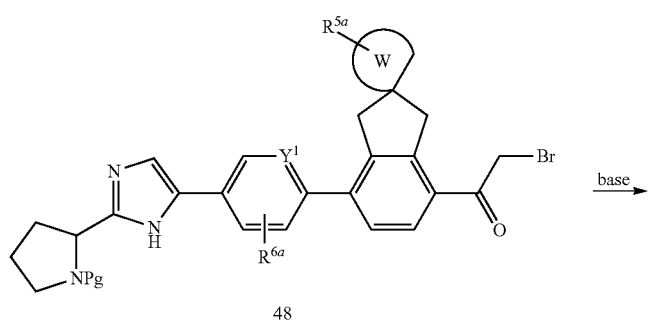
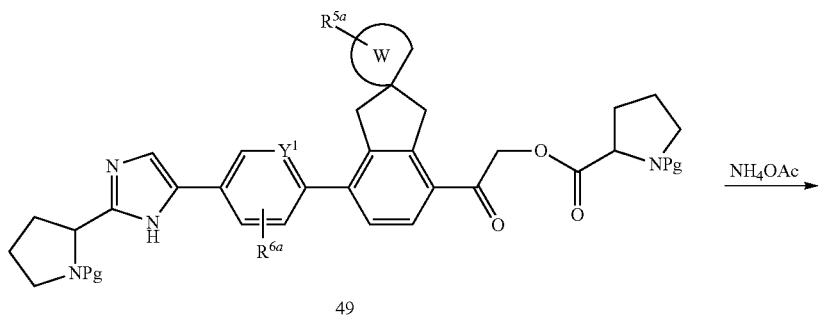
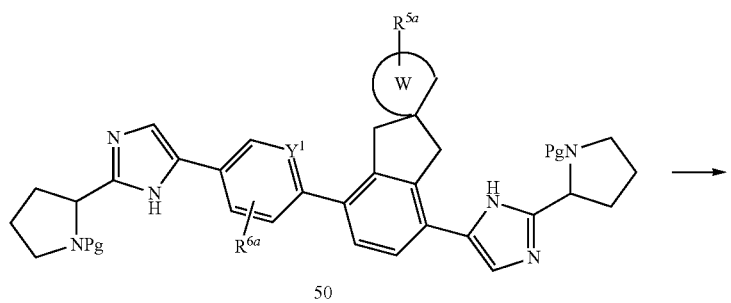

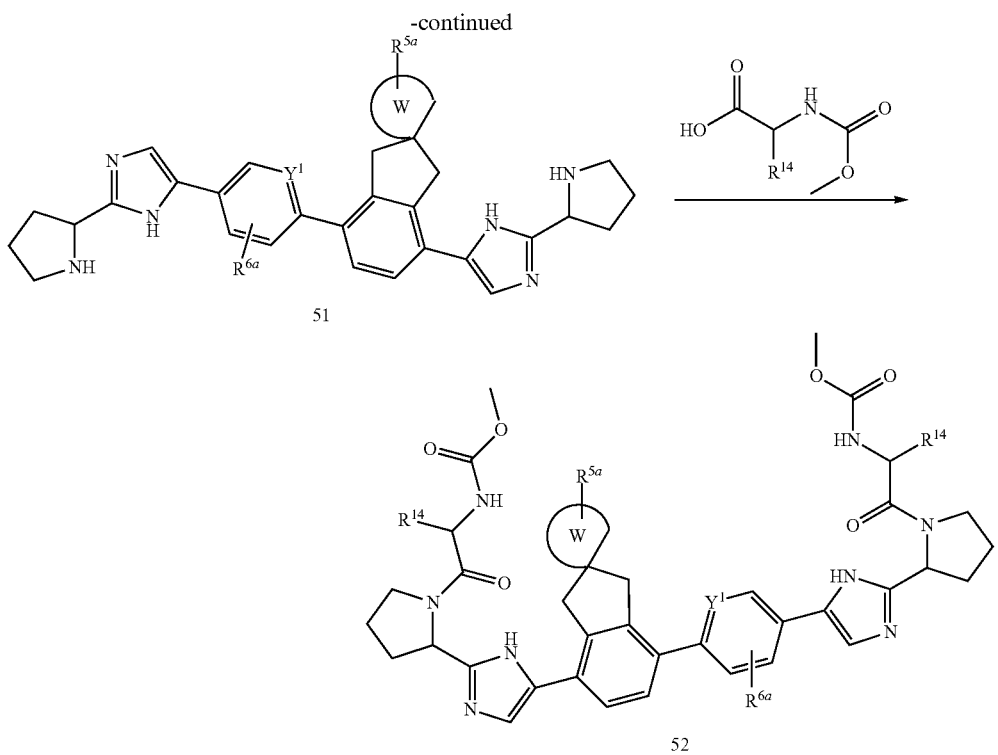

Compound 52 can be prepared by a general synthetic procedure illustrated in Scheme 8, wherein each of $R^{5a}$, $R^{6a}$, $R^{14}$, $Y^1$, Y W and Pg is as defined herein. Compound 41 can be converted to compound 42 in alkali conditions by cyclization. Reduction of compound 42 with a reducing agent in alkali conditions can give compound 43. Compound 43 can be converted to compound 44 by Friedel-Crafts acylation reaction. The methyl in compound 44 can be removed to afford compound 45. Compound 45 can react with trifluoromethanesulfonic anhydride in alkali conditions to afford compound 46. Coupling reaction of compound 46 with compound 22 in the presence of a Pd catalyst can give compound 47. Bromination of compound 47 with $Br_2$ can give compound 48. Compound 48 can react with protected proline in alkali conditions to give compound 49. Cyclization of compound 49 with ammonium acetate under heating conditions can give compound 50. The protecting group Pg in compound 50 can be removed to provide compound 51, which in turn can be condensed with amino acid to give compound 52.

Scheme 9

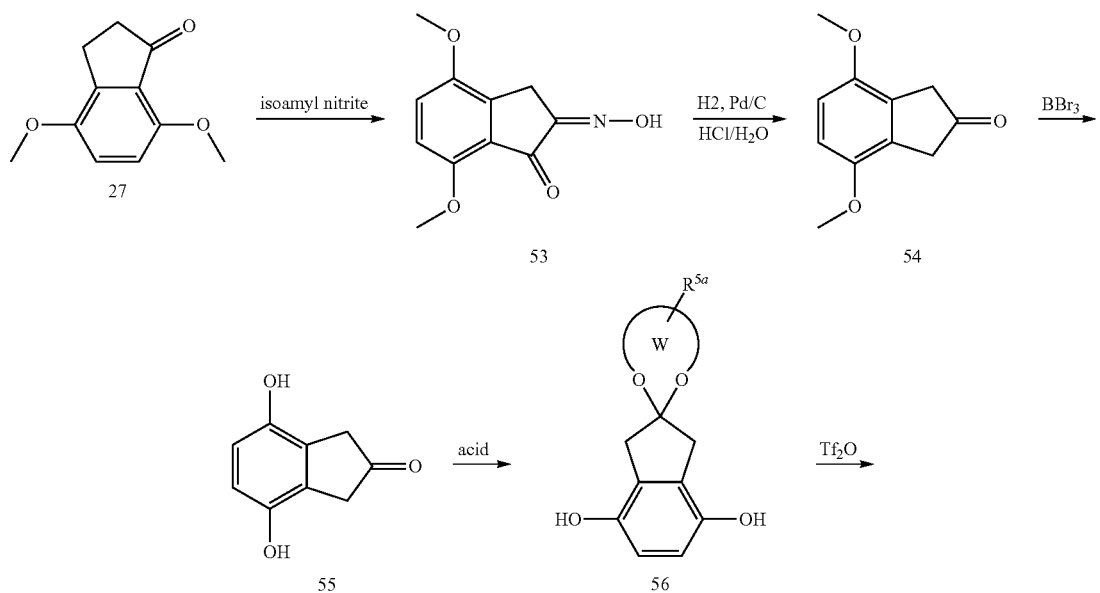

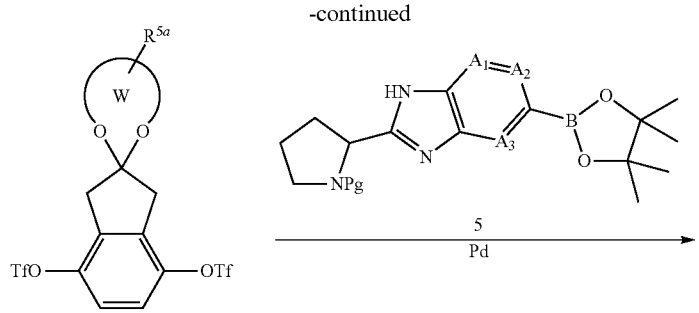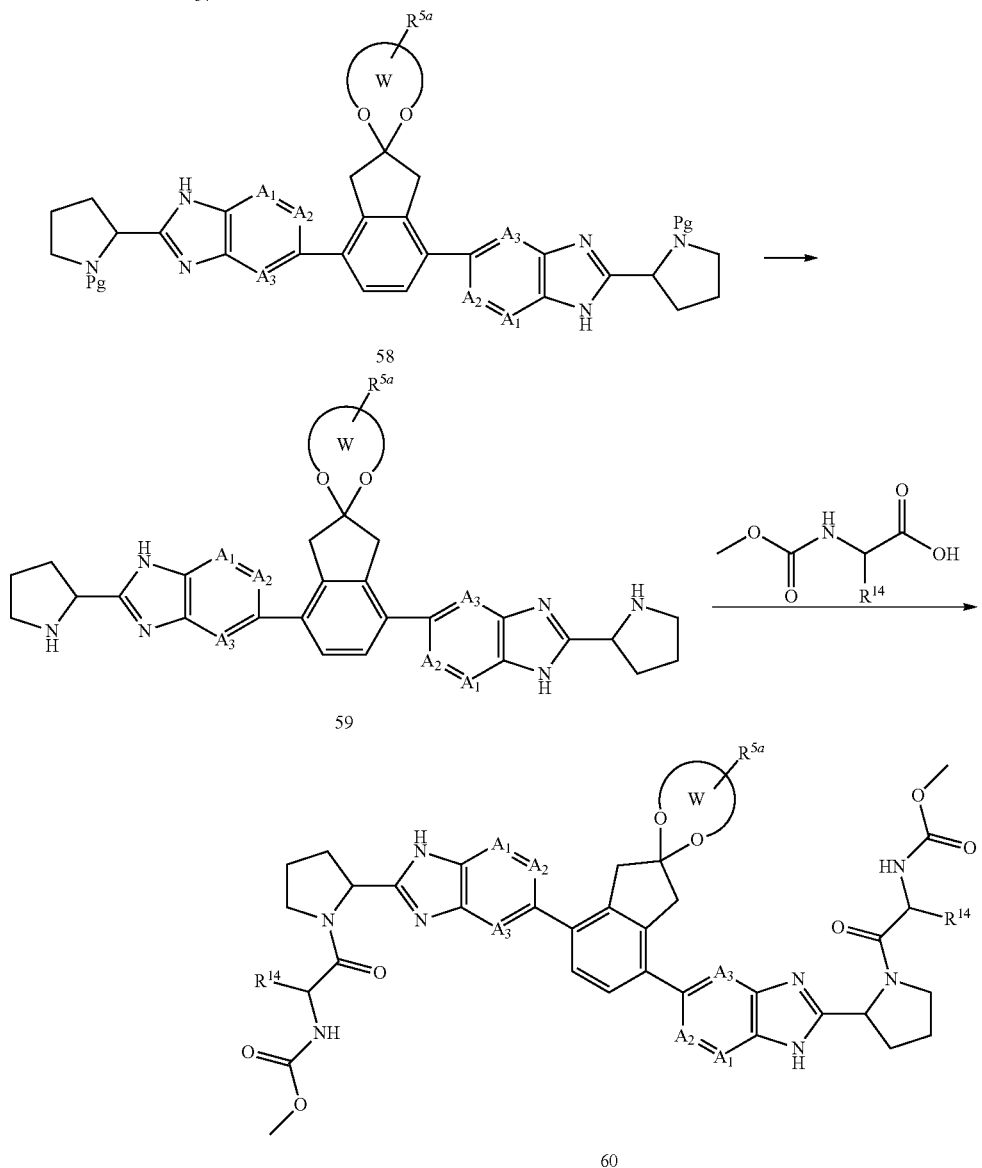

Compound 60 can be prepared by a general synthetic procedure illustrated in Scheme 9, wherein each of $A_1$, $A_2$, $A_3$, $R^{5a}$, Pg and $R^{14}$ is as defined herein. Compound 27 can react with isoamyl nitrite to give compound 53. Compound 53 can be converted to compound 54 by reduction and acidification. The methyl in compound 54 can be removed to give compound 55. Compound 55 can react with ketone to provide compound 56 by acid catalysis. Compound 56 can react with trifluoromethanesulfonic anhydride in alkali conditions to give compound 57. Coupling reaction of compound 57 with compound 5 in the presence of a Pd catalyst can give compound 58. The protecting group Pg in compound 58 can be removed to provide compound 59, which in turn can be condensed with amino acid to give compound 60.

EXAMPLES
Example 1
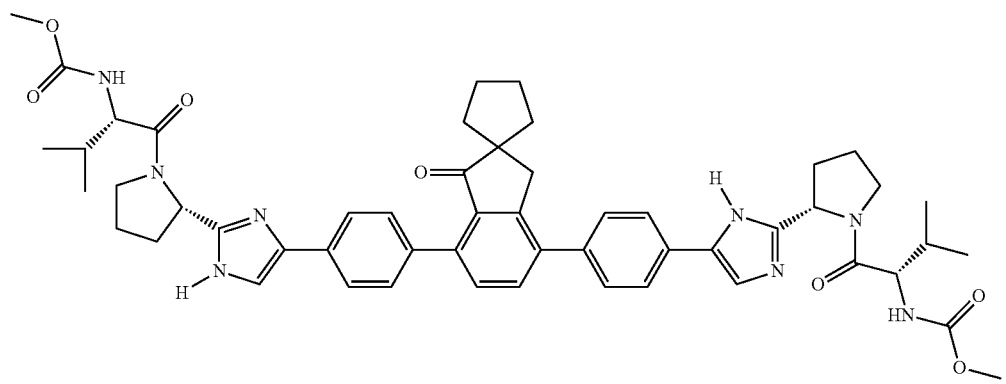
Synthetic Routes
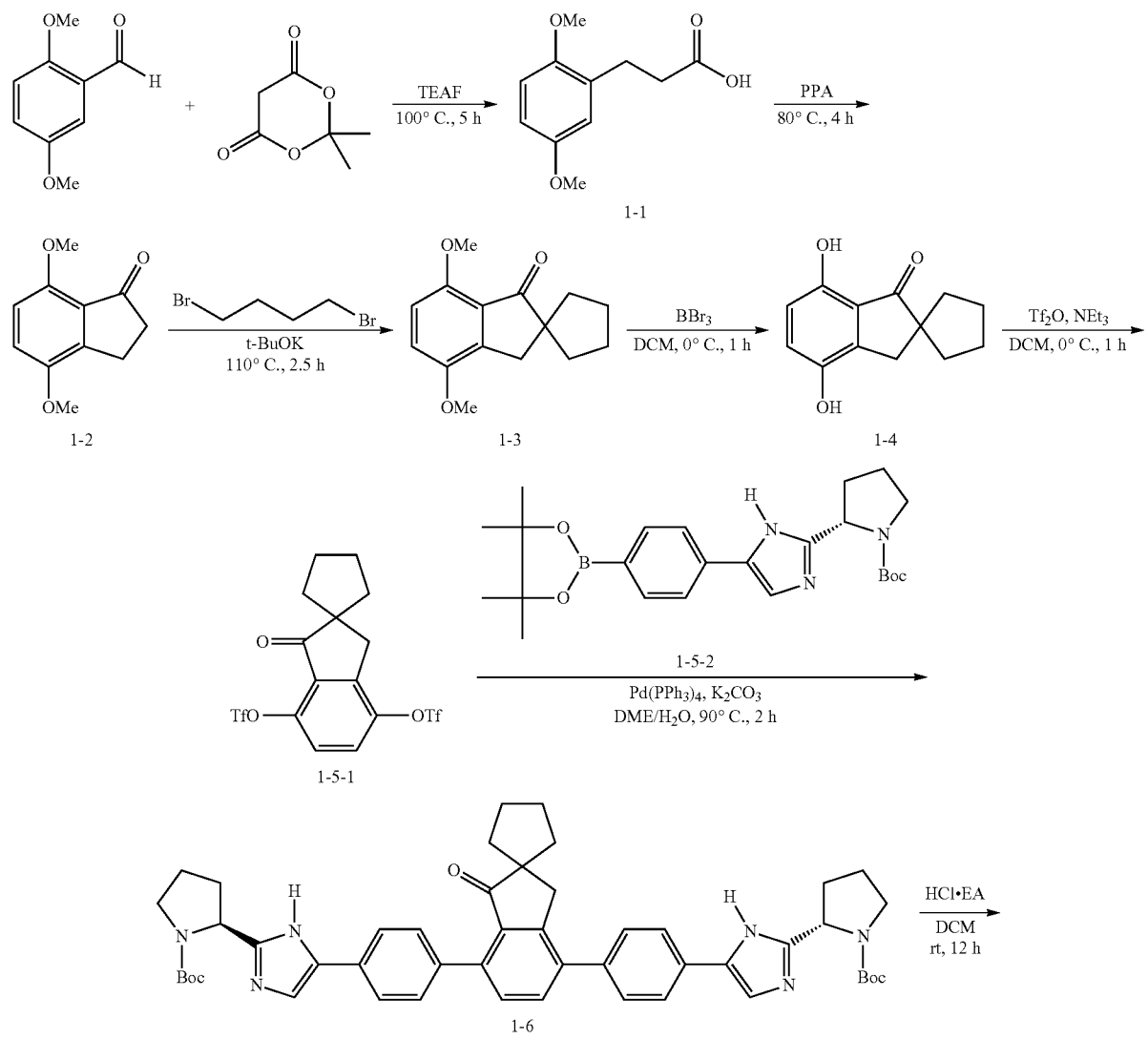

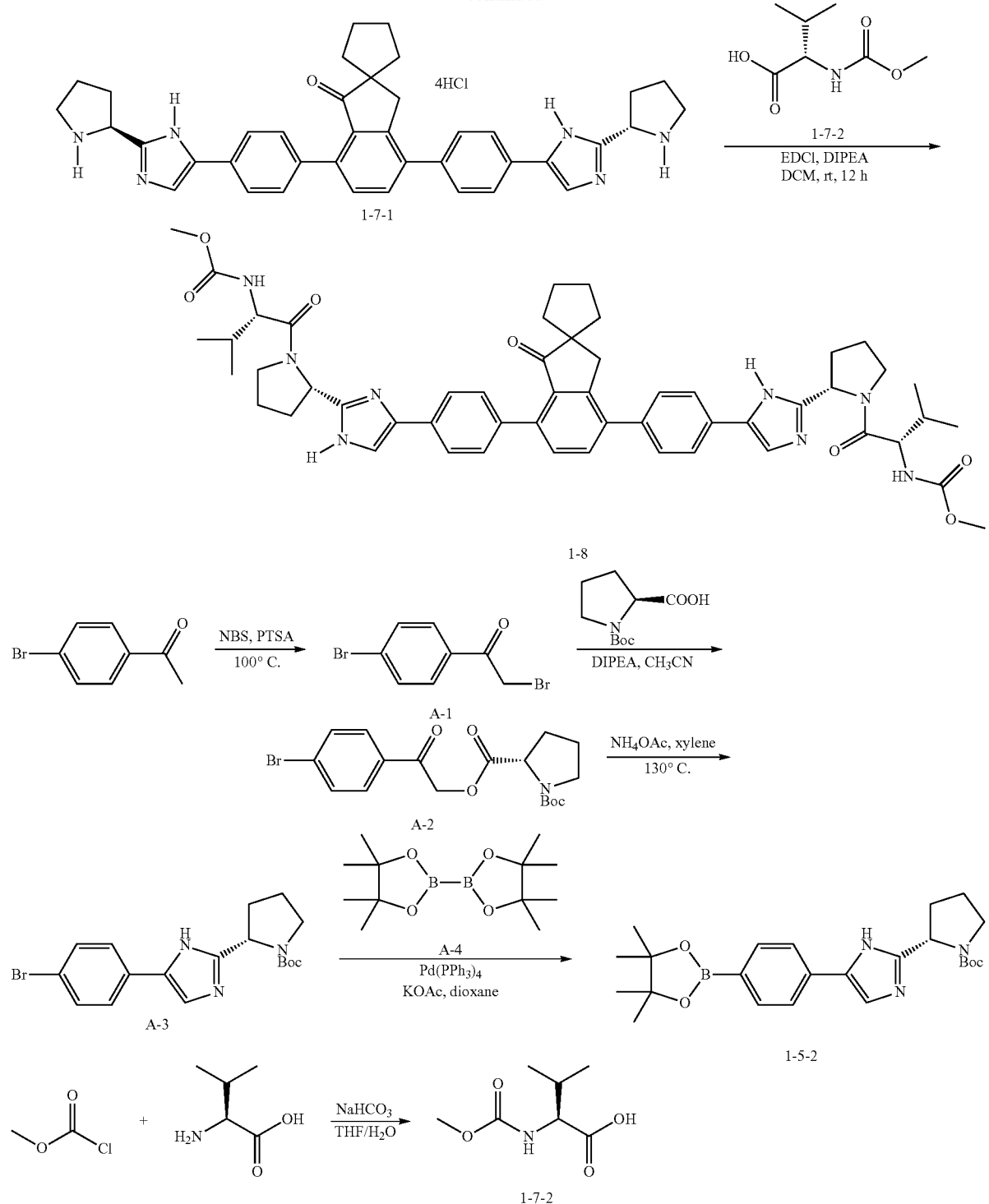

Step 1) The Preparation of Compound 1-1

To methanoic acid (3.7 mL) was added Et$_3$N (5.4 mL) dropwise slowly in an ice bath. At the end of the addition, 2,5-dimethoxybenzaldehyde (2.0 g, 12 mmol) and Meldrum's acid (1.73 g, 12 mmol) were added to the mixture in turn. The reaction mixture was stirred at 100° C. for 5 hours and ice water (20 mL) was added. The mixture was adjusted to pH 1 with HCl aqueous solution (2 N) and extracted with EtOAc (25 mL×3). The combined organic phases were dried over anhydrous Na$_2$SO$_4$ and concentrated in vacuo. The residue was purified by silica gel column chromatography (PE/EtOAc (v/v)=3/1) to give the title compound as a white solid (2.1 g, 83%, HPLC: 95%). The compound was characterized by the following spectroscopic data:

MS-ESI: m/z 211.1 [M+H]$^+$; and $^1$H NMR (400 MHz, CDCl$_3$): δ 6.70-6.78 (m, 6H), 3.78 (s, 3H), 3.75 (s, 3H), 2.91 (t, J=7.8 Hz, 2H), 2.65 (t, J=7.8 Hz, 2H).

Step 2) The Preparation of Compound 1-2

A mixture of compound 1-1 (4.68 g, 22.3 mmol) and PPA (50.87 g, 24.8 mL) in a 100 mL of round-bottomed flask was stirred at 80° C. for 4 hours. Then the mixture was poured into ice water (250 mL) and extracted with EtOAc (100 mL×5). The combined organic phases were dried over anhydrous $Na_2SO_4$ and concentrated in vacuo. The residue was purified by silica gel column chromatography (PE/EtOAc (v/v)=3/1) to give the title compound as a pale yellow solid (3 g, 70%, HPLC: 92.5%). The compound was characterized by the following spectroscopic data:

MS-ESI: m/z 193.2 $[M+H]^+$; and $^1$H NMR (400 MHz, $CDCl_3$): δ 6.98 (d, J=8.7 Hz, 1H), 6.73 (d, J=8.7 Hz, 1H), 3.90 (s, 3H), 3.85 (s, 3H), 2.97-3.00 (m, 2H), 2.65-2.68 (m, 2H).

Step 3) the Preparation of Compound 1-3

To a suspension of potassium tert-butanolate (912.3 mg, 8 mmol) in toluene (10 mL) was added dropwise a solution of compound 1-2 (680 mg, 3.5 mmol) and 1,4-dibromobutane (0.46 mL, 3.8 mmol) in toluene (20 mL) in an ice bath. The reaction mixture was refluxed for 2.5 hours, cooled to rt and quenched with ice water. The toluene was removed under reduced pressure, and the resulting mixture was extracted with EtOAc (25 mL×3). The combined organic phases were dried over anhydrous $Na_2SO_4$ and concentrated in vacuo. The residue was purified by silica gel column chromatography (PE/EtOAc (v/v)=3/1) to give the title compound 1-3 as a pale yellow solid (784.1 mg, 90%, HPLC: 95%). The compound was characterized by the following spectroscopic data:

MS-ESI: m/z 247.2 $[M+H]^+$; and $^1$H NMR (400 MHz, $CDCl_3$): δ 6.98 (d, J=8.7 Hz, 1H), 6.73 (d, J=8.7 Hz, 1H), 3.90 (s, 3H), 3.85 (s, 3H), 2.89 (s, 2H), 2.00-2.02 (m, 2H), 1.91-1.92 (m, 2H), 1.75-1.77 (m, 2H), 1.55-1.60 (m, 2H).

Step 4) The Preparation of Compound 1-4

To a solution of compound 1-3 (1.67 g, 6.8 mmol) in DCM (20 mL) was added dropwise boron tribromide (9 mL, 22.5 mmol, 2.5 mol/L in DCM) in an ice bath. The reaction mixture was stirred for 1 hour, quenched with ice water and extracted with DCM (25 mL×3). The combined organic phases were dried over anhydrous $Na_2SO_4$ and concentrated in vacuo. The residue was purified by silica gel column chromatography (PE/EtOAc (v/v)=3/1) to give the title compound 1-4 as a white solid (1.36 g, 92%, HPLC: 97.9%). The compound was characterized by the following spectroscopic data:

MS-ESI: m/z 219.1 $[M+H]^+$; and $^1$H NMR (400 MHz, $CDCl_3$): δ 8.64 (s, 1H), 6.95 (d, J=8.6 Hz, 1H), 6.68 (d, J=8.6 Hz, 1H), 4.66 (s, 1H), 2.94 (s, 2H), 1.93-2.04 (m, 4H), 1.78-1.83 (m, 2H), 1.64-1.68 (m, 2H).

Step 5) The Preparation of Compound 1-5-1

To a solution of $Et_3N$ (2.3 mL) and compound 1-4 (445 mg, 2 mmol) in DCM (25 mL) was added dropwise trifluoroacetic anhydride (1.7 mL, 12 mmol) in an ice bath. The resulting mixture was stirred for 1 hour, quenched with ice water (25 mL) and extracted with DCM (25 mL×3). The combined organic phases were dried over anhydrous $Na_2SO_4$ and concentrated in vacuo. The residue was purified by silica gel column chromatography (PE/EtOAc (v/v)=20/1) to give the title compound 1-5-1 as yellow oil (916.9 mg, 93.0%, HPLC: 95.5%). The compound was characterized by the following spectroscopic data:

MS-ESI: m/z 483.1 $[M+H]^+$; and $^1$H NMR (400 MHz, $CDCl_3$): δ 7.57 (d, J=8.8 Hz, 1H), 7.30 (d, J=8.8 Hz, 1H), 3.15 (s, 2H), 2.05-3.00 (m, 2H), 1.94-1.98 (m, 2H), 1.78-1.83 (m, 2H), 1.64-1.70 (m, 2H).

Step 6) The Preparation of Compound 1-5-2

A mixture of 4'-bromoacetophenone (25 g, 125.6 mmol), NBS (24.5 g, 138.2 mmol) and PTSA (3.4 g, 20.9 mmol) in a 100 mL of round-bottomed flask was heated to 100° C. under $N_2$ and stirred at 100° C. for 2 hours. After the reaction was completed, the reaction mixture was cooled to rt and diluted with DCM. The mixture was quenched with water and extracted with DCM (50 mL×3). The combined organic phases were dried over anhydrous $Na_2SO_4$ and concentrated in vacuo. The residue was purified by silica gel column chromatography (PE/EtOAc (v/v)=6/1) to give compound A-1 as a white solid (25.0 g, 72%). The compound was characterized by the following spectroscopic data:

MS-ESI: m/z 276.8 $[M+H]^+$; and $^1$H NMR (400 MHz, $CDCl_3$): δ 7.93 (d, 1H), 7.78 (d, 1H), 4.93 (s, 2H).

To a solution of compound A-1 (30 g, 107.9 mmol) and Boc-L-proline (25.6 g, 118.7 mmol) in MeCN (250 mL) was added DIPEA (21.4 mL, 129.5 mmol) dropwise at 0° C. At the end of the addition, the mixture was stirred at rt and the reaction was monitored by TLC. After the reaction was complete, the mixture was quenched with water and extracted with EtOAc (100 mL×3). The combined organic phases were dried over anhydrous $Na_2SO_4$ and concentrated in vacuo. The residue was purified by silica gel column chromatography (PE/EtOAc (v/v)=4/1) to give compound A-2 as colorless oil (40 g, 91%). The compound was characterized by the following spectroscopic data:

MS-ESI: m/z 412.7 $[M+H]^+$; and $^1$H NMR (400 MHz, $CDCl_3$): δ 7.78-7.75 (m, 2H), 7.65-7.63 (m, 2H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

A solution of compound A-2 (15 g, 36.4 mmol) and $NH_4OAc$ (42 g, 711 mmol) in xylene (150 mL) was stirred at 130° C. overnight in a 350 mL of sealed tube until the reaction was completed. The mixture was cooled to rt, quenched with water and extracted with EtOAc (100 mL×3). The combined organic phases were dried over anhydrous $Na_2SO_4$ and concentrated in vacuo. The residue was purified by silica gel column chromatography (PE/EtOAc (v/v)=2/1) to give compound A-3 as a white solid (11.4 g, 80%). The compound was characterized by the following spectroscopic data:

MS-ESI: m/z 392.2 $[M+H]^+$; and $^1$H NMR (400 MHz, $CDCl_3$): δ 7.78-7.75 (m, 2H), 7.65-7.63 (m, 2H), 7.21-7.20 (m, 1H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

To a solution of compound A-3 (1.00 g, 2.55 mmol), compound A-4 (1.35 g, 5.33 mmol) and KOAc (0.640 g, 6.53 mmol) in dioxane (20 mL) under $N_2$ was added $Pd(PPh_3)_4$ (0.147 g, 0.128 mmol), and the resulting mixture was stirred at 80° C. for 14 hours under $N_2$. The reaction was monitored by TLC. After the reaction was completed, the mixture was evaporated in vacuo, and to the residue was added water (20 mL). The aqueous phase was extracted with EtOAc (100 mL×3). The combined organic phases were dried over anhydrous $Na_2SO_4$ and concentrated in vacuo. The residue was purified by silica gel column chromatography (PE/EtOAc (v/v)=2/1) to give the title compound 1-5-2 as a pale yellow solid (0.978 g, 87%). The compound was characterized by the following spectroscopic data:

MS-ESI: m/z 440.39 $[M+H]^+$; and $^1$H NMR (400 MHz, $CDCl_3$): δ 11.03, 10.55 (s, s, 1H), 7.79 (m, 3H), 7.45 (m, 1H), 7.26 (m, 1H), 4.97 (m, 1H), 3.41 (m, 2H), 3.06, 2.91 (2m, 1H), 2.17 (m, 2H), 1.97 (m, 1H), 1.49 (s, 9H), 1.35 (s, 12H).

Step 7) The Preparation of Compound 1-6

To a mixture of compound 1-5-2 (161.54 mg, 0.37 mmol), anhydrous potassium carbonate (105.8 mg, 0.76 mmol) and Pd(PPh$_3$)$_4$ (17.7 mg, 0.015 mmol) in a 50 mL of two-necked flask under N$_2$ was added a solution of compound 1-5-1 (73.9 mg, 0.15 mmol) in DME (4 mL) via syringe followed by distilled water (1 mL). The mixture was stirred at 90° C. under N$_2$ for 2 hours. DME was removed in vacuo and distilled water (15 mL) was added, and the mixture was extracted with DCM (15 mL×3). The combined organic phases were dried over anhydrous Na$_2$SO$_4$ and concentrated in vacuo. The residue was purified by silica gel column chromatography (EtOAc/MeOH (v/v)=60/1) to give the title compound as a yellow solid (99.1 mg, 80%, HPLC: 89%). The compound was characterized by the following spectroscopic data:

MS-ESI: m/z 405.2 [M+2H]$^{2+}$; and $^1$H NMR (400 MHz, CDCl$_3$): δ 7.45-7.90 (m, 12H), 4.99 (br, 2H), 3.42 (br, 4H), 3.10 (s, 2H), 2.16-2.17 (br, 4H), 1.99-2.04 (br, 4H), 1.86 (br, 2H), 1.67 (br, 4H), 1.56-1.62 (br, 2H), 1.51 (s, 18H).

Step 8) The Preparation of Compound 1-7-1

To a solution of compound 1-6 (50 mg, 0.06 mmol) in DCM (4 mL) was added a solution of HCl in EtOAc (2 mL, 4 M). The mixture was stirred at rt for 12 hours and filtered. The filter cake was washed with EtOAc (50 mL) to give the title compound as a yellow solid (42.4 mg, 91%, HPLC: 90%). The compound was characterized by the following spectroscopic data:

MS-ESI: m/z 305.2 [M+2H]$^{2+}$; and $^1$H NMR (400 MHz, CD$_3$OD): δ 8.06-8.07 (br, 2H), 7.99 (d, J=8.8 Hz, 2H), 7.89 (d, J=8.4 Hz, 2H), 7.72-7.77 (m, 3H), 7.63 (d, J=8.3 Hz, 2H), 7.47 (d, J=7.4 Hz, 1H), 5.16-5.22 (m, 2H), 3.59-3.62 (m, 4H), 3.18 (s, 2H), 2.70-2.72 (m, 2H), 2.57 (m, 2H), 2.40 (m, 2H), 2.27 (m, 2H), 1.90-2.00 (m, 2H), 1.78-1.86 (m, 4H), 1.65-1.68 (m, 2H).

Step 9) The Preparation of Compound 1-7-2

To a solution of L-valine (24.9 g, 0.213 mol) in THF (645 mL) was added a solution of NaHCO$_3$ (53.7 g, 0.640 mol) in water (645 mL). At the end of the addition, to the mixture was added methyl chloroformate (22.2 g, 0.235 mol) dropwise. The resulting mixture was stirred at rt overnight, adjusted to pH 3 with HCl aqueous solution (1 N), and extracted with EtOAc (100 mL×3). The combined organic phases were dried over anhydrous Na$_2$SO$_4$ and concentrated in vacuo to give the title compound 1-7-2 as a white solid (33 g, 90%). The compound was characterized by the following spectroscopic data:

MS-ESI: m/z 176 [M+H]$^+$; and $^1$H NMR (400 MHz, DMSO-d$^6$): δ 0.93 (d, J=7.00 Hz, 3H), 1.00 (d, J=7.00 Hz, 3H), 2.23 (m, 1H), 3.70 (s, 3H), 4.33 (m, 1H), 5.26 (brs, 1H), 8.50 (brs, 1H).

Step 10) The Preparation of Compound 1-8

To a mixture of compound 1-7-1 (42.7 mg, 0.056 mmol), compound 1-7-2 (29.8 mg, 0.17 mmol) and EDCI (43.4 mg, 0.22 mmol) in DCM (7 mL) at 0° C. was added DIPEA (0.1 mL) slowly. The resulting mixture was stirred at rt for 12 hours and water (20 mL) was added. The mixture was extracted with DCM (25 mL×3). The combined organic phases were dried over anhydrous Na$_2$SO$_4$ and concentrated in vacuo. The residue was purified by silica gel column chromatography (EtOAc/MeOH (v/v)=60/1) to give the title compound as a yellow solid (36.8 mg, 70.5%, HPLC: 95.5%). The compound was characterized by the following spectroscopic data:

MS-ESI: m/z 462.3 [M+2H]$^{2+}$; and $^1$H NMR (400 MHz, CD$_3$OD): δ 7.88-7.9 (m, 4H), 7.58-7.60 (br, 2H), 7.46-7.50 (m, 6H), 7.35-7.37 (m, 2H), 5.40 (br, 2H), 5.35 (br, 2H), 4.33 (br, 2H), 3.84 (br, 2H), 3.70 (s, 6H), 3.64 (br, 2H), 3.08 (s, 2H), 2.31-2.43 (br, 2H), 2.15-2.25 (m, 2H), 2.08-2.14 (m, 2H), 1.90-2.05 (m, 4H), 1.80-1.90 (br, 2H), 1.65-1.75 (m, 2H), 0.80-0.92 (m, 12H).

Example 2

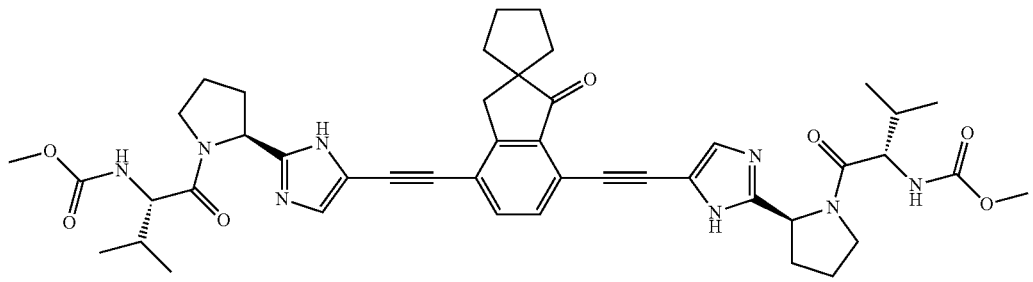

Synthetic Routes

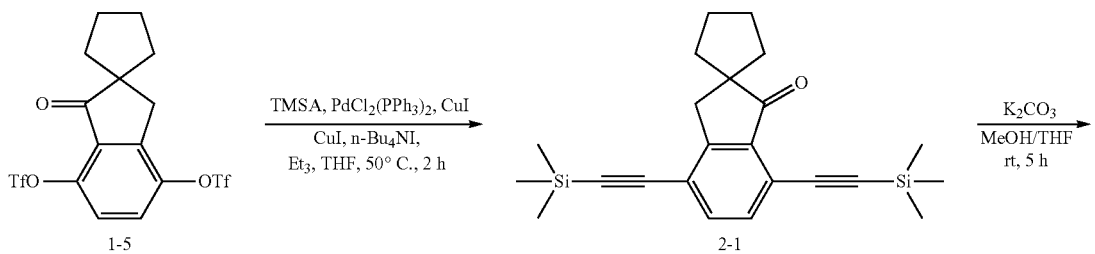

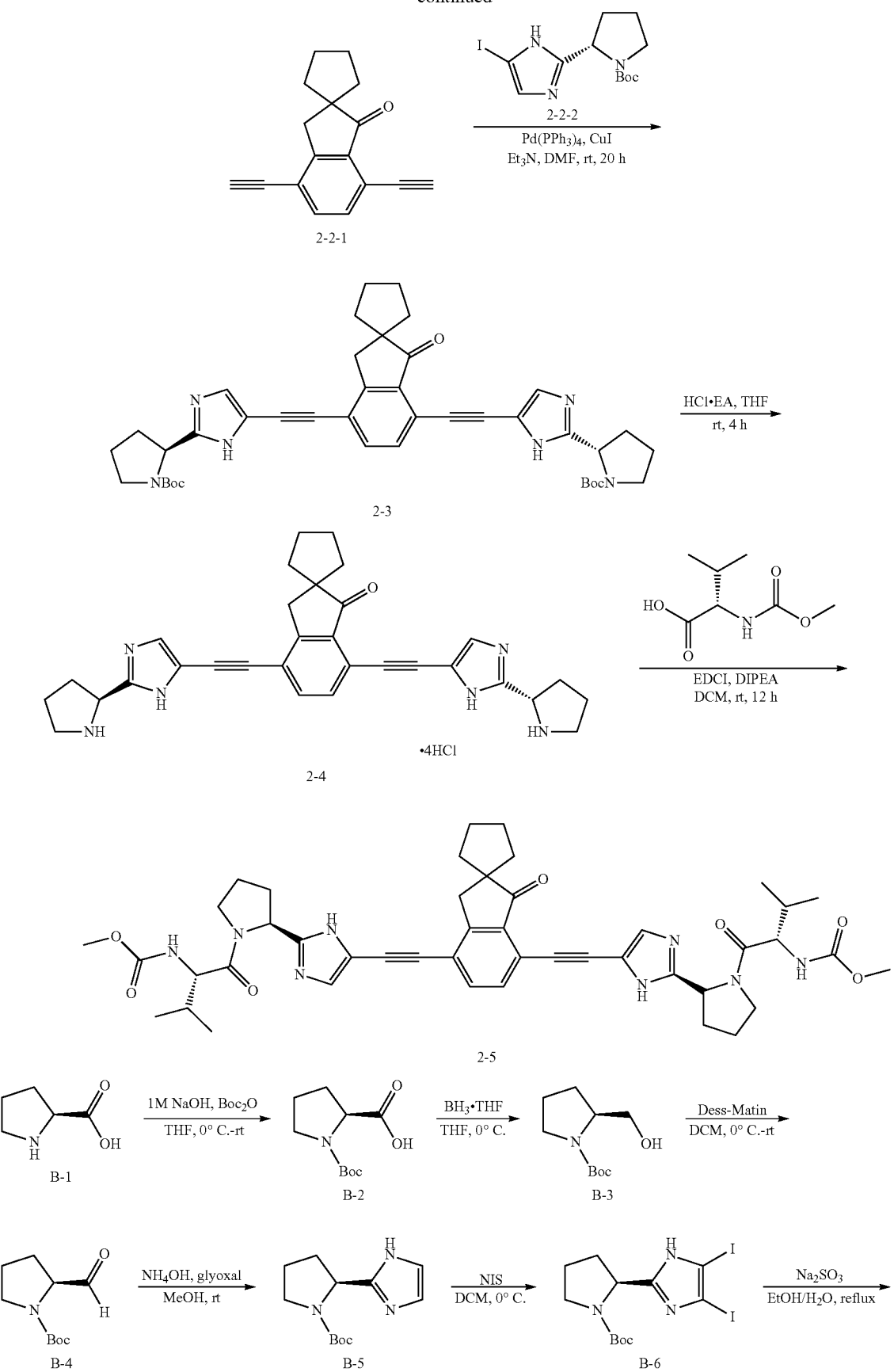

-continued

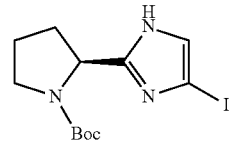

2-2-2

Step 1) The Preparation of Compound 2-1

To a mixture of compound 1-5 (964 mg, 2 mmol), tetrabutylammonium iodide (2214 mg, 6 mmol), cuprous iodide (114 mg, 0.6 mmol) and bis(triphenylphosphine)palladium (II) chloride (140 mg, 0.2 mmol) in a 50 mL of two-necked flask under $N_2$ was added anhydrous THF (8 mL) followed by $Et_3N$ (8 mL) with stirring. After the mixture was stirred for 10 minutes at rt, TMSA (1.4 mL, 10 mmol) was added to the mixture, and the resulting mixture was stirred at 50° C. for 2 hours. The mixture was concentrated in vacuo. The residue was purified by silica gel column chromatography (PE/EtOAc (v/v)=50/1) to give the title compound as a yellow solid (643 mg, 85%, HPLC: 88%). The compound was characterized by the following spectroscopic data:

MS-ESI: m/z 379.2 [M+H]$^+$; and $^1$H NMR (400 MHz, CDCl$_3$): δ 7.56 (d, J=7.8 Hz, 1H), 7.41 (d, J=7.8 Hz, 1H), 2.98 (s, 2H), 2.03-2.06 (m, 2H), 1.93-1.94 (m, 2H), 1.79-1.81 (m, 2H), 1.58-1.63 (m, 2H), 0.31 (d, J=3.5 Hz, 9H), 0.28 (d, J=3.5 Hz, 9H).

Step 2) The Preparation of Compound 2-2-1

To a solution of compound 2-1 (756 mg, 2 mmol) in the mixture of MeOH (4 mL) and THF (4 mL) was added potassium carbonate (1104 mg, 8 mmol) with stirring. The resulting mixture was stirred at rt for 5 hours and filtered. The filtrate was concentrated in vacuo and the residue was purified by silica gel column chromatography (PE/EtOAc (v/v)=20/1) to give the title compound as a brown solid (374.4 mg, 80%, HPLC: 69%). The compound was characterized by the following spectroscopic data:

MS-ESI: m/z 235.1 [M+H]$^+$; and $^1$H NMR (400 MHz, CD$_3$OD): δ 7.64 (d, J=7.8 Hz, 1H), 7.47 (d, J=7.8 Hz, 1H), 3.56 (s, 1H), 3.44 (s, 1H), 3.05 (s, 2H), 2.01-2.06 (m, 2H), 1.93-1.97 (m, 2H), 1.79-1.82 (m, 2H), 1.62-1.64 (m, 2H).

Step 3) The Preparation of Compound 2-2-2

To a suspension of L-proline (15.0 g, 130 mmol) in THF (150 mL) in a 500 mL of dry round-bottomed flask at 0° C. was added NaOH aqueous solution (156.4 mL, 1 M) with stirring. When the mixture was clear, Boc$_2$O (31.3 g, 143.6 mmol) was added dropwise to the mixture. After the end of the addition, the reaction mixture was stirred at rt overnight. After the reaction was completed, THF was removed under reduced pressure. The mixture was adjusted to pH 2 with diluted hydrochloric acid and extracted with EtOAc (100 mL×3). The combined organic phases were washed with brine, dried over anhydrous Na$_2$SO$_4$ and concentrated in vacuo to afford compound B-2 as a white solid (27.7 g, 98.7%).

To a solution of compound B-2 (15.0 g, 130 mmol) in THF (100 mL) in a 500 mL of dry three-necked flask at 0° C. was added dropwise a solution of borane in THF (100 mL, 1 M) under $N_2$ with stirring. After the end of the addition, the reaction mixture was stirred for 3 hours. After the reaction was completed, the reaction mixture was quenched with methanol and concentrated in vacuo. The residue was purified by silica gel column chromatography (PE/EtOAc (v/v)=3/2) to give compound B-3 as colorless oil (7.0 g, 75.2%). The compound was characterized by the following spectroscopic data:

$^1$H NMR (400 MHz, CDCl$_3$): δ 3.87-3.99 (br, 1H), 3.51-3.68 (m, 2H), 3.39-3.48 (m, 1H), 3.25-3.34 (m, 1H), 1.92-2.05 (m, 2H), 1.71-1.88 (m, 2H), 1.45 (s, 9H).

To a solution of compound B-3 (7.0 g, 34.8 mmol) in anhydrous DCM (250 mL) in a 500 mL of dry round-bottomed flask at 0° C. was added Dess-Martin periodinane (20.7 g, 48.8 mmol) in portions with stirring. After the end of the addition, the reaction mixture was stirred at rt for 2 hours. After the reaction was completed, water (250 mL) was added and the resulting mixture was filtered. The layers were separated. The organic layer was washed with brine, dried over anhydrous Na$_2$SO$_4$ and concentrated in vacuo. The residue was purified by silica gel column chromatography (PE/EtOAc (v/v)=3/2) to give compound B-4 as colorless oil (3.5 g, 50.7%). The compound was characterized by the following spectroscopic data:

$^1$H NMR (400 MHz, CDCl$_3$): δ 9.46 (d, J=2.8 Hz, 1H), 4.03-4.08 (m, 1H), 3.42-3.51 (m, 2H), 1.84-1.91 (m, 2H), 1.93-2.01 (m, 2H), 1.43 (s, 9H).

To a solution of compound B-4 (3.5 g, 17.6 mmol) and ammonia (13 mL) in methanol (30 mL) in a 100 mL of dry round-bottomed flask at 0° C. was added glyoxal (8 mL, 40%) dropwise with stirring. After the end of the addition, the reaction mixture was stirred at rt overnight and concentrated in vacuo. The residue was purified by silica gel column chromatography (PE/EtOAc (v/v)=3/2) to give compound B-5 as a white solid (2.0 g, 47.6%). The compound was characterized by the following spectroscopic data:

MS-ESI: m/z 238.2 [M+H]$^+$; and $^1$H NMR (400 MHz, CDCl$_3$): δ 6.96 (s, 1H), 4.94 (dd, J=7.68, 2.40 Hz, 1H), 3.38 (t, J=6.24 Hz, 2H), 2.03-2.17 (m, 2H), 1.91-1.99 (m, 2H), 1.48 (s, 9H).

To a solution of compound B-5 (2.0 g, 8.4 mmol) in DCM (60 mL) in a 100 mL of dry round-bottomed flask at 0° C. was added N-iodosuccinimide (3.8 g, 16.8 mmol) in portions with stirring. After the end of the addition, the reaction mixture was stirred for 1.5 hours, and then the mixture was washed with brine, dried over anhydrous Na$_2$SO$_4$ and concentrated in vacuo. The residue was purified by silica gel column chromatography (PE/EtOAc (v/v)=3/2) to give compound B-6 as a white solid (2.6 g, 63.1%). The compound was characterized by the following spectroscopic data:

MS-ESI: m/z 490.0 [M+H]$^+$, m/z 487.4 [M−2H]$^{2-}$; and $^1$H NMR (400 MHz, CDCl$_3$): δ 4.89 (dd, J=7.64, 2.52 Hz, 1H), 3.36 (t, 2H), 2.02-2.14 (m, 2H), 1.85-1.97 (m, 2H), 1.49 (s, 9H).

To a suspension of compound B-6 (1.6 g, 3.27 mmol) in the mixture of ethanol and water ((v/v)=3/7, 50 mL) in a 100 mL of dry round-bottomed flask was added sodium sulfite (3.7 g, 29 mmol), the resulting mixture was refluxed for 17 hours. Ethanol was removed under reduced pressure and water (20 mL) was added to the mixture. The mixture was extracted with EtOAc (30 mL×3). The combined organic phases were dried over anhydrous Na$_2$SO$_4$ and concentrated in vacuo. The residue was purified by silica gel column chromatography (PE/EtOAc (v/v)=3/2) to give the title compound 2-2-2 as a white solid (1.0 g, 84%). The compound was characterized by the following spectroscopic data:

MS-ESI: m/z 364.1 [M+H]$^+$, m/z 362.1 [M−H]$^-$; and $^1$H NMR (400 MHz, CDCl$_3$): δ 7.04 (d, J=1.84 Hz, 1H), 4.89 (dd, J=7.72, 2.56 Hz, 1H), 3.36 (t, 2H), 2.03-2.18 (m, 2H), 1.82-1.97 (m, 2H), 1.47 (s, 9H).

Step 4) The Preparation of Compound 2-3

To a mixture of compound 2-2-1 (140.4 mg, 0.6 mmol), compound 2-2-2 (479.2 mg, 1.3 mmol), cuprous iodide (2.28 mg, 0.012 mmol) and Pd(PPh$_3$)$_4$ (69.24 mg, 0.06 mmol) in a 50 mL of two-necked flask under N$_2$ was added anhydrous DMF (5 mL) followed by Et$_3$N (0.2 mL). The resulting mixture was stirred at rt for 20 hours and concentrated in vacuo. The residue was purified by silica gel column chromatography (PE/EtOAc (v/v)=2/3) to give the title compound 2-3 as a yellow solid (300 mg, 71.0%, HPLC: 100%). The compound was characterized by the following spectroscopic data:

MS-ESI: m/z 706.3 [M+H]$^+$; and $^1$H NMR (400 MHz, CD$_3$OD): δ 7.64 (s, 1H), 7.44 (s, 1H), 7.35-7.37 (m, 1H), 7.26-7.28 (m, 1H), 4.93-4.94 (br, 2H), 3.11 (s, 2H), 2.14 (br, 4H), 1.94-2.01 (br, 8H), 1.81 (br, 4H), 1.62-1.64 (br, 4H), 1.50 (s, 18H).

Step 5) The Preparation of Compound 2-4

To a solution of compound 2-3 (148 mg, 0.2 mmol) in THF (3 mL) was added a solution of HCl in EtOAc (4 mL, 4 M). The resulting mixture was stirred at rt for 4 hours and filtered. The filter cake was washed with EtOAc (50 mL) to give the title compound as a yellow solid (107 mg, 82.3%, HPLC: 74%). The compound was characterized by the following spectroscopic data:

MS-ESI: m/z 505.3 [M+H]$^+$.

Step 6) The Preparation of Compound 2-5

To a solution of compound 2-4 (42.7 mg, 0.065 mmol), compound 1-7-2 (29.8 mg, 0.17 mmol) and EDCI (43.4 mg, 0.22 mmol) in DCM (7 mL) in an ice bath was added DIPEA (0.1 mL) dropwise. The resulting mixture was stirred at rt for 12 hours. Water (20 mL) was added to the mixture and the mixture was extracted with DCM (25 mL×3). The combined organic phases were dried over anhydrous Na$_2$SO$_4$ and concentrated in vacuo. The residue was purified by silica gel column chromatography (EtOAc/MeOH (v/v)=60/1) to give the title compound 2-5 as a yellow solid (30 mg, 56.3%, HPLC: 91.3%). The compound was characterized by the following spectroscopic data:

MS-ESI: m/z 819.7 [M+H]$^+$; and $^1$H NMR (400 MHz, CD$_3$OD): δ 7.69-7.92 (m, 1H), 7.63 (d, J=7.2 Hz, 1H), 7.52-7.54 (m, 1H), 7.45 (br, 1H), 7.36 (br, 1H), 5.22 (d, J=4.9 Hz, 2H), 4.28-4.33 (m, 4H), 3.60 (s, 6H), 3.04 (s, 2H), 2.31-2.34 (br, 2H), 2.19-2.21 (m, 3H), 2.07-2.14 (m, 5H), 2.00-2.04 (br, 4H), 1.67-1.93 (m, 8H), 1.25-1.32 (m, 12H).

Example 3

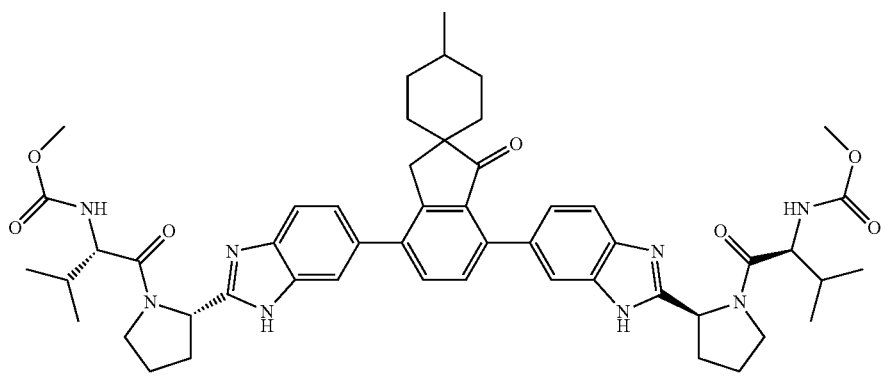 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4c3CC3(CCC(C)CC3)C4=O)cc2[nH]1)C(C)C]

Synthetic Routes

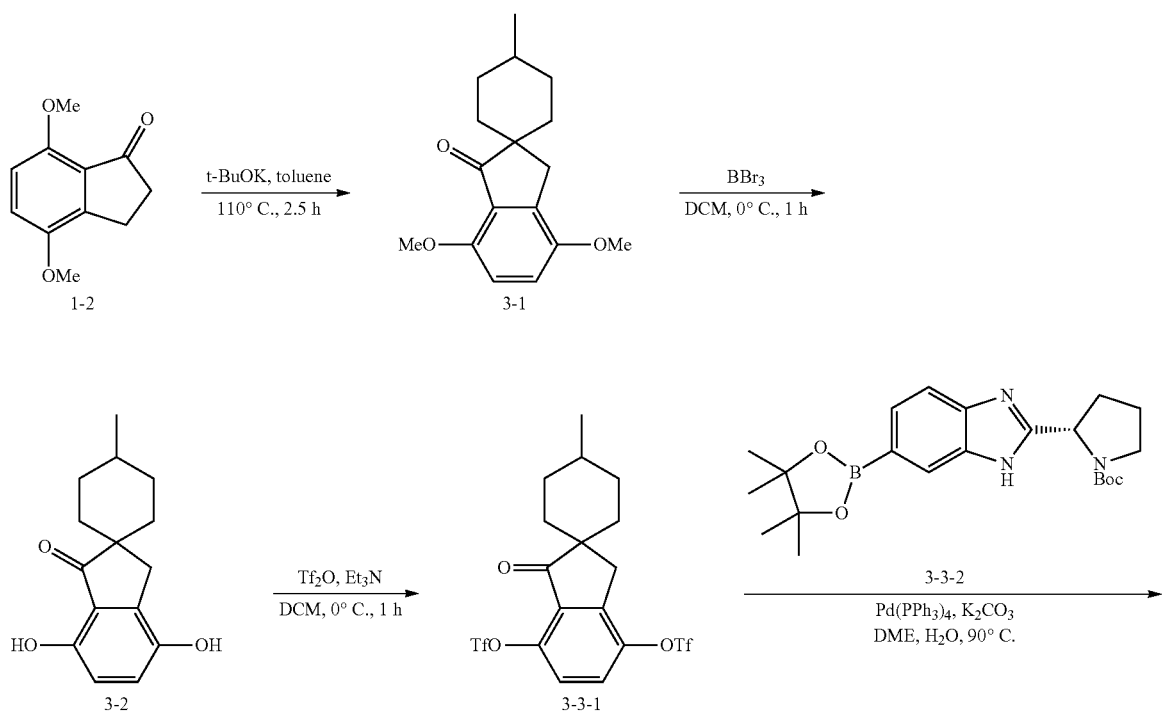

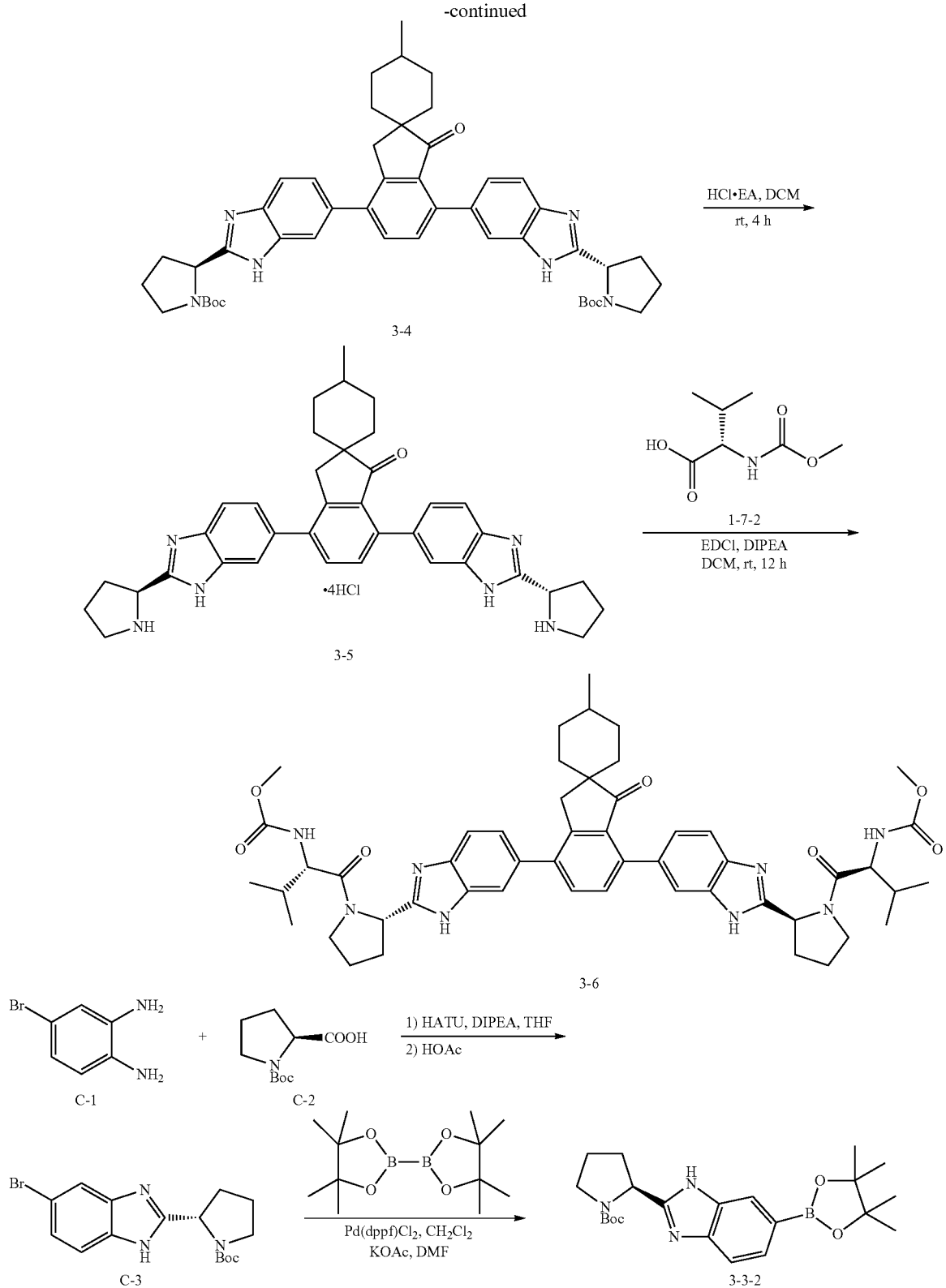

Step 1) The Preparation of Compound 3-1

To a suspension of potassium tert-butanolate (1288 mg, 11.5 mmol) in toluene (10 mL) in an ice bath was added dropwise a solution of compound 1-2 (960 mg, 5 mmol) and 1,5-dibromo-3-methylpentane (0.84 mL, 5.5 mmol) in toluene (25 mL). After the end of the addition, the reaction mixture was refluxed for 2.5 hours and quenched with ice water. The toluene was removed in vacuo, and the mixture was extracted with EtOAc (25 mL×3). The combined organic phases were dried over anhydrous Na$_2$SO$_4$ and concentrated in vacuo. The residue was purified by silica gel column chromatography (PE/EtOAc (v/v)=3/1) to give the title compound 3-1 as a light red solid (1096 mg, 80%, HPLC: 100%). The compound was characterized by the following spectroscopic data:

MS-ESI: m/z 275.2 [M+H]$^+$; and $^1$H NMR (400 MHz, CDCl$_3$): δ 6.99 (d, J=8.7 Hz, 1H), 6.74 (d, J=8.7 Hz, 1H), 3.89 (s, 3H), 3.86 (s, 3H), 2.86 (s, 2H), 1.70-1.79 (m, 4H), 1.47-1.49 (m, 1H), 1.33-1.40 (m, 2H), 1.26-1.28 (m, 2H), 0.97 (d, J=6.5 Hz, 3H).

Step 2) The Preparation of Compound 3-2

To a solution of compound 3-1 (548 mg, 2 mmol) in DCM (10 mL) in an ice bath was added boron tribromide (5 mL, 1.2 mol/L in DCM, 6 mmol) dropwise and the mixture was stirred for 1 hour. The reaction mixture was quenched with ice water and extracted with DCM (15 mL×3). The combined organic phases were dried over anhydrous Na$_2$SO$_4$ and concentrated in vacuo. The residue was purified by silica gel column chromatography (PE/EtOAc (v/v)=4/1) to give the title compound 3-2 as a white solid (478 mg, 97%, HPLC: 94%). The compound was characterized by the following spectroscopic data:

MS-ESI: m/z 247.2 [M+H]$^+$; and $^1$H NMR (400 MHz, CDCl$_3$): δ 9.13 (s, 1H), 9.09 (s, 1H), 6.92 (d, J=8.5 Hz, 1H), 6.60 (d, J=8.5 Hz, 1H), 2.76 (s, 2H), 1.65-1.69 (br, 2H), 1.53-1.58 (br, 2H), 1.33-1.39 (br, 2H), 1.23-1.30 (m, 1H), 1.06-1.13 (br, 2H), 0.92 (d, J=6.5 Hz, 3H).

Step 3) The Preparation of Compound 3-3-1

To a solution of Et$_3$N (2.2 mL) and compound 3-2 (492 mg, 2 mmol) in DCM (20 mL) in an ice bath was added trifluoroacetic anhydride (0.7 mL, 5 mmol) dropwise and the mixture was stirred for 1 hour. The reaction mixture was quenched with ice water (25 mL) and extracted with DCM (20 mL×3). The combined organic phases were dried over anhydrous Na$_2$SO$_4$ and concentrated in vacuo. The residue was purified by silica gel column chromatography (PE/EtOAc (v/v)=8/1) to give the title compound 3-3-1 as yellow oil (612 mg, 60%, HPLC: 95%). The compound was characterized by the following spectroscopic data:

MS-ESI: m/z 511.0 [M+H]$^+$; and $^1$H NMR (400 MHz, CDCl$_3$): δ 7.59 (d, J=8.8 Hz, 1H), 7.31 (d, J=8.8 Hz, 1H), 3.09 (s, 2H), 1.75-1.83 (m, 4H), 1.45-1.49 (m, 1H), 1.24-1.29 (m, 2H), 1.03-1.13 (m, 2H), 0.98 (d, J=6.5 Hz, 3H).

Step 4) The Preparation of Compound 3-3-2

To a solution of compound C-2 (20 g, 93 mmol), compound C-1 (19.1 g, 102 mmol) and HATU (38.9 g, 102 mmol) in THF (500 mL) in an ice bath was added DIPEA (20.5 mL, 118 mmol). The mixture was stirred in the ice bath for 0.5 hour and at rt for 3 hours. The resulting mixture was quenched with water. THF was removed in vacuo. The resulting mixture was extracted with EtOAc (150 mL×3). The combined organic phases were dried over anhydrous Na$_2$SO$_4$ and concentrated in vacuo. The residue was used for the next step without further purification. A solution of the above residue in glacial acetic acid (100 mL) was stirred at 40° C. overnight, basified with NaHCO$_3$ and extracted with EtOAc (150 mL×3). The combined organic phases were dried over anhydrous Na$_2$SO$_4$ and concentrated in vacuo. The residue was purified by silica gel column chromatography (PE/EtOAc (v/v)=2/1) to give compound C-3 (27.6 g, 81%). The compound was characterized by the following spectroscopic data:

$^1$H NMR (400 MHz, CDCl$_3$): δ 7.68 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 2H), 2.01-1.91 (m, 1H), 1.49 (s, 9H).

To a mixture of compound C-3 (3.0 g, 8.2 mmol), bis(pinacolato)diboron (4.29 g, 16.9 mmol), Pd(dppf)Cl$_2$CH$_2$Cl$_2$ (653 mg, 0.8 mmol) and KOAc (2.09 g, 21.3 mmol) in a 50 mL of two-necked flask under N$_2$ was added DMF (30 mL) via syringe. The resulting mixture was stirred at 90° C. overnight, cooled to rt naturally, and water (60 mL) was added. The mixture was extracted with EtOAc (30 mL×3). The combined organic phases were washed with brine, dried over anhydrous Na$_2$SO$_4$ and concentrated in vacuo. The residue was purified by silica gel column chromatography (PE/EtOAc (v/v)=1/2) to give compound 3-3-2 as a beige solid (2.1 g). The compound was characterized by the following spectroscopic data:

$^1$H NMR (400 MHz, CDCl$_3$): δ 7.69 (s, 1H), 7.45-7.43 (m, 1H), 7.32-7.30 (m, 1H), 5.12-5.10 (m, 1H), 3.45-3.43 (m, 2H), 2.95-2.94 (m, 1H), 2.25-2.22 (m, 2H), 2.01-1.91 (m, 1H), 1.49 (s, 9H), 1.35 (s, 12H).

Step 5) The Preparation of Compound 3-4

To a mixture of compound 3-3-2 (619.5 mg, 1.5 mmol), anhydrous potassium carbonate (414 mg, 3 mmol) and Pd(PPh$_3$)$_4$ (69.24 mg, 0.06 mmol) in a 50 mL of two-necked flask under N$_2$ was added a solution of compound 3-3-1 (306 mg, 0.6 mmol) in DME (5 mL) via syringe followed by distilled water (1.5 mL). The resulting mixture was stirred at 90° C. for 2 hours. DME was removed in vacuo and distilled water (15 mL) was added to the mixture. The mixture was extracted with DCM (15 mL×3). The combined organic phases were dried over anhydrous Na$_2$SO$_4$ and concentrated in vacuo. The residue was purified by silica gel column chromatography (PE/EtOAc (v/v)=1/1) to give compound 3-4 as a yellow solid (400 mg, 83.3%, HPLC: 98%). The compound was characterized by the following spectroscopic data:

MS-ESI: m/z 785.3 [M+H]$^+$; and $^1$H NMR (400 MHz, CDCl$_3$): δ 7.85 (s, 1H), 7.72-7.74 (m, 1H), 7.61 (d, J=7.6 Hz, 1H), 7.52-7.53 (m, 2H), 7.35-7.40 (m, 3H), 5.15-5.16 (m, 2H), 3.45 (br, 4H), 3.05 (s, 2H), 2.20-2.24 (br, 4H), 1.67-1.69 (br, 6H), 1.40-1.43 (br, 7H), 1.26 (s, 18H), 1.00 (d, J=6.7 Hz, 3H).

Step 6) The Preparation of Compound 3-5

To a solution of compound 3-4 (235.5 mg, 0.3 mmol) in DCM (5 mL) was added a solution of HCl in EtOAc (5 mL, 4 M) at rt. The mixture was stirred at rt for 4 hours and filtered. The filter cake was washed with EtOAc (60 mL) to give the title compound 3-5 as a yellow solid (152 mg, 66%, HPLC: 100%). The compound was characterized by the following spectroscopic data:

MS-ESI: m/z 585.3 [M+H]$^+$; and $^1$H NMR (400 MHz, CD$_3$OD): δ 7.67 (s, 1H), 7.62 (d, J=7.7 Hz, 2H), 7.39-7.47 (m, 4H), 7.35 (d, J=7.7 Hz, 1H), 5.16-5.23 (m, 2H), 3.53-3.59 (m, 4H), 3.00 (s, 2H), 2.20-2.45 (m, 8H), 1.40-1.50 (m, 4H), 1.24-1.27 (br, 3H), 0.82-0.85 (br, 2H), 0.70 (d, J=6.5 Hz, 3H).

Step 7) The Preparation of Compound 3-6

To a solution of compound 3-5 (150 mg, 0.2 mmol), compound 1-7-2 (110.25 mg, 0.6 mmol) and EDCI (201.28 mg, 1 mmol) in DCM (10 mL) in an ice bath was added DIPEA (0.4 mL) dropwise and the mixture was stirred at rt for 12 hours. Water (20 mL) was added to the mixture and the mixture was extracted with DCM (25 mL×3). The combined organic phases was dried over anhydrous Na$_2$SO$_4$ and concentrated in vacuo. The residue was purified by silica gel column chromatography (EtOAc/MeOH (v/v)=60/1) to give the title compound 3-6 as a pale yellow solid (166 mg, 92%, HPLC: 91.7%). The compound was characterized by the following spectroscopic data:

MS-ESI: m/z 899.7 [M+H]$^+$; and $^1$H NMR (400 MHz, CD$_3$OD): δ 7.78-7.90 (m, 2H), 7.61 (d, J=8.0 Hz, 1H), 7.49 (s, 1H), 7.38 (s, 4H), 5.48-5.50 (m, 2H), 4.39 (d, J=7.0 Hz, 2H), 3.73-3.74 (m, 10H), 3.02 (s, 2H), 2.04-2.06 (m, 2H), 1.69-1.81 (m, 6H), 1.44-1.45 (m, 4H), 1.03-1.05 (m, 5H), 0.87-0.95 (m, 15H).

Example 4
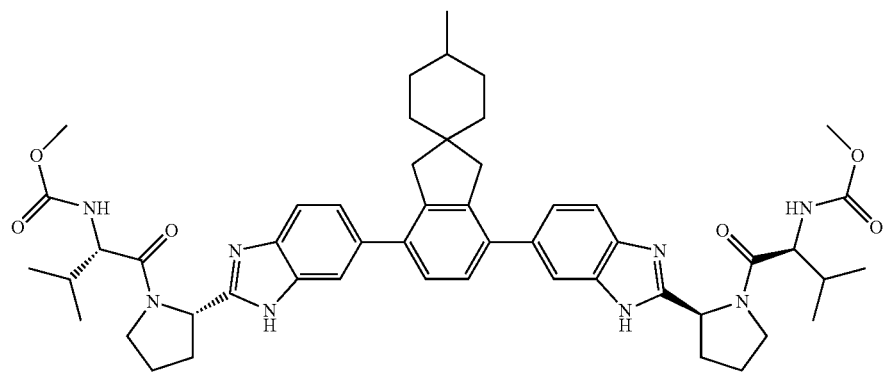 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4c3CC3(CCC(C)CC3)C4)cc2[nH]1)C(C)C]
Synthetic Routes
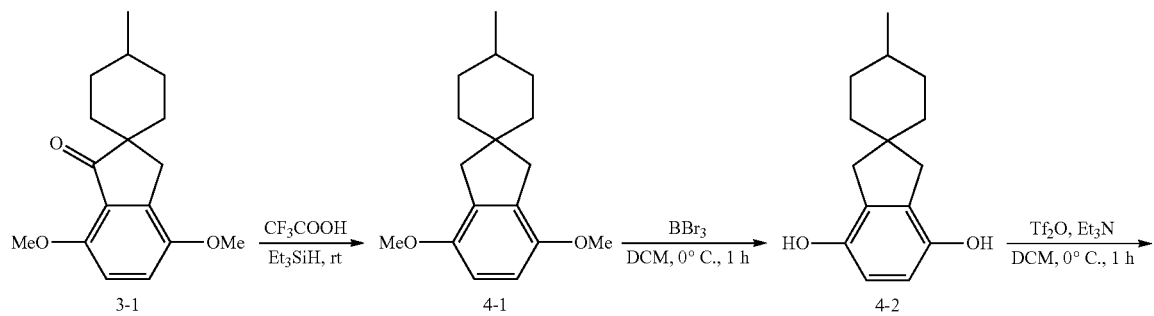
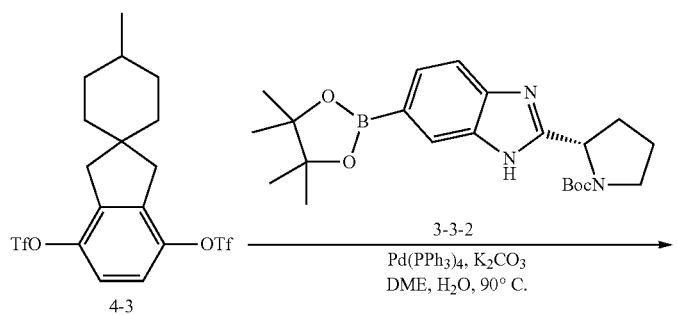
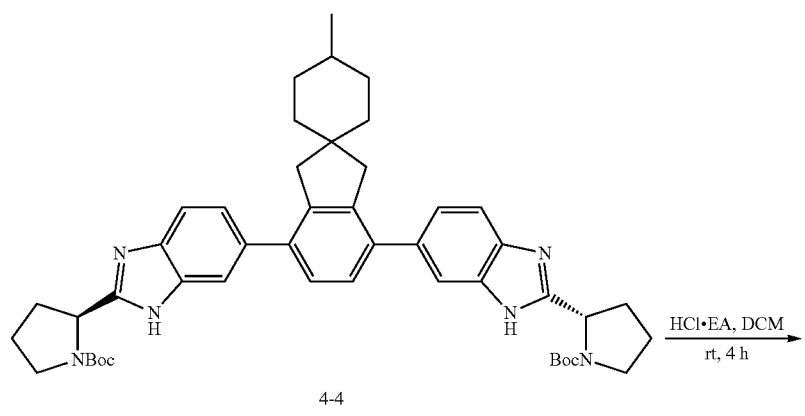

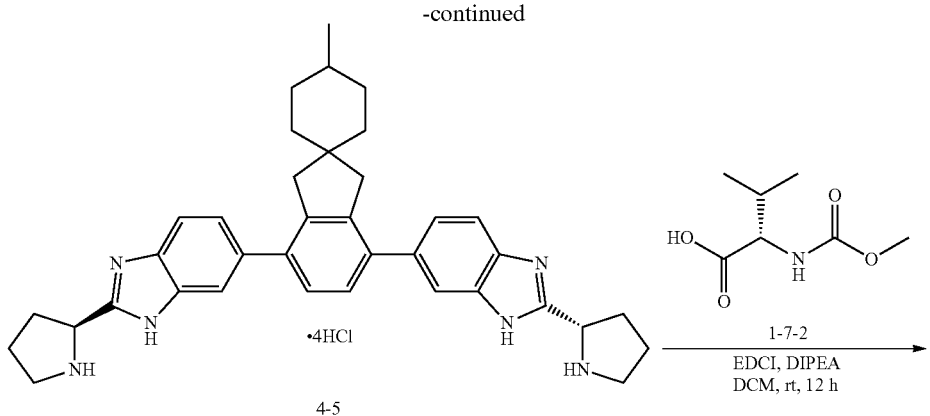

4-5

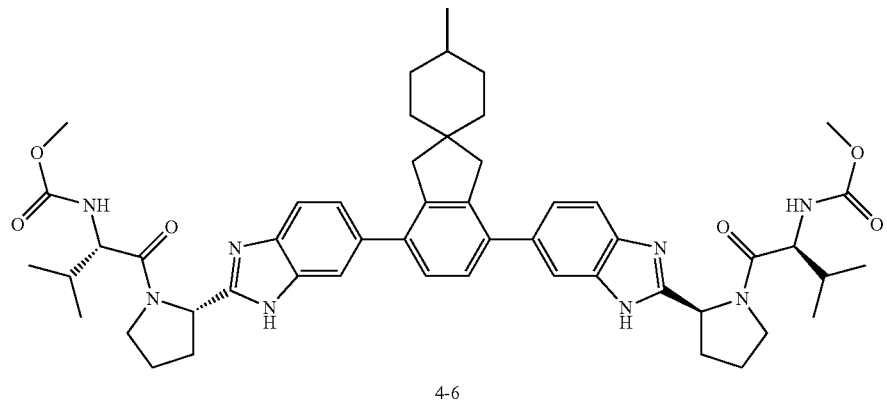 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4c3CC3(CCC(C)CC3)C4)cc2[nH]1)C(C)C]

4-6

Step 1) The Preparation of Compound 4-1

To a mixture of compound 3-1 (959 mg, 3.5 mmol) and triethylsilane (3.3 mL, 21 mmol) in an ice bath was added trifluoroacetic acid (6 mL) dropwise. The resulting mixture was stirred at rt for 8 hours, adjusted to pH 7 with $Na_2CO_3$ saturated solution and extracted with DCM (50 mL×3). The combined organic phases were dried over anhydrous $Na_2SO_4$ and concentrated in vacuo. The residue was purified by silica gel column chromatography (PE/EtOAc (v/v)=3/1) to give the title compound 4-1 as colorless oil (835.5 mg, 92%, HPLC: 64%). The compound was characterized by the following spectroscopic data:

MS-ESI: m/z 261.2 [M+H]$^+$; and $^1$H NMR (400 MHz, CDCl$_3$): δ 6.60 (s, 2H), 3.79 (d, J=5.8 Hz, 6H), 2.76 (s, 2H), 2.70 (s, 2H), 1.66-1.69 (m, 2H), 1.57-1.61 (m, 2H), 1.37-1.41 (m, 3H), 1.10-1.20 (m, 2H), 0.92 (d, J=6.5 Hz, 3H).

Step 2) The Preparation of Compound 4-2

To a solution of compound 4-1 (806 mg, 3.1 mmol) in DCM (20 mL) in an ice bath was added boron tribromide (6 mL, 1.6 mol/L in DCM) dropwise. The resulting mixture was stirred for 1 hour, quenched with ice water (10 mL) and extracted with DCM (20 mL×3). The combined organic phases were dried over anhydrous $Na_2SO_4$ and concentrated in vacuo. The residue was purified by silica gel column chromatography (PE/EtOAc (v/v)=4/1) to give the title compound 4-2 as colorless liquid (700 mg, 97%, HPLC: 65%). The compound was characterized by the following spectroscopic data:

MS-ESI: m/z 233.2 [M+H]$^+$; and $^1$H NMR (400 MHz, CDCl$_3$): δ 8.31 (s, 2H), 6.35 (s, 2H), 2.57 (s, 2H), 2.52 (s, 2H), 1.54-1.56 (m, 4H), 1.35-1.37 (m, 3H), 1.16-1.19 (m, 2H), 0.90 (d, J=6.5 Hz, 3H).

Step 3) The Preparation of Compound 4-3

To a solution of compound 4-2 (696 mg, 3 mmol) and Et$_3$N (3.3 mL) in DCM (25 mL) in an ice bath was added trifluoroacetic anhydride (1.25 mL, 9 mmol) dropwise. The resulting mixture was stirred for 1 hour, quenched with ice water (25 mL) and extracted with DCM (25 mL×3). The combined organic phases were dried over anhydrous $Na_2SO_4$ and concentrated in vacuo. The residue was purified by silica gel column chromatography (PE/EtOAc (v/v)=6/1) to give the title compound 4-3 as pale yellow oil (1041.6 mg, 70%, HPLC: 96%). The compound was characterized by the following spectroscopic data:

$^1$H NMR (400 MHz, CDCl$_3$): δ 7.13 (s, 2H), 2.94 (s, 2H), 2.88 (s, 2H), 1.57-1.64 (m, 5H), 1.37-1.45 (m, 4H), 0.95 (d, J=6.5 Hz, 3H).

Step 4) The Preparation of Compound 4-4

To a mixture of compound 3-3-2 (1032.5 mg, 2.5 mmol), anhydrous potassium carbonate (690 mg, 5 mmol) and Pd(PPh$_3$)$_4$ (115.4 mg, 0.1 mmol) in a 50 mL of two-necked flask under N$_2$ was added a solution of compound 4-3 (496 mg, 1 mmol) in DME (9 mL) via syringe followed by distilled water (3 mL), and the resulting mixture was stirred at 90° C. for 2 hours. DME was removed in vacuo and distilled water (20 mL) was added to the mixture. The mixture was extracted with DCM (20 mL×3). The combined organic phases were dried over anhydrous $Na_2SO_4$ and concentrated in vacuo. The residue was purified by silica gel column chromatography (PE/EtOAc (v/v)=1/1) to give the title compound 4-4 as a pale yellow solid (504 mg, 65%, HPLC: 100%). The compound was characterized by the following spectroscopic data:

MS-ESI: m/z 771.6 [M+H]$^+$; and $^1$H NMR (400 MHz, CDCl$_3$): δ 7.52-7.54 (m, 5H), 7.21-7.43 (m, 3H), 5.20 (br, 2H), 3.47-3.49 (br, 4H), 2.90 (s, 4H), 2.00-2.25 (m, 9H), 1.51 (s, 18H), 1.24-1.28 (m, 8H), 0.80 (d, J=6.4 Hz, 3H).

Step 5) The Preparation of Compound 4-5

To a solution of compound 4-4 (500 mg, 0.65 mmol) in DCM (8 mL) was added a solution of HCl in EtOAc (10 mL, 4 M). The mixture was stirred at rt for 4 hours and filtered. The filter cake was washed with EtOAc (60 mL) to give the title compound 4-5 as a yellow solid (368 mg, 78%, HPLC: 100%). The compound was characterized by the following spectroscopic data:

MS-ESI: m/z 571.5 [M+H]$^+$; and $^1$H NMR (400 MHz, CD$_3$OD): δ 7.64-7.67 (m, 2H), 7.46 (br, 2H), 7.11-7.16 (m, 3H), 6.75-6.92 (m, 1H), 5.04 (br, 2H), 3.47-3.48 (br, 4H), 2.42-2.53 (br, 5H), 2.01-2.09 (m, 7H), 1.09-1.12 (m, 2H), 0.89 (br, 2H), 0.68 (br, 3H), 0.45 (br, 2H), 0.19 (br, 3H).

Step 6) The Preparation of Compound 4-6

To a solution of compound 4-5 (358.5 mg, 0.5 mmol), compound 1-7-2 (262.5 mg, 1.5 mmol) and EDCI (479.25 mg, 2.5 mmol) in DCM (15 mL) in an ice bath was added DIPEA (0.8 mL) dropwise and the mixture was stirred at rt overnight. Water (25 mL) was added to the mixture and the mixture was extracted with DCM (30 mL×3). The combined organic phases were dried over anhydrous Na$_2$SO$_4$ and concentrated in vacuo. The residue was purified by silica gel column chromatography (EtOAc/MeOH (v/v)=50/1) to give the title compound 4-6 as a pale yellow solid (430 mg, 97%, HPLC: 95.9%). The compound was characterized by the following spectroscopic data:

MS-ESI: m/z 885.8 [M+H]$^+$; and $^1$H NMR (400 MHz, CD$_3$OD): δ 10.50-10.57 (m, 2H), 7.76-7.86 (m, 2H), 7.29-7.48 (m, 6H), 5.44-5.45 (br, 4H), 4.35 (br, 2H), 3.86-3.88 (br, 2H), 3.71 (s, 6H), 3.63-3.66 (br, 2H), 2.92-2.96 (br, 4H), 2.37-2.39 (m, 2H), 2.20 (br, 4H), 1.97-1.98 (br, 4H), 1.63 (br, 4H), 1.05-1.09 (m, 3H), 0.88-0.89 (m, 15H).

Example 5

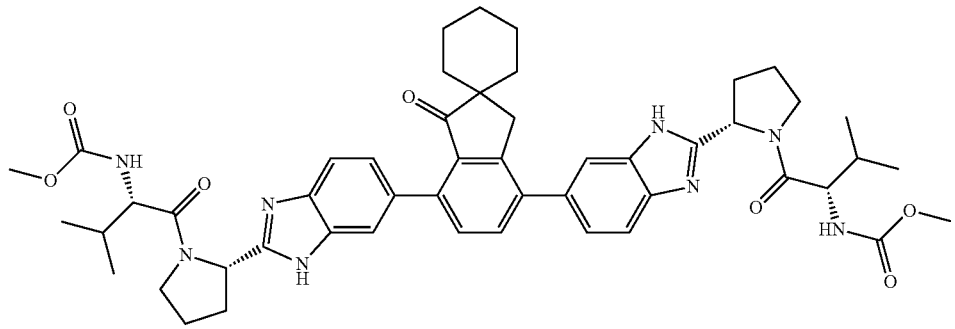

Synthetic Routes

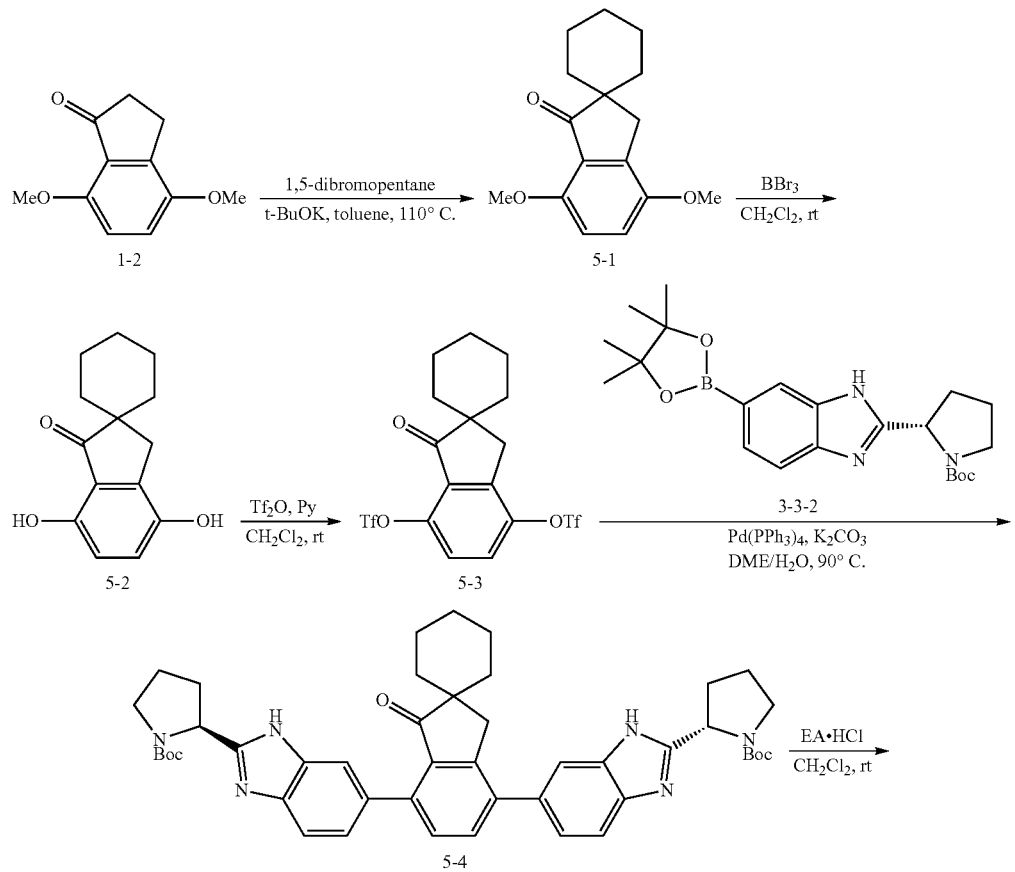

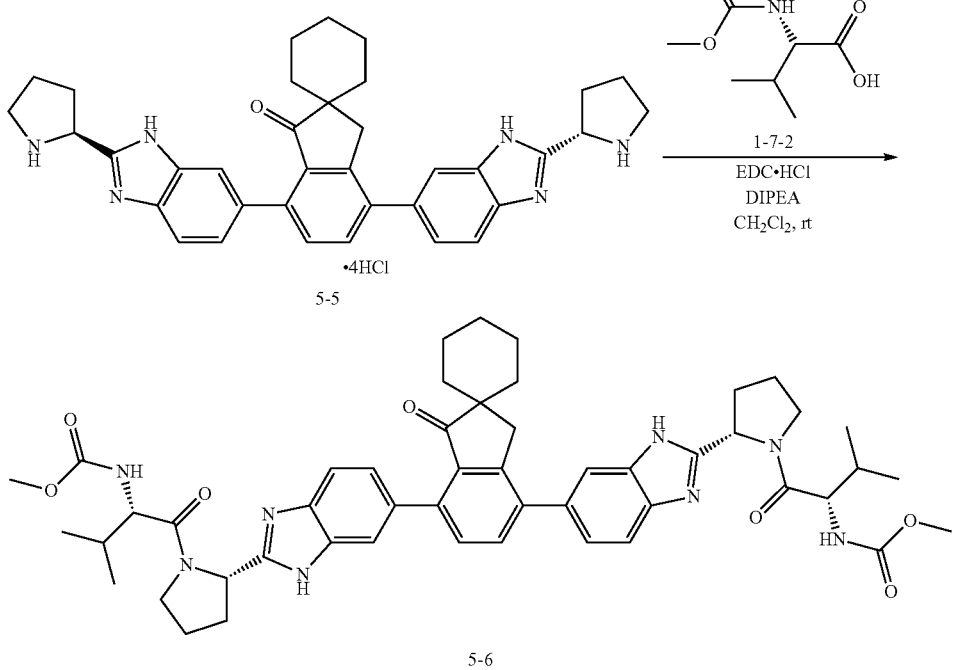

Step 1) the Preparation of Compound 5-1

To a mixture of potassium tert-butanolate (1.17 g, 10.41 mmol) in toluene (5 mL) in an ice bath was added dropwise a solution of compound 1-2 (0.80 g, 4.16 mmol) and 1,5-dibromopentane (0.62 mL, 4.58 mmol) in toluene (20 mL). The reaction mixture was stirred at 110° C. for 2.5 hours, cooled to rt and water (20 mL) was added. The toluene was removed under reduced pressure. To the residue was added water (30 mL) and the resulting mixture was extracted with EtOAc (30 mL×3). The combined organic phases were washed with brine, dried over anhydrous $Na_2SO_4$ and concentrated in vacuo. The residue was purified by silica gel column chromatography (PE/EtOAc (v/v)=4/1) to give the title compound as a pale yellow solid (0.63 g, 58%). The compound was characterized by the following spectroscopic data:

MS-ESI: m/z 261.2 [M+H]$^+$; and $^1$H NMR (400 MHz, CDCl$_3$): δ 6.98 (d, J=8.7 Hz, 1H), 6.73 (d, J=8.7 Hz, 1H), 3.89 (s, 3H), 3.86 (s, 3H), 2.88 (s, 2H), 1.82-1.68 (m, 5H), 1.51-1.26 (m, 5H).

Step 2) The Preparation of Compound 5-2

To a solution of compound 5-1 (0.63 g, 2.42 mmol) in anhydrous DCM (20 mL) was added dropwise boron tribromide (0.92 mL, 9.68 mmol) via syringe in an ice bath. After the reaction mixture was stirred for 20 minutes, the ice bath was removed. The mixture was stirred at rt for 1.5 hours and quenched with ice water (10 mL) in an ice bath. DCM was removed in vacuo and to the residue was added water (20 mL). The resulting mixture was extracted with EtOAc (30 mL×3). The combined organic phases were washed with brine, dried over anhydrous $Na_2SO_4$ and concentrated in vacuo. The residue was purified by silica gel column chromatography (PE/EtOAc (v/v)=6/1) to give the title compound as a white solid (0.52 g, 92%). The compound was characterized by the following spectroscopic data:

MS-ESI: m/z 230.9 [M−H]$^-$; and $^1$H NMR (400 MHz, CDCl$_3$): δ 8.61 (s, 1H), 6.95 (d, J=8.6 Hz, 1H), 6.68 (d, J=8.6 Hz, 1H), 4.75 (s, 1H), 2.92 (s, 2H), 1.88-1.56 (m, 5H), 1.50-1.34 (m, 5H).

Step 3) The Preparation of Compound 5-3

To a solution of compound 5-2 (0.50 g, 2.15 mmol) in anhydrous DCM (20 mL) in an ice bath under $N_2$ was added dropwise Tf$_2$O (0.9 mL, 6.5 mmol) followed by pyridine (4 mL). After the reaction mixture was stirred for 20 minutes, the ice bath was removed. The mixture was stirred at rt for 2 hours and quenched with ice water (10 mL) in an ice bath. DCM was removed in vacuo and to the residue was added water (20 mL). The resulting mixture was extracted with EtOAc (30 mL×3). The combined organic phases were washed with brine, dried over anhydrous $Na_2SO_4$ and concentrated in vacuo. The residue was purified by silica gel column chromatography (PE/EtOAc (v/v)=15/1) to give the title compound as pale yellow oil (0.95 g, 89%). The compound was characterized by the following spectroscopic data:

MS-ESI: m/z 497.0 [M+H]$^+$; and $^1$H NMR (400 MHz, CDCl$_3$): δ 7.58 (d, J=8.8 Hz, 1H), 7.30 (d, J=8.8 Hz, 1H), 3.11 (s, 2H), 1.90-1.69 (m, 5H), 1.51-1.37 (m, 5H).

Step 4) The Preparation of Compound 5-4

To a suspension of compound 3-3-2 (0.916 g, 2.2 mmol), anhydrous potassium carbonate (0.7 g, 5 mmol) and Pd(PPh$_3$)$_4$ (0.12 g, 0.1 mmol) in a 25 mL of two-necked flask under $N_2$ was added a solution of compound 5-3 (0.5 g, 1 mmol) in DME (8 mL) via syringe followed by distilled water (2 mL). The mixture was stirred at 90° C. overnight under $N_2$. After the reaction mixture was cooled to rt, water (40 mL) was added, and the mixture was extracted with EtOAc (30 mL×3). The combined organic phases were washed with brine, dried over anhydrous $Na_2SO_4$ and concentrated in vacuo. The residue was purified by silica gel column chromatography (PE/EtOAc (v/v)=4/1) to give the title compound as a white solid (0.58 g, 75%). The compound was characterized by the following spectroscopic data:

MS-ESI: m/z 768.5 [M−H]$^-$; and $^1$H NMR (400 MHz, CDCl$_3$): δ 10.94-10.58 (m, 2H), 7.93-7.29 (m, 8H), 5.22-5.10 (m, 2H), 3.57-3.38 (br, 4H), 3.11-2.95 (m, 4H), 2.34-2.12 (br, 4H), 2.11-1.92 (m, 4H), 1.87-1.27 (m, 30H).

Step 5) The Preparation of Compound 5-5

To a solution of compound 5-4 (0.53 g, 0.68 mmol) in DCM (3 mL) was added a solution of HCl in EtOAc (10 mL, 4 M) in an ice bath. The resulting mixture was stirred at rt for 2.5 hours and white solid precipitated out. The solvent was removed under reduced pressure. The residue was washed with EtOAc (5 mL) assisted by sonicating in an ultrasonic cleaner, then kept still and the supernatant was discarded. The washing was repeated two more times and the residue was then concentrated in vacuo to give compound 5-5 as a white solid (0.46 g, 97%). The compound was characterized by the following spectroscopic data:

MS-ESI: m/z 568.7 [M−H]−; and $^1$H NMR (400 MHz, D$_2$O): δ 7.82 (d, J=0.8 Hz, 1H), 7.80-7.75 (m, 2H), 7.73 (dd, J=8.6, 0.4 Hz, 1H), 7.67 (d, J=7.7 Hz, 1H), 7.57 (dd, J=8.5, 1.5 Hz, 1H), 7.49 (dd, J=8.6, 1.5 Hz, 1H), 7.39 (d, J=7.7 Hz, 1H), 5.27-5.20 (m, 2H), 3.61-3.50 (m, 4H), 3.02 (s, 2H), 2.77-2.65 (m, 2H), 2.53-2.13 (m, 6H), 1.62-1.10 (m, 10H).

Step 6) The Preparation of Compound 5-6

To a mixture of compound 5-5 (0.25 g, 0.36 mmol), compound 1-7-2 (0.19 g, 1.07 mmol) and EDCI (0.27 g, 1.43 mmol) in DCM (4 mL) in an ice bath was added DIPEA (0.75 mL, 4.29 mmol) slowly under N$_2$. At the end of the addition, the resulting mixture was stirred at rt overnight and DCM was removed under reduced pressure. To the residue was added water (40 mL) and the mixture was extracted with EtOAc (30 mL×3). The combined organic phases were washed with brine, dried over anhydrous Na$_2$SO$_4$ and concentrated in vacuo. The residue was purified by silica gel column chromatography (DCM/MeOH (v/v)=60/1) to give the title compound as a white solid (0.26 g, 81%). The compound was characterized by the following spectroscopic data:

MS-ESI: m/z 882.4 [M−H]−; and $^1$H NMR (400 MHz, CDCl$_3$): δ 10.90-10.55 (m, 2H), 7.94-7.18 (m, 8H), 5.88-5.56 (m, 2H), 5.54-5.33 (m, 2H), 4.46-4.30 (br, 2H), 3.98-3.63 (m, 10H), 3.16-2.93 (m, 4H), 2.53-1.17 (m, 24H), 0.98-0.80 (m, 12H).

Example 6

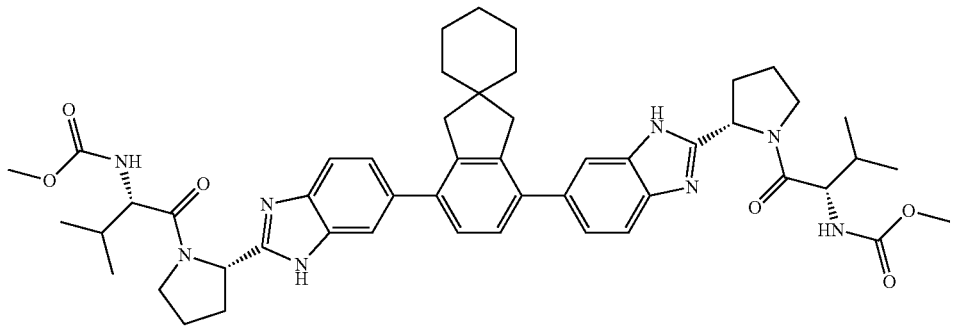

Synthetic Routes

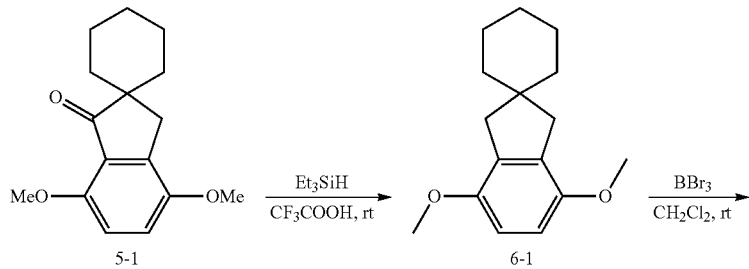

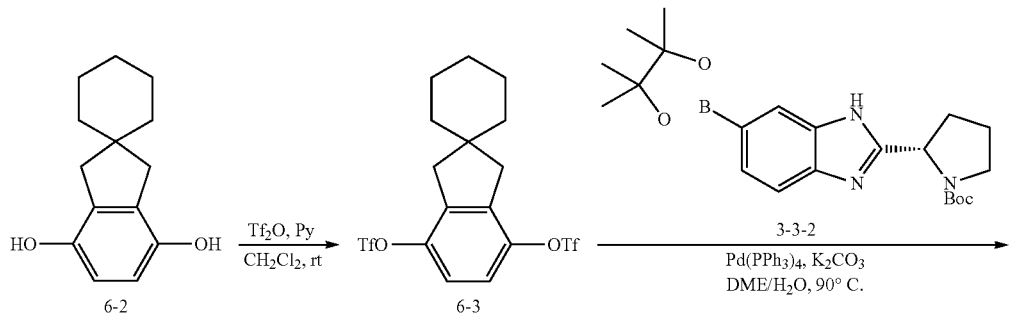

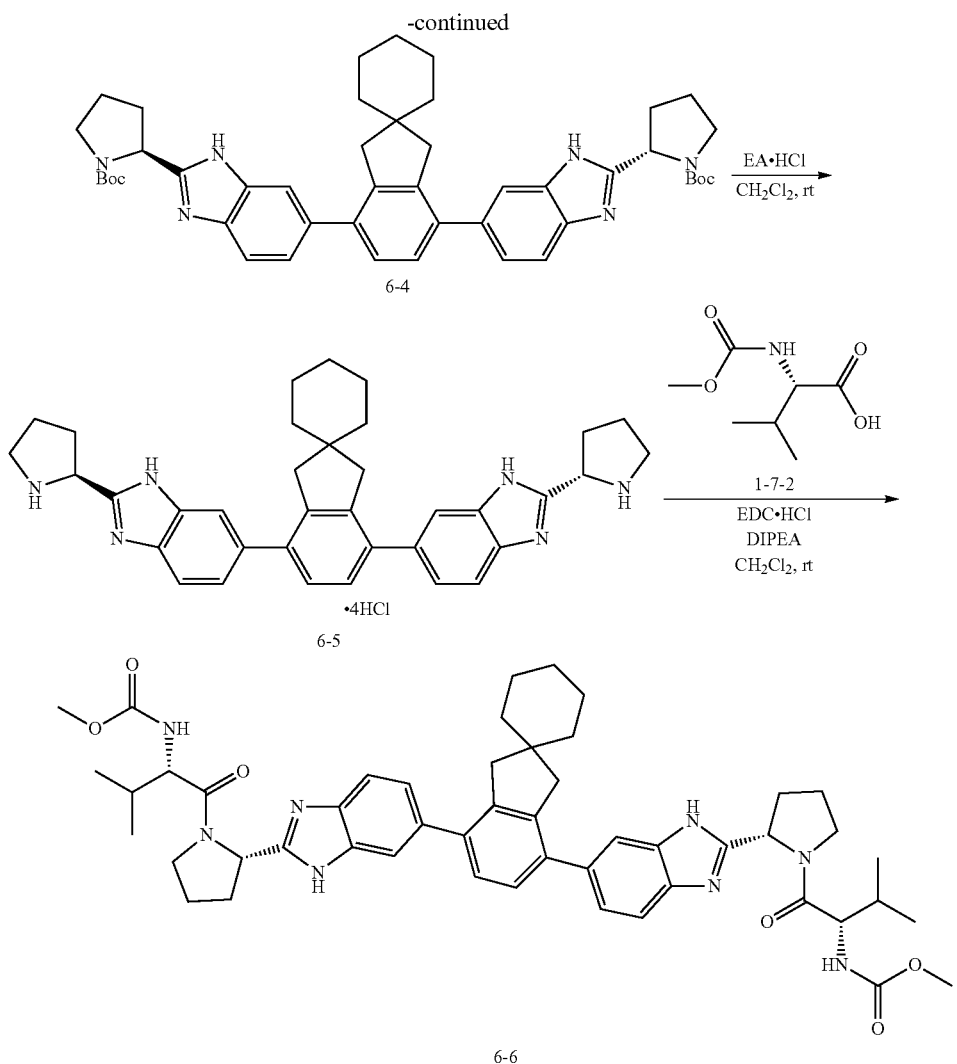

Step 1) The Preparation of Compound 6-1

To a mixture of compound 5-1 (1 g, 3.8 mmol) and triethylsilane (3.7 mL, 23 mmol) in an ice bath was added dropwise trifluoroacetic acid (8 mL) via syringe under $N_2$. After the resulting mixture was stirred for 10 minutes, the ice bath was removed. The mixture was stirred at rt for 7 hours and quenched with $Na_2CO_3$ saturated solution in an ice bath until there was no more gas evolution. Water (40 mL) was added, and the mixture was extracted with EtOAc (30 mL×3). The combined organic phases were washed with brine, dried over anhydrous $Na_2SO_4$ and concentrated in vacuo. The residue was purified by silica gel column chromatography (PE/EtOAc (v/v)=5/1) to give the title compound 6-1 as pale yellow oil (0.81 g, 87%). The compound was characterized by the following spectroscopic data:

MS-ESI: m/z 247.2 [M+H]$^+$; and $^1$H NMR (400 MHz, CDCl$_3$): δ 6.61 (s, 2H), 3.79 (s, 6H), 2.74 (s, 4H), 1.58-1.40 (m, 10H).

Step 2) The Preparation of Compound 6-2

To a solution of compound 6-1 (0.78 g, 3.17 mmol) in anhydrous DCM (20 mL) in an ice bath was added dropwise boron tribromide (1.20 mL, 12.67 mmol) via syringe under $N_2$. After the resulting mixture was stirred for 20 minutes, the ice bath was removed. The resulting mixture was stirred at rt for 2 hours and quenched with ice water in an ice bath. DCM was removed under reduced pressure and to the residue was added water (40 mL). The mixture was extracted with EtOAc (30 mL×3). The combined organic phases were washed with brine, dried over anhydrous $Na_2SO_4$ and concentrated in vacuo. The residue was purified by silica gel column chromatography (PE/EtOAc (v/v)=5/1) to give compound 6-2 as pale yellow oil (0.7 g, 100%). The compound was characterized by the following spectroscopic data:

MS-ESI: m/z 219.2 [M+H]$^+$; and $^1$H NMR (400 MHz, CDCl$_3$): δ 6.49 (s, 2H), 5.07-4.53 (br, 2H), 2.68 (s, 4H), 1.59-1.37 (m, 10H).

Step 3) The Preparation of Compound 6-3

To a solution of compound 6-2 (0.69 g, 3.16 mmol) in anhydrous DCM (20 mL) under $N_2$ in an ice bath was added Tf$_2$O (3.19 mL, 19.97 mmol) via syringe followed by pyridine (2.03 mL, 25.29 mmol). After the resulting mixture was stirred for 20 minutes, the ice bath was removed. The resulting mixture was stirred at rt for 5 hours and quenched with ice water in an ice bath. DCM was removed under reduced pressure and to the residue was added water (40 mL). The mixture was extracted with EtOAc (30 mL×3). The combined organic phases were washed with brine, dried over anhydrous $Na_2SO_4$ and concentrated in vacuo. The residue was purified by silica gel column chromatography (PE/DCM (v/v)=6/1) to give compound 6-3 as colorless oil (1.11 g, 73%). The compound was characterized by the following spectroscopic data:

$^1$H NMR (400 MHz, CDCl$_3$): δ 7.13 (s, 2H), 2.92 (s, 4H), 1.59-1.41 (m, 10H).

Step 4) The Preparation of Compound 6-4

To a mixture of compound 6-3 (0.50 g, 1.04 mmol), compound 3-3-2 (1.03 g, 2.49 mmol), Pd(PPh$_3$)$_4$ (0.12 g, 0.10 mmol) and potassium carbonate (0.43 g, 3.14 mmol) in a 25 mL of two-necked flask under N$_2$ was added DME (8 mL) via syringe followed by pure water (2 mL). The resulting mixture was stirred at 90° C. overnight. After the mixture was cooled to rt, water (40 mL) was added. The mixture was extracted with EtOAc (30 mL×3). The combined organic phases were washed with brine, dried over anhydrous Na$_2$SO$_4$ and concentrated in vacuo. The residue was purified by silica gel column chromatography (DCM/MeOH (v/v)=60/1) to give compound 6-4 as a white solid (0.73 g, 93%). The compound was characterized by the following spectroscopic data:

MS-ESI: m/z 757.6 [M+H]$^+$; and $^1$H NMR (400 MHz, CDCl$_3$): δ 11.10-10.32 (br, 2H), 8.03-7.44 (m, 4H), 7.38 (d, J=8.2 Hz, 2H), 7.30 (s, 2H), 5.22-5.11 (m, 2H), 3.51-3.39 (m, 4H), 3.18-3.02 (m, 2H), 2.93 (s, 4H), 2.32-2.15 (m, 4H), 2.10-1.99 (m, 2H), 1.60-1.30 (m, 28H).

Step 5) The Preparation of Compound 6-5

To a solution of compound 6-4 (0.71 g, 0.94 mmol) in DCM (5 mL) was added a solution of HCl in EtOAc (10 mL, 4 M) in an ice bath. At the end of the addition, the mixture was stirred at rt for 3.5 hours and white solid precipitated out. The solvent was removed under reduced pressure. The residue was washed with EtOAc (5 mL) assisted by sonicating in an ultrasonic cleaner, then kept still and the supernatant was discarded. The washing was repeated two more times and the residue was then concentrated in vacuo to get compound 6-5 as a white solid (0.53 g, 80%). The compound was characterized by the following spectroscopic data:

MS-ESI: m/z 554.8 [M−H]$^-$; and $^1$H NMR (400 MHz, D$_2$O): δ 7.73 (s, 2H), 7.67 (d, J=6.6 Hz, 2H), 7.39 (br, 2H), 7.24 (s, 2H), 5.16 (t, J=8.0 Hz, 2H), 3.60-3.49 (m, 4H), 2.68 (s, 4H), 2.67-2.50 (m, 2H), 2.45-2.17 (m, 6H), 1.30-0.82 (m, 10H).

Step 6) The Preparation of Compound 6-6

To a suspension of compound 6-5 (0.40 g, 0.57 mmol), compound 1-7-2 (0.30 g, 1.71 mmol) and EDC.HCl (0.44 g, 2.28 mmol) in DCM (4 mL) under N$_2$ in an ice bath was added DIPEA (1.19 mL, 6.83 mmol) dropwise via syringe. At the end of the addition, the mixture was stirred at rt overnight. DCM was removed under reduced pressure. Water (20 mL) was added to the mixture and the mixture was extracted with DCM (30 mL×3). The combined organic phases were washed with brine, dried over anhydrous Na$_2$SO$_4$ and concentrated in vacuo. The residue was purified by silica gel column chromatography (DCM/MeOH (v/v)=40/1) to give compound 6-6 as a white solid (0.43 g, 86%). The compound was characterized by the following spectroscopic data:

MS-ESI: m/z 869.4 [M−H]$^-$; and $^1$H NMR (400 MHz, CDCl$_3$): δ 10.72-10.53 (m, 2H), 7.88 (d, J=4.6 Hz, 1H), 7.80 (d, J=8.3 Hz, 1H), 7.47 (s, 1H), 7.45-7.23 (m, 5H), 5.72-5.36 (m, 4H), 4.44-4.34 (m, 2H), 3.98-3.66 (m, 10H), 3.20-3.07 (m, 2H), 3.02-2.87 (m, 4H), 2.50-2.37 (m, 2H), 2.35-2.14 (m, 4H), 2.10-1.95 (m, 2H), 1.55-1.32 (m, 12H), 0.98-0.80 (m, 12H).

Example 7

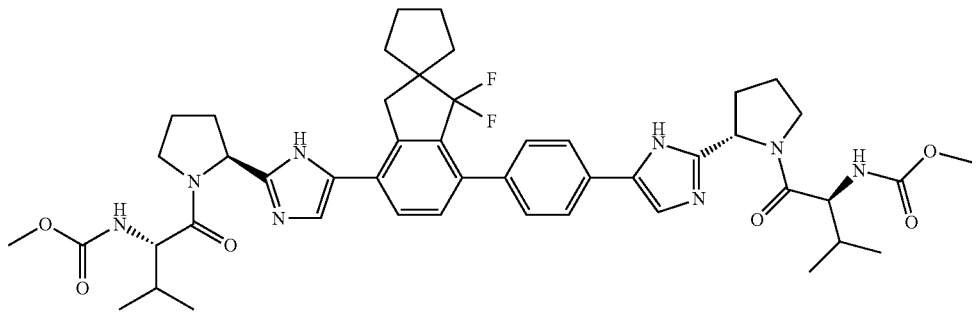

Synthetic routes

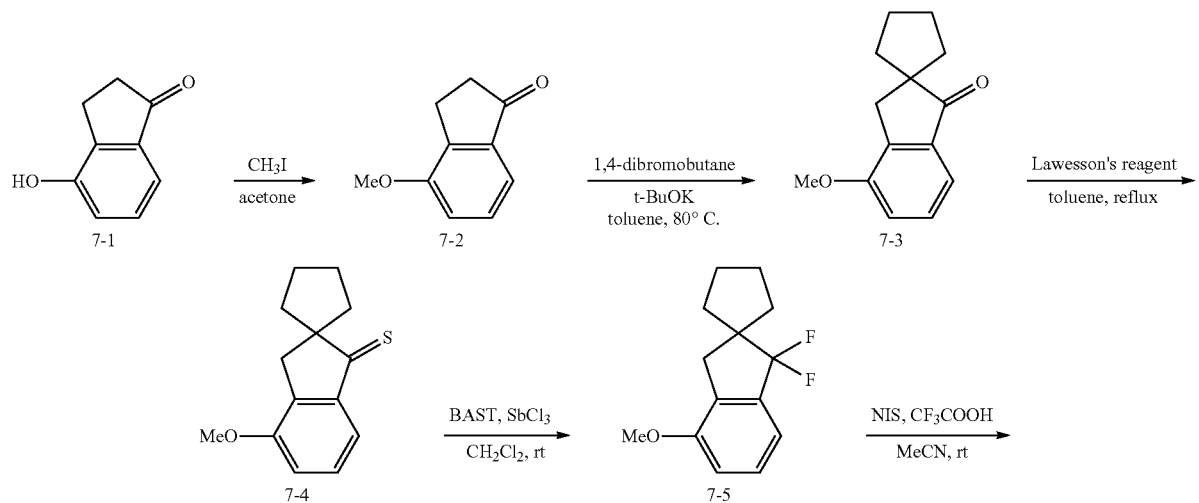

-continued
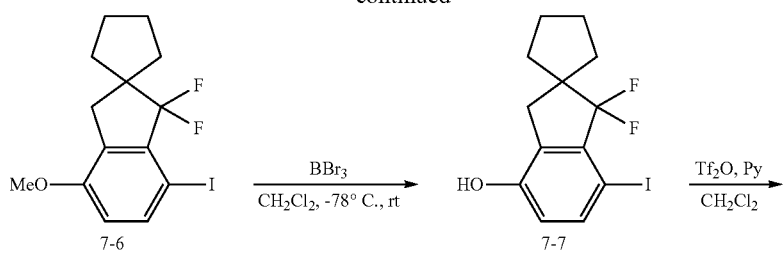
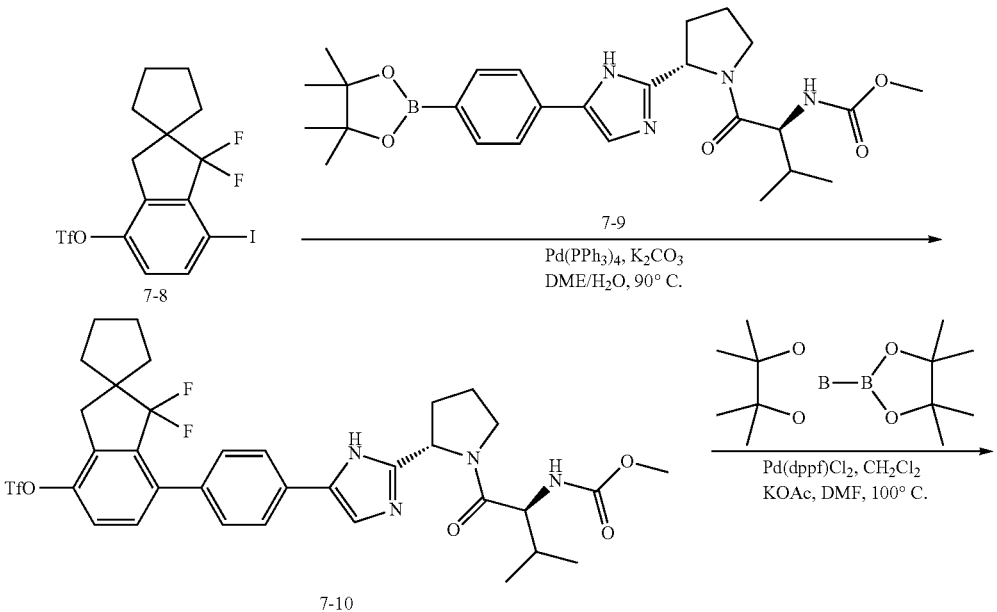
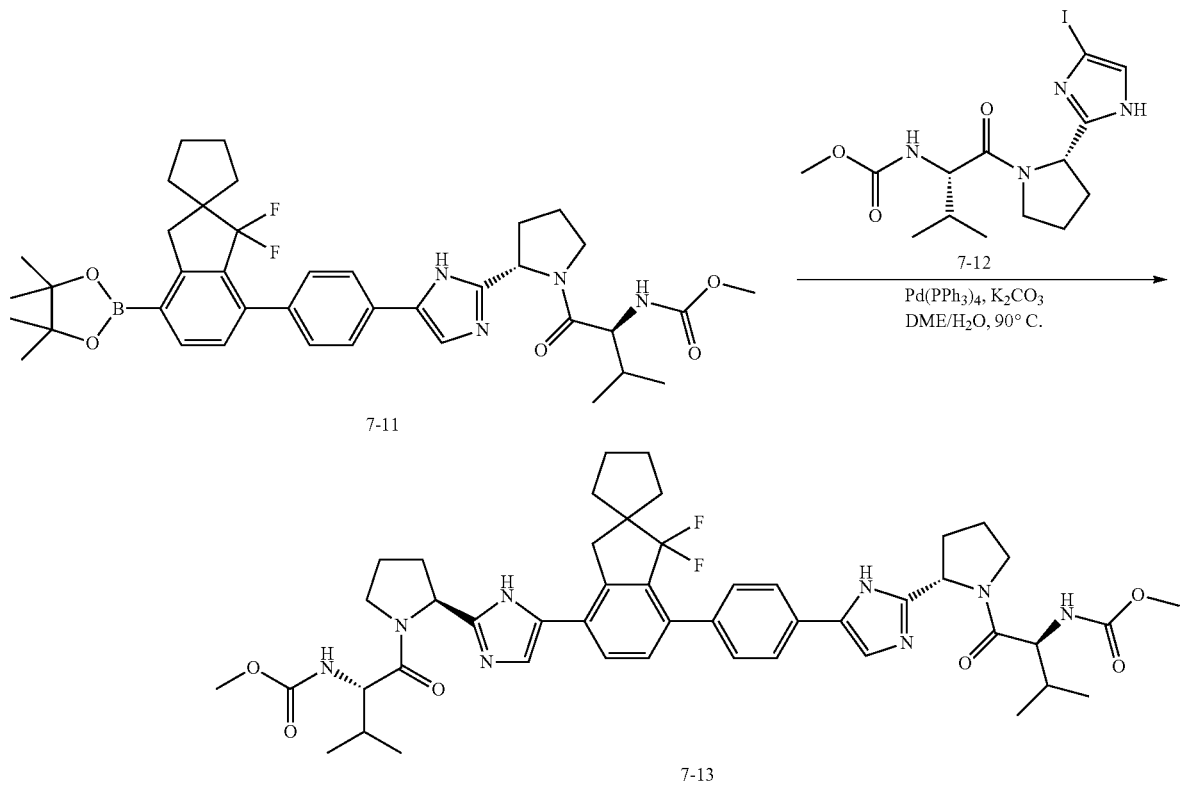

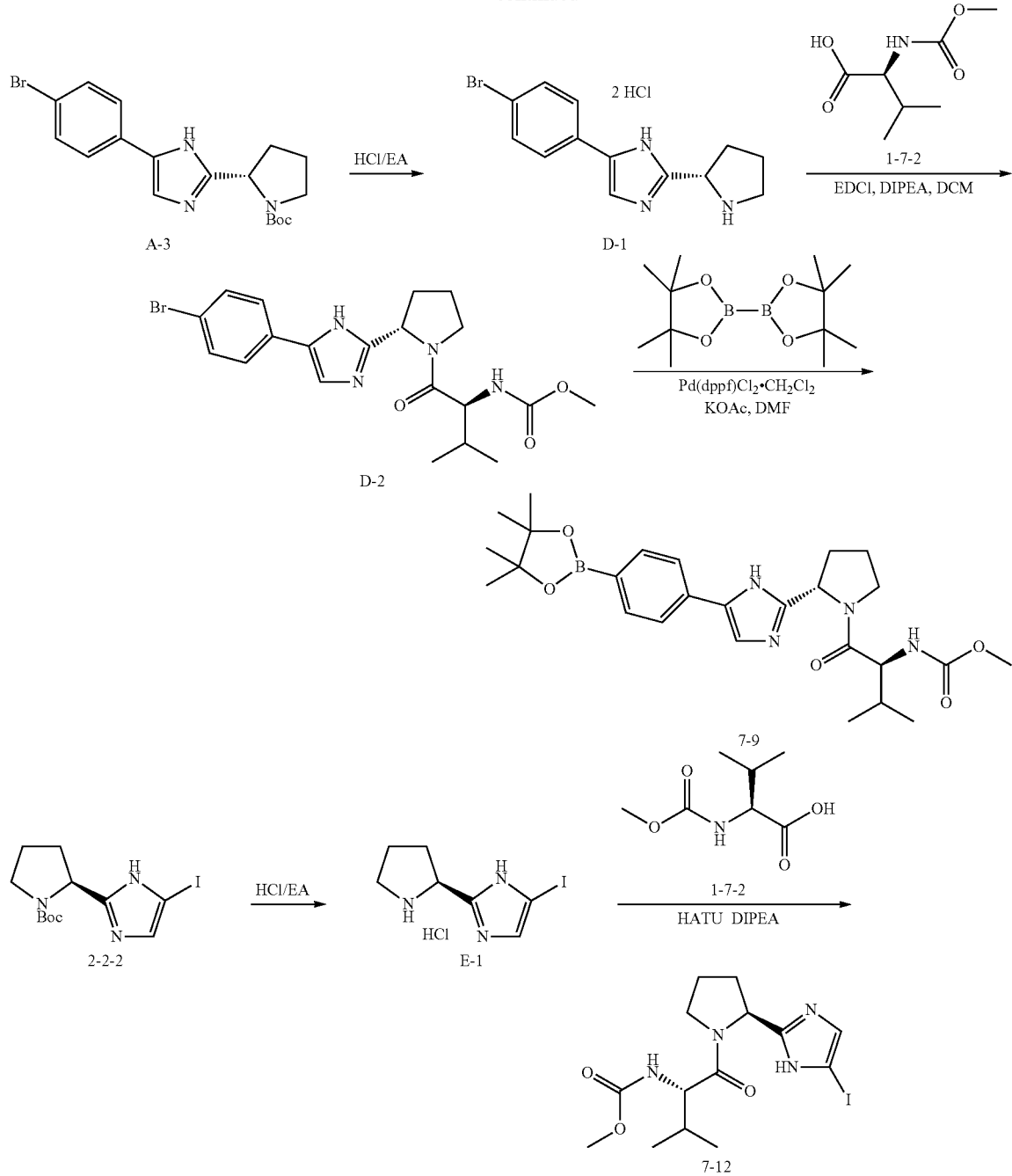

Step 1) The Preparation of Compound 7-2

A mixture of compound 7-1 (5.0 g, 33.7 mmol), K₂CO₃ (23.4 g, 168.5 mmol) and iodomethane in acetone (50 mL) in a sealed tube was stirred at 60° C. for 5 hours. After the mixture was cooled to rt, the solvent was removed in vacuo, and to the residue were added water (150 mL) and EtOAc (150 mL). When the mixture was mixed well, the mixture was filtered through a Celite pad. After the layers were partitioned, the aqueous phase was extracted with EtOAc (150 mL×2). The combined organic phases were washed with brine, dried over anhydrous Na₂SO₄ and concentrated in vacuo. The residue was purified by silica gel column chromatography (PE/EtOAc (v/v)=4/1) to give the title compound 7-2 as a yellow solid (2.5 g, 45%).

Step 2) The Preparation of Compound 7-3

To a suspension of t-BuOK (3.7 g, 32.6 mmol) in toluene (10 mL) under N₂ in an ice bath was added dropwise a solution of compound 7-2 (2.3 g, 14.2 mmol) and 1,4-dibromobutane (3.6 g, 15.6 mmol) in toluene (30 mL). At the end of the addition, the ice bath was removed and the mixture was stirred at 80° C. for 3.5 hours. After the reaction was completed, the mixture was cooled to rt and water (20 mL) was added. The toluene was removed in vacuo, and to the residue was added water (40 mL). The resulting mixture was extracted with EtOAc (50 mL×3). The combined organic phases were washed with brine, dried over anhydrous Na₂SO₄ and concentrated in vacuo. The residue was purified by silica gel column chromatography (PE/EtOAc (v/v)=8/1)

to give compound 7-3 as pale yellow oil (2.3 g, 72%). The compound was characterized by the following spectroscopic data:

MS-ESI: m/z 231.2 [M+H]$^+$; and $^1$H NMR (400 MHz, CDCl$_3$): δ 7.37-7.31 (m, 2H), 7.03 (dd, J=6.2, 2.5 Hz, 1H), 3.91 (s, 3H), 2.93 (s, 2H), 1.83-1.64 (m, 6H), 1.52-1.42 (m, 4H).

Step 3) The Preparation of Compound 7-4

To a solution of compound 7-3 (0.50 g, 2.3 mmol) in toluene (10 mL) under N$_2$ was added Lawesson's reagent (0.47 g, 1.16 mmol). The mixture was refluxed for 18 hours and concentrated in vacuo. The residue was purified by silica gel column chromatography (PE/EtOAc (v/v)=5/1) to give compound 7-4 as purple liquid (0.48 g, 89%). The compound was characterized by the following spectroscopic data:

MS-ESI: m/z 233.2 [M+H]$^+$; and $^1$H NMR (400 MHz, CDCl$_3$): δ 7.57 (d, J=7.8 Hz, 1H), 7.30 (t, J=7.8 Hz, 1H), 7.06 (d, J=7.8 Hz, 1H), 3.91 (s, 3H), 3.03 (s, 2H), 2.20-2.08 (m, 2H), 2.05-1.93 (m, 2H), 1.92-1.79 (m, 2H), 1.73-1.65 (m, 2H).

Step 4) The Preparation of Compound 7-5

To a solution of compound 7-4 (0.50 g, 2.15 mmol) in DCM (20 mL) under N$_2$ in an ice bath were added SbCl$_3$ (0.05 g, 0.22 mmol) and BAST (0.60 mL, 3.23 mmol). At the end of the addition, the ice bath was removed, and the mixture was stirred at rt for 18 hours. The reaction mixture was quenched with NaHCO$_3$ saturated solution in an ice bath and extracted with DCM (50 mL×3). The combined organic phases were washed with brine, dried over anhydrous Na$_2$SO$_4$ and concentrated in vacuo. The residue was purified by silica gel column chromatography (PE/EtOAc (v/v)=6/1) to give compound 7-5 as colorless liquid (0.38 g, 74%). The compound was characterized by the following spectroscopic data:

MS-ESI: m/z 239.2 [M+H]$^+$; and $^1$H NMR (400 MHz, CDCl$_3$): δ 7.29 (t, J=7.8 Hz, 1H), 7.13 (d, J=7.5 Hz, 1H), 6.88 (d, J=8.1 Hz, 1H), 3.84 (s, 3H), 2.83 (s, 2H), 2.12-1.96 (m, 2H), 1.88-1.68 (m, 4H), 1.55-1.42 (m, 2H).

Step 5) The Preparation of Compound 7-6

To a solution of compound 7-5 (1.00 g, 4.20 mmol) and NIS (1.03 g, 4.62 mmol) in acetonitrile (20 mL) in an ice bath was added TFA (0.2 mL) dropwise. Then the mixture was stirred at rt overnight, neutralized with NaHCO$_3$ saturated solution and extracted with EtOAc (20 mL×3). The combined organic phases were washed with brine, dried over anhydrous Na$_2$SO$_4$ and concentrated in vacuo. The residue was purified by silica gel column chromatography (PE/EtOAc (v/v)=6/1) to give the title compound 7-6 as reddish brown oil (0.63 g, 40%). The compound was characterized by the following spectroscopic data:

MS-ESI: m/z 365.0 [M+H]$^+$; and $^1$H NMR (400 MHz, CDCl$_3$): δ 7.65 (d, J=8.5 Hz, 1H), 6.62 (d, J=8.5 Hz, 1H), 3.82 (s, 3H), 2.83 (s, 2H), 2.12-2.00 (m, 2H), 1.88-1.68 (m, 4H), 1.55-1.42 (m, 2H).

Step 6) The Preparation of Compound 7-7

To a solution of compound 7-6 (3.2 g, 8.8 mmol) in anhydrous DCM (50 mL) at −78° C. was added BBr$_3$ (2.5 mL, 26.4 mmol) via syringe under N$_2$. The mixture was stirred at −78° C. for 10 minutes and at rt overnight. The resulting mixture was quenched with ice water in an ice bath. DCM was removed in vacuo and to the residue was added water (80 mL). The resulting mixture was extracted with EtOAc (60 mL×3). The combined organic phases were washed with brine, dried over anhydrous Na$_2$SO$_4$ and concentrated in vacuo. The residue was purified by silica gel column chromatography (PE/EtOAc (v/v)=4/1) to give the title compound 7-7 as a yellow solid (1.3 g, 42%). The compound was characterized by the following spectroscopic data:

MS-ESI: m/z 351.0 [M+H]$^+$; and $^1$H NMR (400 MHz, CDCl$_3$): δ 7.65 (d, J=8.5 Hz, 1H), 6.62 (d, J=8.5 Hz, 1H), 5.01 (s, 1H), 2.83 (s, 2H), 2.12-2.00 (m, 2H), 1.88-1.68 (m, 4H), 1.55-1.42 (m, 2H).

Step 7) The Preparation of Compound 7-8

To a solution of compound 7-7 (2.7 g, 7.7 mmol) in anhydrous DCM (50 mL) in an ice bath was added pyridine (3.1 mL, 38.6 mmol) via syringe followed by Tf$_2$O (3.9 mL, 23.1 mmol) under N$_2$. After the mixture was stirred for 20 minutes, the ice bath was removed and the mixture was stirred at rt for 3 hours. The reaction mixture was quenched with ice water in an ice bath. Water (50 mL) was added to the mixture and the mixture was extracted with DCM (60 mL×3). The combined organic phases were washed with brine, dried over anhydrous Na$_2$SO$_4$ and concentrated in vacuo. The residue was purified by silica gel column chromatography (PE/EtOAc (v/v)=8/1) to give the title compound 7-8 as pale yellow oil (3.1 g, 83%). The compound was characterized by the following spectroscopic data:

MS-ESI: m/z 483.0 [M+H]$^+$; and $^1$H NMR (400 MHz, CDCl$_3$): δ 7.73 (d, J=8.6 Hz, 1H), 7.11 (d, J=8.6 Hz, 1H), 2.85 (s, 2H), 2.16-2.04 (m, 2H), 1.88-1.68 (m, 4H), 1.55-1.42 (m, 2H).

Step 8) The Preparation of Compound 7-9

To a solution of compound A-3 (10.0 g, 25.5 mmol) in EtOAc (50.0 mL) was added a solution of HCl in EtOAc (20.0 mL, 4 M). The mixture was stirred at rt overnight and filtered. The filter cake was washed with EtOAc to give compound D-1 as a pale yellow solid (8.0 g). The compound was characterized by the following spectroscopic data:

$^1$H NMR (400 MHz, CDCl$_3$): δ 7.76-7.73 (m, 2H), 7.66-7.63 (m, 2H), 7.21-7.20 (m, 1H), 5.50-5.22 (m, 2H), 4.49-4.39 (m, 1H), 3.61-3.56 (m, 1H), 3.49-3.39 (m, 1H), 2.31-2.21 (m, 2H), 2.12-2.01 (m, 1H), 1.98-1.85 (m, 1H).

To a solution of compound D-1 (7.03 g, 19.26 mmol), compound 1-7-2 (5.06 g, 28.88 mmol) and EDCI (5.56 g, 28.88 mmol) in DCM (100.0 mL) in an ice bath was added DIPEA (21.0 mL) dropwise. At the end of the addition, the mixture was stirred at rt overnight. Water (100 mL) was added to the mixture and the mixture was extracted with DCM (150 mL×3). The combined organic phases were washed with brine, dried over anhydrous Na$_2$SO$_4$ and concentrated in vacuo. The residue was purified by silica gel column chromatography (PE/EtOAc (v/v)=1/2) to give compound D-2 as a solid (7.6 g). The compound was characterized by the following spectroscopic data:

$^1$H NMR (400 MHz, CDCl$_3$): δ 7.65-7.60 (m, 2H), 7.47-7.43 (m, 2H), 7.22-7.20 (m, 1H), 5.67-5.65 (m, 1H), 5.24-5.22 (m, 1H), 4.34-4.30 (m, 1H), 3.5-3.81 (m, 1H), 3.72 (s, 3H), 3.71-3.64 (m, 1H), 3.00 (s, 1H), 2.34-2.11 (m, 1H), 2.21-1.95 (m, 5H), 1.04-1.02 (m, 1H), 0.88-0.86 (d, 6H).

To a mixture of compound D-2 (5 g, 11.13 mmol), bis(pinacolato)diboron (4.3 g, 16.7 mmol), Pd(dppf)Cl$_2$·CH$_2$Cl$_2$ (0.91 g, 1.11 mmol) and KOAc (3.3 g, 33.4 mmol) under N$_2$ was added DMF (30.0 mL) via syringe. The resulting mixture was stirred at 90° C. overnight, cooled to rt, and water (80 mL) was added. The mixture was extracted with EtOAc (40 mL×3). The combined organic phases were washed with brine, dried over anhydrous Na$_2$SO$_4$ and concentrated in vacuo. The residue was purified by silica gel column chromatography (PE/EtOAc (v/v)=1/2) to give the title compound 7-9 as a beige solid (4 g). The compound was characterized by the following spectroscopic data:

$^1$H NMR (400 MHz, CDCl$_3$): δ 7.65-7.60 (m, 2H), 7.47-7.43 (m, 2H), 7.22-7.20 (m, 1H), 5.67-5.65 (m, 1H), 5.24-5.22 (m, 1H), 4.34-4.30 (m, 1H), 3.5-3.81 (m, 1H), 3.72 (s, 3H), 3.71-3.64 (m, 1H), 3.00 (s, 1H), 2.34-2.11 (m, 1H), 2.21-1.95 (m, 5H), 1.32-1.45 (m, 12H), 1.04-1.02 (m, 1H), 0.88-0.86 (d, 6H).

Step 9) The Preparation of Compound 7-10

To a mixture of compound 7-8 (3.1 g, 6.4 mmol), compound 7-9 (3.3 g, 6.7 mmol), Pd(PPh$_3$)$_4$ (231 mg, 0.2 mmol) and potassium carbonate (2.2 g, 16.0 mmol) under N$_2$ was added DME (50 mL) via syringe followed by pure water (10 mL). The resulting mixture was stirred at 90° C. overnight. DME was removed in vacuo and to the residue was added water (50.0 mL). The resulting mixture was extracted with EtOAc (50.0 mL×3). The combined organic phases were washed with brine, dried over anhydrous Na$_2$SO$_4$ and concentrated in vacuo. The residue was purified by silica gel column chromatography (PE/EtOAc (v/v)=1/1) to give the title compound 7-10 as a beige solid (3.44 g, 74%). The compound was characterized by the following spectroscopic data:

MS-ESI: m/z 724.3 [M+H]$^+$; and $^1$H NMR (400 MHz, CDCl$_3$): δ 7.84-7.82 (m, 1H), 7.69-7.66 (m, 2H), 7.57-7.55 (m, 1H), 7.48-7.44 (m, 2H), 7.40-7.36 (m, 1H), 5.41-5.39 (m, 1H), 5.30-5.28 (m, 1H), 4.35-4.31 (m, 1H), 3.76-3.71 (m, 1H), 3.71 (s, 3H), 3.65-3.63 (m, 1H), 3.21-3.02 (m, 1H), 2.98 (s, 2H), 2.26-2.21 (m, 1H), 2.21-2.14 (m, 2H), 1.97-1.95 (m, 1H), 1.53-1.79 (m, 8H), 0.89-0.87 (m, 6H).

Step 10) The Preparation of Compound 7-11

To a mixture of compound 7-10 (8.0 g, 11.1 mmol), bis(pinacolato)diboron (4.3 g, 16.7 mmol), Pd(dppf)Cl$_2$.CH$_2$Cl$_2$ (0.9 g, 1.1 mmol) and KOAc (3.3 g, 33.4 mmol) under N$_2$ was added DMF (20.0 mL) via syringe. The resulting mixture was stirred at 100° C. overnight, cooled to rt, and water (80 mL) was added. The mixture was extracted with EtOAc (40 mL×3). The combined organic phases were washed with brine, dried over anhydrous Na$_2$SO$_4$ and concentrated in vacuo. The residue was purified by silica gel column chromatography (PE/EtOAc (v/v)=1/1) to give the title compound 7-11 as a beige solid (2.6 g, 33%). The compound was characterized by the following spectroscopic data:

MS-ESI: m/z 703.4 [M+H]$^+$; and $^1$H NMR (400 MHz, CDCl$_3$): δ 7.80-7.79 (m, 1H), 7.65-7.60 (m, 2H), 7.53-7.51 (m, 1H), 7.44-7.41 (m, 2H), 7.38-7.34 (m, 1H), 5.39-5.37 (m, 1H), 5.30-5.28 (m, 1H), 4.35-4.31 (m, 1H), 3.74-3.70 (m, 1H), 3.71 (s, 3H), 3.65-3.63 (m, 1H), 3.21-3.02 (m, 1H), 2.98 (s, 2H), 2.26-2.21 (m, 1H), 2.21-2.14 (m, 2H), 1.97-1.95 (m, 1H), 1.53-1.29 (m, 8H), 1.24 (s, 12H), 0.89-0.87 (m, 6H).

Step 11) The Preparation of Compound 7-12

To a solution of compound 2-2-2 (2.9 g, 7.9 mmol) in EtOAc (10 mL) was added a solution of HCl in EtOAc (10 mL, 4 M) at 0° C. The mixture was stirred at rt overnight and concentrated in vacuo. The residue was washed with EtOAc twice to give compound E-1 as a white solid (2.4 g, 100%).

To a solution of compound E-1 (2.4 g, 7.9 mmol), compound 1-7-2 (2.2 g, 12.7 mmol) and HATU (5.4 g, 14.3 mmol) in DMF (48 mL) was added DIPEA (10.3 g, 13.9 mL, 79.8 mmol) at 0° C. The mixture was stirred at rt overnight. Water and EtOAc were added to the mixture. After the layers were partitioned, the organic layer was dried over anhydrous Na$_2$SO$_4$ and concentrated in vacuo. The residue was purified by silica gel column chromatography (PE/EtOAc (v/v)=3/1) to give the title compound 7-12 (1.3 g, 35%).

Step 12) The Preparation of Compound 7-13

To a mixture of compound 7-11 (2.6 g, 3.7 mmol), compound 7-12 (1.7 g, 4.1 mmol), Pd(PPh$_3$)$_4$ (0.231 g, 0.2 mmol) and potassium carbonate (1.3 g, 9.3 mmol) under N$_2$ was added DME (50 mL) via syringe followed by pure water (10 mL). The resulting mixture was stirred at 90° C. overnight. DME was removed in vacuo, and to the residue was added water (50 mL). The resulting mixture was extracted with EtOAc (50 mL×3). The combined organic phases were washed with brine, dried over anhydrous Na$_2$SO$_4$ and concentrated in vacuo. The residue was purified by silica gel column chromatography (EtOAc) to give the title compound 7-13 as a beige solid (1.2 g, 37%). The compound was characterized by the following spectroscopic data:

MS-ESI: m/z 869.5 [M+H]$^+$; and $^1$H NMR (400 MHz, CDCl$_3$): δ 7.80-7.79 (m, 1H), 7.65-7.60 (m, 2H), 7.53-7.51 (m, 1H), 7.44-7.41 (m, 2H), 7.38-7.34 (m, 1H), 5.66-5.50 (m, 2H), 5.30-5.20 (m, 2H), 4.37-4.28 (m, 2H), 3.90-3.77 (m, 2H), 3.75-3.57 (m, 8H), 3.01-2.77 (m, 6H), 2.43-1.87 (m, 8H), 1.50-1.34 (m, 12H), 0.90-0.73 (m, 12H).

Example 8

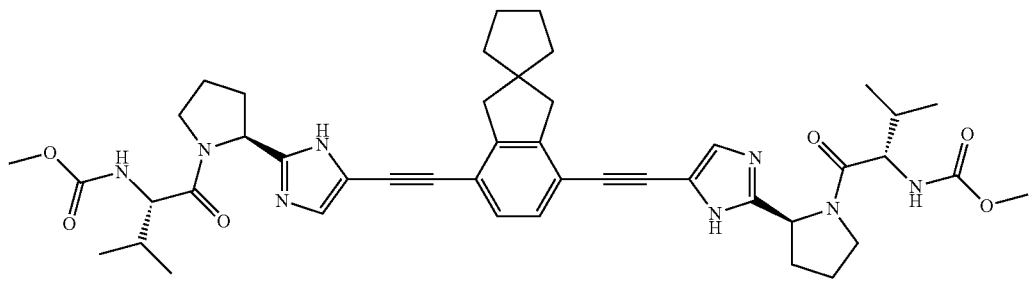

Synthetic routes

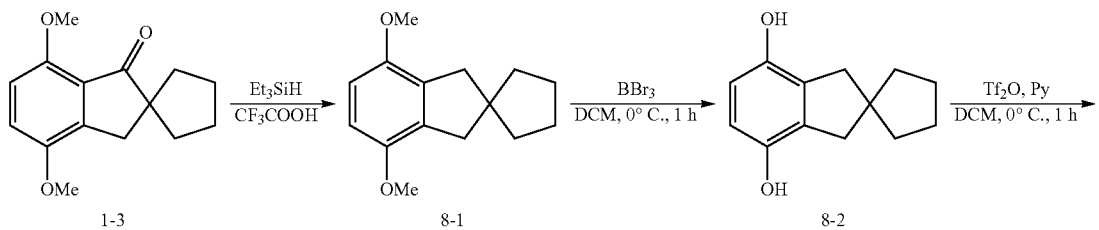

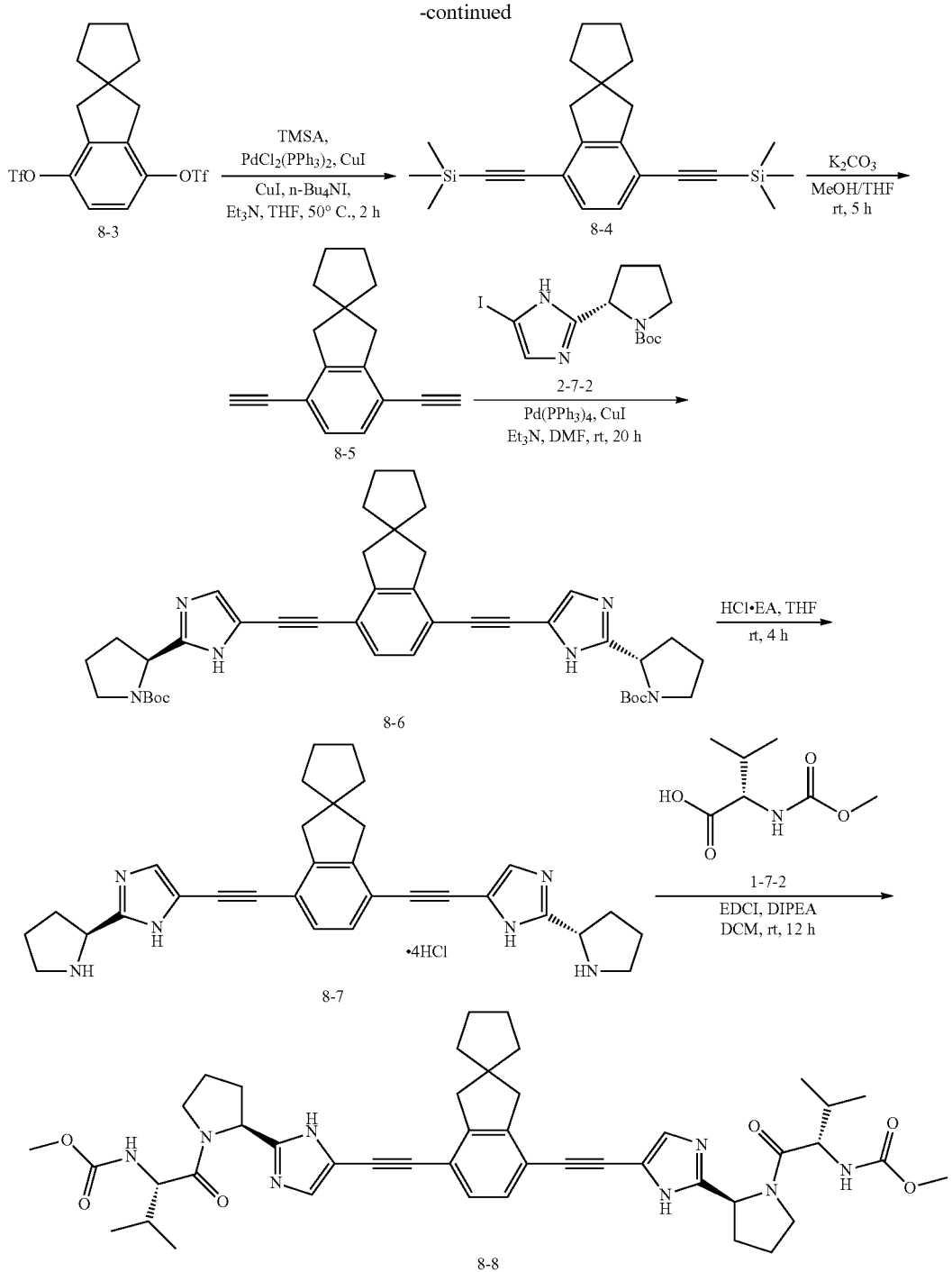

Step 1) The Preparation of Compound 8-1

To a mixture of compound 1-3 (2.0 g, 8.1 mmol) and triethylsilane (7.0 mL, 44 mmol) was added dropwise trifluoroacetic acid (20.0 mL) in an ice bath. The resulting mixture was stirred for 24 hours, quenched with Na$_2$CO$_3$ saturated solution, and extracted with EtOAc (50 mL×3). The combined organic phases were washed with brine, dried over anhydrous Na$_2$SO$_4$ and concentrated in vacuo. The residue was purified by silica gel column chromatography (PE/EtOAc (v/v)=15/1) to give compound 8-1 as colorless oil (1.64 g, 87.2%, HPLC: 97.9%). The compound was characterized by the following spectroscopic data:

MS-ESI: m/z 232.1 [M+H]$^+$; and $^1$H NMR (400 MHz, CDCl$_3$): δ 6.605 (s, 2H), 3.778 (s, 6H), 2.803 (s, 4H), 1.70-1.71 (m, 8H).

Step 2) The Preparation of Compound 8-2

To a solution of compound 8-1 (2.5 g, 10.78 mmol) in anhydrous DCM (30.0 mL) in an ice bath was added dropwise boron tribromide (2.9 mL). The resulting mixture was stirred for 1 hour, quenched with ice water and extracted with DCM (50 mL×3). The combined organic phases were dried over anhydrous Na$_2$SO$_4$ and concentrated in vacuo. The residue was purified by silica gel column chromatography (PE/EtOAc (v/v)=6/1) to give the title compound 8-2 as a white solid (2.0 g, 91%, HPLC: 97.9%). The compound was characterized by the following spectroscopic data:

MS-ESI: m/z 205.1 [M+H]$^+$; and $^1$H NMR (400 MHz, CDCl$_3$): δ 6.52 (s, 2H), 4.3 (s, 1H), 2.7791 (s, 4H), 1.73-1.71 (m, 8H).

Step 3) The Preparation of Compound 8-3

To a solution of compound 8-2 (2.0 g, 9.8 mmol) and pyridine (5.0 mL) in anhydrous DCM (60 mL) was added trifluoroacetic anhydride (5.4 mL, 39.2 mmol) dropwise in an ice bath. The resulting mixture was stirred for 1 hour, quenched with ice water (50 mL) and extracted with DCM (25 mL×3). The combined organic phases were dried over anhydrous Na$_2$SO$_4$ and concentrated in vacuo. The residue was purified by silica gel column chromatography (PE) to give the title compound 8-3 as colorless oil (4.11 g, 89.6%, HPLC: 95.5%). The compound was characterized by the following spectroscopic data:

$^1$H NMR (400 MHz, CDCl$_3$): δ 7.25 (s, 2H), 2.997 (s, 4H), 1.73-1.76 (m, 8H).

Step 4) The Preparation of Compound 8-4

To a mixture of compound 8-3 (964 mg, 2 mmol), tetrabutylammonium iodide (2214 mg, 6 mmol), CuI (114 mg, 0.6 mmol) and bis(triphenylphosphine)palladium(II) chloride (140 mg, 0.2 mmol) in a 50 mL of two-necked flask was added anhydrous THF (8 mL) under N$_2$ via syringe followed by Et$_3$N (8 mL). After the mixture was stirred for 10 minutes, TMSA (1.4 mL, 10 mmol) was added and the mixture was stirred at 50° C. for 2 hours. The mixture was concentrated in vacuo and the residue was purified by silica gel column chromatography (PE) to give the title compound 8-4 as yellow liquid (643 mg, 88.3%, HPLC: 88%). The compound was characterized by the following spectroscopic data:

$^1$H NMR (400 MHz, CDCl$_3$): δ 7.1974 (s, 2H), 4.35 (s, 4H), 1.7541-1.7584 (m, 8H), 0.2882 (s, 18H).

Step 5) The Preparation of Compound 8-5

To a mixture of compound 8-4 (0.610 g, 1.67 mmol) and K$_2$CO$_3$ (1.156 g, 8.3 mmol) in a 50 mL of two-necked flask were added CH$_3$OH (8.0 mL) and THF (8.0 mL) under N$_2$ via syringe. The mixture was stirred at rt for 5 hours and filtered through a Celite pad. The filtrate was concentrated in vacuo and the residue was purified by silica gel column chromatography (PE) to give the title compound 8-5 as yellow liquid (0.324 g, 87.8%, HPLC: 95%). The compound was characterized by the following spectroscopic data:

$^1$H NMR (400 MHz, CDCl$_3$): δ 7.2556 (s, 2H), 3.2616 (s, 2H), 2.9508 (s, 4H), 1.71-1.74 (m, 4H), 1.61-1.64 (m, 4H).

Step 6) The Preparation of Compound 8-6

To a mixture of compound 2-7-2 (472 mg, 1.3 mmol), CuI (22.4 mg, 0.12 mmol) and Pd(PPh$_3$)$_4$ (69.19 mg, 0.06 mmol) in a 50 mL of two-necked flask were added anhydrous DMF (1.0 mL) and Et$_3$N (0.2 mL) under N$_2$ via syringe, then a solution of compound 8-5 (130 mg, 0.6 mmol) in DMF (3.5 mL) was added dropwise to the mixture via syringe. The resulting mixture was stirred at rt for 20 hours, and filtered through a Celite pad. The filtrate was concentrated in vacuo and the residue was purified by silica gel column chromatography (PE) to give the title compound 8-6 as a yellow solid (280 mg, 68.6%, HPLC: 89%). The compound was characterized by the following spectroscopic data:

MS-ESI: m/z 692.3 [M+H]$^+$; and $^1$H NMR (400 MHz, CD$_3$Cl): δ 10.65 (br, 2H), 7.22-7.25 (m, 4H), 4.92 (br, 2H), 3.38 (br, 4H), 3.00 (s, 4H), 2.13 (br, 4H), 1.94 (br, 4H), 1.63 (s, 4H), 1.57 (s, 4H), 1.48 (s, 18H).

Step 7) The Preparation of Compound 8-7

To a solution of compound 8-6 (280 mg, 0.4 mmol) in THF (3 mL) was added a solution of HCl in EtOAc (12 mL, 4 M) in an ice bath. At the end of the addition, the mixture was stirred at rt for 4 hours and filtered. The filter cake was washed with EtOAc (30 mL) to give the title compound 8-7 as a yellow solid (160 mg, 62%, HPLC: 90%). The compound was characterized by the following spectroscopic data:

MS-ESI: m/z 505.3 [M+H]$^+$; and $^1$H NMR (400 MHz, CD$_3$OD): δ 8.01-8.07 (br, 2H), 7.37 (s, 2H), 5.08 (br, 2H), 3.55 (br, 2H), 3.05 (s, 4H), 2.66 (br, 2H), 2.46 (br, 2H), 2.35 (br, 2H), 2.22 (br, 2H), 1.77-1.82 (m, 4H), 1.72-1.65 (m, 4H).

Step 8) The Preparation of Compound 8-8

To a suspension of compound 8-7 (160 mg, 0.25 mmol), compound 1-7-2 (132.1 mg, 0.75 mmol) and EDCI (240.8 mg, 1.2 mmol) in DCM (5.0 mL) in an ice bath was added DIPEA (1.0 mL) dropwise. At the end of the addition, the mixture was stirred at rt for 12 hours. Water (20 mL) was added to the mixture and the mixture was extracted with DCM (50 mL×3). The combined organic phases were washed with brine, dried over anhydrous Na$_2$SO$_4$ and concentrated in vacuo. The residue was purified by silica gel column chromatography (DCM/MeOH (v/v)=200/1) to give the title compound 8-8 as a pale yellow solid (160 mg, 79.5%, HPLC: 99.8%). The compound was characterized by the following spectroscopic data:

MS-ESI: m/z 805.3 [M+H]$^+$; and $^1$H NMR (400 MHz, CD$_3$OD): δ 7.20-7.21 (m, 4H), 5.0-5.1 (br, 2H), 4.8 (br, 2H), 4.18-4.20 (d, J=7.4 Hz, 2H), 3.94 (br, 2H), 3.82 (br, 2H), 3.64 (s, 6H), 2.98 (s, 2H), 2.26-2.28 (br, 2H), 2.17-2.18 (m, 2H), 2.08-2.14 (m, 2H), 1.90-2.05 (m, 4H), 1.75-1.78 (br, 4H), 1.65-1.67 (br, 4H), 0.80-0.92 (m, 12H).

Example 9

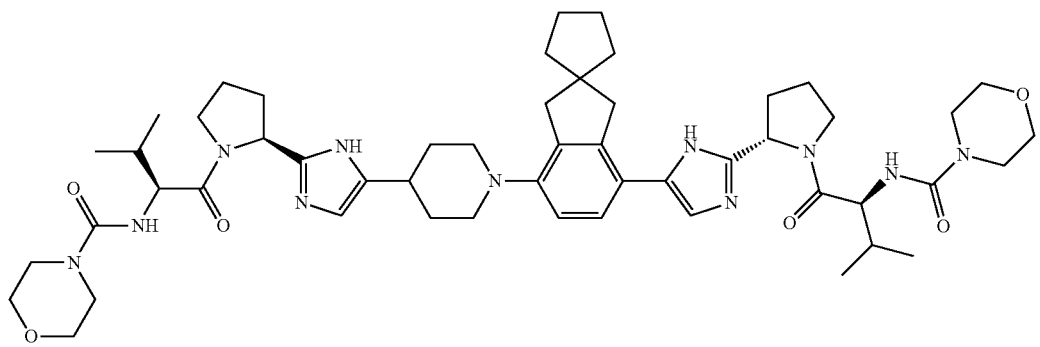 [SMILES: CC(C)[C@H](NC(=O)N1CCOCC1)C(=O)N1CCC[C@H]1c1ncc(-c2ccc(N3CCC(c4cnc([C@@H]5CCCN5C(=O)[C@@H](NC(=O)N5CCOCC5)C(C)C)[nH]4)CC3)c3c2CC2(CCCC2)C3)[nH]1]

Synthetic Routes
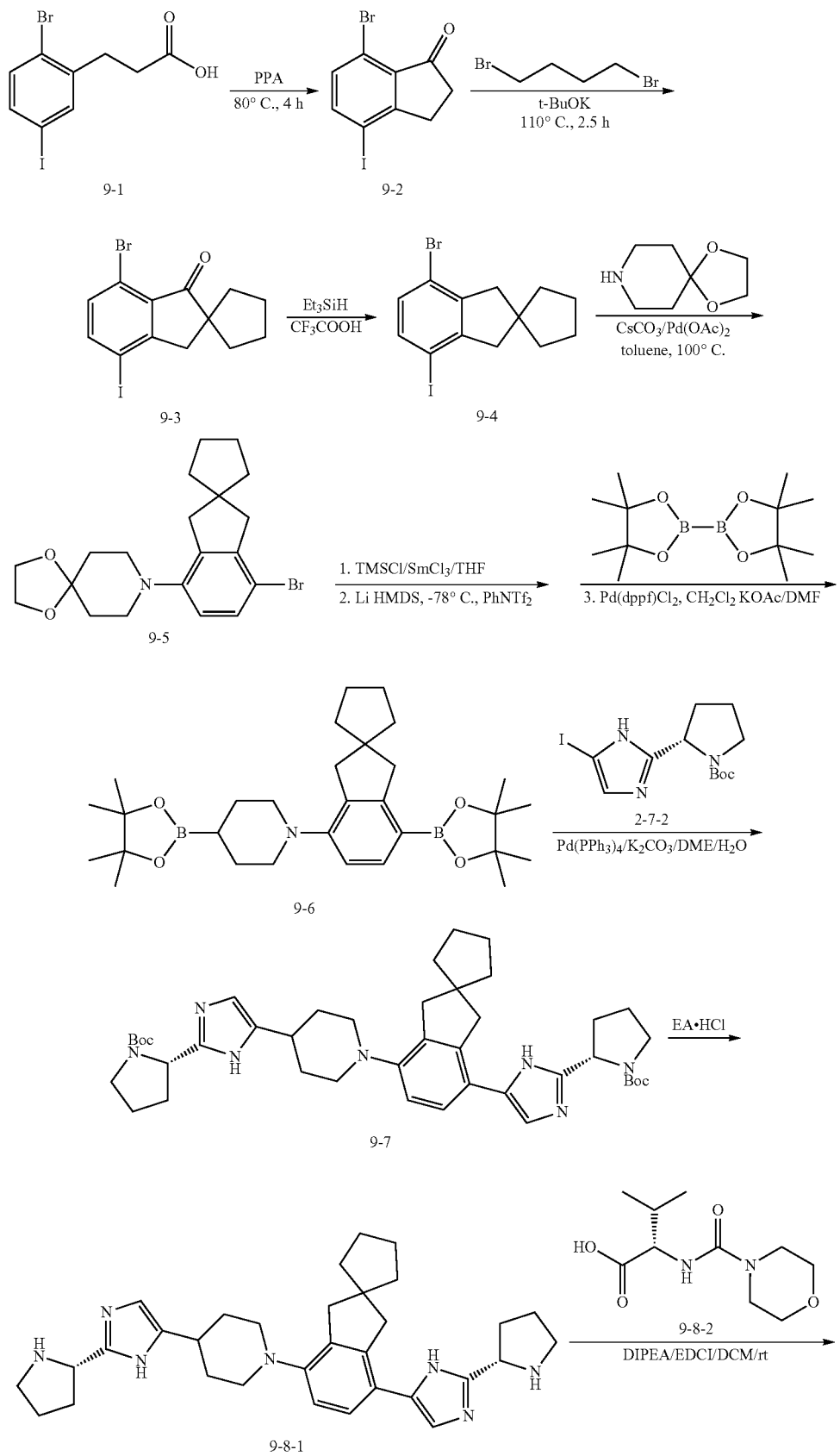

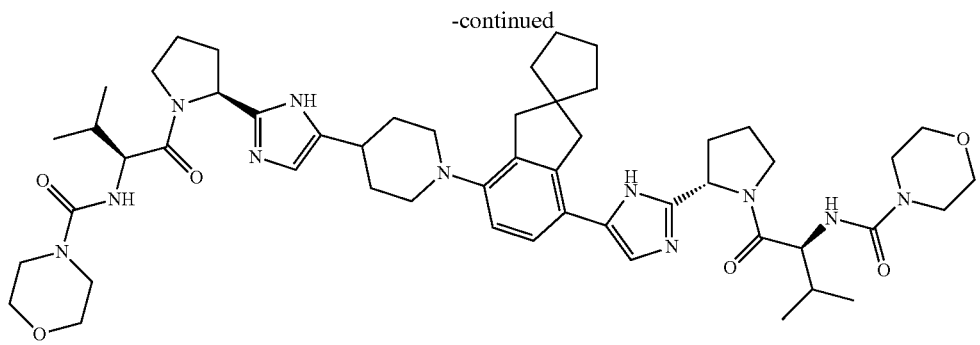

9-9

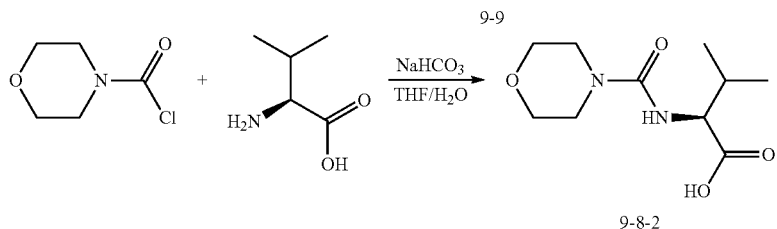

9-8-2

Step 1) The Preparation of Compound 9-2

A mixture of compound 9-1 (4.68 g, 13.18 mmol) and PPA (50.87 g) was stirred at 80° C. for 4 hours and poured into ice water (250 mL). The mixture was extracted with EtOAc (100 mL×5). The combined organic phases were dried over anhydrous $Na_2SO_4$ and concentrated in vacuo. The residue was purified by silica gel column chromatography (PE/EtOAc (v/v)=1/1) to give the title compound 9-2 as a pale yellow solid (3 g). The compound was characterized by the following spectroscopic data:

MS-ESI: m/z 338.2 [M+H]$^+$; and $^1$H NMR (400 MHz, $CDCl_3$): δ 7.5 (d, J=8.7 Hz, 1H), 7.3 (d, J=8.7 Hz, 1H), 2.97-3.00 (m, 2H), 2.65-2.68 (m, 2H).

Step 2) The Preparation of Compound 9-3

To a suspension of t-BuOK (338.28 mg, 3.015 mmol) in toluene (10 mL) under $N_2$ in an ice bath was added dropwise a solution of compound 9-2 (680 mg, 2.01 mmol) and 1,4-dibromobutane (478 mg, 2.21 mmol) in toluene (20 mL). At the end of the addition, the mixture was stirred at 110° C. for 2.5 hours. After the reaction was completed, the mixture was cooled to rt and quenched with ice water. The toluene was removed in vacuo, and the resulting mixture was extracted with EtOAc (25 mL×3). The combined organic phases were washed with brine, dried over anhydrous $Na_2SO_4$ and concentrated in vacuo. The residue was purified by silica gel column chromatography (PE/EtOAc (v/v)=1/1) to give the title compound 9-3 as a pale yellow solid (784.1 mg). The compound was characterized by the following spectroscopic data:

MS-ESI: m/z 392.2 [M+H]$^+$; and $^1$H NMR (400 MHz, $CDCl_3$): δ 7.65 (d, J=8.7 Hz, 1H), 7.24 (d, J=8.7 Hz, 1H), 2.69 (s, 2H), 2.00-2.02 (m, 2H), 1.91-1.92 (m, 2H), 1.75-1.77 (m, 2H), 1.55-1.60 (m, 2H).

Step 3) The Preparation of Compound 9-4

To a mixture of compound 9-3 (2.0 g, 5.12 mmol) and triethylsilane (7.0 mL, 44 mmol) in an ice bath was added dropwise trifluoroacetic acid (20 mL). The resulting mixture was stirred for 4 hours, quenched with $Na_2CO_3$ saturated solution, and extracted with EtOAc (50 mL×3). The combined organic phases were washed with brine, dried over anhydrous $Na_2SO_4$ and concentrated in vacuo. The residue was purified by silica gel column chromatography (PE/EtOAc (v/v)=10/1) to give the title compound 9-4 as a white solid (1.64 g). The compound was characterized by the following spectroscopic data:

MS-ESI: m/z 378.3 [M+H]$^+$; and $^1$H NMR (400 MHz, $CDCl_3$): δ 7.605 (d, J=8.7 Hz, 1H), 7.21 (d, J=8.7 Hz, 1H), 2.803 (s, 4H), 1.56-1.71 (m, 8H).

Step 4) The Preparation of Compound 9-5

To a mixture of compound 9-4 (1.0 g, 2.65 mmol), 1,4-dioxa-8-azaspiro[4.5]decane (0.4178 g, 2.92 mmol), $Cs_2CO_3$ (1.54 g, 7.95 mmol) and $Pd(OAc)_2$ (0.060 g, 0.265 mmol) in a 50 mL of two-necked flask was added toluene (25 mL) via syringe under $N_2$. The mixture was stirred at 100° C. for 10 hours and filtered through a Celite pad. The filtrate was concentrated in vacuo and the residue was purified by silica gel column chromatography (PE/EtOAc (v/v)=1/1) to give the title compound 9-5 as yellow liquid (1.05 g). The compound was characterized by the following spectroscopic data:

MS-ESI: m/z 393.3 [M+H]$^+$; and $^1$H NMR (400 MHz, $CDCl_3$): δ 7.25 (d, J=8.5 Hz, 1H), 6.91 (d, J=8.3 Hz, 1H), 3.88 (s, 4H), 3.65 (m, 4H), 2.803 (s, 4H), 1.65 (m, 4H), 1.56-1.71 (m, 8H).

Step 5) The Preparation of Compound 9-6

To a mixture of compound 9-5 (2.0 g, 5.1 mmol) and $SmCl_3$ (0.131 g, 0.51 mmol) was added THF (20 mL) under $N_2$ via syringe. After the mixture was stirred at rt for 15 minutes, TMSCl (0.610 g, 5.61 mmol) was added slowly. The resulting mixture was stirred at rt for further 10 hours and filtered through a Celite pad. The filtrate was concentrated in vacuo to give the crude product (a) (1.5 g), which was used for the next step without further purification.

To a solution of the above product (a) in THF was added LiHMDS (6.5 mL, 6.46 mmol, 1 M in THF) at −78° C. After the mixture was stirred at −78° C. for 0.5 hour, PhNTf$_2$ (2.77 g, 7.76 mmol) was added dropwise. The resulting mixture was stirred at −78° C. for 0.5 hour and at rt for another 10 hours. The mixture was quenched with water and extracted with EtOAc (50 mL×3). The combined organic phases were washed with brine, dried over anhydrous $Na_2SO_4$ and concentrated in vacuo to give the product (b) (1.0 g), which was used for the next step without further purification.

To a mixture of the above product (b) (1.0 g, 2 mmol), bis(pinacolato)diboron (1.27 g, 5 mmol), Pd(dppf)Cl$_2$.CH$_2$Cl$_2$ (0.16 g, 0.2 mmol) and KOAc (0.78 g, 8 mmol) in a 50 mL of two-necked flask was added DMF (20.0 mL) under $N_2$ via syringe. The mixture was stirred at 90° C. overnight, cooled to rt and water (80 mL) was added. The resulting mixture was extracted with EtOAc (40 mL×3). The combined organic phases were washed with brine, dried over anhydrous $Na_2SO_4$ and concentrated in vacuo. The residue was purified by silica gel column chromatography (PE/EtOAc (v/v)=1/2) to give the title compound 9-6 as a beige solid (0.96 g). The compound was characterized by the following spectroscopic data:

MS-ESI: m/z 508.3 $[M+H]^+$; and
$^1H$ NMR (400 MHz, $CDCl_3$): δ 6.95 (d, J=8.4 Hz, 1H), 6.91 (d, J=8.1 Hz, 1H), 3.48-3.45 (m, 4H), 2.803 (s, 4H), 1.66-1.71 (m, 13H), 1.38 (s, 24H).

Step 6) the preparation of compound 9-7

To a mixture of compound 9-6 (3 g, 5.91 mmol), compound 2-7-2 (4.94 g, 13.6 mmol), $Pd(PPh_3)_4$ (0.342 g, 0.296 mmol) and potassium carbonate (2.47 g, 17.73 mmol) in a 100 mL of two-necked flask under $N_2$ was added DME (60.0 mL) via syringe followed by pure water (12.0 mL). The resulting mixture was stirred at 90° C. overnight, cooled to rt and concentrated in vacuo. To the residue was added water (100.0 mL). The mixture was extracted with EtOAc (100.0 mL×3). The combined organic phases were washed with brine, dried over anhydrous $Na_2SO_4$ and concentrated in vacuo. The residue was purified by silica gel column chromatography (DCM/MeOH (v/v)=200/1) to give the title compound 9-7 as a beige solid (3.9 g). The compound was characterized by the following spectroscopic data:

MS-ESI: m/z 726.93 $[M+H]^+$; and
$^1H$ NMR (400 MHz, $CDCl_3$): δ 10.97 (brs, 1H), 10.49 (brs, 1H), 7.79-7.80 (m, 2H), 7.24 (s, 1H), 7.16 (s, 1H), 4.69-4.89 (m, 2H), 3.31-3.42 (m, 4H), 2.95-3.20 (m, 9H), 1.95-2.35 (m, 10H), 1.80-2.00 (m, 2H), 1.50-1.54 (m, 8H), 1.51 (s, 18H).

Step 7) The Preparation of Compound 9-8-1

To a solution of compound 9-7 (500 mg, 0.689 mmol) in THF (10 mL) was added a solution of HCl in EtOAc (12 mL, 4 M) in an ice bath. At the end of the addition, the mixture was stirred at rt overnight and filtered. The filter cake was washed with EtOAc to give the title compound 9-8-1 as a solid (360 mg). The compound was characterized by the following spectroscopic data:

MS-ESI: m/z 526.7 $[M+H]^+$; and
$^1H$ NMR (400 MHz, $CDCl_3$): δ 10.31 (brs, 2H), 7.69-7.72 (m, 2H), 7.34 (s, 1H), 7.36 (s, 1H), 4.68-4.69 (m, 2H), 3.57 (m, 4H), 2.85-3.07 (m, 9H), 1.85-2.01 (m, 10H), 1.75-1.79 (m, 2H), 1.55-1.65 (m, 8H), 1.5-1.48 (m, 2H).

Step 8) The Preparation of Compound 9-8-2

To a solution of L-valine (2.49 g, 21.3 mmol) in THF (64.5 mL) was added a solution of $NaHCO_3$ (5.37 g, 64 mmol) in water (64.5 mL) followed by 4-morpholinecarbonyl chloride (2.8 mL, 23.5 mmol). The resulting mixture was stirred at rt overnight, adjusted to pH 3 with HCl aqueous solution (1 M) and extracted with EtOAc. The organic layer was dried over anhydrous $Na_2SO_4$ and concentrated in vacuo to give compound 9-8-2 as a white solid (2.9 g, 60%).

Step 9) The Preparation of Compound 9-9

To a suspension of compound 9-8-1 (350 mg, 0.6654 mmol), compound 9-8-2 (246 mg, 0.998 mmol) and EDCI (192 mg, 0.998 mmol) in DCM (10.0 mL) at 0° C. was added DIPEA (0.8 mL) dropwise. After all solid had dissolved, the mixture was stirred at rt for 10 hours. To the mixture was added a small amount of water and the mixture was extracted with DCM (20 mL×3). The combined organic phases were dried over anhydrous $Na_2SO_4$ and concentrated in vacuo. The residue was purified by silica gel column chromatography (DCM/MeOH (v/v)=50/1) to give the title compound 9-9 as a pale yellow solid (150 mg). The compound was characterized by the following spectroscopic data:

MS-ESI: m/z 492.3 $[M+H]^+$; and
$^1H$ NMR (400 MHz, $CDCl_3$): δ 10.74 (d, J=14.0 Hz, 1H), 10.34 (d, J=14.0 Hz, 1H), 7.79-7.81 (m, 2H), 7.43-7.45 (m, 2H), 7.25-7.26 (m, 2H), 5.44-5.47 (m, 2H), 5.27-5.28 (m, 2H), 4.55-4.67 (m, 8H), 4.31-4.34 (m, 2H), 3.82-3.84 (m, 2H), 3.70 (s, 6H), 3.63-3.69 (m, 2H), 2.75-3.08 (m, 13H), 2.35-2.37 (m, 2H), 2.20-2.21 (m, 2H), 2.09-2.12 (m, 2H), 1.95-1.98 (m, 2H), 1.56-1.66 (m, 4H), 1.25 (m, 4H), 1.03-1.05 (m, 2H), 0.88 (s, 12H).

Example 10

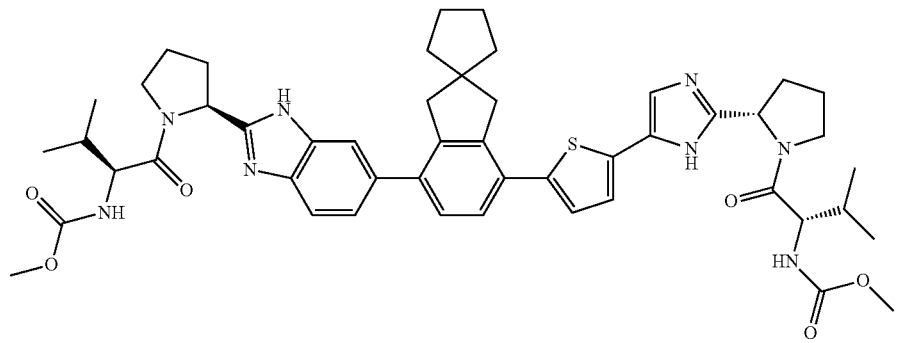

Synthetic Routes

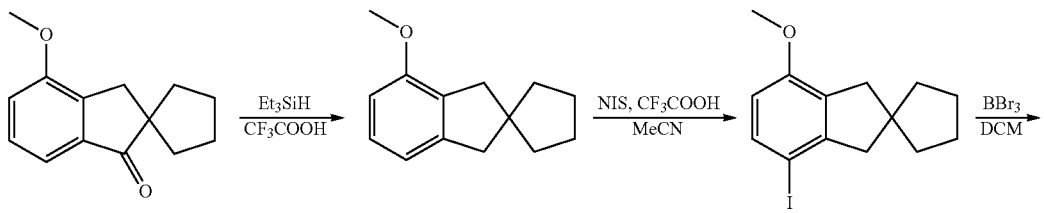

7-3     10-1     10-2

-continued
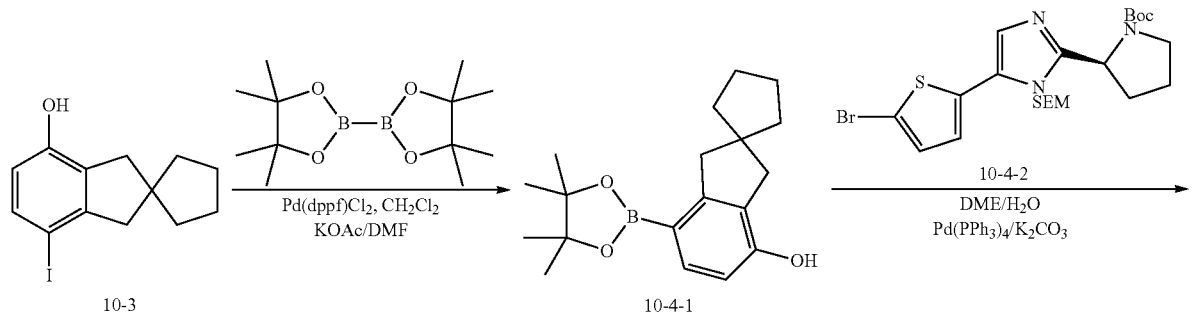
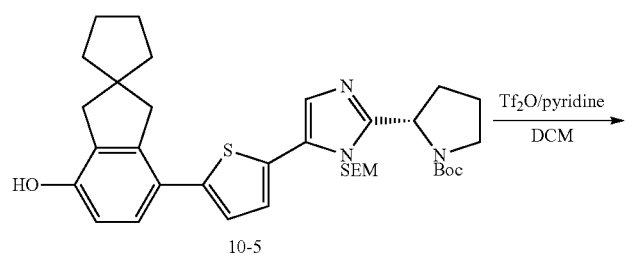
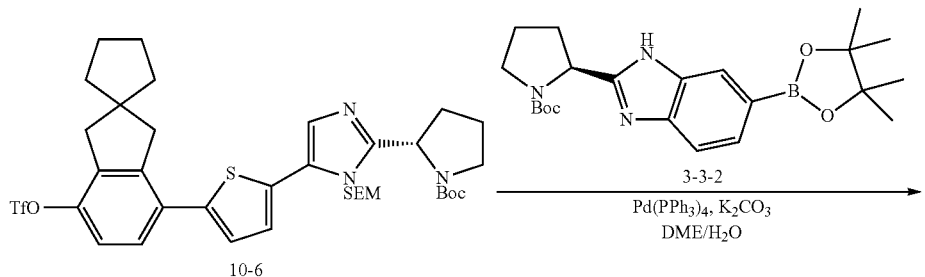
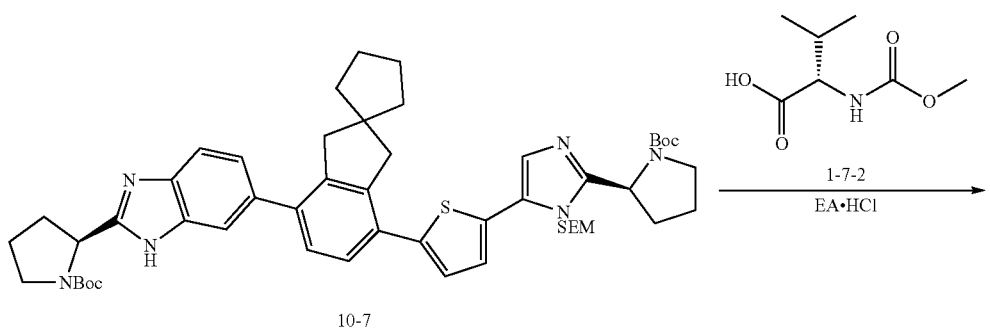
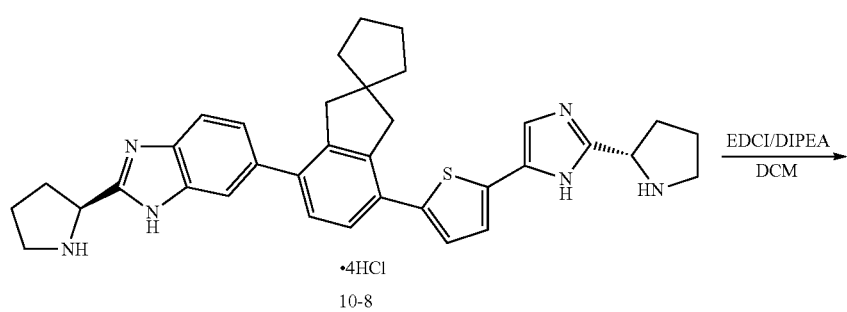

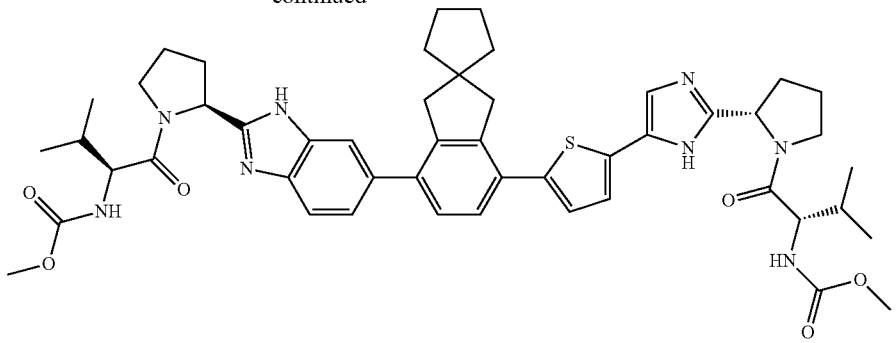

10-9

Step 1) the preparation of compound 10-1

To a mixture of compound 7-3 (9.76 g, 45 mmol) and triethylsilane (28.8 mL, 180 mmol) in an ice bath was added dropwise trifluoroacetic acid (20 mL). The mixture was stirred at 40° C. overnight, neutralized with $NaHCO_3$ saturated solution and extracted with EtOAc (50 mL×3). The combined organic phases were washed with brine, dried over anhydrous $Na_2SO_4$ and concentrated in vacuo. The residue was purified by silica gel column chromatography (PE/EtOAc (v/v)=10/1) to give the title compound 10-1 as colorless oil (7.1 g, 78%). The compound was characterized by the following spectroscopic data:

MS-ESI: m/z 203.14 [M+H]$^+$; and $^1$H NMR (400 MHz, $CDCl_3$): δ 7.10-7.13 (m, 1H), 6.80-6.81 (m, 1H), 6.65-6.67 (m, 1H), 3.83 (s, 1H), 2.85 (s, 2H), 2.80 (s, 2H), 1.57-1.72 (m, 8H).

Step 2) The Preparation of Compound 10-2

To a solution of compound 10-1 (14.1 g, 69.8 mmol) and NIS (17.2 g, 76.8 mmol) in acetonitrile (200 mL) was added TFA (1.55 mL, 20.9 mmol) slowly in an ice bath. The mixture was stirred at rt overnight, neutralized with $NaHCO_3$ saturated solution and extracted with EtOAc (100 mL×3). The combined organic phases were washed with brine, dried over anhydrous $Na_2SO_4$ and concentrated in vacuo. The residue was purified by silica gel column chromatography (PE/EtOAc (v/v)=20/1) to give the title compound 10-2 as colorless oil (19.2 g, 84%). The compound was characterized by the following spectroscopic data:

MS-ESI: m/z 329.2 [M+H]$^+$; and $^1$H NMR (400 MHz, $CDCl_3$): δ 7.45 (d, 1H), 6.43 (d, 1H), 3.77 (s, 3H), 2.90 (s, 2H), 2.81 (s, 2H), 1.73-1.69 (m, 4H), 1.63-1.59 (m, 4H).

Step 3) The Preparation of Compound 10-3

To a solution of compound 10-2 (19.6 g, 59.7 mmol) in anhydrous DCM (15 mL) at −78° C. was added dropwise boron tribromide (74.7 g, 298.8 mmol). At the end of the addition, the mixture was stirred at rt for 6 hours, quenched with ice water and extracted with EtOAc (100 mL×3). The combined organic phases were dried over anhydrous $Na_2SO_4$ and concentrated in vacuo. The residue was purified by silica gel column chromatography (PE/EtOAc (v/v)=3/1) to give the title compound 10-3 as a gray solid (17 g, 92%). The compound was characterized by the following spectroscopic data:

MS-ESI: m/z 315.2 [M+H]$^+$; and $^1$H NMR (400 MHz, $CDCl_3$): δ 7.36 (d, 1H), 6.41 (d, 1H), 4.91 (s, 1H), 2.89 (s, 2H), 2.82 (s, 2H), 1.73-1.69 (m, 4H), 1.67-1.63 (m, 4H).

Step 4) The Preparation of Compound 10-4-1

To a mixture of compound 10-3 (6.5 g, 20.7 mmol), bis (pinacolato)diboron (7.4 g, 28.9 mmol), $Pd(dppf)Cl_2 \cdot CH_2Cl_2$ (0.84 g, 1.03 mmol) and KOAc (6.1 g, 62.1 mmol) under $N_2$ was added DMF (80.0 mL) via syringe. The resulting mixture was stirred at 90° C. overnight, cooled to rt, and water (80 mL) was added. The mixture was extracted with EtOAc (100.0 mL×3). The combined organic phases were washed with brine, dried over anhydrous $Na_2SO_4$ and concentrated in vacuo. The residue was purified by silica gel column chromatography (PE/EtOAc (v/v)=1/1) to give the title compound 10-4-1 (8 g). The compound was characterized by the following spectroscopic data:

$^1$H NMR (400 MHz, $CDCl_3$): δ 7.49 (d, 1H), 6.60 (d, 1H), 3.06 (s, 2H), 2.72 (s, 2H), 1.70-1.60 (m, 8H), 1.34-1.36 (m, 12H).

Step 5) The Preparation of Compound 10-5

To a mixture of compound 10-4-1 (1.5 g, 4.77 mmol), compound 10-4-2 (2.24 g, 4.54 mmol), $Pd(PPh_3)_4$ (0.2625 g, 0.227 mmol) and potassium carbonate (1.577 g, 1.134 mmol) in a 25 mL of two-necked flask under $N_2$ was added DME (10.0 mL) via syringe followed by pure water (2.5 mL). The mixture was stirred at 90° C. overnight. After the mixture was cooled to rt, the solvent was removed in vacuo, and to the residue was added water (30.0 mL). The resulting mixture was extracted with EtOAc (30.0 mL×3). The combined organic phases were washed with brine, dried over anhydrous $Na_2SO_4$ and concentrated in vacuo. The residue was purified by silica gel column chromatography (PE/EtOAc (v/v)=8/1) to give the title compound 10-5 as a red brown solid (1.114 g, 41.38%). The compound was characterized by the following spectroscopic data:

MS-ESI: m/z 636.3 [M+H]$^+$; and $^1$H NMR (400 MHz, $CDCl_3$): δ 7.19-7.30 (m, 2H), 7.01-7.05 (br, 1H), 6.96-6.99 (br, 1H), 6.09 (br, 1H), 5.79-5.82 (d, J=10.48 Hz, 1H), 5.34-5.36 (br, 1H), 5.10-5.17 (t, J=11 Hz, 1H), 4.982 (br, 1H), 4.909 (br, 1H), 2.20-2.21 (br, 2H), 1.95 (br, 4H), 1.698 (br, 12H), 1.39 (s, 9H), 1.24-1.25 (br, 2H), 0.0017 (s, 9H).

Step 6) The Preparation of Compound 10-6

To a solution of compound 10-5 (1.106 g, 0.174 mmol) and pyridine (0.7 mL, 0.869 mmol) in anhydrous DCM (5 mL) under $N_2$ in an ice bath was added trifluoroacetic anhydride (0.88 mL, 6.3 mmol). After the resulting mixture was stirred for 1 hour, the reaction mixture was quenched with ice water (15 mL) and extracted with DCM (25 mL×3). The combined organic phases were dried over anhydrous $Na_2SO_4$ and concentrated in vacuo. The residue was purified by silica gel column chromatography (PE/EtOAc (v/v)=5/1) to give the title compound 10-6 as a pale yellow solid (0.593 g, 42%, HPLC: 95.5%). The compound was characterized by the following spectroscopic data:

$^1$H NMR (400 MHz, $CDCl_3$): δ 7.39-7.42 (m, 2H), 7.229 (br, 1H), 7.09-7.10 (br, 1H), 6.44-6.55 (br, 1H), 5.83-5.85 (d, J=9.36 Hz, 1H), 5.35-5.38 (br, 1H), 5.13-5.14 (br, 1H), 4.96-4.99 (br, 1H), 4.90-4.91 (br, 1H), 3.10-3.11 (d, J=6.4 Hz, 2H), 2.97 (s, 2H), 2.18-2.27 (br, 2H), 1.91-1.93 (br, 2H), 1.70-1.72 (br, 4H), 1.63-1.64 (br, 8H), 1.39 (s, 9H), 0.0017 (s, 9H).

Step 7) the Preparation of Compound 10-7

To a mixture of compound 10-6 (530 mg, 0.69 mmol), compound 3-3-2 (270.76 mg, 0.655 mmol), Pd(PPh₃)₄ (39.85 mg, 0.0345 mmol) and potassium carbonate (287.77 mg, 2.07 mmol) in a 25 mL of two-necked flask under N₂ was added DME (10 mL) via syringe followed by pure water (2.5 mL). The mixture was stirred at 90° C. overnight. After the mixture was cooled to rt, the solvent was removed in vacuo, and to the residue was added water (30.0 mL). The resulting mixture was extracted with EtOAc (30.0 mL×3). The combined organic phases were washed with brine, dried over anhydrous Na₂SO₄ and concentrated in vacuo. The residue was purified by silica gel column chromatography (PE/EtOAc (v/v)=1/1) to give the title compound 10-7 as a pale yellow solid (360 mg, 58%). The compound was characterized by the following spectroscopic data:

MS-ESI: m/z 453.3 [M+2H]²⁺; and

¹H NMR (400 MHz, CDCl₃): δ 7.84 (br, 1H), 7.76-7.78 (d, J=8.12 Hz, 2H), 7.46-7.48 (br, 2H), 7.34-7.35 (br, 1H), 7.15 (br, 2H), 7.098 (s, 1H), 5.85-5.875 (br, 2H), 5.36 (br, 1H), 5.14-5.16 (br, 2H), 5.002 (br, 1H), 3.64 (br, 1H), 3.52-3.56 (br, 2H), 3.4258 (br, 2H), 3.16 (s, 2H), 3.09 (br, 1H), 2.97-3.00 (br, 2H), 2.19-2.22 (m, 4H), 2.03-2.04 (br, 2H), 1.75 (br, 4H), 1.59-1.63 (br, 9H), 1.518 (br, 9H), 1.417 (s, 6H), 0.0107 (s, 9H).

Step 8) the Preparation of Compound 10-8

To a solution of compound 10-7 (360 mg, 0.4 mmol) in EtOAc (3.0 mL) was added a solution of HCl in EtOAc (15 mL, 4 M). The mixture was stirred at rt overnight and filtered. The filter cake was washed with EtOAc (30 mL) to give the title compound 10-8 as a beige solid (280 mg, 97%, HPLC: 90%). The compound was characterized by the following spectroscopic data:

MS-ESI: m/z 589.3 [M+H]⁺; and

¹H NMR (400 MHz, CDCl₃): δ 7.72-7.76 (m, 1H), 7.51-7.55 (m, 2H), 7.46-7.48 (br, 1H), 7.34-7.35 (br, 1H), 7.15 (br, 2H), 7.098 (s, 1H), 5.85-5.875 (br, 2H), 5.046 (br, 1H), 4.87 (br, 2H), 3.37-3.38 (br, 4H), 3.13 (s, 2H), 2.96 (s, 2H), 2.32-2.35 (m, 4H), 2.14-2.17 (br, 2H), 1.90-2.05 (m, 2H), 1.57-1.60 (br, 8H).

Step 9) The Preparation of Compound 10-9

To a solution of compound 10-8 (212 mg, 0.294 mmol), compound 1-7-2 (155 mg, 0.883 mmol) and EDCI (198 mg, 1.029 mmol) in DCM (10.0 mL) in an ice bath was added DIPEA (0.5 mL, 2.353 mmol) dropwise. The mixture was stirred at rt overnight. Water (20 mL) was added to the mixture and the mixture was extracted with DCM (50 mL×3). The combined organic phases were dried over anhydrous Na₂SO₄ and concentrated in vacuo. The residue was purified by silica gel column chromatography (DCM/MeOH (v/v)=100/1) to give the title compound 10-9 as a solid (77.5 mg, 29.96%, HPLC: 90.38%). The compound was characterized by the following spectroscopic data:

MS-ESI: m/z 445.3 [M+2H]²⁺; and

¹H NMR (400 MHz, CDCl₃): δ 7.68-7.70 (m, 1H), 7.57-7.59 (m, 2H), 7.49-7.52 (br, 2H), 7.37-7.39 (m, 1H), 7.22-7.26 (m, 2H), 5.25-5.35 (br, 2H), 5.10-5.18 (br, 1H), 4.22-4.27 (m, 2H), 4.18-4.20 (m, 2H), 3.86-3.92 (br, 4H), 3.64 (s, 6H), 3.07-3.09 (br, 2H), 2.84-2.85 (br, 2H), 2.00-2.06 (br, 6H), 1.43-1.66 (m, 8H), 1.28-1.33 (br, 2H), 0.88-0.92 (m, 12H).

Example 11

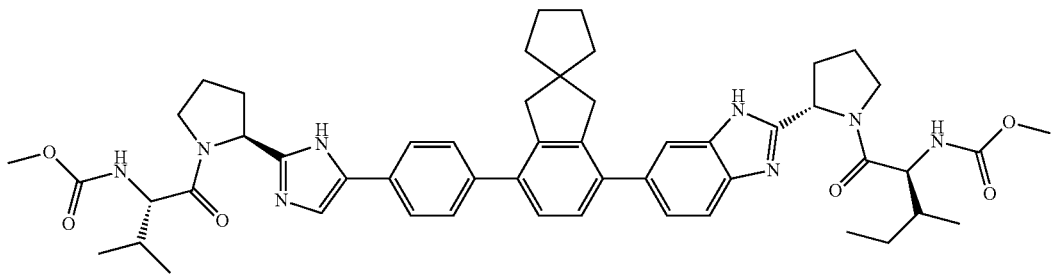

Synthetic Routes

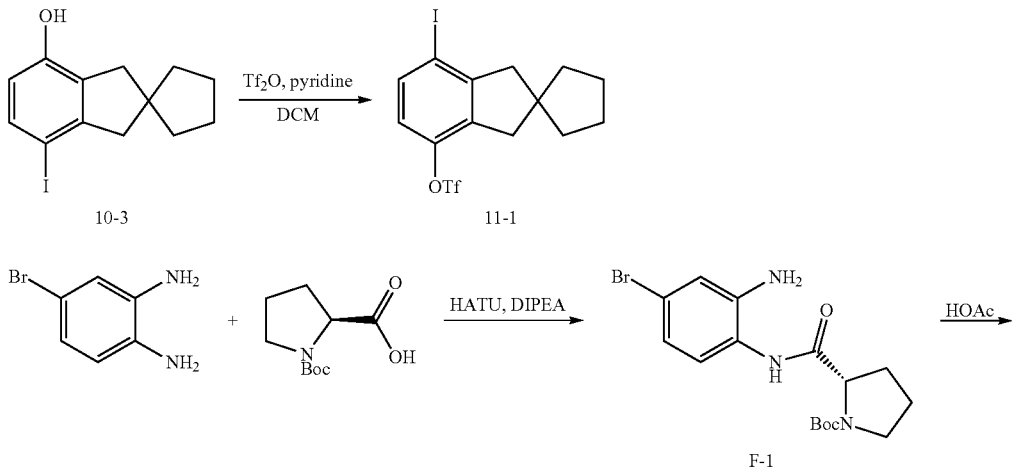

-continued
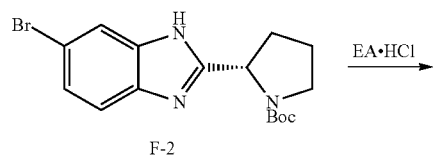 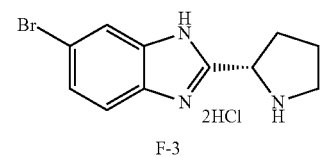 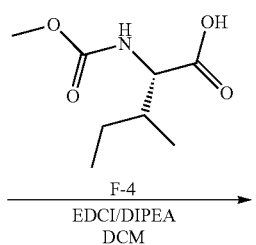
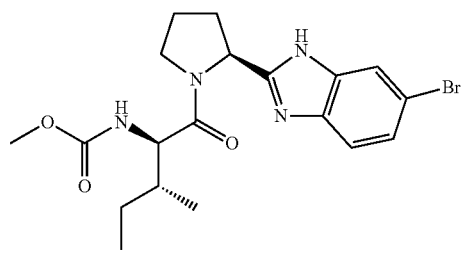 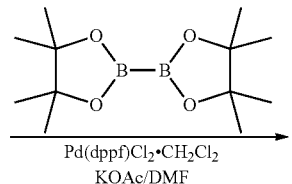
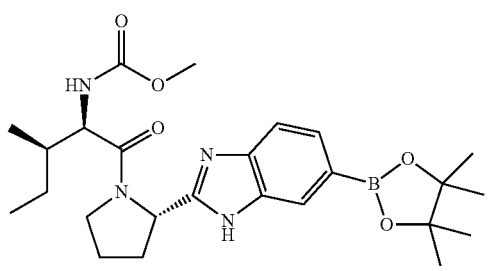
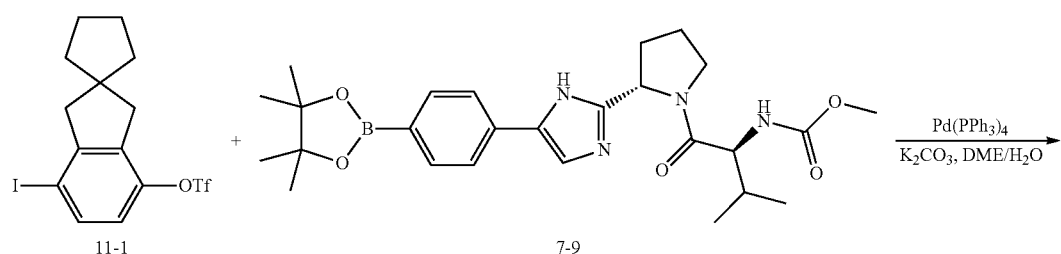
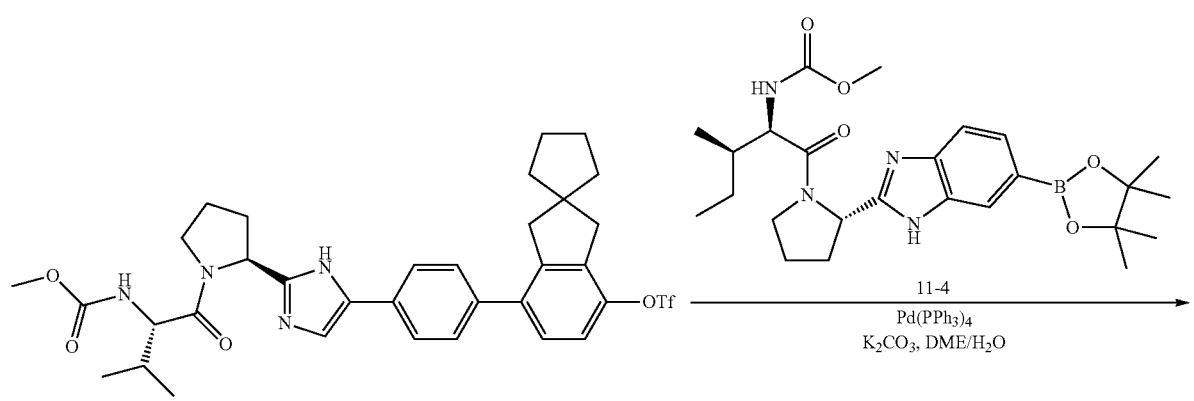

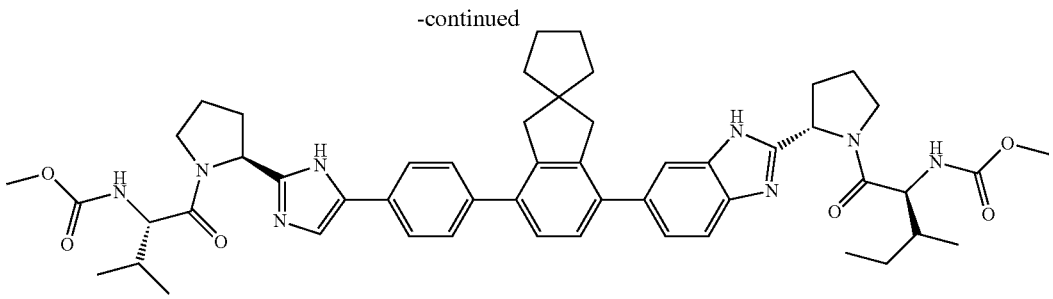

11-5

Step 1) The Preparation of Compound 11-1

To a solution of compound 10-3 (5 g, 15.92 mmol) in anhydrous DCM (50 mL) under $N_2$ in an ice bath was added slowly $Tf_2O$ (8.0 mL, 47.77 mmol) via syringe followed by pyridine (6.5 mL, 79.62 mmol). The resulting mixture was stirred in the ice bath for 20 minutes and stirred at rt for another 3 hours, then quenched with ice water in an ice bath. Water (50 mL) was added to the mixture and the mixture was extracted with DCM (60 mL×3). The combined organic phases were washed with brine, dried over anhydrous $Na_2SO_4$ and concentrated in vacuo. The residue was purified by silica gel column chromatography (PE/EtOAc (v/v)=10/1) to give the title compound 11-1 as pale yellow oil (5.98 g). The compound was characterized by the following spectroscopic data:

$^1$H NMR (400 MHz, $CDCl_3$): δ 7.57 (d, 1H), 6.79 (d, 1H), 3.07 (s, 2H), 2.88 (s, 2H), 1.75-1.72 (m, 4H), 1.65-1.63 (m, 4H).

Step 2) The Preparation of Compound 11-3

To a mixture of compound 11-1 (4.56 g, 10.21 mmol), compound 7-9 (4.22 g, 8.5 mmol), $Pd(PPh_3)_4$ (0.983 g, 0.85 mmol) and potassium carbonate (4.27 g, 25.5 mmol) in a 100 mL of two-necked flask under $N_2$ was added DME (50.0 mL) via syringe followed by pure water (10.0 mL). The mixture was stirred at 90° C. overnight. After the mixture was cooled to rt, the solvent was removed in vacuo, and to the residue was added water (50.0 mL). The resulting mixture was extracted with EtOAc (30.0 mL×3). The combined organic phases were washed with brine, dried over anhydrous $Na_2SO_4$ and concentrated in vacuo. The residue was purified by silica gel column chromatography (PE/EtOAc (v/v)=1/2) to give the title compound 11-3 as a beige solid (3.45 g, 58%). The compound was characterized by the following spectroscopic data:

MS-ESI: m/z 690.3 $[M+H]^+$; and $^1$H NMR (400 MHz, $CDCl_3$): δ 7.84-7.82 (m, 1H), 7.69-7.66 (m, 2H), 7.57-7.55 (m, 1H), 7.48-7.44 (m, 2H), 7.40-7.36 (m, 1H), 5.41-5.39 (m, 1H), 5.29-5.27 (m, 1H), 4.34-4.30 (m, 1H), 3.75-3.70 (m, 1H), 3.70 (s, 3H), 3.64-3.62 (m, 1H), 3.20-3.01 (m, 1H), 2.99 (s, 2H), 2.95 (s, 2H), 2.25-2.20 (m, 1H), 2.20-2.13 (m, 2H), 1.96-1.94 (m, 1H), 1.52-1.78 (m, 8H), 0.88-0.86 (m, 6H).

Step 3) The Preparation of Compound 11-4

To a mixture of Boc-L-proline (29.0 g, 134.7 mmol) and HATU (53.93 g, 141.46 mmol) in THF (300 mL) was added DIPEA (28.2 mL, 161.6 mmol) under $N_2$ in an ice bath. At the end of the addition, the ice bath was removed, and the mixture was stirred at rt for 0.5 hour. Then the reaction mixture was cooled down in an ice bath, and a solution of 4-bromo-1,2-benzenediamine (27.71 g, 148.2 mmol) in THF (140 mL) was added dropwise. The mixture was stirred at rt for 2.0 hours. To the mixture was added water (20 mL), and most of the THF was removed in vacuo. To the residue was added water (200 mL), and the resulting mixture was extracted with EtOAc (250 mL×3). The combined organic phases were washed with brine, dried over anhydrous $Na_2SO_4$ and concentrated in vacuo to give compound F-1 as brown oil (60.1 g).

A mixture of compound F-1 (60.1 g, 156.5 mmol) in glacial acetic acid (140 mL) was heated at 40° C. overnight, cooled to rt and concentrated in vacuo. The residue was neutralized with $Na_2CO_3$ saturated solution, and water (200 mL) was added. The mixture was extracted with EtOAc (250 mL×3). The combined organic phases were washed with brine, dried over anhydrous $Na_2SO_4$ and concentrated in vacuo. The residue was purified by silica gel column chromatography (PE/EtOAc (v/v)=1/1) to give compound F-2 as a brown solid (40 g). The compound was characterized by the following spectroscopic data:

MS-ESI: m/z 267.3 $[M+H]^+$; and $^1$H NMR (400 MHz, $CDCl_3$): δ 7.68 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 2H), 2.01-1.91 (m, 1H), 1.49 (s, 9H).

To a solution of compound F-2 (366 mg, 1.0 mmol) in EtOAc (3.0 mL) was added a solution of HCl in EtOAc (15 mL, 4 M). The mixture was stirred at rt overnight and filtered. The filter cake was washed with EtOAc (30 mL) to give compound F-3 as a beige solid (280 mg). The compound was characterized by the following spectroscopic data:

MS-ESI: m/z 313.2 $[M+H]^+$; and $^1$H NMR (400 MHz, $CDCl_3$): δ 8.01 (s, 1H), 7.70-7.76 (m, 2H), 5.25-5.27 (m, 1H), 3.30-3.31 (m, 2H), 2.74-2.77 (m, 1H), 2.54-2.52 (m, 1H), 2.40-2.37 (m, 1H), 2.30-2.10 (m, 1H).

To a solution of isoleucine (1.0 g, 7.62 mmol) in THF (10 mL) was added a solution of NaOH (1.0 g, 25.2 mmol) in water (5 mL) followed by methyl chloroformate (1.18 mL, 15.25 mmol) dropwise. The mixture was stirred at rt overnight, adjusted to pH 3 with hydrochloric acid (1 N) and extracted with EtOAc (50 mL×3). The combined organic phases were dried over anhydrous $Na_2SO_4$ and concentrated in vacuo to give compound F-4 as a white solid (1.4 g, 7.4 mmol, 97%). The compound was characterized by the following ¹H NMR (400 MHz, CDCl₃): δ 1.27-1.39 (m, 1H), 1.38-1.53 (m, 2H), 1.58-1.72 (m, 3H), 1.82-1.94 (m, 2H), 2.04 (d, J=3.8 Hz, 2H), 3.70 (s, 3H), 4.94 (brs, 1H).

To a suspension of compound F-3 (771 mg, 2.274 mmol), compound F-4 (644.77 mg, 3.412 mmol) and EDCI (654 mg, 3.412 mmol) in DCM (15.0 mL) in an ice bath was added DIPEA (0.7 mL, 13.646 mmol) dropwise. The mixture was stirred at rt overnight. Water (20 mL) was added to the mixture and the mixture was extracted with DCM (50 mL×3). The combined organic phases were dried over anhydrous Na₂SO₄ and concentrated in vacuo. The residue was purified by silica gel column chromatography (PE/EtOAc (v/v)=1/2) to give the title compound F-5 as a solid (421 mg). The compound was characterized by the following spectroscopic data:

MS-ESI: m/z 438.3 [M+H]⁺; and

¹H NMR (400 MHz, CDCl₃): δ 7.57-7.59 (m, 1H), 7.52 (s, 1H), 7.31-7.33 (m, 1H), 5.33-5.40 (m, 2H), 4.30-4.34 (t, J=8.72 Hz, 1H), 4.11-4.13 (m, 1H), 3.70 (s, 3H), 3.66-3.62 (m, 1H), 3.04-3.05 (m, 1H), 2.80-3.04 (m, 1H), 2.17-2.23 (m, 1H), 2.04-2.16 (m, 2H), 1.70 (br, 1H), 1.24-1.28 (m, 2H), 0.88-0.84 (m, 6H).

To a solution of compound F-5 (420 mg, 0.961 mmol), bis(pinacolato)diboron (366 mg, 1.44 mmol), Pd(dppf)Cl₂·CH₂Cl₂ (79 mg, 0.0961 mmol) and KOAc (283 mg, 2.88 mmol) under N₂ was added DMF (6 mL). The resulting mixture was stirred at 90° C. overnight, cooled to rt, and water (50 mL) was added. The mixture was extracted with EtOAc (30.0 mL×3). The combined organic phases were washed with brine, dried over anhydrous Na₂SO₄ and concentrated in vacuo. The residue was purified by silica gel column chromatography (PE/EtOAc (v/v)=1/2) to give the title compound 11-4 as a beige solid (280 mg). The compound was characterized by the following spectroscopic data:

MS-ESI: m/z 485.3 [M+H]⁺; and

¹H NMR (400 MHz, CDCl₃): δ 7.88 (s, 1H), 7.71-7.73 (m, 1H), 7.66-7.67 (m, 1H), 5.33-5.40 (br, 2H), 4.30-4.34 (t, J=8.72 Hz, 1H), 3.89-3.91 (m, 1H), 3.70 (s, 3H), 3.64-3.62 (m, 1H), 3.07-3.09 (m, 1H), 2.21-2.22 (m, 1H), 2.20-2.13 (m, 2H), 1.50-1.53 (m, 1H), 1.35 (s, 12H), 1.27-1.30 (m, 2H), 0.88-0.84 (m, 6H).

Step 4) The Preparation of Compound 11-5

To a mixture of compound 11-3 (328.5 mg, 0.477 mmol), compound 11-4 (254 mg, 0.5244 mmol), Pd(PPh₃)₄ (55 mg, 0.0477 mmol) and potassium carbonate (200 mg, 1.431 mmol) in a 25 mL of two-necked flask under N₂ was added DME (5.0 mL) via syringe followed by pure water (1.0 mL). The resulting mixture was stirred at 90° C. overnight. After the mixture was cooled to rt, the solvent was removed under reduced pressure, and to the residue was added water (50.0 mL). The mixture was extracted with EtOAc (30.0 mL×3). The combined organic phases were washed with brine, dried over anhydrous Na₂SO₄ and concentrated in vacuo. The residue was purified by silica gel column chromatography (DCM/MeOH (v/v)=100/2) to give the title compound 11-5 as a beige solid (200 mg, 40%, HPLC: 96.65%). The compound was characterized by the following spectroscopic data:

MS-ESI: m/z 449.3 [M+2H]²⁺; and

¹H NMR (400 MHz, CDCl₃): δ 7.78-7.84 (m, 3H), 7.65-7.75 (m, 1H), 7.48-7.50 (m, 1H), 7.38-7.43 (m, 5H), 5.44-5.46 (m, 2H), 5.37-5.42 (m, 1H), 5.23-5.31 (br, 1H), 4.33-4.37 (m, 2H), 3.81-3.93 (m, 3H), 3.82-3.84 (m, 1H), 3.71 (br, 6H), 3.63-3.65 (m, 2H), 3.12-3.15 (m, 2H), 3.00 (br, 4H), 2.32-2.41 (m, 2H), 2.15-2.28 (m, 3H), 2.09-2.14 (m, 1H), 1.90-1.94 (m, 1H), 1.71-1.80 (br, 3H), 1.51-1.64 (br, 6H), 1.24-1.27 (br, 2H), 0.81-0.89 (m, 12H).

Example 12

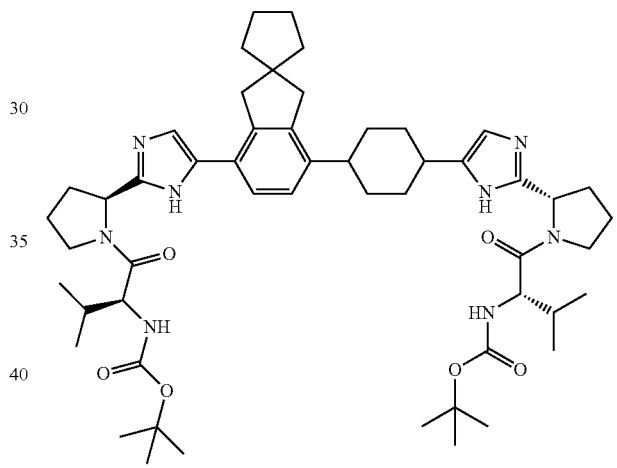

Synthetic Routes

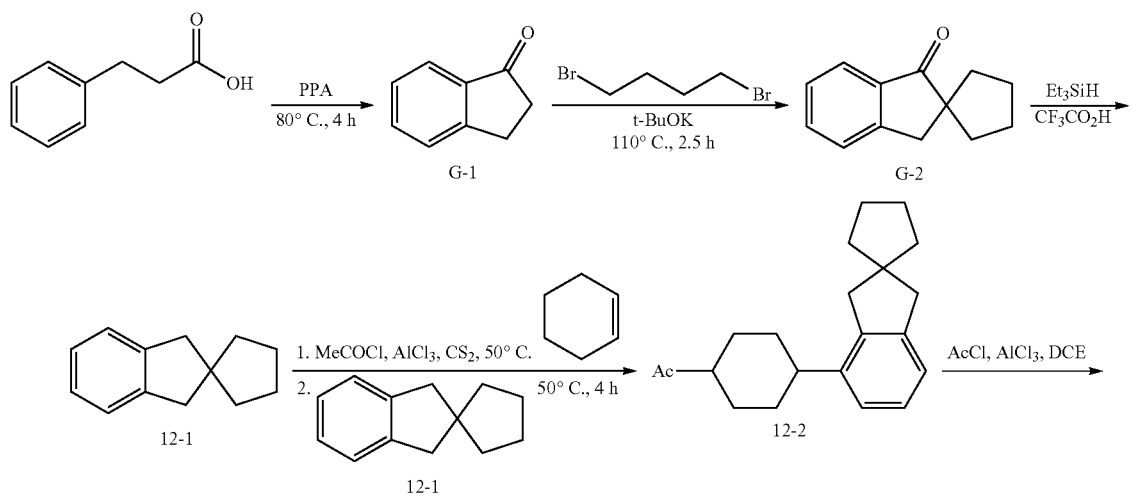

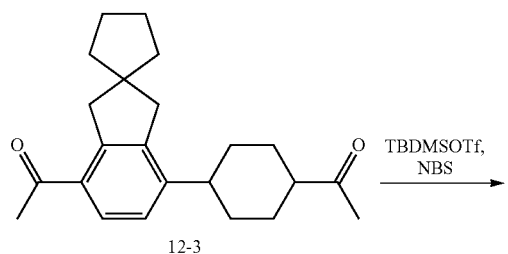
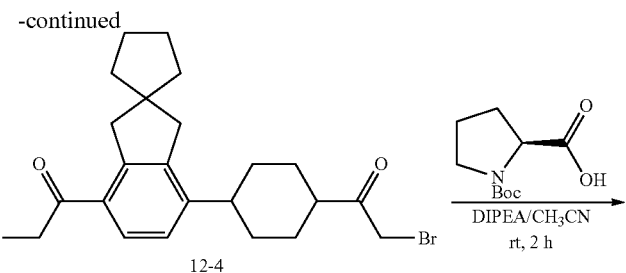
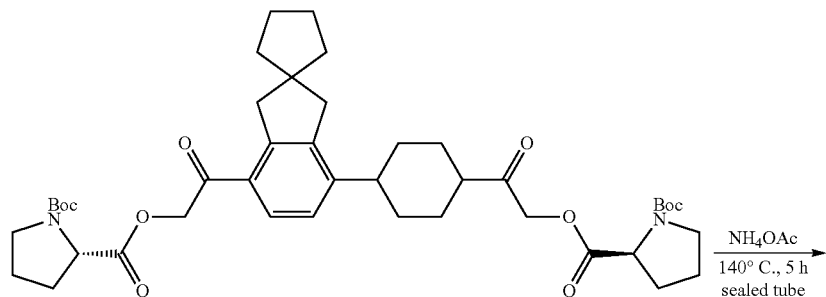
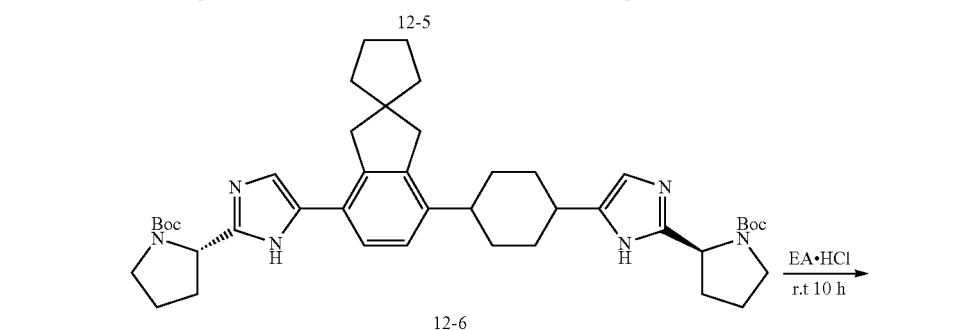
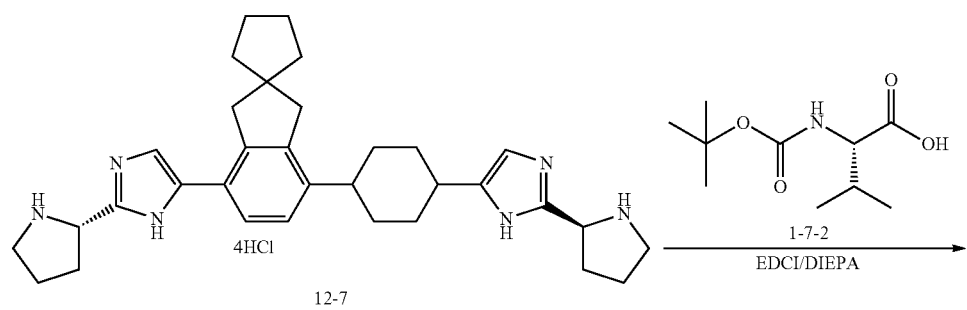
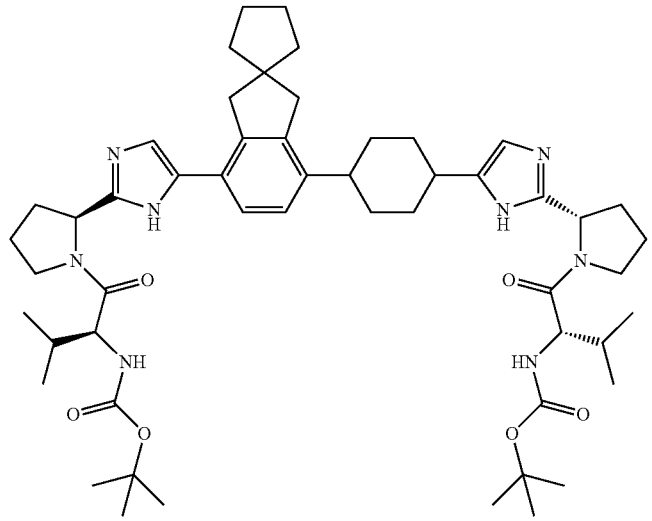

Step 1) The Preparation of Compound 12-1

A mixture of 3-phenylpropionic acid (4.68 g, 31.16 mmol) and PPA (50.87 g) in a 100 mL of round-bottomed flask was stirred at 80° C. for 4 hours, and ice water (250 mL) was added. The mixture was extracted with EtOAc (100 mL×5). The combined organic phases were dried over anhydrous $Na_2SO_4$ and concentrated in vacuo. The residue was purified by silica gel column chromatography (PE/EtOAc (v/v)=3/1) to give the title compound G-1 as a pale yellow solid (3 g). The compound was characterized by the following spectroscopic data:

MS-ESI: m/z 133.2 [M+H]$^+$; and $^1$H NMR (400 MHz, CDCl$_3$): δ 7.82 (m, 1H), 7.60 (m, 1H), 7.36 (m, 1H), 7.16 (m, 1H), 3.97-3.94 (m, 2H), 2.85-2.86 (m, 2H).

To a suspension of t-BuOK (3.81 g, 34.1 mmol) in toluene (40 mL) in an ice bath was added dropwise a solution of compound G-1 (3.0 g, 22.73 mmol) and 1,4-dibromobutane (5.4 g, 25.0 mmol) in toluene (40 mL). At the end of the addition, the mixture was stirred at 110° C. for 2.5 hours. After the mixture was cooled to rt, poured into ice water (50 mL) and extracted with EtOAc (100 mL×3). The combined organic phases were dried over anhydrous $Na_2SO_4$ and concentrated in vacuo. The residue was purified by silica gel column chromatography (PE/DCM (v/v)=3/1) to give the title compound G-2 as yellow slurry (2.9 g). The compound was characterized by the following spectroscopic data:

MS-ESI: m/z 187.3 [M+H]$^+$; and $^1$H NMR (400 MHz, CDCl$_3$): δ 7.71-7.69 (m, 1H), 7.53-7.51 (m, 1H), 7.34-7.32 (m, 2H), 2.89 (s, 2H), 1.93-1.91 (m, 4H), 1.76-1.81 (m, 2H), 1.56-1.62 (m, 2H).

To a mixture of compound G-2 (2.9 g, 15.57 mmol) and triethylsilane (7.4 mL) in an ice bath was added dropwise trifluoroacetic acid (20 mL). The mixture was stirred at 40° C. for 24 hours, neutralized with $Na_2CO_3$ saturated solution, and extracted with DCM (100 mL×4). The combined organic phases were dried over anhydrous $Na_2SO_4$ and concentrated in vacuo. The residue was purified by silica gel column chromatography (PE/DCM (v/v)=15/1) to give the title compound 12-1 as colorless oil (2.5 g). The compound was characterized by the following spectroscopic data:

MS-ESI: m/z 173.3 [M+H]$^+$; and $^1$H NMR (400 MHz, CDCl$_3$): δ 7.13 (s, 4H), 2.85 (s, 4H), 1.51-1.53 (m, 4H), 1.43-1.45 (m, 4H).

Step 2) The Preparation of Compound 12-2

To a suspension of anhydrous aluminium chloride (2.15 g, 16.2 mmol) in carbon disulfide (40 mL) was added dropwise acetyl chloride (1.4 mL, 19.7 mmol) to afford a pale yellow solution. Then to the above mixture was added a solution of cyclohexene (1 mL, 10 mmol) in carbon disulfide (20 mL) dropwise. At the end of the addition, the resulting mixture was stirred at rt for 2 hours. The solvent was removed in vacuo, and to the residue was added compound 12-1 (2.58 g, 15 mmol). The mixture was stirred at 50° C. for 4 hours, quenched with a small amount of ice water and extracted with EtOAc (100 mL×3). The combined organic phases were dried over anhydrous $Na_2SO_4$ and concentrated in vacuo. The residue was purified by silica gel column chromatography (PE/DCM (v/v)=10/1) to give the title compound 12-2 as colorless oil (1.5 g). The compound was characterized by the following spectroscopic data:

MS-ESI: m/z 297.3 [M+H]$^+$; and $^1$H NMR (400 MHz, CDCl$_3$): δ 7.02-7.05 (m, 3H), 2.95 (s, 4H), 2.75-2.77 (m, 1H), 2.31-2.33 (m, 1H), 1.95 (s, 3H), 1.57-1.59 (m, 8H), 1.35-1.46 (m, 8H).

Step 3) The Preparation of Compound 12-3

To a suspension of anhydrous aluminium chloride (2.12 g, 15.9 mmol) in 1,2-dichloroethane (40 mL) was added acetyl chloride (1.2 mL, 16.8 mmol) dropwise to afford a pale yellow solution. Then to the above mixture was added a solution of compound 12-2 (3.8 g, 13 mmol) in 1,2-dichloroethane (20 mL) dropwise. At the end of the addition, the resulting mixture was stirred at rt for 2 hours, quenched with a small amount of ice water and extracted with EtOAc (100 mL×3). The combined organic phases were dried over anhydrous $Na_2SO_4$ and concentrated in vacuo. The residue was purified by silica gel column chromatography (PE/EtOAc (v/v)=15/1) to give the title compound 12-3 as a white solid (1.63 g). The compound was characterized by the following spectroscopic data:

MS-ESI: m/z 339.3 [M+H]$^+$; and $^1$H NMR (400 MHz, CDCl$_3$): δ 7.69 (d, J=8.56 Hz, 1H), 7.09 (d, J=8.96 Hz, 1H), 2.98 (s, 4H), 2.75-2.77 (m, 1H), 2.68 (s, 3H), 2.31-2.33 (m, 1H), 1.95 (s, 3H), 1.57-1.59 (m, 8H), 1.35-1.46 (m, 8H).

Step 4) The Preparation of Compound 12-4

To a solution of compound 12-3 (1.6 g, 4.73 mmol) in anhydrous DCM (30 mL) was added DIPEA (2.5 mL) in an ice bath followed by TBDMSOTf (3.5 mL, 11.5 mmol). At the end of the addition, the mixture was stirred at rt for 2 hours, and a small amount of water was added. The resulting mixture was extracted with DCM (40 mL×3). The combined organic phases were dried over anhydrous $Na_2SO_4$ and concentrated in vacuo. The residue was dissolved in THF (20 mL) and the solution was cooled to 0° C. in an ice bath. To the solution was added NBS (1.56 g, 8.76 mmol) and the mixture was stirred for 4 hours at 0° C. The solvent was removed in vacuo, a small amount of water was added to the mixture and the mixture was extracted with EtOAc (50 mL×3). The combined organic phases were dried over anhydrous $Na_2SO_4$ and concentrated in vacuo. The residue was purified by silica gel column chromatography (PE/EtOAc (v/v)=10/1) to give the title compound 12-4 as white slurry (1.6 g). The compound was characterized by the following spectroscopic data:

MS-ESI: m/z 497.3 [M+H]$^+$; and $^1$H NMR (400 MHz, CDCl$_3$): δ 7.65 (d, J=8.66 Hz, 1H), 7.12 (d, J=9.05 Hz, 1H), 5.35 (s, 2H), 5.25 (s, 2H), 2.89 (s, 4H), 2.65-2.67 (m, 1H), 2.28-2.30 (m, 1H), 1.57-1.59 (m, 8H), 1.35-1.46 (m, 8H).

Step 5) The Preparation of Compound 12-5

To a solution of compound 12-4 (1.08 g, 2.18 mmol) in anhydrous acetonitrile (22 mL) in an ice bath was added DIPEA (1.1 mL) followed by Boc-L-proline (1.08 g, 5.014 mmol). The mixture was stirred at rt for 2 hour and concentrated in vacuo. The residue was purified by silica gel column chromatography (PE/EtOAc (v/v)=2/3) to give the title compound 12-5 as pale yellow slurry (1.6 g). The compound was characterized by the following spectroscopic data:

MS-ESI: m/z 765.9 [M+H]$^+$; and $^1$H NMR (400 MHz, CDCl$_3$): δ 7.67 (d, J=8.0 Hz, 1H), 7.28 (d, J=8.0 Hz, 1H), 5.20-5.59 (m, 4H), 4.49-4.51 (m, 1H), 4.10-4.15 (m, 1H), 3.58-3.60 (m, 2H), 3.40-3.49 (m, 2H), 3.24 (s, 2H), 2.86 (s, 2H), 2.62-2.64 (m, 2H), 2.32-2.34 (m, 2H), 2.05-2.20 (m, 4H), 1.80-2.00 (m, 4H), 1.50-1.54 (m, 10H), 1.46-1.48 (m, 4H), 1.45 (s, 9H), 1.47 (s, 9H).

Step 6) The Preparation of Compound 12-6

A mixture of compound 12-5 (1.4 g, 1.83 mmol) and ammonium acetate (2.82 g, 36.6 mmol) in xylene (20 mL) in a sealed tube was stirred at 140° C. for 5 hours. After the mixture was cooled to rt, a small amount of water was added, and the resulting mixture was extracted with EtOAc (50 mL×3). The combined organic phases were dried over anhydrous Na$_2$SO$_4$ and concentrated in vacuo. The residue was purified by silica gel column chromatography (DCM/MeOH (v/v)=50/1) to give the title compound 12-6 as a pale yellow solid (0.95 g). The compound was characterized by the following spectroscopic data:

MS-ESI: m/z 725.9 [M+H]$^+$; and $^1$H NMR (400 MHz, CDCl$_3$): δ 10.97 (brs, 1H), 10.49 (brs, 1H), 7.63 (d, J=8.0 Hz, 1H), 7.18 (d, J=8.0 Hz, 1H), 4.99-5.00 (m, 2H), 3.41-3.42 (m, 2H), 3.15 (s, 1H), 2.95-3.13 (m, 4H), 2.97 (s, 2H), 2.75-2.77 (m, 1H), 2.31-2.33 (m, 1H), 2.10-2.20 (m, 4H), 1.95-1.98 (m, 3H), 1.80-2.00 (m, 2H), 1.57-1.59 (m, 8H), 1.50-1.54 (m, 8H), 1.51 (s, 18H).

Step 7) The Preparation of Compound 12-7

To a solution of compound 12-6 (950 mg) in THF (30 mL) was added a solution of HCl in EtOAc (22 mL, 4 M). The mixture was stirred at rt for 10 hours and pale yellow solid precipitated. The mixture was filtered, and the filter cake was washed with EtOAc (50 mL) to get the title compound 12-7 as a pale yellow solid (730 mg). The compound was characterized by the following spectroscopic data:

MS-ESI: m/z 519.7 [M+H]$^+$; and $^1$H NMR (400 MHz, CDCl$_3$): δ 10.21 (brs, 2H), 9.72 (brs, 2H), 7.60 (d, J=8.0 Hz, 2H), 7.39 (d, J=8.0 Hz, 2H), 4.98 (s, 2H), 3.57 (m, 4H), 3.07 (s, 2H), 3.00 (s, 2H), 2.75 (m, 1H), 2.50-2.51 (m, 2H), 2.35-2.45 (m, 2H), 2.31-2.33 (m, 1H), 2.19-2.21 (m, 2H), 1.99-2.04 (m, 2H), 1.57-1.60 (m, 8H), 1.55-1.65 (m, 8H).

Step 8) The Preparation of Compound 12-8

To a mixture of compound 12-7 (400 mg, 0.6 mmol), compound 1-7-2 (341 mg, 1.56 mmol) and EDCI (300.56 mg, 1.56 mmol) in DCM (30 mL) at 0° C. was added DIPEA (1.09 mL, 6.264 mmol) dropwise. The mixture was stirred at rt for 10 hours. Then a small amount of water was added, and the resulting mixture was extracted with DCM (50 mL×3). The combined organic phases were dried over anhydrous Na$_2$SO$_4$ and concentrated in vacuo. The residue was purified by silica gel column chromatography (DCM/MeOH (v/v)=50/1) to give the title compound 12-8 as a pale yellow solid (350 mg, HPLC: 98%). The compound was characterized by the following spectroscopic data:

MS-ESI: m/z 924.3 [M+H]$^+$; and $^1$H NMR (400 MHz, CDCl$_3$): δ 10.74 (d, J=14.0 Hz, 1H), 10.34 (d, J=14.0 Hz, 1H), 7.25-7.26 (m, 2H), 7.10-7.12 (m, 2H), 5.44-5.47 (m, 2H), 5.27-5.28 (m, 2H), 4.31-4.34 (m, 2H), 3.82-3.84 (m, 2H), 3.70 (s, 6H), 3.63-3.69 (m, 2H), 2.94-3.03 (m, 6H), 2.75-2.77 (m, 1H), 2.35-2.37 (m, 2H), 2.31-2.33 (m, 1H), 2.20-2.21 (m, 2H), 2.09-2.12 (m, 2H), 1.95-1.98 (m, 2H), 1.56-1.66 (m, 14H), 1.38 (m, 12H), 1.36-1.46 (m, 8H), 1.25 (m, 4H), 1.03-1.05 (m, 2H).

Example 13

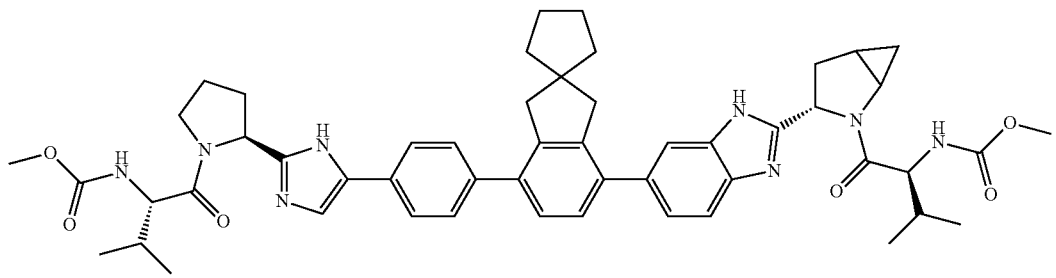

Synthetic Routes

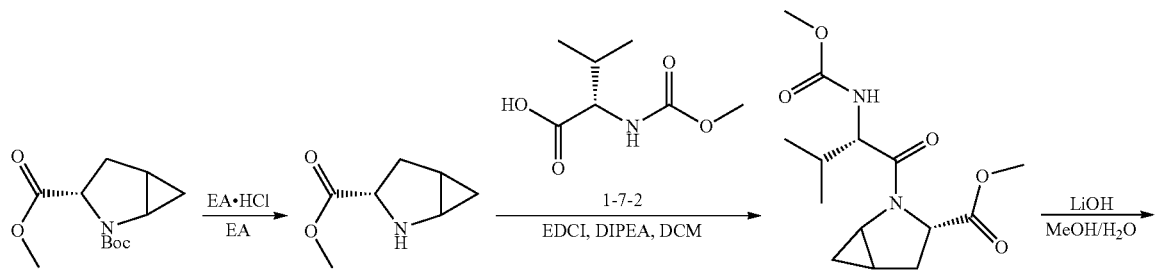

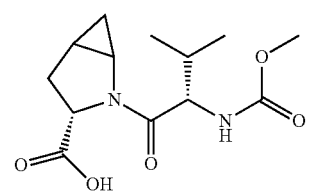

13-1

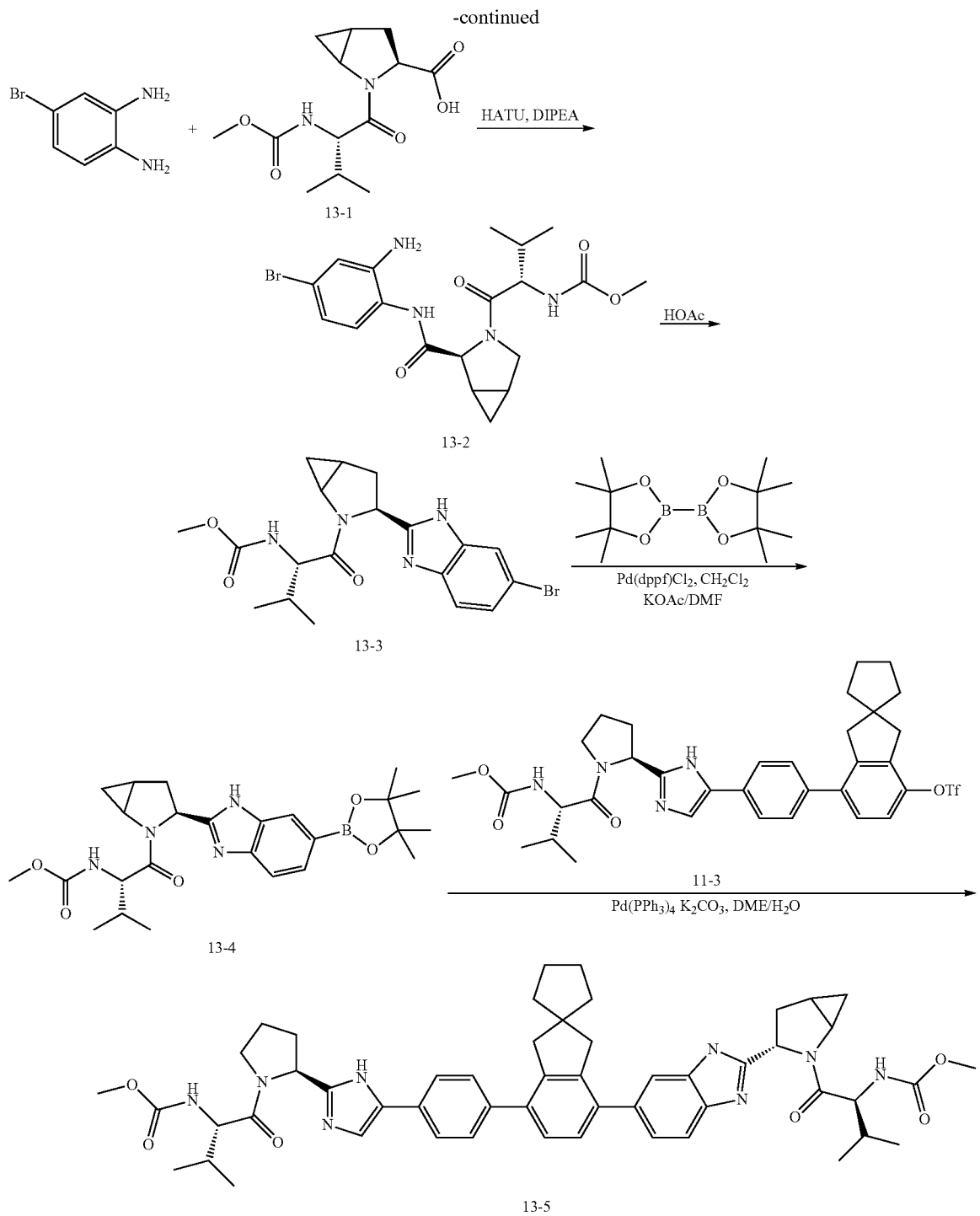

Step 1) The Preparation of Compound 13-1

To a solution of compound H-1 (1.5 g, 6.22 mmol) in EtOAc (10.0 mL) was added a solution of HCl in EtOAc (20 mL, 4 M). The mixture was stirred at rt overnight and filtered. The filter cake was washed with EtOAc (80 mL) to give compound H-2 as a white solid (1.3 g, HPLC: 90%). The compound was characterized by the following spectroscopic data:

MS-ESI: m/z 142.3 [M+H]$^+$; and $^1$H NMR (400 MHz, CDCl$_3$): δ 4.02 (m, 1H), 3.58 (s, 3H), 2.89 (m, 1H), 2.17-2.20 (m, 2H), 0.95 (m, 1H), 0.53 (m, 1H), 0.21 (m, 1H).

To a solution of compound H-2 (1.007 g, 5.67 mmol), compound 1-7-2 (1.70 g, 9.682 mmol) and EDCI (1.856 g, 9.682 mmol) in DCM (40.0 mL) was added dropwise DIPEA (6.75 mL, 38.73 mmol) in an ice bath. After the mixture was stirred at rt overnight, water (20 mL) was added and the mixture was extracted with DCM (50 mL×3). The combined organic phases were dried over anhydrous Na$_2$SO$_4$ and concentrated in vacuo. The residue was purified by silica gel column chromatography (PE/EtOAc (v/v)=4/1) to give compound H-3 as a solid (1.17 g). The compound was characterized by the following spectroscopic data:

MS-ESI: m/z 300.3 [M+H]$^+$; and $^1$H NMR (400 MHz, CDCl$_3$): δ 5.46 (m, 1H), 4.78-4.82 (m, 2H), 3.69 (s, 6H), 2.56 (m, 1H), 2.19-2.23 (m, 2H), 0.91-0.95 (m, 7H), 0.52 (m, 1H), 0.23 (m, 1H).

A suspension of compound H-3 (1.165 g, 3.9 mmol) and LiOH.H$_2$O (0.470 g, 11.2 mmol) in mixed solvents of MeOH (10 mL) and H$_2$O (10 mL) was stirred at rt overnight. MeOH was removed in vacuo, and water (10 mL) was added to the mixture. The aqueous layer was washed with EtOAc (50 mL), adjusted to pH 3, and extracted with EtOAc (50 mL×3). The combined organic phases were washed with brine, dried over anhydrous Na$_2$SO$_4$ and concentrated in vacuo to give the title compound 13-1 as a white solid (1.14 g). The compound was characterized by the following spectroscopic data:

MS-ESI: m/z 285.3 [M+H]$^+$; and $^1$H NMR (400 MHz, CDCl$_3$): δ 5.36 (m, 1H), 4.75-4.80 (m, 2H), 3.65 (s, 3H), 2.54 (m, 1H), 2.17-2.21 (m, 2H), 0.89-0.92 (m, 7H), 0.51 (m, 1H), 0.21 (m, 1H).

Step 2) the preparation of compound 13-2

To a mixture of compound 13-1 (2.5 g, 8.824 mmol) and HATU (2.6 g, 9.265 mmol) in THF (30 mL) in an ice bath was added DIPEA (1.85 mL, 10.589 mmol) under N$_2$. At the end of the addition, the ice bath was removed. The mixture was stirred at rt for 0.5 hour, then cooled in an ice bath and a solution of 4-bromo-1,2-benzenediamine (1.815 g, 9.7 mmol) in THF (30 mL) was added dropwise. The resulting mixture was stirred at rt for 2.0 hours and water (20 mL) was added. Most of the THF was removed in vacuo, and to the residue was added water (200 mL). The mixture was extracted with EtOAc (250 mL×3). The combined organic phases were washed with brine, dried over anhydrous Na$_2$SO$_4$ and concentrated in vacuo. The residue was purified by silica gel column chromatography (PE/EtOAc (v/v)=3/1) to give the title compound 13-2 as brown oil (2.5 g).

Step 3) The Preparation of Compound 13-3

A solution of compound 13-2 (2.5 g, 5.5 mmol) in glacial acetic acid (40 mL) was stirred at 40° C. overnight. After the mixture was cooled to rt, the mixture was concentrated in vacuo and quenched with Na$_2$CO$_3$ saturated solution until there was no more CO$_2$ gas evolution. Water (100 mL) was added to the mixture and the mixture was extracted with EtOAc (150 mL×3). The combined organic phases were washed with brine, dried over anhydrous Na$_2$SO$_4$ and concentrated in vacuo. The residue was purified by silica gel column chromatography (PE/EtOAc (v/v)=1/1) to give the title compound 13-3 as a brown solid (1.05 g). The compound was characterized by the following spectroscopic data:

MS-ESI: m/z 436.0 [M+H]$^+$; and $^1$H NMR (400 MHz, CD$_3$OD): δ 7.656 (s, 1H), 7.403-7.425 (d, J=8.48 Hz, 1H), 7.28-7.31 (dd, 1H), 5.59-5.63 (dd, 1H), 4.42-4.44 (d, J=7.52 Hz, 1H), 4.07-4.12 (m, 1H), 3.666 (s, 3H), 2.78 (s, 2H), 2.70-2.74 (br, 1H), 2.46-2.50 (m, 1H), 1.94 (s, 1H), 1.87-1.91 (br, 1H), 0.95-1.01 (m, 2H), 0.87-0.89 (br, 6H).

Step 4) The Preparation of Compound 13-4

To a mixture of compound 13-3 (1.05 g, 2.41 mmol), bis(pinacolato)diboron (0.919 g, 3.618 mmol), Pd(dppf)Cl$_2$.CH$_2$Cl$_2$ (0.197 g, 0.241 mmol) and KOAc (0.710 g, 7.236 mmol) under N$_2$ was added DMF (15 mL) via syringe. The resulting mixture was stirred at 90° C. overnight, cooled to rt, and water (60 mL) was added. The mixture was extracted with EtOAc (30.0 mL×3). The combined organic phases were washed with brine, dried over anhydrous Na$_2$SO$_4$ and concentrated in vacuo. The residue was purified by silica gel column chromatography (PE/EtOAc (v/v)=1/2) to give the title compound 13-4 as a beige solid (0.542 g, 46.72%). The compound was characterized by the following spectroscopic data:

MS-ESI: m/z 483.3 [M+H]$^+$; and $^1$H NMR (400 MHz, CDCl$_3$): δ 10.50-10.54 (br, 1H), 7.72-7.74 (d, J=8.12 Hz, 1H), 7.66-7.68 (d, J=8.08 Hz, 1H), 7.33-7.35 (d, J=7.64 Hz, 1H), 5.70-5.73 (d, J=10.32 Hz, 1H), 5.61-5.63 (br, 1H), 4.55-4.59 (t, J=7.12 Hz, 1H), 4.09-4.13 (m, 1H), 3.72 (s, 3H), 3.37-3.40 (d, J=13.08 Hz, 1H), 2.55-2.58 (br, 1H), 2.049 (s, 1H), 1.347 (s, 12H), 1.24-1.26 (br, 2H), 0.81-0.83 (br, 6H).

Step 5) The Preparation of Compound 13-5

To a mixture of compound 11-3 (260 mg, 0.3769 mmol), compound 13-4 (200 mg, 0.4146 mmol), Pd(PPh$_3$)$_4$ (44 mg, 0.03769 mmol) and potassium carbonate (158 mg, 1.132 mmol) in a 25 mL of two-necked flask under N$_2$ was added DME (5.0 mL) via syringe followed by pure water (1.0 mL). The resulting mixture was stirred at 90° C. overnight, then cooled to rt and concentrated in vacuo. To the residue was added water (50.0 mL). The mixture was extracted with EtOAc (30.0 mL×3). The combined organic phases were washed with brine, dried over anhydrous Na$_2$SO$_4$ and concentrated in vacuo. The residue was purified by silica gel column chromatography (DCM/MeOH (v/v)=100/2) to give the title compound 13-5 as a beige solid (190 mg, 56.4%, HPLC: 97.39%). The compound was characterized by the following spectroscopic data:

MS-ESI: m/z 448.3 [M+H]$^+$; and $^1$H NMR (400 MHz, CDCl$_3$): δ 7.69-7.86 (m, 3H), 7.31-7.54 (m, 8H), 5.72-5.75 (d, J=12.12 Hz, 1H), 5.27-5.42 (m, 3H), 4.61 (m, 1H), 4.21-4.30 (br, 1H), 3.73 (s, 6H), 3.49-3.549 (m, 2H), 3.00-3.03 (br, 5H), 2.51-2.60 (br, 1H), 2.32-2.41 (br, 1H), 2.17-2.20 (br, 2H), 2.10 (s, 1H), 2.04 (s, 1H), 1.91-1.96 (br, 2H), 1.58-1.66 (br, 9H), 1.24-1.27 (m, 2H), 1.05-1.11 (br, 1H), 0.81-0.85 (m, 12H).

Example 14

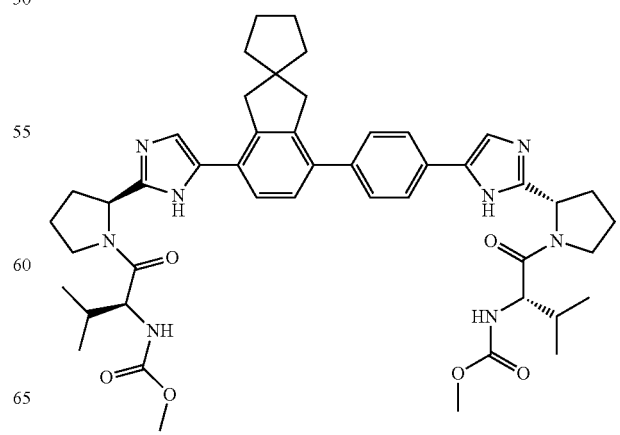

Synthetic Routes
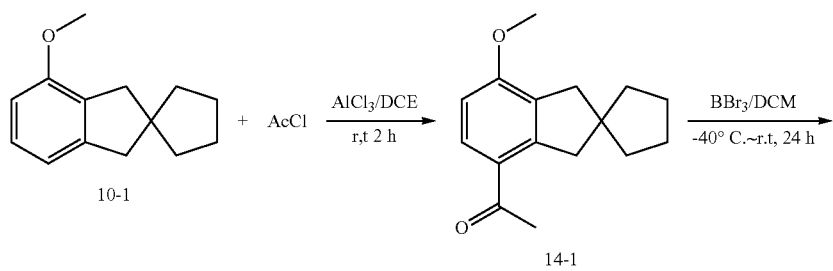
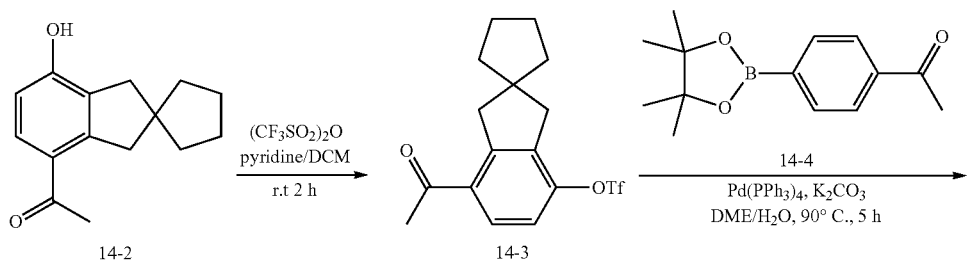
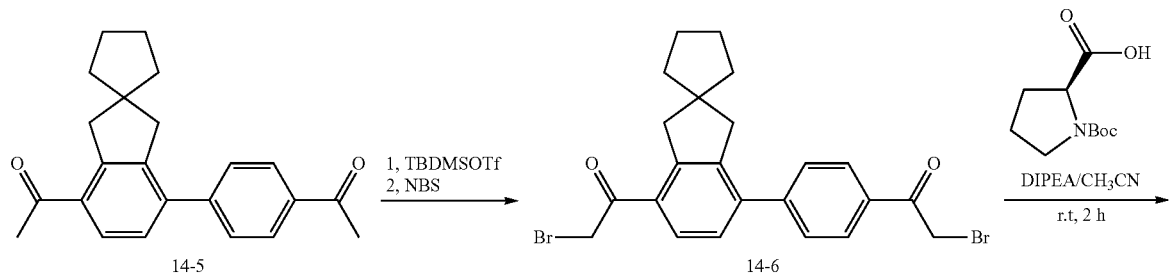
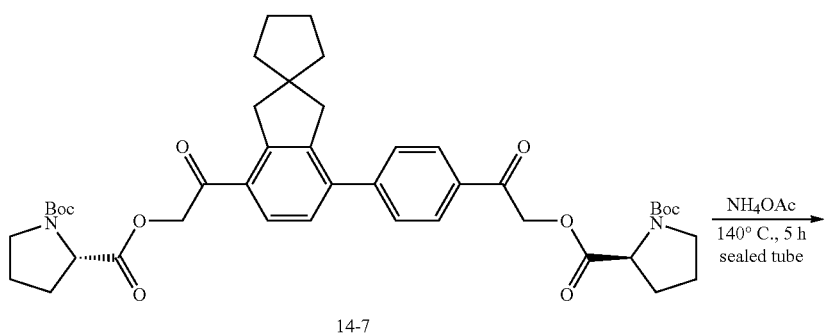
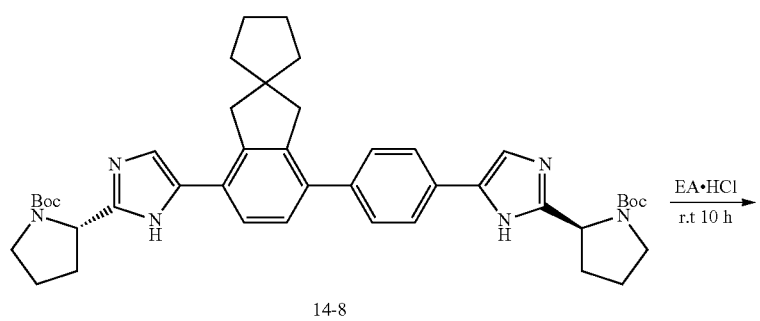

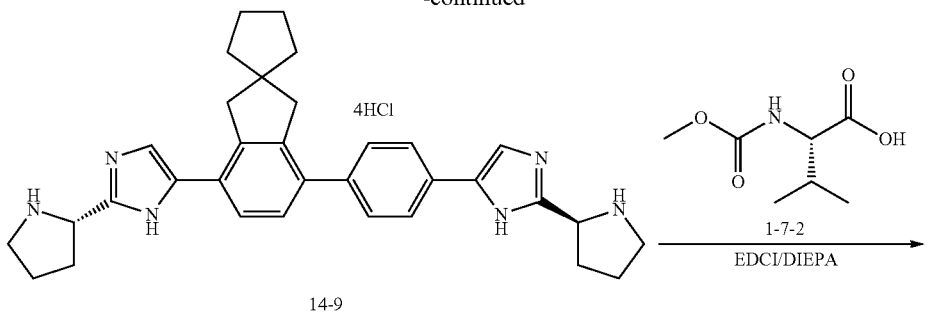

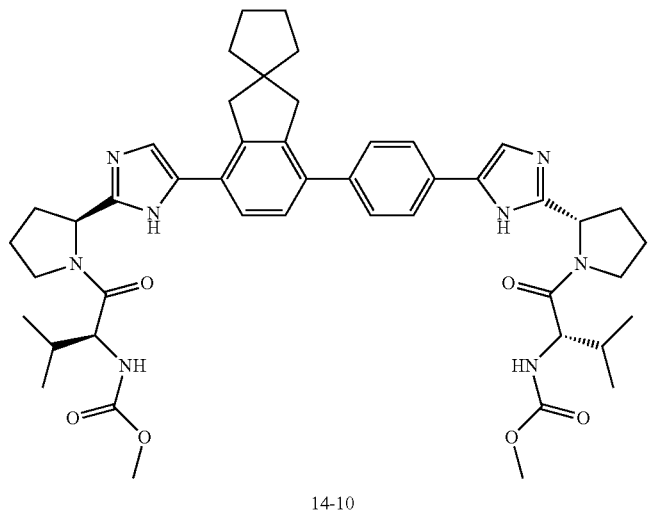

14-10

Step 1) The Preparation of Compound 14-1

To a suspension of anhydrous aluminium chloride (2.12 g, 15.9 mmol) in 1,2-dichloroethane (40 mL) was added acetyl chloride (1.2 mL) dropwise to afford a pale yellow solution. Then to the above mixture was added a solution of compound 10-1 (1.59 g, 7.8 mmol) in 1,2-dichloroethane (20 mL) dropwise. At the end of the addition, the resulting mixture was stirred at rt for 2 hours, quenched with a small amount of ice water and extracted with EtOAc (100 mL×3). The combined organic phases were dried over anhydrous $Na_2SO_4$ and filtered. The filtrate was concentrated in vacuo. The residue was purified by silica gel column chromatography (PE/EtOAc (v/v)=15/1) to give the title compound 14-1 as a white solid (1.63 g, 85%, HPLC: 95%). The compound was characterized by the following spectroscopic data:

MS-ESI: m/z 245.3 $[M+H]^+$; and $^1$H NMR (400 MHz, $CDCl_3$): δ 7.73 (d, J=8.0 Hz, 1H), 6.71 (d, J=8.0 Hz, 1H), 3.89 (s, 3H), 3.23 (s, 2H), 2.75 (s, 2H), 1.70-1.73 (m, 4H), 1.60-1.62 (m, 4H).

Step 2) The Preparation of Compound 14-2

To a solution of compound 14-1 (0.97 g, 3.97 mmol) in anhydrous DCM (40 mL) at −40° C. was added dropwise a solution of boron tribromide (6.0 g, 24 mmol) in DCM (20 mL) to get a reddish brown mixture. At the end of the addition, the reaction mixture was stirred at rt for 24 hours, quenched with a small amount of ice water, and extracted with DCM (30 mL×3). The combined organic phases were dried over anhydrous $Na_2SO_4$ and concentrated in vacuo. The residue was purified by silica gel column chromatography (PE/EtOAc (v/v)=4/1) to give the title compound 14-2 as a white solid (0.82 g, 90%, HPLC: 98%). The compound was characterized by the following spectroscopic data:

MS-ESI: m/z 231.3 $[M+H]^+$; and $^1$H NMR (400 MHz, $CDCl_3$): δ 7.64 (d, J=8.0 Hz, 1H), 6.68 (d, J=8.0 Hz, 1H), 5.22 (s, 1H), 3.24 (s, 2H), 2.74 (s, 2H), 2.53 (s, 3H), 1.71-1.74 (m, 4H), 1.61-1.64 (m, 4H).

Step 3) The Preparation of Compound 14-3

To a solution of compound 14-2 (0.80 g, 3.48 mmol) in anhydrous DCM (30 mL) was added pyridine (1.4 mL) dropwise at 0° C. to get a pale yellow mixture, and to the above mixture was added trifluoromethanesulfonic anhydride (1.76 mL, 10 mmol) slowly. The mixture was stirred at rt for 2 hours, then a small amount of water was added, and the resulting mixture was extracted DCM (50 mL×3). The combined organic phases were dried over anhydrous $Na_2SO_4$ and concentrated in vacuo. The residue was purified by silica gel column chromatography (PE/DCM (v/v)=4/1) to give the title compound 14-3 as pale yellow slurry (1.25 g, 100%, HPLC: 95%). The compound was characterized by the following spectroscopic data:

MS-ESI: m/z 363.6 $[M+H]^+$; and $^1$H NMR (400 MHz, $CDCl_3$): δ 7.72 (d, J=8.0 Hz, 1H), 7.15 (d, J=8.0 Hz, 1H), 3.25 (s, 2H), 2.92 (s, 2H), 2.58 (s, 3H), 2.63 (s, 3H), 1.61-1.74 (m, 8H).

Step 4) The Preparation of Compound 14-4

To a mixture of 4-bromoacetophenone (2.0 g, 10 mmol), bis(pinacolato)diboron (3.81 g, 15 mmol), Pd(dppf)$Cl_2 \cdot CH_2Cl_2$ (0.41 g, 0.5 mmol) and anhydrous KOAc (2.94 g, 30 mmol) under $N_2$ was added DMF (50 mL) via syringe. The resulting mixture was stirred at 90° C. for 4 hours and cooled to rt. Water (100 mL) was added, and the mixture was extracted with EtOAc (100 mL×3). The combined organic phases were washed with water followed by brine, dried over anhydrous $Na_2SO_4$ and concentrated in vacuo. The residue was purified by silica gel column chromatography (PE/DCM (v/v)=4/1) to give the title compound 14-4 as a white solid (2.35 g, 95%, HPLC: 95%). The compound was characterized by the following spectroscopic data:

MS-ESI: m/z 247.1 [M+H]$^+$; and $^1$H NMR (400 MHz, CDCl$_3$): δ 7.87-7.93 (m, 4H), 2.60 (s, 3H), 1.35 (s, 12H).

Step 5) The Preparation of Compound 14-5

To a mixture of compound 14-4 (506 mg, 2 mmol), Pd(PPh$_3$)$_4$ (140 mg, 0.12 mmol) and potassium carbonate (600 mg, 4.3 mmol) under N$_2$ was added a solution of compound 14-3 (620 mg, 1.7 mmol) in DME (15 mL) followed by pure water (5 mL). The resulting mixture was refluxed at 90° C. for 5 hours. After the mixture was cooled to rt, a small amount of water was added. The mixture was extracted with EtOAc (30 mL×3). The combined organic phases were dried over anhydrous Na$_2$SO$_4$ and concentrated in vacuo. The residue was purified by silica gel column chromatography (PE/EtOAc (v/v)=10/1) to give the title compound 14-5 as a white solid (450 mg, 80%, HPLC: 95%). The compound was characterized by the following spectroscopic data:

MS-ESI: m/z 333.4 [M+H]$^+$; and $^1$H NMR (400 MHz, CDCl$_3$): δ 8.04 (d, J=8.0 Hz, 1H), 7.75 (d, J=8.0 Hz, 1H), 7.53 (d, J=8.0 Hz, 1H), 7.27 (d, J=8.0 Hz, 1H), 3.27 (s, 1H), 2.87 (s, 2H), 2.65 (s, 3H), 2.63 (s, 3H), 1.60-1.62 (m, 8H).

Step 6) The Preparation of Compound 14-6

To a solution of compound 14-5 (675 mg, 2 mmol) in anhydrous DCM (20 mL) was added DIPEA (1.32 mL) in an ice bath followed by TBDMSOTf (1.4 mL, 6 mmol). At the end of the addition, the mixture was stirred at rt for 2 hours, and a small amount of water was added. The resulting mixture was extracted with DCM (20 mL×3). The combined organic phases were dried over anhydrous Na$_2$SO$_4$ and concentrated in vacuo. The residue was dissolved in THF (20 mL) and the solution was cooled to 0° C. in an ice bath. To the solution was added NBS (723 mg, 4 mmol) and the mixture was stirred for 4 hours at 0° C. The solvent was removed in vacuo, a small amount of water was added to the mixture and the mixture was extracted with EtOAc (30 mL×3). The combined organic phases were dried over anhydrous Na$_2$SO$_4$ and concentrated in vacuo. The residue was purified by silica gel column chromatography (PE/EtOAc (v/v)=8/1) to give the title compound 14-6 as white slurry (0.87 g, 88%, HPLC: 95%). The compound was characterized by the following spectroscopic data:

MS-ESI: m/z 491.23 [M+H]$^+$; and $^1$H NMR (400 MHz, CDCl$_3$): δ 8.07 (d, J=8.0 Hz, 2H), 7.76 (d, J=8.0 Hz, 1H), 7.57 (d, J=8.0 Hz, 2H), 7.30 (d, J=8.0 Hz, 1H), 4.48 (s, 4H), 3.27 (s, 2H), 2.89 (s, 2H), 1.57-1.65 (m, 8H).

Step 7) The Preparation of Compound 14-7

To a solution of compound 14-6 (1.08 g, 2.2 mmol) in anhydrous acetonitrile (22 mL) in an ice bath was added DIPEA (1.1 mL) followed by Boc-L-proline (1.04 g, 4.8 mmol). The mixture was stirred at rt for 2 hours and concentrated in vacuo. The residue was purified by silica gel column chromatography (PE/EtOAc (v/v)=2/3) to give the title compound 14-7 as pale yellow slurry (1.4 g, 84%, HPLC: 99%). The compound was characterized by the following spectroscopic data:

MS-ESI: m/z 759.9 [M+H]$^+$; and $^1$H NMR (400 MHz, CDCl$_3$): δ 7.79-7.80 (m, 2H), 7.67 (d, J=8.0 Hz, 1H), 7.53-7.56 (m, 2H), 7.28 (d, J=8.0 Hz, 1H), 5.20-5.59 (m, 4H), 4.49-4.51 (m, 1H), 4.10-4.15 (m, 1H), 3.58-3.60 (m, 2H), 3.40-3.49 (m, 2H), 3.24 (s, 2H), 2.86 (s, 2H), 2.32-2.34 (m, 4H), 2.05-2.20 (m, 2H), 1.80-2.00 (m, 2H), 1.50-1.54 (m, 8H), 1.45 (s, 9H), 1.47 (s, 9H).

Step 8) The Preparation of Compound 14-8

A mixture of compound 14-7 (1.4 g, 1.8 mmol) and ammonium acetate (2.2 g, 28 mmol) in xylene (20 mL) in a sealed tube was refluxed at 140° C. for 5 hours. After the mixture was cooled to rt, a small amount of water was added, and the mixture was extracted with EtOAc (50 mL×3). The combined organic phases were dried over anhydrous Na$_2$SO$_4$ and concentrated in vacuo. The residue was purified by silica gel column chromatography (DCM/MeOH (v/v)=50/1) to give the title compound 14-8 as a pale yellow solid (0.73 g, 55%, HPLC: 95%). The compound was characterized by the following spectroscopic data:

MS-ESI: m/z 719.93 [M+H]$^+$; and $^1$H NMR (400 MHz, CDCl$_3$): δ 10.97 (brs, 1H), 10.49 (brs, 1H), 7.79-7.80 (m, 2H), 7.45 (d, J=8.0 Hz, 1H), 7.27 (d, J=8.0 Hz, 1H), 7.14 (s, 1H), 7.26 (s, 1H), 4.99-5.00 (m, 2H), 3.41-3.42 (m, 2H), 2.95-3.20 (m, 4H), 3.05 (s, 1H), 2.97 (s, 2H), 2.10-2.20 (m, 4H), 1.95-1.98 (m, 2H), 1.80-2.00 (m, 2H), 1.50-1.54 (m, 8H), 1.51 (s, 18H).

Step 9) The Preparation of Compound 14-9

To a solution of compound 14-8 (205 mg, 0.28 mmol) in THF (3 mL) was added a solution of HCl in EtOAc (11 mL, 4 M). The mixture was stirred at rt for 10 hours and filtered. The filter cake was washed with EtOAc to get the title compound 14-9 as a pale yellow solid (0.186 g, 100%, HPLC: 100%). The compound was characterized by the following spectroscopic data:

MS-ESI: m/z 519.7 [M+H]$^+$; and $^1$H NMR (400 MHz, CDCl$_3$): δ 10.21 (brs, 2H), 9.72 (brs, 2H), 8.04 (s, 1H), 7.96 (d, J=8.0 Hz, 2H), 7.76 (d, J=8.0 Hz, 2H), 7.60 (d, J=8.0 Hz, 2H), 7.39 (d, J=8.0 Hz, 2H), 4.98 (s, 2H), 3.57 (m, 4H), 3.07 (s, 2H), 3.00 (s, 2H), 2.50-2.51 (m, 2H), 2.35-2.45 (m, 2H), 2.19-2.21 (m, 2H), 1.99-2.04 (m, 2H), 1.55-1.65 (m, 8H).

Step 10) The Preparation of Compound 14-10

To a suspension of compound 14-9 (147 mg, 0.22 mmol), compound 1-7-2 (150 mg, 0.86 mmol) and EDCI (220 mg, 1.1 mmol) in DCM (3 mL) in an ice bath was added DIPEA (0.5 mL) dropwise. At the end of the addition, the mixture was stirred at rt for 10 hours. A small amount of water was added to the mixture and the mixture was extracted with DCM (10 mL×3). The combined organic phases were dried over anhydrous Na$_2$SO$_4$ and concentrated in vacuo. The residue was purified by silica gel column chromatography (DCM/MeOH (v/v)=50/1) to give the title compound 14-10 as a pale yellow solid (50 mg, 25%, HPLC: 99%). The compound was characterized by the following spectroscopic data:

MS-ESI: m/z 834.03 [M+H]$^+$; and $^1$H NMR (400 MHz, CDCl$_3$): δ 10.74 (d, J=14.0 Hz, 1H), 10.34 (d, J=14.0 Hz, 1H), 7.80-7.82 (m, 2H), 7.43-7.45 (m, 3H), 7.25-7.26 (m, 2H), 7.10-7.12 (m, 1H), 5.44-5.47 (m, 2H), 5.27-5.28 (m, 2H), 4.31-4.34 (m, 2H), 3.82-3.84 (m, 2H), 3.70 (s, 6H), 3.63-3.69 (m, 2H), 2.94-3.03 (m, 6H), 2.35-2.37 (m, 2H), 2.20-2.21 (m, 2H), 2.09-2.12 (m, 2H), 1.95-1.98 (m, 2H), 1.56-1.66 (m, 4H), 1.25 (m, 4H), 1.03-1.05 (m, 2H), 0.88 (s, 12H).

Example 15
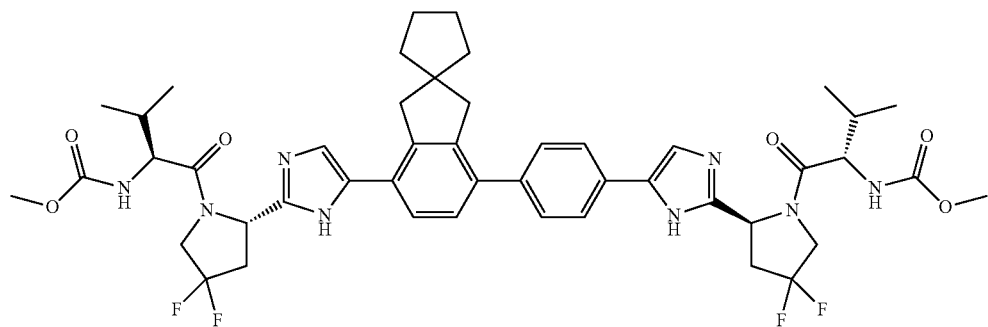
Synthetic Routes
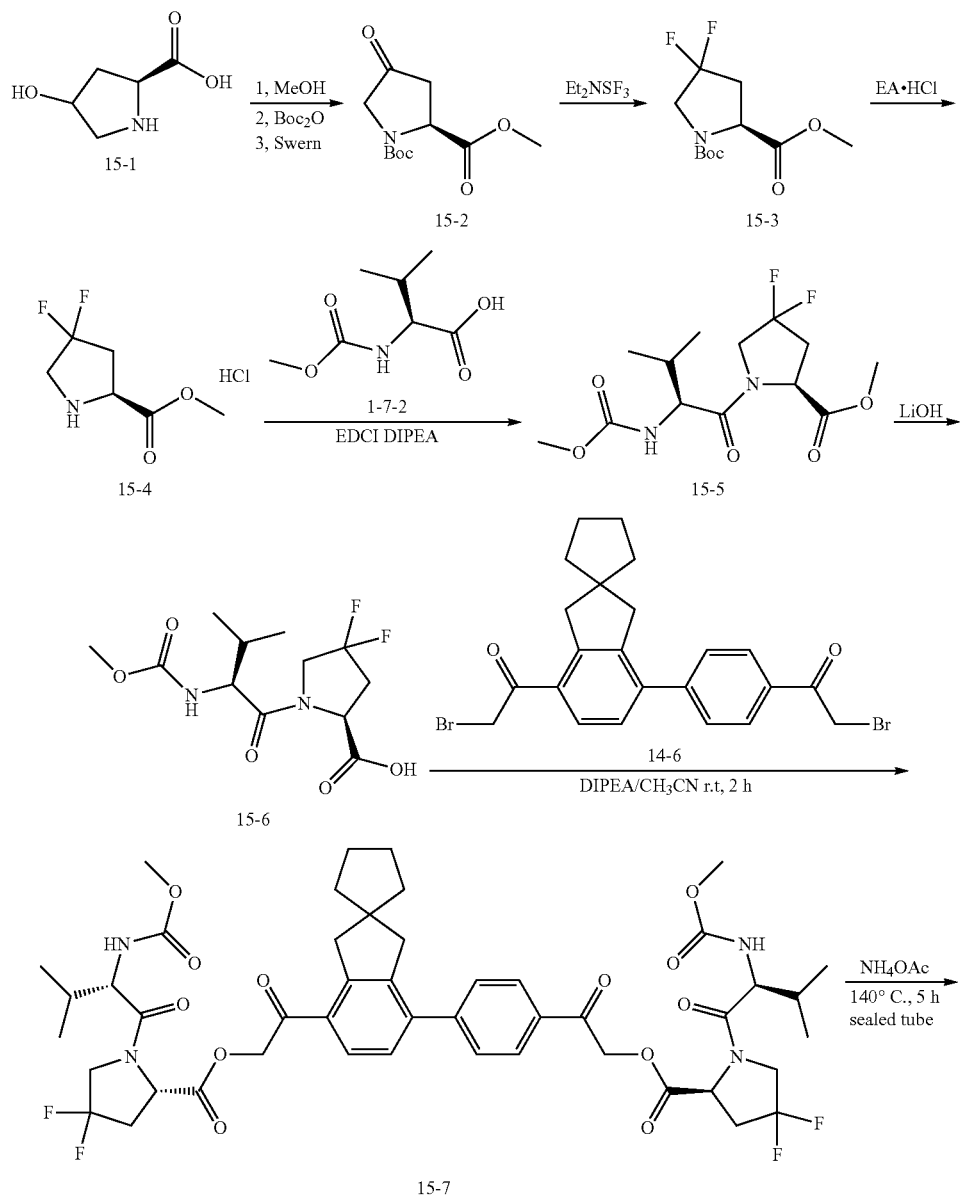

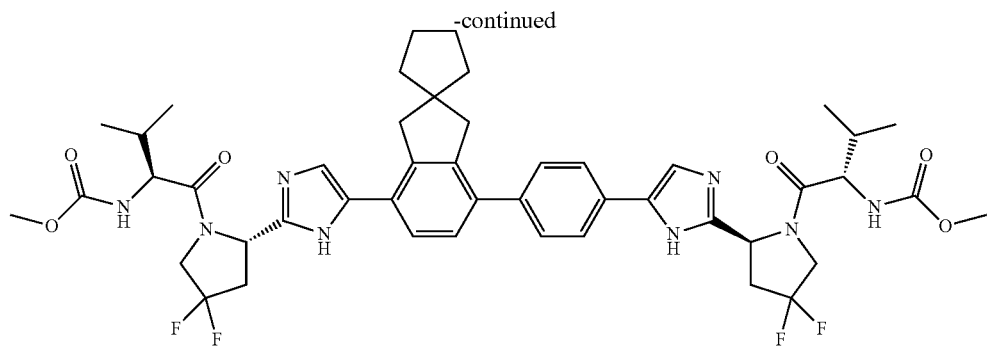

15-8

Step 1) The Preparation of Compound 15-2

To a solution of (2R)-4-hydroxypyrrolidine-2-carboxylic acid (compound 15-1) (10.0 g, 76.2 mmol) in anhydrous MeOH (100 mL) under $N_2$ at 0° C. was added $SOCl_2$ (11 mL) dropwise. At the end of the addition, the mixture was refluxed at 70° C. for 3 hours and concentrated in vacuo to give the crude product as pale yellow oil (13.78 g), which was used for the next step directly.

To a suspension of the above crude product and DMAP (2.0 g, 16.4 mmol) in DCM (110 mL) at 0° C. was added $Et_3N$ (13 mL, 91.7 mmol) dropwise followed by a solution of $Boc_2O$ (20.0 g, 91.7 mmol) in DCM (50 mL). The mixture was stirred at rt overnight. A small amount of water was added to the mixture. The mixture was adjusted to pH 2-3 with diluted hydrochloric acid (10%) and extracted with DCM (100 mL×3). The combined organic phases were dried over anhydrous $Na_2SO_4$ and concentrated in vacuo. The residue was purified by silica gel column chromatography (PE/EtOAc (v/v)=2/1) to give a crude product as pale yellow slurry (15.7 g).

To a mixture of oxalyl chloride (9.0 mL), DCM (100 mL) and DMSO (9.5 mL) was added a solution of the above crude product in DCM (120 mL) dropwise at −78° C. After the mixture was stirred at −78° C. for 2 hours, $Et_3N$ (28 mL) was added dropwise, and the mixture was allowed to warm to rt. Water (60 mL) was added to the mixture, and the mixture was extracted with DCM (150 mL×3). The combined organic phases were dried over anhydrous $Na_2SO_4$ and concentrated in vacuo. The residue was purified by silica gel column chromatography (PE/EtOAc (v/v)=1/1) to give the title compound 15-2 as colorless slurry (11 g, 59%). The compound was characterized by the following spectroscopic data:

$^1$H NMR (400 MHz, $CDCl_3$): δ 4.83-4.70 (dd, J=10 Hz, 10 Hz, 1H), 3.91-3.88 (d, J=8 Hz, 2H), 3.77 (s, 3H), 2.98-2.88 (m, 1H), 2.62-2.55 (m, 1H), 1.48-1.47 (s, 9H).

Step 2) The Preparation of Compound 15-3

To a solution of compound 15-2 (0.5 g, 2 mmol) in DCM (10 mL) at −78° C. was added dropwise $Et_2NSF_3$ (0.82 mL, 6 mmol). The mixture was stirred at −78° C. for 2 hours and at rt for another 12 hours. A small amount of water was added to the mixture, and the resulting mixture was extracted with DCM (30 mL×3). The combined organic phases were dried over anhydrous $Na_2SO_4$ and concentrated in vacuo. The residue was purified by silica gel column chromatography (PE/EtOAc (v/v)=9/1) to give the title compound 15-3 (0.42 g, 79%). The compound was characterized by the following spectroscopic data:

MS-ESI: m/z 266.25 [M+H]$^+$; and $^1$H NMR (400 MHz, $CDCl_3$): δ 4.43-4.47 and 4.55-4.53 (m, 1H), 3.80-3.83 (m, 2H), 3.77 (s, 3H), 2.66-2.74 (m, 1H), 2.40-2.52 (m, 1H), 1.42-1.47 (d, J=20 Hz, 9H).

Step 3) The Preparation of Compound 15-4

A mixture of compound 15-3 (3 g, 11.3 mmol) and a solution of HCl in EtOAc (15 mL, 4 M) was stirred at rt for 4 hours and concentrated in vacuo to give the title compound 15-4 as a white solid (2.27 g, 100%). The compound was characterized by the following spectroscopic data:

MS-ESI: m/z 166.14 [M+H]$^+$; and $^1$H NMR (400 MHz, $CDCl_3$): δ 4.70-4.69 (m, 1H), 3.75-3.87 (m, 2H), 3.71 (s, 3H), 2.91-3.00 (m, 1H), 2.70-2.81 (m, 1H).

Step 4) The Preparation of Compound 15-5

To a solution of compound 15-4 (1.2 g, 5.9 mmol), compound 1-7-2 (1.2 g, 6.8 mmol) and EDCI (1.73 g, 9.1 mmol) in anhydrous DCM (20 mL) was added DIPEA (3.5 mL) dropwise at 0° C. under $N_2$. At the end of the addition, the mixture was stirred at rt for 8 hours. A small amount of water was added to the mixture and the mixture was extracted with DCM (10 mL×3). The combined organic phases were dried over anhydrous $Na_2SO_4$ and concentrated in vacuo. The residue was purified by silica gel column chromatography (PE/EtOAc (v/v)=1/1) to give the title compound 15-5 as colorless slurry (1.28 g, 67%). The compound was characterized by the following spectroscopic data:

MS-ESI: m/z 323.32 [M+H]$^+$; and $^1$H NMR (400 MHz, $CDCl_3$): δ 5.34-5.36 (d, J=8.0 Hz, 1H), 4.77-4.81 (m, 1H), 4.22-4.31 (m, 1H), 4.10-4.17 (m, 1H), 3.94-4.03 (m, 1H), 3.76 (s, 3H), 3.67 (s, 3H), 2.67-2.77 (m, 1H), 2.43-2.56 (m, 1H), 2.04-2.05 (m, 1H), 1.06-1.05 (d, J=6.0 Hz, 1H), 0.97-0.98 (d, J=6.0 Hz, 1H).

Step 5) The Preparation of Compound 15-6

To a solution of compound 15-5 (1.0 g, 3.1 mmol) in THF (12 mL) was added Lithium hydroxide (0.65 g, 4 mL) aqueous solution at 0° C. The mixture was stirred at 30° C. for 5 fours. THF was removed in vacuo. The mixture was extracted with MTBE (50 mL×3) and the organic layer was discarded. The aqueous layer was adjusted to pH 2 with diluted hydrochloric acid (10%) and extracted with DCM (50 mL×3). The combined organic phases were dried over anhydrous Na$_2$SO$_4$ and concentrated in vacuo to give the title compound 15-6 as colorless slurry (0.86 g, 90%). The compound was characterized by the following spectroscopic data:

MS-ESI: m/z 309.28 [M+H]$^+$; and $^1$H NMR (400 MHz, CDCl$_3$): δ 5.71-5.73 (d, J=8.0 Hz, 1H), 4.78-4.82 (m, 1H), 4.28-4.33 (m, 1H), 4.10-4.17 (m, 1H), 3.94-4.00 (m, 1H), 3.67 (s, 3H), 2.80-2.84 (m, 1H), 2.55-2.65 (m, 1H), 2.03-2.05 (m, 1H), 1.01-1.03 (d, J=6.0 Hz, 1H), 0.94-0.96 (d, J=6.0 Hz, 1H).

Step 6) The Preparation of Compound 15-7

To a solution of compound 14-6 (0.49 g, 1 mmol) in anhydrous acetonitrile (10 mL) was added DIPEA (0.7 mL) in an ice bath followed by compound 15-6 (0.72 g, 2.3 mmol). The mixture was stirred at rt for 2 hours and concentrated in vacuo. The residue was purified by silica gel column chromatography (PE/EtOAc (v/v)=1/2) to give the title compound 15-7 as a white solid (0.3 g, 30%, HPLC: 99%). The compound was characterized by the following spectroscopic data:

MS-ESI: m/z 946 [M+H]$^+$; and $^1$H NMR (400 MHz, CDCl$_3$): δ 7.97 (d, J=8.0 Hz, 2H), 7.64 (d, J=8.0 Hz, 1H), 7.54 (d, J=8.0 Hz, 2H), 7.28 (d, J=8.0 Hz, 1H), 5.25-5.64 (m, 2H), 5.19-5.34 (m, 4H), 4.91 (q, J=8.0 Hz, 2H), 4.00-4.30 (m, 6H), 3.68 (s, 6H), 3.23-3.24 (d, J=4.0 Hz, 2H), 2.77-2.85 (m, 6H), 2.31 (s, 1H), 1.55-1.75 (m, 8H), 1.24-1.26 (m, 2H), 1.04 (d, J=4.0 Hz, 6H), 0.95 (d, J=4.0 Hz, 6H).

Step 7) The Preparation of Compound 15-8

A mixture of compound 15-7 (0.28 g, 0.29 mmol) and ammonium acetate (0.35 g, 4.5 mmol) in xylene (5 mL) in a sealed tube was refluxed at 140° C. for 5 hours. A small amount of water was added to the mixture and the mixture was extracted with EtOAc (20 mL×3). The combined organic phases were dried over anhydrous Na$_2$SO$_4$ and concentrated in vacuo. The residue was purified by silica gel column chromatography (PE/EtOAc (v/v)=1/5) to give the title compound 15-8 as a pale yellow solid (65 mg, 25%, HPLC: 96%). The compound was characterized by the following spectroscopic data:

MS-ESI: m/z 906 [M+H]$^+$; and $^1$H NMR (400 MHz, CDCl$_3$): δ 10.30 (brs, 1H), 10.63 (brs, 1H), 7.80-7.82 (m, 2H), 7.45-7.52 (m, 3H), 7.26-7.37 (m, 2H), 7.16 (s, 1H), 5.40-5.49 (m, 4H), 4.30-4.34 (m, 2H), 4.22 (m, 2H), 3.71-3.89 (m, 2H), 3.70 (s, 6H), 2.82-3.07 (m, 6H), 1.92-2.04 (m, 4H), 1.65-1.91 (m, 8H), 1.26 (s, 6H), 0.84 (s, 12H).

Example 16

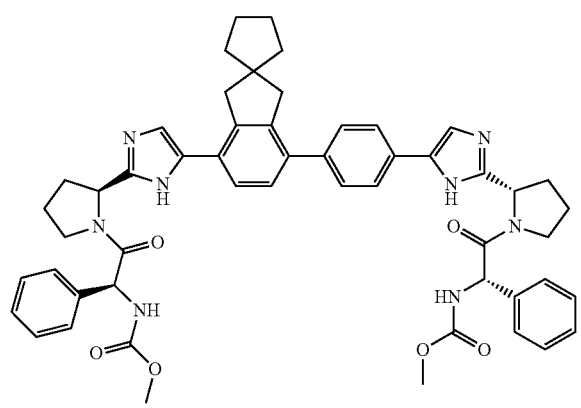 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)c5ccccc5)[nH]4)c4c3CC3(CCCC3)C4)cc2)[nH]1)c1ccccc1]

Synthetic Routes

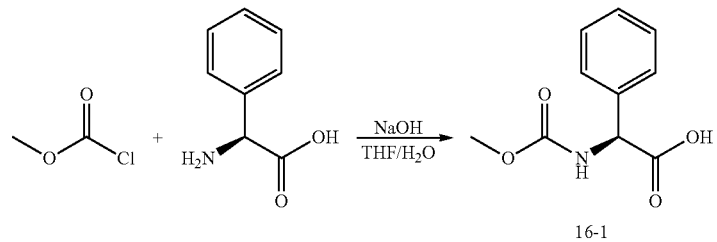

16-1

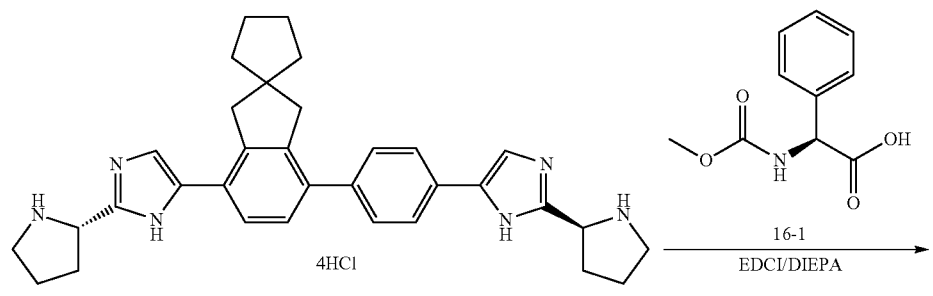

14-9

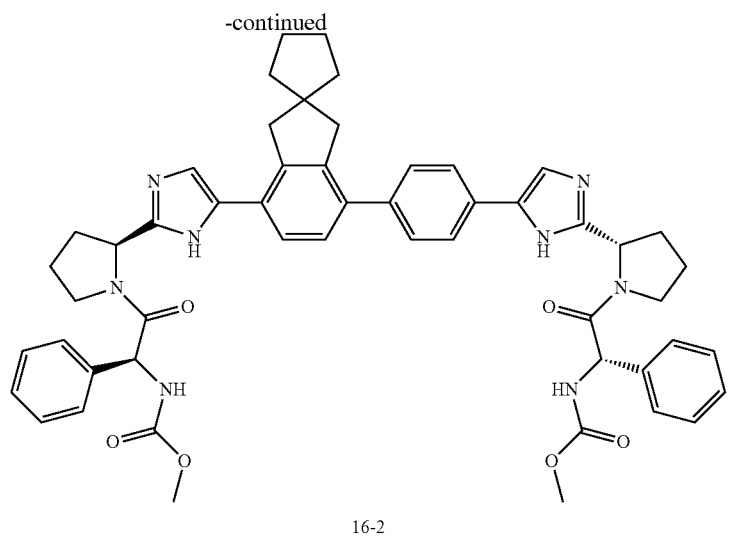

16-2

Step 1) The Preparation of Compound 16-1

To a solution of L-phenylglycine (10.0 g, 66.1 mmol) in THF (10 mL) was added a solution of NaOH (10.6 g, 265 mmol) in H$_2$O (60 mL) followed by methyl chloroformate (10.2 mL, 133 mmol) dropwise at 0° C. The mixture was stirred at rt overnight, adjusted to pH 3 with hydrochloric acid (1 M) and extracted with EtOAc. The organic layer was dried over anhydrous Na$_2$SO$_4$ and concentrated in vacuo to give the title compound 16-1 as a white solid (12.6 g, 91%). The compound was characterized by the following spectroscopic data:

$^1$H NMR (400 MHz, DMSO-d$^6$): δ 12.84 (brs, 1H), 7.96 (d, J=8.3 Hz, 1H), 7.41-7.29 (m, 5H), 5.14 (d, J=8.3 Hz, 1H), 3.55 (s, 3H).

Step 2) The Preparation of Compound 16-2

To a suspension of compound 14-9 (345 mg, 0.52 mmol), compound 16-1 (327 mg, 1.56 mmol) and EDCI (401 mg, 2 mmol) in DCM (8 mL) in an ice bath was added DIPEA (1.0 mL) dropwise. At the end of the addition, the mixture was stirred at rt for 10 hours. A small amount of water was added to the mixture and the mixture was extracted with DCM (10 mL×3). The combined organic phases were dried over anhydrous Na$_2$SO$_4$ and concentrated in vacuo. The residue was purified by silica gel column chromatography (PE/EtOAc (v/v)=1/10) to give the title compound 16-2 as a white solid (170 mg, 40%, HPLC: 98%). The compound was characterized by the following spectroscopic data:

MS-ESI: m/z 902.03 [M+H]$^+$; and $^1$H NMR (400 MHz, CDCl$_3$): δ 7.73-7.74 (m, 2H), 7.45-7.47 (m, 6H), 7.39-7.41 (m, 7H), 7.14-7.26 (m, 1H), 5.99-6.05 (m, 2H), 5.40-5.43 (m, 2H), 5.30-5.32 (m, 2H), 3.74-3.75 (m, 2H), 3.66 (d, J=8.0 Hz, 6H), 3.20-3.21 (m, 2H), 3.06 (s, 2H), 2.98 (s, 4H), 2.05-2.32 (m, 8H), 1.62-1.67 (m, 8H).

Example 17

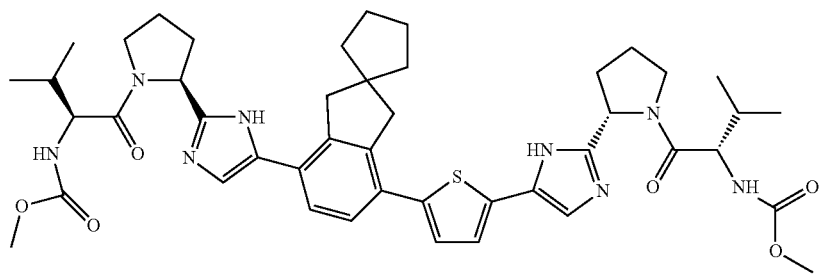 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)c4c3CC3(CCCC3)C4)s2)[nH]1)C(C)C]

Synthetic Routes

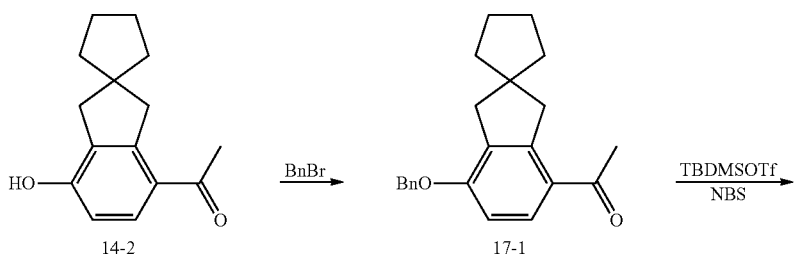

-continued
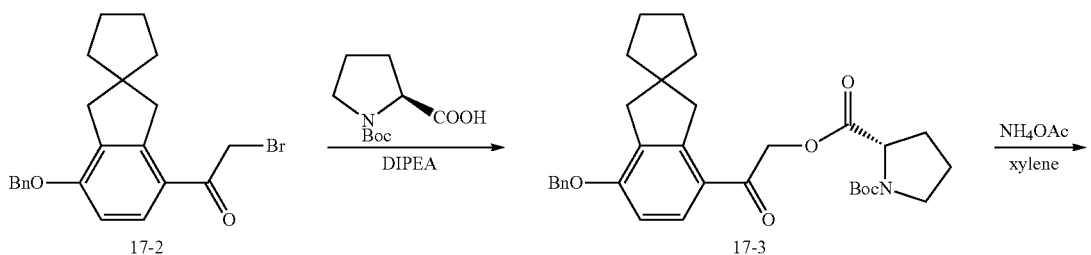
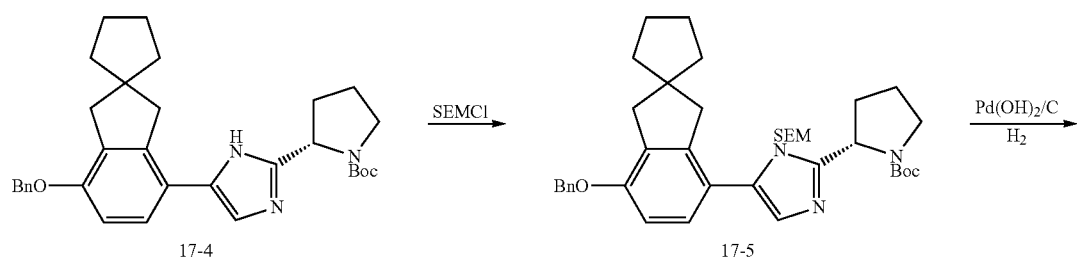
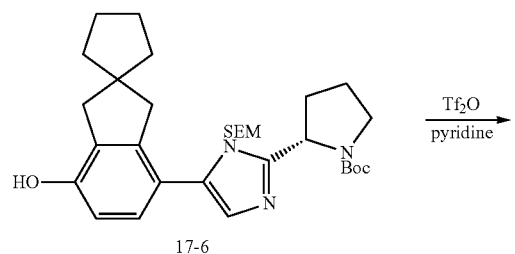
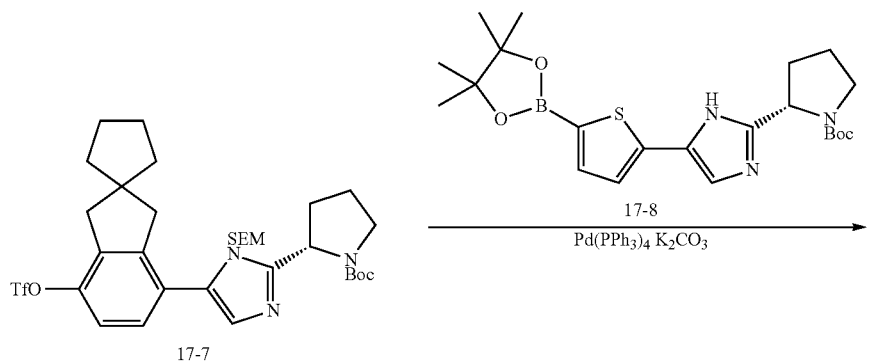
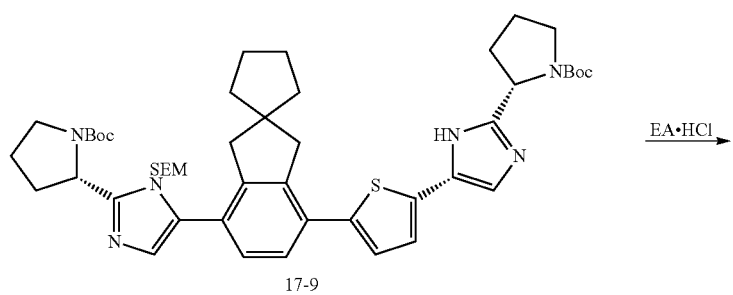

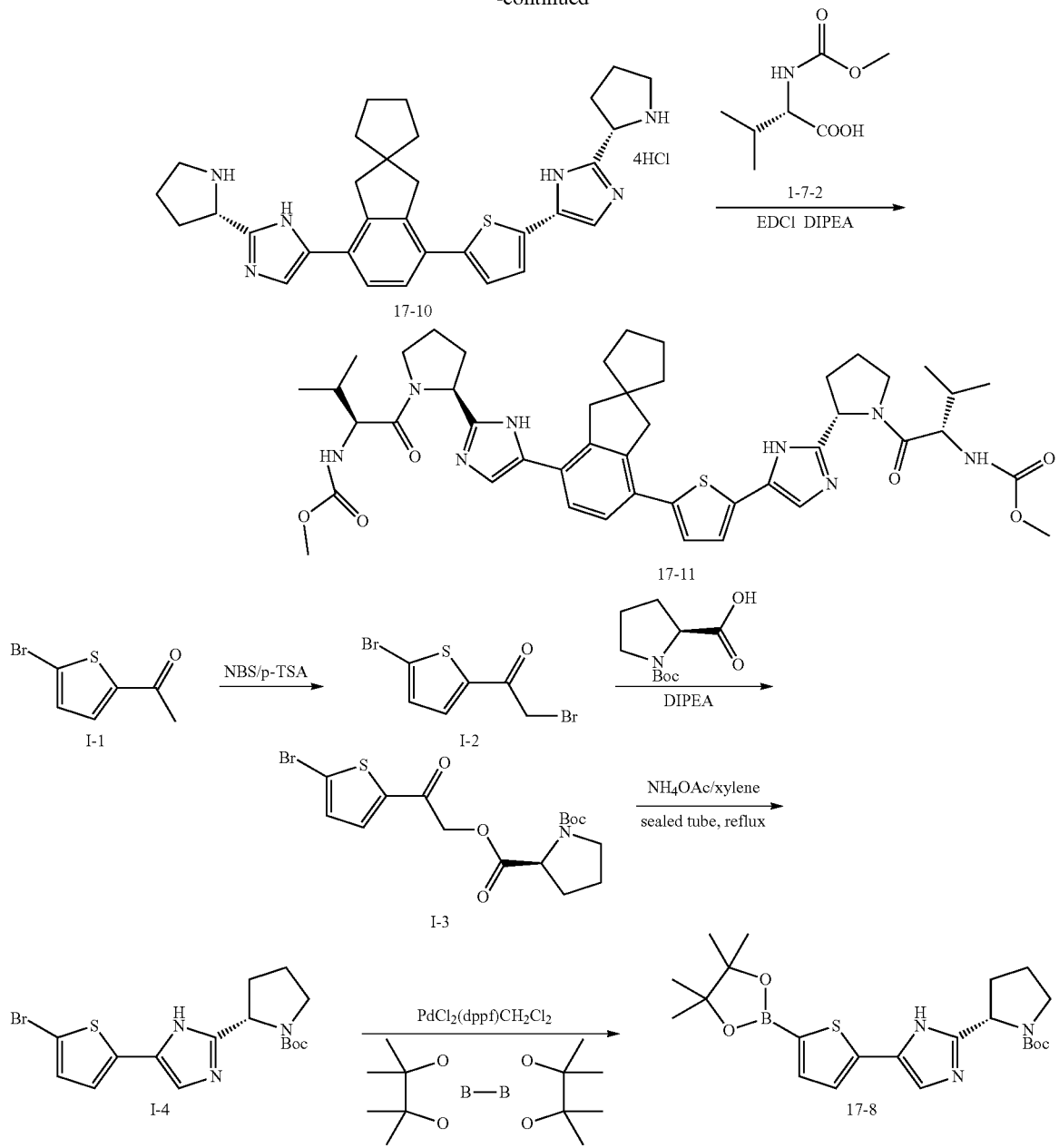

Step 1) The Preparation of Compound 17-1

To a solution of compound 14-2 (0.7 g, 3 mmol) in acetone (20 mL) was added potassium carbonate (0.85 g, 6 mmol) dropwise followed by benzyl bromide (0.75 mL, 6.3 mmol). At the end of the addition, the mixture was stirred at 60° C. for 3 hours and filtered. The filtrate was concentrated in vacuo. The residue was purified by silica gel column chromatography (PE/EtOAc (v/v)=20/1) to give the title compound 17-1 as a white solid (0.85 g, 90%, HPLC: 98%). The compound was characterized by the following spectroscopic data:

MS-ESI: m/z 321.3 [M+H]$^+$; and $^1$H NMR (400 MHz, CDCl$_3$): δ 7.69 (d, J=8.0 Hz, 1H), 7.33-7.44 (m, 5H), 6.75 (d, J=8.0 Hz, 1H), 5.15 (s, 2H), 3.24 (s, 2H), 2.82 (s, 2H), 2.53 (s, 3H), 1.70-1.73 (m, 4H), 1.60-1.62 (m, 4H).

Step 2) The Preparation of Compound 17-2

To a solution of compound 17-1 (850 mg, 2.6 mmol) in anhydrous DCM (20 mL) was added DIPEA (0.86 mL) in an ice bath followed by TBDMSOTf (0.92 mL, 4 mmol). At the end of the addition, the mixture was stirred at rt for 2 hours. Then a small amount of water was added, and the resulting mixture was extracted with DCM (20 mL×3). The combined organic phases were dried over anhydrous Na$_2$SO$_4$ and concentrated in vacuo. The residue was dissolved in THF (20 mL) and the solution was cooled to 0° C. in an ice bath. To the solution was added NBS (470 mg, 2.6 mmol) and the mixture was stirred at 0° C. for 4 hours. The solvent was removed in vacuo, a small amount of water was added to the mixture and the mixture was extracted with EtOAc (30 mL×3). The combined organic phases were dried over anhydrous Na$_2$SO$_4$ and concentrated in vacuo. The residue was purified by silica gel column chromatography (PE/EtOAc (v/v)=20/1) to give the title compound 17-2 as a white solid (1.0 g, 88%, HPLC: 94%). The compound was characterized by the following spectroscopic data:

MS-ESI: m/z 400.32 [M+H]$^+$; and $^1$H NMR (400 MHz, CDCl$_3$): δ 7.71 (d, J=8.0 Hz, 2H), 7.34-7.44 (m, 5H), 6.77 (d, J=8.0 Hz, 1H), 4.41 (s, 2H), 3.24 (s, 2H), 2.83 (s, 2H), 1.70-1.73 (m, 4H), 1.60-1.62 (m, 4H).

Step 3) The Preparation of Compound 17-3

To a solution of compound 17-2 (1.0 g, 2.5 mmol) in anhydrous acetonitrile (15 mL) was added DIPEA (0.82 mL) in an ice bath followed by Boc-L-proline (0.64 g, 3 mmol). The mixture was stirred at rt for 1 hour and concentrated in vacuo. The residue was purified by silica gel column chromatography (PE/EtOAc (v/v)=5/1) to give the title compound 17-3 as a pale yellow solid (1.1 g, 82%, HPLC: 99%). The compound was characterized by the following spectroscopic data:

MS-ESI: m/z 534.66 [M+H]$^+$; and $^1$H NMR (400 MHz, CDCl$_3$): δ 7.60 (d, J=8.0 Hz, 1H), 7.33-7.43 (m, 5H), 6.76 (d, J=8.0 Hz, 1H), 5.09-5.52 (m, 2H), 5.21 (s, 2H), 4.38-4.41 (m, 1H), 3.56-3.58 (m, 1H), 3.41-3.48 (m, 1H), 3.41 (s, 2H), 2.82 (s, 2H), 2.28-2.35 (m, 2H), 2.03-2.05 (m, 1H), 1.89-1.92 (m, 1H), 1.72 (s, 4H), 1.61 (s, 4H), 1.47 (s, 9H).

Step 4) the preparation of compound 17-4

A mixture of compound 17-3 (1.1 g, 2 mmol) and ammonium acetate (2.4 g, 31 mmol) in xylene (150 mL) in a sealed tube was stirred at 140° C. for 4 hours. After the mixture was cooled to rt, a small amount of water was added to the mixture and the mixture was extracted with EtOAc (50 mL×3). The combined organic phases were dried over anhydrous Na$_2$SO$_4$ and concentrated in vacuo. The residue was purified by silica gel column chromatography (PE/EtOAc (v/v)=3/2) to give the title compound 17-4 as a pale yellow solid (0.64 g, 60%, HPLC: 95%). The compound was characterized by the following spectroscopic data:

MS-ESI: m/z 514.67 [M+H]$^+$; and $^1$H NMR (400 MHz, CDCl$_3$): δ 7.78-7.75 (m, 2H), 7.65-7.63 (m, 2H), 7.34-7.40 (m, 5H), 7.21-7.20 (m, 1H), 5.53-5.15 (m, 2H), 4.45-4.60 (s, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Step 5) The Preparation of Compound 17-5

To a solution of compound 17-4 (0.64 g, 1.2 mmol) in anhydrous DMF (10 mL) was added sodium hydride (0.25 g, 6 mmol, 60% dispersed in oil) at 0° C. After the mixture was stirred at 0° C. for 30 minutes, SEMCl (0.45 mL, 2.5 mmol) was added. The mixture was stirred at rt for 2 hours, quenched with a small amount of ice water and extracted with EtOAc (30 mL×3). The combined organic phases were dried over anhydrous Na$_2$SO$_4$ and concentrated in vacuo. The residue was purified by silica gel column chromatography (PE/EtOAc (v/v)=6/1) to give the title compound 17-5 as a white solid (0.4 g, 50%, HPLC: 97%). The compound was characterized by the following spectroscopic data:

MS-ESI: m/z 644.38 [M+H]$^+$; and $^1$H NMR (400 MHz, CDCl$_3$): δ 7.71 (d, J=8.0 Hz, 1H), 7.28-7.44 (m, 5H), 6.92 (s, 1H), 6.79 (s, 1H), 5.39 and 5.84 (2m, 1H), 5.19 (d, J=8.0 Hz, 1H), 5.10 (s, 2H), 4.92-5.02 (m, 1H), 3.47-3.70 (m, 4H), 3.0 (s, 2H), 2.88 (s, 2H), 1.63-2.29 (m, 4H), 1.63-1.72 (m, 8H), 1.41 (s, 9H), 0.91-0.93 (m, 2H), 0.02 (s, 9H).

Step 6) The Preparation of Compound 17-6

A suspension of compound 17-5 (0.4 g, 0.62 mmol) and Pd(OH)$_2$/C (0.1 g) in a mixture of EtOAc (4 mL) and methanol (10 mL) was stirred under H$_2$ (normal pressure) at rt for 5 hours. The mixture was filtered and the filtrate was concentrated in vacuo to give the title compound 17-6 as a white solid (360 mg, 100%). The compound was characterized by the following spectroscopic data:

MS-ESI: m/z 554.81 [M+H]$^+$; and $^1$H NMR (400 MHz, CDCl$_3$): δ 7.64 (m, 1H), 6.89 (s, 1H), 6.65-6.66 (m, 1H), 5.84 and 5.40 (2m, 1H), 5.19 (d, J=8.0 Hz, 1H), 4.90-5.05 (m, 1H), 3.55-3.80 (m, 2H), 3.54-3.56 (m, 2H), 2.99 (s, 2H), 2.79-2.80 (m, 2H), 1.90-2.35 (m, 4H), 1.66-1.71 (m, 8H), 1.28-1.30 (d, J=8.0 Hz, 9H), 0.87-0.89 (m, 2H), 0.02 (s, 9H).

Step 7) The Preparation of Compound 17-7

To a solution of compound 17-6 (0.5 g, 0.9 mmol) in anhydrous DCM (10 mL) in an ice bath was added pyridine (0.4 mL) followed by Tf$_2$O (0.5 mL, 3 mmol). The mixture was stirred at rt for 2 hours, quenched with a small amount of water and extracted with DCM (20 mL×3). The combined organic phases were dried over anhydrous Na$_2$SO$_4$ and concentrated in vacuo. The residue was purified by silica gel column chromatography (PE/EtOAc (v/v)=8/1) to give the title compound 17-7 as pale yellow oil (0.48 g, 77.8%). The compound was characterized by the following spectroscopic data:

$^1$H NMR (400 MHz, CDCl$_3$): δ 7.82 (d, J=8.0 Hz, 1H), 7.06 (d, J=8.0 Hz, 1H), 7.02 (s, 1H), 5.84 and 5.40 (2m, 1H), 5.19 (d, J=8.0 Hz, 1H), 4.90-5.05 (m, 1H), 3.55-3.80 (m, 2H), 3.54-3.56 (m, 2H), 2.99 (s, 2H), 2.79-2.80 (m, 2H), 1.90-2.35 (m, 4H), 1.66-1.71 (m, 8H), 1.28-1.30 (d, J=8.0 Hz, 9H), 0.87-0.89 (m, 2H), 0.02 (s, 9H).

Step 8) The Preparation of Compound 17-8

A mixture of compound I-1 (6.0 g, 29 mmol), NBS (5.76 g, 32 mmol) and p-toluenesulfonic acid (1.0 g, 5.2 mmol) was stirred at 100° C. for 0.5 hour. It was then cooled to rt followed by adding DCM and water. The mixture was extracted with DCM (50 mL×3). The combined organic phases were dried over anhydrous Na$_2$SO$_4$ and concentrated in vacuo. The residue was purified by silica gel column chromatography (PE/DCM (v/v)=8/1) to give the title compound 1-2 as yellow slurry (5.64 g, 70%, HPLC: 95%). The compound was characterized by the following spectroscopic data:

MS-ESI: m/z 284.97 [M+H]$^+$; and $^1$H NMR (400 MHz, CDCl$_3$): δ 7.55 (d, J=4.0 Hz, 1H), 7.14 (d, J=4.0 Hz, 1H), 4.29 (s, 2H).

To a solution of compound 1-2 (5.64 g, 19.8 mmol) and N-Boc-L-proline (4.7 g, 21.8 mmol) in anhydrous acetonitrile (100 mL) was added DIPEA (3.62 mL). The mixture was stirred at rt for 3 hours, and water (50 mL) was added. The resulting mixture was extracted with EtOAc (50 mL×3). The combined organic phases were dried over anhydrous Na$_2$SO$_4$ and concentrated in vacuo. The residue was purified by silica gel column chromatography (PE/EtOAc (v/v)=3/1) to give the title compound 1-3 as a yellow solid (5.8 g, 70%, HPLC: 95%). The compound was characterized by the following spectroscopic data:

MS-ESI: m/z 418.3 [M+H]$^+$; and $^1$H NMR (400 MHz, CDCl$_3$): δ 7.49 (d, J=4.0 Hz, 1H), 7.13 (t, J=4.0 Hz, 1H), 5.02-5.23 (m, 2H), 4.37-4.48 (m, 1H), 3.38-3.60 (m, 2H), 2.26-2.29 (m, 2H), 1.92-2.11 (m, 2H), 1.44 (s, 9H).

A mixture of compound I-3 (8.0 g, 19 mmol) and ammonium acetate (22.2 g, 288 mmol) in xylene (100 mL) in a sealed tube was stirred at 140° C. for 5 hours. The mixture was cooled to rt and concentrated in vacuo. The residue was purified by silica gel column chromatography (PE/EtOAc (v/v)=4/1) to give the title compound I-4 as a yellow solid (7.0 g, 92%, HPLC: 99%). The compound was characterized by the following spectroscopic data:

MS-ESI: m/z 398.32 [M+H]$^+$; and $^1$H NMR (400 MHz, CDCl$_3$): δ 10.51 (br, 1H), 7.07 (s, 1H), 6.94 (s, 2H), 4.90-4.91 (m, 1H), 3.39 (s, 2H), 2.98 (s, 1H), 2.12 (s, 2H), 1.95 (s, 1H), 1.48 (s, 9H).

To a mixture of compound I-4 (1.0 g, 2.5 mmol), bis(pinacolato)diboron (0.96 g, 3.8 mmol), Pd(dppf)Cl$_2$.CH$_2$Cl$_2$ (0.11 g, 0.13 mmol) and anhydrous KOAc (0.74 g, 7.5 mmol) under N$_2$ was added DMF (12 mL) via syringe. The resulting mixture was stirred at 90° C. for 4 hours, cooled to rt, and water (50 mL) was added. The mixture was extracted with EtOAc (30 mL×3). The combined organic phases were washed with water followed by brine, dried over anhydrous Na$_2$SO$_4$ and concentrated in vacuo. The residue was purified by silica gel column chromatography (PE/EtOAc (v/v)=3/1) to give the title compound 17-8 as a white solid (0.89 g, 80%, HPLC: 96%). The compound was characterized by the following spectroscopic data:

$^1$H NMR (400 MHz, CDCl$_3$): δ 10.51 (br, 1H), 7.53 (s, 1H), 7.27 (s, 1H), 7.15 (s, 1H), 4.93-4.94 (m, 1H), 3.39 (s, 2H), 2.99 (s, 1H), 1.94-2.12 (m, 4H), 1.49 (s, 9H), 1.34 (s, 12H), 1.24 (m, 8H).

Step 9) The Preparation of Compound 17-9

To a mixture of compound 17-8 (470 mg, 1 mmol), Pd(PPh$_3$)$_4$ (80 mg, 0.07 mmol) and potassium carbonate (250 mg, 1.8 mmol) under N$_2$ was added a solution of compound 17-7 (480 mg, 0.7 mmol) in 1,2-dimethoxyethane (6 mL) followed by pure water (1.5 mL). The resulting mixture was stirred at 90° C. for 3 hours. After the mixture was cooled to rt, a small amount of water was added. The mixture was extracted with EtOAc (20 mL×3). The combined organic phases were dried over anhydrous Na$_2$SO$_4$ and concentrated in vacuo. The residue was purified by silica gel column chromatography (PE/EtOAc (v/v)=2/1) to give the title compound 17-9 as a pale yellow solid (350 mg, 60%, HPLC: 95%). The compound was characterized by the following spectroscopic data:

MS-ESI: m/z 856.2 [M+H]$^+$; and $^1$H NMR (400 MHz, CDCl$_3$): δ 7.80 (d, J=8.0 Hz, 1H), 7.44 (d, J=8.0 Hz, 1H), 7.13-7.14 (m, 3H), 7.03 (s, 1H), 5.41 and 5.86 (2m, 1H), 5.21-5.23 (m, 1H), 4.95-5.04 (m, 2H), 3.41-3.73 (m, 6H), 3.12 (s, 2H), 3.0 (s, 2H), 1.95-2.31 (m, 8H), 1.64-1.71 (m, 8H), 1.41-1.50 (m, 18H), 0.89-0.90 (m, 2H), 0.02 (s, 9H).

Step 10) The Preparation of Compound 17-10

To a solution of compound 17-9 (350 mg, 0.4 mmol) in EtOAc (2 mL) was added a solution of HCl in EtOAc (10 mL, 4 M). The mixture was stirred at rt overnight and filtered. The filter cake was washed with EtOAc to give the title compound 17-10 as a pale yellow solid (290 mg, 100%, HPLC: 100%). The compound was characterized by the following spectroscopic data:

MS-ESI: m/z 671.72 [M+H]$^+$; and $^1$H NMR (400 MHz, CDCl$_3$): δ 7.87 (s, 1H), 7.78-7.80 (m, 2H), 7.62-7.66 (m, 2H), 7.43 (d, J=4.0 Hz, 1H), 5.43 (t, J=8.0 Hz, 1H), 5.26-5.27 (m, 1H), 3.70-3.76 (m, 4H), 3.18 (s, 2H), 3.16 (s, 2H), 2.29-2.85 (m, 8H), 1.68-1.73 (m, 8H).

Step 11) The Preparation of Compound 17-11

To a suspension of compound 17-10 (260 mg, 0.39 mmol), compound 1-7-2 (200 mg, 1.1 mmol) and EDCI (300 mg, 1.6 mmol) in DCM (8 mL) at 0° C. was added DIPEA (0.64 mL) dropwise. At the end of the addition, the mixture was stirred at rt for 10 hours. A small amount of water was added to the mixture and the mixture was extracted with DCM (10 mL×3). The combined organic phases were washed with brine, dried over anhydrous Na$_2$SO$_4$ and concentrated in vacuo. The residue was purified by silica gel column chromatography (PE/EtOAc (v/v)=1/10) to give the title compound 17-11 as a pale yellow solid (198 mg, 60.5%, HPLC: 96%). The compound was characterized by the following spectroscopic data:

MS-ESI: m/z 839.06 [M+H]$^+$; and $^1$H NMR (400 MHz, CDCl$_3$): δ 10.49 (brs, 2H), 7.39 (m, 1H), 7.07-7.08 (m, 5H), 6.60-6.62 (m, 2H), 5.15-5.25 (m, 2H), 4.33 (t, J=8.0 Hz, 2H), 3.84-3.86 (m, 2H), 3.74 (s, 6H), 3.67-3.80 (m, 2H), 2.95-3.15 (m, 6H), 2.34-2.36 (m, 2H), 1.97-2.22 (m, 8H), 1.59-1.70 (m, 8H), 0.89 (d, J=8.4 Hz, 12H).

Example 18

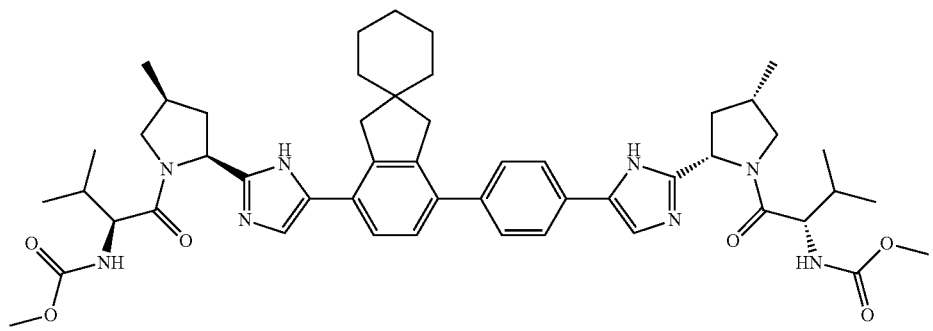

Synthetic Routes

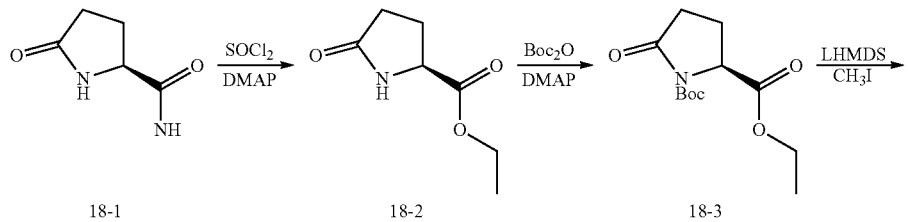

18-1     18-2     18-3

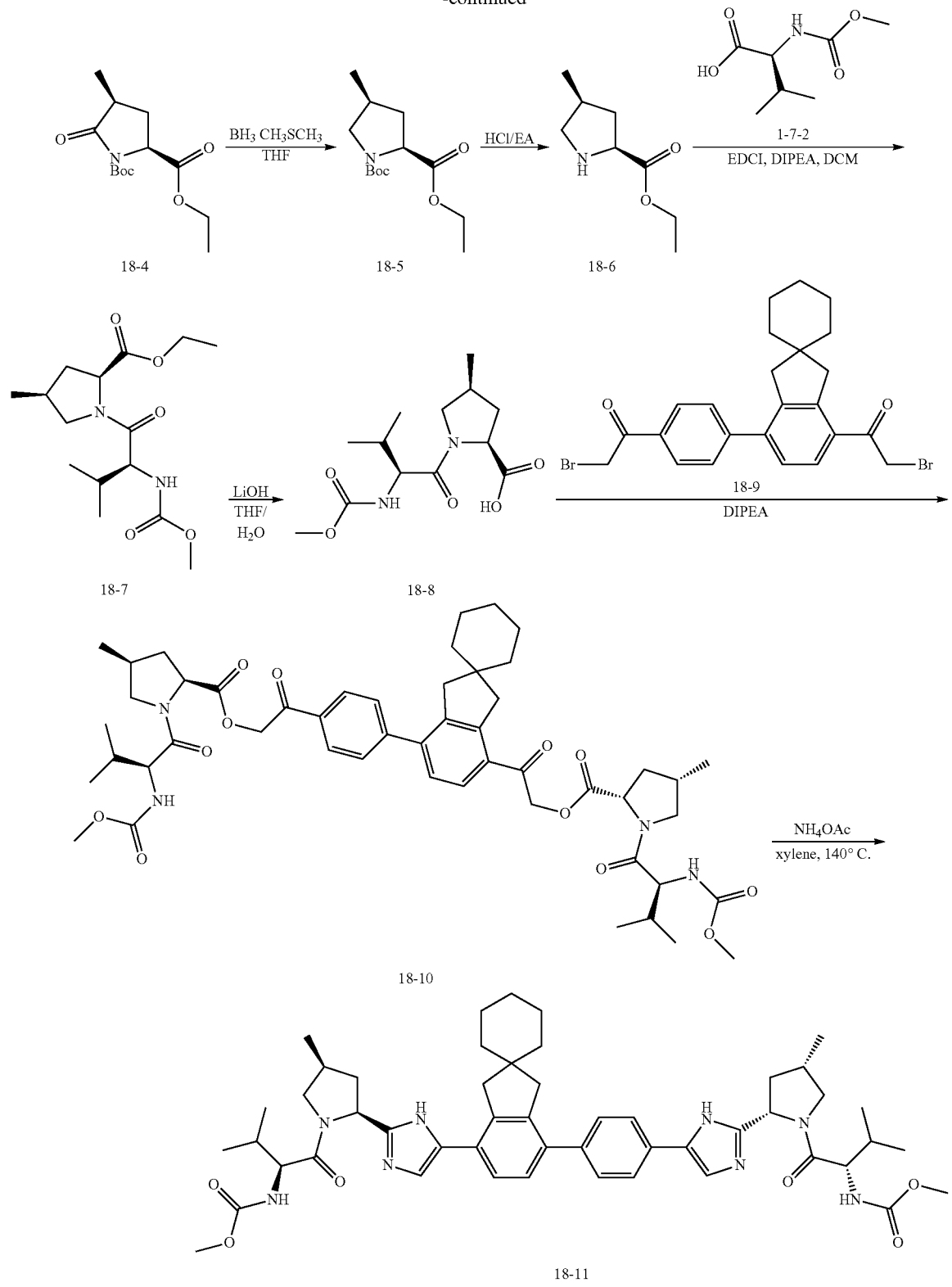

Step 1) The Preparation of Compound 18-2

To a solution of compound 18-1 (10.0 g, 77.5 mmol) in ethanol (150 mL) was added SOCl₂ (9.22 g, 77.5 mmol) dropwise at 0° C. The mixture was stirred at 0° C. for 0.5 hour and at rt for another 3 hours. The reaction was monitored by TLC and the mixture was concentrated in vacuo after the process stopped. The residue was purified by silica gel column chromatography (EtOAc/MeOH (v/v)=15/1) to give the title compound 18-2 as oil (8.5 g, 70%). The compound was characterized by the following spectroscopic data:

¹H NMR (400 MHz, CDCl₃): δ 7.04 (br, 1H), 4.10-4.22 (m, 3H), 2.22-2.48 (m, 3H), 2.07-2.22 (m, 1H), 1.22 (t, J=7.1 Hz, 3H).

Step 2) The Preparation of Compound 18-3

To a solution of compound 18-2 (25.2 g, 0.176 mol) and DMAP (2.20 g, 0.018 mol) in CH₃CN (150 mL) was added Boc₂O (40.0 g, 0.178 mol) in two portions. The mixture was stirred at rt for 18 hours. The reaction was monitored by TLC and the mixture was concentrated in vacuo after the process stopped. To the residue were added NaHSO₄ aqueous solution (1 M, 75 mL) and EtOAc (200 mL). After the layers were partitioned, the aqueous phase was extracted with EtOAc (250 mL×3). The combined organic phases were washed with brine (300 mL), dried over anhydrous Na₂SO₄ and concentrated in vacuo. The residue was purified by silica gel column chromatography (PE/EtOAc (v/v)=1/1) to give the title compound 18-3 (23.2 g, 88%). The compound was characterized by the following spectroscopic data:

¹H NMR (400 MHz, CDCl₃): δ 4.58 (dd, J=9.4, 2.8 Hz, 1H), 4.20 (m, 2H), 2.59 (m, 1H), 2.48 (m, 1H), 2.30 (m, 1H), 2.01 (m, 1H), 1.47 (s, 9H), 1.27 (t, J=7.1 Hz, 3H).

Step 3) The Preparation of Compound 18-4

To a solution of compound 18-3 (20 g, 77.8 mmol) in THF (200 mL) was added LiN(SiMe₃)₂ (80 mL, 1.0 M in THF) at −78° C. dropwise. The mixture was stirred for 45 minutes, and iodomethane (12 mL) was added in one portion. The resulting mixture was stirred at −78° C. for 2 hours and at rt overnight. The reaction mixture was quenched with acetic acid (2 eq) and water (30 mL), extracted with EtOAc (100 mL×3). The combined organic phases were dried over anhydrous Na₂SO₄ and concentrated in vacuo. The residue was purified by silica gel column chromatography (PE/EtOAc (v/v)=2/1) to give the title compound 18-4 as oil (6.0 g, 28%). The compound was characterized by the following spectroscopic data:

¹H NMR (400 MHz, CDCl₃): δ 4.46 (m, 1H), 4.21 (m, 2H), 2.56 (m, 2H), 1.60 (m, 1H), 1.48 (s, 9H), 1.23-1.29 (m, 6H).

Step 4) The Preparation of Compound 18-5

To a solution of compound 18-4 (0.2 g, 0.74 mmol) in THF (10 mL) was added BH₃·Me₂S(1 mL, 2 M in THF, 2 mmol) at 40° C. The mixture was stirred for 10 hours and concentrated in vacuo. The residue was purified by silica gel column chromatography (PE/EtOAc (v/v)=10/1) to give the title compound 18-5 as oil (100 mg, 52%). The compound was characterized by the following spectroscopic data:

MS-ESI: m/z 280.1 [M+23]⁺; and

¹H NMR (400 MHz, CDCl₃): δ 4.24-4.13 (m, 3H), 3.75-3.62 (m, 1H), 2.96 (t, J=10.16 Hz, 1H), 2.38 (m, 1H), 2.21 (m, 1H), 1.53 (m, 1H), 1.48 (s, 9H), 1.26 (m, 3H), 1.03 (m, 3H).

Step 5) The Preparation of Compound 18-6

To a solution of compound 18-5 (0.2 g, 0.78 mmol) in EtOAc (3 mL) was added a solution of HCl in EtOAc (5 mL, 4 M) in an ice bath. At the end of the addition, the mixture was stirred at rt overnight and concentrated in vacuo to afford the title compound 18-6 as colorless oil (150 mg), which was used for next step directly.

Step 6) The Preparation of Compound 18-7

To a mixture of compound 18-6 (1.0 g, 5.2 mmol), compound 1-7-2 (1.5 g, 8.6 mmol) and EDCI (1.95 g, 10 mmol) in an ice bath under N₂ was added DCM (5 mL) via syringe followed by DIPEA (5.2 mL, 32 mmol). At the end of the addition, the mixture was stirred at rt overnight. Water (15 mL) and DCM (15 mL) were added to the mixture and the mixture was extracted with DCM (15 mL×2). The combined organic phases were washed with brine, dried over anhydrous Na₂SO₄ and concentrated in vacuo. The residue was purified by silica gel column chromatography (PE/EtOAc (v/v)=1/1) to give the title compound 18-7 (0.98 g, 60%). The compound was characterized by the following spectroscopic data:

MS-ESI: m/z 315.2 [M+H]⁺; and

¹H NMR (400 MHz, CDCl₃): δ 5.44 (d, J=9.04 Hz, 2H), 4.40 (m, 3H), 4.32 (m, 1H), 4.18 (dd, J=3 Hz, 7 Hz, 2H), 4.00 (m, 1H), 3.65 (s, 1H), 2.43 (m, 1H), 2.33 (m, 1H), 2.04 (m, 1H), 1.26 (t, J=7.1 Hz, 3H), 1.05 (m, 3H), 1.02 (m, 3H), 0.94 (m, 3H).

Step 7) The Preparation of Compound 18-8

To a solution of compound 18-7 (1.45 g, 4.6 mmol) in THF (10 mL) was added LiOH (2.1 g) followed by water (8 mL) at 0° C. The mixture was stirred at rt overnight and THF was removed in vacuo. The mixture was extracted with EtOAc (50 mL×3) and the organic layer was discarded. The aqueous layer was adjusted to pH 2 with diluted hydrochloric acid (10%) and extracted with EtOAc (50 mL×3). The combined organic phases were dried over anhydrous Na₂SO₄ and concentrated in vacuo to give the title compound 18-8 as colorless slurry (1.18 g, 90%). The compound was characterized by the following spectroscopic data:

¹H NMR (400 MHz, CDCl₃): δ 5.32 (d, J=8.74 Hz, 2H), 4.37 (m, 3H), 4.28 (m, 1H), 4.00 (m, 1H), 3.62 (s, 1H), 2.41 (m, 1H), 2.32 (m, 1H), 2.04 (m, 1H), 1.03 (m, 3H), 1.01 (m, 3H), 0.92 (m, 3H).

Step 8) The Preparation of Compound 18-9

The title compound 18-9 (HPLC: 95%) was prepared by an analogous procedure to that described for compound 14-6 (Example 14). The compound was characterized by the following spectroscopic data:

MS-ESI: m/z 505.1 [M+3H]³⁺; and

¹H NMR (400 MHz, CDCl₃): δ 8.09 (dd, J=6.7, 1.9 Hz, 2H), 7.76 (d, J=8.1 Hz, 1H), 7.57 (dd, J=6.7, 1.9 Hz, 2H), 7.30 (d, J=8.1 Hz, 1H), 4.49 (s, 4H), 3.19 (s, 2H), 2.80 (s, 2H), 1.58-1.36 (m, 10H).

Step 9) The Preparation of Compound 18-10

To a solution of compound 18-9 (0.25 g, 0.5 mmol) in acetonitrile (10 mL) was added DIPEA (0.35 mL, 2.0 mmol). The mixture was stirred for 5 minutes, and compound 18-8 (0.34 g, 1.2 mmol) was added. The resulting mixture was stirred at rt for 3 hours and concentrated in vacuo. The residue was purified by silica gel column chromatography (PE/EtOAc (v/v)=3/1) to give the title compound 18-10 as a pale yellow solid (0.26 g, 56%). The compound was characterized by the following spectroscopic data:

MS-ESI: m/z 915.4 [M+H]⁺; and

¹H NMR (400 MHz, CDCl₃): δ 8.03-7.96 (m, 2H), 7.67 (d, J=8.0 Hz, 1H), 7.57 (dd, J=8.2, 3.0 Hz, 2H), 7.27 (d, J=8.0 Hz, 1H), 5.62-5.51 (m, 2H), 5.39 (d, J=9.16 Hz, 2H), 5.30-5.16 (m, 2H), 4.62-4.56 (m, 2H), 4.36-4.32 (m, 2H), 4.05-4.02 (m, 2H), 3.67 (s, 6H), 3.15 (s, 2H), 2.77 (s, 2H), 2.63-2.57 (m, 2H), 2.36-2.44 (m, 2H), 2.08-2.01 (m, 2H), 1.92-1.83 (m, 2H), 1.53-1.40 (m, 10H), 1.17 (d, J=6.24 Hz, 6H), 1.03 (d, J=6.68 Hz, 6H), 0.93 (d, J=6.72 Hz, 6H).

Step 10) the Preparation of Compound 18-11

A mixture of compound 18-10 (250 mg, 0.27 mmol) and ammonium acetate (210 mg, 2.7 mmol) in xylene (10 mL) in a sealed tube was stirred at 140° C. for 4 hours, cooled to rt and concentrated in vacuo. To the residue was added water (10 mL) and the mixture was extracted with EtOAc (30 mL×3). The combined organic phases were washed with brine, dried over anhydrous Na₂SO₄ and concentrated in vacuo. The residue was purified by silica gel column chromatography (EtOAc) to give the title compound 18-11 as a pale yellow solid (0.12 g, 51%). The compound was characterized by the following spectroscopic data:

MS-ESI: m/z 876.5 [M+H]⁺; and

¹H NMR (400 MHz, CDCl₃): δ 7.82-7.58 (m, 2H), 7.50-7.36 (m, 3H), 7.25-7.17 (m, 2H), 7.11 (s, 1H), 5.70-5.59 (m, 2H), 5.32-5.22 (m, 2H), 4.38-4.29 (m, 2H), 3.91-3.80 (m, 2H), 3.78-3.60 (m, 8H), 3.04-2.80 (m, 6H), 2.46-1.90 (m, 8H), 1.52-1.35 (m, 12H), 0.93-0.78 (m, 18H).

Example 19
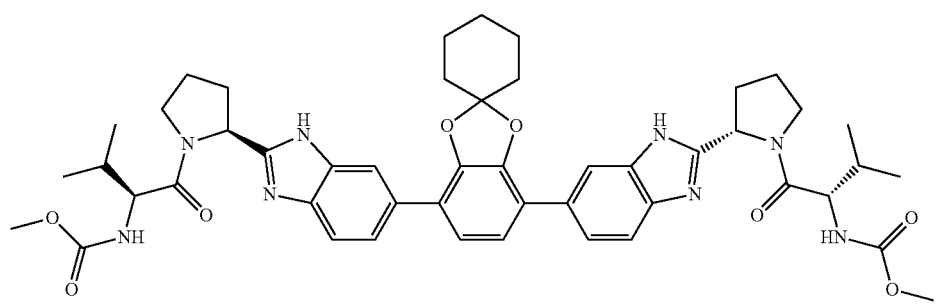
Synthetic Routes
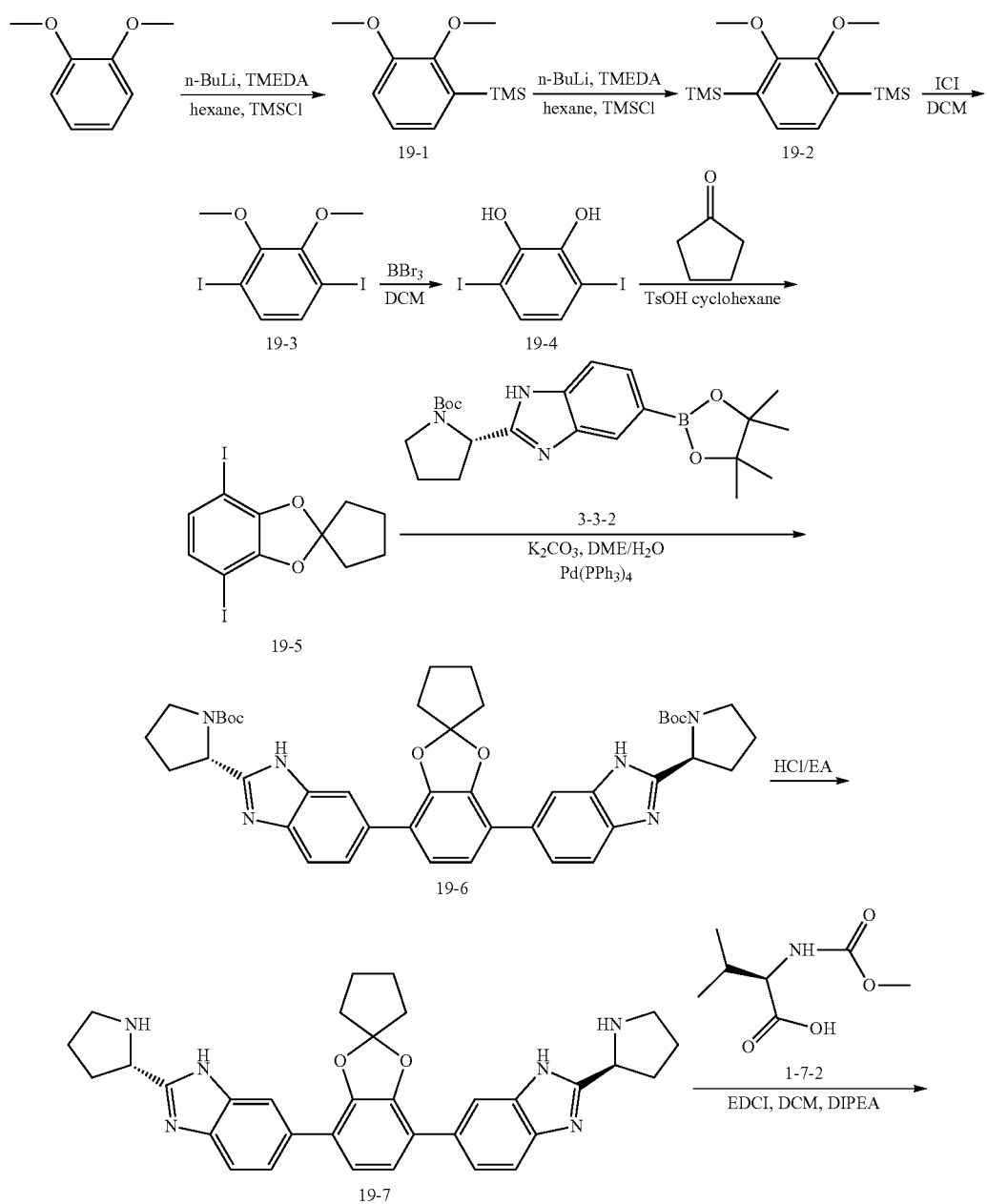

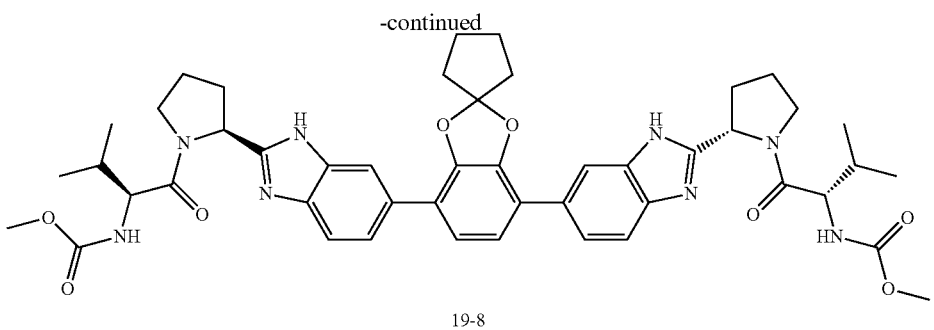

19-8

Step 1) The Preparation of Compound 19-1

To a mixture of hexane (100 mL) and N,N,N',N'-tetramethylethylenediamine (40 mL) was added 1,2-dimethoxybenzene (40.0 g, 0.29 mol) followed by n-BuLi (200 mL, 0.32 mol, 1.6 M in hexane) dropwise at rt. The mixture was stirred at rt for 28 hours and cooled to −78° C., then ClSiMe$_3$ (45 mL) was added dropwise. The reaction mixture was heated to rt over a period of 5 hours, quenched with water and extracted with hexane. The organic layer was dried over anhydrous Na$_2$SO$_4$ and concentrated in vacuo. The residue was purified by silica gel column chromatography (hexane/DCM (v/v)=10/1) to give the title compound 19-1 as colorless oil (51.5 g, 85%). The compound was characterized by the following spectroscopic data:

$^1$H NMR (400 MHz, CDCl$_3$): δ 0.28 (s, 9H), 3.86 (s, 6H), 6.93-6.97 (m, 2H), 7.02-7.06 (m, 1H).

Step 2) The Preparation of Compound 19-2

To a solution of compound 19-1 (69.0 g, 0.33 mol) in N,N,N',N'-tetramethylethylenediamine (60 mL) was added n-BuLi (250 mL, 0.40 mol, 1.6 M in hexane) dropwise at 0° C. The mixture was stirred at rt for 25 hours and cooled to −78° C., then ClSiMe$_3$ (60 mL) was added dropwise. The reaction mixture was heated to rt over a period of 5 hours, quenched with water and extracted with hexane (100 mL×3). The combined organic phases were dried over anhydrous Na$_2$SO$_4$ and concentrated in vacuo. The residue was purified by silica gel column chromatography (hexane/DCM (v/v)=10/1) to give the title compound 19-2 as colorless oil (82.5 g, 89%). The compound was characterized by the following spectroscopic data:

$^1$H NMR (400 MHz, CDCl$_3$): δ 0.29 (s, 18H), 3.83 (s, 6H), 7.11 (s, 2H).

Step 3) The Preparation of Compound 19-3

To a solution of compound 19-2 (19.2 g, 68.1 mmol) in DCM (100 mL) at 0° C. was added a solution of ICl (23.1 g, 0.14 mol) in DCM (100 mL) dropwise. The mixture was stirred at rt for 30 minutes and quenched with Na$_2$S$_2$O$_3$ aqueous solution. The organic layer was dried over anhydrous Na$_2$SO$_4$ and concentrated in vacuo. The residue was purified by silica gel column chromatography (hexane/DCM (v/v)=10/1) to give the title compound 19-3 as a pale yellow solid (21.5 g, 81%). The compound was characterized by the following spectroscopic data:

$^1$H NMR (400 MHz, CDCl$_3$): δ 3.87 (s, 6H), 7.24 (s, 2H).

Step 4) The Preparation of Compound 19-4

To a solution of compound 19-3 (1.80 g, 4.62 mmol) in DCM (20 mL) at −78° C. was added BBr$_3$ (2 mL, 21.2 mmol). The mixture was stirred at rt overnight and poured into ice water. The resulting mixture was extracted with DCM (30 mL×3). The combined organic phases were dried over anhydrous Na$_2$SO$_4$ and concentrated in vacuo. The residue was purified by silica gel column chromatography (DCM) to give the title compound 19-4 as a white solid (1.50 g, 90%). The compound was characterized by the following spectroscopic data:

$^1$H NMR (400 MHz, CDCl$_3$): δ 5.66 (s, 2H), 7.00 (s, 2H).

Step 5) The Preparation of Compound 19-5

A mixture of compound 19-4 (400 mg, 1 mmol), cyclopentanone (280 mg, 3 mmol) and p-toluenesulfonic acid (19 mg, 0.1 mmol) in hexane (50 mL) in a 100 mL of round-bottomed flask equipped with Dean-Stark trap was refluxed for 5 hours, poured into water and extracted with EtOAc. The organic layer was dried over anhydrous Na$_2$SO$_4$ and concentrated in vacuo. The residue was purified by silica gel column chromatography (hexane/DCM (v/v)=1/1) to give the title compound 19-5 as a beige white solid (200 mg, 46%). The compound was characterized by the following spectroscopic data:

$^1$H NMR (400 MHz, CDCl$_3$): δ 6.84 (s, 1H), 2.17 (m, 4H), 1.87 (m, 4H).

Step 6) The Preparation of Compound 19-6

To a mixture of compound 19-5 (170 mg, 0.41 mmol), Pd(PPh$_3$)$_4$ (46 mg, 0.041 mmol) and anhydrous potassium carbonate (286 mg, 2 mmol) under N$_2$ was added a solution of compound 3-3-2 (423 mg, 0.99 mmol) in DME (8 mL) via syringe followed by distilled water (2 mL). The resulting mixture was stirred at 90° C. for 2 hours and DME was removed in vacuo. To the residue was added distilled water (15 mL) and the mixture was extracted with DCM (15 mL×3). The combined organic phases were dried over anhydrous Na$_2$SO$_4$ and concentrated in vacuo. The residue was purified by silica gel column chromatography (DCM/MeOH (v/v)=20/1) to give the title compound 19-6 as a yellow solid (200 mg, 65%). The compound was characterized by the following spectroscopic data:

$^1$H NMR (400 MHz, CDCl$_3$): δ 8.19 (s, 1H), 7.83 (s, 1H), 7.78 (d, J=8.36 Hz, 1H), 7.65 (m, 2H), 7.47 (d, J=8.36 Hz, 1H), 7.15 (s, 2H), 5.14 (d, J=5.90 Hz, 1H), 3.43 (m, 4H), 2.21 (m, 8H), 2.03 (m, 4H), 1.88 (m, 4H), 1.55 (s, 18H).

Step 7) The Preparation of Compound 19-7

To a solution of compound 19-6 (200 mg, 0.27 mmol) in EtOAc (4 mL) was added a solution of HCl in EtOAc (5 mL, 4 M). The mixture was stirred at rt overnight and filtered. The filter cake was washed with EtOAc (30 mL) to give the title compound 19-7 as a yellow solid (180 mg, 96%). The compound was characterized by the following spectroscopic data:

MS-ESI: m/z 547.2 [M+H]+; and

1H NMR (400 MHz, D2O): δ 7.95 (m, 2H), 7.72 (m, 4H), 7.14 (m, 2H), 5.09 (m, 2H), 3.54 (m, 4H), 2.59 (m, 2H), 2.38 (m, 4H), 2.26 (m, 6H), 1.81 (m, 4H).

Step 8) the Preparation of Compound 19-8

To a suspension of compound 19-7 (220 mg, 0.32 mmol), compound 1-7-2 (167 mg, 0.95 mmol) and EDCI (300 mg, 1.6 mmol) in DCM (10.0 mL) in an ice bath was added DIPEA (0.7 mL) dropwise. At the end of the addition, the mixture was stirred at rt overnight. Water (20 mL) was added to the mixture and the mixture was extracted with DCM (25 mL×3). The combined organic phases were dried over anhydrous Na2SO4 and concentrated in vacuo. The residue was purified by silica gel column chromatography (EtOAc) to give the title compound 19-8 as a white solid (120 mg, 43%, HPLC: 95.5%). The compound was characterized by the following spectroscopic data:

MS-ESI: m/z 861.6 [M+H]+; and

1H NMR (400 MHz, CDCl3): δ 10.52 (m, 2H), 8.17 (s, 1H), 7.78 (s, 2H), 7.63 (brs, 2H), 7.40 (d, J=8.36 Hz, 1H), 7.12 (s, 2H), 5.45 (m, 2H), 4.35 (m, 2H), 3.89 (m, 2H), 3.12 (m, 2H), 2.40 (m, 2H), 2.28-2.10 (m, 12H), 1.86 (m, 4H), 0.88 (m, 12H).

Example 20

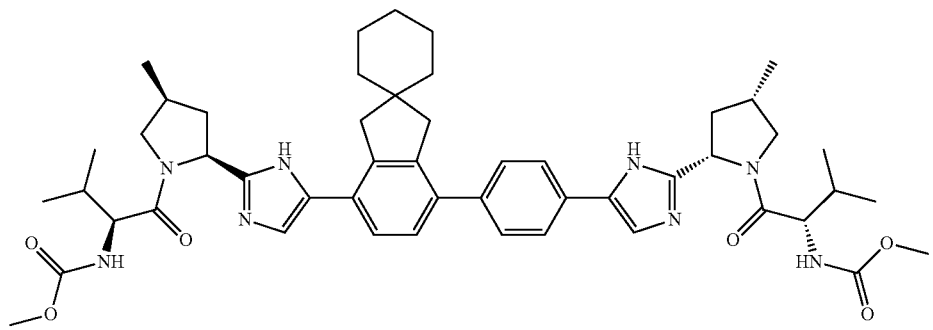

Synthetic Routes

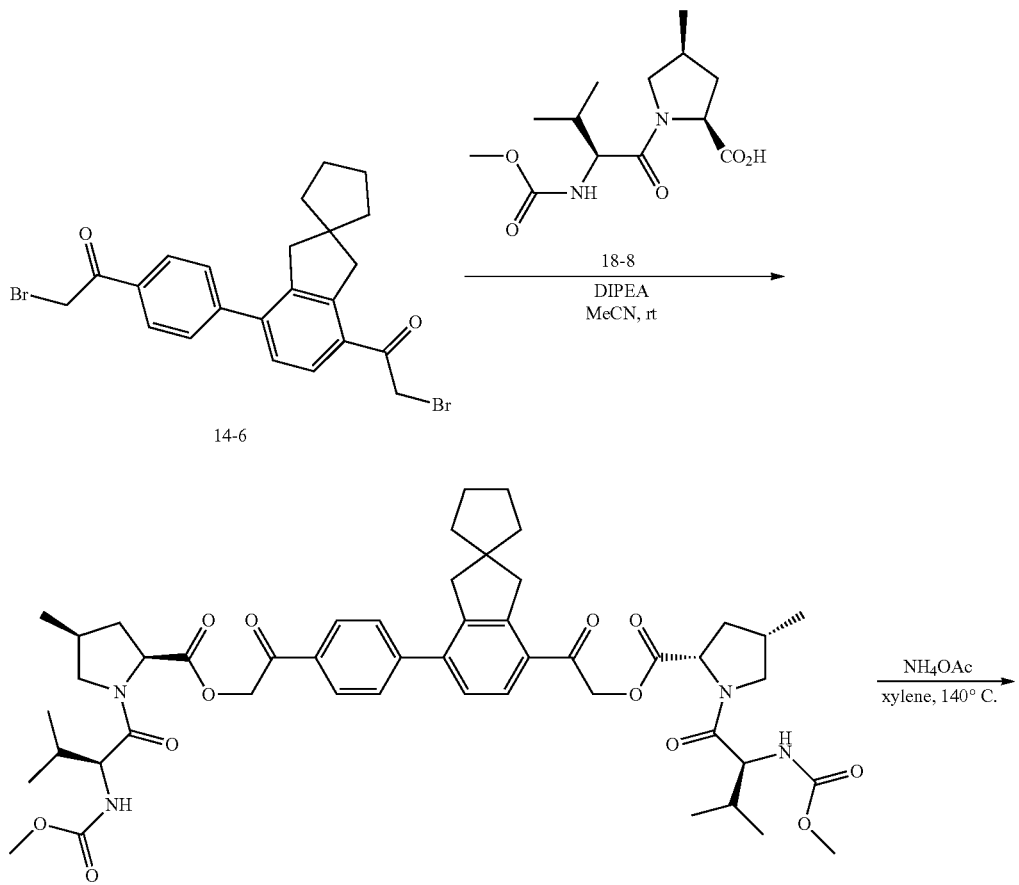

20-1

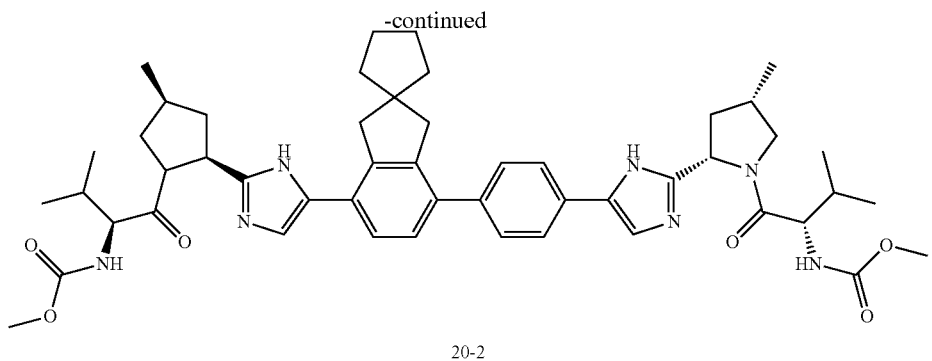

20-2

Step 1) The Preparation of Compound 20-1

To a solution of compound 14-6 (0.20 g, 0.4 mmol) in anhydrous acetonitrile (10 mL) in an ice bath was added DIPEA (0.5 mL) followed by compound 18-8 (0.30 g, 1 mmol). The mixture was stirred at rt for 3 hours and concentrated in vacuo. The residue was purified by silica gel column chromatography (PE/EtOAc (v/v)=1/3) to give the title compound 20-1 as yellow slurry (0.21 g, 58%). The compound was characterized by the following spectroscopic data:

MS-ESI: m/z 901.4 [M+H]$^+$; and $^1$H NMR (400 MHz, CDCl$_3$): δ 8.03-7.96 (m, 2H), 7.67 (d, J=8.0 Hz, 1H), 7.57 (dd, J=8.2, 3.0 Hz, 2H), 7.27 (d, J=8.0 Hz, 1H), 5.62-5.51 (m, 2H), 5.39 (d, J=9.16 Hz, 2H), 5.30-5.16 (m, 2H), 4.62-4.56 (m, 2H), 4.36-4.32 (m, 2H), 4.05-4.02 (m, 2H), 3.67 (s, 6H), 3.15 (s, 2H), 2.77 (s, 2H), 2.63-2.57 (m, 2H), 2.36-2.44 (m, 2H), 2.08-2.01 (m, 2H), 1.92-1.83 (m, 2H), 1.53-1.40 (m, 8H), 1.17 (d, J=6.24 Hz, 6H), 1.03 (d, J=6.68 Hz, 6H), 0.93 (d, J=6.72 Hz, 6H).

Step 2) The Preparation of Compound 20-2

A suspension of compound 20-1 (0.18 g, 0.2 mmol) and ammonium acetate (0.31 g, 4 mmol) in xylene (5 mL) in a sealed tube under N$_2$ was stirred at 130° C. for 3 hours, cooled to rt and diluted with EtOAc (15 mL). The organic layer was washed with water and brine, dried over anhydrous Na$_2$SO$_4$ and concentrated in vacuo. The residue was purified by silica gel column chromatography (EtOAc) to give the title compound 20-2 as a white solid (60 mg, 35%). The compound was characterized by the following spectroscopic data:

MS-ESI: m/z 861.5 [M+H]$^+$; and $^1$H NMR (400 MHz, CDCl$_3$): δ 11.00 (bs, 1H), 10.63 (bs, 1H), 7.90-7.69 (m, 2H), 7.48-7.38 (m, 2H), 7.28-7.22 (m, 2H), 7.13 (s, 2H), 5.43 (d, J=8.08 Hz, 2H), 5.21 (d, J=8.08 Hz, 2H), 4.38 (t, J=7.16 Hz, 2H), 4.21 (s, 2H), 3.70 (s, 6H), 3.13-2.93 (m, 6H), 2.76-2.34 (m, 6H), 1.93-1.55 (m, 8H), 1.32-0.79 (m, 18H).

Example 21

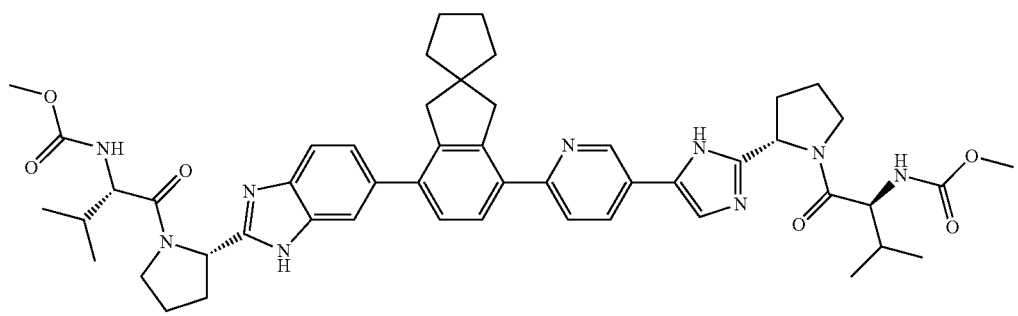

Synthetic Routes

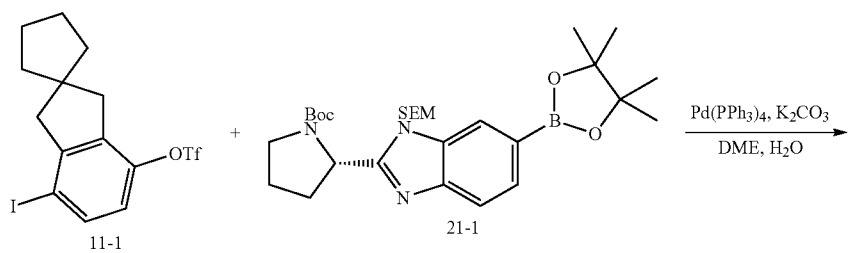

-continued
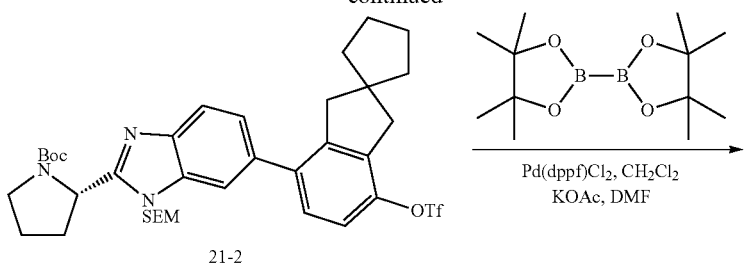
21-2
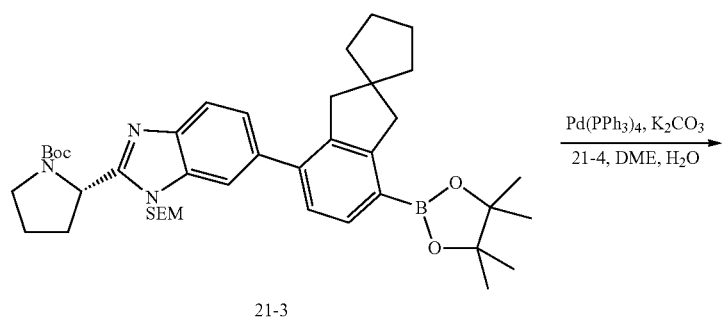
21-3
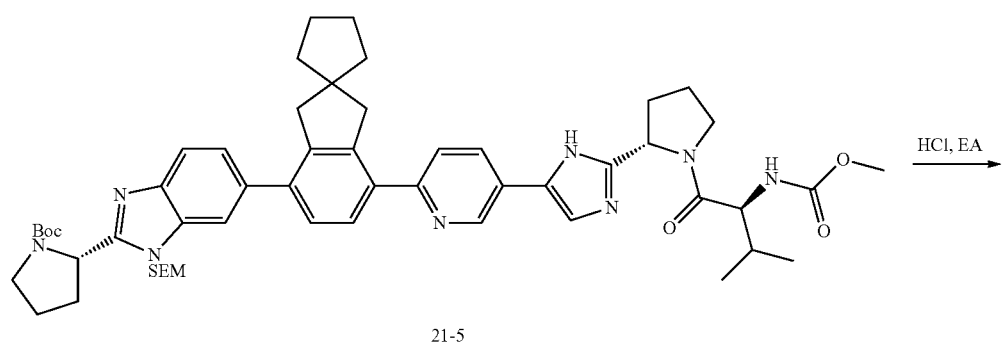
21-5
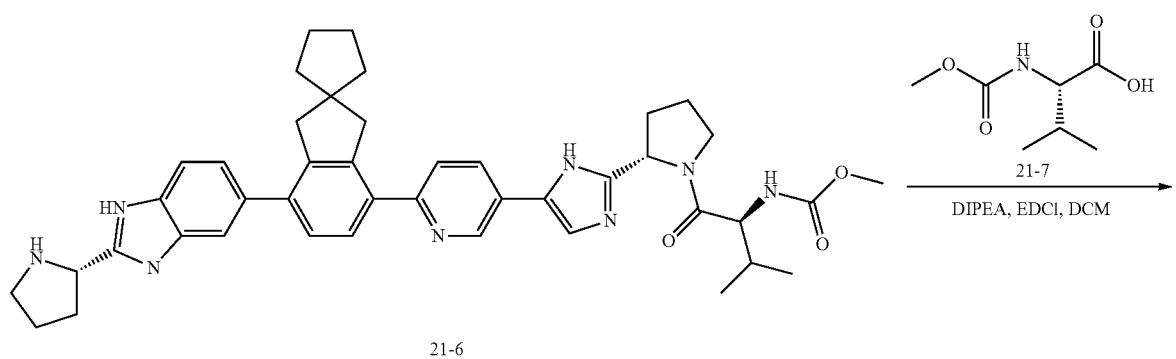
21-6
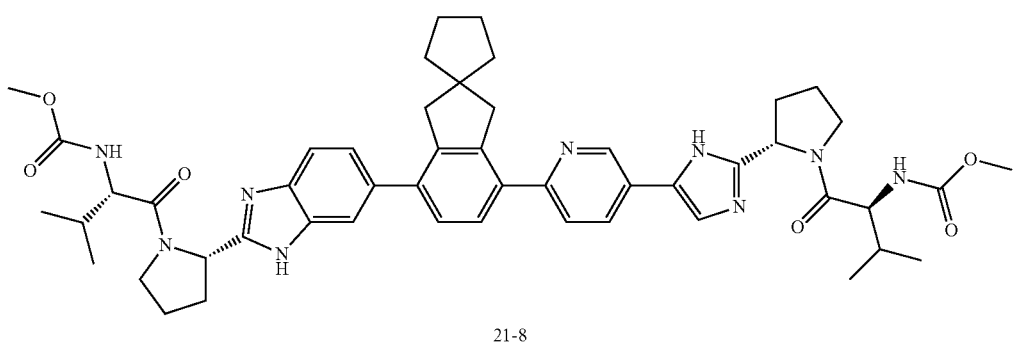
21-8

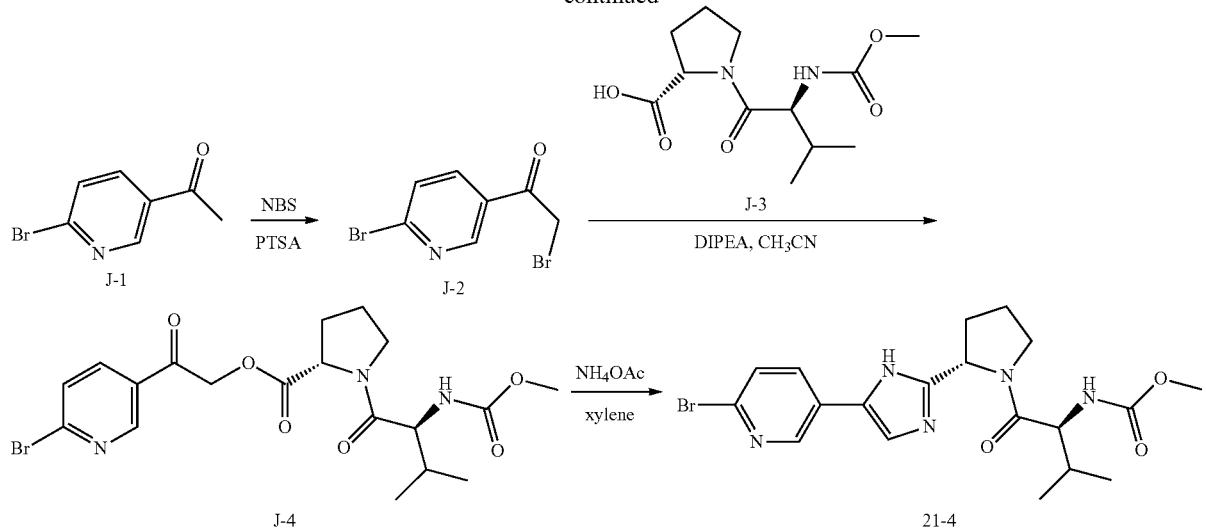

Step 1) The Preparation of Compound 21-1

The title compound 21-1 was prepared by an analogous procedure to that described for compound 3-3-2 (Example 3). The compound was characterized by the following spectroscopic data:

MS-ESI: m/z 544.3 [M+H]$^+$; and $^1$H NMR (400 MHz, CDCl$_3$): δ 8.22 (s, 0.5H), 7.86-7.87 (m, 0.5H), 7.37-7.39 (m, 2H), 5.89-5.94 (m, 0.5H), 5.53-5.58 (m, 1H), 5.46-5.48 (m, 0.5H), 5.05-5.16 (m, 1H), 3.61-3.77 (m, 2H), 3.52-3.61 (m, 2H), 1.89-2.49 (m, 4H), 1.34 (s, 12H), 1.25 (s, 9H), 0.87-0.88 (m, 2H), 0.06 (s, 9H).

Step 2) The Preparation of Compound 21-2

To a solution of compound 11-1 (353 mg, 0.79 mmol), compound 21-1 (390 mg, 0.72 mmol) and potassium carbonate (300 mg, 2.12 mmol) in mixed solvents of DME (4 mL) and water (1 mL) was added Pd(PPh$_3$)$_4$ (83 mg, 0.07 mmol) under N$_2$. The resulting mixture was stirred at 90° C. for 4 hours. The mixture was quenched with water and extracted with EtOAc (20 mL×3). The combined organic phases were washed with brine, dried over anhydrous Na$_2$SO$_4$ and concentrated in vacuo. The residue was purified by silica gel column chromatography (PE/EtOAc (v/v)=2/1) to give the title compound 21-2 (0.424 g, 80%). The compound was characterized by the following spectroscopic data:

$^1$H NMR (400 MHz, CDCl$_3$): δ 7.78 (d, J=8.0 Hz, 1H), 7.39 (s, 1H), 7.26-7.27 (m, 2H), 7.11-7.13 (m, 1H), 5.91-5.94 (m, 0.5H), 5.59-5.70 (m, 0.5H), 5.48-5.50 (m, 1H), 5.10-5.19 (m, 1H), 3.61-3.82 (m, 2H), 3.57-3.59 (m, 2H), 3.00 (s, 2H), 2.94 (s, 2H), 1.98-2.43 (m, 4H), 1.51-1.72 (m, 8H), 1.16-1.23 (m, 9H), 0.87-0.88 (m, 2H), 0.04 (s, 9H).

Step 3) The Preparation of Compound 21-3

A mixture of compound 21-2 (670 mg, 0.91 mmol), bis(pinacolato)diboron (463 mg, 1.82 mmol), Pd(dppf)Cl$_2$·CH$_2$Cl$_2$ (71 mg, 0.09 mmol) and KOAc (268 mg, 2.73 mmol) in DMF (10 mL) was stirred at 90° C. for 3 hours under N$_2$, cooled to rt and quenched with water. The mixture was extracted with EtOAc (20 mL×3). The combined organic phases were washed with brine, dried over anhydrous Na$_2$SO$_4$ and concentrated in vacuo. The residue was purified by silica gel column chromatography (PE/EtOAc (v/v)=2/1) to give the title compound 21-3 (559 mg, 86%). The compound was characterized by the following spectroscopic data:

MS-ESI: m/z 714.4 [M+H]$^+$; and $^1$H NMR (400 MHz, CDCl$_3$): δ 7.79 (d, J=8.0 Hz, 1H), 7.42 (s, 1H), 7.25-7.26 (m, 2H), 7.11-7.13 (m, 1H), 5.85-5.86 (m, 0.5H), 5.51-5.55 (m, 0.5H), 5.48-5.50 (m, 1H), 5.10-5.19 (m, 1H), 3.62-3.84 (m, 2H), 3.57-3.59 (m, 2H), 3.00 (s, 2H), 2.94 (s, 2H), 1.98-2.43 (m, 4H), 1.51-1.72 (m, 8H), 1.36-1.50 (m, 12H), 1.16-1.23 (m, 9H), 0.87-0.88 (m, 2H), 0.04 (s, 9H).

Step 4) The Preparation of Compound 21-4

A mixture of compound J-1 (25 g, 125.6 mmol), NBS (24.5 g, 138.2 mmol) and p-TSA (3.4 g, 20.9 mmol) was stirred at 100° C. under N$_2$ for 2 hours. The mixture was then cooled to rt and dissolved in DCM. The resulting mixture was quenched with water and extracted with DCM (50 mL×3). The combined organic phases were dried over anhydrous Na$_2$SO$_4$ and concentrated in vacuo. The residue was purified by silica gel column chromatography (PE/EtOAc (v/v)=5/1) to give the title compound J-2 (25 g, 71%). The compound was characterized by the following spectroscopic data:

MS-ESI: m/z 279.9 [M+H]$^+$; and $^1$H NMR (400 MHz, CDCl$_3$): δ 8.95 (d, J=1.12 Hz, 1H), 8.11-8.14 (m, 1H), 7.66-7.68 (m, 1H), 4.41 (s, 2H).

To a solution of compound J-2 (5 g, 17.9 mmol) and compound J-3 (5.4 g, 19.7 mmol) in MeCN (100 mL) at 0° C. was added DIPEA (3.3 mL, 19.7 mmol) dropwise. The mixture was stirred at rt and the reaction was monitored by TLC. After the reaction was completed, the mixture was poured into ice water and extracted with EtOAc (100 mL×3). The combined organic phases were dried over anhydrous Na$_2$SO$_4$ and concentrated in vacuo. The residue was purified by silica gel column chromatography (PE/EtOAc (v/v)=3/1) to give the title compound J-4 (8.0 g, 96%). The compound was characterized by the following spectroscopic data:

MS-ESI: m/z 470.1 [M+H]$^+$; and $^1$H NMR (400 MHz, CDCl$_3$): δ 8.88 (s, 1H), 8.04 (d, J=3.88 Hz, 1H), 7.65 (d, J=4.16 Hz, 1H), 5.59-5.61 (m, 1H), 5.48 (d, J=8.32 Hz, 1H), 5.23 (d, J=8.3 Hz, 1H), 4.67 (t, J=5.72 Hz, 1H), 4.31 (t, J=7.52 Hz, 1H), 3.84-3.86 (m, 1H), 3.71-3.73 (m, 1H), 3.66 (s, 3H), 2.34-2.15 (m, 4H), 1.01 (t, 3H), 0.93-0.94 (m, 3H), 0.85-0.88 (m, 1H).

A solution of compound J-4 (2.0 g, 4.25 mmol) and ammonium acetate (4.9 g, 83 mmol) in xylene (50 mL) in a sealed tube was stirred at 130° C. overnight. Then the mixture was cooled to rt, quenched with water and extracted with EtOAc (50 mL×3). The combined organic phases were dried over anhydrous Na$_2$SO$_4$ and concentrated in vacuo. The residue was purified by silica gel column chromatography (PE/EtOAc (v/v)=2/1) to give the title compound 21-4 (1.39 g, 73%). The compound was characterized by the following spectroscopic data:

MS-ESI: m/z 450.1 [M+H]+; and

¹H NMR (400 MHz, CDCl₃): δ 8.70 (s, 1H), 7.93 (d, J=6.92 Hz, 1H), 7.45 (d, J=8.28 Hz, 1H), 5.41 (d, J=4.6 Hz, 1H), 5.22-5.24 (m, 1H), 4.32 (m, 1H), 3.83-3.85 (m, 1H), 3.67 (s, 3H), 3.62-3.63 (m, 3H), 3.03-3.05 (m, 1H), 2.31-1.93 (m, 4H), 1.03-1.04 (m, 1H), 0.88 (s, 3H), 0.86 (s, 3H).

Step 5) The Preparation of Compound 21-5

To a solution of compound 21-3 (435 mg, 0.61 mmol), compound 21-4 (274 mg, 0.6 mmol) and potassium carbonate (254 mg, 1.83 mmol) in mixed solvents of DME (5 mL) and water (1 mL) was added Pd(PPh₃)₄ (70 mg, 0.05 mmol) under N₂. The mixture was stirred at 90° C. for 4 hours, cooled to rt and quenched with water. The mixture was extracted with EtOAc (20 mL×3). The combined organic phases were washed with brine, dried over anhydrous Na₂SO₄ and concentrated in vacuo. The residue was purified by silica gel column chromatography (PE/EtOAc (v/v)=1/1) to give the title compound 21-5 (528 mg, 92%). The compound was characterized by the following spectroscopic data:

MS-ESI: m/z 957.5 [M+H]+; and

¹H NMR (400 MHz, CDCl₃): δ 9.10-9.13 (m, 1H), 7.82-7.84 (m, 1H), 7.75-7.74 (m, 1H), 7.60-7.68 (m, 1H), 7.51-7.68 (m, 2H), 7.31-7.45 (m, 3H), 5.99-5.96 (d, 0.5H), 5.75-5.77 (m, 1H), 5.56-5.58 (m, 0.5H), 5.29-5.31 (m, 1H), 5.13-5.25 (m, 1H), 4.34-4.39 (m, 1H), 4.12-4.18 (m, 1H), 3.86-3.91 (m, 2H), 3.79 (s, 3H), 3.66-3.78 (m, 2H), 3.17 (s, 2H), 3.01 (s, 2H), 2.12-2.46 (m, 4H), 1.86-2.07 (m, 4H), 1.52-1.63 (m, 8H), 1.31-1.32 (m, 1H), 1.29 (s, 9H), 1.05-1.12 (m, 2H), 0.88-0.95 (m, 12H), 1.51-1.72 (m, 8H), 1.36-1.50 (m, 12H), 1.16-1.23 (m, 9H), 0.87-0.88 (m, 2H), 0.00 (s, 9H).

Step 6) The Preparation of Compound 21-6

A solution of compound 21-5 (75 mg, 0.08 mmol) in a solution of HCl in EtOAc (5 mL, 4 M) was stirred at rt overnight and concentrated in vacuo. The residue was washed with EtOAc to give the title compound 21-6 as a pale yellow solid (65 mg, 99%), which was used for the next step without further purification. The compound was characterized by the following spectroscopic data:

MS-ESI: m/z 727.4 [M+H]+; and

¹H NMR (400 MHz, CDCl₃): δ 9.09-9.11 (m, 1H), 7.81-7.83 (m, 1H), 7.76-7.78 (m, 1H), 7.58-7.60 (m, 1H), 7.51-7.68 (m, 2H), 7.40-7.46 (m, 3H), 5.29-5.31 (m, 1H), 5.13-5.25 (m, 1H), 4.34-4.39 (m, 1H), 4.11-4.17 (m, 1H), 3.79 (s, 3H), 3.66-3.78 (m, 2H), 3.15 (s, 2H), 3.06 (s, 2H), 2.10-2.46 (m, 4H), 1.83-2.06 (m, 4H), 1.53-1.64 (m, 8H), 1.31-1.32 (m, 1H), 1.29 (s, 9H), 1.05-1.12 (m, 2H), 0.88-0.95 (m, 12H), 1.51-1.72 (m, 8H), 1.36-1.50 (m, 12H).

Step 7) The Preparation of Compound 21-7

To a solution of compound 21-6 (56.3 mg, 0.067 mmol), compound 21-7 (21 mg, 0.116 mmol) and EDCI (30 mg, 0.154 mmol) in DCM (1 mL) in an ice bath was added DIPEA (0.09 mL, 0.539 mmol) dropwise. At the end of the addition, the mixture was stirred at rt overnight, quenched with NaHCO₃ saturated solution and extracted with EtOAc (10 mL×3). The combined organic phases were washed with brine, dried over anhydrous Na₂SO₄ and concentrated in vacuo. The residue was purified by silica gel column chromatography (EtOAc) to give the title compound 21-8 (30 mg, 51%, HPLC: 95%). The compound was characterized by the following spectroscopic data:

MS-ESI: m/z 884.5 [M+H]+; and

¹H NMR (400 MHz, CDCl₃): δ 9.03-9.08 (m, 1H), 7.69-7.84 (m, 2H), 7.41-7.52 (m, 3H), 7.51-7.68 (m, 3H), 7.31-7.45 (m, 3H), 5.71-5.73 (m, 1H), 5.26-5.45 (m, 1H), 4.34-4.37 (m, 2H), 3.87-3.91 (m, 2H), 3.71-3.76 (m, 2H), 3.71 (s, 3H), 3.70 (s, 3H), 3.10 (s, 2H), 2.98 (s, 2H), 2.00-2.41 (m, 10H), 1.54-1.65 (m, 8H), 0.85-0.91 (m, 12H).

Example 22

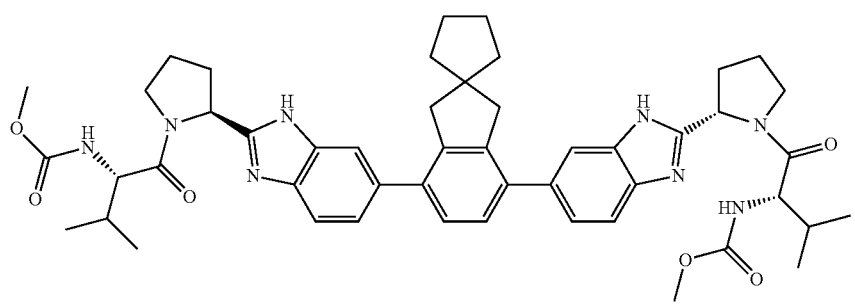 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4c3CC3(CCCC3)C4)cc2[nH]1)C(C)C]

Synthetic Routes

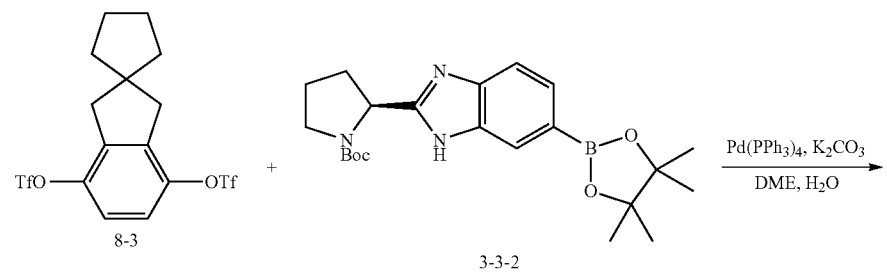

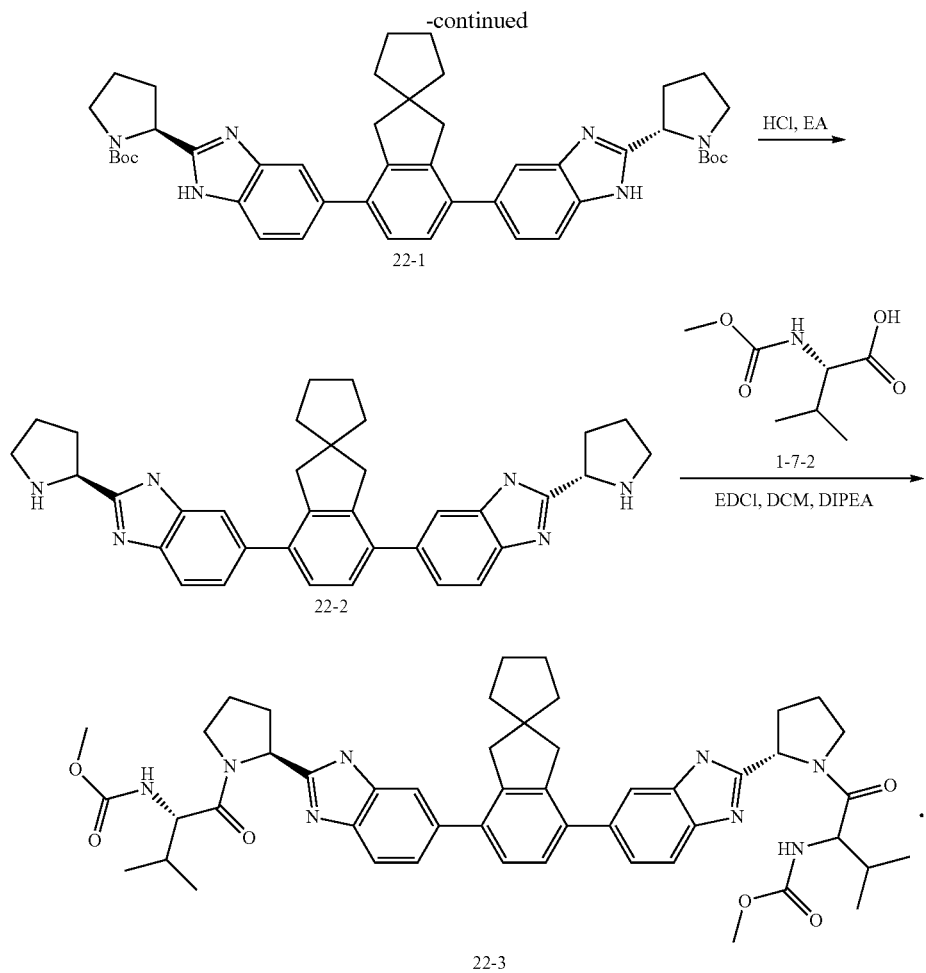

Step 1) The Preparation of Compound 22-1

A solution of compound 8-3 (528 mg, 1.13 mmol), compound 3-3-2 (1.12 g, 2.71 mmol), Pd(PPh₃)₄ (57 mg, 0.05 mmol) and potassium carbonate (778 mg, 5.64 mmol) in mixed solvents DME (5 mL) and water (5 mL) under $N_2$ was stirred at 90° C. overnight. Water (10 mL) was then added and the mixture was extracted with EtOAc (20 mL×3). The combined organic phases were washed with brine, dried over anhydrous $Na_2SO_4$ and concentrated in vacuo. The residue was purified by silica gel column chromatography (PE/EtOAc (v/v)=1/2) to give the title compound 22-1 (430 mg, 51%). The compound was characterized by the following spectroscopic data:

MS-ESI: m/z 743.4 [M+H]⁺; and

¹H NMR (400 MHz, CDCl₃): δ 1.491-1.696 (m, 26H), 1.982-2.093 (m, 4H), 2.226-2.242 (m, 4H), 3.046 (s, 4H), 3.315-3.510 (m, 4H), 5.175-5.189 (m, 2H), 7.283 (s, 2H), 7.344-7.487 (m, 6H).

Step 2) The Preparation of Compound 22-2

To a solution of HCl in EtOAc (10 mL, 4M) was added compound 22-1 (430 mg, 0.58 mmol). The mixture was concentrated in vacuo to give the title compound 22-2 as a pale yellow solid (320 mg, 80%), which was used for the next step without further purification. The compound was characterized by the following spectroscopic data:

MS-ESI: m/z 543.3 [M+H]⁺; and

¹H NMR (400 MHz, CDCl₃): δ 1.139-1.230 (m, 8H), 1.987-2.354 (m, 6H), 2.591-2.605 (m, 2H), 2.743-2.782 (m, 4H), 3.511-3.568 (m, 4H), 5.139-5.236 (m, 2H), 7.141 (s, 2H), 7.412 (s, 2H), 7.611-7.718 (m, 4H).

Step 3) The Preparation of Compound 22-3

To a solution of compound 22-2 (150 mg, 0.22 mmol), compound 1-7-2 (115 mg, 0.66 mmol) in DCM (25 mL) was added EDCI (169 mg, 0.88 mmol) followed by DIPEA (0.38 mL) under $N_2$. At the end of the addition, the mixture was stirred at rt overnight, quenched with $NaHCO_3$ solution and extracted with EtOAc (10 mL×3). The combined organic phases were washed with brine, dried over anhydrous $Na_2SO_4$ and concentrated in vacuo. The residue was purified by silica gel column chromatography (DCM/MeOH (v/v)=40/1) to give the title compound 22-3 (80 mg, 43%, HPLC: 95.7%). The compound was characterized by the following spectroscopic data:

MS-ESI: m/z 625.2[M+H]⁺; and

¹H NMR (400 MHz, CDCl₃): δ 0.844-0.919 (m, 12H), 1.253-2.283 (m, 8H), 1.975-2.406 (m, 8H), 3.027-3.121 (m, 4H), 3.715 (s, 6H), 3.659-3.777 (m, 4H), 5.438-5.464 (m, 2H), 7.285-7.298 (m, 2H), 7.355-7.375 (m, 3H), 7.460-7.480 (m, 1H), 7.773-7.781 (m, 1H), 7.831-7.885 (m, 1H).

Example 23
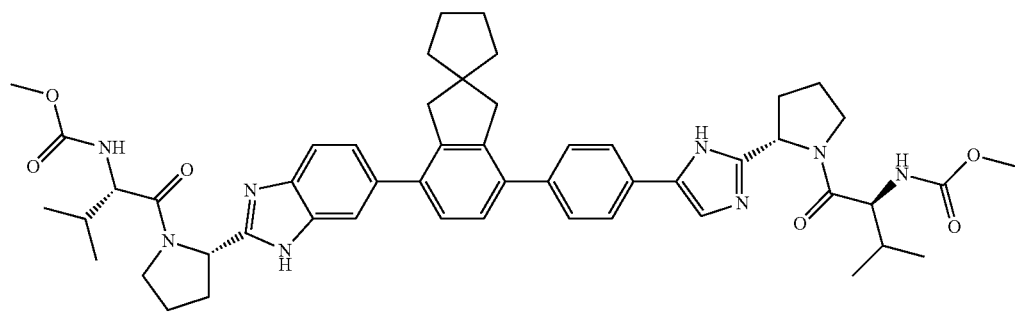
Synthetic Routes
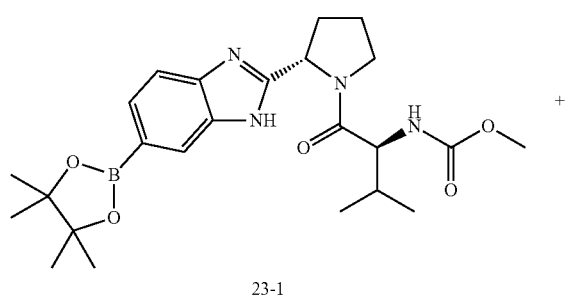
23-1
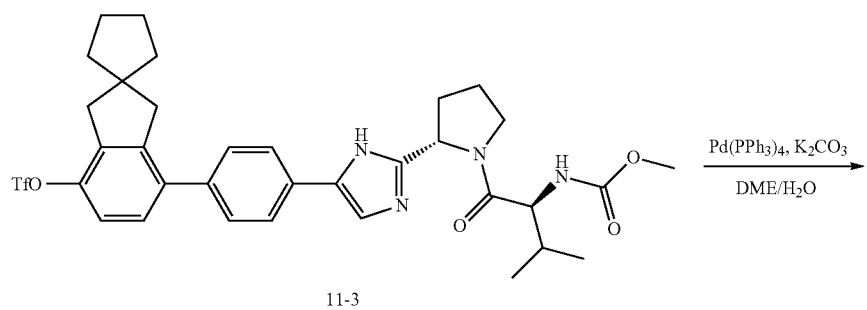
11-3
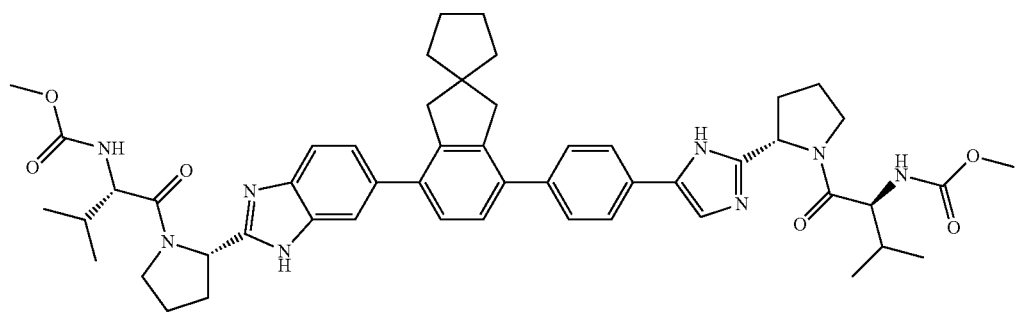
23-2

Step 1) The Preparation of Compound 23-1

The title compound 23-1 was prepared by an analogous procedure to that described for compound 11-4 (Example 11). The compound was characterized by the following spectroscopic data:

MS-ESI: m/z 470.3 [M+H]$^+$; and $^1$H NMR (400 MHz, CDCl$_3$): δ 7.87-7.80 (m, 1H), 7.71-7.66 (m, 2H), 5.47-5.42 (m, 2H), 4.34-4.30 (m, 1H), 3.86-3.84 (m, 1H), 3.70 (s, 3H), 3.64-3.62 (m, 1H), 3.04-2.98 (m, 1H), 2.25-2.20 (m, 1H), 2.20-2.13 (m, 2H), 1.96-1.94 (m, 1H), 1.35 (s, 12H), 0.88-0.84 (m, 6H).

Step 2) the Preparation of Compound 23-2

To a mixture of compound 11-3 (2.407 g, 3.5 mmol), compound 23-1 (1.84 g, 3.9 mmol), Pd(PPh$_3$)$_4$ (404 mg, 0.35 mmol) and potassium carbonate (1.23 g, 8.8 mmol) under N$_2$ was added DME (20.0 mL) via syringe followed by pure water (4.0 mL). The mixture was stirred at 90° C. overnight, cooled to rt and concentrated in vacuo. To the residue was added water (50.0 mL) and the mixture was extracted with EtOAc (50.0 mL×3). The combined organic phases were washed with brine, dried over anhydrous Na$_2$SO$_4$ and concentrated in vacuo. The residue was purified by silica gel column chromatography (DCM/MeOH (v/v)=50/1) to give the title compound 23-2 as a beige solid (1.19 g, HPLC: 97.39%). The compound was characterized by the following spectroscopic data:

MS-ESI: m/z 884.1 [M+H]$^+$; and $^1$H NMR (400 MHz, CDCl$_3$): δ 7.70-7.68 (m, 2H), 7.52-7.56 (m, 2H), 7.42-7.48 (m, 2H), 7.28-7.34 (m, 2H), 7.25-7.26 (m, 2H), 5.26-5.29 (m, 1H), 5.16-5.19 (m, 1H), 4.21-4.26 (m, 2H), 3.94-4.08 (m, 2H), 3.88-3.93 (m, 2H), 3.65 (s, 6H), 2.97 (s, 2H), 2.94 (s, 2H), 2.04-2.34 (m, 10H), 1.53-1.59 (m, 8H), 0.86-0.93 (m, 12H).

Example 24

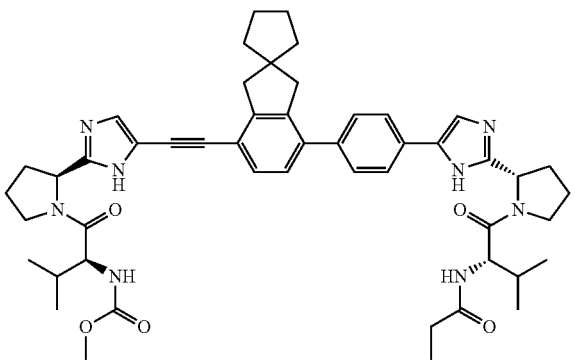 [SMILES: CCC(=O)N[C@H](C(=O)N1CCC[C@H]1c1ncc(-c2ccc(-c3ccc(C#Cc4cnc([C@@H]5CCCN5C(=O)[C@@H](NC(=O)OC)C(C)C)[nH]4)c4c3CC3(CCCC3)C4)cc2)[nH]1)C(C)C]

Synthetic Routes

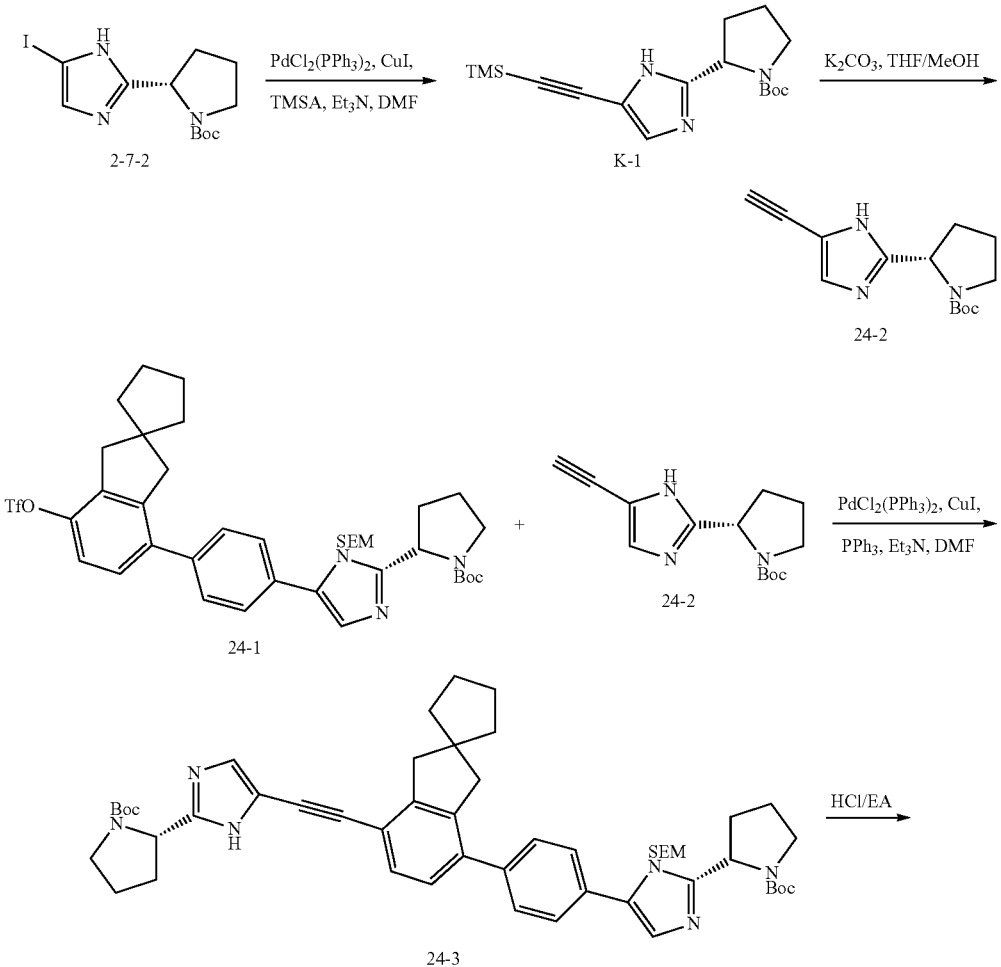

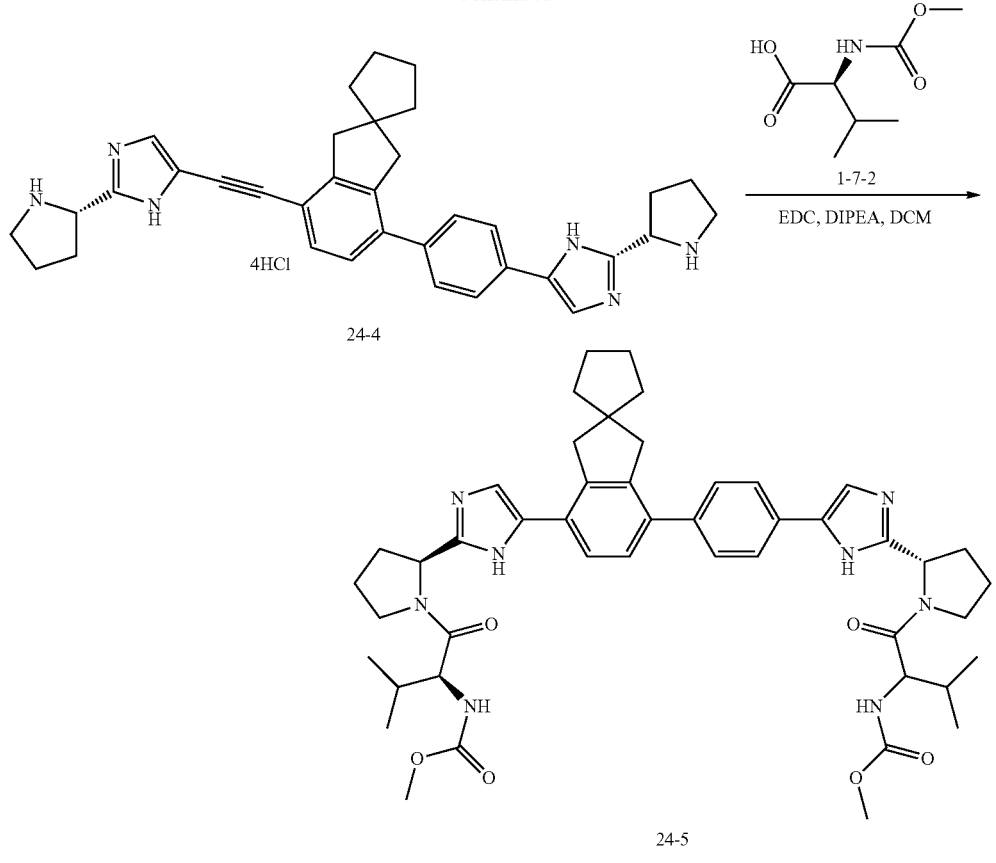

Step 1) The Preparation of Compound 24-1

The title compound 24-1 was prepared by an analogous procedure to that described for compound 17-7 (Example 17). The compound was characterized by the following spectroscopic data:

$^1$H NMR (400 MHz, CDCl$_3$): δ 7.82-7.80 (m, 2H), 7.39-7.37 (m, 2H), 7.26-7.24 (m, 2H), 7.11-7.09 (m, 1H), 6.45-6.47 (m, 1H), 5.80-5.88 (m, 0.5H), 5.40-5.42 (m, 0.5H), 5.18-5.21 (m, 1H), 4.93-5.01 (m, 1H), 3.64-3.73 (m, 2H), 3.49-3.55 (m, 2H), 2.99 (s, 2H), 2.95 (s, 2H), 1.82-2.23 (m, 4H), 1.58-1.69 (m, 8H), 1.1-1.28 (m, 9H), 0.89-0.93 (m, 2H), 0.01 (s, 9H).

Step 2) The Preparation of Compound 24-2

To a solution of compound 2-7-2 (500 mg, 1.38 mmol), PdCl$_2$(PPh$_3$)$_2$ (98 mg, 0.14 mmol) and CuI (78 mg, 0.41 mmol) in DMF (15 mL) under N$_2$ was added Et$_3$N (2 mL) dropwise. The mixture was stirred at rt for 10 minutes, and TMSA (0.98 mL, 6.89 mmol) was added dropwise. The resulting mixture was stirred at rt for another 10 minutes and at 70° C. overnight, then filtered through a Celite pad. The filtrate was diluted with water and extracted with EtOAc (10 mL×3). The combined organic phases were dried over anhydrous Na$_2$SO$_4$ and concentrated in vacuo. The residue was purified by silica gel column chromatography (hexane/EtOAc (v/v)=3/1) to give compound K-1 (290 mg, 63%). The compound was characterized by the following spectroscopic data:

MS-ESI: m/z 334.2 [M+H]$^+$; and $^1$H NMR (400 MHz, CDCl$_3$): δ 7.15 (s, 1H), 4.86-4.88 (m, 1H), 3.34-3.36 (m, 2H), 2.91 (m, 1H), 2.28-1.91 (m, 4H), 1.23 (s, 9H), 0.01 (s, 9H).

A solution of compound K-1 (290 mg, 0.87 mmol) and K$_2$CO$_3$ (601 mg, 4.35 mmol) in mixed solvents of MeOH (2 mL) and THF (2 mL) was stirred at rt for 6 hours and concentrated in vacuo. To the residue was added water (10 mL), and the mixture was extracted with EtOAc (5 mL×3). The combined organic phases were dried over anhydrous Na$_2$SO$_4$ and concentrated in vacuo. The residue was purified by silica gel column chromatography (hexane/EtOAc (v/v)=2/1) to give the title compound 24-2 (208 mg, 91%). The compound was characterized by the following spectroscopic data:

MS-ESI: m/z 262.2 [M+H]$^+$; and $^1$H NMR (400 MHz, CDCl$_3$): δ 7.18 (s, 1H), 4.87-4.89 (m, 1H), 3.31-3.38 (m, 2H), 3.04 (s, 1H), 2.11-2.14 (m, 2H), 1.95-1.91 (m, 2H), 1.43 (s, 9H).

Step 3) The Preparation of Compound 24-3

To a mixture of compound 24-1 (300 mg, 0.39 mmol), PdCl$_2$(PPh$_3$)$_2$ (66 mg, 0.094 mmol), CuI (33 mg, 0.172 mmol) and PPh$_3$ (226 mg, 0.86 mmol) in an 25 mL of round-bottomed flask under N$_2$ was added DMF (10 mL) via syringe followed by Et$_3$N (5 mL). The mixture was stirred at rt for 10 minutes and heated to 90° C. Then to the mixture was added a solution of compound 24-2 (113 mg, 0.43 mmol) in DMF (3 mL) using a syringe pump over a period of more than 1 hour. The mixture was stirred at 90° C. for another 30 minutes, and the reaction was monitored by TLC. The resulting mixture was filtered through a Celite pad. The filtrate was diluted with water and extracted with EtOAc. The organic layer was dried over anhydrous Na$_2$SO$_4$ and concentrated in vacuo. The residue was purified by silica gel column chromatography (hexane/EtOAc (v/v)=1/2) to give the title compound 24-3 (200 mg, 58.7%). The compound was characterized by the following spectroscopic data:

MS-ESI: m/z 874.5 [M+H]⁺; and

¹H NMR (400 MHz, CDCl₃): δ 7.99 (s, 1H), 7.80 (d, J=4.12 Hz, 2H), 7.43-7.41 (m, 2H), 7.18-7.17 (m, 3H), 5.85-5.87 (m, 0.5H), 5.39-5.42 (m, 0.5H), 5.19 (d, J=5.44 Hz, 1H), 4.93-5.01 (m, 2H), 3.49-3.73 (m, 4H), 3.35-3.42 (m, 2H), 3.02 (s, 2H), 2.95 (s, 2H), 1.82-2.38 (m, 8H), 1.58-1.69 (m, 8H), 1.1-1.28 (m, 18H), 0.89-0.93 (m, 2H), 0.01 (s, 9H).

Step 4) The Preparation of Compound 24-4

A solution of compound 24-3 (200 mg, 0.23 mmol) in a solution of HCl in EtOAc (8 mL, 4 M) was stirred at rt overnight and concentrated in vacuo. The residue was washed with EtOAc (10 mL) to give the title compound 24-4 as a white solid (158 mg, 100%). The compound was characterized by the following spectroscopic data:

MS-ESI: m/z 544.3 [M+H]⁺; and

¹H NMR (400 MHz, D₂O): δ 7.71-7.69 (m, 3H), 7.55-7.38 (m, 3H), 7.19-7.25 (m, 2H), 4.93-5.01 (m, 2H), 3.49-3.43 (m, 4H), 2.81-2.98 (m, 4H), 2.01-2.70 (m, 8H), 1.48-1.61 (m, 8H).

Step 5) The Preparation of Compound 24-5

To a solution of compound 24-4 (202 mg, 0.3 mmol), compound 1-7-2 (158 mg, 0.907 mmol) and EDCI (201 mg, 1.05 mmol) in DCM (30.0 mL) in an ice bath was added DIPEA (0.42 mL) dropwise under N₂. At the end of the addition, the mixture was stirred at rt overnight, quenched with NaHCO₃ saturated solution, and extracted with EtOAc (10 mL×3). The combined organic phases were dried over anhydrous Na₂SO₄ and concentrated in vacuo. The residue was purified by silica gel column chromatography (DCM/MeOH (v/v)=60/1) to give the title compound 24-5 as a white solid (100 mg, HPLC: 93.3%). The compound was characterized by the following spectroscopic data:

MS-ESI: m/z 857.5 [M+H]¹; and

¹H NMR (400 MHz, D₂O): δ 7.72-7.82 (m, 1H), 7.35-7.42 (m, 3H), 7.31-7.33 (m, 1H), 7.14-7.22 (m, 3H), 5.71-5.76 (m, 2H), 5.21-5.23 (m, 2H), 3.83-3.87 (m, 2H), 3.69 (s, 6H), 3.65-3.68 (m, 2H), 3.01 (s, 2H), 2.92 (s, 2H), 2.31-2.42 (m, 2H), 2.14-2.21 (m, 2H), 2.06-2.11 (m, 2H), 1.97-2.04 (m, 2H), 1.58-1.67 (m, 10H), 0.83-0.96 (m, 12H).

Example 25

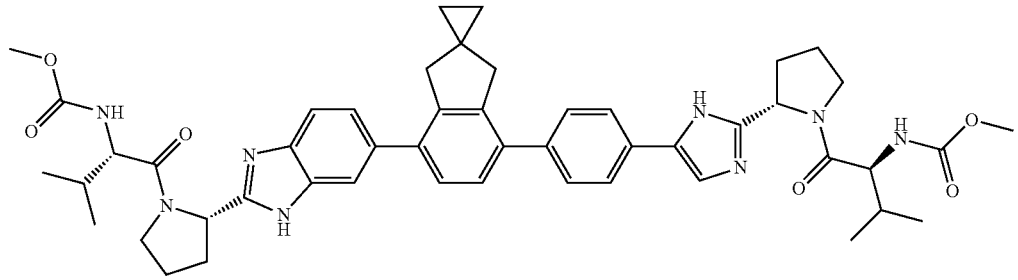

Synthetic Routes

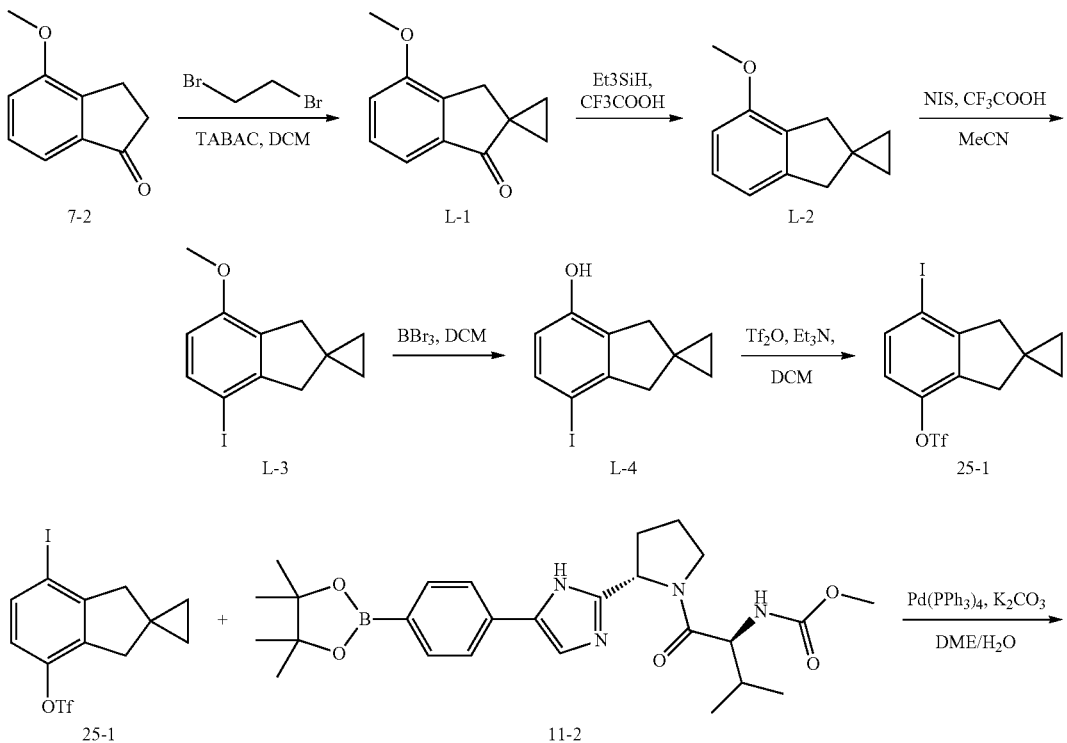

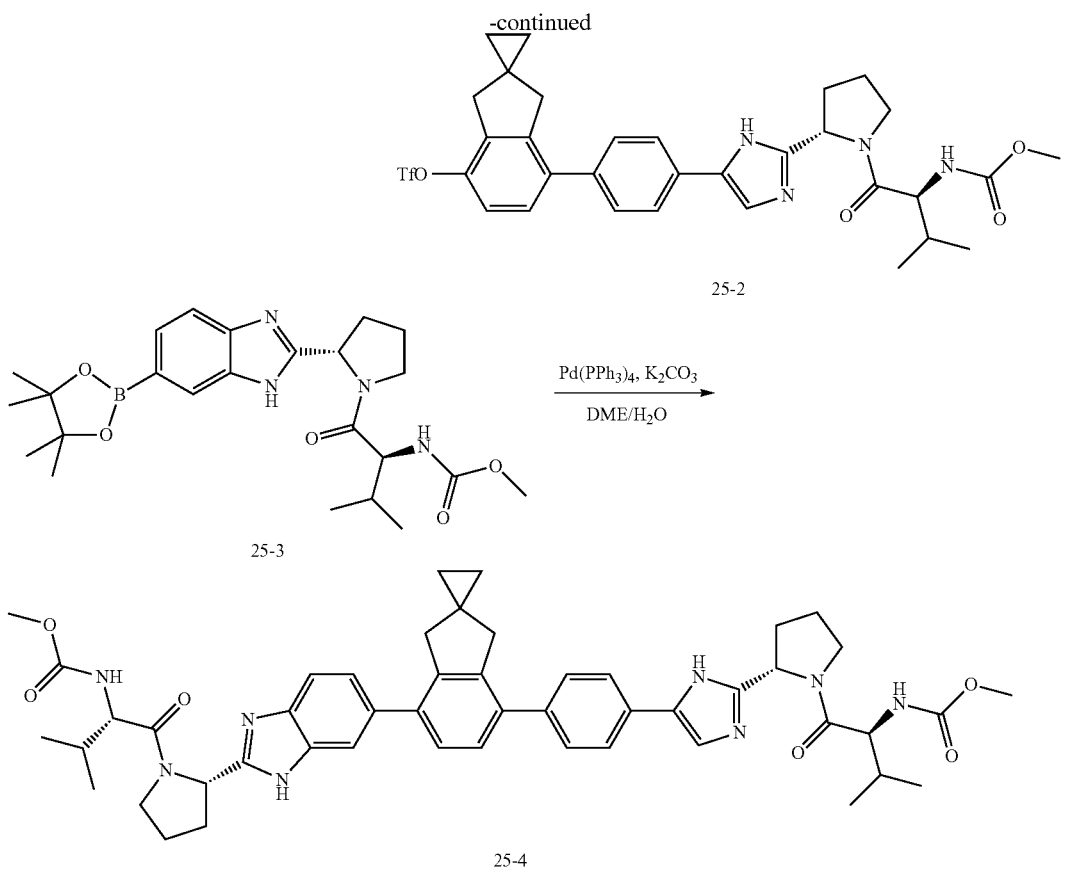

Compounds disclosed herein can be prepared by an analogous procedure to that described in Example 11.

Compound 25-1 was characterized by the following spectroscopic data:
$^1$H NMR (400 MHz, CDCl$_3$): δ 7.56-7.57 (m, 1H), 6.78-6.79 (m, 1H), 3.01-3.07 (m, 2H), 2.48-2.64 (m, 2H), 1.49-1.55 (m, 2H), 1.23-1.29 (m, 2H).

Compound 25-2 was characterized by the following spectroscopic data:
$^1$H NMR (400 MHz, CDCl$_3$): δ 7.84-7.82 (m, 1H), 7.69-7.66 (m, 2H), 7.57-7.55 (m, 1H), 7.48-7.44 (m, 2H), 7.40-7.36 (m, 1H), 5.41-5.39 (m, 1H), 5.29-5.27 (m, 1H), 4.34-4.30 (m, 1H), 3.75-3.70 (m, 1H), 3.70 (s, 3H), 3.64-3.62 (m, 1H), 3.20-3.01 (m, 1H), 3.01-3.08 (m, 2H), 2.45-2.61 (m, 2H), 2.25-2.20 (m, 1H), 2.20-2.13 (m, 2H), 1.96-1.94 (m, 1H), 1.50-1.54 (m, 2H), 1.21-1.33 (m, 2H), 0.88-0.86 (m, 6H).

Compound 25-3 was characterized by the following spectroscopic data:
MS-ESI: m/z 471.2 [M+H]$^+$; and
$^1$H NMR (400 MHz, CDCl$_3$): δ 7.87-7.80 (m, 1H), 7.71-7.66 (m, 2H), 5.47-5.42 (m, 2H), 4.34-4.30 (m, 1H), 3.86-3.84 (m, 1H), 3.70 (s, 3H), 3.64-3.62 (m, 1H), 3.04-2.98 (m, 1H), 2.25-2.20 (m, 1H), 2.20-2.13 (m, 2H), 1.96-1.94 (m, 1H), 1.35 (s, 12H), 0.88-0.84 (m, 6H).

Compound 25-4 (HPLC: 95.6%) was characterized by the following spectroscopic data:
MS-ESI: m/z 855.4 [M+H]$^+$; and
$^1$H NMR (400 MHz, CDCl$_3$): δ 7.70-7.68 (m, 2H), 7.52-7.56 (m, 2H), 7.42-7.48 (m, 2H), 7.28-7.34 (m, 2H), 7.25-7.26 (m, 2H), 5.26-5.29 (m, 1H), 5.16-5.19 (m, 1H), 4.21-4.26 (m, 2H), 3.94-4.08 (m, 2H), 3.88-3.93 (m, 2H), 3.65 (s, 6H), 3.01-3.08 (m, 2H), 2.45-2.61 (m, 2H), 2.04-2.34 (m, 10H), 1.51-1.55 (m, 2H), 1.20-1.32 (m, 2H), 0.86-0.93 (m, 12H).

Example 26

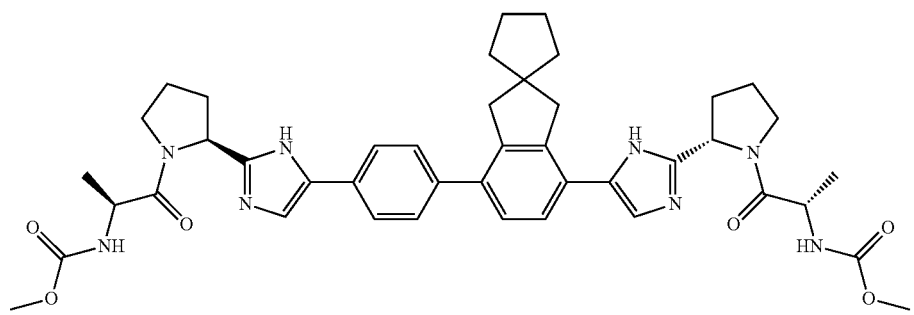

Synthetic Routes

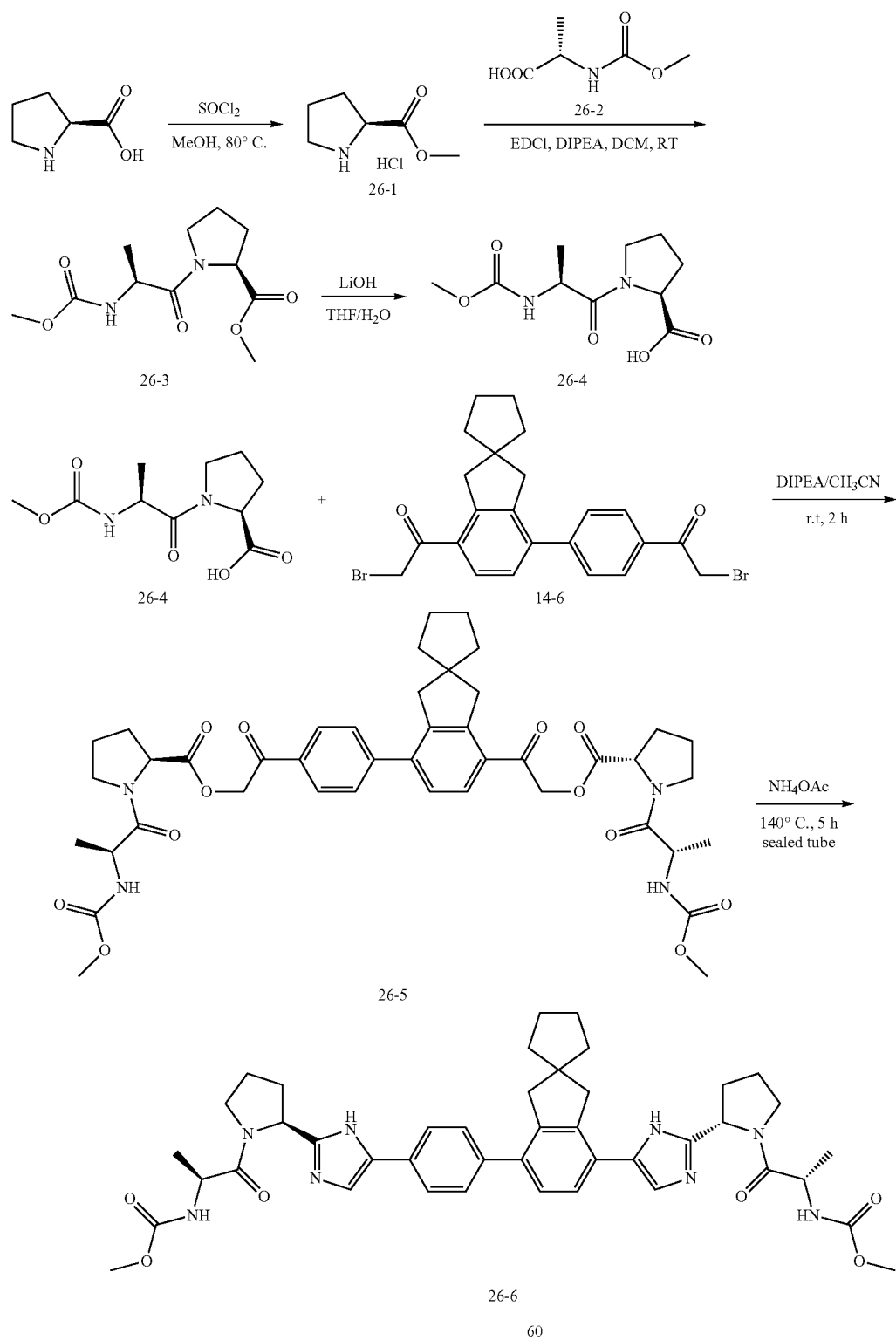

Step 1) The Preparation of Compound 26-1

To a solution of L-proline (10 g, 86.9 mmol) in MeOH (100 mL) was added SOCl$_2$ (12.6 mL, 174 mmol) at 0° C. The mixture was stirred at 80° C. for 1.5 hours and concentrated in vacuo to afford the title compound 26-1 as a white solid (14.3 g, 100%). The compound was characterized by the following spectroscopic data:

MS-ESI: m/z 130.2 [M+H]$^+$; and $^1$H NMR (400 MHz, CD$_3$OD): δ 4.45 (m, 1H), 3.85 (s, 1H), 3.40 (m, 2H), 2.42 (m, 1H), 2.12 (m, 1H), 2.07 (m, 1H).

Step 2) The Preparation of Compound 26-3

To a mixture of compound 26-1 (1 g, 6 mmol), compound 26-2 (1.5 g, 10 mmol) and EDCI (2.2 g, 11.5 mmol) in DCM (50.0 mL) at 0° C. was added DIPEA (2.55 mL, 15.5 mmol) dropwise under $N_2$. At the end of the addition, the mixture was stirred at rt overnight, washed with water (30 mL×2), dried over anhydrous $Na_2SO_4$ and concentrated in vacuo. The residue was purified by silica gel column chromatography (hexane/EtOAc (v/v)=3/1) to give the title compound 26-3 as water white viscous liquid (0.98 g, 63%). The compound was characterized by the following spectroscopic data:

MS-ESI: m/z 259.12 [M+H]$^+$; and $^1$H NMR (400 MHz, CDCl$_3$): δ 5.40 (d, J=8.96 Hz, 1H), 4.53 (m, 1H), 4.31 (m, 1H), 3.81 (m, 1H), 3.78 (s, 3H), 3.74 (s, 3H), 2.24 (m, 1H), 2.23 (m, 1H), 2.22 (m, 1H), 2.07 (m, 1H), 2.04 (m, 3H).

Step 3) The Preparation of Compound 26-4

To a solution of compound 26-3 (0.98 g, 3.8 mmol) in mixed solvents (THF/water (v/v)=3/2, 25 mL) was added LiOH.H$_2$O (0.46 g, 11 mmol). The mixture was stirred at rt for 12 hours, adjusted to pH 2-3 and extracted with EtOAc (30 mL×3). The combined organic phases were dried over anhydrous $Na_2SO_4$ and concentrated in vacuo to give the title compound 26-4 as water white viscous liquid (0.93 g, 100%). The compound was characterized by the following spectroscopic data:

MS-ESI: m/z 245.11 [M+H]$^+$; and $^1$H NMR (400 MHz, CDCl$_3$): δ 5.40 (d, J=8.96 Hz, 1H), 4.53 (m, 1H), 4.31 (m, 1H), 3.81 (m, 1H), 3.78 (s, 3H), 2.24 (m, 1H), 2.23 (m, 1H), 2.22 (m, 1H), 2.07 (m, 1H), 2.04 (m, 3H).

Step 4) The Preparation of Compound 26-5

To a mixture of compound 26-4 (0.93 g, 3.8 mmol) and compound 14-6 (0.49 g, 1 mmol) in acetonitrile (20 mL) was added DIPEA (5.1 mL, 31 mmol) dropwise at low temperature under $N_2$. The mixture was stirred at rt for 2 hours and concentrated in vacuo. To the residue was added water (10 mL), and the mixture was extracted with EtOAc (30 mL×3). The combined organic phases were dried over anhydrous $Na_2SO_4$ and concentrated in vacuo. The residue was purified by silica gel column chromatography (hexane/EtOAc (v/v)=1/3) to give the title compound 26-5 as a pale yellow solid (1.2 g, 38%). The compound was characterized by the following spectroscopic data:

MS-ESI: m/z 817.12 [M+H]$^+$; and $^1$H NMR (400 MHz, CDCl$_3$): δ 7.97 (d, J=8.4 Hz, 2H), 7.65 (d, J=8.12 Hz, 1H), 7.53 (d, J=8.4 Hz, 2H), 7.29 (d, J=8.12 Hz, 1H), 5.59-5.16 (m, 4H), 5.54 (m, 2H), 4.72 (m, 2H), 5.53 (m, 2H), 3.71 (m, 4H), 3.68 (s, 3H), 3.67 (s, 3H), 3.23 (m, 2H), 2.85 (s, 2H), 2.38 (m, 4H), 2.35 (m, 2H), 2.09 (m, 2H), 1.55 (m, 4H), 1.37 (m, 6H), 1.26 (t, 3H).

Step 5) The Preparation of Compound 26-6

A mixture of compound 26-5 (0.3 g, 0.37 mmol) and ammonium acetate (1.2 g, 15.5 mmol) in xylene (10 mL) in a sealed tube was stirred at 140° C. for 5 hours, cooled to rt, and water (10 mL) was added. The mixture was extracted with EtOAc (30 mL×3). The combined organic phases were dried over anhydrous $Na_2SO_4$ and concentrated in vacuo. The residue was purified by silica gel column chromatography (hexane/EtOAc (v/v)=1/5) to give the title compound 26-6 as a pale yellow solid (0.24 g, 65%). The compound was characterized by the following spectroscopic data:

MS-ESI: m/z 777.4 [M+H]$^+$; and $^1$H NMR (400 MHz, CDCl$_3$): δ 7.97 (d, J=8.4 Hz, 2H), 7.65 (d, 1H, J=8.12 Hz), 7.53 (d, J=8.4 Hz, 2H), 7.29 (d, J=8.12 Hz, 1H), 5.54 (m, 2H), 4.72 (m, 2H), 5.53 (m, 2H), 3.71 (m, 4H), 3.68 (s, 3H), 3.67 (s, 3H), 3.23 (m, 2H), 2.85 (s, 2H), 2.38 (m, 4H), 2.35 (m, 2H), 2.09 (m, 2H), 1.55 (m, 4H), 1.37 (m, 6H), 1.26 (t, 3H).

Example 27

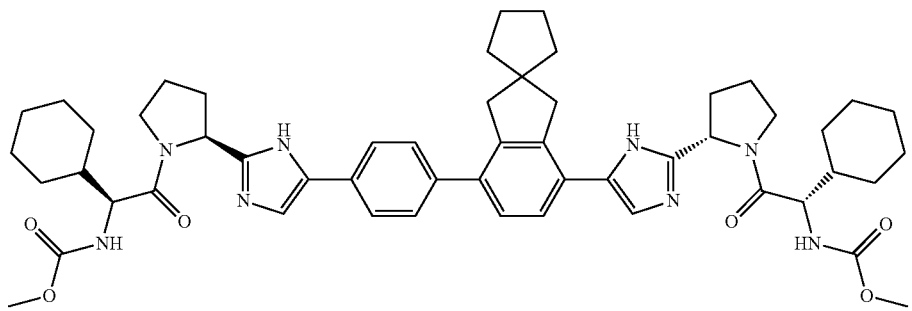

Synthetic Routes

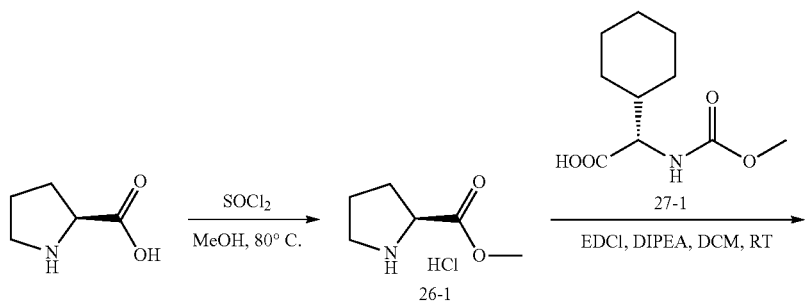

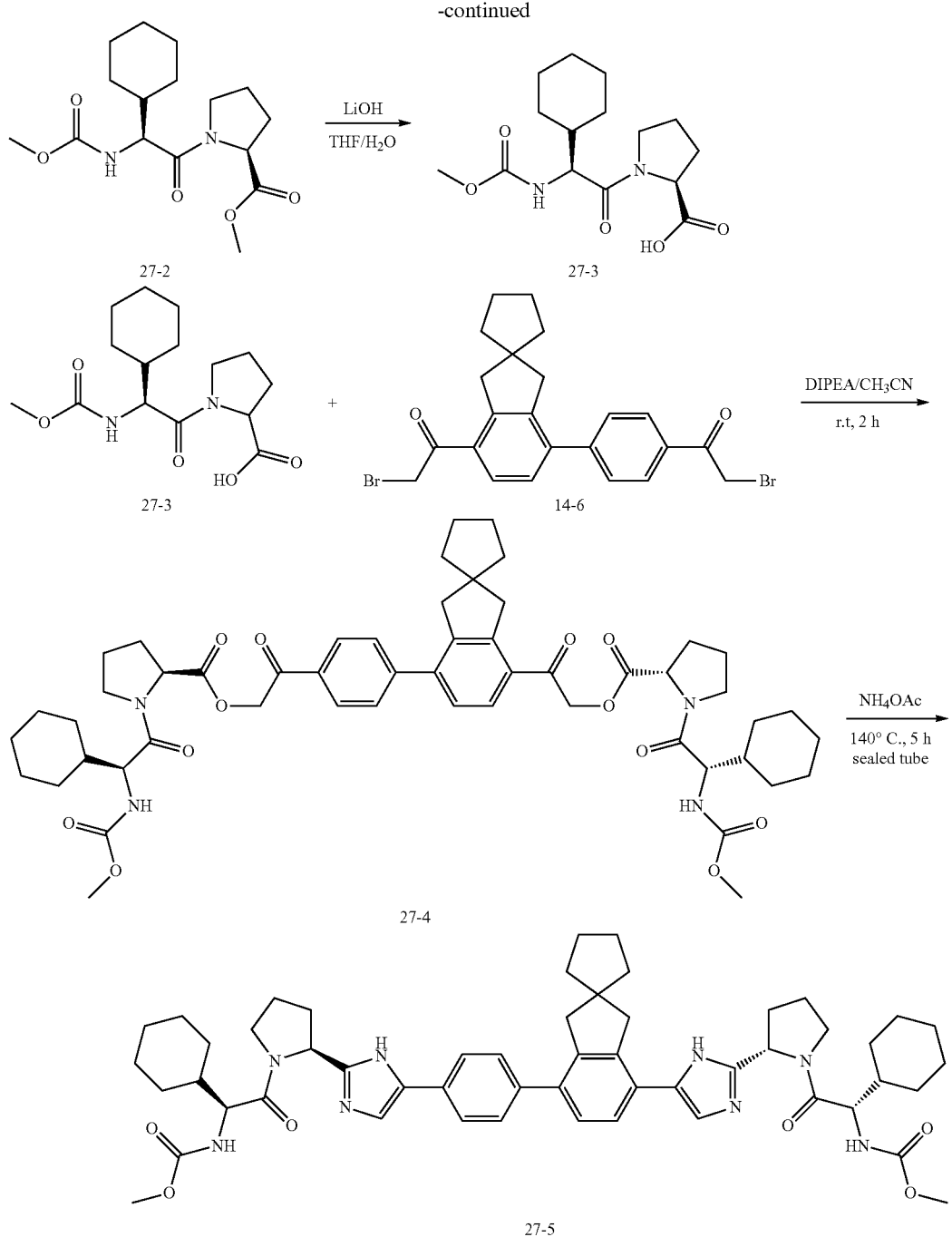

Step 1) The Preparation of Compound 27-2

To a mixture of compound 26-1 (1 g, 6 mmol), compound 27-1 (1.3 g, 6 mmol) and EDCI (2.2 g, 11.5 mmol) in DCM (50.0 mL) was added DIPEA (2.5 mL, 15.5 mmol) dropwise at 0° C. under $N_2$. At the end of the addition, the mixture was stirred at rt overnight, washed with water (30 mL×2), dried over anhydrous $Na_2SO_4$ and concentrated in vacuo. The residue was purified by silica gel column chromatography (hexane/EtOAc (v/v)=2/1) to give the title compound 27-2 as water white viscous liquid (0.95 g, 48%). The compound was characterized by the following spectroscopic data:

MS-ESI: m/z 328.2 [M+H]+; and $^1$H NMR (400 MHz, CDCl$_3$): δ 5.40 (d, J=8.96 Hz, 1H), 4.53 (m, 1H), 4.31 (m, 1H), 3.81 (m, 1H), 3.78 (s, 3H), 3.74 (s, 3H), 2.24 (m, 1H), 2.23 (m, 1H), 2.22 (m, 1H), 2.07 (m, 1H), 2.04 (m, 1H), 1.98 (m, 4H), 1.87 (m, 4H), 1.56 (m, 2H).

Step 2) The Preparation of Compound 27-3

To a solution of compound 27-2 (0.95 g, 2.9 mmol) in mixed solvents (THF/water (v/v)=3/2, 25 mL) was added LiOH.H$_2$O (0.45 g, 11 mmol). The mixture was stirred at rt for 12 hours, adjusted to pH 2-3 and extracted with EtOAc (30 mL×3). The combined organic phases were dried over anhydrous Na$_2$SO$_4$ and concentrated in vacuo to give the title compound 27-3 as water white viscous liquid (0.87 g, 96%). The compound was characterized by the following spectroscopic data:

MS-ESI: m/z 313.2 [M+H]$^+$; and $^1$H NMR (400 MHz, CDCl$_3$): δ 5.40 (d, J=8.96 Hz, 1H), 4.53 (m, 1H), 4.31 (m, 1H), 3.81 (m, 1H), 3.78 (s, 3H), 2.24 (m, 1H), 2.23 (m, 1H), 2.22 (m, 1H), 2.07 (m, 1H), 2.04 (m, H), 1.98 (m, 4H), 1.87 (m, 4H), 1.56 (m, 2H).

Step 3) The Preparation of Compound 27-4

To a mixture of compound 27-3 (0.87 g, 2.79 mmol) and compound 14-6 (0.44 g, 0.9 mmol) in acetonitrile (20 mL) was added DIPEA (5.2 mL, 31 mmol) dropwise at low temperature under N$_2$. The mixture was stirred at rt for 2 hours and concentrated in vacuo. To the residue was added water (10 mL), and the mixture was extracted with EtOAc (30 mL×3). The combined organic phases were dried over anhydrous Na$_2$SO$_4$ and concentrated in vacuo. The residue was purified by silica gel column chromatography (hexane/EtOAc (v/v)=1/2) to give the title compound 27-4 as a pale yellow solid (0.79 g, 29.7%). The compound was characterized by the following spectroscopic data:

MS-ESI: m/z 953.5 [M+H]$^+$; and $^1$H NMR (400 MHz, CDCl$_3$): δ 7.97 (d, J=8.4 Hz, 2H), 7.65 (d, J=8.12 Hz, 1H), 7.53 (d, J=8.4 Hz, 2H), 7.29 (d, J=8.12 Hz, 1H), 5.59-5.16 (m, 4H), 5.54 (m, 2H), 4.72 (m, 2H), 5.53 (m, 2H), 3.71 (m, 4H), 3.68 (s, 3H), 3.67 (s, 3H), 3.23 (m, 2H), 2.85 (s, 2H), 2.38 (m, 4H), 2.35 (m, 2H), 2.09 (m, 2H), 2.04 (m, 1H), 1.98 (m, 4H), 1.87 (m, 4H), 1.56 (m, 2H), 1.55 (m, 4H), 1.37 (m, 3H), 1.26 (t, 3H).

Step 4) The Preparation of Compound 27-5

A mixture of compound 27-4 (0.3 g, 0.31 mmol) and ammonium acetate (1.2 g, 15.6 mmol) in xylene (10 mL) in a sealed tube was stirred at 140° C. for 5 hours, cooled to rt, and water (10 mL) was added. The mixture was extracted with EtOAc (30 mL×3). The combined organic phases were dried over anhydrous Na$_2$SO$_4$ and concentrated in vacuo. The residue was purified by silica gel column chromatography (hexane/EtOAc (v/v)=1/8) to give the title compound 27-5 as a pale yellow solid (0.22 g, 77.7%). The compound was characterized by the following spectroscopic data:

MS-ESI: m/z 913.4 [M+H]$^+$; and $^1$H NMR (400 MHz, CDCl$_3$): δ 7.97 (d, J=8.4 Hz, 2H), 7.65 (d, J=8.12 Hz, 1H), 7.53 (d, J=8.4 Hz, 2H), 7.29 (d, J=8.12 Hz, 1H), 5.54 (m, 2H), 4.72 (m, 2H), 5.53 (m, 2H), 3.71 (m, 4H), 3.68 (s, 3H), 3.67 (s, 3H), 3.23 (m, 2H), 2.85 (s, 2H), 2.38 (m, 4H), 2.35 (m, 2H), 2.09 (m, 2H), 2.04 (m, H), 1.98 (m, 4H), 1.87 (m, 4H), 1.56 (m, 2H), 1.55 (m, 4H), 1.37 (m, 3H), 1.26 (t, 3H).

Example 28

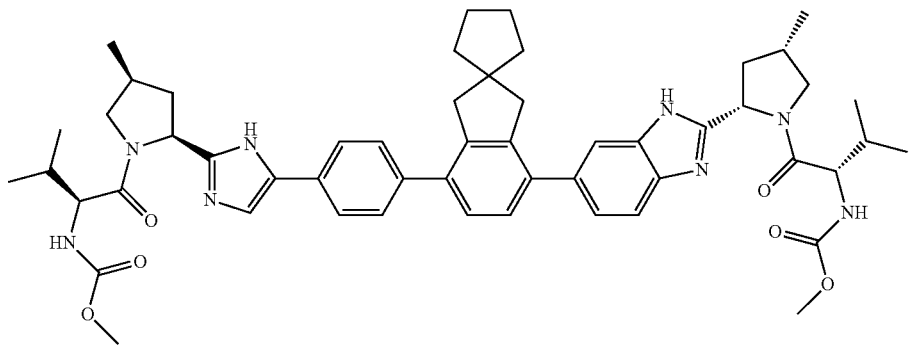 [SMILES: COC(=O)N[C@H](C(=O)N1C[C@@H](C)C[C@H]1c1ncc(-c2ccc(-c3ccc(-c4ccc5nc([C@@H]6C[C@H](C)CN6C(=O)[C@@H](NC(=O)OC)C(C)C)[nH]c5c4)c4c3CC3(CCCC3)C4)cc2)[nH]1)C(C)C]

Synthetic Routes

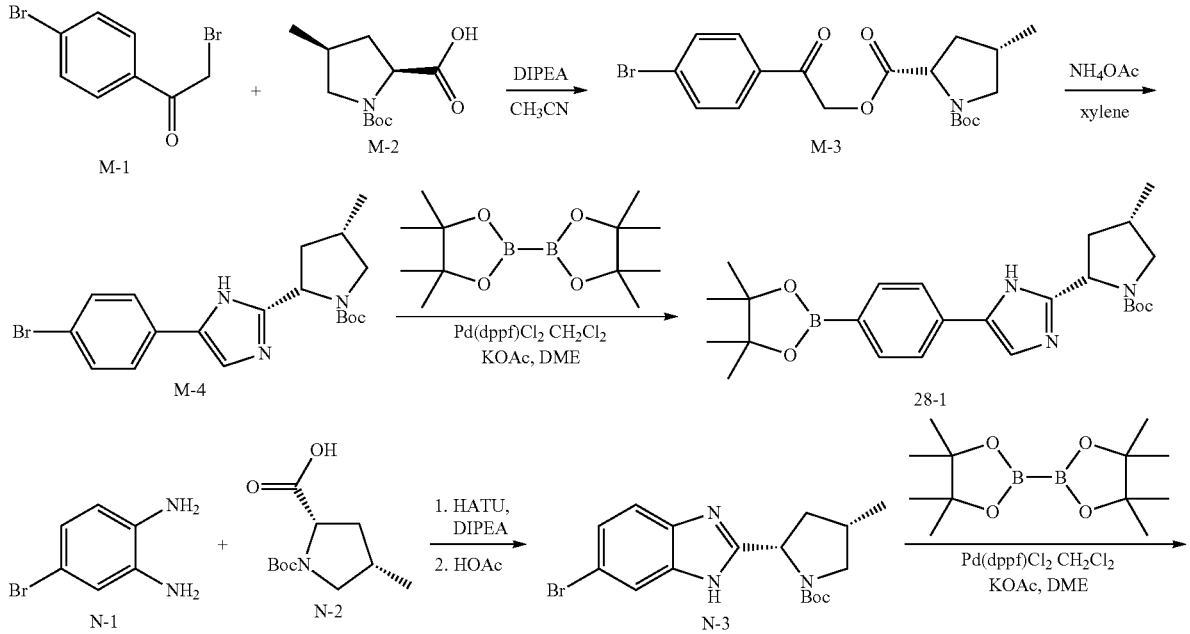

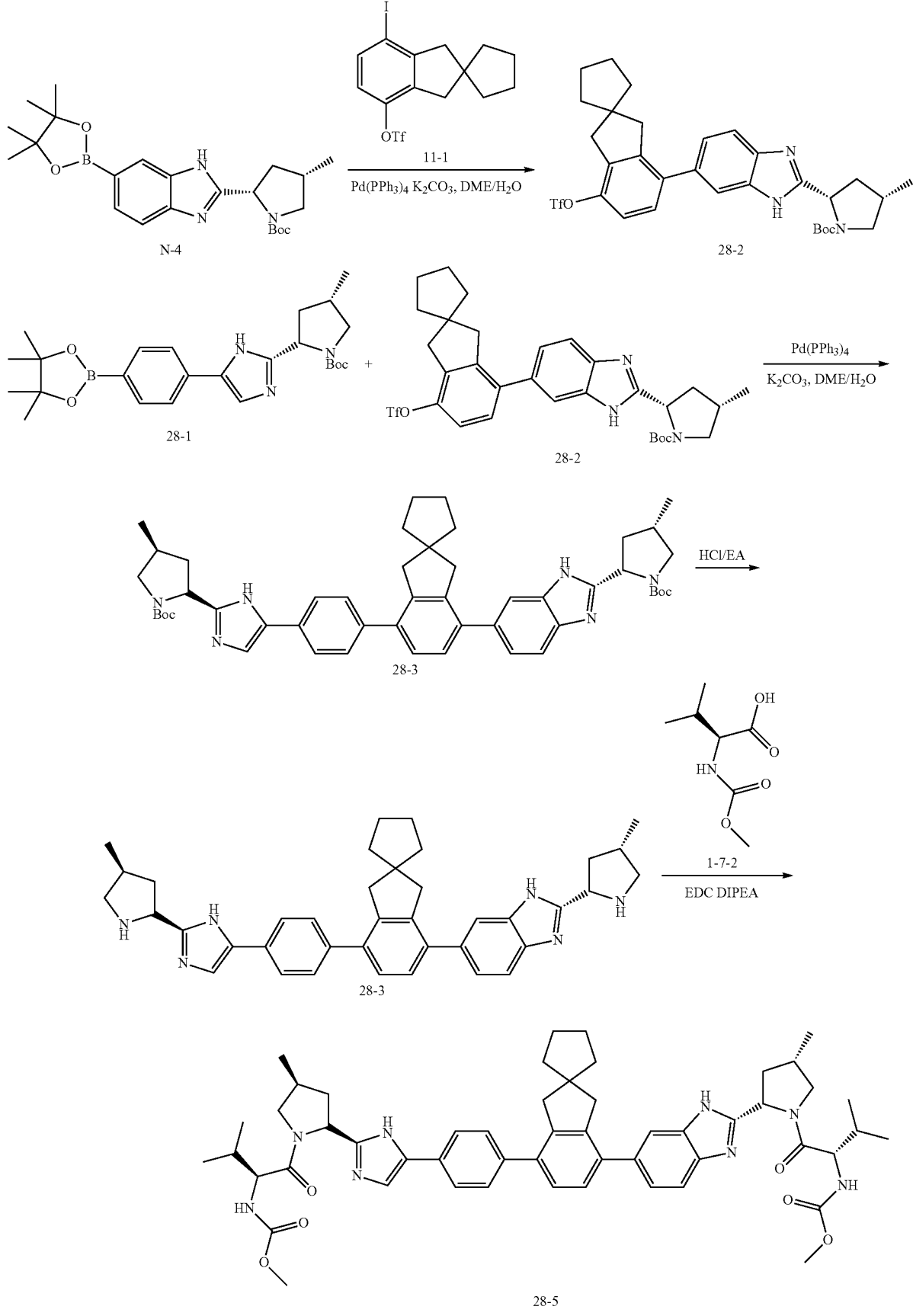

Step 1) The Preparation of Compound 28-1

To a solution of compound M-1 (2 g, 7.2 mmol) and M-2 (1.5 g, 6.55 mmol) in MeCN (50 mL) was added DIPEA (1.3 mL) at 0° C. At the end of the addition, the mixture was stirred at rt and the reaction was monitored by TLC. After the reaction was completed, the mixture was quenched with ice water (10 mL) and extracted with EtOAc (100 mL×3). The combined organic phases were dried over anhydrous $Na_2SO_4$ and concentrated in vacuo. The residue was purified by silica gel column chromatography (hexane/EtOAc (v/v)=4/1) to give compound M-3 (2.55 g, 94%). The compound was characterized by the following spectroscopic data:

$^1$H NMR (400 MHz, $CDCl_3$): δ 7.78 (m, 2H), 7.65 (m, 2H), 5.54-5.15 (m, 2H), 4.39 (m, 1H), 3.76 (m, 1H), 3.03 (m, 1H), 2.53 (m, 1H), 2.27 (m, 1H), 1.84 (m, 1H), 1.43 (m, 9H), 1.24 (m, 1H), 1.09 (m, 3H).

A mixture of compound M-3 (2.55 g, 6.2 mmol) and ammonium acetate (4.6 g, 59.7 mmol) in xylene (100 mL) in a sealed tube was stirred at 130° C. for 5 hours, cooled to rt and washed with water. The organic layers were dried over anhydrous $Na_2SO_4$ and concentrated in vacuo. The residue was purified by silica gel column chromatography (hexane/EtOAc (v/v)=4/1) to give compound M-4 (1.63 g, 64.7%). The compound was characterized by the following spectroscopic data:

$^1$H NMR (400 MHz, $CDCl_3$): δ 7.78 (m, 2H), 7.65 (m, 2H), 4.39 (m, 1H), 3.76 (m, 1H), 3.03 (m, 1H), 2.53 (m, 1H), 2.27 (m, 1H), 1.84 (m, 1H), 1.43 (m, 9H), 1.24 (m, 1H), 1.09 (m, 3H).

To a mixture of compound M-4 (1.63 g, 4 mmol), bis(pinacolato)diboron (1.12 g, 4.4 mmol), $Pd(dppf)Cl_2.CH_2Cl_2$ (71 mg, 0.09 mmol) and KOAc (0.98 g, 10 mmol) was added DME (20 mL) under $N_2$ via syringe. The resulting mixture was stirred at 90° C. for 5 hours in an oil bath and concentrated in vacuo. To the residue was added a small amount of water, and the mixture was extracted with EtOAc (30 mL×3). The combined organic phases were dried over anhydrous $Na_2SO_4$ and concentrated in vacuo. The residue was purified by silica gel column chromatography (hexane/EtOAc (v/v)=2/1) to give the title compound 28-1 as a pale yellow solid (1.77 g, 97.6%). The compound was characterized by the following spectroscopic data:

$^1$H NMR (400 MHz, $CDCl_3$): δ 7.78 (m, 2H), 7.65 (m, 2H), 4.39 (m, 1H), 3.76 (m, 1H), 3.03 (m, 1H), 2.53 (m, 1H), 2.27 (m, 1H), 1.84 (m, 1H), 1.43 (m, 9H), 1.24 (m, 1H), 1.09 (m, 3H).

Step 2) The Preparation of Compound 28-2

To a mixture of compound N-2 (2 g, 8.7 mmol) and HATU (3.5 g, 9.2 mmol) in THF (30 mL) was added DIPEA (6 mL) at 0° C. under $N_2$. The mixture was stirred at rt for 0.5 hour, and compound N-1 (1.8 g, 9.6 mmol) was added. The mixture was stirred at rt for another 2 hours and quenched with water (10 mL). THF was removed in vacuo, and the aqueous layer was extracted with EtOAc (50 mL×3). The combined organic phases were washed with brine and concentrated in vacuo. To the above residue was added acetic acid (35 mL) and the mixture was stirred at 40° C. overnight. The mixture was then neutralized with $NaHCO_3$ saturated solution and extracted with EtOAc (50 mL×3). The combined organic phases were dried over anhydrous $Na_2SO_4$ and concentrated in vacuo. The residue was purified by silica gel column chromatography (hexane/EtOAc (v/v)=4/1) to give compound N-3 as a reddish brown solid (2.4 g, 72%). The compound was characterized by the following spectroscopic data:

$^1$H NMR (400 MHz, $CDCl_3$): δ 7.87 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 1H), 2.01-1.91 (m, 1H), 1.49 (s, 9H), 1.23 (d, 3H).

To a mixture of compound N-3 (2.4 g, 6.3 mmol), bis(pinacolato)diboron (1.8 g, 7 mmol), $Pd(dppf)Cl_2.CH_2Cl_2$ (0.1 g, 0.12 mmol) and KOAc (1.6 g, 16 mmol) was added DME (30 mL) under $N_2$ via syringe. The mixture was stirred at 90° C. in an oil bath for 3 hours and concentrated in vacuo. To the residue was added water (5 mL), and the mixture was extracted with EtOAc (50 mL×3). The combined organic phases were washed with brine, dried over anhydrous $Na_2SO_4$ and concentrated in vacuo. The residue was purified by silica gel column chromatography (hexane/EtOAc (v/v)=4/1) to give compound N-4 (2.1 g, 78%). The compound was characterized by the following spectroscopic data:

$^1$H NMR (400 MHz, $CDCl_3$): δ 7.87 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 1H), 2.01-1.91 (m, 1H), 1.49 (s, 9H), 1.23 (d, 3H).

To a mixture of compound 11-1 (54 mg, 0.12 mmol), compound N-4 (50 mg, 0.11 mmol), $Pd(PPh_3)_4$ (12.7 mg, 0.01 mmol) and potassium carbonate (46 mg, 0.33 mmol) was added DME (5 mL) under $N_2$ via syringe followed by pure water (1 mL). The mixture was stirred at 90° C. overnight and concentrated in vacuo. To the residue was added water (3 mL) and the mixture was extracted with EtOAc (20 mL×3). The combined organic phases were dried over anhydrous $Na_2SO_4$ and concentrated in vacuo. The residue was purified by silica gel column chromatography (hexane/EtOAc (v/v)=2/1) to give the title compound 28-2 as a yellow solid (32 mg, 46.9%). The compound was characterized by the following spectroscopic data:

$^1$H NMR (400 MHz, $CDCl_3$): δ 7.82 (s, 2H), 7.52 (s, 2H), 7.39 (d, J=8.24 Hz, 2H), 7.11 (d, J=8.24 Hz, 2H), 4.94 (m, H), 3.78 (m, H), 3.44 (m, 1H), 3.19 (m, 1H), 2.83 (s, 4H), 1.82 (m, 2H), 1.76 (m, 1H), 1.55 (m, 17H), 0.96 (d, 3H).

Step 3) The Preparation of Compound 28-3

To a solution of compound 28-2 (0.46 g, 0.74 mmol), compound 28-1 (0.32 g, 0.7 mmol) and potassium carbonate (0.3 g, 2.1 mmol) in mixed solvents of DME (10 mL) and water (1 mL) was added $Pd(PPh_3)_4$ (0.04 g, 0.03 mmol) under $N_2$. The mixture was stirred at 90° C. for 4 hours, cooled to rt and quenched with water (5 mL). The mixture was extracted with EtOAc (50 mL×3). The combined organic phases were washed with brine, dried over anhydrous $Na_2SO_4$ and concentrated in vacuo. The residue was purified by silica gel column chromatography (hexane/EtOAc (v/v)=1/4) to give the title compound 28-3 as a claybank solid (480 mg, 85%). The compound was characterized by the following spectroscopic data:

$^1$H NMR (400 MHz, $CDCl_3$): δ 13 (s, 1H), 8.33 (m, 2H), 8.07 (s, 1H), 7.92 (s, 1H), 7.65 (s, 1H), 7.48 (m, 2H), 7.35 (m, 1H), 7.25 (s, 2H), 5.0 (s, 1H), 4.63 (m, 2H), 3.44-3.12 (m, 4H), 2.83 (m, 4H), 1.97-1.72 (m, 4H), 1.56 (m, 10H), 1.50 (m, 8H), 1.38 (m, 18H), 0.96 (m, 6H).

Step 4) The Preparation of Compound 28-4

A solution of compound 28-3 (480 mg, 0.6 mmol) in a solution of HCl in EtOAc (10 mL, 4 M) was stirred at rt overnight and concentrated in vacuo. The residue was washed with EtOAc to give the title compound 28-4 as a white solid (260 mg, 58%), which was used for the next step without further purification. The compound was characterized by the following spectroscopic data:

$^1$H NMR (400 MHz, $CDCl_3$): δ 13 (s, 1H), 8.33 (m, 2H), 8.07 (s, 1H), 7.92 (s, 1H), 7.65 (s, 1H), 7.48 (m, 2H), 7.35 (m, 1H), 7.25 (s, 2H), 5.0 (s, 1H), 4.63 (m, 2H), 3.44-3.12 (m, 4H), 2.83 (m, 4H), 1.97-1.72 (m, 4H), 1.56 (m, 10H), 1.50 (m, 8H), 0.96 (m, 6H).

Step 5) The Preparation of Compound 28-5

To a solution of compound 28-4 (260 mg, 0.35 mmol), compound 1-7-2 (176 mg, 1 mmol) and EDCI (210 mg, 1.1 mmol) in DCM (10.0 mL) was added DIPEA (0.7 mL) dropwise at 0° C. At the end of the addition, the mixture was stirred at rt overnight, quenched with $NaHCO_3$ saturated solution and extracted with EtOAc (50 mL×3). The combined organic phases were washed with brine, dried over anhydrous Na₂SO₄ and concentrated in vacuo. The residue was purified by silica gel column chromatography (EtOAc) to give the title compound 28-5 as a white solid (280 mg, 87.8%). The compound was characterized by the following spectroscopic data:

$^1$H NMR (400 MHz, CDCl₃): δ 13 (s, 1H), 8.33 (m, 2H), 8.07 (s, 1H), 7.92 (s, 1H), 7.65 (s, 1H), 7.48 (m, 2H), 7.35 (m, 1H), 7.25 (s, 2H), 5.40 (d, 2H), 5.0 (s, 1H), 4.63 (m, 2H), 4.47 (m, 2H), 4.33 (m, 2H), 4.16 (m, 4H), 4.09 (m, 6H), 3.61 (d, 2H), 3.34 (d, 2H), 3.44-3.12 (m, 4H), 2.83 (m, 4H), 1.97-1.72 (m, 4H), 1.56 (m, 10H), 1.50 (m, 8H), 0.96 (m, 6H).

Example 29

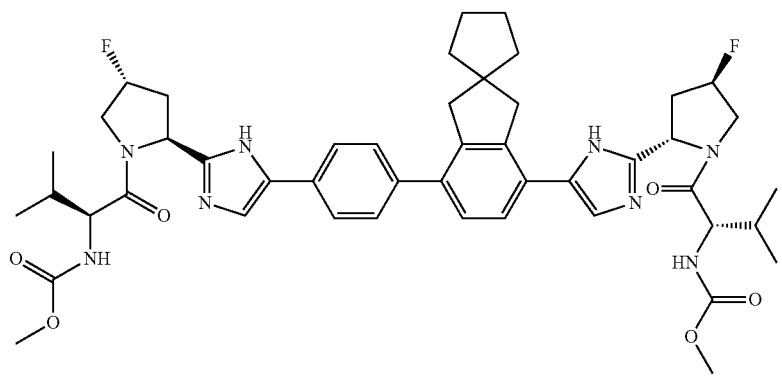 [SMILES: COC(=O)N[C@H](C(=O)N1C[C@H](F)C[C@H]1c1ncc(-c2ccc(-c3ccc(-c4cnc([C@@H]5C[C@@H](F)CN5C(=O)[C@@H](NC(=O)OC)C(C)C)[nH]4)c4c3CC3(CCCC3)C4)cc2)[nH]1)C(C)C]

Synthetic Routes

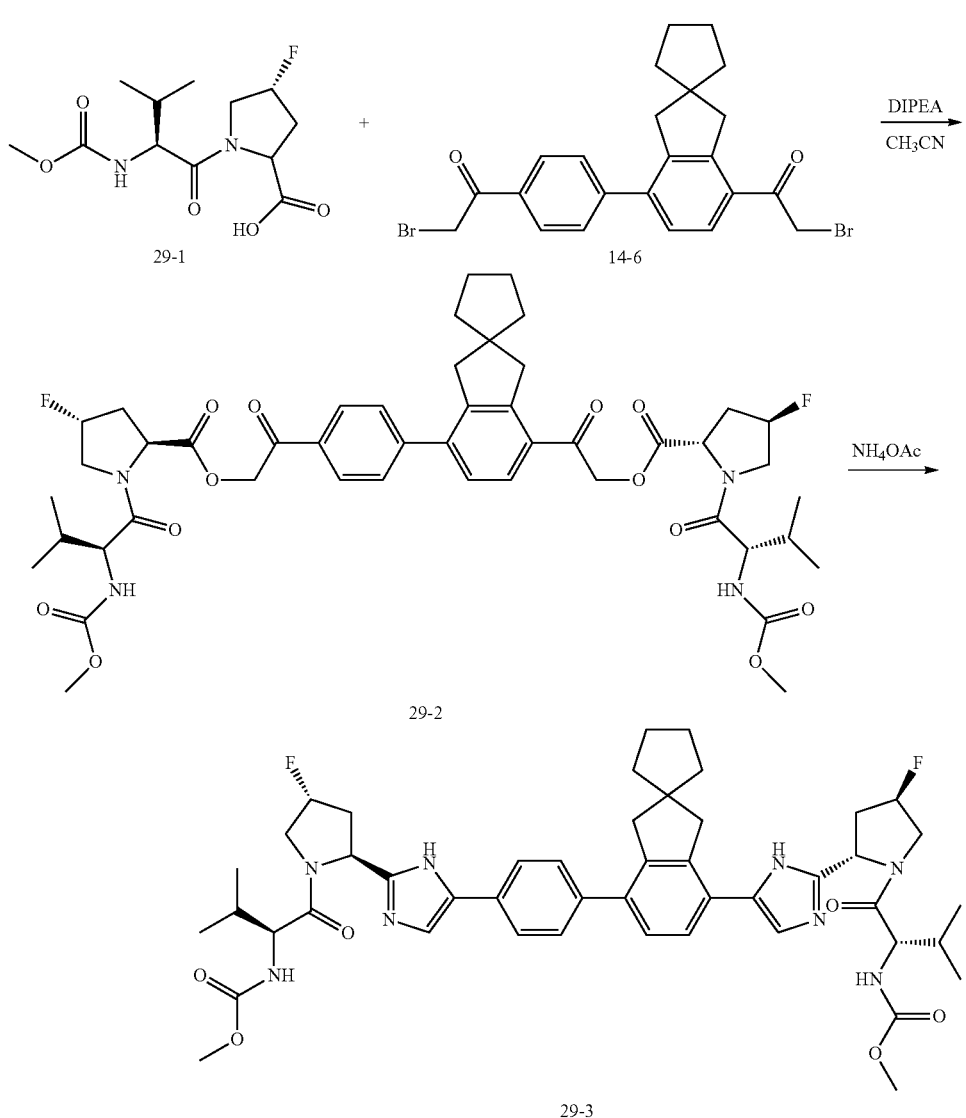

Step 1) the Preparation of Compound 29-1

The title compound 29-1 was prepared by an analogous procedure to that described for compound 18-8 (Example 18). The compound was characterized by the following spectroscopic data:

MS-ESI: m/z 291 [M+H]$^+$; and $^1$H NMR (400 MHz, CD$_3$Cl): δ 5.38 (m, 2H), 4.63 (m, 1H), 4.29 (m, 1H), 4.20 (m, 1H), 3.85 (m, 1H), 3.73 (m, 3H), 2.67 (m, 1H), 2.17 (m, 2H), 1.02 (m, 3H), 0.94 (m, 3H).

Step 2) The Preparation of Compound 29-2

To a solution of compound 29-1 (0.2 g, 1.0 mmol) and compound 14-6 (0.233 g, 0.47 mmol) in MeCN (10 mL) at 0° C. was added DIPEA (0.2 mL, 1.2 mmol). The mixture was stirred at rt overnight and concentrated in vacuo. To the residue was added water (10 mL), and the mixture was extracted with EtOAc (50 mL×3). The combined organic phases were dried over anhydrous Na$_2$SO$_4$ and concentrated in vacuo. The residue was purified by silica gel column chromatography (EtOAc) to give the title compound 29-2 (0.29 g, 67.9%). The compound was characterized by the following spectroscopic data:

MS-ESI: m/z 909.1 [M+H]$^+$; and $^1$H NMR (400 MHz, CD$_3$Cl): δ 7.96 (d, J=8.24 Hz, 2H), 7.66 (d, J=8.12 Hz, 1H), 7.54 (d, J=8.28 Hz, 2H), 7.27 (d, J=8.12 Hz, 1H), 5.62-5.21 (m, 4H), 5.44 (m, 2H), 4.84 (m, 2H), 4.33 (m, 2H), 4.31 (m, 2H), 3.72 (m, 1H), 3.68 (s, 3H), 3.65 (s, 3H), 3.22 (s, 2H), 2.85 (m, 4H), 2.55 (m, 2H), 1.65 (m, 3H), 1.56 (m, 4H), 1.25 (m, 9H), 1.02 (m, 6H).

Step 3) The Preparation of Compound 29-3

A mixture of compound 29-2 (0.29 g, 0.32 mmol) and ammonium acetate (0.25 g, 3.2 mmol) in xylene (15 mL) in a sealed tube was stirred at 130° C. overnight. The mixture was diluted with EtOAc (50 mL) and washed with water (10 mL×3). The combined organic phases were dried over anhydrous Na$_2$SO$_4$ and concentrated in vacuo. The residue was purified by silica gel column chromatography (hexane/EtOAc (v/v)=1/10) to give the title compound 29-3 as an offwhite solid (0.155 g, 56.0%). The compound was characterized by the following spectroscopic data:

MS-ESI: m/z 870 [M+H]$^+$; and $^1$H NMR (400 MHz, CD$_3$Cl): δ 7.96 (d, J=8.24 Hz, 2H), 7.66 (d, J=8.12 Hz, 1H), 7.54 (d, J=8.28 Hz, 2H), 7.27 (d, J=8.12 Hz, 1H), 5.44 (m, 2H), 4.84 (m, 2H), 4.33 (m, 2H), 4.31 (m, 2H), 3.72 (m, 1H), 3.68 (s, 3H), 3.65 (s, 3H), 3.22 (s, 2H), 2.85 (m, 4H), 2.55 (m, 2H), 1.65 (m, 3H), 1.56 (m, 4H), 1.25 (m, 9H), 1.02 (m, 6H).

Example 30

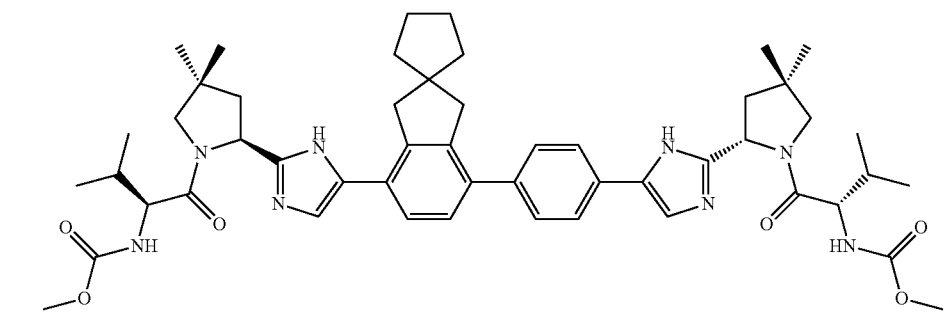

Synthetic Routes

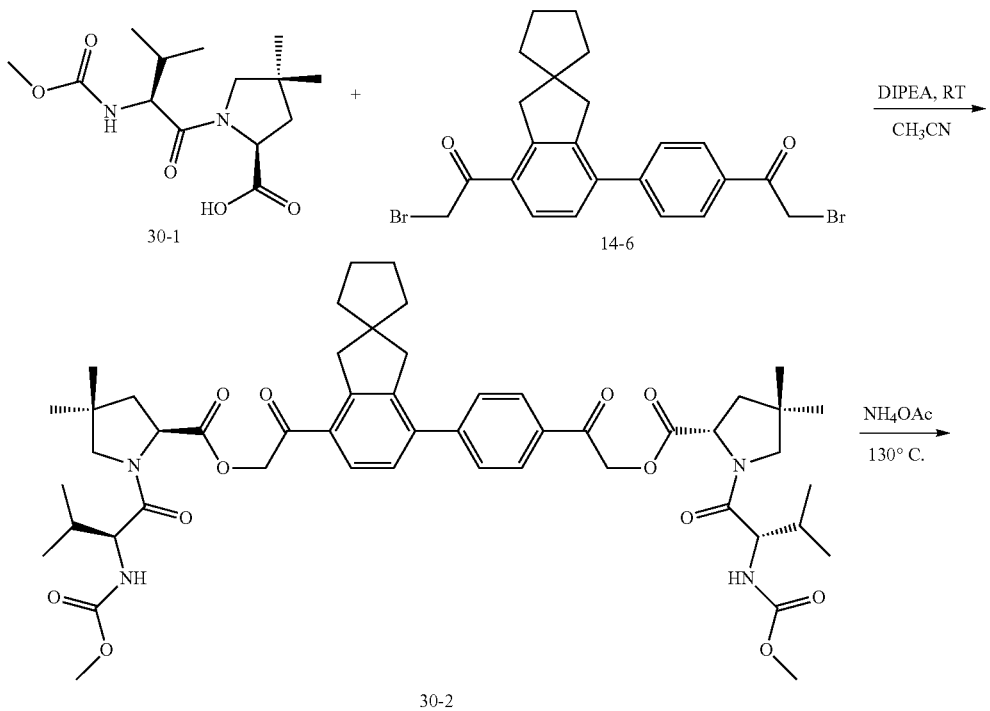

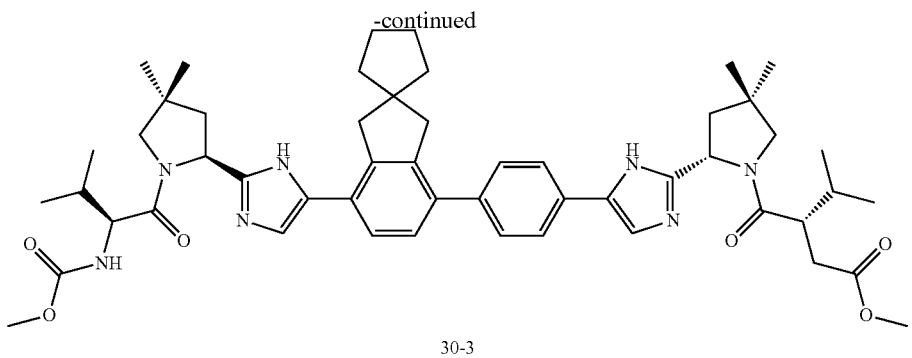

30-3

Step 1) The Preparation of Compound 30-1

The title compound 30-1 was prepared by an analogous procedure to that described for compound 18-8 (Example 18). The compound was characterized by the following spectroscopic data:

$^1$H NMR (400 MHz, CD$_3$Cl): δ 5.41 (d, J=8.96 Hz, 1H), 4.49 (m, 1H), 4.46 (m, 1H), 3.65 (s, 3H), 3.58 (d, J=9.64 Hz, 1H), 3.35 (d, J=9.63 Hz, 1H), 2.07 (m, 3H), 1.76 (m, 1H), 1.27 (m, 4H), 1.03 (m, 6H), 0.93 (m, 3H).

Step 2) The Preparation of Compound 30-2

To a solution of compound 30-1 (1.14 g, 3.8 mmol) and compound 14-6 (0.88 g, 1.8 mmol) in MeCN (15 mL) at 0° C. was added DIPEA (1.58 mL, 9.6 mmol). The mixture was stirred at rt overnight and concentrated in vacuo. The residue was purified by silica gel column chromatography (hexane/EtOAc (v/v)=1/5) to give the title compound 29-2 (0.83 g, 49.8%). The compound was characterized by the following spectroscopic data:

MS-ESI: m/z 930.5 [M+H]$^+$; and $^1$H NMR (400 MHz, CD$_3$Cl): δ 7.96 (d, J=8.24 Hz, 2H), 7.66 (d, J=8.12 Hz, 1H), 7.54 (d, J=8.28 Hz, 2H), 7.27 (d, J=8.12 Hz, 1H), 5.62-5.21 (m, 4H), 5.44 (m, 2H), 4.84 (m, 2H), 4.33 (m, 2H), 4.31 (m, 2H), 3.72 (m, 1H), 3.68 (s, 3H), 3.65 (s, 3H), 3.22 (s, 2H), 2.85 (m, 4H), 2.55 (m, 2H), 1.65 (m, 3H), 1.56 (m, 4H), 1.25 (m, 9H), 1.08 (m, 12H), 1.02 (m, 6H).

Step 3) The Preparation of Compound 30-3

A mixture of compound 30-2 (0.83 g, 0.89 mmol) and ammonium acetate (2.3 g, 29.8 mmol) in xylene (15 mL) in a sealed tube was stirred at 130° C. for 4 hours. After the mixture was cooled to rt, water (10 mL) was added to the mixture and the mixture was extracted with EtOAc (50 mL×3). The combined organic phases were dried over anhydrous Na$_2$SO$_4$ and concentrated in vacuo. The residue was purified by silica gel column chromatography (DCM/MeOH (v/v)=40/1) to give the title compound 30-3 as a white solid (0.52 g, 65.5%). The compound was characterized by the following spectroscopic data:

MS-ESI: m/z 890.5 [M+H]$^+$; and $^1$H NMR (400 MHz, CD$_3$Cl): δ 7.96 (d, J=8.24 Hz, 2H), 7.66 (d, J=8.12 Hz, 1H), 7.54 (d, J=8.28 Hz, 2H), 7.27 (d, J=8.12 Hz, 1H), 5.44 (m, 2H), 4.84 (m, 2H), 4.33 (m, 2H), 4.31 (m, 2H), 3.72 (m, 1H), 3.68 (s, 3H), 3.65 (s, 3H), 3.22 (s, 2H), 2.85 (m, 4H), 2.55 (m, 2H), 1.65 (m, 3H), 1.56 (m, 4H), 1.25 (m, 9H), 1.08 (m, 12H), 1.02 (m, 6H).

Example 31

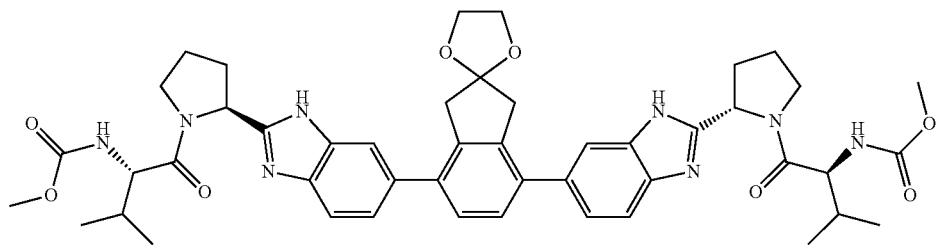 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4c3CC3(C4)OCCO3)cc2[nH]1)C(C)C]

Synthetic Routes

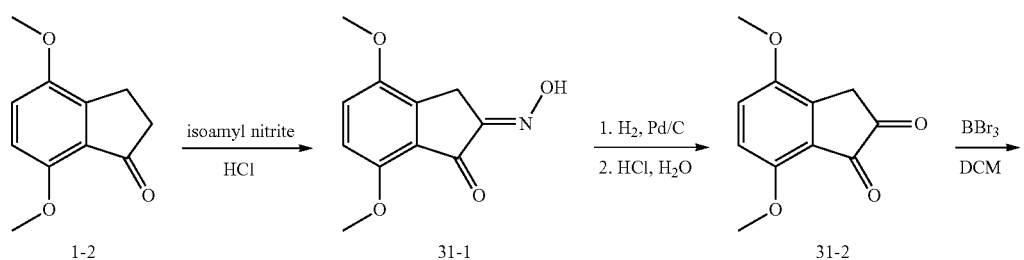

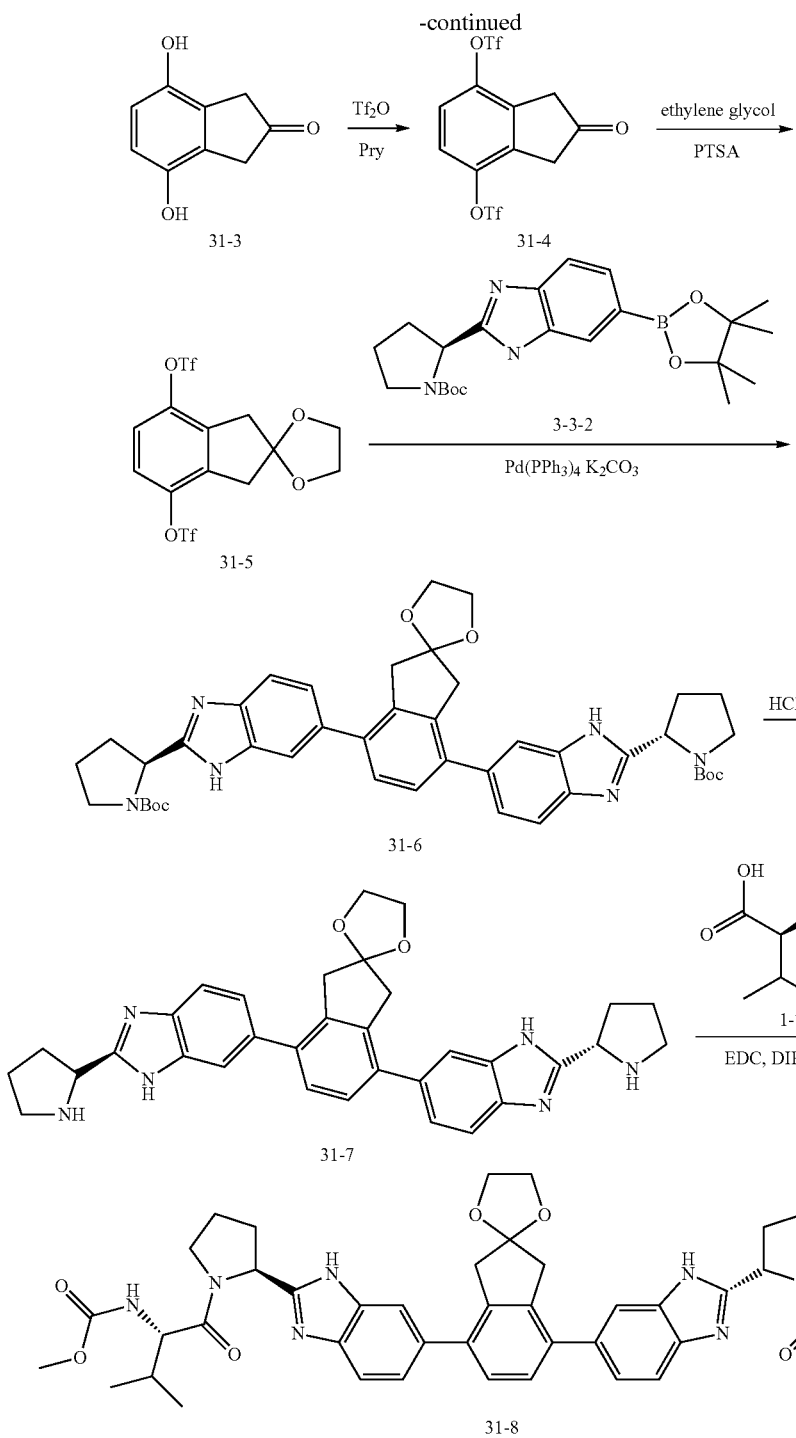

Step 1) The Preparation of Compound 31-1

To a solution of compound 1-2 (2.48 g, 12.90 mmol) in anhydrous MeOH (10 mL) was added concentrated hydrochloric acid (2 mL) under $N_2$. Then to the mixture was added isoamyl nitrite (6 mL) at 60-62° C. The mixture was stirred at 50° C. for 3 hours, cooled to rt and filtered. The solid recrystallized from ethanol to afford the title compound 31-1 as a yellow solid (2.6 g, 91.2%). The compound was characterized by the following spectroscopic data:

$^1$H NMR (400 MHz, DMSO-d$^6$): δ 3.53 (s, 2H), 3.82 (d, 6H), 6.97 (d, J=8.8 Hz, 1H), 7.29 (d, J=8.8 Hz, 2H), 12.45 (s, 1H).

Step 2) The Preparation of Compound 31-2

A suspension of compound 31-1 (1.18 g, 5.3 mmol), NaOH (25 mL, 10% in water) and Pd/C (0.3 g, 10%) in ethanol (15 mL) was stirred at rt for 4.5 hours under $H_2$ (50 Pa), filtered through a Celite pad and the Celite pad was washed with ethanol. The filtrate was concentrated in vacuo. To the residue were added concentrated hydrochloric acid (20 mL) and water (10 mL). The resulting mixture was refluxed for 0.5 hour and extracted with DCM (70 mL×3). The combined organic phases were dried over anhydrous $Na_2SO_4$ and concentrated in vacuo to afford the title compound 31-2 (0.81 g, 79.2%). The compound was characterized by the following spectroscopic data:

$^1$H NMR (400 MHz, CDCl$_3$): δ 3.46 (s, 4H), 3.81 (s, 6H), 6.73 (s, 2H).

Step 3) The Preparation of Compound 31-3

To a solution of compound 31-2 (1.0 g, 5.2 mmol) in anhydrous DCM (20 mL) at −78° C. was added dropwise boron tribromide (1.6 mL, 16.6 mmol) under N$_2$. The mixture was stirred at rt for 3 hours, and quenched with ice water (5 mL) in an ice bath. Then water (20 mL) was added to the mixture and the mixture was extracted with EtOAc (20 mL×3). The combined organic phases were washed with brine, dried over anhydrous Na$_2$SO$_4$ and concentrated in vacuo. The residue was purified by silica gel column chromatography (hexane/EtOAc (v/v)=6/1) to give the title compound 31-3 as a white solid (0.77 g, 90.2%). The compound was characterized by the following spectroscopic data:

$^1$H NMR (400 MHz, CDCl$_3$): δ 3.43 (s, 4H), 6.70 (s, 2H).

Step 4) The Preparation of Compound 31-4

To a solution of compound 31-3 (0.5 g, 3.04 mmol) in DCM (20 mL) was added Tf$_2$O (1.2 mL, 7.1 mmol) at 0° C. under N$_2$ via syringe followed by Et$_3$N (2.4 mL, 17.7 mmol). The mixture was stirred at rt overnight, poured into ice water (20 mL) and extracted with EtOAc (50 mL×3). The combined organic phases were washed with brine, dried over anhydrous Na$_2$SO$_4$ and concentrated in vacuo. The residue was purified by silica gel column chromatography (hexane/EtOAc (v/v)=20/1) to give the title compound 31-4 as colorless oil (0.9 g, 69.2%). The compound was characterized by the following spectroscopic data:

$^1$H NMR (400 MHz, CDCl$_3$): δ 3.51 (s, 4H), 7.05 (s, 2H).

Step 5) The Preparation of Compound 31-5

A solution of compound 31-4 (0.43 g, 1 mmol), ethylene glycol (0.186 g, 3 mmol) and p-TSA (0.019 g, 0.1 mmol) in toluene (50 mL) in a flask equipped with Dean-Stark trap was refluxed for 5 hours, poured into water and extracted with EtOAc (50 mL×3). The combined organic phases were dried over anhydrous Na$_2$SO$_4$ and concentrated in vacuo. The residue was purified by silica gel column chromatography (hexane/EtOAc (v/v)=10/1) to give the title compound 31-5 (0.17 g, 36%). The compound was characterized by the following spectroscopic data:

$^1$H NMR (400 MHz, CDCl$_3$): δ 3.38 (s, 4H), 3.87 (s, 4H), 7.03 (s, 2H).

Step 6) The Preparation of Compound 31-6

To a mixture of compound 31-5 (0.19 g, 0.41 mmol), Pd(PPh$_3$)$_4$ (46 mg, 0.040 mmol) and potassium carbonate (0.29 g, 2.1 mmol) under N$_2$ was added a solution of compound 3-3-2 (423 mg, 1.02 mmol) in DME (8 mL) followed by pure water (2 mL). The mixture was stirred at 90° C. for 2 hours and DME was removed in vacuo. To the residue was added water (15 mL) and the mixture was extracted with DCM (15 mL×3). The combined organic phases were dried over anhydrous Na$_2$SO$_4$ and concentrated in vacuo. The residue was purified by silica gel column chromatography (DCM/MeOH (v/v)=20/1) to give the title compound 31-6 as a pale yellow solid (0.17 g, 55.5%). The compound was characterized by the following spectroscopic data:

MS-ESI: m/z 747.3 [M+H]$^+$; and $^1$H NMR (400 MHz, CDCl$_3$): δ 1.491-1.696 (m, 26H), 1.982-2.093 (m, 2H), 3.046 (s, 4H), 3.315-3.510 (m, 4H), 3.87 (m, 4H), 5.175-5.189 (m, 2H), 7.283 (s, 2H), 7.344-7.487 (m, 6H).

Step 7) The Preparation of Compound 31-7

To a solution of compound 31-6 (0.3 g, 0.4 mmol) in EtOAc (5 mL) was added a solution of HCl in EtOAc (5 mL, 4 M). At the end of the addition, the mixture was stirred at rt overnight and filtered. The filter cake was washed with EtOAc to give the title compound 31-7 as a pale yellow solid (0.22 g, 79.1%), which was used for the next step directly.

Step 8) The Preparation of Compound 31-8

To a solution of compound 31-7 (0.22 g, 0.32 mmol), compound 1-7-2 (167 mg, 0.95 mmol) and EDCI (300 mg, 1.6 mmol) in DCM (10.0 mL) was added DIPEA (0.7 mL, 4.23 mmol) dropwise in an ice bath. At the end of the addition, the mixture was stirred at rt overnight. Water (20 mL) was then added to the mixture and the mixture was extracted with DCM (25 mL×3). The combined organic phases were dried over anhydrous Na$_2$SO$_4$ and concentrated in vacuo. The residue was purified by silica gel column chromatography (EtOAc) to give the title compound 31-8 as a white solid (0.11 g, 40.2%, HPLC: 96%). The compound was characterized by the following spectroscopic data:

MS-ESI: m/z 861.6 [M+H]$^+$; and $^1$H NMR (400 MHz, CDCl$_3$): δ 10.52 (m, 2H), 8.17 (s, 1H), 7.78 (s, 2H), 7.63 (brs, 2H), 7.40 (d, J=8.36 Hz, 1H), 7.12 (s, 2H), 5.45 (m, 2H), 4.35 (m, 2H), 3.63 (m, 4H), 3.17 (m, 4H), 2.28-2.10 (m, 10H), 1.86 (m, 4H), 0.88 (m, 12H).

Example 32

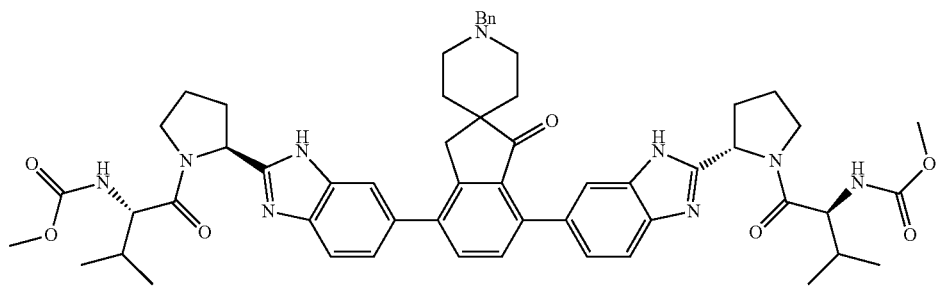 [SMILES: COC(=O)N[C@H](C(=O)N1CCC[C@H]1c1nc2ccc(-c3ccc(-c4ccc5nc([C@@H]6CCCN6C(=O)[C@@H](NC(=O)OC)C(C)C)[nH]c5c4)c4c3CC3(CCN(Cc5ccccc5)CC3)C4=O)cc2[nH]1)C(C)C]

Synthetic Routes

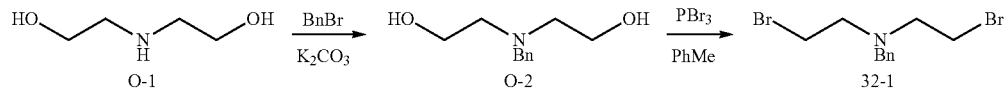

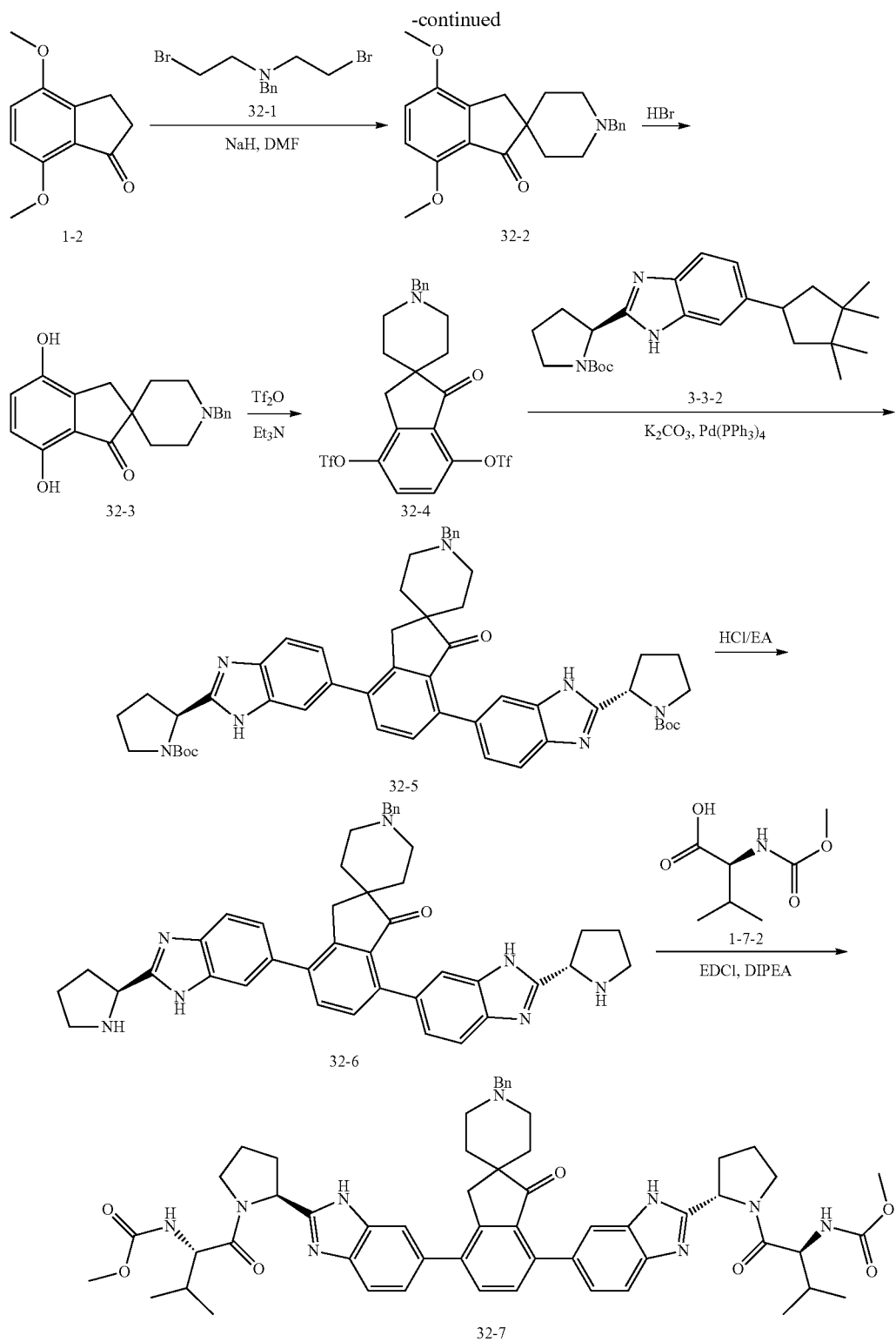

Step 1) The Preparation of Compound 32-1

A mixture of compound O-1 (12.10 g, 115.1 mmol), benzyl bromide (13.70 mL, 115.3 mmol) and potassium carbonate (31.81 g, 230.2 mmol) in acetone (120 mL) was refluxed for 18 hours, cooled to rt and filtered. The filtrate was concentrated in vacuo. The residue was purified by silica gel column chromatography (DCM/MeOH (v/v)=20/1) to give compound O-2 as pale yellow liquid (16.39 g, 72.9%). The compound was characterized by the following spectroscopic data:

$^1$H NMR (400 MHz, CDCl$_3$): δ 7.36-7.23 (m, 5H), 3.70 (s, 2H), 3.62 (t, J=5.3 Hz, 4H), 2.72 (t, J=5.3 Hz, 4H), 2.48 (brs, 2H).

To a solution of compound O-2 (14.60 g, 74.77 mmol) in toluene (140 mL) was added phosphorus tribromide (21.1 mL, 224.5 mmol) dropwise at 0° C. under N$_2$. At the end of the addition, the mixture was refluxed for 6 hours, cooled to rt, quenched with ice water (400 mL) and filtered. The filtrate was washed with NaOH solution and extracted with DCM (100 mL×3). The combined organic phases were dried over anhydrous $Na_2SO_4$ and concentrated in vacuo. The residue was purified by silica gel column chromatography (hexane/EtOAc (v/v)=10/1) to give the title compound 32-1 as colorless oil (13.30 g, 54.6%). The compound was characterized by the following spectroscopic data:

$^1$H NMR (400 MHz, $CDCl_3$): δ 7.36-7.25 (m, 5H), 3.73 (s, 2H), 3.34 (t, J=7.3 Hz, 4H), 2.98 (t, J=7.3 Hz, 4H).

Step 2) The Preparation of Compound 32-2

To a solution of compound 1-2 (2.56 g, 14.34 mmol) and compound 32-1 (6.905 g, 21.51 mmol) in DMF (15 mL) under $N_2$ was added NaH (1.434 g, 35.85 mmol, 60% dispersed in Mineral oil). The mixture was stirred at 50° C. for 18 hours, cooled to rt, and quenched with water (20 mL). The mixture was extracted with EtOAc (150 mL×3). The combined organic phases were washed with water, dried over anhydrous $Na_2SO_4$ and concentrated in vacuo. The residue was purified by silica gel column chromatography (hexane/EtOAc (v/v)=8/1) to give the title compound 32-2 (0.752 g, 14.9%). The compound was characterized by the following spectroscopic data:

MS-ESI: m/z 352.1 $[M+H]^+$; and $^1$H NMR (400 MHz, $CDCl_3$): δ 7.63-7.56 (m, 1H), 7.41-7.22 (m, 6H), 3.82 (d, 6H), 3.56 (s, 2H), 3.03 (s, 2H), 2.98-2.89 (m, 2H), 2.24-2.00 (m, 4H), 1.37 (d, J=11.8 Hz, 2H).

Step 3) The Preparation of Compound 32-3

To a solution of compound 32-2 (1.5 g, 4.3 mmol) in acetic acid (40 mL) was added hydrobromic acid (9.6 mL, 85 mmol). The mixture was refluxed for 12 hours, quenched with $NaHCO_3$ saturated solution and extracted with EtOAc (10 mL×3). The combined organic phases were washed with brine, dried over anhydrous $Na_2SO_4$ and filtered. The filtrate was concentrated in vacuo. The residue was purified by silica gel column chromatography (hexane/EtOAc (v/v)=4/1) to give the title compound 32-3 as a white solid (0.55 g, 39.9%). The compound was characterized by the following spectroscopic data:

$^1$H NMR (400 MHz, $CDCl_3$): δ 7.53-7.42 (m, 1H), 7.21-7.02 (m, 6H), 3.53 (s, 2H), 3.01 (s, 2H), 2.95-2.83 (m, 2H), 2.24-2.00 (m, 4H), 1.37 (d, J=11.8 Hz, 2H).

Step 4) The Preparation of Compound 32-4

To a solution of compound 32-3 (0.5 g, 1.5 mmol) in anhydrous DCM (20 mL) at 0° C. was added $Tf_2O$ (1.2 mL, 7.1 mmol) under $N_2$ followed by $Et_3N$ (2.4 mL, 17.27 mmol). The mixture was stirred at rt overnight, quenched with ice water (10 mL) and extracted with EtOAc (50 mL×3). The combined organic phases were washed with brine, dried over anhydrous $Na_2SO_4$ and concentrated in vacuo. The residue was purified by silica gel column chromatography (hexane/EtOAc (v/v)=10/1) to give the title compound 32-4 (0.66 g, 72.7%). The compound was characterized by the following spectroscopic data:

$^1$H NMR (400 MHz, $CDCl_3$): δ 8.03-7.88 (m, 1H), 7.69-7.52 (m, 6H), 3.76 (s, 2H), 3.08 (s, 2H), 2.99-2.91 (m, 2H), 2.26-2.03 (m, 4H), 1.39 (d, J=11.8 Hz, 2H).

Step 5) The Preparation of Compound 32-5

To a mixture of compound 32-4 (0.50 g, 0.85 mmol), $Pd(PPh_3)_4$ (46 mg, 0.0398 mmol) and potassium carbonate (286 mg, 2.07 mmol) under $N_2$ was added a solution of compound 3-3-2 (0.85 g, 2.06 mmol) in DME (8 mL) followed by distilled water (2 mL). The mixture was stirred at 90° C. for 3 hours and DME was removed in vacuo. To the residue was added water (15 mL). The mixture was extracted with DCM (20 mL×3). The combined organic phases were washed with brine, dried over anhydrous $Na_2SO_4$ and concentrated in vacuo. The residue was purified by silica gel column chromatography (hexane/EtOAc (v/v)=1/3) to give the title compound 32-5 as a yellow solid (0.51 g, 69.5%). The compound was characterized by the following spectroscopic data:

$^1$H NMR (400 MHz, $CDCl_3$): δ 7.23-7.73 (m, 13H), 5.17 (br, 2H), 3.70 (s, 2H), 3.43 (br, 2H), 3.06 (br, 2H), 2.22-2.24 (m, 8H), 1.95-2.06 (m, 4H), 1.82 (br, 4H), 1.64 (br, 4H), 1.52 (s, 18H).

Step 6) The Preparation of Compound 32-6

To a solution of compound 32-5 (500 mg, 0.58 mmol) in EtOAc (4 mL) was added a solution of HCl in EtOAc (5 mL, 4 M). The mixture was stirred at rt overnight and filtered. The filter cake was washed with EtOAc (20 mL) to give the title compound 32-6 as a yellow solid (350 mg, 74.7%), which was used for the next step directly.

Step 7) The Preparation of Compound 32-7

To a solution of compound 32-6 (350 mg, 0.43 mmol), compound 1-7-2 (167 mg, 0.95 mmol) and EDCI (300 mg, 1.6 mmol) in DCM (10.0 mL) in an ice bath was added DIPEA (0.9 mL, 5.44 mmol) dropwise. The mixture was stirred at rt overnight. Water (10 mL) was added to the mixture and the mixture was extracted with DCM (30 mL×3). The combined organic phases were dried over anhydrous $Na_2SO_4$ and concentrated in vacuo. The residue was purified by silica gel column chromatography (EtOAc) to give the title compound 32-7 as a white solid (102 mg, 24.1%, HPLC: 93%). The compound was characterized by the following spectroscopic data:

MS-ESI: m/z 977.3 $[M+H]^+$; and $^1$H NMR (400 MHz, $CDCl_3$): δ 10.69 (br, 2H), 7.21-7.74 (m, 13H), 5.45-5.50 (m, 4H), 4.36 (m, 2H), 3.82-3.92 (m, 2H), 3.72 (s, 6H), 3.60-3.70 (m, 2H), 3.68 (s, 2H), 3.10 (s, 2H), 1.85-2.45 (m, 14H), 1.57-1.75 (m, 4H), 0.90 (br, 12H).

Example 33

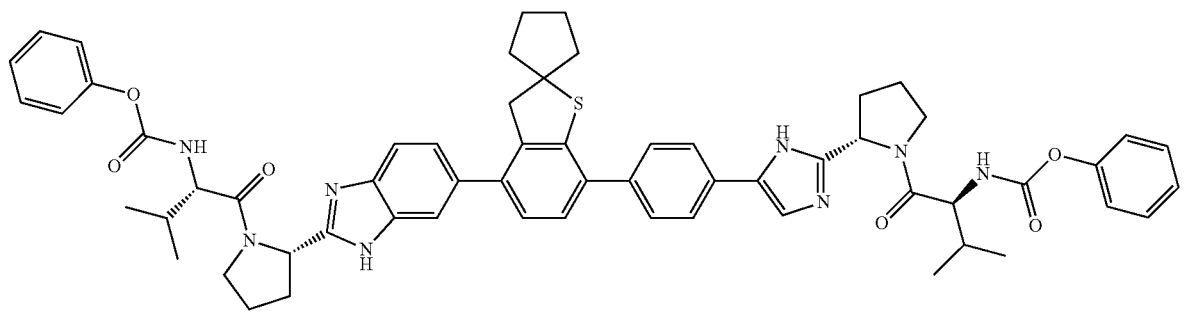 [SMILES: CC(C)[C@H](NC(=O)Oc1ccccc1)C(=O)N1CCC[C@H]1c1ncc(-c2ccc(-c3ccc(-c4ccc5nc([C@@H]6CCCN6C(=O)[C@@H](NC(=O)Oc6ccccc6)C(C)C)[nH]c5c4)c4c3SC3(CCCC3)C4)cc2)[nH]1]

Synthetic Routes
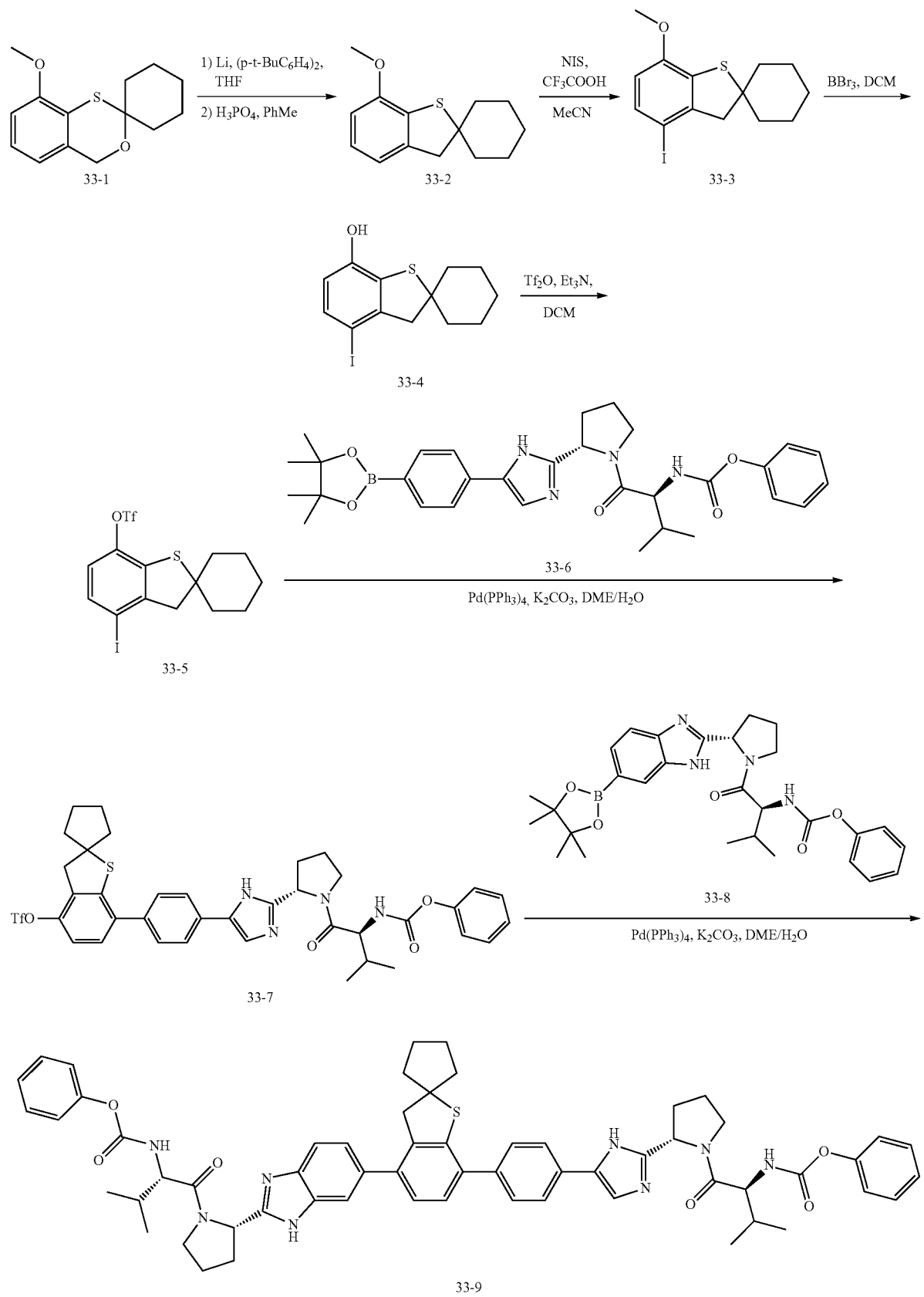

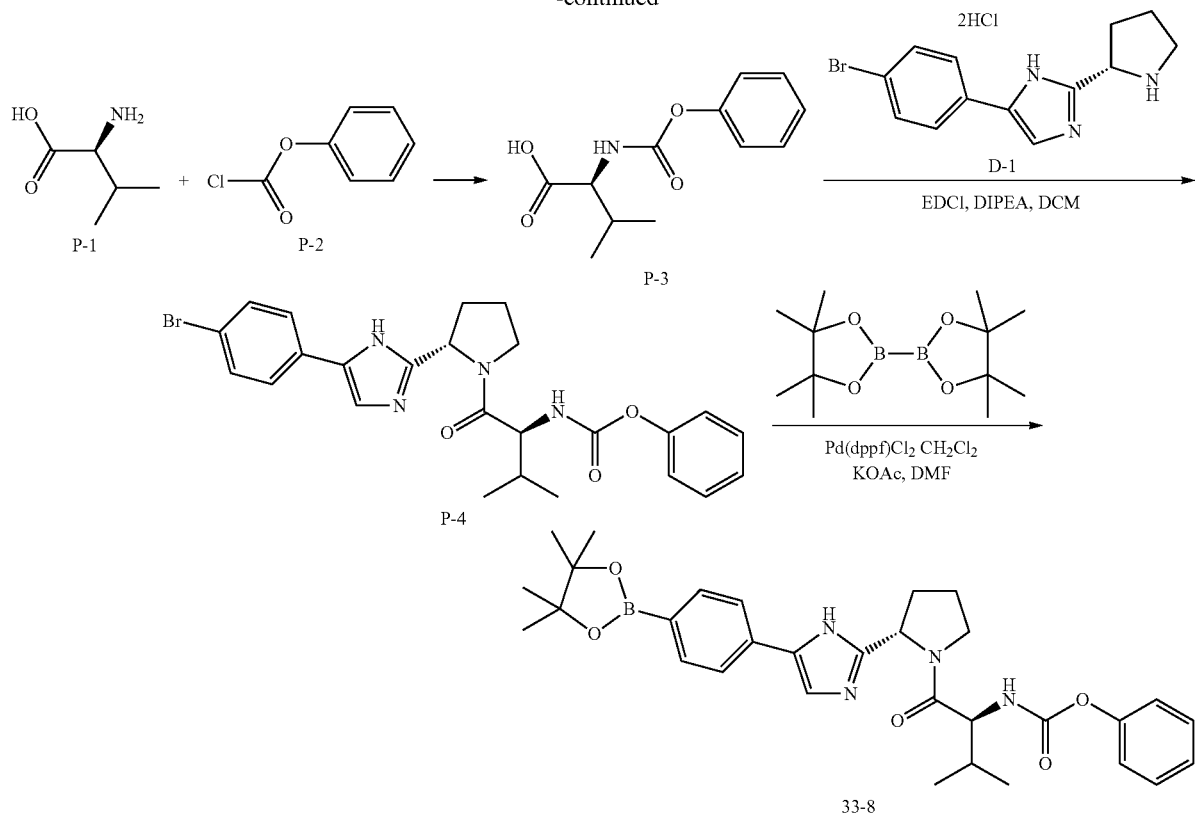

Step 1) The Preparation of Compound 33-2

To a mixture of Li (1 mg, 0.1 mmol) in anhydrous THF (10 mL) was added compound 33-1 (1 g, 4 mmol). The mixture was cooled to 0° C., and (p-t-BuC$_6$H$_4$)$_2$ (11 mg, 0.04 mmol) was added. The resulting mixture was stirred at rt overnight and quenched with ice water. THF was removed in vacuo, and the mixture was extracted with EtOAc (10 mL×3). The combined organic phases were washed with brine, dried over anhydrous Na$_2$SO$_4$ and concentrated in vacuo to give the residue, which was used for the next step without further purification.

To a solution of the above residue in toluene (10 mL) was added H$_3$PO$_4$ (784 mg, 8 mmol). The mixture was refluxed for 8 hours, quenched with NaHCO$_3$ saturated solution (20 mL) and extracted with EtOAc (10 mL×3). The combined organic phases were washed with brine, dried over anhydrous Na$_2$SO$_4$ and concentrated in vacuo. The residue was purified by silica gel column chromatography (PE/EtOAc (v/v)=20/1) to give the title compound 33-2 (280 mg, 29.9%). The compound was characterized by the following spectroscopic data:

MS-ESI: m/z 235.1 [M+H]$^+$; and $^1$H NMR (400 MHz, CDCl$_3$): δ 7.38-7.39 (m, 1H), 7.25-7.24 (m, 1H), 7.22-7.23 (m, 1H), 3.87 (s, 3H), 3.52 (s, 2H), 1.41-1.72 (m, 10H).

Step 2) The Preparation of Compound 33-3

To a solution of compound 33-2 (2.0 g, 8.5 mmol) and NIS (2.1 g, 9.35 mmol) in acetonitrile (50 mL) in an ice bath was added TFA (30 mL) dropwise. The mixture was stirred at rt overnight, neutralized with NaHCO$_3$ saturated solution and extracted with EtOAc (50 mL×3). The combined organic phases were washed with brine, dried over anhydrous Na$_2$SO$_4$ and concentrated in vacuo. The residue was purified by silica gel column chromatography (PE/EtOAc (v/v)=10/1) to give the title compound 33-3 as pale yellow oil (2.4 g, 78.1%). The compound was characterized by the following spectroscopic data:

MS-ESI: m/z 361.0 [M+H]$^+$; and $^1$H NMR (400 MHz, CDCl$_3$): δ 7.35-7.36 (m, 1H), 7.28-7.29 (m, 1H), 3.88 (s, 3H), 3.53 (s, 2H), 1.39-1.65 (m, 10H).

Step 3) The Preparation of Compound 33-4

To a solution of compound 33-3 (1.5 g, 4.2 mmol) in DCM (15 mL) was added BBr$_3$ (4 g, 16 mmol) dropwise at −78° C. At the end of the addition, the mixture was stirred at rt for 6 hours, quenched with ice water (20 mL) and extracted with EtOAc (10 mL×3). The combined organic phases were dried over anhydrous Na$_2$SO$_4$ and concentrated in vacuo. The residue was purified by silica gel column chromatography (PE/EtOAc (v/v)=5/1) to give the title compound 33-4 as a white solid (1.3 g, 90.2%). The compound was characterized by the following spectroscopic data:

MS-ESI: m/z 347.0 [M+H]$^+$; and $^1$H NMR (400 MHz, CDCl$_3$): δ 7.36-7.37 (m, 1H), 7.28-7.29 (m, 1H), 3.55 (s, 2H), 1.40-1.64 (m, 10H).

Step 4) The Preparation of Compound 33-5

To a solution of compound 33-4 (5.0 g, 14.4 mmol) in anhydrous DCM (50 mL) under N$_2$ in an ice bath was added Tf$_2$O (3.6 mL, 21.6 mmol) via syringe followed by pyridine (2.4 mL, 28.8 mmol). The mixture was stirred in the ice bath for 20 minutes and at rt for another 3 hours. The resulting mixture was quenched with ice water in an ice bath. Water (50 mL) was added to the mixture and the mixture was extracted with DCM (60 mL×3). The combined organic phases were washed with brine, dried over anhydrous Na$_2$SO$_4$ and concentrated in vacuo. The residue was purified by silica gel column chromatography (PE/EtOAc (v/v)=10/1) to give the title compound 33-5 as colorless oil (6.2 g, 89.8%). The compound was characterized by the following spectroscopic data:

MS-ESI: m/z 478.9 [M+H]+; and $^1$H NMR (400 MHz, CDCl$_3$): δ 7.37-7.38 (m, 1H), 7.29-7.30 (m, 1H), 3.55 (s, 2H), 1.39-1.65 (m, 10H).

Step 5) The Preparation of Compound 33-6

The title compound 33-6 was prepared by an analogous procedure to that described for compound 7-9 (Example 7). The compound was characterized by the following spectroscopic data:

MS-ESI: m/z 559.3 [M+H]+; and $^1$H NMR (400 MHz, CDCl$_3$): δ 7.65-7.60 (m, 2H), 7.47-7.43 (m, 2H), 7.38-7.39 (m, 5H), 7.22-7.20 (m, 1H), 5.67-5.65 (m, 1H), 5.24-5.22 (m, 1H), 4.34-4.30 (m, 1H), 3.5-3.81 (m, 1H), 3.71-3.64 (m, 1H), 3.00 (s, 1H), 2.34-2.11 (m, 1H), 2.21-1.95 (m, 5H), 1.32-1.45 (m, 12H), 1.04-1.02 (m, 1H), 0.88-0.86 (d, 6H).

Step 6) The Preparation of Compound 33-7

To a mixture of compound 33-5 (3.81 g, 7.98 mmol), compound 33-6 (3.71 g, 6.65 mmol), Pd(PPh$_3$)$_4$ (768 mg, 0.66 mmol) and potassium carbonate (2.77 g, 20.1 mmol) in a 100 mL of two-necked flask under N$_2$ was added DME (50.0 mL) via syringe followed by pure water (10.0 mL). The resulting mixture was stirred at 90° C. overnight. After the mixture was cooled to rt and concentrated in vacuo, to the residue was added water (50.0 mL). The mixture was extracted with EtOAc (50.0 mL×3). The combined organic phases were washed with brine, dried over anhydrous Na$_2$SO$_4$ and concentrated in vacuo. The residue was purified by silica gel column chromatography (DCM/MeOH (v/v)=50/1) to give the title compound 33-7 as a beige solid (4.1 g, 82.3%). The compound was characterized by the following spectroscopic data:

MS-ESI: m/z 751.3 [M+H]+; and $^1$H NMR (400 MHz, CDCl$_3$): δ 7.84-7.82 (m, 1H), 7.69-7.66 (m, 2H), 7.57-7.55 (m, 1H), 7.48-7.44 (m, 2H), 7.43-7.41 (m, 5H), 7.40-7.36 (m, 6H), 5.41-5.39 (m, 1H), 5.29-5.27 (m, 1H), 4.34-4.30 (m, 1H), 3.75-3.70 (m, 1H), 3.64-3.62 (m, 1H), 3.20-3.01 (m, 1H), 2.95 (s, 2H), 2.25-2.20 (m, 1H), 2.20-2.13 (m, 2H), 1.96-1.94 (m, 1H), 1.79-1.52 (m, 10H), 0.88-0.86 (m, 6H).

Step 7) The Preparation of Compound 33-8

The title compound 33-8 was prepared by an analogous procedure to that described for compound 11-4 (Example 11). The compound was characterized by the following spectroscopic data:

MS-ESI: m/z 690.3 [M+H]+; and $^1$H NMR (400 MHz, CDCl$_3$): δ 7.84-7.82 (m, 1H), 7.69-7.66 (m, 2H), 7.57-7.55 (m, 1H), 7.48-7.44 (m, 2H), 7.40-7.36 (m, 1H), 5.41-5.39 (m, 1H), 5.29-5.27 (m, 1H), 4.34-4.30 (m, 1H), 3.75-3.70 (m, 1H), 3.70 (s, 3H), 3.64-3.62 (m, 1H), 3.20-3.01 (m, 1H), 2.99 (s, 2H), 2.95 (s, 2H), 2.25-2.20 (m, 1H), 2.20-2.13 (m, 2H), 1.96-1.94 (m, 1H), 1.52-1.78 (m, 8H), 0.88-0.86 (m, 6H).

Step 8) the preparation of compound 33-9

To a mixture of compound 33-7 (2.74 g, 3.65 mmol), compound 33-8 (1.84 g, 3.46 mmol), Pd(PPh$_3$)$_4$ (404 mg, 0.35 mmol) and potassium carbonate (1.23 g, 0.89 mmol) in a 100 mL of two-necked flask under N$_2$ was added DME (20.0 mL) via syringe followed by pure water (4.0 mL). The mixture was stirred at 90° C. overnight, cooled to rt and concentrated in vacuo. To the residue was added water (50.0 mL). The mixture was extracted with EtOAc (50.0 mL×3). The combined organic phases were washed with brine, dried over anhydrous Na$_2$SO$_4$ and concentrated in vacuo. The residue was purified by silica gel column chromatography (DCM/MeOH (v/v)=50/1) to give the title compound 33-9 as a pale yellow solid (1.21 g, 34.2%, HPLC: 95.4%). The compound was characterized by the following spectroscopic data:

MS-ESI: m/z 1039.5 [M+H]+; and $^1$H NMR (400 MHz, CDCl$_3$): δ 7.70-7.68 (m, 2H), 7.52-7.56 (m, 2H), 7.42-7.48 (m, 2H), 7.45-7.42 (m, 5H), 7.35-7.37 (m, 5H), 7.28-7.34 (m, 2H), 7.25-7.26 (m, 2H), 5.26-5.29 (m, 1H), 5.16-5.19 (m, 1H), 4.21-4.26 (m, 2H), 3.88-3.93 (m, 2H), 2.97 (s, 2H), 2.94 (s, 2H), 2.04-2.34 (m, 10H), 1.53-1.59 (m, 10H), 0.86-0.93 (m, 12H).

Example 34

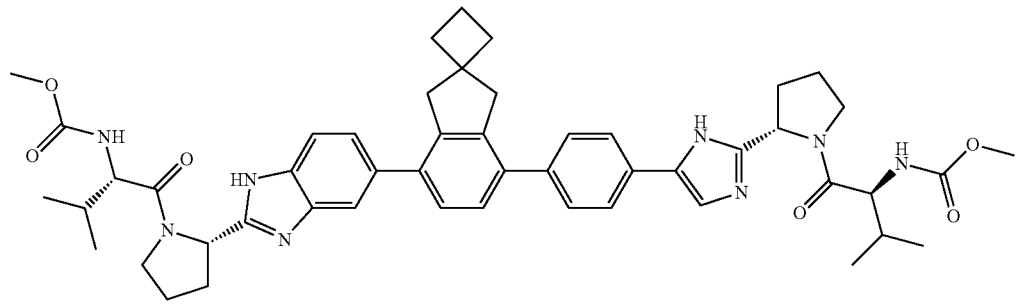

Synthetic Routes

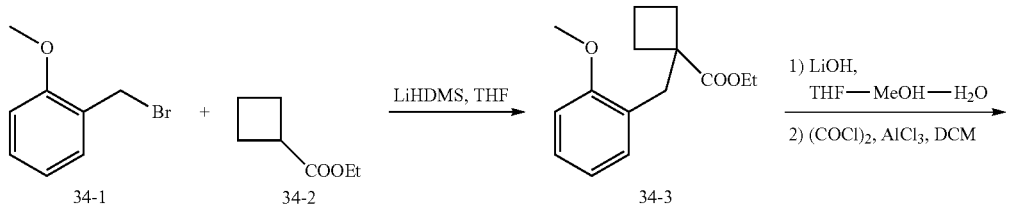

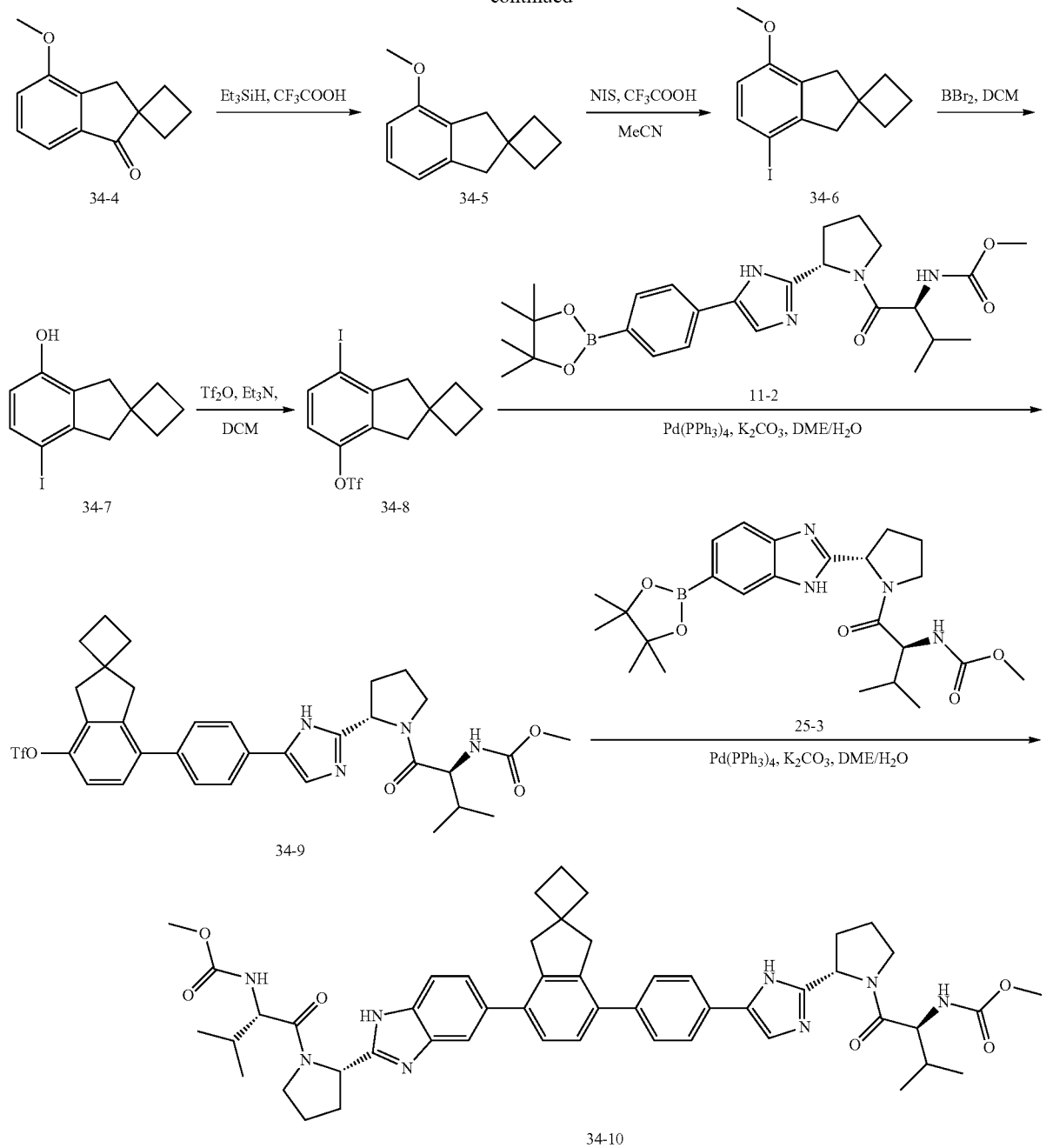

Step 1) The Preparation of Compound 34-3

To a solution of compound 34-2 (530 mg, 4.14 mmol) in THF (20 mL) was added LiHMDS (5.8 mL, 1 M) dropwise at −25° C. The mixture was stirred at −25° C. for 1 hour, and a solution of compound 34-1 (1.08 g, 5.38 mmol) in THF was added slowly. The resulting mixture was allowed to warm to 0° C. and stirred for another 2 hours. The reaction mixture was quenched with NH$_4$Cl saturated solution (10 mL) and extracted with EtOAc (50 mL×3). The combined organic phases were washed with brine, dried over anhydrous Na$_2$SO$_4$ and concentrated in vacuo. The residue was purified by silica gel column chromatography (PE/EtOAc (v/v)=10/1) to give the title compound 34-3 (510 mg, 49.7%). The compound was characterized by the following spectroscopic data:

MS-ESI: m/z 249.1 [M+H]$^+$; and $^1$H NMR (400 MHz, CDCl$_3$): δ 7.14-7.19 (m, 1H), 7.02-7.03 (m, 1H), 6.81-6.85 (m, 2H), 4.07-4.13 (m, 2H), 3.78 (s, 3H), 2.36-2.43 (m, 2H), 2.04-2.07 (m, 4H), 1.84-1.88 (m, 2H), 1.19 (t, J=7.12 Hz, 3H).

Step 2) The Preparation of Compound 34-4

To a solution of compound 34-3 (0.51 g, 2.05 mmol) in mixed solvents of THF (8 mL), MeOH (4 mL) and H$_2$O (2 mL) was added LiOH (215 mg, 5.12 mmol). The mixture was stirred at 50° C. overnight and concentrated in vacuo. To the residue was added water (10 mL) and the mixture was extracted with EtOAc (50 mL). The aqueous layer was adjusted to pH 3 and extracted with EtOAc (50 mL×3). The combined organic phases were washed with brine, dried over anhydrous Na$_2$SO$_4$ and concentrated in vacuo to give the crude product, which was used for next step without further purification.

To a solution of the above crude product in anhydrous DCM (20 mL) was added aluminium chloride (549 mg, 4.12 mmol) followed by oxalyl chloride (260 mg, 2.05 mmol) dropwise at 0° C. The mixture stirred at 0° C. for 4 hours, quenched with hydrochloric acid (1 M) and extracted with DCM (50 mL×3). The combined organic phases were washed with brine, dried over anhydrous Na$_2$SO$_4$ and concentrated in vacuo. The residue was purified by silica gel column chromatography (PE/EtOAc (v/v)=15/1) to give the title compound 34-4 as pale yellow oil (125 mg, 30.1%). The compound was characterized by the following spectroscopic data:

MS-ESI: m/z 203.1 [M+H]$^+$; and
$^1$H NMR (400 MHz, CDCl$_3$): δ 7.35-7.37 (m, 2H), 7.03-7.05 (m, 1H), 3.92 (s, 3H), 3.23 (s, 2H), 2.51-2.55 (m, 2H), 2.04-2.16 (m, 4H).

Step 3) The Preparation of Compound 34-5

To a mixture of compound 34-4 (0.82 g, 4.05 mmol) and triethylsilane (1.86 g, 16.0 mmol) in an ice bath was added trifluoroacetic acid (10 mL) dropwise. The mixture was stirred at 40° C. overnight, neutralized with NaHCO$_3$ saturated solution and extracted with EtOAc (50 mL×3). The combined organic phases were washed with brine, dried over anhydrous Na$_2$SO$_4$ and concentrated in vacuo. The residue was purified by silica gel column chromatography (PE/EtOAc (v/v)=20/1) to give the title compound 34-5 as colorless oil (0.60 g, 78.7%). The compound was characterized by the following spectroscopic data:

MS-ESI: m/z 189.1 [M+H]$^+$; and
$^1$H NMR (400 MHz, CDCl$_3$): δ 7.36-7.37 (m, 2H), 7.04-7.06 (m, 1H), 3.93 (s, 3H), 3.24 (s, 2H), 3.22 (s, 2H), 2.51-2.54 (m, 2H), 2.05-2.14 (m, 4H).

Step 4) The Preparation of Compound 34-6

To a solution of compound 34-5 (0.85 g, 4.5 mmol) and NIS (1.1 g, 5.9 mmol) in acetonitrile (20 mL) was added TFA (10 mL) dropwise in an ice bath. The mixture was stirred at rt overnight, neutralized with NaHCO$_3$ saturated solution and extracted with EtOAc (20 mL×3). The combined organic phases were washed with brine, dried over anhydrous Na$_2$SO$_4$ and concentrated in vacuo. The residue was purified by silica gel column chromatography (PE/EtOAc (v/v)=20/1) to give the title compound 34-6 as colorless oil (1.2 g, 84.6%). The compound was characterized by the following spectroscopic data:

MS-ESI: m/z 315.2 [M+H]$^+$; and
$^1$H NMR (400 MHz, CDCl$_3$): δ 7.34-7.36 (m, 2H), 3.94 (s, 3H), 3.23 (s, 2H), 3.21 (s, 2H), 2.51-2.54 (m, 2H), 2.06-2.16 (m, 4H).

Step 5) The Preparation of Compound 34-7

To a solution of compound 34-6 (1.1 g, 3.5 mmol) in DCM (15 mL) at −78° C. was added boron tribromide (3.5 g, 14 mmol) dropwise. The mixture was stirred at rt for 6 hours, and added dropwise to ice water (20 mL). The mixture was extracted with EtOAc (20 mL×3). The combined organic phases were dried over anhydrous Na$_2$SO$_4$ and concentrated in vacuo. The residue was purified by silica gel column chromatography (PE/EtOAc (v/v)=5/1) to give the title compound 34-7 as a gray solid (0.95 g, 90.4%). The compound was characterized by the following spectroscopic data:

MS-ESI: m/z 301.0 [M+H]$^+$; and
$^1$H NMR (400 MHz, CDCl$_3$): δ 7.35-7.37 (m, 2H), 3.24 (s, 2H), 3.22 (s, 2H), 2.50-2.53 (m, 2H), 2.05-2.15 (m, 4H).

Step 6) The Preparation of Compound 34-8

To a solution of compound 34-7 (2.5 g, 8.3 mmol) in anhydrous DCM (30 mL) under N$_2$ in an ice bath was added Tf$_2$O (2.7 mL, 16.4 mmol) slowly via syringe followed by pyridine (1.3 mL, 16.4 mmol). After the resulting mixture was stirred for 20 minutes, the ice bath was removed. The resulting mixture was stirred at rt for 3 hours, and quenched with ice water (10 mL) in an ice bath. Then water (10 mL) was added to the mixture and the mixture was extracted with DCM (20 mL×3). The combined organic phases were washed with brine, dried over anhydrous Na$_2$SO$_4$ and concentrated in vacuo. The residue was purified by silica gel column chromatography (PE/EtOAc (v/v)=10/1) to give the title compound 34-8 as colorless oil (3.2 g, 88.9%). The compound was characterized by the following spectroscopic data:

MS-ESI: m/z 432.9 [M+H]$^+$; and
$^1$H NMR (400 MHz, CDCl$_3$): δ 7.34-7.36 (m, 2H), 3.25 (s, 2H), 3.23 (s, 2H), 2.51-2.53 (m, 2H), 2.04-2.14 (m, 4H).

Step 7) The Preparation of Compound 34-9

To a mixture of compound 34-8 (3.44 g, 7.98 mmol), compound 11-2 (3.3 g, 6.65 mmol), Pd(PPh$_3$)$_4$ (768 mg, 0.79 mmol) and potassium carbonate (2.77 g, 19.9 mmol) in a 100 mL of two-necked flask under N$_2$ was added DME (50.0 mL) via syringe followed by pure water (10.0 mL). The mixture was stirred at 90° C. overnight, cooled to rt and concentrated in vacuo. To the residue was added water (50.0 mL), and the mixture was extracted with EtOAc (50.0 mL×3). The combined organic phases were washed with brine, dried over anhydrous Na$_2$SO$_4$ and concentrated in vacuo. The residue was purified by silica gel column chromatography (DCM/MeOH (v/v)=70/1) to give the title compound 34-9 as a pale yellow solid (3.5 g, 78.0%). The compound was characterized by the following spectroscopic data:

MS-ESI: m/z 675.2 [M+H]$^+$; and
$^1$H NMR (400 MHz, CDCl$_3$): δ 7.84-7.82 (m, 1H), 7.69-7.66 (m, 2H), 7.57-7.55 (m, 1H), 7.47-7.45 (m, 2H), 7.40-7.36 (m, 1H), 5.41-5.39 (m, 1H), 5.29-5.27 (m, 1H), 4.34-4.30 (m, 1H), 3.75-3.70 (m, 1H), 3.70 (s, 3H), 3.64-3.62 (m, 1H), 3.23 (s, 2H), 3.21 (s, 2H), 3.20-3.01 (m, 1H), 2.25-2.20 (m, 1H), 2.20-2.13 (m, 2H), 2.11-2.01 (m, 6H), 1.96-1.94 (m, 1H), 0.88-0.86 (m, 6H).

Step 8) The Preparation of Compound 34-10

To a mixture of compound 34-9 (2.407 g, 3.5 mmol), compound 25-3 (1.84 g, 3.9 mmol), Pd(PPh$_3$)$_4$ (404 mg, 0.35 mmol) and potassium carbonate (1.23 g, 8.8 mmol) in a 100 mL of two-necked flask under N$_2$ was added DME (20.0 mL) via syringe followed by pure water (4.0 mL). The mixture was stirred at 90° C. overnight, cooled to rt and concentrated in vacuo. To the residue was added water (50.0 mL), and the mixture was extracted with EtOAc (50.0 mL×3). The combined organic phases were washed with brine, dried over anhydrous Na$_2$SO$_4$ and concentrated in vacuo. The residue was purified by silica gel column chromatography (DCM/MeOH (v/v)=50/1) to give the title compound 34-10 as a beige solid (1.19 g, 39.1%, HPLC: 97.39%). The compound was characterized by the following spectroscopic data:

MS-ESI: m/z 869.4 [M+H]$^+$; and
$^1$H NMR (400 MHz, CDCl$_3$): δ 7.71-7.67 (m, 2H), 7.54-7.58 (m, 2H), 7.42-7.48 (m, 2H), 7.29-7.34 (m, 2H), 7.24-7.27 (m, 2H), 5.26-5.29 (m, 1H), 5.15-5.18 (m, 1H), 4.20-4.25 (m, 2H), 3.95-4.06 (m, 2H), 3.87-3.91 (m, 2H), 3.64 (s, 6H), 3.22 (s, 2H), 3.20 (S, 2H), 2.14-2.34 (m, 10H), 2.13-2.01 (m, 6H), 0.86-0.93 (m, 12H).

Example 35
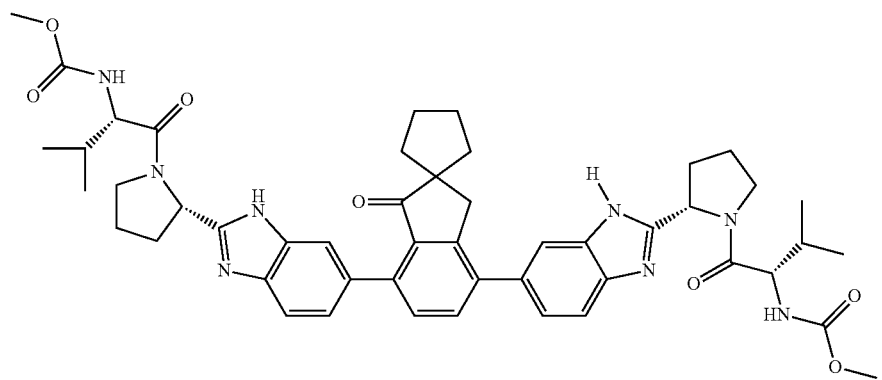
Synthetic Routes
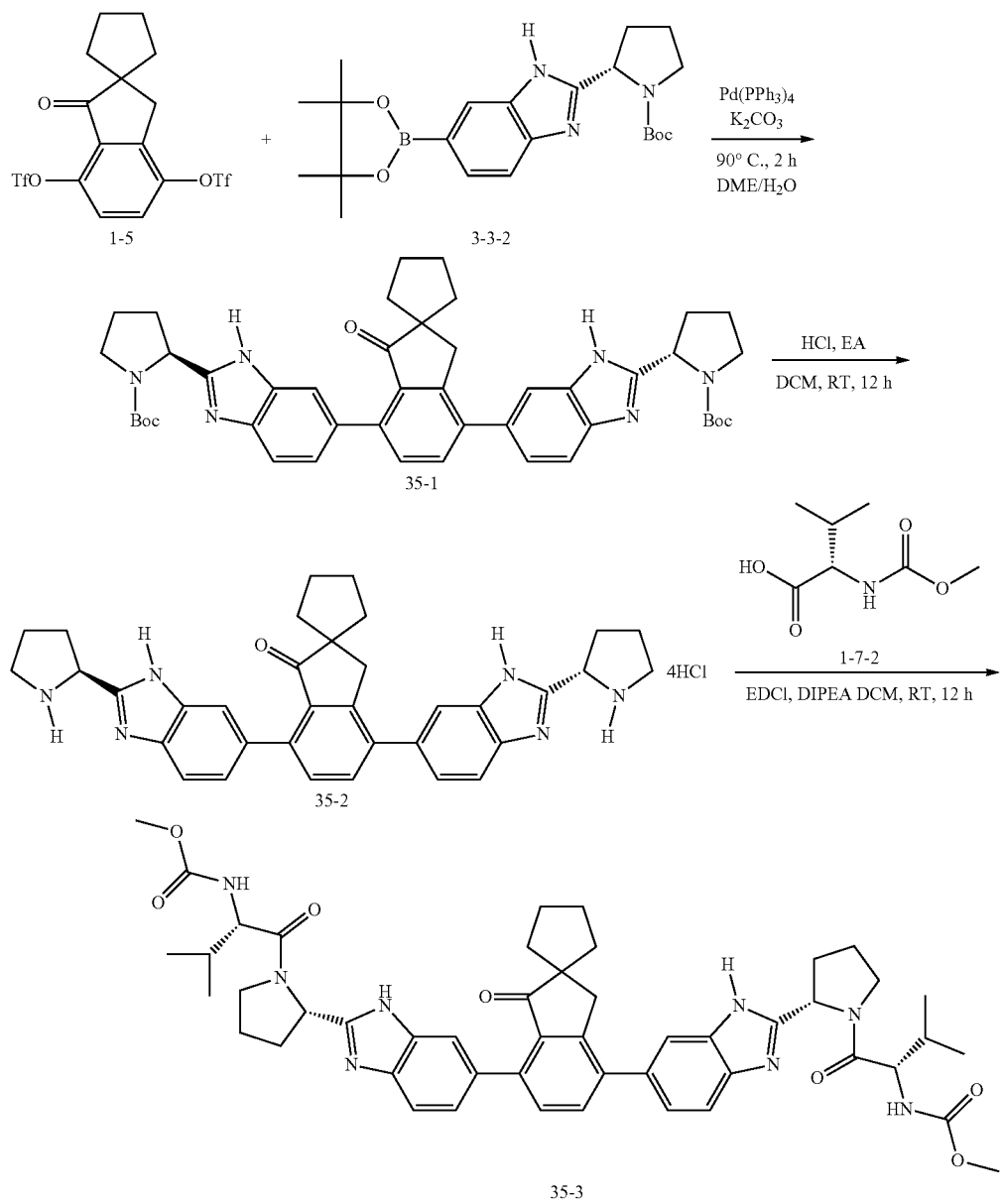

Compounds disclosed herein can be prepared by an analogous procedure to that described in Example 1.

Compound 35-1 was characterized by the following spectroscopic data:

MS-ESI: m/z 379.3 [M+2H]$^{2+}$; and $^1$H NMR (400 MHz, CDCl$_3$): δ 7.34-7.73 (m, 8H), 5.17 (br, 2H), 3.43 (br, 2H), 3.06 (br, 2H), 2.22-2.24 (m, 4H), 1.95-2.06 (m, 8H), 1.82 (br, 4H), 1.64 (br, 4H), 1.52 (s, 18H).

Compound 35-2 was characterized by the following spectroscopic data:

MS-ESI: m/z 557.4 [M−4HCl+H]$^{+1}$; and

H NMR (400 MHz, CD$_3$OD): δ 7.98-8.00 (m, 2H), 7.90-7.94 (m, 2H), 7.80-7.83 (m, 2H), 7.73-7.76 (m, 1H), 7.54-7.56 (m, 1H), 5.34-5.40 (m, 2H), 3.65-3.68 (m, 4H), 3.18 (s, 2H), 2.80-2.85 (m, 2H), 2.61-2.67 (m, 2H), 2.43-2.47 (m, 2H), 2.30-2.35 (m, 2H), 1.62-1.95 (m, 8H).

Compound 35-3 was characterized by the following spectroscopic data:

MS-ESI: m/z 436.3 [M+2H]$^{2+}$; and $^1$H NMR (400 MHz, CDCl$_3$): δ 10.69 (br, 2H), 7.41-7.74 (m, 8H), 5.45-5.50 (m, 4H), 4.36 (m, 2H), 3.82-3.92 (m, 2H), 3.72 (s, 6H), 3.60-3.70 (m, 2H), 3.10 (s, 2H), 1.85-2.45 (m, 10H), 1.57-1.75 (m, 8H), 0.90 (br, 12H).

Example 36

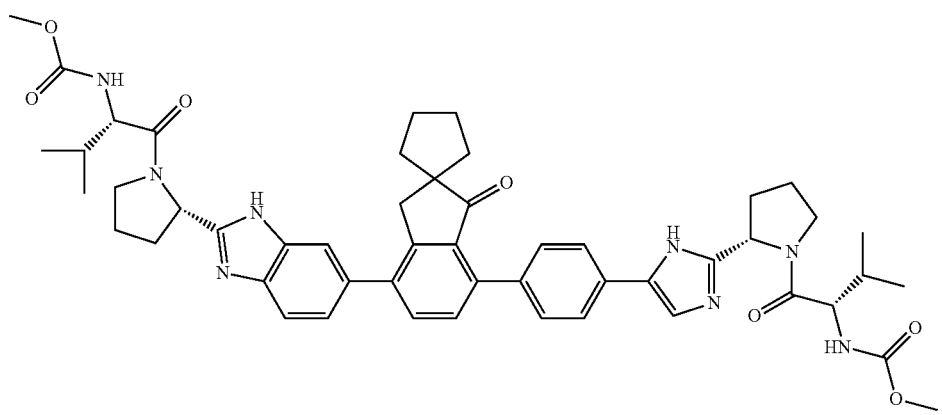

Synthetic Routes

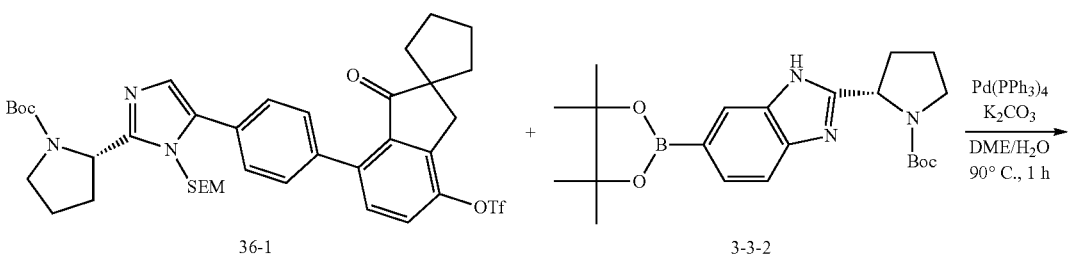

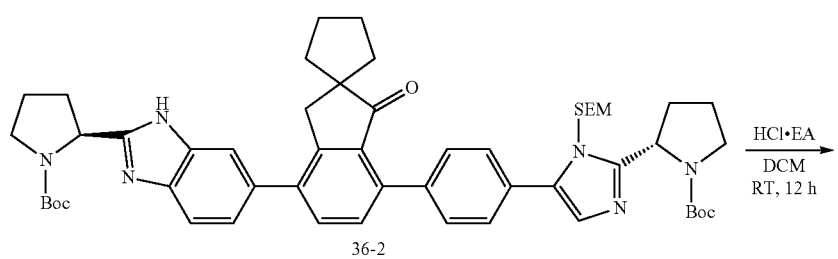

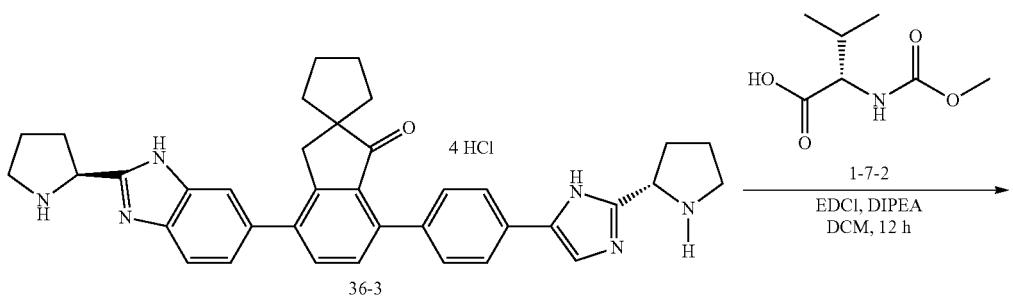

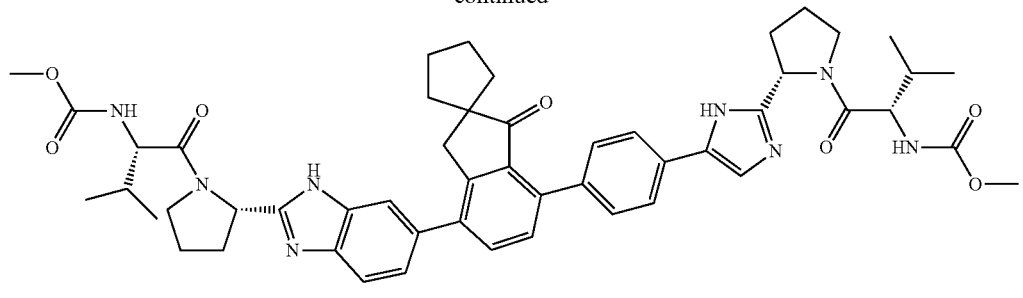

36-4

Step 1) The Preparation of Compound 36-1

The title compound 36-1 was prepared by an analogous procedure to that described for compound 17-7 (Example 17). The compound was characterized by the following spectroscopic data:

MS-ESI: m/z 776.2 [M+H]$^+$; and $^1$H NMR (400 MHz, CDCl$_3$): δ 7.80 (m, 2H), 7.30-7.50 (m, 4H), 7.13 (s, 1H), 5.80 (br, 1H), 5.35 (br, 1H), 5.15 (br, 1H), 3.45 (m, 2H), 3.05 (s, 2H), 2.12-2.25 (br, 2H), 1.72-1.96 (m, 6H), 1.57-1.63 (m, 2H), 1.40 (br, 4H), 1.26 (s, 9H), 0.89-0.93 (m, 2H), 0.05 (s, 9H).

Step 2) The Preparation of Compound 36-2

To a mixture of anhydrous potassium carbonate (37.5 mg, 0.271 mmol) and Pd(PPh$_3$)$_4$ (6.3 mg, 0.00545 mmol) in a 25 mL of two-necked flask under N$_2$ was added a solution of compound 36-1 (84.3 mg, 0.1086 mmol) and compound 3-3-2 (53.9 mg, 0.1304 mmol) in DME (4 mL) followed by distilled water (1 mL). After the mixture was stirred at 90° C. for 1 hour, DME was removed in vacuo and distilled water (15 mL) was added. The mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (PE/EtOAc (v/v)=1/2) to give the title compound 36-2 as a yellow solid (87.4 mg, 88.1%, HPLC: 95.0%). The compound was characterized by the following spectroscopic data:

MS-ESI: m/z 457.3 [M+2H]$^{2+}$; and $^1$H NMR (400 MHz, CDCl$_3$): δ 10.81 (br, 1H), 7.88 (br, 1H), 7.84 (br, 2H), 7.63 (br, 1H), 7.50-7.54 (m, 3H), 7.39 (br, 1H), 7.34 (br, 1H), 7.18 (s, 1H), 5.85 (br, 1H), 5.43 (br, 1H), 5.19 (br, 2H), 3.54 (m, 2H), 3.00 (s, 2H), 2.21-2.25 (m, 4H), 1.93-2.05 (m, 4H), 1.85 (br, 2H), 1.53 (br, 6H), 1.43 (br, 4H), 1.26 (s, 18H), 0.88-0.92 (m, 2H), 0.07 (s, 9H).

Step 3) The Preparation of Compound 36-3

To a solution of compound 36-2 (55.6 mg, 0.0609 mmol) in CH$_2$Cl$_2$ (6 mL) was added a solution of HCl in EtOAc (4 M, 3.5 mL). The reaction mixture was stirred at rt for 12 hours and filtered. The filter cake was washed with EtOAc (10 mL) to give the title compound 36-3 as a yellow solid (42.1 mg, 94.9%, HPLC: 100%). The compound was characterized by the following spectroscopic data:

MS-ESI: m/z 583.4 [M−4HCl+H]$^+$; and $^1$H NMR (400 MHz, CD$_3$OD): δ 8.11 (s, 1H), 7.89-7.93 (m, 4H), 7.79 (br, 1H), 7.72 (br, 1H), 7.66 (br, 2H), 7.50 (br, 1H), 5.22-5.28 (m, 2H), 3.60-3.66 (m, 4H), 3.16 (s, 2H), 2.74-2.77 (m, 2H), 2.56-2.59 (m, 2H), 2.39-2.42 (m, 2H), 2.28-2.31 (m, 2H), 1.92-1.97 (m, 2H), 1.85 (br, 2H), 1.74-1.77 (m, 2H), 1.63-1.69 (m, 2H).

Step 4) The Preparation of Compound 36-4

To a solution of compound 36-3 (0.0401 g, 0.055 mmol), compound 1-7-2 (0.029 g, 0.1655 mmol) and EDCI (0.0423 g, 0.221 mmol) in DCM (8 mL) was added dropwise DIPEA (0.1 mL, 0.605 mmol) in an ice bath. After the mixture was stirred at rt overnight, H$_2$O (20 mL) was added. Then the mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (EtOAc/MeOH (v/v)=60/1) to give the title compound 36-4 as a yellow solid (0.0462 g, 93.6%, HPLC: 98.1%). The compound was characterized by the following spectroscopic data:

MS-ESI: m/z 449.3 [M+2H]$^{2+}$; and $^1$H NMR (400 MHz, CDCl$_3$): δ 10.83 (br, 1H), 10.45 (br, 1H), 7.82-7.84 (m, 2H), 7.49-7.54 (m, 5H), 7.33-7.35 (m, 3H), 5.45-5.46 (m, 2H), 5.25-5.35 (m, 2H), 4.92-5.07 (m, 2H), 4.34-4.36 (m, 2H), 3.85-3.95 (m, 2H), 3.72 (s, 3H), 3.70 (s, 3H), 3.09 (s, 2H), 1.91-2.40 (m, 10H), 1.65-1.78 (m, 8H), 0.88-0.90 (m, 12H).

Example 37

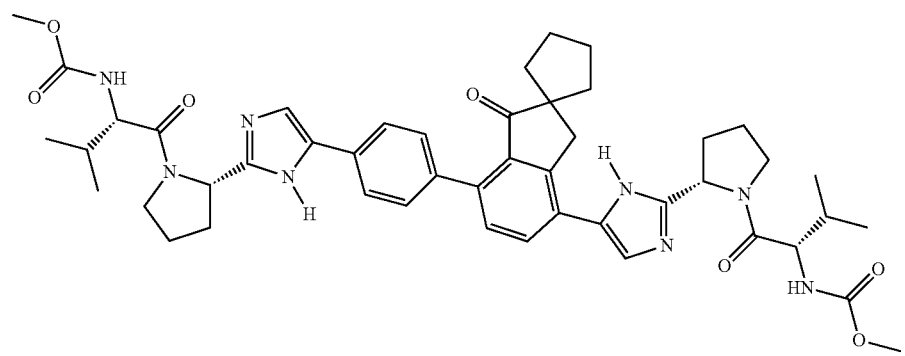

Synthetic Routes

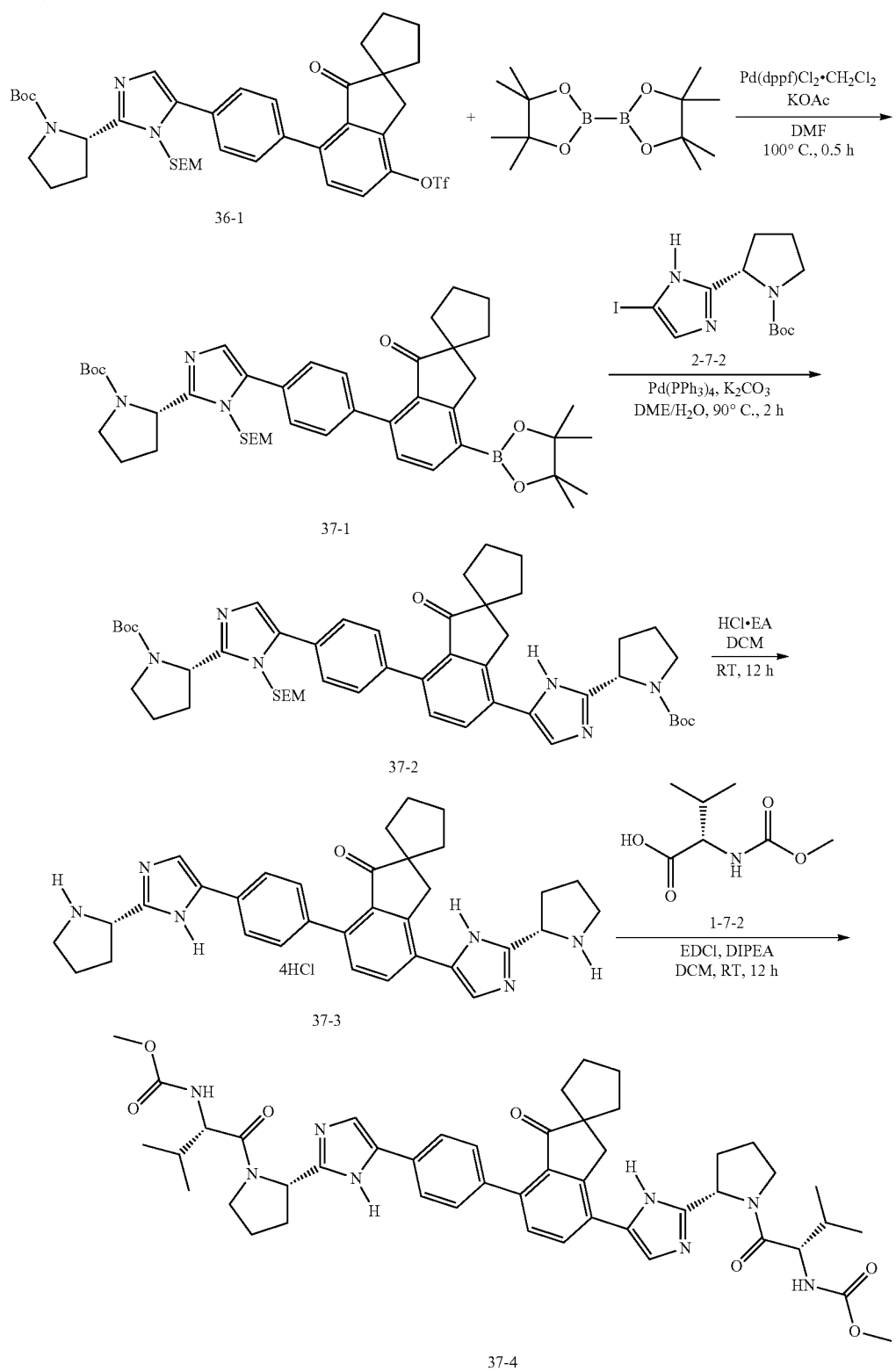

Step 1) The Preparation of Compound 37-1

A solution of compound 36-1 (0.0739 g, 0.0952 mmol), bis(pinacolato)diboron (0.0726 g, 0.286 mmol), Pd(dppf)Cl$_2$·CH$_2$Cl$_2$ (0.0078 g, 0.00955 mmol) and KOAc (0.0374 g, 0.381 mmol) in anhydrous DMF (10 mL) under N$_2$ was stirred at 100° C. for 0.5 hour. After DMF was removed, H$_2$O (20 mL) was added and the mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (PE/EtOAc (v/v)=3/1) to give the title compound 37-1 as a yellow solid (0.06 g, 83.6%, HPLC:

85.0%). The compound was characterized by the following spectroscopic data:

MS-ESI: m/z 754.4 [M+H]$^+$; and $^1$H NMR (400 MHz, CDCl$_3$): δ 8.02 (d, J=7.5 Hz, 1H), 7.79-7.81 (m, 2H), 7.46 (m, 2H), 7.28 (d, J=7.5 Hz, 1H), 7.17 (s, 1H), 5.85 (br, 1H), 5.35 (br, 1H), 5.21 (br, 1H), 3.53 (m, 2H), 3.26 (s, 2H), 2.19-2.31 (m, 2H), 1.90-1.99 (m, 2H), 1.78-1.88 (m, 4H), 1.65 (m, 2H), 1.43 (m, 4H), 1.39 (s, 12H), 1.25 (s, 9H), 0.87-0.93 (m, 2H), 0.07 (s, 9H).

Step 2) The Preparation of Compound 37-2

To a mixture of anhydrous potassium carbonate (0.055 g, 0.398 mmol) and Pd(PPh$_3$)$_4$ (0.0092 g, 0.00796 mmol) in a 25 mL of two-ports flask under N$_2$ was added a solution of compound 37-1 (0.12 g, 0.159 mmol) and compound 2-7-2 (0.1157 g, 0.318 mmol) in DME (12 mL) followed by distilled water (3 mL). After the mixture was stirred at 90° C. under N$_2$ for 2 hours, DME was removed in vacuo and distilled water (25 mL) was added. The mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (PE/EtOAc (v/v)=1/2) to give the title compound 37-2 as a yellow solid (0.0847 g, 61.6%, HPLC: 90.0%). The compound was characterized by the following spectroscopic data:

MS-ESI: m/z 432.3 [M+2H]$^{2+}$; and $^1$H NMR (400 MHz, CDCl$_3$): δ 8.21 (br, 1H), 7.81 (br, 2H), 7.69-7.74 (m, 1H), 7.52-7.55 (m, 1H), 7.47 (br, 2H), 7.24 (s, 1H), 7.17 (s, 1H), 5.85 (m, 1H), 5.34-5.41 (m, 1H), 5.21 (m, 2H), 3.52-3.56 (m, 2H), 3.19 (s, 2H), 2.17-2.19 (m, 4H), 2.00-2.06 (m, 4H), 1.88 (m, 4H), 1.80 (m, 4H), 1.42 (m, 4H), 1.25 (s, 18H), 0.88 (m, 2H), 0.07 (s, 9H).

Step 3) The Preparation of Compound 37-3

To a solution of compound 37-2 (84.7 mg, 0.0981 mmol) in CH$_2$Cl$_2$ (2 mL) was added a solution of HCl in EtOAc (4 M, 5 mL). The reaction mixture was stirred at rt for 12 hours and filtered. The filter cake was washed with EtOAc to give the title compound 37-3 as a yellow solid (63 mg, 94.9%, HPLC: 100%). The compound was characterized by the following spectroscopic data:

MS-ESI: m/z 267.2 [M−4HCl+2H]$^{2+}$; and $^1$H NMR (400 MHz, CD$_3$OD): δ 8.16 (d, J=7.8 Hz, 1H), 8.07 (s, 1H), 7.92 (m, 2H), 7.88 (s, 1H), 7.63 (m, 2H), 7.51 (d, J=7.8 Hz, 1H), 5.14-5.23 (m, 2H), 3.57-3.65 (m, 4H), 3.00 (s, 2H), 2.67-2.76 (m, 2H), 2.51-2.60 (m, 2H), 2.38-2.43 (m, 2H), 2.21-2.29 (m, 2H), 1.93-1.98 (m, 2H), 1.89-1.90 (m, 4H), 1.70-1.73 (m, 2H).

Step 4) The Preparation of Compound 37-4

To a solution of compound 37-3 (0.075 g, 0.111 mmol), compound 1-7-2 (0.0583 g, 0.333 mmol) and EDCI (0.0851 g, 0.444 mmol) in DCM (5 mL) was added dropwise DIPEA (0.2 mL, 1.21 mmol) slowly. After the mixture was stirred at rt for 12 hours, water (20 mL) was added. Then the mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (EtOAc/MeOH (v/v)=60/1) to give the title compound 37-4 as a yellow solid (0.086 g, 91.8%, HPLC: 96.1%). The compound was characterized by the following spectroscopic data:

MS-ESI: m/z 424.3 [M+2H]$^{2+}$; and $^1$H NMR (400 MHz, CDCl$_3$): δ 10.78 (br, 1H), 10.51 (br, 1H), 8.25 (br, 1H), 7.81 (br, 1H), 7.51-7.54 (m, 1H), 7.45-7.47 (m, 3H), 7.31-7.35 (m, 1H), 7.21 (s, 1H), 5.42-5.48 (m, 2H), 5.24-5.34 (m, 2H), 4.30-4.34 (m, 2H), 3.82-3.85 (m, 2H), 3.71 (s, 6H), 3.62-3.68 (m, 2H), 3.20 (s, 2H), 1.90-2.35 (m, 10H), 1.67-1.79 (m, 8H), 0.98 (m, 12H).

Example 38

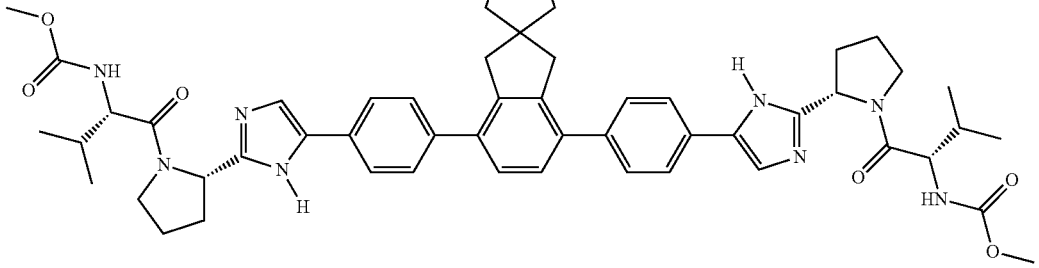

Synthetic Routes

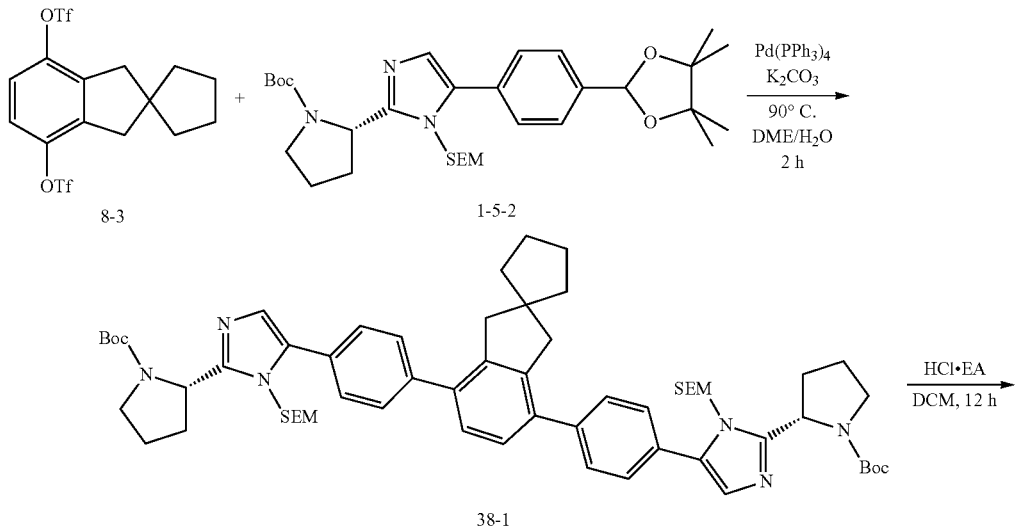

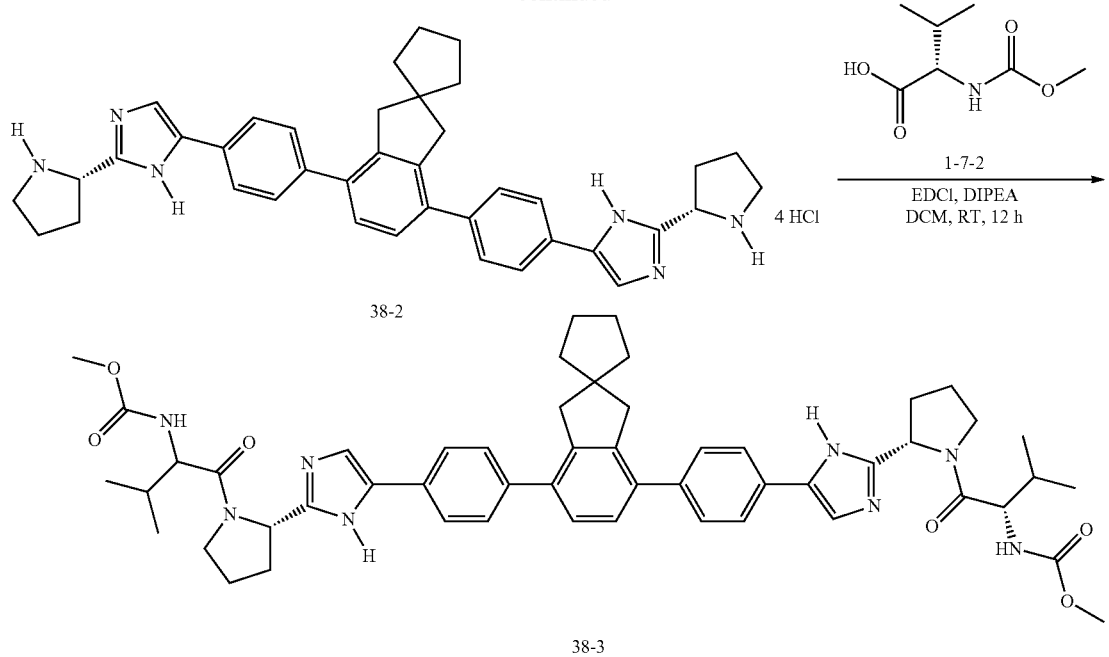

Compounds disclosed herein can be prepared by an analogous procedure to that described in Example 1.

Compound 38-1 was characterized by the following spectroscopic data:

MS-ESI: m/z 528.7 [M+2H]$^{2+}$; and $^1$H NMR (400 MHz, CDCl$_3$): δ 7.83 (d, J=8.3 Hz, 4H), 7.48 (d, J=8.3 Hz, 4H), 7.30 (s, 2H), 7.18 (s, 2H), 5.40-5.43 (m, 2H), 5.22 (br, 2H), 4.93-5.02 (m, 2H), 3.65-3.73 (m, 4H), 3.52-3.56 (m, 4H), 2.99 (s, 4H), 1.89-2.24 (m, 8H), 1.61-1.62 (m, 8H), 1.25 (s, 18H), 0.88-0.94 (m, 4H), 0.07 (s, 18H).

Compound 38-2 was characterized by the following spectroscopic data:

MS-ESI: m/z 595.6 [M−4HCl+H]$^+$; and $^1$H NMR (400 MHz, CD$_3$OD): δ 8.08 (s, 2H), 7.93 (d, J=8.4 Hz, 4H), 7.67 (d, J=8.4 Hz, 4H), 7.36 (s, 2H), 5.21-5.24 (m, 2H), 3.60-3.63 (m, 4H), 3.01 (s, 4H), 2.72-2.75 (m, 2H), 2.59-2.61 (m, 2H), 2.41-2.42 (m, 2H), 2.21-2.27 (m, 2H), 1.58-1.65 (m, 8H).

Compound 38-3 was characterized by the following spectroscopic data:

MS-ESI: m/z 455.3 [M+2H]$^{2+}$; and $^1$H NMR (400 MHz, CDCl$_3$): δ 10.50 (br, 2H), 7.75 (br, 4H), 7.49 (br, 4H), 7.30 (s, 2H), 7.17 (s, 2H), 5.46 (br, 2H), 5.26-5.29 (m, 2H), 4.32-4.34 (m, 2H), 3.81-3.88 (m, 2H), 3.74 (s, 6H), 3.67-3.70 (m, 2H), 2.98 (s, 4H), 2.38-2.40 (m, 2H), 2.22-2.29 (m, 2H), 1.93-2.18 (m, 6H), 1.55-1.68 (m, 8H), 0.88 (br, 12H).

Example 39

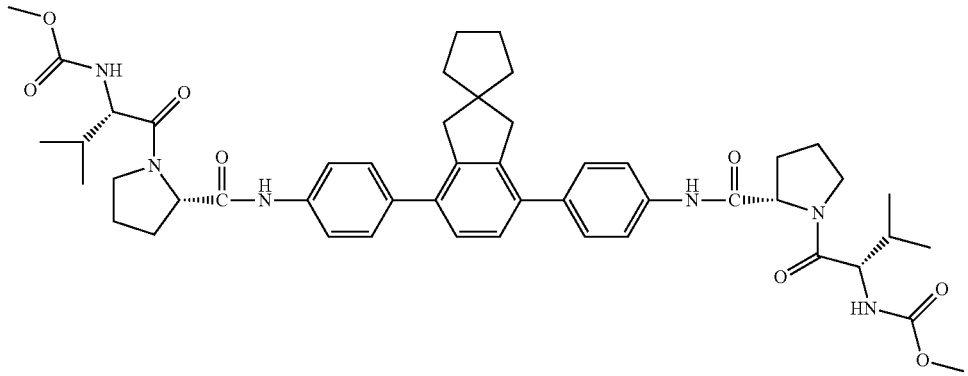

Synthetic Routes

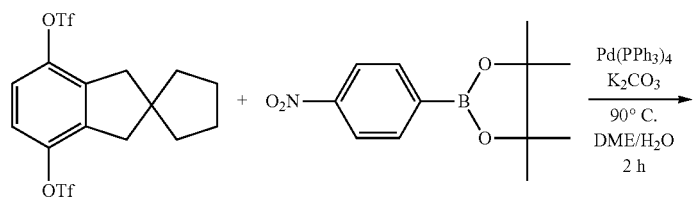

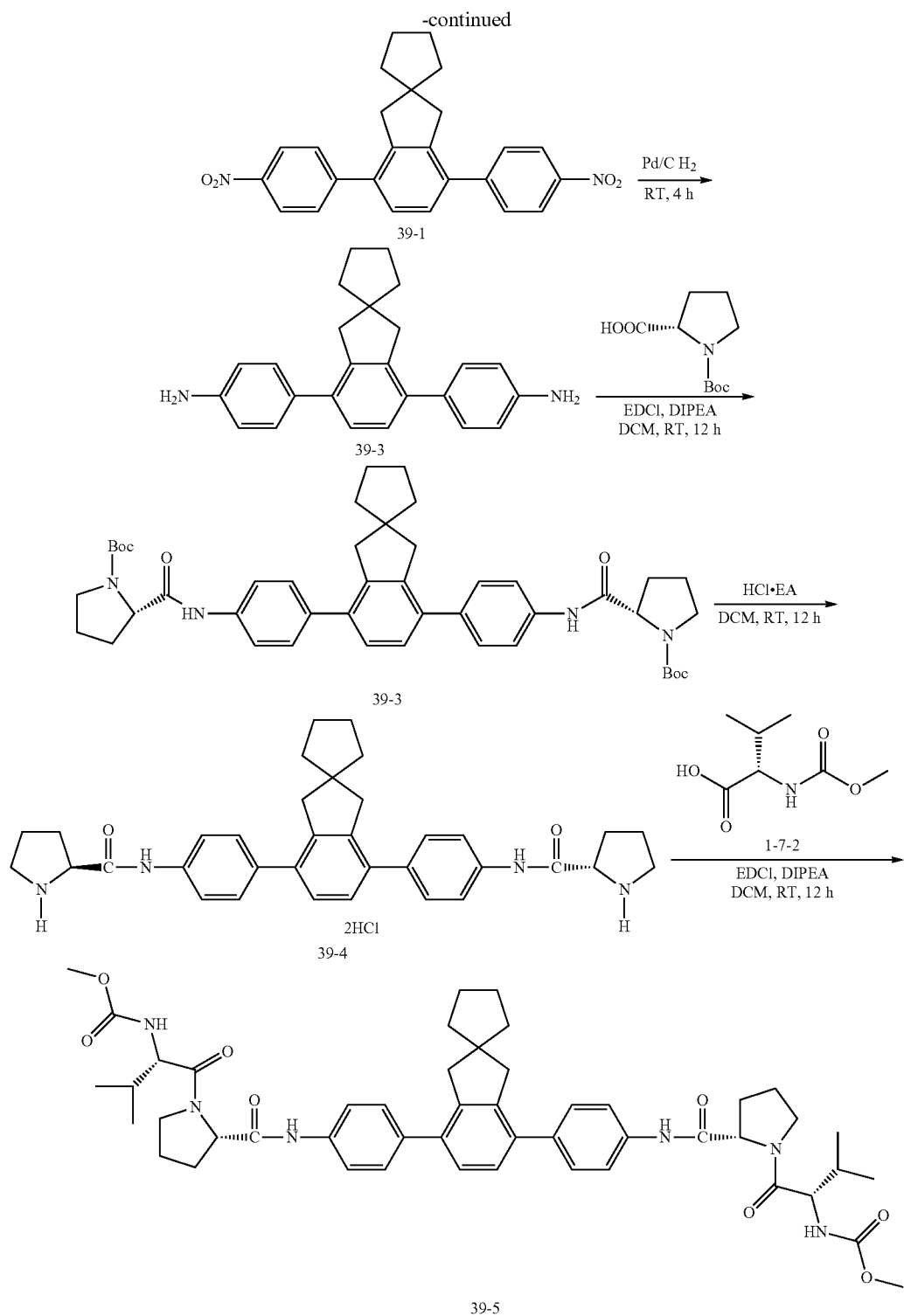

Step 1) The Preparation of Compound 39-1

To a mixture of 4,4,5,5-tetramethyl-2-(4-nitrophenyl)-1,3,2-dioxaborolane (0.38 g, 1.526 mmol), anhydrous potassium carbonate (0.4786 g, 3.463 mmol) and Pd(PPh$_3$)$_4$ (0.0801 g, 0.0693 mmol) in a 50 mL of two-necked flask under N$_2$ was added a solution of compound 8-3 (0.3246 g, 0.693 mmol) in DME (8 mL) followed by distilled water (2 mL). The mixture was stirred at 90° C. under N$_2$ for 2 hours and DME was removed in vacuo. To the residue was added distilled water (15 mL), and the mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (PE/EtOAc (v/v)=50/1) to give the title compound 39-1 as a yellow solid (0.273 g, 95.1%, HPLC: 95%). The compound was characterized by the following spectroscopic data:

MS-ESI: m/z 415.1 [M+H]$^+$; and

¹H NMR (400 MHz, CDCl₃): δ 8.31-8.33 (m, 4H), 7.62-7.64 (m, 4H), 7.34 (s, 2H), 2.97 (s, 4H), 1.56 (s, 8H).

Step 2) The Preparation of Compound 39-2

To a solution of compound 39-1 (0.27 g, 0.651 mmol) in mixed solvents of DCM (10 mL) and MeOH (15 mL) was added Pd/C (0.2 g). The mixture was stirred at rt for 4 hours under H₂, and then Pd/C was filtered off. The filtrate was concentrated in vacuo to give the title compound 39-2 as a white solid (0.221 g, 95.7%, HPLC: 100%). The compound was characterized by the following spectroscopic data:

MS-ESI: m/z 355.3 [M+H]⁺; and

¹H NMR (400 MHz, CDCl₃): δ 7.27-7.30 (m, 4H), 7.22 (s, 2H), 6.74-6.76 (m, 4H), 3.65 (br, 4H), 2.97 (s, 4H), 1.57 (s, 8H).

Step 3) The Preparation of Compound 39-3

To a solution of compound 39-2 (0.12 g, 0.339 mmol), Boc-L-proline (0.2186 g, 1.016 mmol) and EDCI (0.2599 g, 1.356 mmol) in DCM (10 mL) was added dropwise DIPEA (0.336 mL, 2.033 mmol) slowly. After the mixture was stirred at rt for 12 hours, water (20 mL) was added. Then the mixture was extracted with CH₂Cl₂ (25 mL×3). The combined organic phases were dried over anhydrous Na₂SO₄ and filtered. The filtrate was concentrated in vacuo and the residue was purified by silica gel column chromatography (PE/EtOAc (v/v)=1/1) to give the title compound 39-3 as a white solid (0.2058 g, 81.2%, HPLC: 95.0%). The compound was characterized by the following spectroscopic data:

MS-ESI: m/z 649.3 [M−99]⁺; and

¹H NMR (400 MHz, CDCl₃): δ 9.54 (br, 2H), 7.57-7.59 (m, 4H), 7.41-7.43 (m, 4H), 7.24 (s, 2H), 4.49 (br, 2H), 3.44 (br, 4H), 2.95 (s, 4H), 1.95 (br, 4H), 1.59 (br, 12H), 1.51 (s, 18H).

Step 4) The Preparation of Compound 39-4

To a solution of compound 39-3 (0.095 g, 0.1268 mmol) in CH₂Cl₂ (5 mL) was added a solution of HCl in EtOAc (4 M, 5 mL). The reaction mixture was stirred at rt for 12 hours and filtered. The filter cake was washed with EtOAc to give the title compound 39-4 as a white solid (0.0684 g, 86.8%, HPLC: 96.8%). The compound was characterized by the following spectroscopic data:

MS-ESI: m/z 275.3 [M−2HCl+2H]²⁺; and

¹H NMR (400 MHz, CD₃OD): δ 7.68-7.70 (m, 4H), 7.45-7.47 (m, 4H), 7.25 (s, 2H), 4.42-4.46 (m, 2H), 3.48-3.51 (m, 2H), 3.39-3.42 (m, 2H), 2.95 (s, 4H), 2.54-2.60 (m, 2H), 2.12-2.17 (m, 6H), 1.62-1.65 (m, 4H), 1.57 (m, 4H).

Step 5) The Preparation of Compound 39-5

To a solution of compound 39-4 (0.1124 g, 0.181 mmol), compound 1-7-2 (0.0952 g, 0.543 mmol) and EDCI (0.139 g, 0.725 mmol) in DCM (10 mL) was added dropwise DIPEA (0.3 mL, 1.815 mmol) slowly in an ice bath. After the mixture was stirred at rt for 12 hours, water (20 mL) was added. Then the mixture was extracted with CH₂Cl₂ (25 mL×3). The combined organic phases were dried over anhydrous Na₂SO₄ and filtered. The filtrate was concentrated in vacuo and the residue was purified by silica gel column chromatography (EtOAc/MeOH (v/v)=60/1) to give the title compound 39-5 as a white solid (0.1496 g, 95.8%, HPLC: 93.2%). The compound was characterized by the following spectroscopic data:

MS-ESI: m/z 863.3 [M+H]⁺; and

¹H NMR (400 MHz, CDCl₃): δ 9.41 (s, 2H), 7.50-7.52 (br, 4H), 7.33-7.36 (br, 4H), 7.14 (s, 2H), 5.41-5.43 (m, 2H), 4.81-4.84 (m, 2H), 4.35-4.39 (m, 2H), 3.80 (m, 2H), 3.70 (s, 6H), 3.64-3.67 (m, 2H), 2.92 (s, 4H), 2.54-2.57 (m, 2H), 2.21 (m, 2H), 2.06-2.09 (m, 2H), 1.93 (m, 2H), 1.51 (br, 4H), 1.26 (m, 4H), 0.97-1.02 (m, 12H).

Example 40

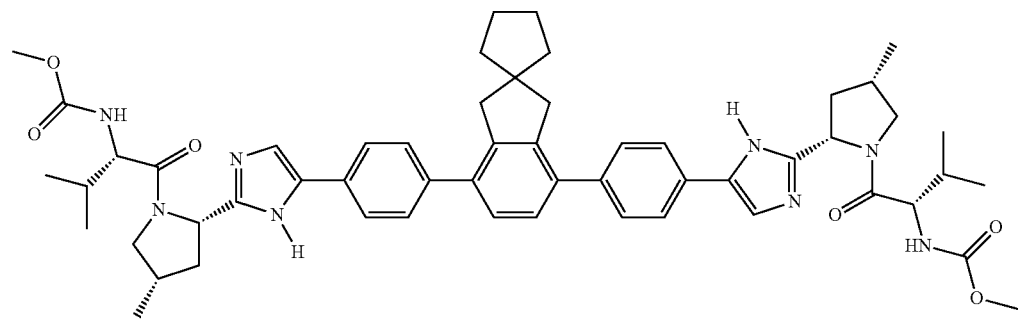

Synthetic Routes

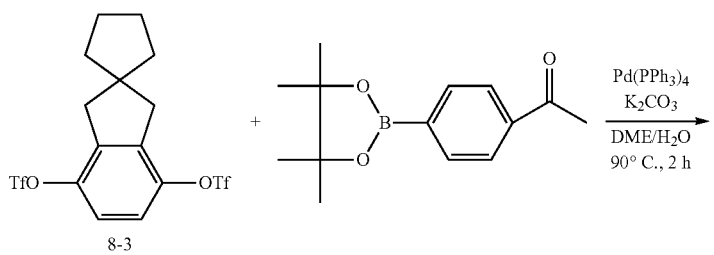

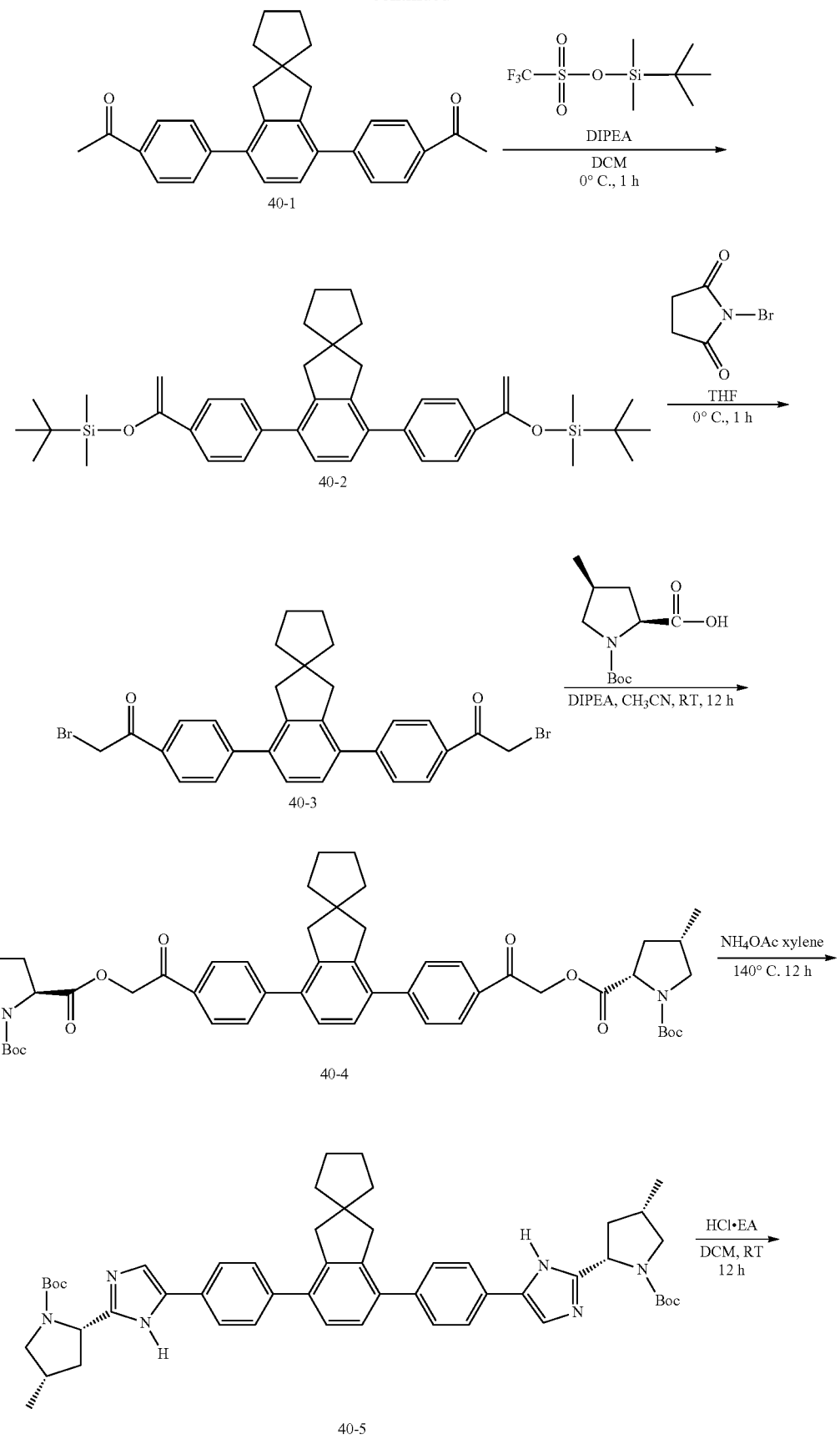

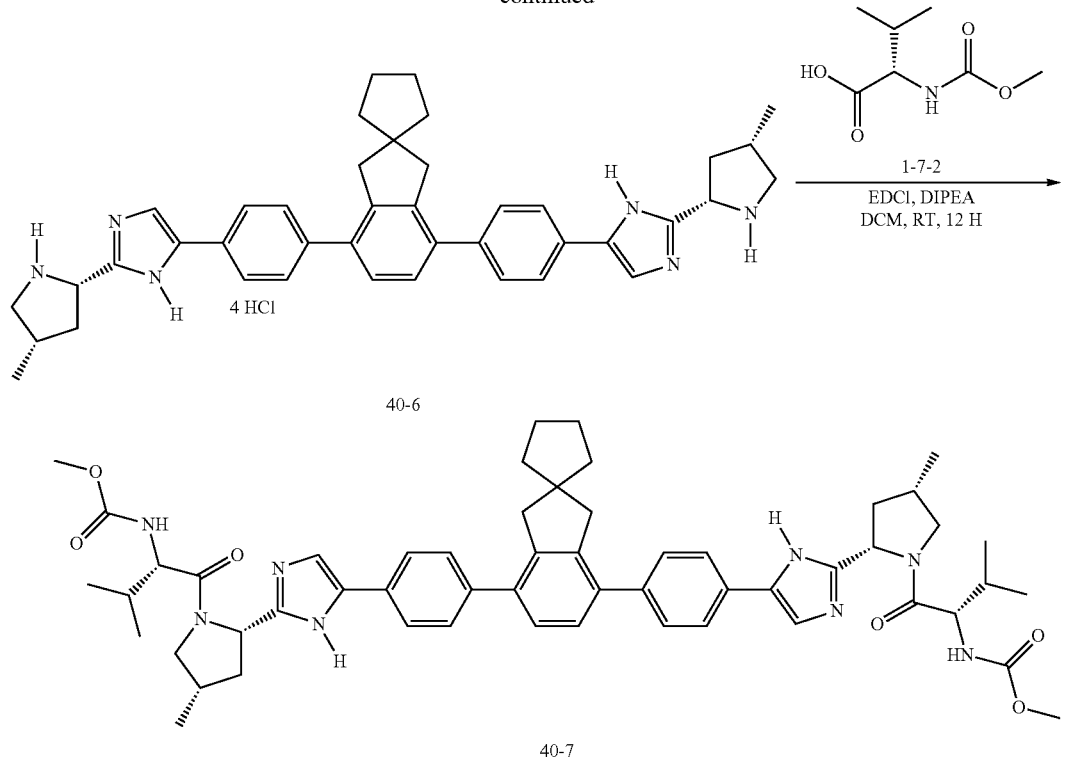

Step 1) The Preparation of Compound 40-1

To a mixture of 1-(4-(4,4,5,5-tetramethyl-1,3,2-dioxaborolan-2-yl)phenyl)ethanone (0.9937 g, 4.04 mmol), anhydrous potassium carbonate (1.267 g, 9.17 mmol) and Pd(PPh$_3$)$_4$ (0.212 g, 0.183 mmol) in a 50 mL of two-necked flask under N$_2$ was added a solution of compound 8-3 (0.8593 g, 1.835 mmol) in DME (16 mL) followed by distilled water (4 mL). The mixture was stirred at 90° C. under N$_2$ for 2 hours. DME was removed in vacuo and distilled water (15 mL) was added, the mixture was extracted with CH$_2$Cl$_2$ (25 mL×3). The combined organic phases were dried over anhydrous Na$_2$SO$_4$ and concentrated in vacuo. The residue was purified by silica gel column chromatography (PE/EtOAc (v/v)=5/1) to give the title compound 40-1 as a white solid (0.68 g, 90.8%, HPLC: 95%). The compound was characterized by the following spectroscopic data:

MS-ESI: m/z 409.2 [M+H]$^+$; and $^1$H NMR (400 MHz, CDCl$_3$): δ 8.05 (d, J=8.3 Hz, 4H), 7.58 (d, J=8.3 Hz, 4H), 7.33 (s, 2H), 2.98 (s, 4H), 2.66 (s, 6H), 1.56-1.64 (m, 8H).

Step 2) The Preparation of Compound 40-2

To a solution of compound 40-1 (0.39 g, 0.955 mmol) and DIPEA (0.563 mL, 3.822 mmol) in CH$_2$Cl$_2$ (20 mL) was added TBDMSOTf (0.7571 g, 2.864 mmol) in an ice bath. After the mixture was stirred for 1 hour, water (20 mL) was added. Then the mixture was extracted with CH$_2$Cl$_2$ (25 mL×3). The combined organic phases were dried over anhydrous Na$_2$SO$_4$ and filtered. The filtrate was concentrated in vacuo to give the title compound 40-2 as a yellow solid. The crude product was used for the next step without further purification.

Step 3) The Preparation of Compound 40-3

To a solution of compound 40-2 (0.609 g, 0.956 mmol) in THF (10 mL) was added dropwise a solution of NBS (0.3404 g, 1.912 mmol) in THF (10 mL) slowly in the ice bath. After the mixture was stirred for 1 hour, water (20 mL) was added. Then the mixture was extracted with EtOAc (25 mL×3). The combined organic phases were dried over anhydrous Na$_2$SO$_4$ and filtered. The filtrate was concentrated in vacuo and the residue was purified by silica gel column chromatography (PE/EtOAc (v/v)=10/1) to give the title compound 40-3 as a white solid (0.52 g, 96.1%, HPLC: 95%). The compound was characterized by the following spectroscopic data:

$^1$H NMR (400 MHz, CDCl$_3$): δ 8.08 (d, J=8.3 Hz, 4H), 7.60 (d, J=8.3 Hz, 4H), 7.34 (s, 2H), 4.50 (s, 4H), 2.98 (s, 4H), 1.58-1.62 (m, 8H).

Step 4) The Preparation of Compound 40-4

To a solution of compound 40-3 (0.3072 g, 0.542 mmol) and (2R,4S)-1-(tert-butoxycarbonyl)-4-methylpyrrolidine-2-carboxylic acid (0.3118 g, 1.36 mmol) in CH$_3$CN was added dropwise DIPEA (0.1759 g, 1.361 mmol) slowly in an ice bath. The mixture was stirred at rt for 12 hours and concentrated in vacuo. The residue was purified by silica gel column chromatography (PE/EtOAc (v/v)=3/1) to give the title compound 40-4 as a white solid (0.4089 g, 87.4%, HPLC: 100%). The compound was characterized by the following spectroscopic data:

MS-ESI: m/z 763.8 [M−99]$^+$; and $^1$H NMR (400 MHz, CDCl$_3$): δ 7.98-8.01 (m, 4H), 7.58-7.61 (m, 4H), 7.33 (s, 2H), 5.24-5.66 (m, 4H), 4.37-4.46 (m, 2H), 3.68-3.82 (m, 2H), 3.01-3.06 (m, 2H), 2.97 (s, 4H), 2.54-2.61 (m, 2H), 2.25-2.33 (m, 2H), 1.85-1.93 (m, 2H), 1.56-1.63 (m, 8H), 1.47, 1.44 (s, 18H), 1.11-1.13 (m, 6H).

Step 5) The Preparation of Compound 40-5

To a solution of compound 40-4 (0.102 g, 0.102 mmol) in xylene (15 mL) was added NH$_4$OAc (0.6934 g, 9.0 mmol). The mixture was heated at 140° C. for 12 hours in a sealed tube and concentrated in vacuo. To the residue was added H₂O (20 mL). The mixture was extracted with CH₂Cl₂ (25 mL×3). The combined organic phases were dried over anhydrous Na₂SO₄ and filtered. The filtrate was concentrated in vacuo and the residue was purified by silica gel column chromatography (CH₂Cl₂/MeOH (v/v)=60/1) to give the title compound 41-5 as a yellow solid (0.2577 g, 69.5%, HPLC: 99.5%). The compound was characterized by the following spectroscopic data:

MS-ESI: m/z 412.3 [M+2H]²⁺; and

¹H NMR (400 MHz, CDCl₃): δ 10.48 (br, 2H), 7.78 (m, 4H), 7.48-7.52 (m, 4H), 7.32 (s, 2H), 7.28 (s, 2H), 4.97-4.99 (m, 2H), 3.79 (m, 2H), 3.00 (s, 4H), 2.88-2.91 (m, 2H), 2.61-2.67 (m, 2H), 2.51-2.52 (m, 2H), 2.24-2.32 (m, 2H), 1.56-1.62 (m, 8H), 1.50, 1.46 (s, 18H), 1.13 (d, J=6.2 Hz, 6H).

Step 6) The Preparation of Compound 40-6

To a solution of compound 40-5 (0.081 g, 0.0984 mmol) in CH₂Cl₂ (3 mL) was added a solution of HCl in EtOAc (4 M, 2 mL). The reaction mixture was stirred at rt for 12 hours and filtered. The filter cake was washed with EtOAc to give the title compound 40-6 as a yellow solid (0.0704 g, 93.1%, HPLC: 95%). The compound was characterized by the following spectroscopic data:

MS-ESI: m/z 312.3 [M−4HCl+2H]²⁺; and

¹H NMR (400 MHz, CD₃OD): δ 8.12 (s, 2H), 7.96 (d, J=7.6 Hz, 4H), 7.68 (d, J=7.6 Hz, 4H), 7.36 (s, 2H), 5.27-5.31 (m, 2H), 3.65-3.74 (m, 2H), 3.19-3.25 (m, 2H), 3.01 (s, 4H), 2.75-2.84 (m, 2H), 2.60-2.69 (m, 2H), 2.31-2.35 (m, 2H), 1.58-1.65 (m, 8H), 1.12-1.19 (m, 6H).

Step 7) The Preparation of Compound 40-7

To a solution of compound 40-6 (0.1561 g, 0.203 mmol), compound 1-7-2 (0.1071 g, 0.611 mmol) and EDCI (0.1563 g, 0.815 mmol) in DCM (7 mL) was added dropwise DIPEA (0.4 mL, 2.4 mmol) slowly in an ice bath. After the mixture was stirred at rt for 12 hours, water (20 mL) was added. The mixture was extracted with CH₂Cl₂ (25 mL×3). The combined organic phases were dried over anhydrous Na₂SO₄ and filtered. The filtrate was concentrated in vacuo and the residue was purified by silica gel column chromatography (CH₂Cl₂/MeOH (v/v)=60/1) to give the title compound 40-7 as a yellow solid (0.1253 g, 65.8%, HPLC: 90.1%). The compound was characterized by the following spectroscopic data:

MS-ESI: m/z 469.3 [M+2H]²⁺; and

¹H NMR (400 MHz, CDCl₃): δ 10.60 (br, 2H), 7.70-7.73 (m, 4H), 7.47-7.52 (m, 4H), 7.32 (s, 2H), 7.18 (s, 2H), 5.46 (br, 2H), 5.21-5.36 (m, 4H), 3.88-4.08 (m, 2H), 3.70 (s, 6H), 3.12-3.33 (m, 2H), 2.98 (s, 4H), 2.65-2.75 (m, 2H), 2.49-2.54 (m, 2H), 2.20-2.29 (m, 2H), 1.55-1.66 (m, 8H), 1.11-1.18 (m, 6H), 0.85-0.98 (m, 12H).

Example 41

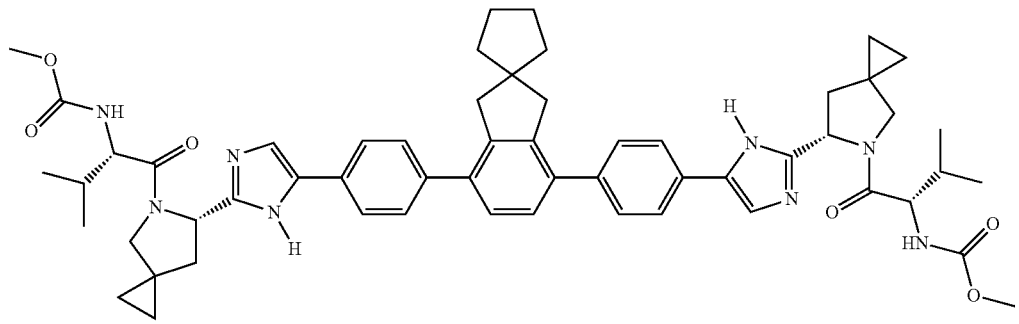

Synthetic Routes

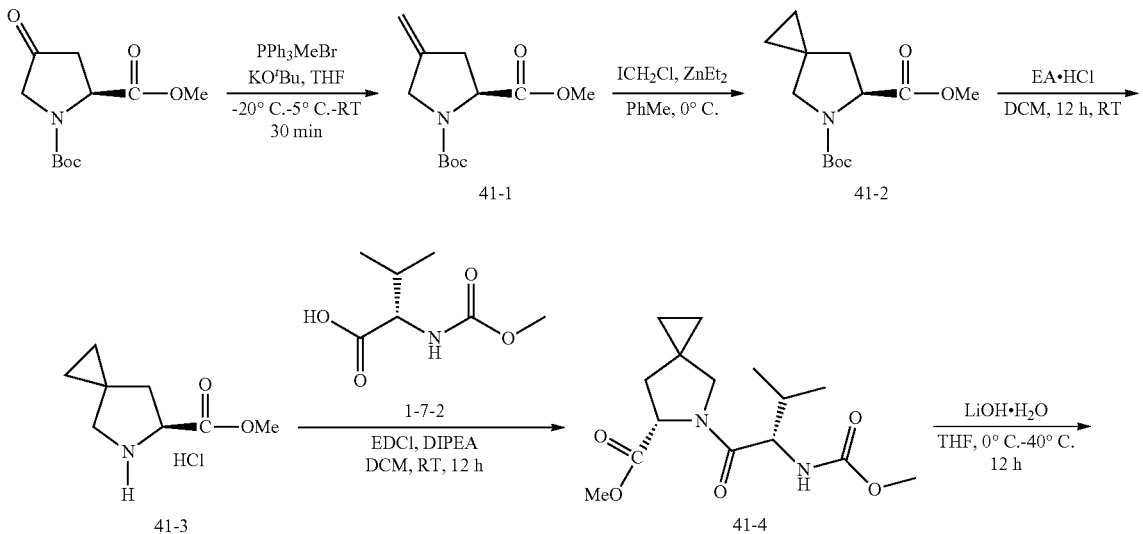

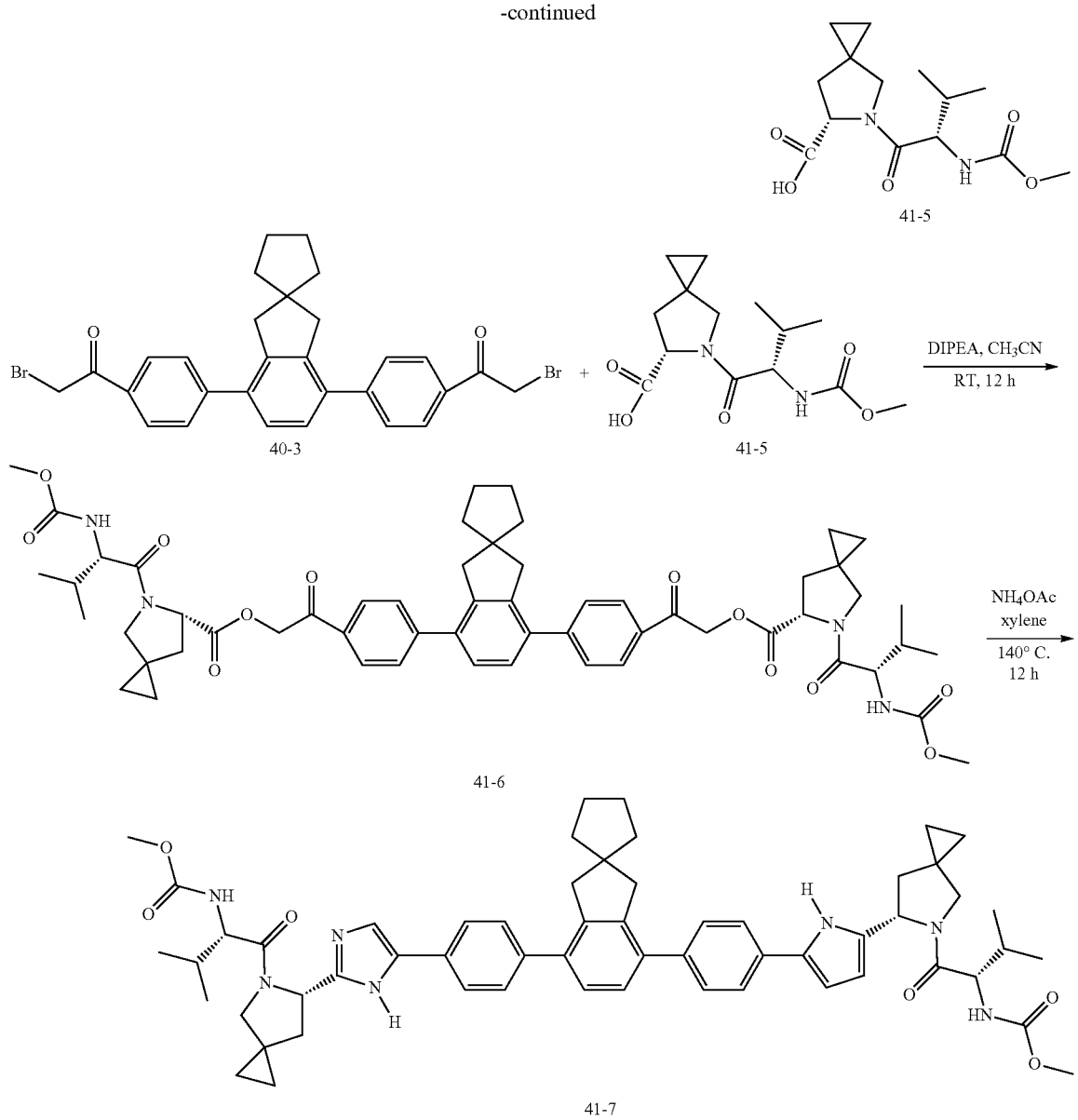

Step 1) The Preparation of Compound 41-1

PPh₃MeBr (5.05 g, 14.2 mmol) in a round-bottomed flask was cooled to −20° C., then to which was added potassium tert-butanolate (14.9 mL, 1.0 M in THF, 14.9 mmol). The mixture was stirred at −5° C. for 30 minutes. To the mixture was added compound 8-1 (1.72 g, 7.07 mmol). The mixture was stirred at rt until the reaction was completed as monitored by TLC. The mixture was quenched with H₂O (10 mL) and extracted with EtOAc (100 mL×3). The combined organic phases were dried over anhydrous Na₂SO₄ and filtered. The filtrate was concentrated in vacuo and the residue was purified by silica gel column chromatography (PE/EtOAc (v/v)=5/1) to give the title compound 41-1 as pale yellow oil (1.07 g, 62.9%). The compound was characterized by the following spectroscopic data:

MS-ESI: m/z 242.12 [M+H]$^+$; and $^1$H NMR (400 MHz, DMSO-d$^6$): δ 5.01 (d, J=10.8 Hz, 2H), 4.36 (t, J=11.2 Hz, 1H), 3.95 (2s, 2H), 3.64 (2s, 3H), 3.01 (q, J=14.6 Hz, 1H), 2.57-2.50 (m, 1H), 1.38 (2s, 9H).

Step 2) The Preparation of Compound 41-2

To a solution of diethylzinc (2.297 g, 18.60 mmol) in toluene (30 mL) was added chloroiodomethane (6.569 g, 37.24 mmol) slowly in an ice bath. After the mixture was stirred for 45 minutes, a solution of compound 41-1 (1.5 g, 6.22 mmol) in toluene (15 mL) was added. The mixture was stirred at 0° C. for another 18 hours, then quenched with NH₄Cl saturated solution (20 mL) and extracted with EtOAc (25 mL×4). The combined organic phases were dried over anhydrous Na₂SO₄ for 1 hour and filtered. The filtrate was concentrated in vacuo and the residue was purified by silica gel column chromatography (PE/EtOAc (v/v)=10/1) to give the title compound 41-2 as white liquid (0.58 g, 36.5%, HPLC: 95%). The compound was characterized by the following spectroscopic data:

MS-ESI: m/z 156.2 [M−99]$^+$; and $^1$H NMR (400 MHz, CDCl₃): δ 4.33-4.47 (m, 1H), 3.71 (s, 3H), 3.29-3.37 (m, 2H), 2.17-2.25 (m, 1H), 1.75-1.86 (m, 1H), 1.44, 1.40 (s, s, 9H), 0.50-0.62 (m, 4H).

Step 3) The Preparation of Compound 41-3

To a solution of compound 41-2 (0.69 g, 2.7 mmol) in $CH_2Cl_2$ (6 mL) was added a solution of HCl in EtOAc (4 M, 10 mL). The reaction mixture was stirred at rt for 12 hours and concentrated in vacuo to give the title compound 41-3 as colorless oil (0.5 g, 96.5%, HPLC: 100%). The compound was characterized by the following spectroscopic data:

MS-ESI: m/z 156.2 [M−HCl+H]$^+$; and $^1$H NMR (400 MHz, $CD_3OD$): δ 4.62-4.66 (m, 1H), 4.44-4.45 (m, 1H), 3.86 (s, 3H), 3.60-3.61 (m, 1H), 2.34-2.39 (m, 1H), 2.14-2.19 (m, 1H), 1.46-1.49 (m, 1H), 1.16-1.19 (m, 1H), 0.87-0.88 (m, 1H), 0.79-0.81 (m, 1H).

Step 4) The Preparation of Compound 41-4

To a solution of compound 41-3 (0.53 g, 2.77 mmol), compound 1-7-2 (0.729 g, 4.16 mmol) and EDCI (1.063 g, 5.55 mmol) in DCM (20 mL) was added dropwise DIPEA (2.4 mL, 14.52 mmol) slowly in an ice bath. After the mixture was stirred at rt for 12 hours, water (20 mL) was added. The mixture was extracted with $CH_2Cl_2$ (25 mL×3). The combined organic phases were dried over anhydrous $Na_2SO_4$ and filtered. The filtrate was concentrated in vacuo and the residue was purified by silica gel column chromatography (PE/EtOAc (v/v)=1/1) to give the title compound 41-4 as white liquid (0.6067 g, 70.2%, HPLC: 100%). The compound was characterized by the following spectroscopic data:

MS-ESI: m/z 313.2 [M+H]$^+$; and $^1$H NMR (400 MHz, $CDCl_3$): δ 5.42-5.44 (br, 1H), 4.68-4.71 (m, 1H), 4.20-4.29 (m, 1H), 3.73 (s, 3H), 3.69-3.72 (m, 1H), 3.67 (s, 3H), 3.54-3.59 (m, 1H), 2.15-2.20 (m, 1H), 2.01-2.06 (m, 1H), 1.90-1.95 (m, 1H), 0.93-1.05 (m, 6H), 0.61-0.66 (m, 4H).

Step 5) The Preparation of Compound 41-5

To a solution of compound 41-4 (0.2 g, 0.64 mmol) in THF (10 mL) was added dropwise a solution of $LiOH \cdot H_2O$ (0.1346 g, 3.2 mmol) in $H_2O$ (5 mL) slowly in an ice bath. The mixture was stirred at 40° C. for 12 hours and concentrated in vacuo. To the residue was added $H_2O$ (10 mL). The mixture was extracted with EtOAc (25 mL×3). The aqueous phase was adjusted to pH 1 with HCl (10%) and extracted with EtOAc (25 mL×3). The combined organic phases were dried over anhydrous $Na_2SO_4$ and filtered. The filtrate was concentrated in vacuo to give the title compound 41-5 as a white solid (0.1581 g, 82.8%, HPLC: 95%). The compound was characterized by the following spectroscopic data:

MS-ESI: m/z 299.2 [M+H]$^+$; and $^1$H NMR (400 MHz, $CDCl_3$): δ 7.06 (br, 1H), 5.76 (br, 1H), 4.69-4.73 (m, 1H), 4.18-4.23 (m, 1H), 3.79 (d, J=9.7 Hz, 1H), 3.66 (s, 3H), 3.49 (d, J=9.7 Hz, 1H), 2.18-2.26 (m, 1H), 1.93-2.07 (m, 2H), 0.94-1.00 (m, 6H), 0.64-0.68 (m, 4H).

Step 6) The Preparation of Compound 41-6

To a solution of compound 41-5 (0.1136 g, 0.38 mmol) and compound 40-3 (0.1027 g, 0.181 mmol) in $CH_3CN$ (5 mL) was added dropwise DIPEA (0.083 mL, 0.504 mmol) slowly in an ice bath. The mixture was stirred at rt for 12 hours and concentrated in vacuo. The residue was purified by silica gel column chromatography (PE/EtOAc (v/v)=1/2) to give the title compound 41-6 as a yellow solid (0.1089 g, 60.0%, HPLC: 94.6%). The compound was characterized by the following spectroscopic data:

MS-ESI: m/z 1001.4 [M+H]$^+$; and $^1$H NMR (400 MHz, $CDCl_3$): δ 7.98 (d, J=8.3 Hz, 4H), 7.59 (d, J=8.3 Hz, 4H), 7.32 (s, 2H), 5.68 (m, 2H), 5.41 (br, 2H), 5.24 (m, 2H), 4.86-4.88 (m, 2H), 4.23-4.27 (m, 2H), 3.77 (d, J=9.5 Hz, 2H), 3.67 (s, 6H), 3.58 (d, J=9.5 Hz, 2H), 2.96 (s, 4H), 2.27-2.32 (m, 4H), 2.05 (m, 2H), 1.56-1.64 (m, 8H), 0.84-1.05 (m, 20H).

Step 7) The Preparation of Compound 41-7

To a solution of compound 41-6 (0.102 g, 0.102 mmol) in xylene (10 mL) was added $NH_4OAc$ (0.1569 g, 2.04 mmol). The mixture was heated at 140° C. for 12 hours in a sealed tube and concentrated in vacuo. The residue was purified by silica gel column chromatography ($CH_2Cl_2$/MeOH (v/v)=60/1) to give the title compound 41-7 as a white solid (0.04 g, 40.8%, HPLC: 96.2%). The compound was characterized by the following spectroscopic data:

MS-ESI: m/z 481.3 [M+2H]$^{2+}$; and $^1$H NMR (400 MHz, $CDCl_3$): δ 10.81 (br, 1H), 10.45 (br, 1H), 7.72-7.74 (m, 5H), 7.50-7.56 (m, 5H), 7.33 (s, 2H), 5.37-5.51 (m, 4H), 4.23-4.26 (m, 2H), 3.73-3.82 (m, 2H), 3.68 (s, 6H), 3.50-3.52 (m, 2H), 3.02 (s, 4H), 2.24-2.33 (m, 2H), 2.05-2.07 (m, 2H), 2.05-2.13 (m, 2H), 1.58-1.69 (m, 8H), 0.90-1.10 (m, 20H).

Example 42

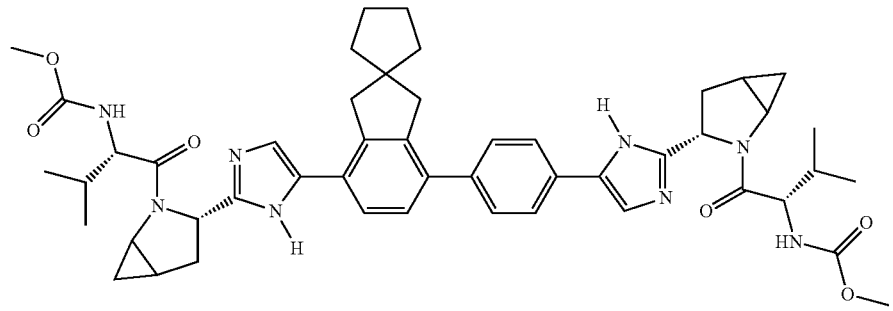

Synthetic Routes

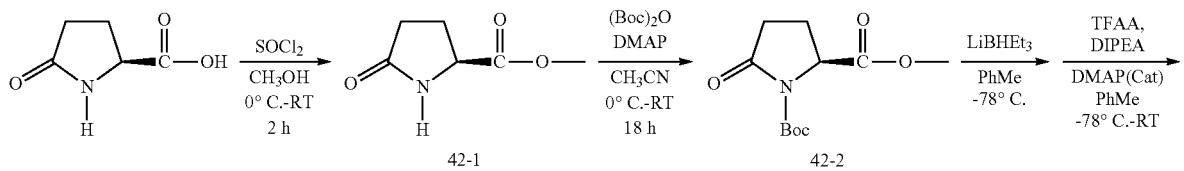

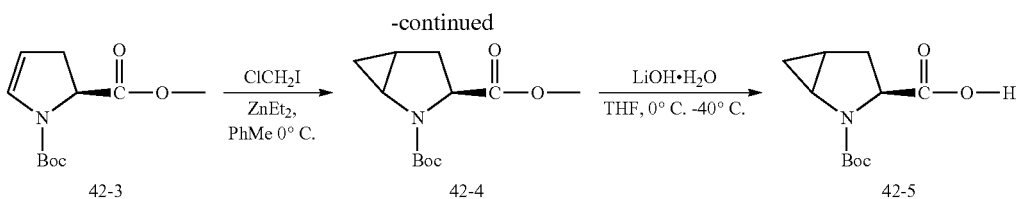
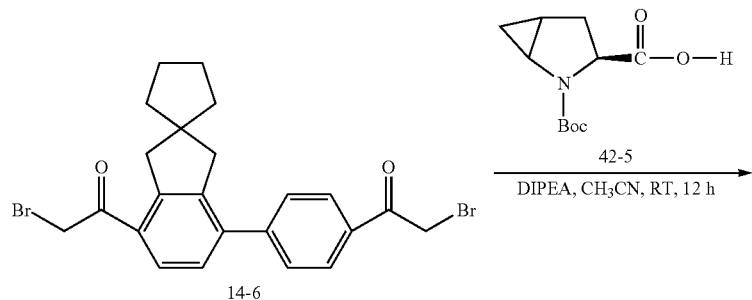
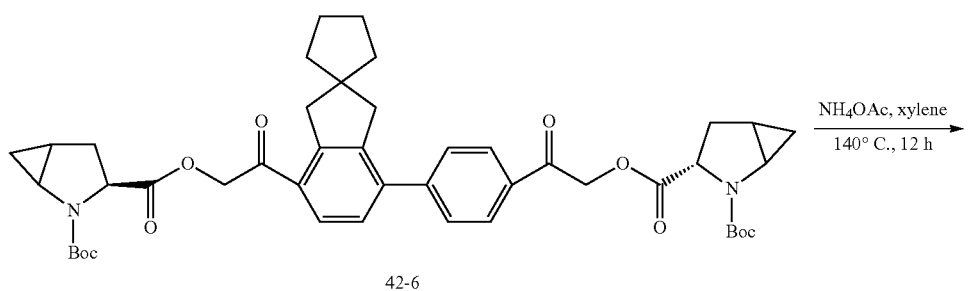
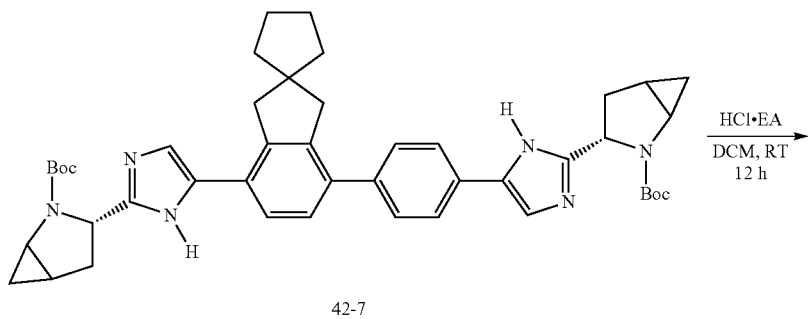
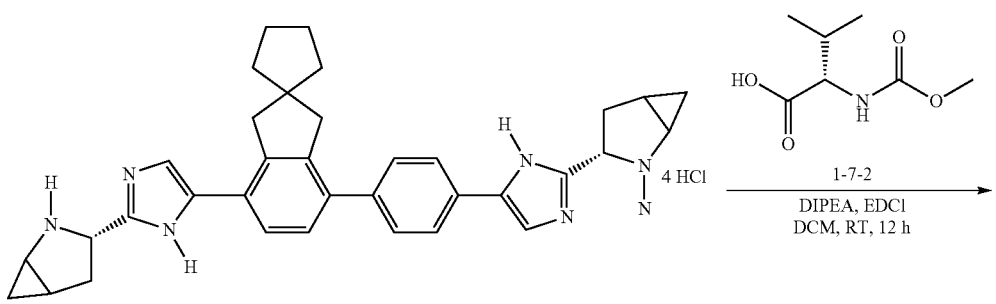

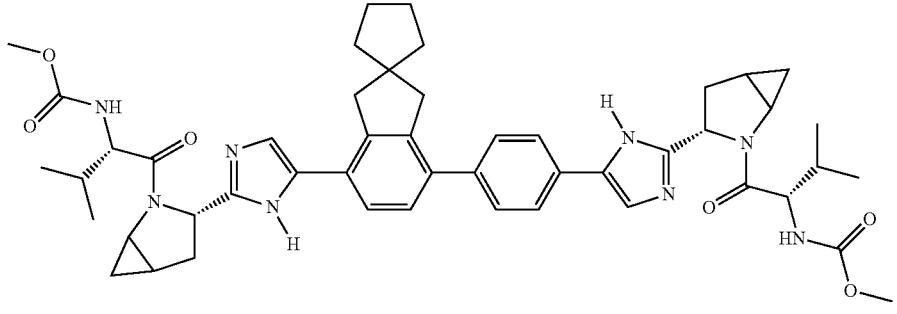

42-9

Step 1) The Preparation of Compound 42-1

To a solution of L-pyroglutamic acid (10 g, 77.5 mmol) in MeOH (50 mL) was added dropwise thionyl chloride (5.5 mL, 75.8 mmol) slowly in an ice bath. The mixture was stirred at 0° C. for 1 hour and at rt for another 2 hours. To the resulting mixture was added solid $NaHCO_3$, MeOH was removed and water (30 mL) was added. The mixture was extracted with $CH_2Cl_2$ (35 mL×3). The combined organic phases were dried over anhydrous $Na_2SO_4$ for 1 hour and filtered. The filtrate was concentrated in vacuo and the residue was purified by silica gel column chromatography (EtOAc) to give the title compound 42-1 as colorless liquid (7.5 g, 67.6%, HPLC: 95%). The compound was characterized by the following spectroscopic data:

MS-ESI: m/z 144.2 $[M+H]^+$; and
$^1$H NMR (400 MHz, $CDCl_3$): δ 7.38 (br, 1H), 4.16-4.20 (m, 1H), 3.67 (s, 3H), 2.23-2.39 (m, 3H), 2.07-2.14 (m, 1H).

Step 2) The Preparation of Compound 42-2

To a solution of compound 42-1 (6.45 g, 45.06 mmol) in MeCN (30 mL) was added DMAP (0.5503 g, 4.5 mmol) and di-tert-butyl dicarbonate (10.816 g, 49.56 mmol) slowly in turn in an ice bath. The mixture was stirred at 0° C. for 30 minutes and at rt for another 18 hours and concentrated in vacuo. The residue was purified by silica gel column chromatography (PE/EtOAc (v/v)=1/1) to give the title compound 42-2 as colorless liquid (5.0 g, 45.6%, HPLC: 95%). The compound was characterized by the following spectroscopic data:

MS-ESI: m/z 144.2 $[M-99]^+$; and
$^1$H NMR (400 MHz, $CDCl_3$): δ 4.57-4.60 (m, 1H), 3.75 (s, 3H), 2.55-2.65 (m, 1H), 2.42-2.50 (m, 1H), 2.24-2.36 (m, 1H), 1.96-2.04 (m, 1H), 1.45 (s, 9H).

Step 3) The Preparation of Compound 42-3

To a solution of compound 42-2 (3.74 g, 15.4 mmol) in toluene (50 mL) was added lithium triethylborohydride (1.793 g, 16.9 mmol) slowly at −78° C. After stirring for 70 minutes at −78° C., to the mixture was added DIPEA (3.2 mL, 19.4 mmol), DMAP (0.1877 g, 1.54 mmol) and TFAA (3 mL, 40.4 mmol) in turn. The mixture was stirred at rt for another 2 hours and concentrated in vacuo. The residue was purified by silica gel column chromatography (PE/EtOAc (v/v)=10/1) to give the title compound 42-3 as yellow liquid (2.26 g, 64.8%, HPLC: 97%). The compound was characterized by the following spectroscopic data:

MS-ESI: m/z 128.2 $[M-99]^+$; and
$^1$H NMR (400 MHz, $CDCl_3$): δ 6.52-6.65 (br, 1H), 4.91-4.96 (br, 1H), 4.57-4.68 (m, 1H), 3.76 (s, 3H), 3.00-3.12 (m, 1H), 2.61-2.71 (m, 1H), 1.44-1.49 (br, 9H).

Step 4) The Preparation of Compound 42-4

To a solution of diethylzinc (0.4871 g, 3.94 mmol) in toluene (6 mL) was added chloroiodomethane (1.394 g, 7.9 mmol) slowly in an ice bath. After the mixture was stirred for 45 minutes, a solution of compound 42-3 (0.3 g, 1.32 mmol) in toluene (4 mL) was added. The mixture was stirred at 0° C. for another 18 hours, quenched with $NH_4Cl$ saturated solution (15 mL) and extracted with EtOAc (25 mL×3). The combined organic phases were dried over anhydrous $Na_2SO_4$ and filtered. The filtrate was concentrated in vacuo and the residue was purified by silica gel column chromatography (PE/EtOAc (v/v)=10/1) to give the title compound 42-4 as yellow liquid (0.19 g, 59.7%, HPLC: 95%). The compound was characterized by the following spectroscopic data:

MS-ESI: m/z 142.2 $[M-99]^+$; and
$^1$H NMR (400 MHz, $CDCl_3$): δ 4.51-4.64 (m, 1H), 3.70 (s, 3H), 3.45-3.56 (m, 1H), 2.54-2.64 (m, 1H), 2.01-2.05 (m, 1H), 1.50, 1.41 (s, 9H), 0.65-0.75 (m, 3H).

Step 5) The Preparation of Compound 42-5

To a solution of compound 42-4 (1.02 g, 4.23 mmol) in THF (20 mL) was added dropwise a solution of $LiOH.H_2O$ (0.8888 g, 21.2 mmol) in $H_2O$ (10 mL) slowly in an ice bath. The mixture was stirred at 40° C. for 12 hours and concentrated in vacuo. To the residue was added $H_2O$ (10 mL). The mixture was extracted with EtOAc (25 mL×3). The aqueous phase was adjusted to pH 1 with HCl (10%) and extracted with EtOAc (25 mL×3). The combined organic phases were dried over anhydrous $Na_2SO_4$ and filtered. The filtrate was concentrated in vacuo to give the title compound 42-5 as a white solid (0.8371 g, 87.0%, HPLC: 95%). The compound was characterized by the following spectroscopic data:

MS-ESI: m/z 226.2 $[M-H]^-$; and
$^1$H NMR (400 MHz, $CD_3OD$): δ 4.46-4.53 (m, 1H), 3.42-3.48 (m, 1H), 2.57-2.70 (m, 1H), 2.01-2.05 (m, 1H), 1.54-1.60 (m, 1H), 1.48, 1.41 (s, 9H), 0.80-0.89 (m, 1H), 0.66-0.73 (m, 1H).

Step 6) The Preparation of Compound 42-6

To a solution of compound 14-6 (0.344 g, 0.7 mmol) and compound 42-5 (0.4 g, 1.76 mmol) in $CH_3CN$ (10 mL) was added dropwise DIPEA (0.3 mL, 1.76 mmol) slowly in an ice bath. The mixture was stirred at rt for 12 hours and concentrated in vacuo. The residue was purified by silica gel column chromatography (PE/EtOAc (v/v)=2/1) to give the title compound 42-6 as a white solid (0.44 g, 80.1%, HPLC: 95%). The compound was characterized by the following spectroscopic data:

MS-ESI: m/z 683.9 $[M-99]^+$; and
$^1$H NMR (400 MHz, $CDCl_3$): δ 7.97-8.00 (m, 2H), 7.66 (d, J=8.1 Hz, 1H), 7.53-7.56 (m, 2H), 7.29 (d, J=8.1 Hz, 1H), 5.10-5.64 (m, 4H), 4.74-4.81 (m, 2H), 3.58-3.59 (m, 1H), 3.50 (m, 1H), 3.24 (s, 2H), 2.86 (s, 2H), 2.62-2.70 (m, 2H), 2.40-2.49 (m, 2H), 1.59-1.69 (m, 8H), 1.50 (s, 9H), 1.45 (s, 9H), 1.01-1.06 (m, 2H), 0.83-0.88 (m, 2H), 0.71-0.78 (m, 2H).

Step 7) The Preparation of Compound 42-7

To a solution of compound 42-6 (0.42 g, 0.536 mmol) in xylene (10 mL) was added $NH_4OAc$ (0.826 g, 10.72 mmol). The mixture was heated at 140° C. for 12 hours in a sealed tube. The mixture was concentrated in vacuo and the residue was purified by silica gel column chromatography (PE/

EtOAc (v/v)=2/1) to give the title compound 42-7 as a yellow solid (0.2 g, 50.2%, HPLC: 95%). The compound was characterized by the following spectroscopic data:

MS-ESI: m/z 372.3 [M+2H]$^{2+}$; and $^1$H NMR (400 MHz, CDCl$_3$): δ 10.81 (br, 1H), 10.36 (br, 1H), 7.44-7.79 (m, 6H), 7.13-7.23 (m, 2H), 5.30 (br, 2H), 3.55 (br, 2H), 3.26 (br, 2H), 3.04 (s, 2H), 2.96 (s, 2H), 2.49 (m, 2H), 1.62-1.69 (m, 8H), 1.55 (br, 18H), 0.85-0.89 (m, 2H), 0.76 (m, 2H), 0.64 (m, 2H).

Step 8) The Preparation of Compound 42-8

To a solution of compound 42-7 (0.07 g, 0.094 mmol) in CH$_2$Cl$_2$ (3 mL) was added a solution of HCl in EtOAc (4 M, 2 mL). The reaction mixture was stirred at rt for 12 hours and filtered. The filter cake was washed with EtOAc (10 mL) to give the title compound 42-8 as a yellow solid (0.059 g, 90.8%, HPLC: 94.5%). The compound was characterized by the following spectroscopic data:

MS-ESI: m/z 272.2 [M−4HCl+2H]$^{2+}$; and $^1$H NMR (400 MHz, CD$_3$OD): δ 8.11 (br, 1H), 7.86-7.94 (m, 3H), 7.65-7.66 (m, 3H), 7.42-7.44 (br, 1H), 5.73 (br, 2H), 3.61 (br, 2H), 3.02-3.11 (br, 4H), 2.69-2.71 (m, 2H), 2.19 (m, 2H), 1.64-1.68 (m, 8H), 1.29-1.31 (m, 4H), 1.22 (m, 2H).

Step 9) The Preparation of Compound 42-9

To a solution of compound 42-8 (0.15 g, 0.22 mmol), compound 1-7-2 (0.1149 g, 0.66 mmol) and EDCI (0.1667 g, 0.875 mmol) in DCM (15 mL) was added dropwise DIPEA (0.4 mL, 2.4 mmol) slowly in an ice bath. Then the mixture was stirred at rt for 12 hours. To the resulting mixture was added H$_2$O (20 mL). The mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (EtOAc) to give the title compound 42-9 as a yellow solid (0.0844 g, 45.2%, HPLC: 97.7%). The compound was characterized by the following spectroscopic data:

MS-ESI: m/z 429.3 [M+2H]$^{2+}$; and $^1$H NMR (400 MHz, CDCl$_3$): δ 10.70 (br, 1H), 10.35 (br, 1H), 7.81 (m, 2H), 7.70-7.73 (m, 1H), 7.52-7.54 (m, 1H), 7.43-7.45 (m, 2H), 7.21 (s, 1H), 7.10 (br, 1H), 5.52-5.58 (m, 4H), 4.56-4.58 (m, 2H), 3.71 (s, 6H), 3.25 (br, 2H), 3.02 (s, 2H), 2.96 (s, 2H), 2.52-2.54 (m, 2H), 1.89-2.11 (m, 6H), 1.58-1.62 (m, 6H), 0.85-0.94 (m, 18H).

Example 43

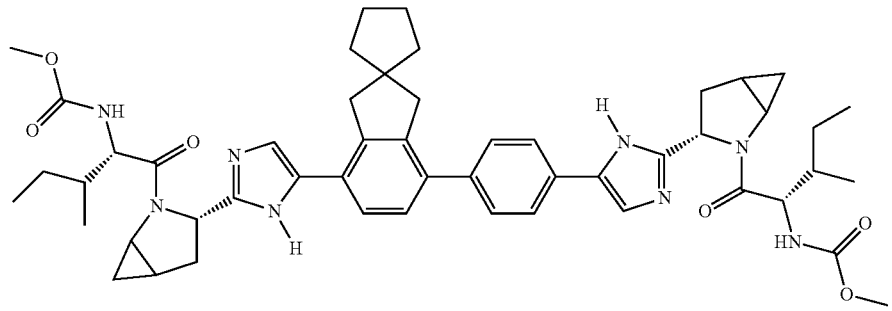

Synthetic Routes

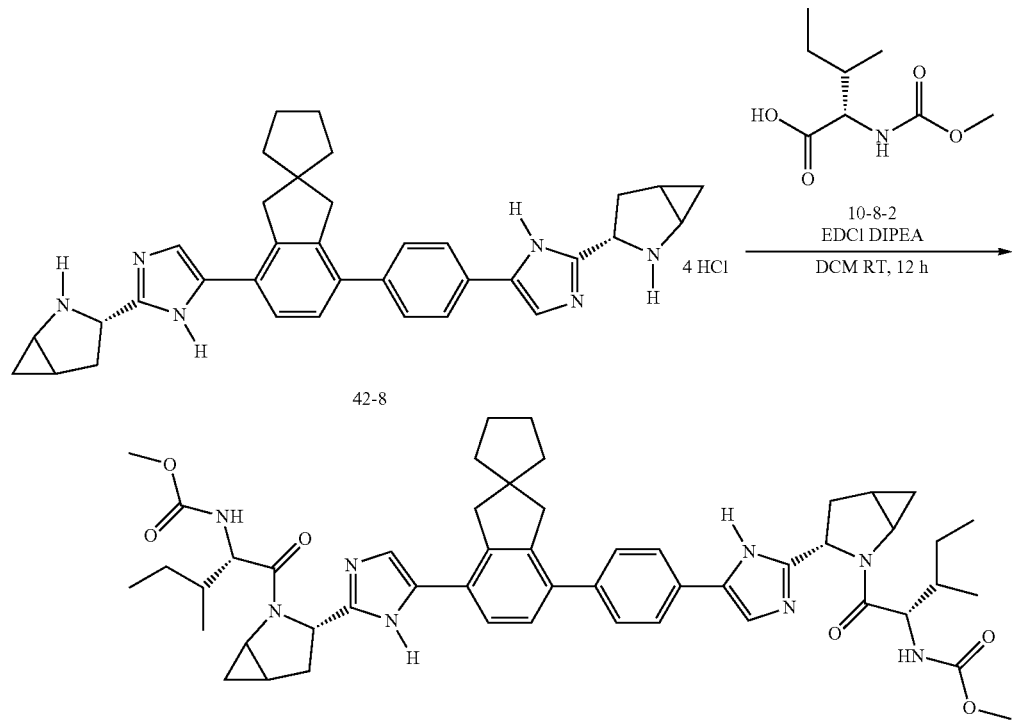

Step 1) The Preparation of Compound 43

To a solution of compound 42-8 (0.1648 g, 0.244 mmol), chloroacetyl-L-isoleucine (0.1393 g, 0.736 mmol) and EDCI (0.1882 g, 0.982 mmol) in DCM (15 mL) was added dropwise DIPEA (0.5 mL, 3.03 mmol) slowly in an ice bath. Then the mixture was stirred at rt for 12 hours. To the resulting mixture was added H$_2$O (20 mL). The mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (EtOAc) to give the title compound 43 as a yellow solid (0.09 g, 41.4%, HPLC: 98.8%). The compound was characterized by the following spectroscopic data:

MS-ESI: m/z 443.3 [M+2H]$^{2+}$; and $^1$H NMR (400 MHz, CDCl$_3$): δ 10.69 (br, 1H), 10.32 (br, 1H), 7.81-7.83 (br, 2H), 7.70-7.72 (m, 1H), 7.52-7.54 (m, 1H), 7.46 (br, 2H), 7.21 (s, 1H), 7.07-7.11 (br, 1H), 5.48-5.58 (m, 4H), 4.57-4.59 (m, 2H), 3.71 (s, 6H), 3.23-3.34 (m, 2H), 2.95-3.07 (m, 4H), 2.53 (br, 2H), 1.85-2.09 (m, 6H), 1.57-1.63 (m, 6H), 0.79-0.94 (m, 18H).

Example 44

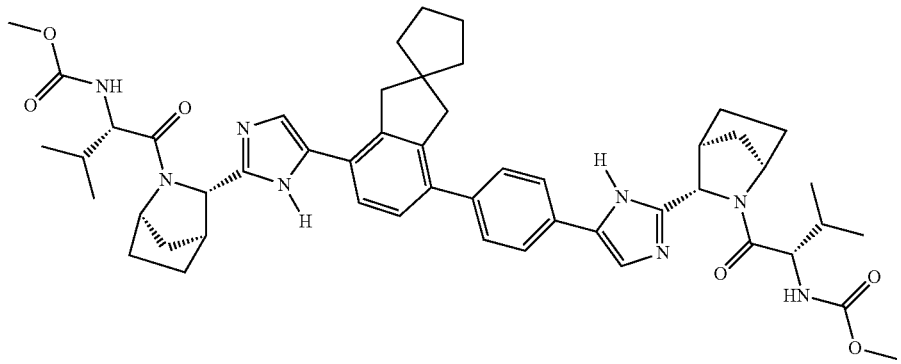

Synthetic Routes

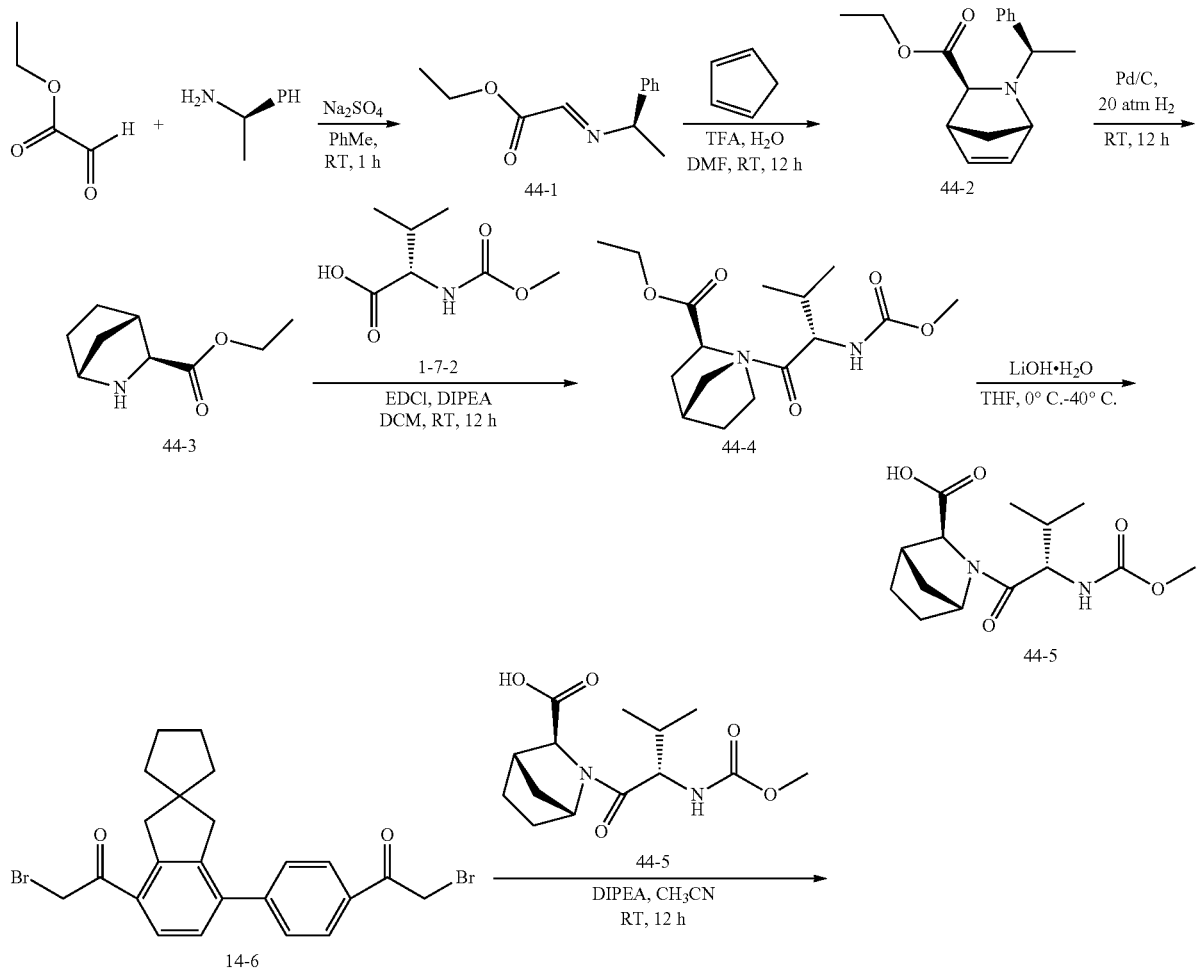

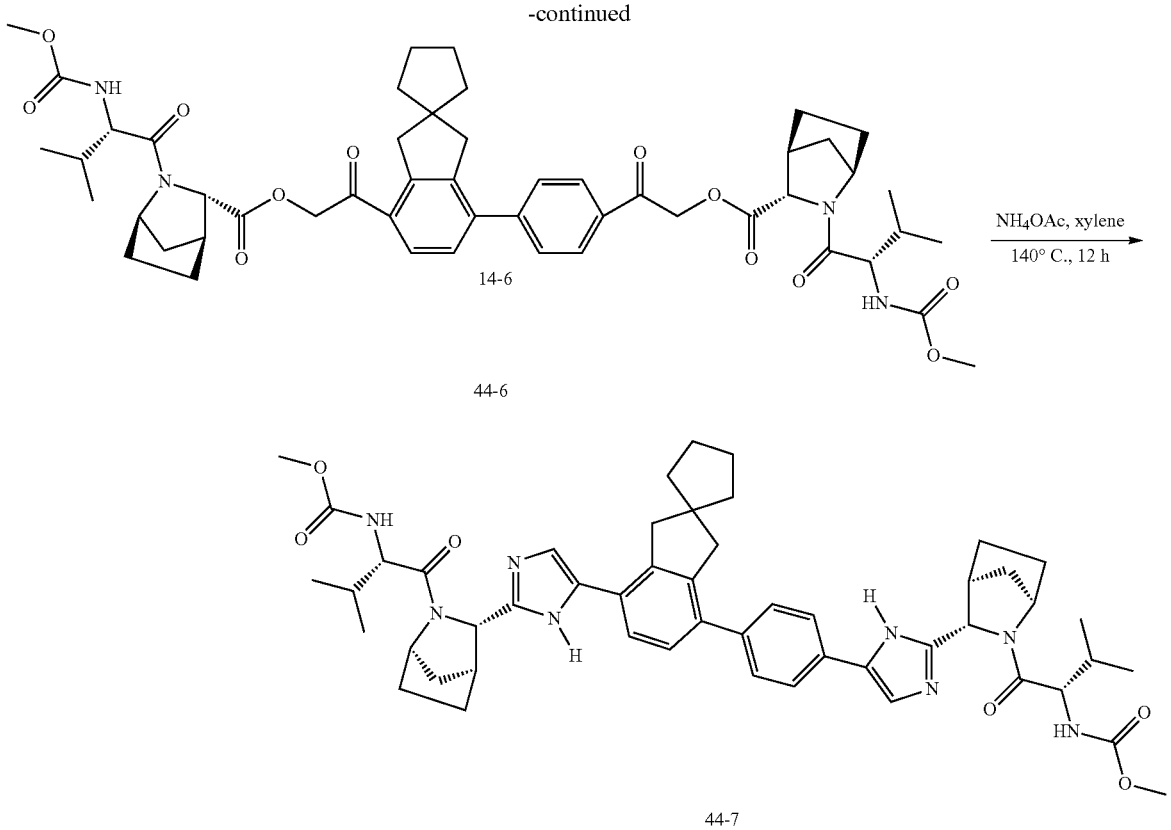

Step 1) The Preparation of Compound 44-1

To a solution of R-1-phenylethylamine (1.3 mL, 10.1 mmol) in toluene (15 mL) was added anhydrous $Na_2SO_4$ (3.48 g, 24.5 mmol) at rt. Then to the mixture was added ethyl glyoxalate (1 mL, 10.1 mmol) slowly. The mixture was stirred at rt for 1 hour and filtered. The filtrate was concentrated in vacuo to give the title compound 44-1 as yellow liquid (1.9 g, 91.8%, HPLC: 95%), which was used for the next step without further purification.

Step 2) The Preparation of Compound 44-2

To a solution of compound 44-1 (2.0 g, 9.7 mmol) in DMF (15 mL) was added TFA (0.75 mL, 10.1 mmol) at rt. After 2 minutes, to the mixture were added freshly distilled cyclopenta-1,3-diene (1.29 g, 19.5 mmol) and two drops of water. The mixture was stirred for another 12 hours and concentrated in vacuo. To the residue was added $NaHCO_3$ solution (10%, 20 mL). The mixture was adjusted to pH 8 with solid $Na_2CO_3$ and extracted with PE (25 mL×3). The combined organic phases were dried over anhydrous $Na_2SO_4$ and filtered. The filtrate was concentrated in vacuo and the residue was purified by silica gel column chromatography (PE/EtOAc (v/v)=10/1) to give the title compound 44-2 as pale yellow liquid (2.38 g, 90.0%, HPLC: 95%). The compound was characterized by the following spectroscopic data:

$^1$H NMR (400 MHz, CDCl$_3$): δ 7.17-7.35 (m, 5H), 6.42 (br, 1H), 6.26-6.28 (br, 1H), 4.30-4.34 (m, 2H), 3.78-3.82 (m, 2H), 3.02-3.04 (m, 1H), 2.90 (br, 1H), 2.20 (br, 1H), 2.13 (m, 1H), 1.41 (d, J=6.6 Hz, 3H), 0.95 (t, J=7.2 Hz, 3H).

Step 3) The Preparation of Compound 44-3

To a solution of compound 44-2 (2.0 g, 7.37 mmol) in EtOH (60 mL) was added Pd/C (0.7 g). The mixture was stirred under $H_2$ (20 atm) at rt for 12 hours and filtered. The filtrate was concentrated in vacuo to give the title compound 44-3 as yellow liquid (1.2 g, 96.2%, HPLC: 100%). The compound was characterized by the following spectroscopic data:

MS-ESI: m/z 170.2 [M+H]$^+$; and $^1$H NMR (400 MHz, CDCl$_3$): δ 4.15-4.21 (m, 2H), 3.55 (br, 1H), 3.33 (br, 1H), 2.63 (br, 1H), 2.32 (br, 1H), 1.60-1.64 (m, 2H), 1.47-1.53 (m, 2H), 1.36-1.42 (m, 2H), 1.28 (t, J=7.1 Hz, 3H).

Step 4) The Preparation of Compound 44-4

To a solution of compound 44-3 (0.68 g, 4.02 mmol), compound 1-7-2 (1.057 g, 6.03 mmol) and EDCI (1.543 g, 8.05 mmol) in DCM (25 mL) was added dropwise DIPEA (2.1 mL, 12.7 mmol) slowly in an ice bath. Then the mixture was stirred at rt for 12 hours. To the resulting mixture was added $H_2O$ (30 mL). The mixture was extracted with $CH_2Cl_2$ (35 mL×3). The combined organic phases were dried over anhydrous $Na_2SO_4$ and filtered. The filtrate was concentrated in vacuo and the residue was purified by silica gel column chromatography (PE/EtOAc (v/v)=2/1) to give the title compound 44-4 as a white solid (0.74 g, 56.4%, HPLC: 95%). The compound was characterized by the following spectroscopic data:

MS-ESI: m/z 327.2 [M+H]$^+$; and $^1$H NMR (400 MHz, CDCl$_3$): δ 5.44 (br, 1H), 4.40 (br, 1H), 4.30-4.33 (m, 1H), 4.14-4.19 (m, 2H), 4.02 (br, 1H), 3.66 (s, 3H), 2.74 (br, 1H), 2.04 (br, 1H), 1.88-1.91 (m, 2H), 1.74-1.80 (m, 2H), 1.54-1.56 (m, 1H), 1.38-1.43 (m, 1H), 1.26 (t, J=7.1 Hz, 3H), 1.07 (d, J=6.8 Hz, 3H), 0.97 (d, J=6.8 Hz, 3H).

Step 5) The Preparation of Compound 44-5

To a solution of compound 44-4 (0.74 g, 2.27 mmol) in THF (25 mL) was added dropwise a solution of lithium hydroxide (0.4767 g, 11.35 mmol) in H$_2$O (10 mL) slowly in an ice bath. The mixture was stirred at 40° C. for 12 hours and concentrated in vacuo. To the residue was added H$_2$O (10 mL). The mixture was extracted with EtOAc (25 mL×3). The aqueous phase was adjusted to pH 1 with HCl (10%) and extracted with EtOAc (25 mL×3). The combined organic phases were dried over anhydrous Na$_2$SO$_4$ and filtered. The filtrate was concentrated in vacuo to give the title compound 44-5 as a white solid (0.55 g, 81.3%). The compound was characterized by the following spectroscopic data:

MS-ESI: m/z 299.2 [M+H]$^+$; and $^1$H NMR (400 MHz, CD$_3$OD): δ 4.52 (br, 1H), 4.20 (d, J=7.8 Hz, 1H), 3.93 (br, 1H), 3.63 (s, 3H), 2.73 (br, 1H), 1.98-2.01 (m, 4H), 1.75-1.85 (m, 2H), 1.46-1.54 (m, 2H), 1.05 (d, J=6.8 Hz, 3H), 0.98 (d, J=6.8 Hz, 3H).

Step 6) The Preparation of Compound 44-6

To a solution of compound 14-6 (0.36 g, 0.73 mmol) and compound 44-5 (0.55 g, 1.84 mmol) in CH$_3$CN (15 mL) was added dropwise DIPEA (0.305 mL, 1.84 mmol) slowly in an ice bath. The mixture was stirred at rt for 12 hours and concentrated in vacuo. The residue was purified by silica gel column chromatography (PE/EtOAc (v/v)=1/2) to give the title compound 44-6 as a white solid (0.48 g, 70.6%, HPLC: 92.3%). The compound was characterized by the following spectroscopic data:

MS-ESI: m/z 463.3 [M+2H]$^{2+}$; and $^1$H NMR (400 MHz, CDCl$_3$): δ 7.97 (d, J=8.4 Hz, 2H), 7.66 (d, J=8.1 Hz, 1H), 7.53 (d, J=8.4 Hz, 2H), 7.29 (d, J=8.1 Hz, 1H), 5.54-5.63 (m, 2H), 5.43 (br, 2H), 5.14-5.26 (m, 2H), 4.43 (br, 2H), 4.32-4.36 (m, 2H), 4.20-4.21 (m, 2H), 3.67 (s, 6H), 3.23-3.24 (m, 2H), 3.10 (s, 2H), 2.85 (s, 2H), 2.18-2.21 (m, 2H), 1.51-2.07 (m, 20H), 0.95-1.06 (m, 12H).

Step 7) The Preparation of Compound 44-7

To a solution of compound 44-6 (0.26 g, 0.28 mmol) in xylene (15 mL) was added NH$_4$OAc (0.4328 g, 5.6 mmol). The mixture was heated at 140° C. for 12 hours in a sealed tube. The mixture was concentrated in vacuo and the residue was purified by silica gel column chromatography (EtOAc) to give the title compound 44-7 as a white solid (0.124 g, 49.8%, HPLC: 99.2%). The compound was characterized by the following spectroscopic data:

MS-ESI: m/z 443.4 [M+2H]$^{2+}$; and $^1$H NMR (400 MHz, CDCl$_3$): δ 10.85 (br, 1H), 10.44 (br, 1H), 7.71-7.79 (m, 2H), 7.42-7.44 (m, 3H), 7.21-7.25 (m, 2H), 7.13 (s, 1H), 5.54 (br, 2H), 4.73 (br, 2H), 4.36-4.40 (m, 4H), 3.71 (s, 6H), 3.47-3.54 (m, 2H), 2.91-3.08 (m, 4H), 2.24-2.33 (m, 2H), 1.89-2.05 (m, 12H), 1.59-1.65 (m, 8H), 0.85-0.97 (m, 12H).

Example 45

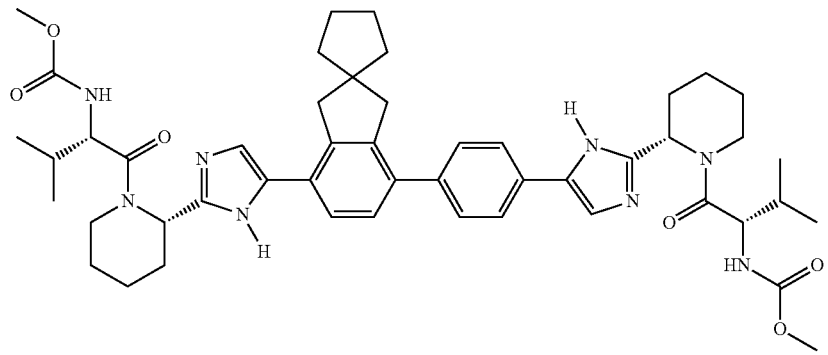 [SMILES: COC(=O)N[C@H](C(=O)N1CCCC[C@H]1c1ncc(-c2ccc(-c3ccc(-c4cnc([C@@H]5CCCCN5C(=O)[C@@H](NC(=O)OC)C(C)C)[nH]4)c4c3CC3(CCCC3)C4)cc2)[nH]1)C(C)C]

Synthetic Routes

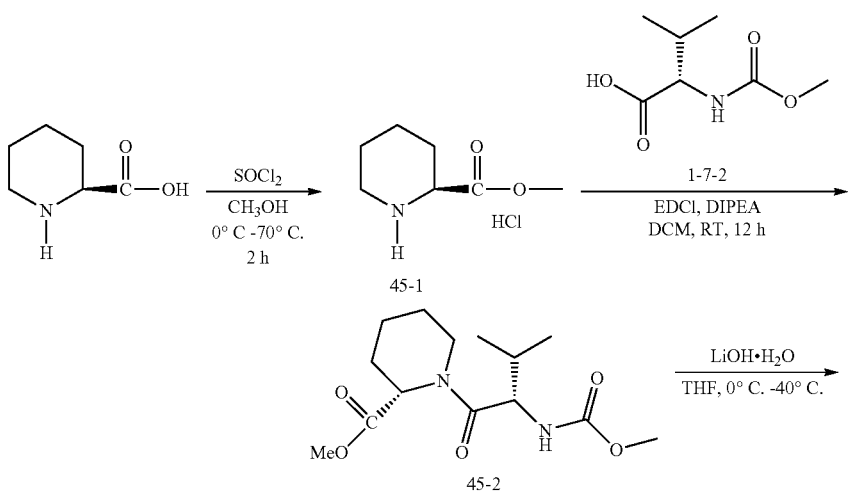

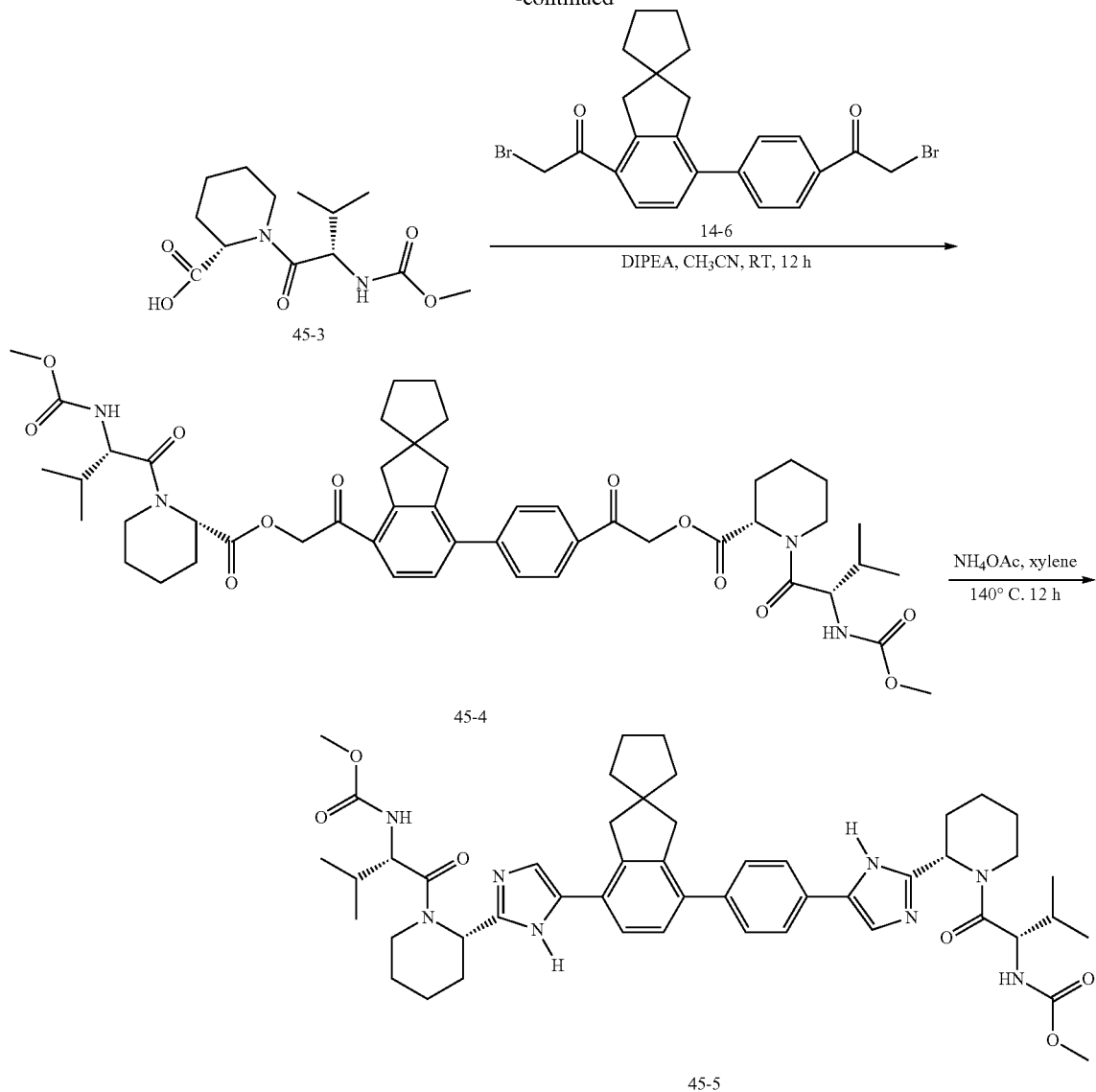

Step 1) The Preparation of Compound 45-1

To a solution of L-pipecolinic acid (10 g, 77.4 mmol) in MeOH (50 mL) was added dropwise thionyl chloride (8.5 mL, 117.2 mmol) slowly in an ice bath. The mixture was stirred at 0° C. for 1 hour, then stirred at 70° C. for another 1 hour and concentrated in vacuo to give the title compound 45-1 as a white solid (11.0 g, 79.1%, HPLC: 65%). The compound was characterized by the following spectroscopic data:

MS-ESI: m/z 144.1 [M−HCl+H]$^+$; and $^1$H NMR (400 MHz, CDCl$_3$): δ 5.02 (br, 1H), 4.00 (br, 1H), 3.85 (s, 3H), 3.63 (br, 1H), 3.15 (br, 1H), 2.28 (m, 1H), 2.08 (m, 2H), 1.86 (m, 2H), 1.63 (br, 1H).

Step 2) The Preparation of Compound 45-2

To a solution of compound 45-1 (1.0 g, 5.57 mmol), compound 1-7-2 (1.468 g, 8.38 mmol) and EDCI (2.142 g, 11.17 mmol) in DCM (40 mL) was added dropwise DIPEA (5 mL, 30.25 mmol) slowly in an ice bath. Then the mixture was stirred at rt for 12 hours. To the resulting mixture was added H$_2$O (40 mL). The mixture was extracted with CH$_2$Cl$_2$ (35 mL×3). The combined organic phases were dried over anhydrous Na$_2$SO$_4$ and filtered. The filtrate was concentrated in vacuo and the residue was purified by silica gel column chromatography (PE/EtOAc (v/v)=2/1) to give the title compound 45-2 as colorless liquid (1.5 g, 89.8%, HPLC: 95%). The compound was characterized by the following spectroscopic data:

MS-ESI: m/z 301.2 [M+H]$^+$; and $^1$H NMR (400 MHz, CDCl$_3$): δ 5.62 (br, 1H), 5.43 (br, 1H), 4.61-4.65 (m, 1H), 3.91 (m, 1H), 3.18-3.33 (m, 1H), 2.27-2.30 (br, 1H), 1.97 (m, 1H), 1.73-1.77 (m, 2H), 1.61-1.68 (m, 1H), 1.46-1.52 (m, 1H), 1.32-1.37 (m, 1H), 0.96-1.03 (m, 3H), 0.87-0.91 (m, 3H).

Step 3) The Preparation of Compound 45-3

To a solution of compound 45-2 (1.41 g, 4.7 mmol) in THF (40 mL) was added dropwise a solution of lithium hydroxide (0.987 g, 23.5 mmol) in H$_2$O (20 mL) slowly in an ice bath. The mixture was stirred at 40° C. for 12 hours and concentrated in vacuo. To the residue was added H$_2$O (10 mL). The mixture was extracted with EtOAc (25 mL×3). The aqueous phase was adjusted to pH 1 with HCl (10%) and extracted with EtOAc (35 mL×3). The combined organic phases were dried over anhydrous Na$_2$SO$_4$ and filtered. The filtrate was concentrated in vacuo to give the title compound 45-3 as a white solid (1.22 g, 90.8%, HPLC: 95%). The compound was characterized by the following spectroscopic data:

MS-ESI: m/z 285.1 [M−H]⁻; and $^1$H NMR (400 MHz, CDCl$_3$): δ 7.15 (br, 1H), 5.97 (d, J=9.1 Hz, 1H), 5.45 (br, 1H), 4.62-4.66 (m, 1H), 4.10-4.15 (m, 1H), 3.67 (s, 3H), 3.24-3.30 (m, 1H), 2.33 (br, 1H), 2.03-2.05 (m, 1H), 1.62-1.79 (m, 3H), 1.41-1.56 (m, 2H), 0.99 (d, J=6.7 Hz, 3H), 0.87 (d, J=6.6 Hz, 3H).

Step 4) The Preparation of Compound 45-4

To a solution of compound 14-6 (0.3685 g, 0.75 mmol) and compound 45-3 (0.54 g, 1.89 mmol) in CH$_3$CN (15 mL) was added dropwise DIPEA (0.4 mL, 2.4 mmol) slowly in an ice bath. The mixture was stirred at rt for 12 hours and concentrated in vacuo. The residue was purified by silica gel column chromatography (PE/EtOAc (v/v)=1/2) to give the title compound 45-4 as a white solid (0.42 g, 61.7%, HPLC: 100%). The compound was characterized by the following spectroscopic data:

MS-ESI: m/z 901.5 [M+H]⁺; and $^1$H NMR (400 MHz, CDCl$_3$): δ 7.99 (d, J=8.3 Hz, 2H), 7.70 (d, J=8.1 Hz, 1H), 7.56 (d, J=8.3 Hz, 2H), 7.29 (d, J=8.1 Hz, 1H), 5.61 (br, 4H), 5.42 (br, 2H), 5.35 (br, 2H), 4.65-4.69 (m, 2H), 3.90-3.93 (m, 2H), 3.68 (s, 6H), 3.47-3.53 (m, 2H), 3.24 (s, 2H), 2.86 (s, 2H), 2.45 (br, 2H), 1.54-1.81 (m, 20H), 0.99-1.01 (m, 6H), 0.84-0.87 (m, 6H).

Step 5) The Preparation of Compound 45-5

To a solution of compound 45-4 (0.42 g, 0.466 mmol) in xylene (15 mL) was added NH$_4$OAc (0.7178 g, 9.3 mmol). The mixture was heated at 140° C. for 12 hours in a sealed tube. The mixture was concentrated in vacuo and the residue was purified by silica gel column chromatography (EtOAc) to give the title compound 45-5 as a yellow solid (0.2618 g, 65.2%, HPLC: 96.5%). The compound was characterized by the following spectroscopic data:

MS-ESI: m/z 431.3 [M+2H]$^{2+}$; and $^1$H NMR (400 MHz, CDCl$_3$): δ 11.78 (br, 1H), 11.39 (br, 1H), 7.70-7.85 (m, 2H), 7.43 (m, 2H), 7.36 (s, 1H), 7.22 (m, 3H), 5.82-5.85 (br, 2H), 5.53 (br, 2H), 5.34 (br, 2H), 4.60 (br, 2H), 4.41-4.43 (m, 2H), 3.77 (s, 3H), 3.66 (s, 3H), 3.07 (s, 2H), 2.95 (s, 2H), 2.82 (br, 2H), 2.42-2.48 (m, 2H), 2.22-2.37 (m, 2H), 2.02-2.06 (m, 2H), 1.59-1.81 (m, 14H), 1.10-1.11 (m, 6H), 0.87-0.88 (m, 6H).

Example 46

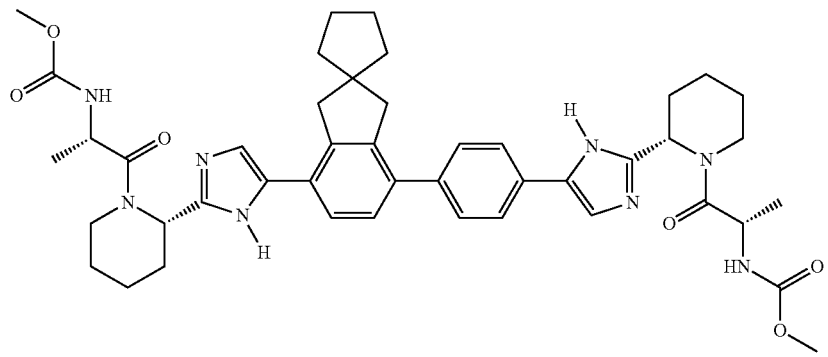 [SMILES: COC(=O)N[C@@H](C)C(=O)N1CCCC[C@H]1c1ncc(-c2ccc(-c3ccc(-c4cnc([C@@H]5CCCCN5C(=O)[C@H](C)NC(=O)OC)[nH]4)c4c3CC3(CCCC3)C4)cc2)[nH]1]

Synthetic Routes

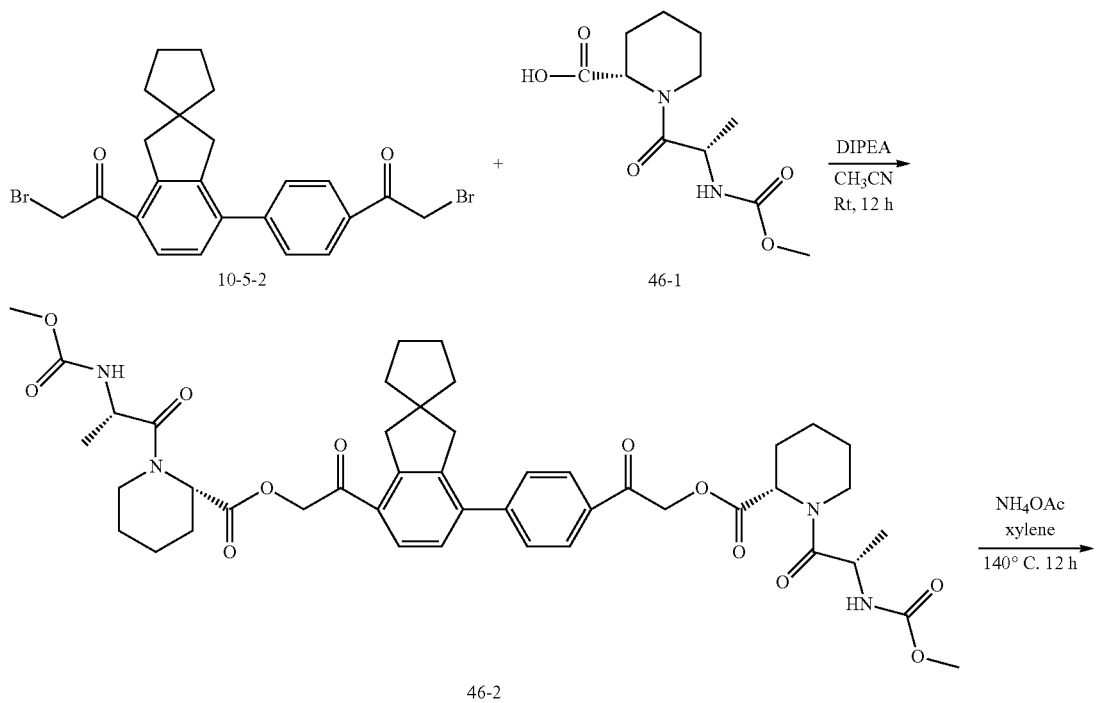

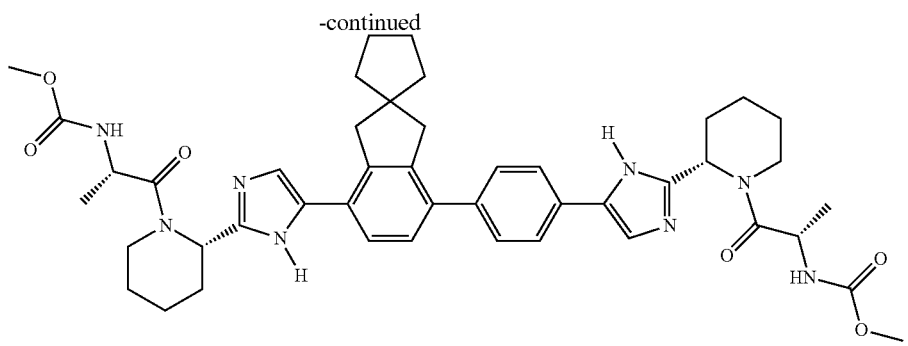

46-3

Step 1) The Preparation of Compound 46-1

The title compound 46-1 was prepared by an analogous procedure to that described for compound 45-2 (Example 45). The compound was characterized by the following spectroscopic data:

MS-ESI: m/z 257.1 [M−H]−; and $^1$H NMR (400 MHz, CDCl$_3$): δ 7.82 (br, 1H), 6.14 (br, 1H), 5.40 (br, 1H), 4.74-4.82 (m, 1H), 3.87 (m, 1H), 3.67 (s, 3H), 3.27 (m, 1H), 2.34 (m, 1H), 1.66-1.78 (m, 3H), 1.41-1.54 (m, 2H), 1.33 (d, J=6.9 Hz, 3H).

Step 2) The Preparation of Compound 46-2

To a solution of compound 10-5-2 (0.5372 g, 1.01 mmol) and compound 46-1 (0.71 g, 2.75 mmol) in CH$_3$CN (25 mL) was added DIPEA (0.5 mL, 3.02 mmol) slowly in an ice bath. The mixture was stirred at rt for 12 hours and concentrated in vacuo. The residue was purified by silica gel column chromatography (PE/EtOAc (v/v)=1/2) to give the title compound 46-2 as a white solid (0.33 g, 35.6%, HPLC: 100%). The compound was characterized by the following spectroscopic data:

MS-ESI: m/z 845.4 [M+H]+; and $^1$H NMR (400 MHz, CDCl$_3$): δ 7.99 (d, J=8.3 Hz, 2H), 7.67 (d, J=8.1 Hz, 1H), 7.55 (d, J=8.3 Hz, 2H), 7.29 (d, J=8.1 Hz, 1H), 5.80 (br, 2H), 5.54 (br, 2H), 5.43 (s, 2H), 5.34 (br, 2H), 4.75-4.78 (m, 2H), 3.82-3.86 (m, 2H), 3.68 (s, 6H), 3.47-3.50 (m, 2H), 3.24 (s, 2H), 2.86 (s, 2H), 2.44-2.47 (m, 2H), 1.54-1.80 (m, 18H), 1.33-1.35 (m, 6H).

Step 3) The Preparation of Compound 46-3

To a solution of compound 46-2 (0.33 g, 0.39 mmol) in xylene (15 mL) was added NH$_4$OAc (0.6014 g, 7.8 mmol). The mixture was heated at 140° C. for 12 hours in a sealed tube. The mixture was concentrated in vacuo and the residue was purified by silica gel column chromatography (EtOAc) to give the title compound 46-3 as a yellow solid (0.2429 g, 77.3%, HPLC: 93.0%). The compound was characterized by the following spectroscopic data:

MS-ESI: m/z 403.4 [M+2H]$^{2+}$; and $^1$H NMR (400 MHz, CDCl$_3$): δ 11.76 (br, 1H), 11.38 (br, 1H), 7.83 (br, 2H), 7.45 (br, 2H), 7.37 (s, 1H), 7.23-7.25 (m, 3H), 5.99 (br, 2H), 5.83 (br, 2H), 5.61 (br, 2H), 4.69-4.73 (m, 2H), 4.54-4.57 (m, 2H), 3.76 (s, 6H), 3.07 (s, 2H), 2.93 (s, 2H), 2.41-2.50 (m, 2H), 2.02-2.07 (m, 4H), 1.79-1.82 (m, 4H), 1.59-1.67 (m, 10H), 1.26-1.30 (m, 6H).

Example 47

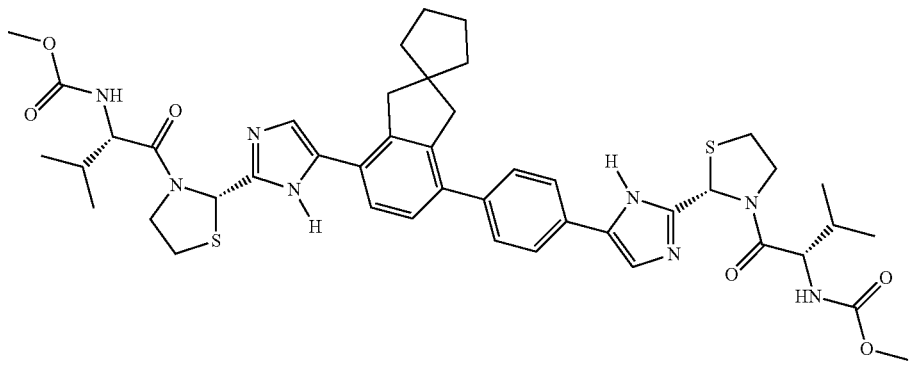

Synthetic Routes

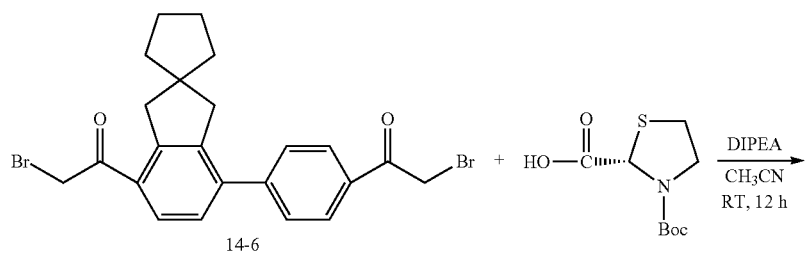

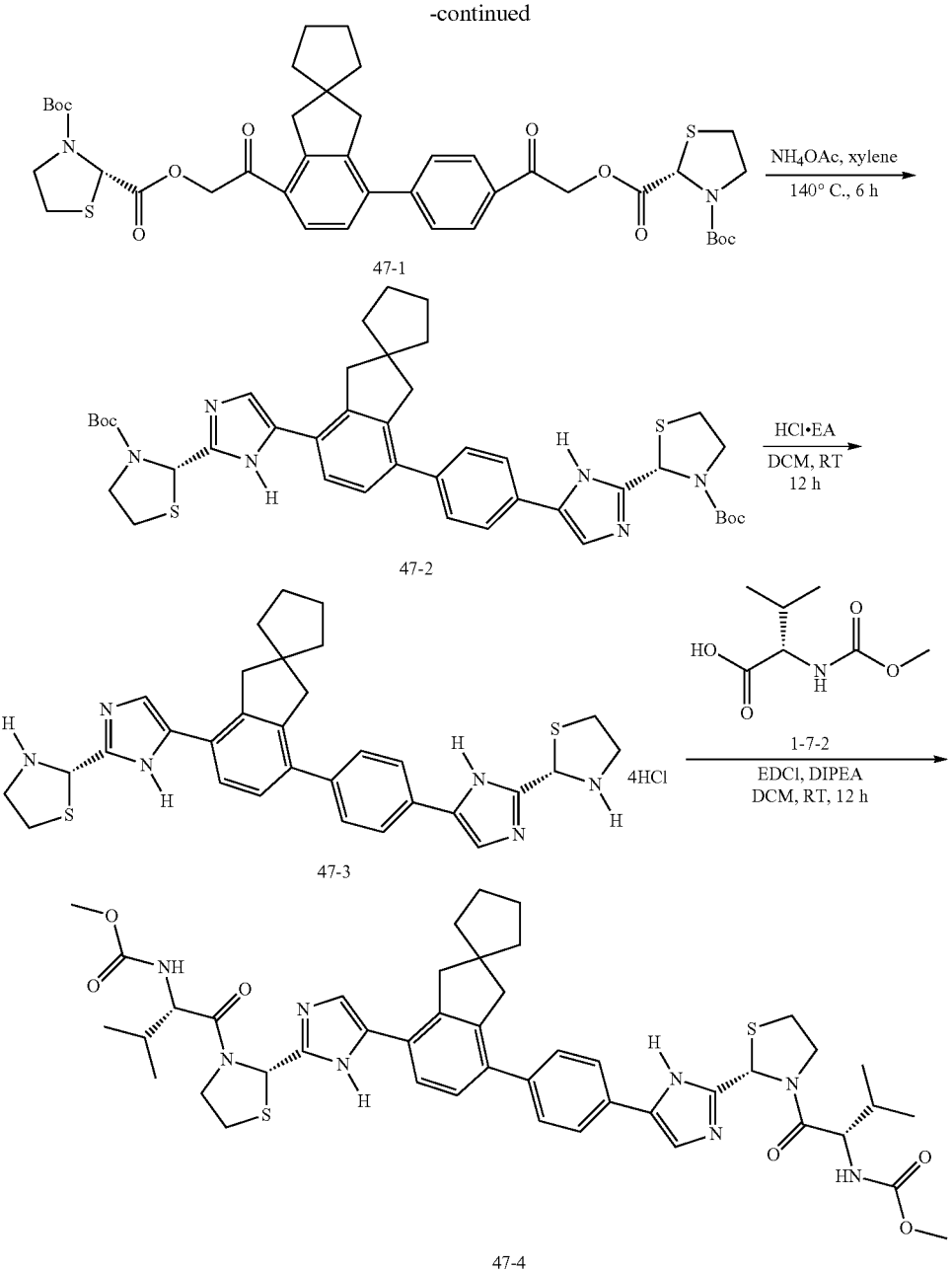

47-1

47-2

47-3

47-4

Step 1) The Preparation of Compound 47-1

To a solution of (S)-3-(tert-butoxycarbonyl)thiazolidine-2-carboxylic acid (0.419 g, 1.8 mmol) and compound 14-6 (0.5 g, 1.02 mmol) in $CH_3CN$ (15 mL) was added DIPEA (0.4 mL, 2.4 mmol) slowly in an ice bath. The mixture was stirred at rt for 12 hours and concentrated in vacuo. The residue was purified by silica gel column chromatography (PE/EtOAc (v/v)=2/1) to give the title compound 47-1 as a white solid (0.49 g, 60.4%, HPLC: 97.1%). The compound was characterized by the following spectroscopic data:

$^1$H NMR (400 MHz, $CDCl_3$): δ 8.00 (d, J=8.2 Hz, 2H), 7.67 (d, J=8.1 Hz, 1H), 7.55 (d, J=8.2 Hz, 2H), 7.29 (d, J=8.1 Hz, 1H), 5.29-5.49 (m, 6H), 3.82-3.93 (m, 4H), 3.31-3.36 (m, 2H), 3.29 (s, 2H), 3.05 (br, 2H), 2.87 (s, 2H), 1.54-1.69 (m, 8H), 1.49 (s, 18H).

Step 2) The Preparation of Compound 47-2

To a solution of compound 47-1 (0.49 g, 0.62 mmol) in xylene (25 mL) was added $NH_4OAc$ (0.95 g, 12.3 mmol). The mixture was heated at 140° C. for 6 hours in a sealed tube. The mixture was concentrated in vacuo and the residue was purified by silica gel column chromatography (EtOAc) to give the title compound 47-2 as a red solid (0.3 g, 64.4%, HPLC: 95%). The compound was characterized by the following spectroscopic data:

MS-ESI: m/z 378.0 $[M+2H]^{2+}$; and $^1$H NMR (400 MHz, $CDCl_3$): δ 11.74 (br, 1H), 11.35 (br, 1H), 7.30-7.62 (m, 4H), 7.12-7.22 (m, 4H), 6.22 (br, 2H), 3.87-3.88 (m, 4H), 3.32 (m, 2H), 2.93-3.13 (m, 6H), 1.59-1.64 (m, 8H), 1.47 (s, 18H).

Step 3) The Preparation of Compound 47-3

To a solution of compound 47-2 (0.3 g, 0.4 mmol) in CH$_2$Cl$_2$ (3 mL) was added a solution of HCl in EtOAc (4 M, 5 mL). The reaction mixture was stirred at rt for 12 hours and filtered. The filter cake was washed with EtOAc (15 mL) to give the title compound 47-3 as a red solid (0.25 g, 89.8%, HPLC: 95%). The compound was characterized by the following spectroscopic data:

MS-ESI: m/z 278.0 [M−4HCl+2H]$^{2+}$; and $^1$H NMR (400 MHz, CD$_3$OD): δ 7.86-7.91 (m, 3H), 7.63-7.66 (m, 3H), 7.57 (d, J=7.8 Hz, 1H), 7.41 (d, J=7.8 Hz, 1H), 6.21 (br, 2H), 3.84 (br, 2H), 3.42 (br, 2H), 3.14-3.23 (m, 4H), 3.08 (s, 2H), 3.02 (s, 2H), 1.64-1.69 (m, 8H).

Step 4) The Preparation of Compound 47-4

To a solution of compound 47-3 (0.15 g, 0.214 mmol), compound 1-7-2 (0.113 g, 0.64 mmol) and EDCI (0.165 g, 0.86 mmol) in DCM (15 mL) was added dropwise DIPEA (0.4 mL, 2.4 mmol) slowly in an ice bath. Then the mixture was stirred at rt for 12 hours. To the resulting mixture was added H$_2$O (20 mL). The mixture was extracted with CH$_2$Cl$_2$ (25 mL×3). The combined organic phases were dried over anhydrous Na$_2$SO$_4$ and filtered. The filtrate was concentrated in vacuo and the residue was purified by silica gel column chromatography (EtOAc) to give the title compound 47-4 as a red solid (0.0934 g, 50.2%, HPLC: 95.3%). The compound was characterized by the following spectroscopic data:

MS-ESI: m/z 435.2 [M+2H]$^{2+}$; and $^1$H NMR (400 MHz, CDCl$_3$): δ 11.73 (br, 1H), 11.35 (br, 1H), 7.31-7.71 (m, 4H), 7.11-7.25 (m, 4H), 6.25 (br, 2H), 5.81 (br, 2H), 5.56 (br, 2H), 3.85-3.87 (m, 4H), 3.76 (s, 6H), 3.28 (br, 2H), 3.25 (s, 2H), 3.05-3.13 (m, 2H), 2.95 (s, 2H), 2.68-2.73 (m, 2H), 1.57-1.62 (m, 8H), 1.09-1.12 (m, 6H), 0.87-0.89 (m, 6H).

Example 48

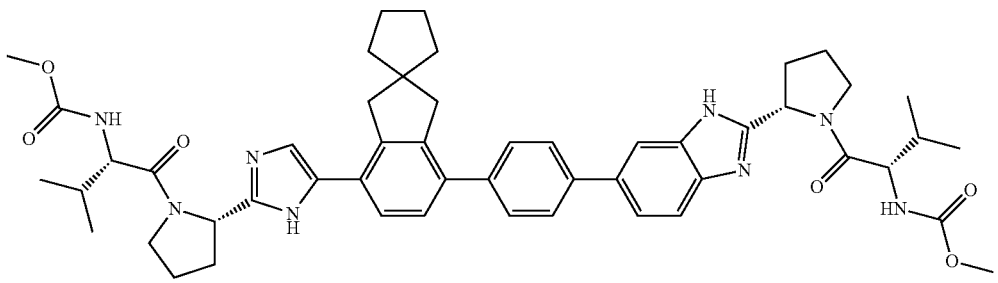

Synthetic Routes

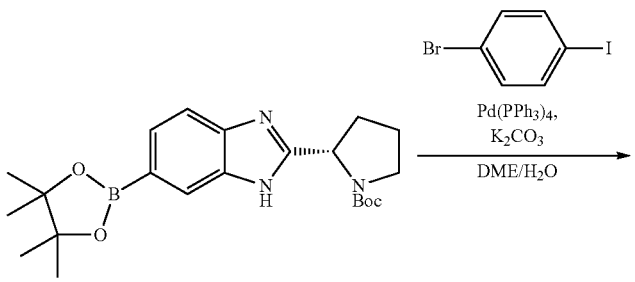

3-3-2

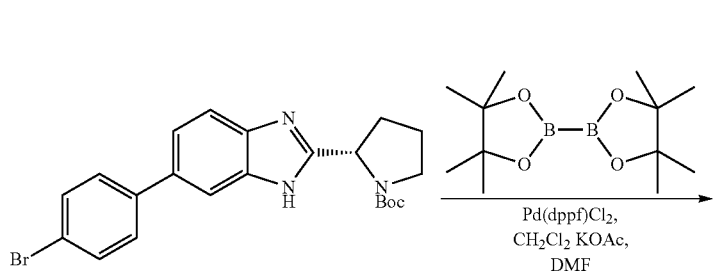

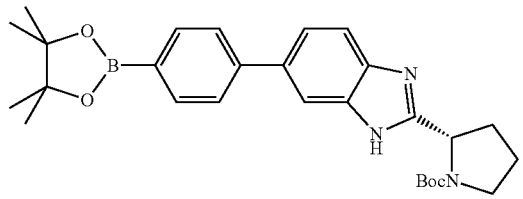

48-6

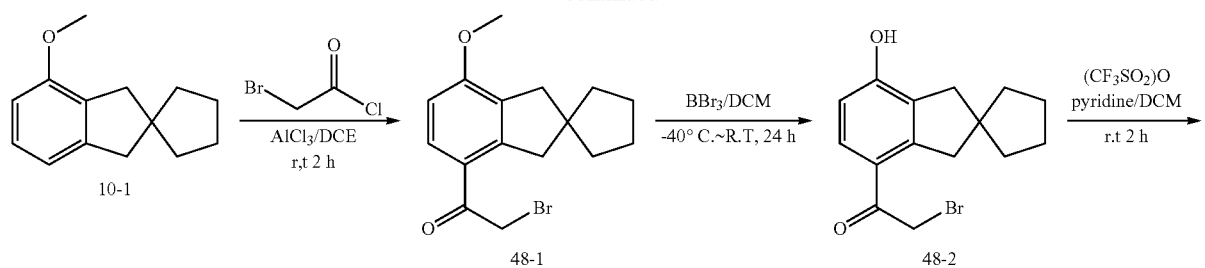
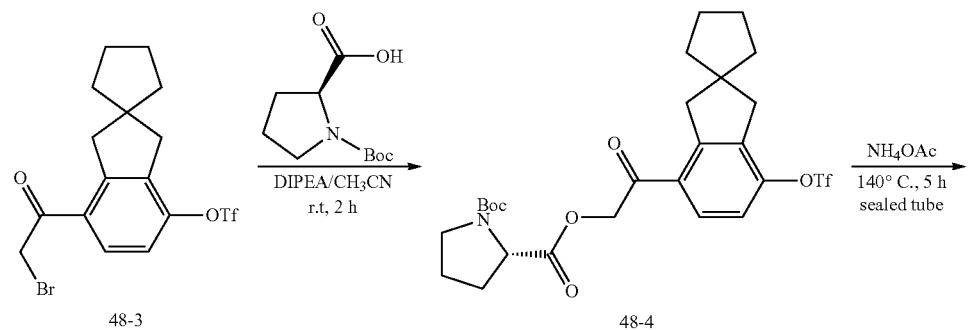
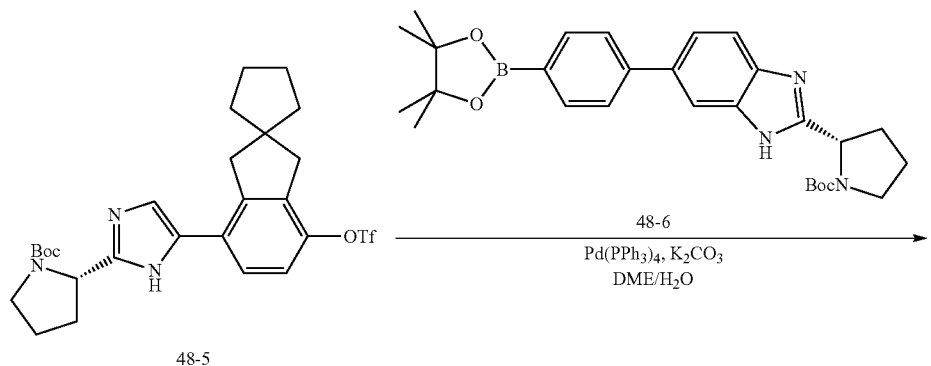
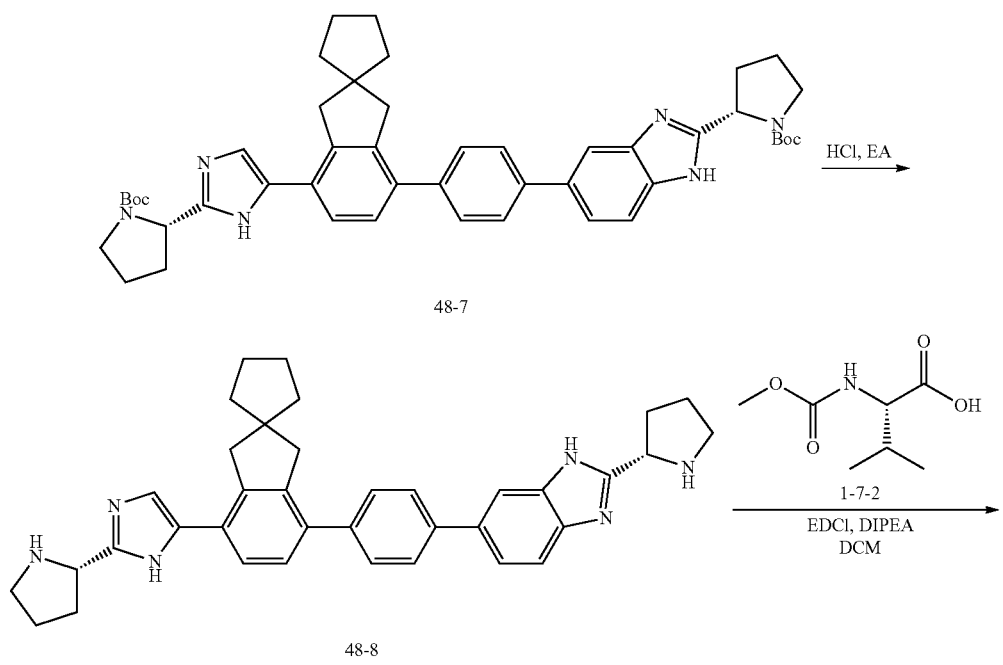

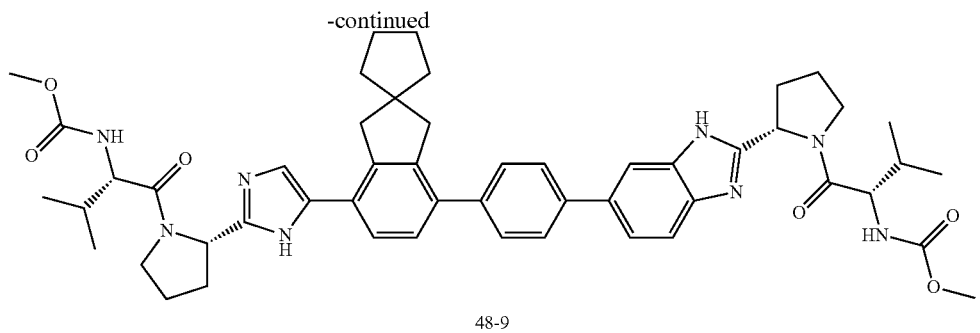

48-9

Step 1) The Preparation of Compound 48-1

To a suspension of aluminium chloride (2.12 g, 16.0 mmol) in 1,2-dichloroethane (40 mL) was added bromoacetyl chloride (1.2 mL, 14.4 mmol). To the mixture was added a solution of compound 10-1 (1.29 g, 6.37 mmol) in 1,2-dichloroethane (20 mL) slowly. The mixture was stirred for 2 hours at rt, then quenched with ice water (5 mL) and extracted with EtOAc (100 mL×3). The combined organic phases were dried over anhydrous $Na_2SO_4$ and filtered. The filtrate was concentrated in vacuo and the residue was purified by silica gel column chromatography (PE/EtOAc (v/v)=15/1) to give the title compound 48-1 as a white solid (1.75 g, 85.0%, HPLC: 95%). The compound was characterized by the following spectroscopic data:

MS-ESI: m/z 324.1 $[M+H]^+$; and $^1$H NMR (400 MHz, $CDCl_3$): δ 7.73 (d, J=8.0 Hz, 1H), 6.71 (d, J=8.0 Hz, 1H), 3.89 (s, 3H), 3.23 (s, 2H), 2.75 (s, 2H), 2.52 (s, 2H), 1.70-1.73 (m, 4H), 1.60-1.62 (m, 4H).

Step 2) The Preparation of Compound 48-2

A solution of compound 48-1 (0.97 g, 3.0 mmol) in $CH_2Cl_2$ (40 mL) was cooled to −40° C. And to the solution was added a solution of boron tribromide (6.0 g, 23.95 mmol) in $CH_2Cl_2$ (20 mL) slowly at −40° C. Then the mixture was stirred at rt for 24 hours, quenched with ice water (10 mL) and extracted with $CH_2Cl_2$ (30 mL×3). The combined organic phases were dried over anhydrous $Na_2SO_4$ and filtered. The filtrate was concentrated in vacuo and the residue was purified by silica gel column chromatography (PE/EtOAc (v/v)=4/1) to give the title compound 48-2 as a white solid (0.84 g, 90.3%, HPLC: 98%). The compound was characterized by the following spectroscopic data:

MS-ESI: m/z 310.1 $[M+H]^+$; and $^1$H NMR (400 MHz, $CDCl_3$): δ 7.64 (d, J=8.0 Hz, 1H), 6.68 (d, J=8.0 Hz, 1H), 5.22 (s, 1H), 3.24 (s, 2H), 2.74 (s, 2H), 2.53 (s, 2H), 1.71-1.74 (m, 4H), 1.61-1.64 (m, 4H).

Step 3) The Preparation of Compound 48-3

To a solution of compound 48-2 (0.80 g, 2.59 mmol) in $CH_2Cl_2$ (30 mL) were added pyridine (1.4 mL, 17.4 mmol) and trifluoromethanesulfonic anhydride (1.76 mL, 10.46 mmol) slowly at 0° C. Then the mixture was stirred at rt for 2 hours, quenched with a small amount of water and extracted with $CH_2Cl_2$ (50 mL×3). The combined organic phases were dried over anhydrous $Na_2SO_4$ and filtered. The filtrate was concentrated in vacuo and the residue was purified by silica gel column chromatography (PE/DCM (v/v)=4/1) to give the title compound 48-3 as pale yellow slurry (1.14 g, 99.8%, HPLC: 95%). The compound was characterized by the following spectroscopic data:

MS-ESI: m/z 442.1 $[M+H]^+$; and $^1$H NMR (400 MHz, $CDCl_3$): δ 7.72 (d, J=8.0 Hz, 1H), 7.15 (d, J=8.0 Hz, 1H), 3.25 (s, 2H), 2.92 (s, 2H), 2.58 (s, 3H), 2.63 (s, 2H), 1.61-1.74 (m, 8H).

Step 4) The Preparation of Compound 48-4

To a solution of compound 48-3 (1.08 g, 2.45 mmol) in anhydrous $CH_3CN$ (22 mL) were added DIPEA (1.1 mL, 6.66 mmol) and Boc-L-proline (1.04 g, 4.83 mmol) in an ice bath. The reaction mixture was stirred at rt for 2 hours and concentrated in vacuo. The residue was purified by silica gel column chromatography (PE/EtOAc (v/v)=2/3) to give the title compound 48-4 as pale yellow slurry (1.4 g, 99.3%, HPLC: 99%). The compound was characterized by the following spectroscopic data:

MS-ESI: m/z 576.2 $[M+H]^+$; and $^1$H NMR (400 MHz, $CDCl_3$): δ 7.72 (d, J=8.0 Hz, 1H), 7.15 (d, J=8.0 Hz, 1H), 5.34 (s, 2H), 4.49-4.51 (m, 1H), 4.10-4.15 (m, 1H), 3.40-3.49 (m, 2H), 3.24 (s, 2H), 2.86 (s, 2H), 2.05-2.20 (m, 2H), 1.80-2.00 (m, 2H), 1.50-1.54 (m, 8H), 1.47 (s, 9H).

Step 5) The Preparation of Compound 48-5

To a solution of compound 48-4 (1.4 g, 2.43 mmol) in xylene (20 mL) was added $NH_4OAc$ (2.2 g, 28.54 mmol). The mixture was refluxed at 140° C. for 5 hours in a sealed tube. To the mixture was added $H_2O$ (30 mL). The mixture was extracted with EtOAc (50 mL×3). The combined organic phases were dried over anhydrous $Na_2SO_4$ and filtered. The filtrate was concentrated in vacuo and the residue was purified by silica gel column chromatography (DCM/MeOH (v/v)=50/1) to give the title compound 48-5 as a pale yellow solid (0.73 g, 54.1%, HPLC: 95%). The compound was characterized by the following spectroscopic data:

MS-ESI: m/z 556.2 $[M+H]^+$; and $^1$H NMR (400 MHz, $CDCl_3$): δ 10.49 (brs, 1H), 7.45 (d, J=8.0 Hz, 1H), 7.27 (d, J=8.0 Hz, 1H), 7.26 (s, 1H), 4.99-5.00 (m, 1H), 3.41-3.42 (m, 2H), 3.05 (s, 2H), 2.97 (s, 2H), 1.95-1.98 (m, 2H), 1.80-2.00 (m, 2H), 1.50-1.54 (m, 8H), 1.51 (s, 9H).

Step 6) The Preparation of Compound 48-6

A mixture of compound 3-3-2 (3.30 g, 7.98 mmol), 1-bromo-4-iodobenzene (1.88 g, 6.65 mmol), $Pd(PPh_3)_4$ (0.768 g, 0.66 mmol) and $K_2CO_3$ (2.77 g, 2.00 mmol) in mixed solvents of DME (50.0 mL) and $H_2O$ (10.0 mL) was stirred at 90° C. under $N_2$ overnight and then cooled down naturally. To the resulting mixture was added $H_2O$ (50.0 mL). The mixture was extracted with EtOAc (50.0 mL×3). The combined organic phases were washed with brine, dried over anhydrous $Na_2SO_4$ and filtered. The filtrate was concentrated in vacuo and the residue was purified by silica gel column chromatography (DCM/MeOH (v/v)=50/1) to give the title compound as a beige solid (2.62 g, 89.1%). The compound was characterized by the following spectroscopic data:

MS-ESI: m/z 444.1 $[M+H]^+$; and $^1$H NMR (400 MHz, $CDCl_3$): δ 8.22 (s, 0.5H), 7.86-7.87 (m, 0.5H), 7.61-7.66 (m, 2H), 7.51-7.53 (m, 2H), 7.37-7.39 (m, 2H), 5.05-5.16 (m, 1H), 3.52-3.61 (m, 2H), 1.86-2.46 (m, 4H), 1.27 (s, 9H).

A solution of the beige compound (4.53 g, 10.2 mmol), bis(pinacolato)diboron (3.88 g, 15.3 mmol), Pd(dppf)Cl$_2$·CH$_2$Cl$_2$ (0.833 g, 1.02 mmol) and KOAc (3.0 g, 30.6 mmol) in DMF (40 mL) was stirred at 90° C. under N$_2$ for 3 hours. The mixture was quenched with H$_2$O (20 mL) and extracted with EtOAc (20 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=3/1) to give the title compound 48-6 as a white solid (4.67 g, 93.2%). The compound was characterized by the following spectroscopic data:

MS-ESI: m/z 490.3 [M+H]$^+$; and $^1$H NMR (400 MHz, CDCl$_3$): δ 8.23 (s, 0.5H), 7.87-7.88 (m, 0.5H), 7.60-7.65 (m, 2H), 7.51-7.53 (m, 2H), 7.36-7.38 (m, 2H), 5.04-5.12 (m, 1H), 3.52-3.61 (m, 2H), 1.84-2.41 (m, 4H), 1.34 (s, 12H), 1.25 (s, 9H).

Step 7) The Preparation of Compound 48-7

A mixture of compound 48-5 (2.21 g, 3.98 mmol), compound 48-6 (1.63 g, 3.33 mmol), Pd(PPh$_3$)$_4$ (0.384 g, 0.33 mmol) and K$_2$CO$_3$ (1.38 g, 9.98 mmol) in mixed solvents of DME (50.0 mL) and H$_2$O (10.0 mL) was stirred at 90° C. under N$_2$ overnight, then cooled down naturally and concentrated in vacuo. To the residue was added H$_2$O (50.0 mL). The mixture was extracted with EtOAc (50.0 mL×3). The combined organic phases were washed with brine, dried over anhydrous Na$_2$SO$_4$ and filtered. The filtrate was concentrated in vacuo and the residue was purified by silica gel column chromatography (DCM/MeOH (v/v)=50/1) to give the title compound 48-7 as a beige solid (2.26 g, 88.3%). The compound was characterized by the following spectroscopic data:

$^1$H NMR (400 MHz, CDCl$_3$): δ 7.74-7.71 (m, 2H), 7.66-7.68 (m, 2H), 7.51-7.54 (m, 2H), 7.33-7.35 (m, 2H), 7.28-7.29 (m, 2H), 5.35-5.37 (m, 1H), 5.20-5.21 (m, 1H), 3.96-4.08 (m, 2H), 3.31 (s, 2H), 3.01 (s, 2H), 2.05-2.24 (m, 8H), 1.55-1.59 (m, 8H), 1.27 (s, 18H).

Step 8) The Preparation of Compound 48-8

To a solution of compound 48-7 (10.0 g, 13.0 mmol) in EtOAc (50.0 mL) was added a solution of HCl in EtOAc (4 M, 60.0 mL). The reaction mixture was stirred at rt overnight and filtered. The filter cake was washed with EtOAc (50 mL) to give the title compound 48-8 as a pale yellow solid (8.0 g, 86.1%). The compound was characterized by the following spectroscopic data:

$^1$H NMR (400 MHz, CDCl$_3$): δ 7.72-7.75 (m, 2H), 7.64-7.68 (m, 2H), 7.50-7.52 (m, 2H), 7.33-7.34 (m, 2H), 7.27-7.29 (m, 2H), 5.31-5.32 (m, 1H), 5.21-5.23 (m, 1H), 3.96-4.08 (m, 2H), 3.30 (s, 2H), 3.11 (s, 2H), 2.06-2.25 (m, 8H), 1.56-1.59 (m, 8H).

Step 9) The Preparation of Compound 48-9

A suspension of compound 48-8 (0.151 g, 0.21 mmol), EDCI (0.22 g, 1.15 mmol) and compound 1-7-2 (0.15 g, 0.86 mmol) in CH$_2$Cl$_2$ (3 mL) was cooled to 0° C. in an ice bath. To the mixture was added dropwise DIPEA (0.5 mL, 3.02 mmol) slowly. The mixture was stirred at rt for 10 hours. To the mixture was added H$_2$O (10 mL). The mixture was extracted with CH$_2$Cl$_2$ (10 mL×3). The combined organic phases were dried over anhydrous Na$_2$SO$_4$ and filtered. The filtrate was concentrated in vacuo and the residue was purified by silica gel column chromatography (DCM/MeOH (v/v)=40/1) to give the title compound 48-9 as a pale yellow solid (0.05 g, 26.8%, HPLC: 95.3%). The compound was characterized by the following spectroscopic data:

MS-ESI: m/z 884.1 [M+H]$^+$; and $^1$H NMR (400 MHz, CDCl$_3$): δ 7.71-7.73 (m, 2H), 7.65-7.68 (m, 2H), 7.50-7.52 (m, 2H), 7.31-7.33 (m, 2H), 7.28-7.29 (m, 2H), 5.35-5.37 (m, 1H), 5.20-5.21 (m, 1H), 4.20-4.25 (m, 2H), 3.96-4.08 (m, 2H), 3.90-3.92 (m, 2H), 3.61 (s, 6H), 3.31 (s, 2H), 3.01 (s, 2H), 2.05-2.24 (m, 10H), 1.55-1.59 (m, 8H), 0.84-0.91 (m, 12H).

Example 49

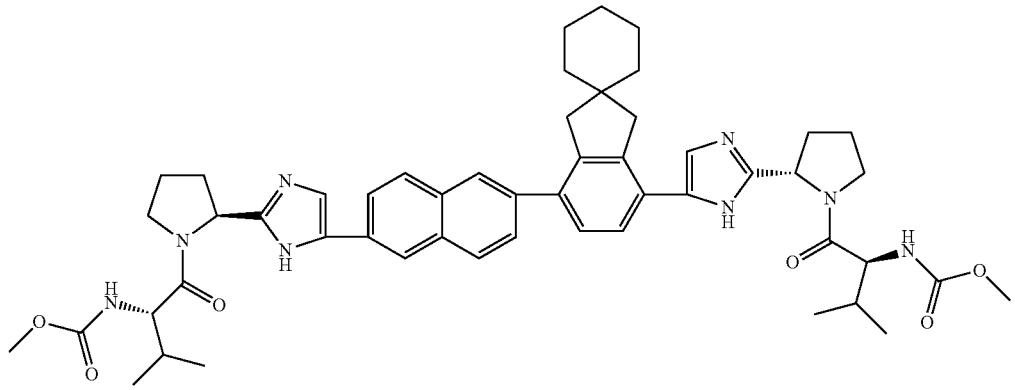

Synthetic Routes

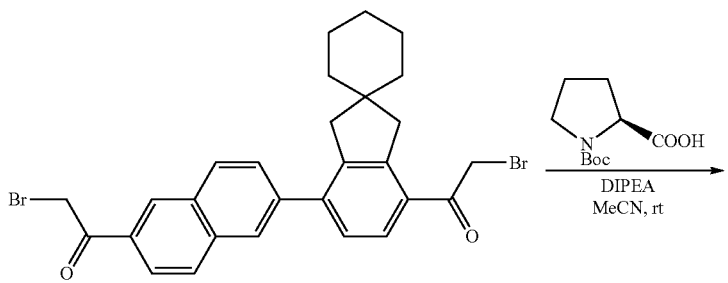

49-1

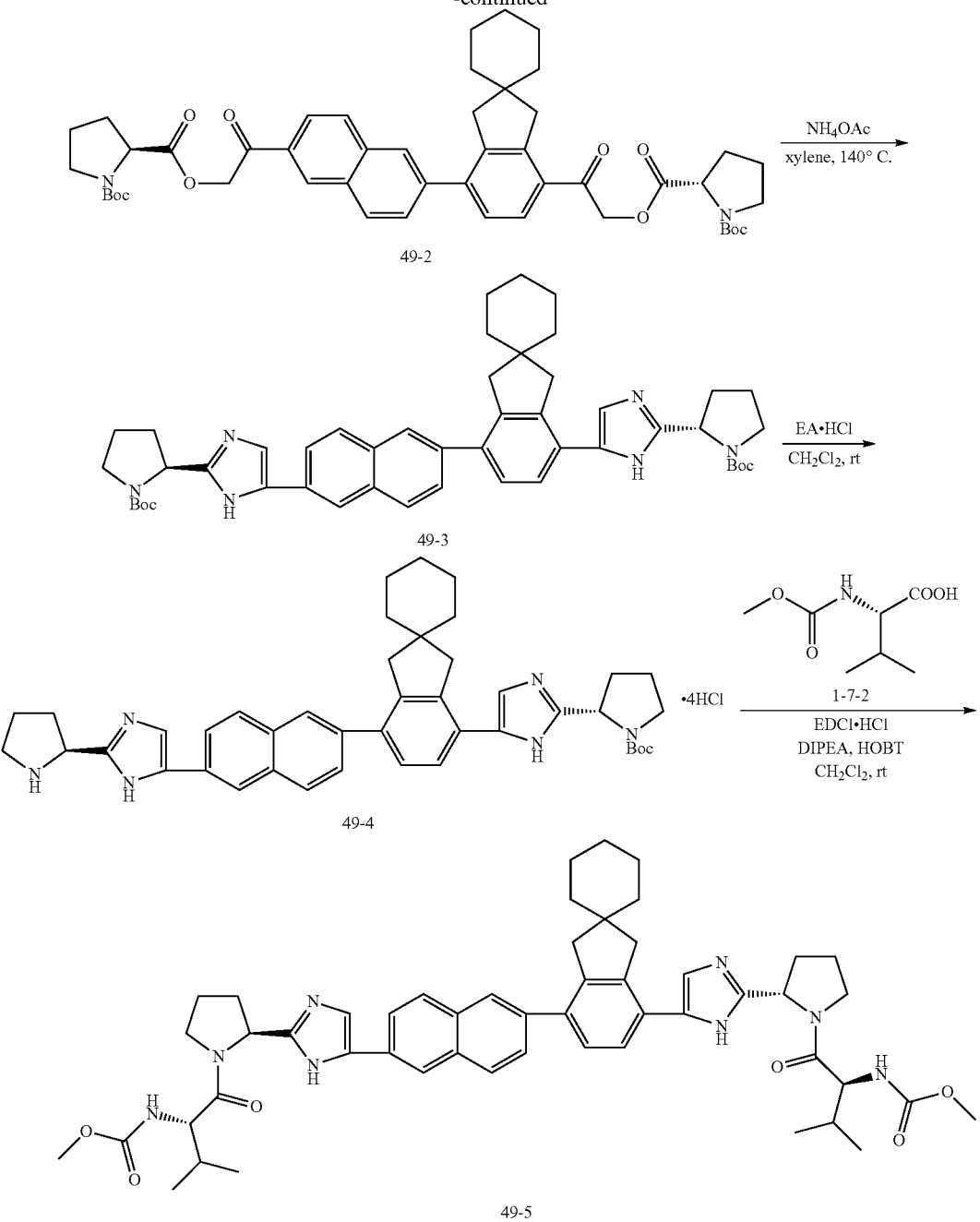

Step 1) The Preparation of Compound 49-1

The title compound 49-1 was prepared by an analogous procedure to that described for compound 14-6 (Example 14). The compound was characterized by the following spectroscopic data:

MS-ESI: m/z 555.2 [M+H]$^+$; and $^1$H NMR (400 MHz, CDCl$_3$): δ 8.57 (s, 1H), 8.11-8.05 (m, 2H), 7.98 (d, J=8.7 Hz, 1H), 7.93 (s, 1H), 7.79 (d, J=8.1 Hz, 1H), 7.67 (dd, J=8.5, 1.7 Hz, 1H), 7.39 (d, J=8.0 Hz, 1H), 4.60 (s, 2H), 4.51 (s, 2H), 3.22 (s, 2H), 2.86 (s, 2H), 1.58-1.30 (m, 10H).

Step 2) The Preparation of Compound 49-2

To a solution of compound 49-1 (4.4 g, 7.9 mmol) in CH$_3$CN (30 mL) were added CH$_2$Cl$_2$ (20 mL) and DIPEA (4.1 mL, 24.8 mmol). The mixture was stirred for 5 minutes and to which was added Boc-L-proline (3.8 g, 17.6 mmol). The mixture was stirred at rt overnight and concentrated in vacuo. To the residue was added H$_2$O (60 mL). The mixture was extracted with EtOAc (50 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=2/1) to give the title compound 49-2 as a pale yellow solid (4.4 g, 67.7%). The compound was characterized by the following spectroscopic data:

MS-ESI: m/z 846.1 [M+Na]$^+$; and $^1$H NMR (400 MHz, CDCl$_3$): δ 8.46 (d, J=3.1 Hz, 1H), 8.06-7.93 (m, 3H), 7.90 (d, J=3.0 Hz, 1H), 7.69 (d, J=8.0 Hz, 1H), 7.68-7.60 (m, 1H), 7.36 (d, J=8.0 Hz, 1H), 5.76-5.45 (m, 2H), 5.45-5.13 (m, 2H), 4.55-4.39 (m, 2H), 3.66-3.52 (m, 2H), 3.52-3.38 (m, 2H), 3.17 (s, 2H), 2.83 (s, 2H), 2.42-2.25 (m, 4H), 2.17-1.86 (m, 4H), 1.58-1.30 (m, 28H).

Step 3) The Preparation of Compound 49-3

To a solution of compound 49-2 (1.01 g, 1.22 mmol) in xylene (12 mL) was added NH$_4$OAc (1.51 g, 19.60 mmol). The mixture was heated at 140° C. overnight in a sealed tube, then cooled down naturally and concentrated in vacuo. To the residue was added H$_2$O (20 mL). The mixture was extracted with EtOAc (30 mL×3). The combined organic phases were washed with brine, dried over anhydrous Na$_2$SO$_4$ and filtered. The filtrate was concentrated in vacuo and the residue was purified by silica gel column chromatography (DCM/MeOH (v/v)=30/1) to give the title compound 49-3 as a yellowish-brown solid (0.59 g, 61.7%). The compound was characterized by the following spectroscopic data:

MS-ESI: m/z 785.1 [M+H]$^+$; and $^1$H NMR (400 MHz, CDCl$_3$): δ 11.13 (s, br, 1H), 10.59 (s, br, 1H), 7.98-7.78 (m, 4H), 7.58 (d, J=8.0 Hz, 1H), 7.39-7.30 (m, 2H), 7.18 (s, 1H), 5.03 (s, 2H), 3.62-3.35 (m, 4H), 3.14-2.87 (m, 6H), 2.30-2.12 (m, 4H), 2.12-1.88 (m, 4H), 1.58-1.32 (m, 28H).

Step 4) The Preparation of Compound 49-4

To a solution of compound 49-3 (0.56 g, 0.72 mmol) in CH$_2$Cl$_2$ (3 mL) was added a solution of HCl in EtOAc (4 M, 13 mL) in an ice bath. The mixture was stirred at rt overnight, and pale yellow solid precipitated out. The reaction was monitored by LC-MS until a trace amount of the desired compound was detected. The mixture was then kept still, and the supernatant was discarded. The residue was washed with EtOAc (5 mL) assisted by sonicating in an ultrasonic cleaner, then kept still and the supernatant was discarded. The washing was repeated four more times and the residue was then concentrated in vacuo to give compound 49-4 as a pale yellow solid (0.51 g, 97.1%). The compound was characterized by the following spectroscopic data:

MS-ESI: m/z 583.3 [M+H]$^+$; and $^1$H NMR (400 MHz, D$_2$O): δ 8.30-7.00 (m, 8H), 5.25-4.55 (m, 4H), 3.67-3.33 (m, 4H), 2.80-1.95 (m, 14H), 1.30-0.50 (m, 10H).

Step 5) The Preparation of Compound 49-5

To a mixture of compound 49-4 (0.20 g, 0.27 mmol), compound 1-7-2 (0.15 g, 0.86 mmol), EDCI (0.23 g, 1.20 mmol) and HOBT (0.12 g, 0.89 mmol) was added CH$_2$Cl$_2$ (5 mL) via syringe followed by DIPEA (0.62 mL, 3.75 mmol) under N$_2$ in an ice bath. The reaction mixture was stirred at rt overnight. To the resulting mixture was added H$_2$O (15 mL) and CH$_2$Cl$_2$ (15 mL). The aqueous phase was extracted with CH$_2$Cl$_2$ (15 mL×2). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/10) to give the title compound 49-5 as white powder (0.10 g, 40.7%). The compound was characterized by the following spectroscopic data:

MS-ESI: m/z 449.4 [M+2H]$^{2+}$; and $^1$H NMR (400 MHz, CDCl$_3$): δ 11.13 (s, br, 1H), 10.59 (s, br, 1H), 7.95-7.70 (m, 4H), 7.55 (s, 1H), 7.40-7.29 (m, 2H), 7.15 (s, 1H), 5.53 (d, J=8.8 Hz, 2H), 5.38-5.20 (m, 2H), 4.40-4.30 (m, 2H), 3.92-3.60 (m, 10H), 2.48-1.90 (m, 8H), 1.90-1.60 (m, 6H), 1.58-1.35 (m, 10H), 0.98-0.75 (m, 12H).

Example 50

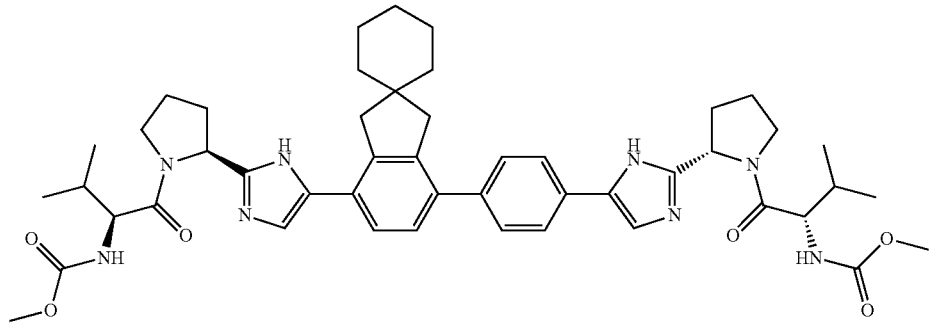

Synthetic Routes

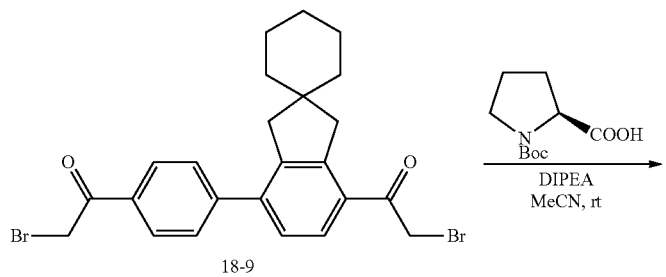

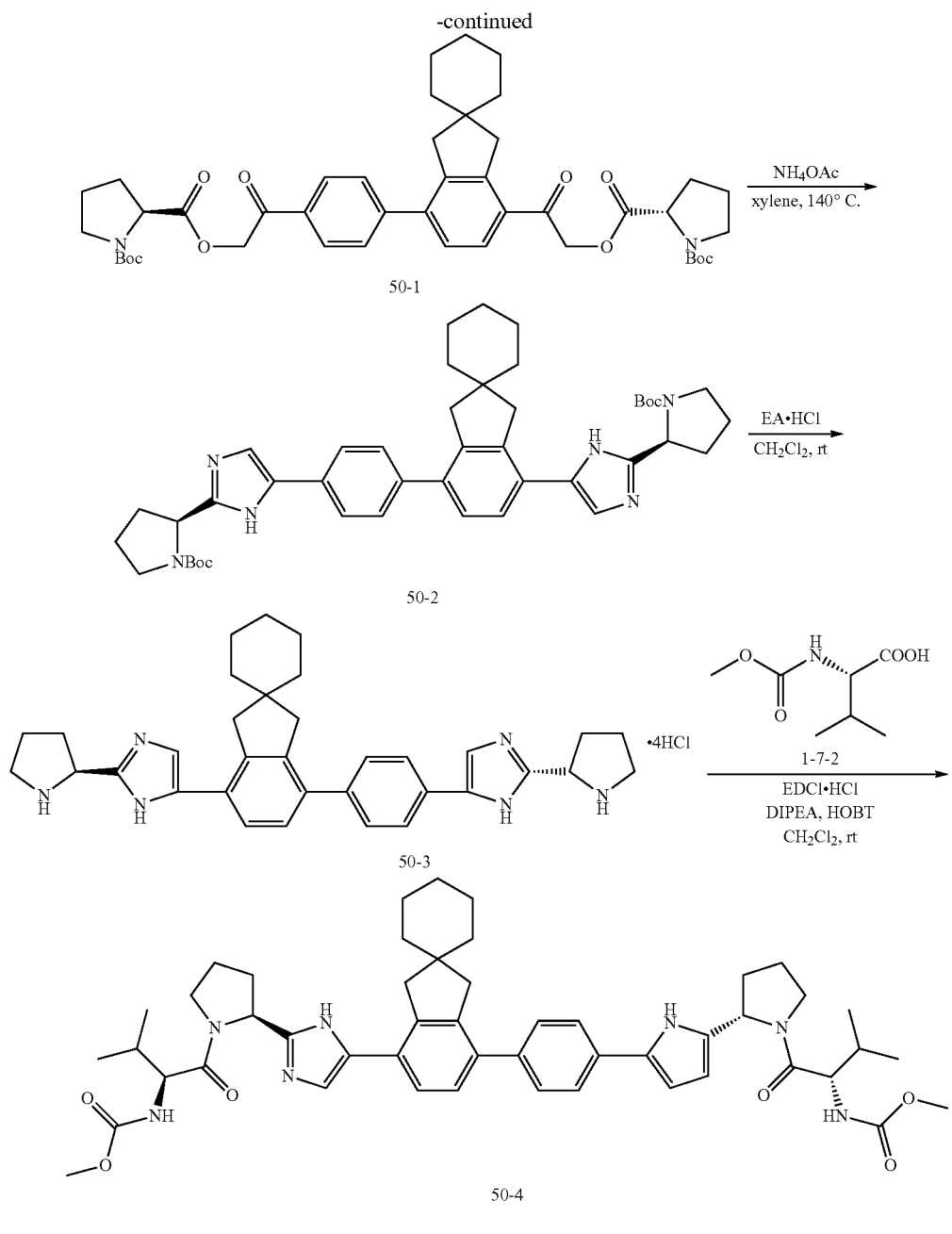

Step 1) The Preparation of Compound 50-1

To a solution of compound 18-9 (0.94 g, 1.86 mmol) in CH$_3$CN (20 mL) was added DIPEA (0.97 mL, 5.59 mmol). After the mixture was stirred for 5 minutes, Boc-L-proline (0.88 g, 4.10 mmol) was added. The mixture was stirred at rt for 3 hours and concentrated in vacuo. The residue was purified by silica gel column chromatography (PE/EtOAc (v/v)=3/1) to give the title compound 50-1 as pale yellow dope (1.01 g, 70.2%). The compound was characterized by the following spectroscopic data:

MS-ESI: m/z 772.4 [M+H]$^+$; and $^1$H NMR (400 MHz, CDCl$_3$): δ 8.03-7.96 (m, 2H), 7.67 (d, J=8.0 Hz, 1H), 7.57 (dd, J=8.2, 3.0 Hz, 2H), 7.27 (d, J=8.0 Hz, 1H), 5.65-5.15 (m, 4H), 4.52-4.39 (m, 2H), 3.65-3.53 (m, 2H), 3.53-3.38 (m, 2H), 3.16 (s, 2H), 2.78 (s, 2H), 2.41-2.20 (m, 4H), 2.18-1.88 (m, 4H), 1.55-1.38 (m, 28H).

Step 2) The Preparation of Compound 50-2

To a solution of compound 50-1 (1.01 g, 1.31 mmol) in xylene (12 mL) was added NH$_4$OAc (1.51 g, 19.60 mmol). The mixture was heated at 140° C. in a sealed tube, then cooled down naturally and concentrated in vacuo. To the residue was added H$_2$O (20 mL). The mixture was extracted with EtOAc (30 mL×3). The combined organic phases were washed with brine, dried over anhydrous Na$_2$SO$_4$ and filtered. The filtrate was concentrated in vacuo and the residue was purified by silica gel column chromatography (DCM/MeOH (v/v)=30/1) to give the title compound 50-2 as a yellowish-brown solid (0.59 g, 61.5%). The compound was characterized by the following spectroscopic data:

MS-ESI: m/z 733.4 [M+H]$^+$; and

¹H NMR (400 MHz, CDCl₃): δ 7.78-7.59 (m, 2H), 7.53-7.40 (m, 3H), 7.31-7.20 (m, 2H), 7.20-7.13 (m, 1H), 5.01 (br, 2H), 3.63-3.36 (m, 4H), 3.02-2.85 (m, 4H), 2.42-1.90 (m, 8H), 1.62-1.30 (m, 28H).

Step 3) The Preparation of Compound 50-3

To a solution of compound 50-2 (0.56 g, 0.76 mmol) in CH₂Cl₂ (3 mL) was added a solution of HCl in EtOAc (4 M, 13 mL). The mixture was stirred at rt overnight and pale yellow solid precipitated out. The reaction was monitored by LC-MS until a trace amount of the desired compound was detected. The mixture was then kept still, and the supernatant was discarded. The residue was washed with EtOAc (5 mL) assisted by sonicating in an ultrasonic cleaner, then kept still and the supernatant was discarded. The washing was repeated four more times and the residue was then concentrated in vacuo to give the title compound 50-3 as a pale yellow solid (0.51 g, 98.8%). The compound was characterized by the following spectroscopic data:

MS-ESI: m/z 533.3 [M+H]⁺; and

¹H NMR (400 MHz, CDCl₃): δ 7.81-7.74 (m, 3H), 7.66-7.59 (m, 2H), 7.51 (d, J=8.0 Hz, 1H), 7.40 (d, J=8.0 Hz, 1H), 5.18-5.10 (m, 2H), 3.60-3.48 (m, 4H), 2.88 (d, J=2.3 Hz, 4H), 2.72-2.60 (m, 2H), 2.51-2.39 (m, 2H), 2.39-2.29 (m, 2H), 2.25-2.10 (m, 2H), 1.45-1.35 (m, 10H).

Step 4) The Preparation of Compound 50-4

To a mixture of compound 50-3 (0.20 g, 0.29 mmol), compound 1-7-2 (0.15 g, 0.88 mmol), EDCI (0.23 g, 1.18 mmol) and HOBT (0.12 g, 0.88 mmol) was added CH₂Cl₂ (5 mL) via syringe followed by DIPEA (0.62 mL, 3.54 mmol) under N₂ in an ice bath. The reaction mixture was stirred at rt overnight. To the resulting mixture were added H₂O (15 mL) and CH₂Cl₂ (15 mL). The aqueous phase was extracted with CH₂Cl₂ (15 mL×2). The combined organic phases were washed with brine, dried over anhydrous Na₂SO₄ and filtered. The filtrate was concentrated in vacuo and the residue was purified by silica gel column chromatography (PE/EtOAc (v/v)=1/10) to give the title compound 50-4 as white powder (0.10 g, 40.5%). The compound was characterized by the following spectroscopic data:

MS-ESI: m/z 845.5 [M−H]⁻; and

¹H NMR (400 MHz, CDCl₃): δ 7.82-7.58 (m, 2H), 7.50-7.36 (m, 3H), 7.25-7.17 (m, 2H), 7.11 (s, 1H), 5.70-5.59 (m, 2H), 5.32-5.22 (m, 2H), 4.38-4.29 (m, 2H), 3.91-3.80 (m, 2H), 3.78-3.60 (m, 8H), 3.04-2.80 (m, 6H), 2.46-1.90 (m, 8H), 1.52-1.35 (m, 12H), 0.93-0.78 (m, 12H).

Example 51

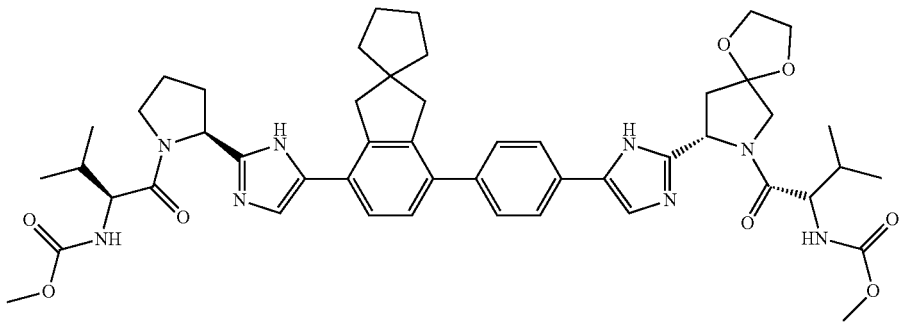

Synthetic Routes

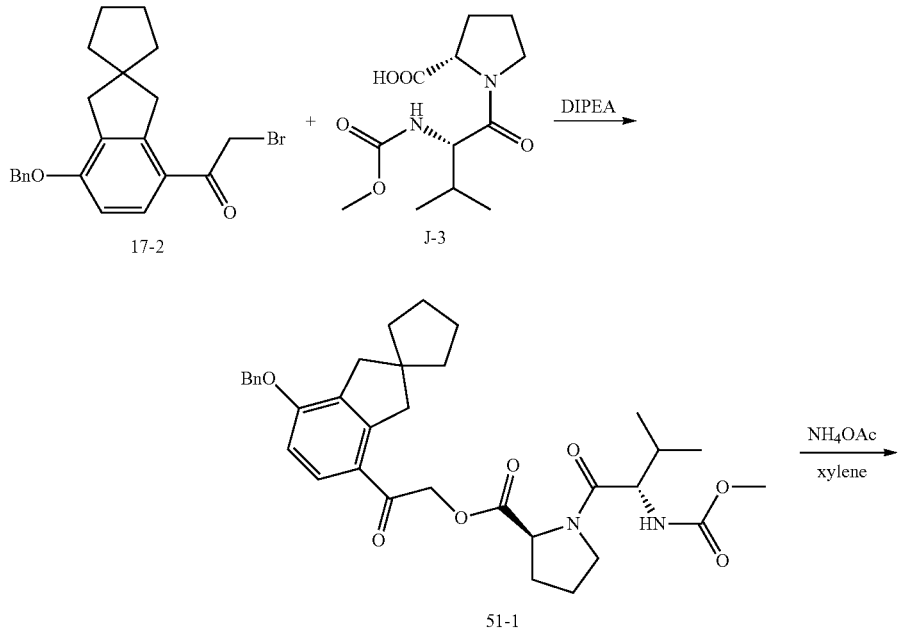

-continued
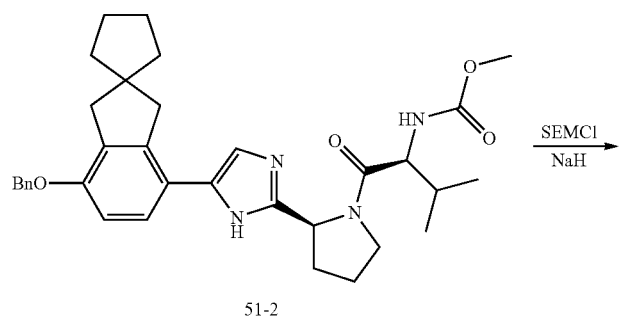
51-2
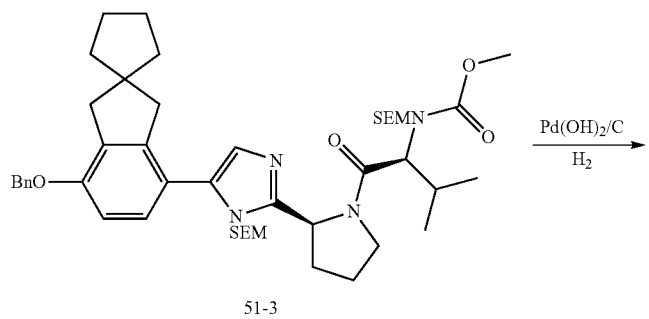
51-3
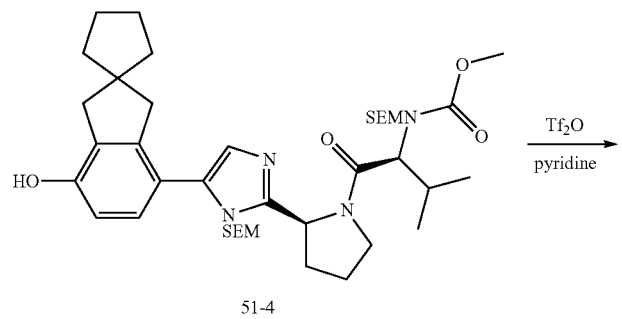
51-4
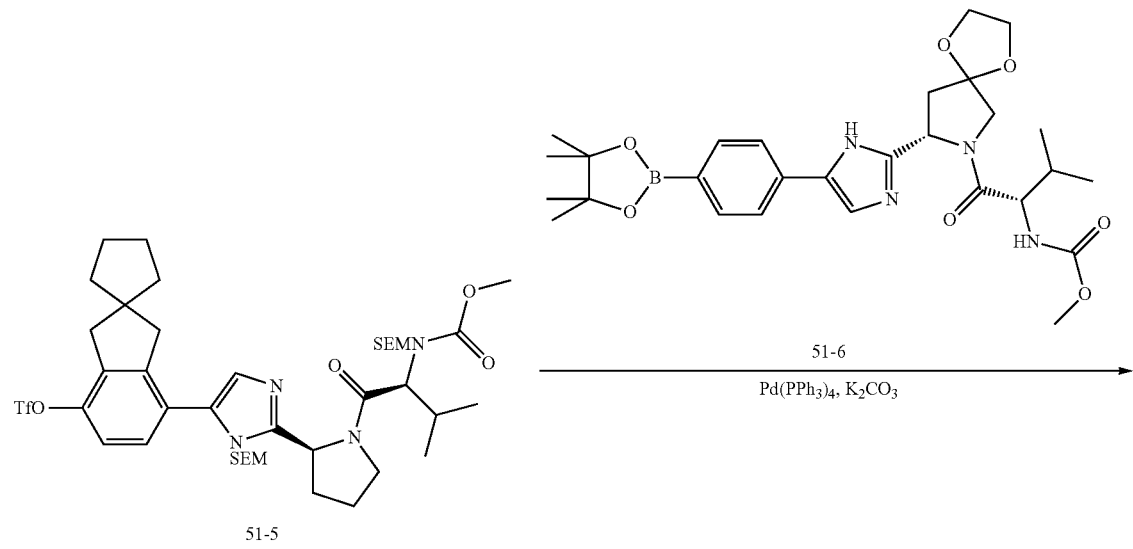
51-5

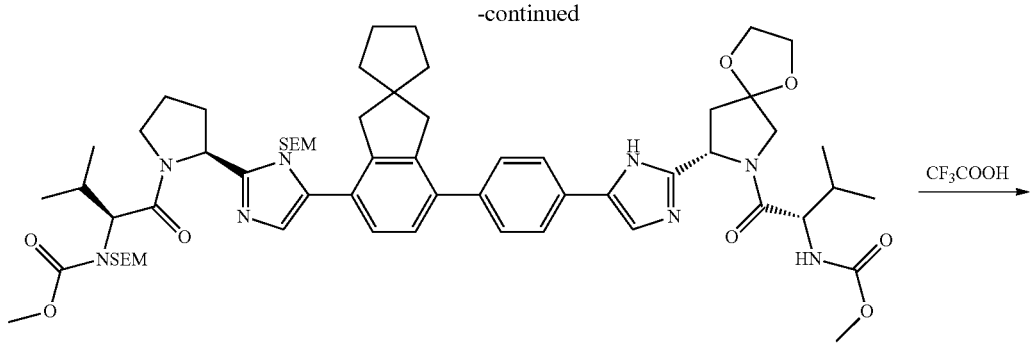
51-7
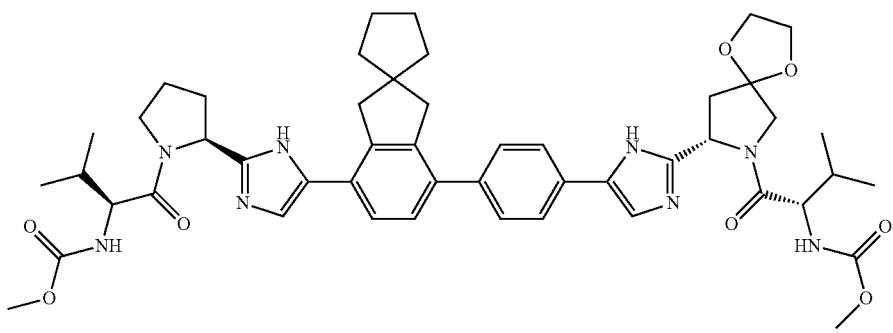
51-8
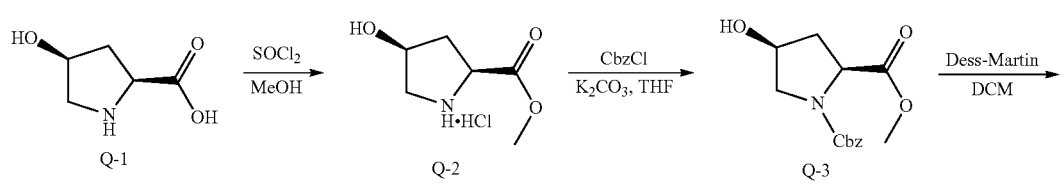
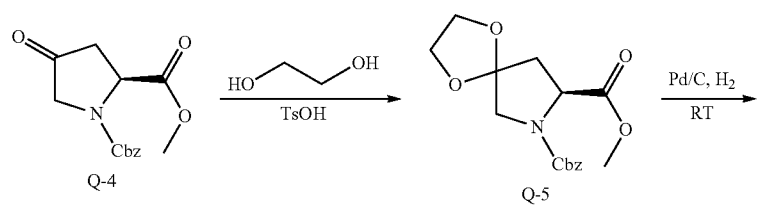
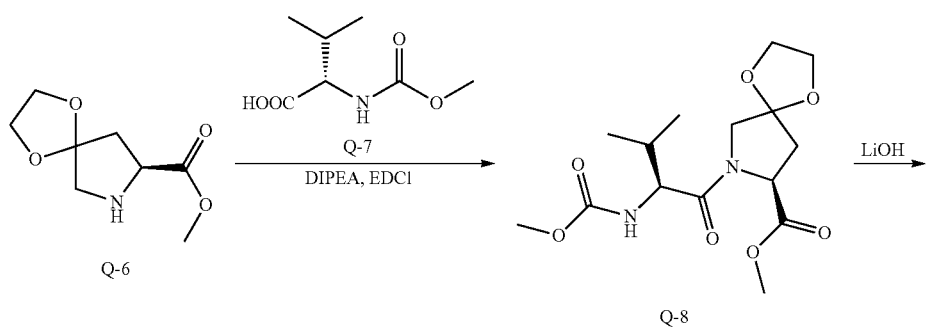

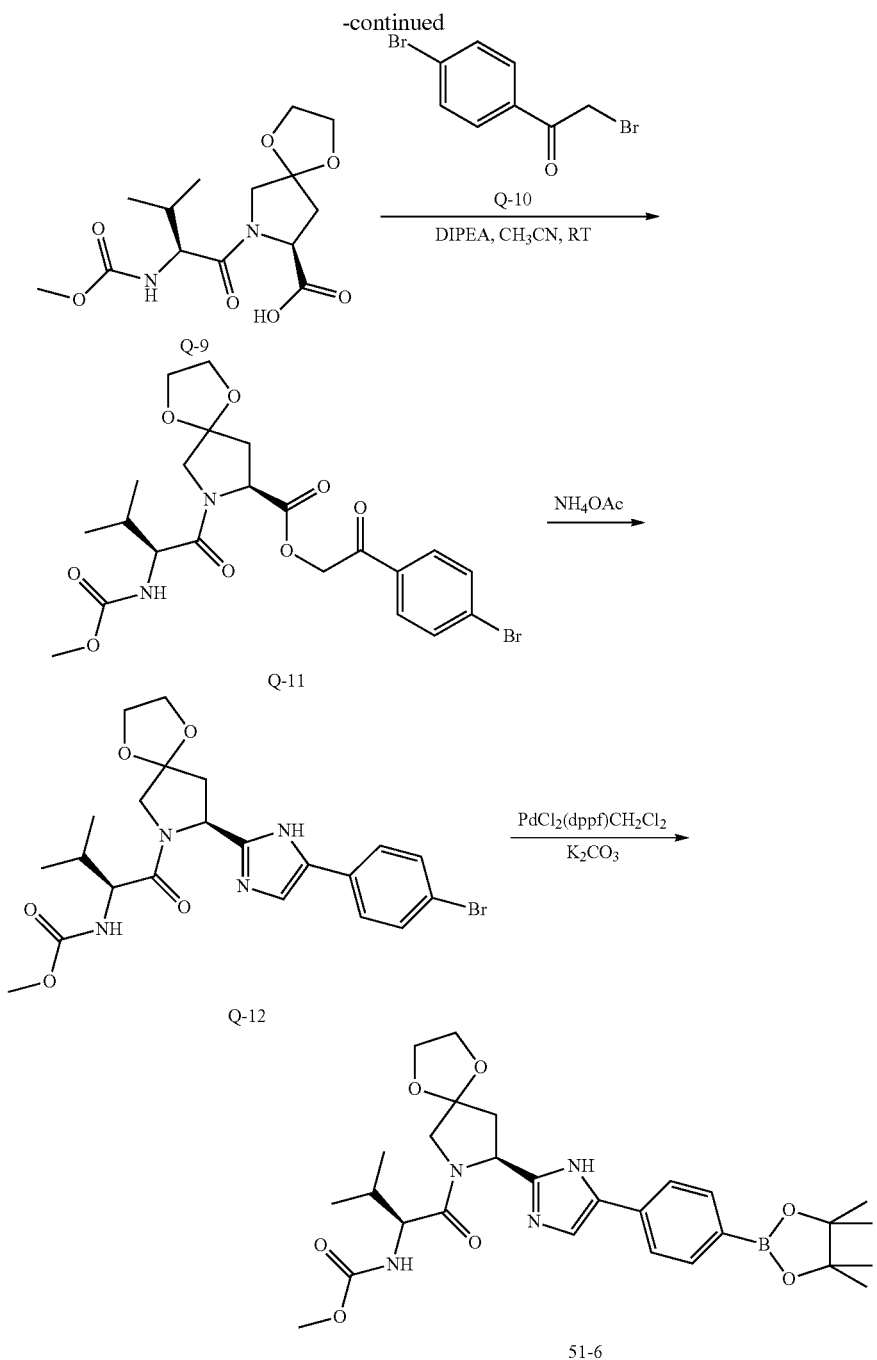

Step 1) The Preparation of Compound 51-1

To a solution of compound 17-2 (1.0 g, 2.5 mmol) in anhydrous $CH_3CN$ (15 mL) in an ice bath were added DIPEA (0.82 mL, 5.0 mmol) and compound J-3 (0.64 g, 2.4 mmol) in turn. The mixture was stirred at rt for 1 hour and concentrated in vacuo. The residue was purified by silica gel column chromatography (PE/EtOAc (v/v)=5/1) to give the title compound 51-1 as a pale yellow solid (1.1 g, 77.5%, HPLC: 99%). The compound was characterized by the following spectroscopic data:

MS-ESI: m/z 534.66 [M+H]$^+$; and $^1$H NMR (400 MHz, $CDCl_3$): δ 7.60 (d, J=8.0 Hz, 1H), 7.33-7.43 (m, 5H), 6.76 (d, J=8.0 Hz, 1H), 5.09-5.52 (m, 2H), 5.46 (d, J=8.0 Hz, 1H), 5.24 (q, J=8.0 Hz, 1H), 4.30-4.34 (m, 1H), 3.79-3.83 (m, 1H), 3.69 (s, 3H), 3.09 (s, 2H), 2.87 (s, 2H), 1.93-2.35 (m, 4H), 1.63-1.71 (m, 8H), 1.02-1.07 (m, 1H), 0.88 (d, J=8.0 Hz, 6H).

Step 2) The Preparation of Compound 51-2

To a solution of compound 51-1 (3.74 g, 6.3 mmol) in xylene (25 mL) was added ammonium acetate (4.9 g, 63.3 mmol). The reaction mixture was refluxed at 140° C. for 5 hours in a sealed tube and cooled to rt. To the resulting mixture was added $H_2O$ (20 mL). The mixture was extracted with EtOAc (50 mL×3). The combined organic phases were dried over anhydrous $Na_2SO_4$ and filtered. The filtrate was concentrated in vacuo and the residue was purified by silica gel column chromatography (PE/EtOAc (v/v)=1/4) to give the title compound 51-2 as a pale yellow solid (2.5 g, 69.4%, HPLC: 96%). The compound was characterized by the following spectroscopic data:

MS-ESI: m/z 571.72 [M+H]$^+$; and $^1$H NMR (400 MHz, CDCl$_3$): δ 10.60 (brs, 1H), 10.63 (brs, 1H), 7.31-7.44 (m, 6H), 6.99 (s, 1H), 6.76 (d, J=8.0 Hz, 1H), 5.46 (d, J=8.0 Hz, 1H), 5.24 (q, J=8.0 Hz, 1H), 5.09 (s, 2H), 4.30-4.34 (m, 1H), 3.79-3.83 (m, 1H), 3.69 (s, 3H), 3.59-3.64 (m, 1H), 2.95-3.01 (m, 3H), 2.87 (s, 2H), 1.93-2.35 (m, 4H), 1.63-1.71 (m, 8H), 1.02-1.07 (m, 1H), 0.88 (d, J=8.0 Hz, 6H).

Step 3) The Preparation of Compound 51-3

To a solution of compound 51-2 (1.5 g, 2.6 mmol) in DMF (15 mL) was added NaCl (0.42 g, 10.5 mmol) in an ice bath. The reaction mixture was stirred at 0° C. for 30 minutes. To the mixture was added SEMCl (0.94 mL, 5.3 mmol). The mixture was stirred at rt for 2 hours, quenched with ice water (10 mL) and extracted with EtOAc (30 mL×3). The combined organic phases were dried over anhydrous Na$_2$SO$_4$ and filtered. The filtrate was concentrated in vacuo and the residue was purified by silica gel column chromatography (PE/EtOAc (v/v)=5/1) to give the title compound 51-3 as colorless slurry (1.26 g, 58.3%, HPLC: 95%). The compound was characterized by the following spectroscopic data:

MS-ESI: m/z 832.24 [M+H]$^+$; and $^1$H NMR (400 MHz, CDCl$_3$): δ 7.63 (d, J=8.0 Hz, 1H), 7.30-7.44 (m, 5H), 6.89 (s, 1H), 6.76 (d, J=8.0 Hz, 1H), 5.85 (d, J=8.0 Hz, 1H), 5.02-5.18 (m, 5H), 4.59-4.67 (m, 2H), 3.92-3.96 (m, 2H), 3.76 (s, 3H), 3.47-3.57 (m, 4H), 2.90-3.04 (q, J=16.0 Hz, 2H), 2.02 (s, 2H), 1.56-1.77 (m, 8H), 0.02 (d, J=2.0 Hz, 18H).

Step 4) The Preparation of Compound 51-4

To a solution of compound 51-3 (1.25 g, 1.5 mmol) in EtOAc (5 mL) were added CH$_3$OH (15 mL) and Pd(OH)$_2$/C (0.4 g) in turn. The reaction mixture was stirred at rt for 5 hours under H$_2$ (1 atm) and filtered. The filtrate was concentrated in vacuo to give the title compound 51-4 as a white solid (1.03 g, 92.8%). The compound was characterized by the following spectroscopic data:

MS-ESI: m/z 742 [M+H]$^+$; and $^1$H NMR (400 MHz, CDCl$_3$): δ 7.48 (d, J=8.0 Hz, 1H), 6.85 (s, 1H), 6.55 (d, J=8.0 Hz, 1H), 5.83 (d, J=8.0 Hz, 1H), 5.00-5.17 (m, 3H), 4.59-4.66 (m, 2H), 3.92-3.95 (m, 2H), 3.76 (s, 3H), 2.87-3.01 (m, 2H), 2.76 (s, 2H), 2.50-2.55 (m, 1H), 2.15-2.19 (m, 3H), 1.96-1.99 (m, 1H), 1.66-1.70 (m, 8H), 0.87-0.95 (m, 6H), 0.79-0.80 (m, 2H), 0.02 (d, J=2.0 Hz, 18H).

Step 5) The Preparation of Compound 51-5

To a solution of compound 51-4 (1.0 g, 1.3 mmol) in anhydrous CH$_2$Cl$_2$ (20 mL) was added dropwise pyridine (0.7 mL, 8.7 mmol) slowly at 0° C. Then to the pale yellow mixture was added dropwise Tf$_2$O (0.9 mL, 5.3 mmol) slowly at 0° C. The mixture was stirred at rt for 2 hours. To the resulting mixture was added a little water, and the mixture was extracted with CH$_2$Cl$_2$ (20 mL×3). The combined organic phases were dried over anhydrous Na$_2$SO$_4$ and filtered. The filtrate was concentrated in vacuo and the residue was purified by silica gel column chromatography (PE/EtOAc (v/v)=4/1) to give the title compound 51-5 as colorless and transparent slurry (0.48 g, 42.3%). The compound was characterized by the following spectroscopic data:

$^1$H NMR (400 MHz, CDCl$_3$): δ 7.74 (d, J=8.0 Hz, 1H), 7.04 (d, J=8.0 Hz, 1H), 6.99 (s, 1H), 5.84 (d, J=8.0 Hz, 1H), 5.19 (d, J=8.0 Hz, 1H), 5.10-5.11 (m, 1H), 5.00-5.03 (m, 1H), 4.59-4.65 (m, 2H), 3.93-3.94 (m, 2H), 3.76 (s, 3H), 3.47-3.57 (m, 4H), 2.93-3.02 (m, 4H), 2.53-2.56 (m, 1H), 2.04-2.28 (m, 4H), 1.67-1.71 (m, 8H), 0.79-0.94 (m, 8H), 0.02 (d, J=2.0 Hz, 18H).

Step 6) The Preparation of Compound 51-6

To a mixture of compound Q-1 (2 g, 15.3 mmol) in CH$_3$OH (25 mL) was added thionyl chloride (3.4 mL, 46.9 mmol) slowly at 0° C. The reaction mixture was refluxed at 80° C. for 3.5 hours and concentrated in vacuo to give compound Q-2 as a white solid (2.76 g, 99.5%). The crude product was used for the next step without further purification. The compound was characterized by the following spectroscopic data:

$^1$H NMR (400 MHz, CD$_3$Cl): δ 3.68 (s, 3H), 3.58 (t, 1H), 3.56 (s, 1H), 3.32 (m, 1H), 3.02 (m, 1H), 2.77 (m, 1H), 2.52 (s, 1H), 2.21 (m, 1H), 1.96 (m, 1H).

To a solution of benzyl chloroformate (3.7 mL, 26.3 mmol) and K$_2$CO$_3$ (10.6 g, 76.7 mmol) in mixed solvents of THF (20 mL) and H$_2$O (10 mL) was added compound Q-2 (3.1 g, 17.1 mmol) in one portion while the mixture was stirred vigorously. At the end of the addition, the mixture was stirred at rt overnight, adjusted to pH 3 with diluted hydrochloric acid and extracted with EtOAc (50 mL×3). The combined organic phases were dried over anhydrous Na$_2$SO$_4$ and filtered. The filtrate was concentrated in vacuo and the residue was purified by silica gel column chromatography (PE/EtOAc (v/v)=4/1) to give compound Q-3 as pale yellow oil (3 g, 62.8%). The compound was characterized by the following spectroscopic data:

$^1$H NMR (400 MHz, CD$_3$Cl): δ 7.47 (d, J=8.24 Hz, 2H), 7.38 (d, J=8.24 Hz, 2H), 7.24 (m, 1H), 5.09 (s, 2H), 4.18 (t, 1H), 3.68 (s, 3H), 3.63 (m, 1H), 3.58 (s, 1H), 3.38 (m, 1H), 3.32 (m, 1H), 2.21 (m, 1H), 1.96 (m, 1H).

To a solution of compound Q-3 (1.0 g, 3.6 mmol) in DCM (20 mL) was added Dess-Martin (3.0 g, 7.1 mmol) slowly in an ice bath. The reaction mixture was stirred at rt for 1 hour and filtered. The filtrate was concentrated in vacuo and the residue was purified by silica gel column chromatography (PE/EA (v/v)=5/1) to give compound Q-4 as yellow oil (0.79 g, 79.5%). The compound was characterized by the following spectroscopic data:

$^1$H NMR (400 MHz, CD$_3$Cl): δ 7.47 (d, J=8.24 Hz, 2H), 7.38 (d, J=8.24 Hz, 2H), 7.24 (m, 1H), 5.09 (s, 2H), 4.18 (t, 1H), 3.68 (s, 3H), 3.38 (m, 1H), 3.32 (m, 1H), 2.21 (m, 1H), 1.96 (m, 1H).

To a solution of compound Q-4 (1.0 g, 3.6 mmol) in toluene (20 mL) in a flask equipped with Dean-Stock trap were added ethylene glycol (0.8 mL, 15.7 mmol) and TsOH (0.14 g, 0.8 mmol) in turn. The reaction mixture was refluxed overnight. After the reaction was complete, the mixture was diluted with EtOAc (10 mL), and washed with saturated NaHCO$_3$ aqueous solution (10 mL) and brine (15 mL) separately. The organic phase was dried over anhydrous Na$_2$SO$_4$ and filtered. The filtrate was concentrated in vacuo and the residue was purified by silica gel column chromatography (PE/EtOAc (v/v)=6/1) to give compound Q-5 as colorless and sticky liquid (0.54 g, 46.7%). The compound was characterized by the following spectroscopic data:

$^1$H NMR (400 MHz, CD$_3$Cl): δ 7.47 (d, 2H, J=8.24 Hz), 7.38 (d, 2H, J=8.24 Hz), 7.24 (m, 1H), 5.09 (s, 2H), 4.18 (t, 1H), 4.05 (m, 2H), 3.95 (m, 2H), 3.68 (s, 3H), 3.38 (m, 1H), 3.32 (m, 1H), 2.21 (m, 1H), 1.96 (m, 1H).

To a solution of compound Q-5 (0.59 g, 1.8 mmol) in CH$_3$OH (150 mL) was added Pd/C (0.5 g). The reaction mixture was stirred at rt under H$_2$ overnight and filtered. The filtrate was concentrated in vacuo to give compound Q-6 (0.34 g, 98.9%). The crude product was used for the next step without further purification. The compound was characterized by the following spectroscopic data:

$^1$H NMR (400 MHz, CD$_3$Cl): δ 4.18 (t, 1H), 4.05 (m, 2H), 3.95 (m, 2H), 3.68 (s, 3H), 3.38 (m, 1H), 3.32 (m, 1H), 2.21 (m, 1H), 1.96 (m, 1H).

To a solution of compound Q-6 (3.48 g, 18.6 mmol) in DCM (50 mL) in an ice bath were added compound Q-7 (3.26 g, 18.6 mmol), DIPEA (12.3 mL, 74.4 mmol) and EDCI (7.1 g, 37.0 mmol) in turn. The reaction mixture was stirred at rt overnight, washed with H$_2$O (20 mL), dried over anhydrous Na$_2$SO$_4$ and filtered. The filtrate was concentrated in vacuo and the residue was purified by silica gel column chromatography (PE/EtOAc (v/v)=3/1) to give compound Q-8 as pale yellow oil (2.5 g, 39.1%). The compound was characterized by the following spectroscopic data:

$^1$H NMR (400 MHz, CD$_3$Cl): δ 9.80 (s, 1H), 4.54 (d, 1H, J=7.25 Hz), 4.28 (m, 1H), 4.06 (m, 4H), 3.76 (m, 2H), 3.50 (s, 3H), 3.45 (s, 3H), 2.71 (m, 2H), 2.65 (m, 1H), 0.87 (m, 3H), 0.81 (m, 3H).

To a solution of compound Q-8 (0.9 g, 2.6 mmol) in mixed solvents of THF (5 mL) and H$_2$O (5 mL) was added LiOH (0.12 g, 5.0 mmol). The reaction mixture was stirred at rt overnight, then adjusted to pH 2 with diluted hydrochloric acid and extracted with EtOAc (50 mL×3). The combined organic phases were dried over anhydrous Na$_2$SO$_4$ and filtered. The filtrate was concentrated in vacuo to give compound Q-9 as a white solid (0.85 g, 99.0%). The crude product was used for the next step without further purification. The compound was characterized by the following spectroscopic data:

$^1$H NMR (400 MHz, CD$_3$Cl): δ 9.80 (s, 1H), 4.54 (d, 1H, J=7.25 Hz), 4.28 (m, 1H), 4.06 (m, 4H), 3.76 (m, 2H), 3.50 (s, 3H), 2.71 (m, 2H), 2.65 (m, 1H), 0.87 (m, 3H), 0.81 (m, 3H).

To a solution of compound Q-9 (1.78 g, 5.4 mmol) in CH$_3$CN (30 mL) was added compound Q-10 (1.65 g, 5.9 mmol). Then to the mixture was added DIPEA (1.1 mL, 6.7 mmol) slowly at 0° C. The reaction mixture was stirred at rt overnight and concentrated in vacuo. The residue was purified by silica gel column chromatography (PE/EtOAc (v/v)=3/1) to give compound Q-11 as a pale yellow solid (2.76 g, 97.3%). The compound was characterized by the following spectroscopic data:

$^1$H NMR (400 MHz, CD$_3$Cl): δ 9.30 (s, 1H), 7.95 (d, 2H, J=8.27 Hz), 7.71 (d, 2H, J=8.25 Hz), 5.34-5.72 (m, 2H), 4.52 (d, 1H), 4.29 (m, 1H), 4.19 (m, 4H), 3.77 (m, 2H), 3.69 (s, 3H), 2.71 (m, 1H), 2.65 (m, 2H), 0.91 (m, 3H), 0.89 (m, 3H).

A suspension of compound Q-11 (3.0 g, 5.7 mmol) and ammonium acetate (4.4 g, 57.1 mmol) in xylene (20 mL) was heated at 130° C. overnight in a sealed tube. The resulting mixture was diluted with EtOAc (40 mL), washed with brine, dried over anhydrous Na$_2$SO$_4$ and filtered. The filtrate was concentrated in vacuo and the residue was purified by silica gel column chromatography (PE/EtOAc (v/v)=3/1) to give compound Q-12 as a claybank solid (2.6 g, 89.9%). The compound was characterized by the following spectroscopic data:

$^1$H NMR (400 MHz, CD$_3$Cl): δ 9.30 (s, 1H), 7.95 (d, 2H, J=8.27 Hz), 7.71 (d, 2H, J=8.25 Hz), 4.52 (d, 1H), 4.29 (m, 1H), 4.19 (m, 4H), 3.77 (m, 2H), 3.69 (s, 3H), 2.71 (m, 1H), 2.65 (m, 2H), 0.91 (m, 3H), 0.89 (m, 3H).

A mixture of compound Q-12 (4.0 g, 7.9 mmol), PdCl$_2$(dppf).CH$_2$Cl$_2$ (0.64 g, 0.8 mmol), anhydrous potassium acetate (1.94 g, 19.8 mmol) and bis(pinacolato)diboron (3.11 g, 12.2 mmol) in DMF (50 mL) was stirred at 90° C. for 4 hours under N$_2$ and cooled to rt. To the resulting mixture was added H$_2$O (100 mL). The mixture was extracted with EtOAc (100 mL×3). The combined organic phases were washed with water and brine, dried over anhydrous Na$_2$SO$_4$ and filtered. The filtrate was concentrated in vacuo and the residue was purified by silica gel column chromatography (PE/DCM (v/v)=4/1) to give the title compound 51-6 as a white solid (4.15 g, 94.7%, HPLC: 95%). The compound was characterized by the following spectroscopic data:

$^1$H NMR (400 MHz, CD$_3$Cl): δ 9.30 (s, 1H), 7.95 (d, 2H, J=8.27 Hz), 7.71 (d, 2H, J=8.25 Hz), 4.52 (d, 1H), 4.29 (m, 1H), 4.19 (m, 4H), 3.77 (m, 2H), 3.69 (s, 3H), 2.71 (m, 1H), 2.65 (m, 2H), 1.35 (s, 12H), 0.91 (m, 3H), 0.89 (m, 3H).

Step 7) The Preparation of Compound 51-7

To a mixture of compound 51-5 (0.47 g, 0.54 mmol), Pd(PPh$_3$)$_4$ (0.037 g, 0.03 mmol) and K$_2$CO$_3$ (0.22 g, 1.6 mmol) under N$_2$ were added a solution of compound 51-6 (0.53 g, 0.96 mmol) in 1,2-dimethoxyethane (6 mL) and H$_2$O (1.5 mL) via syringe. The reaction mixture was refluxed at 90° C. for 3 hours and cooled to rt. To the resulting mixture was added H$_2$O (15 mL). The mixture was extracted with EtOAc (20 mL×3). The combined organic phases were dried over anhydrous Na$_2$SO$_4$ and filtered. The filtrate was concentrated in vacuo and the residue was purified by silica gel column chromatography (PE/CH$_3$COCH$_3$ (v/v)=2/1) to give the title compound 51-7 as a pale yellow solid (0.18 g, 28.9%, HPLC: 95%). The compound was characterized by the following spectroscopic data:

MS-ESI: m/z 1022.33 [M+H]$^+$; and $^1$H NMR (400 MHz, CDCl$_3$): δ 7.77-7.78 (m, 2H), 7.44-7.46 (m, 4H), 7.01 (s, 2H), 5.87 (d, J=12.0 Hz, 1H), 5.45 (d, J=12.0 Hz, 1H), 5.37 (m, 1H), 5.21 (m, 1H), 5.21 (d, J=12.0 Hz, 1H), 5.14 (t, J=4.0 Hz, 1H), 5.03 (d, J=12.0 Hz, 1H), 4.61-4.68 (m, 2H), 4.11-4.13 (m, 1H), 3.96-4.07 (m, 7H), 3.77 (s, 3H), 3.70 (s, 3H), 3.51-3.59 (m, 6H), 2.93-3.06 (m, 4H), 2.58-2.65 (m, 1H), 2.45-2.50 (m, 1H), 2.04-2.17 (m, 6H), 1.53-1.64 (m, 8H), 0.78-0.95 (m, 12H), 0.02 (d, J=2.0 Hz, 18H).

Step 8) The Preparation of Compound 51-8

To a solution of compound 51-7 (0.13 g, 0.11 mmol) in CH$_2$Cl$_2$ (8 mL) was added trifluoroacetic acid (4 mL). The reaction mixture was stirred at rt for 24 hours, then concentrated in vacuo, adjusted to pH 7-8 with saturated Na$_2$CO$_3$ aqueous solution and extracted with EtOAc (20 mL×3). The combined organic phases were dried over anhydrous Na$_2$SO$_4$ and filtered. The filtrate was concentrated in vacuo and the residue was purified by silica gel column chromatography (PE/EtOAc (v/v)=1/10) to give the title compound 51-8 as a pale yellow solid (0.07 g, 69.6%, HPLC: 95.25%). The compound was characterized by the following spectroscopic data:

MS-ESI: m/z 892.2 [M+H]$^+$; and $^1$H NMR (400 MHz, CDCl$_3$): δ 7.63 (brs, 1H), 7.33-7.36 (m, 2H), 7.08-7.15 (m, 4H), 6.97-7.00 (m, 1H), 5.47-5.50 (m, 2H), 5.36 (m, 1H), 5.28-5.30 (m, 1H), 4.28-4.47 (m, 2H), 4.04-4.08 (m, 4H), 3.84-3.95 (m, 2H), 3.73 (s, 6H), 2.91-2.97 (m, 6H), 2.05-2.32 (m, 8H), 1.61-1.65 (m, 8H), 0.90-0.93 (d, J=2.0 Hz, 12H).

Example 52

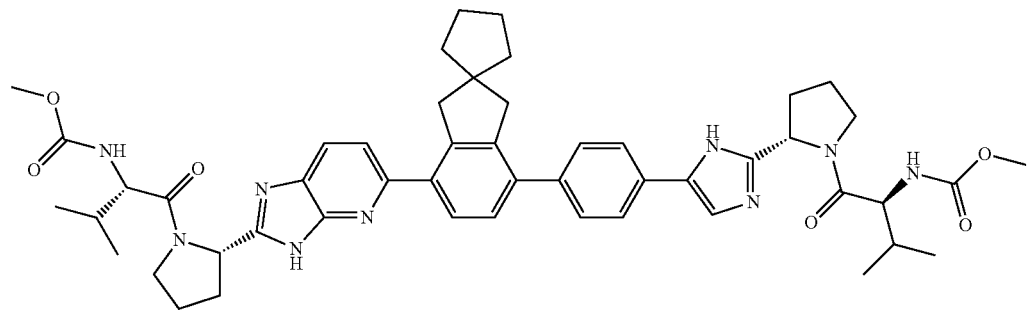

Synthetic Routes
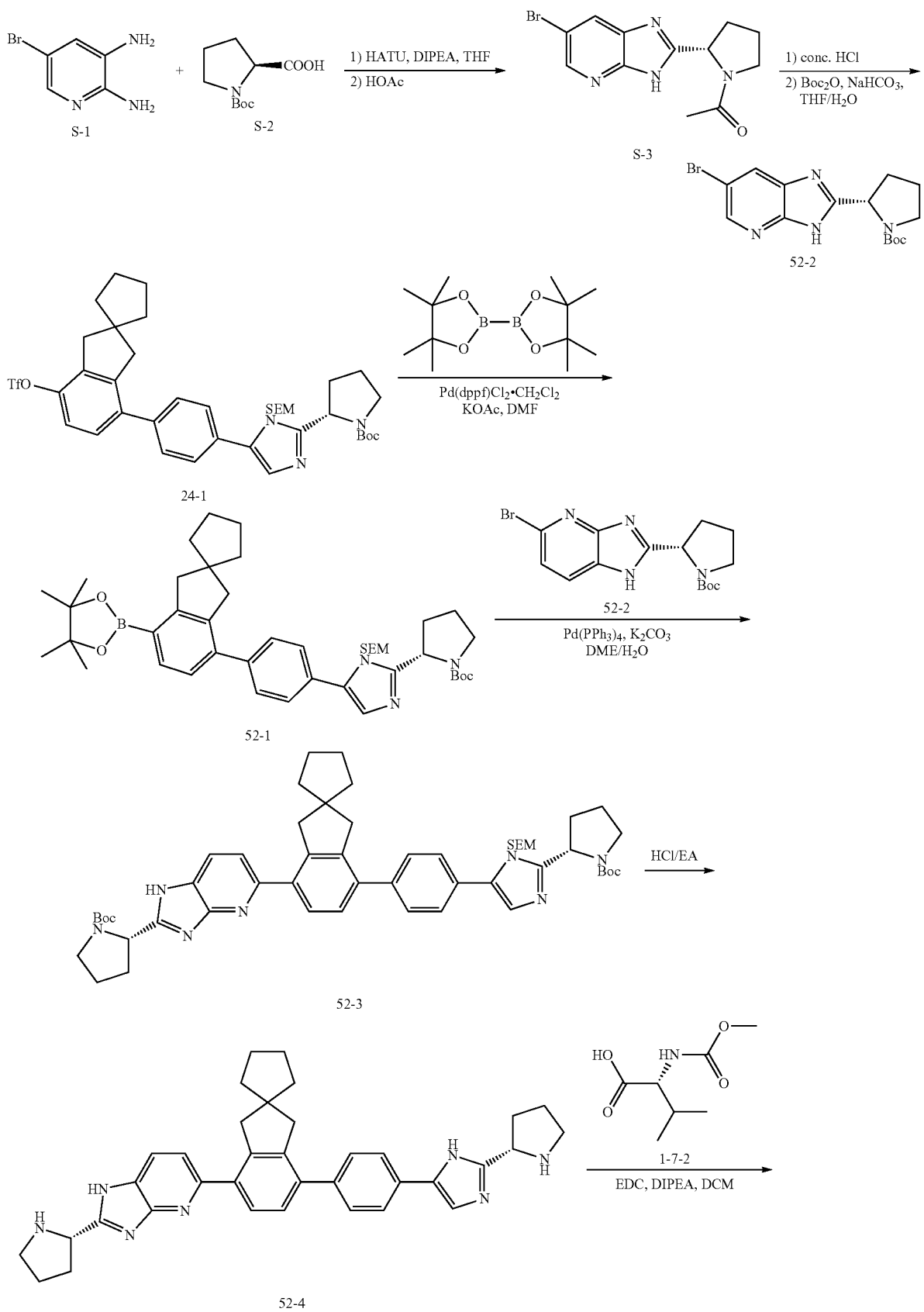

-continued

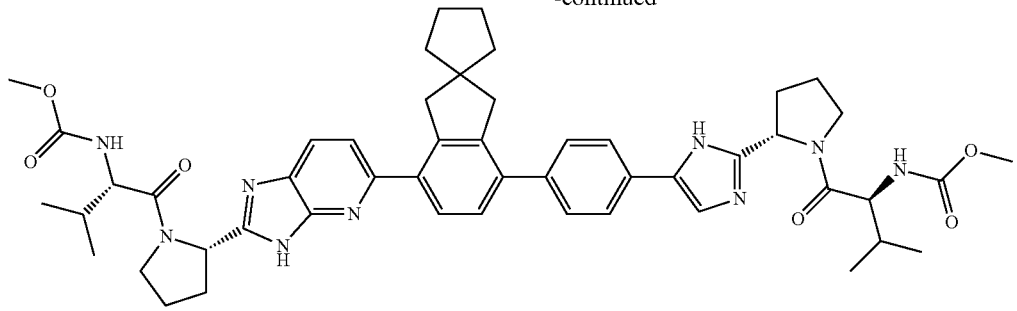

52-5

Step 1) The Preparation of Compound 52-1

A solution of compound 24-1 (0.5 g, 0.66 mmol), bis(pinacolato)diboron (0.233 g, 0.92 mmol), Pd(dppf)Cl$_2$·CH$_2$Cl$_2$ (0.054 g, 0.07 mmol) and KOAc (0.193 g, 1.97 mmol) in DMF (10 mL) was stirred at 90° C. for 4 hours under N$_2$. Insoluble solid was filtered off through a Celite pad. The filtrate was diluted with H$_2$O (3 mL) and extracted with EtOAc (10 mL×3). The combined organic phases were dried over anhydrous Na$_2$SO$_4$ and filtered. The filtrate was concentrated in vacuo and the residue was purified by silica gel column chromatography (PE/EtOAc (v/v)=1/1) to give compound 52-1 (0.4 g, 81.9%). The compound was characterized by the following spectroscopic data:

MS-ESI: m/z 740.5 [M+H]$^+$; and $^1$H NMR (400 MHz, CDCl$_3$): δ 7.82-7.80 (m, 2H), 7.83-7.86 (m, 2H), 7.41-7.42 (m, 2H), 7.28-7.29 (m, 1H), 7.22-7.23 (m, 1H), 7.12-7.14 (m, 1H), 5.87-5.88 (m, 0.5H), 5.44-5.45 (m, 0.5H), 5.23-5.24 (m, 1H), 5.00-5.01 (m, 1H), 3.66-3.76 (m, 2H), 3.51-3.59 (m, 2H), 3.02 (s, 2H), 2.95 (s, 2H), 2.31-2.22 (m, 4H), 1.71-1.62 (m, 8H), 1.36-1.44 (m, 9H), 1.26-1.28 (m, 12H), 0.88-0.89 (m, 2H), 0.03 (s, 9H).

Step 2) The Preparation of Compound 52-2

To a solution of compound S-1 (10.0 g, 53.2 mmol), compound S-2 (11.5 g, 53.4 mmol) and HATU (40.46 g, 106.4 mmol) in THF (150 mL) was added DIPEA (10.0 mL, 60.5 mmol) in an ice bath. The mixture was stirred for 0.5 hour in the ice bath and at rt for another 3 hours. The mixture was quenched with water (30 mL), concentrated in vacuo and extracted with EtOAc (100 mL×3). The combined organic phases were dried over anhydrous Na$_2$SO$_4$ and filtered. The filtrate was concentrated in vacuo to give crude product, which was used for the next step without further purification.

A solution of the crude product in acetic acid glacial (100 mL) was stirred at 120° C. for 16 hours, then basified with solid NaHCO$_3$ and extracted with EtOAc (80 mL×3). The combined organic phases were dried over anhydrous Na$_2$SO$_4$ and filtered. The filtrate was concentrated in vacuo and the residue was purified by silica gel column chromatography (PE/EtOAc (v/v)=1/3) to give compound S-3 (3.6 g, 21.89%). The compound was characterized by the following spectroscopic data:

MS-ESI: m/z 310.0 [M+H]$^1$; and $^1$H NMR (400 MHz, CDCl$_3$): δ 8.37-8.38 (m, 1H), 8.10-8.12 (m, 1H), 5.39-5.41 (m, 1H), 3.53-3.65 (m, 2H), 2.12-2.26 (m, 7H).

A mixture of compound S-3 (6.4 g, 20.7 mmol) in concentrated hydrochloric acid (25 mL) was stirred at 100° C. for 15 hours and concentrated in vacuo to give crude product, which was used for the next step without further purification. To a solution of the crude product in mixed solvents of THF (60 mL) and H$_2$O (10 mL) was added NaHCO$_3$ (19.8 g, 235.7 mmol). After the mixture was stirred for 10 minutes, Boc$_2$O (5.4 mL, 23.5 mmol) was added dropwise. The mixture was stirred overnight, then concentrated in vacuo and extracted with EtOAc (60 mL×3). The combined organic phases were dried over anhydrous Na$_2$SO$_4$ and filtered. The filtrate was concentrated in vacuo and the residue was purified by silica gel column chromatography (PE/EtOAc (v/v)=1/2) to give compound 52-2 (6.0 g, 78.9%). The compound was characterized by the following spectroscopic data:

MS-ESI: m/z 368.1 [M+H]$^+$; and $^1$H NMR (400 MHz, CDCl$_3$): δ 8.43-8.52 (m, 1H), 8.08-8.12 (m, 1H), 5.12-5.14 (m, 1H), 3.46-3.48 (m, 2H), 2.00-2.25 (m, 4H), 1.49 (s, 9H).

Step 3) The Preparation of Compound 52-3

A suspension of compound 52-1 (0.03 g, 0.04 mmol), Pd(PPh$_3$)$_4$ (0.0047 g, 0.004 mmol), compound 52-2 (0.016 g, 0.044 mmol) and K$_2$CO$_3$ (0.017 g, 0.12 mmol) in mixed solvents of DME (1 mL) and H$_2$O (0.2 mL) was stirred at 90° C. for 5 hours. Insoluble solid was filtered off through a Celite pad. The filtrate is diluted with H$_2$O (5 mL) and extracted with EtOAc (20 mL×3). The combined organic phases were dried over anhydrous Na$_2$SO$_4$ and filtered. The filtrate was concentrated in vacuo and the residue was purified by silica gel column chromatography (PE/EtOAc (v/v)=1/4) to give compound 52-3 (0.032 g, 89.2%). The compound was characterized by the following spectroscopic data:

MS-ESI: m/z 900.5 [M+H]$^+$; and $^1$H NMR (400 MHz, CDCl$_3$): δ 7.85-7.83 (m, 1H), 7.74-7.70 (m, 4H), 7.44-7.57 (m, 4H), 5.87-5.88 (m, 0.5H), 5.43-5.44 (m, 0.5H), 5.23 (m, 2H), 5.00-5.01 (m, 1H), 3.66-3.76 (m, 2H), 3.51-3.59 (m, 4H), 3.02 (s, 2H), 2.95 (s, 2H), 2.42-1.98 (m, 8H), 1.71-1.62 (m, 8H), 1.36-1.44 (m, 18H), 0.88-0.89 (m, 2H), 0.03 (s, 9H).

Step 4) The Preparation of Compound 52-4

To a solution of compound 52-3 (0.21 g, 0.23 mmol) in EtOAc (5 mL) was added a solution of HCl in EtOAc (6 M, 20 mL) at rt. The mixture was stirred for 4 hours and concentrated in vacuo. The residue was washed with EtOAc (30 mL) to give compound 52-4 as a white solid (0.163 g, 98.9%). The compound was characterized by the following spectroscopic data:

MS-ESI: m/z 570.3 [M+H]$^+$; and $^1$H NMR (400 MHz, CDCl$_3$): δ 8.22 (s, 1H), 8.04 (d, 2H), 7.66-7.52 (m, 6H), 5.38-5.44 (m, 2H), 3.68-3.59 (m, 4H), 3.08 (s, 2H), 3.03 (s, 2H), 2.89-2.68 (m, 4H), 2.41-2.20 (m, 4H), 1.61-1.58 (m, 8H), 1.36-1.44 (m, 18H), 0.88-0.89 (m, 2H), 0.03 (s, 9H).

Step 5) The Preparation of Compound 52-5

To a suspension of compound 52-4 (0.206 g, 0.29 mmol), compound 1-7-2 (10.15 g, 0.86 mmol) and EDCI (0.192 g, 1.0 mmol) in DCM (10 mL) was added DIPEA (0.50 mL) slowly in an ice bath. The mixture was stirred at rt overnight, quenched with saturated NaHCO₃ aqueous solution (10 mL) and extracted with EtOAc (10 mL×3). The combined organic phases were dried over anhydrous Na₂SO₄ and filtered. The filtrate was concentrated in vacuo and the residue was purified by silica gel column chromatography (EtOAc) to give the title compound 52-5 as a white solid (0.08 g, 31.2%, HPLC: 94.9%). The compound was characterized by the following spectroscopic data:

MS-ESI: m/z 884.5 [M+H]⁺; and

¹H NMR (400 MHz, CDCl₃): δ 8.45 (s, 1H), 8.09 (s, 1H), 7.73-7.83 (m, 1H), 7.69-7.72 (m, 1H), 7.54-7.52 (m, 1H), 7.48-7.46 (m, 2H), 7.36-7.22 (m, 2H), 5.67-5.69 (m, 1H), 5.51-5.22 (m, 1H), 4.32-4.30 (m, 2H), 4.07-4.09 (m, 2H), 3.85-3.89 (m, 2H), 3.69 (s, 6H), 3.00 (s, 2H), 2.98 (s, 2H), 1.91-2.42 (m, 8H), 1.61-1.69 (m, 2H), 1.54-1.58 (m, 8H), 1.23-1.29 (m, 12H).

Example 53

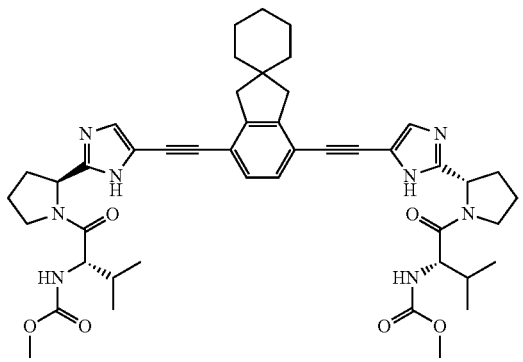 [SMILES: COC(=O)N[C@H](C(=O)N1CCC[C@H]1c1ncc(C#Cc2ccc(C#Cc3cnc([C@@H]4CCCN4C(=O)[C@@H](NC(=O)OC)C(C)C)[nH]3)c3c2CC2(CCCCC2)C3)[nH]1)C(C)C]

Synthetic Routes

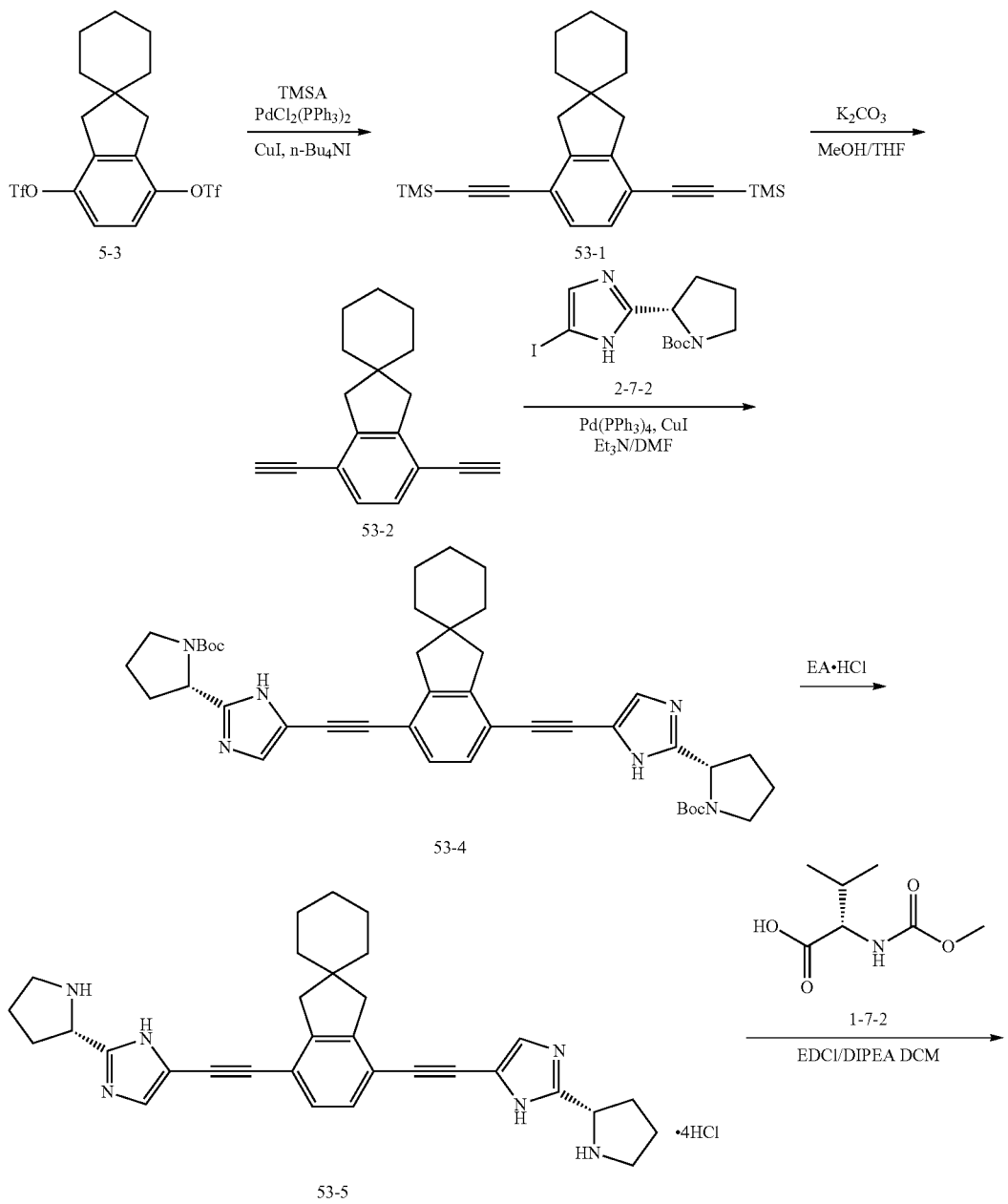

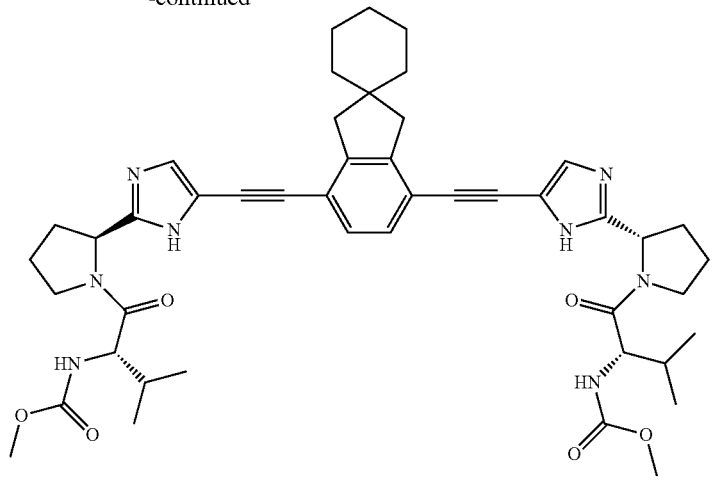

53-6

Compounds disclosed herein can be prepared by an analogous procedure to that described in Example 8.

Compound 53-1 was characterized by the following spectroscopic data:
$^1$H NMR (400 MHz, CDCl$_3$): δ 7.1518 (s, 2H), 2.8309 (s, 4H), 1.5131-1.5572 (m, 10H), 0.2519 (s, 18H).

Compound 53-2 was characterized by the following spectroscopic data:
$^1$H NMR (400 MHz, CDCl$_3$): δ 7.2118 (s, 2H), 3.2739 (s, 2H), 2.8739 (s, 4H), 1.254-1.4643 (m, 10H).

Compound 53-3 was characterized by the following spectroscopic data:
MS-ESI: m/z 705.3 [M+H]$^+$; and
$^1$H NMR (400 MHz, CD$_3$Cl): δ 10.62-10.67 (br, 2H), 7.22-7.25 (m, 4H), 4.92 (br, 2H), 3.379 (br, 4H), 2.94 (s, 4H), 2.123 (br, 4H), 1.896 (br, 4H), 1.24-1.49 (m, 28H).

Compound 53-4 was characterized by the following spectroscopic data:
MS-ESI: m/z 505.3 [M+H]$^+$; and
$^1$H NMR (400 MHz, CD$_3$OD): δ 8.02-8.08 (br, 2H), 7.39 (s, 2H), 5.10 (br, 2H), 3.57 (br, 4H), 3.06 (s, 4H), 2.66 (br, 2H), 2.46 (br, 2H), 2.35 (br, 2H), 2.22 (br, 2H), 1.254-1.4643 (m, 10H).

Compound 53-5 was characterized by the following spectroscopic data:
MS-ESI: m/z 820.3 [M+H]$^+$; and
$^1$H NMR (400 MHz, CD$_3$OD): δ 7.19-7.23 (m, 4H), 5.07-5.09 (br, 2H), 4.57 (br, 2H), 4.18-4.20 (d, 2H, J=7.36 Hz), 3.94-3.96 (br, 2H), 3.80-3.83 (br, 2H), 3.64 (s, 6H), 2.90-2.91 (br, 4H), 2.26-2.28 (br, 4H), 2.16-2.18 (m, 2H), 1.99-2.05 (m, 6H), 1.27-1.32 (m, 10H), 0.87-0.91 (m, 12H).

Example 54

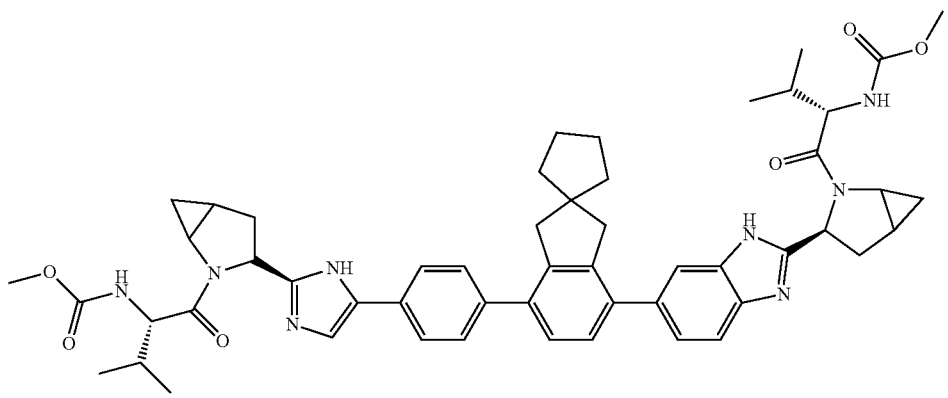

Synthetic Routes

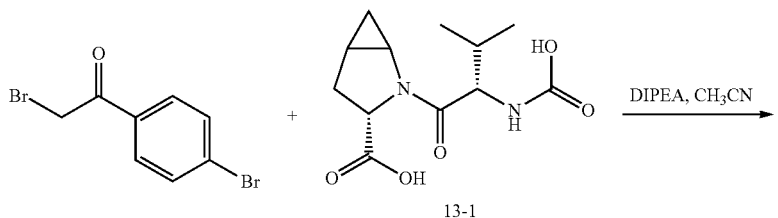

13-1

-continued
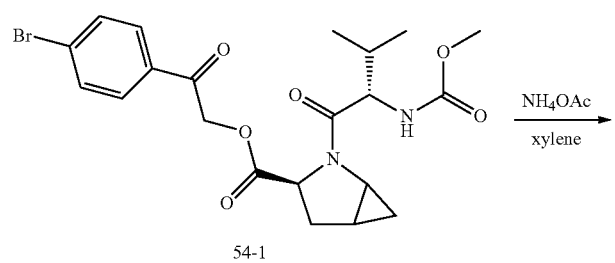
54-1
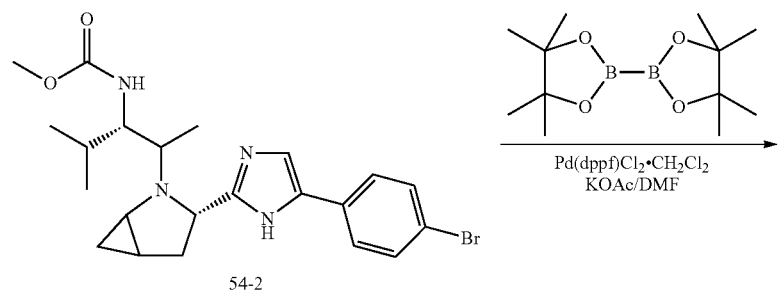
54-2
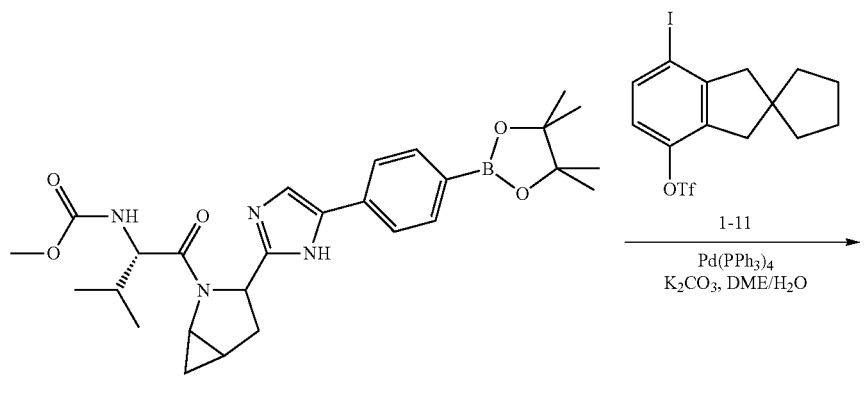
54-3
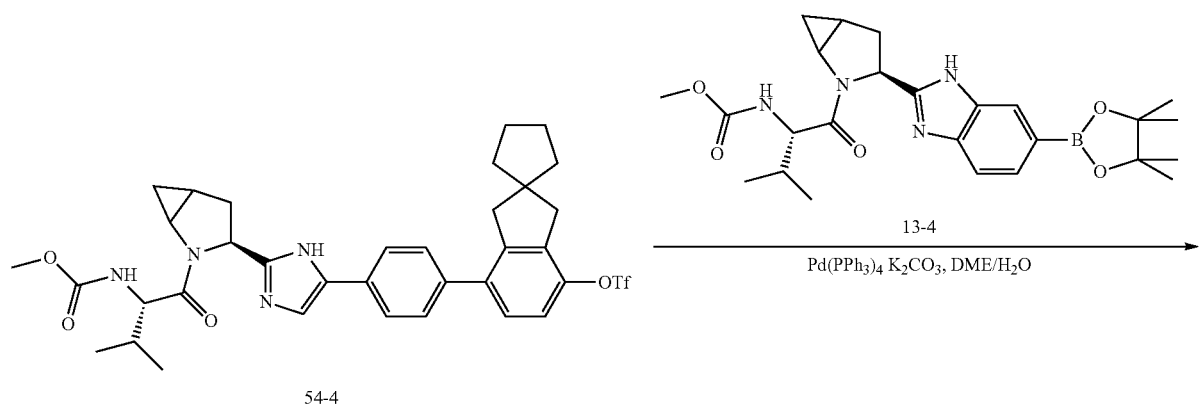
54-4

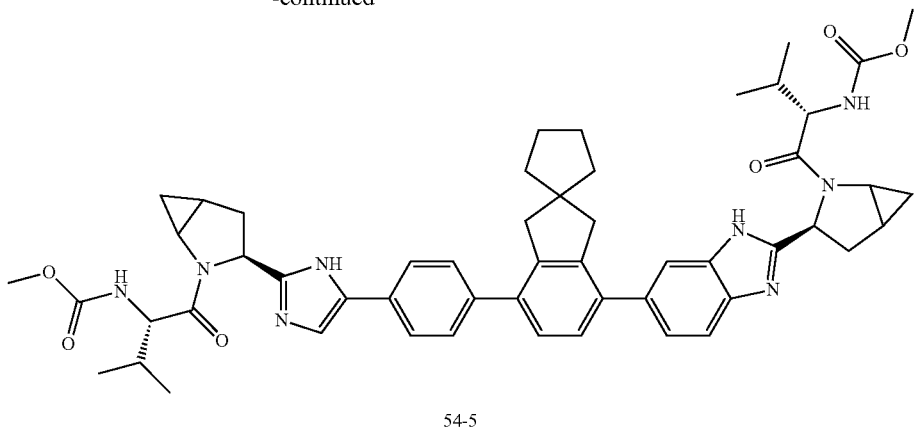

54-5

Step 1) The Preparation of Compound 54-1

A mixture of 2-bromo-1-(4-bromophenyl)ethanone (1.62 g, 5.829 mmol), compound 13-1 (1.5 g, 5.550 mmol) in CH$_3$CN (40.0 mL) was cooled down in an ice bath under N$_2$. To the mixture was added DIPEA (1.1 mL, 6.656 mmol) slowly. At the end of the addition, the ice bath was removed and the mixture was stirred at rt for 4.0 hours. To the mixture was added H$_2$O (20 mL) and the mixture was concentrated in vacuo. To the residue was added H$_2$O (20 mL). The mixture was extracted with EtOAc (100 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/2) to give the title compound 54-1 as a pale yellow solid (1.94 g, 72.6%). The compound was characterized by the following spectroscopic data:

MS-ESI: m/z 482.1 [M+2H]$^{2+}$; and $^1$H NMR (400 MHz, CDCl$_3$): δ 7.73 (d, J=8.52 Hz, 2H), 7.62 (d, J=8.56 Hz, 2H), 5.48 (d, J=16.44 Hz, 1H), 5.38 (d, J=9.4 Hz, 1H), 5.14 (d, J=16.56 Hz, 1H), 4.97 (d, J=11.68 Hz, 1H), 4.55-4.59 (t, J=6.36 Hz, 1H), 3.71 (br, 1H), 3.67 (s, 3H), 2.65-2.73 (m, 1H), 2.45-2.50 (d, J=13.8 Hz, 1H), 2.19-2.27 (m, 1H), 2.04 (s, 1H), 1.77-1.84 (m, 1H), 1.24-1.27 (t, J=7.2 Hz, 1H), 1.07-1.08 (br, 1H), 1.03-1.05 (d, J=6.76 Hz, 3H), 0.92-0.93 (d, J=6.76 Hz, 3H).

Step 2) The Preparation of Compound 54-2

To a solution of compound 54-1 (1.94 g, 4.030 mmol) in xylene (40.0 mL) was added NH$_4$OAc (6.226 g, 80.77 mmol). The mixture was refluxed at 135° C. overnight, cooled down naturally and concentrated in vacuo. To the residue was added H$_2$O (40 mL). The mixture was extracted with EtOAc (50 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/2) to give the title compound 54-2 as a yellow solid (1.58 g, 85.0%). The compound was characterized by the following spectroscopic data:

MS-ESI: m/z 462.1 [M+H]$^+$; and $^1$H NMR (400 MHz, CDCl$_3$): δ 10.35 (s, 1H), 7.62-7.64 (d, J=8.52 Hz, 2H), 7.45-7.454 (d, J=1.84 Hz, 2H), 7.157 (s, 1H), 5.46-5.54 (br, 2H), 4.53-4.57 (m, 1H), 3.70 (s, 3H), 2.48-2.54 (m, 1H), 2.04-2.09 (m, 2H), 1.85-1.89 (br, 1H), 1.24-1.28 (t, J=7.08 Hz, 2H), 1.02-1.04 (br, 1H), 0.81-0.85 (m, 6H).

Step 3) The Preparation of Compound 54-3

To a mixture of compound 54-2 (1.545 g, 3.349 mmol), bis(pinacolato)diboron (1.225 g, 4.8246 mmol), Pd(dppf)Cl$_2$.CH$_2$Cl$_2$ (0.263 g, 0.3216 mmol) and KOAc (0.947 g, 9.65 mmol) was added DMF (20.0 mL) via syringe under N$_2$. The reaction mixture was stirred at 90° C. overnight and cooled down naturally. To the resulting mixture was added H$_2$O (80.0 mL). The mixture was extracted with EtOAc (40.0 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/2) to give the title compound 54-3 as a beige solid (1.34 g, 78.68%). The compound was characterized by the following spectroscopic data:

MS-ESI: m/z 511.3 [M+H]$^+$; and $^1$H NMR (400 MHz, CDCl$_3$): δ 10.31 (s, 1H), 7.74-7.81 (m, 4H), 7.39-7.41 (d, J=8.0 Hz, 1H), 5.49-5.59 (m, 2H), 4.53-4.58 (m, 1H), 3.67 (s, 3H), 2.47-2.54 (m, 1H), 2.04-2.10 (m, 2H), 1.89-1.91 (br, 1H), 1.35 (s, 12H), 1.24-1.27 (t, J=7.08 Hz, 2H), 1.02-1.04 (br, 1H), 0.81-0.85 (m, 6H).

Step 4) The Preparation of Compound 54-4

To a mixture of compound 1-11 (0.772 g, 1.73 mmol), compound 54-3 (0.8 g, 1.5735 mmol), Pd(PPh$_3$)$_4$ (0.182 g, 0.15749 mmol) and K$_2$CO$_3$ (0.656 g, 4.7464 mmol) under N$_2$ were added DME (15.0 mL) and H$_2$O (3.0 mL) via syringe. The mixture was stirred at 90° C. overnight, cooled down naturally and concentrated in vacuo. To the residue was added H$_2$O (50.0 mL). The mixture was extracted with EtOAc (30.0 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/2) to give the title compound 54-4 as a beige solid (0.6288 mg, 57.03%). The compound was characterized by the following spectroscopic data:

MS-ESI: m/z 701.7 [M+H]$^+$; and $^1$H NMR (400 MHz, CDCl$_3$): δ 7.82-7.84 (d, J=8.16 Hz, 1H), 7.64-7.69 (m, 3H), 7.53-7.57 (m, 1H), 7.44-7.48 (m, 2H), 7.38-7.40 (m, 2H), 5.48-5.56 (m, 2H), 4.53-4.57 (m, 1H), 3.69 (s, 3H), 2.95-2.99 (d, J=14.12 Hz, 2H), 2.50-2.51 (br, 1H), 1.85-1.95 (br, 1H), 1.64-1.68 (br, 5H), 1.256 (s, 3H), 0.81-0.88 (br, 7H).

Step 5) The Preparation of Compound 54-5

To a mixture of compound 54-4 (0.1981 g, 0.2827 mmol), compound 13-4 (0.15 g, 0.311 mmol), Pd(PPh$_3$)$_4$ (0.033 g, 0.0285 mmol) and K$_2$CO$_3$ (0.118 g, 0.854 mmol) under N$_2$ were added DME (5.0 mL) and H$_2$O (1.0 mL) via syringe. The mixture was stirred at 90° C. overnight, cooled down naturally and concentrated in vacuo. To the residue was added H₂O (50.0 mL). The mixture was extracted with EtOAc (30.0 mL×3). The combined organic phases were washed with brine, dried over anhydrous Na₂SO₄ and filtered. The filtrate was concentrated in vacuo and the residue was purified by silica gel column chromatography (DCM/MeOH (v/v)=50/1) to give the title compound 54-5 as a beige solid (166.5 mg, 64.9%, HPLC: 97.07%). The compound was characterized by the following spectroscopic data:

MS-ESI: m/z 454.2 [M+2H]²⁺; and

¹H NMR (400 MHz, CDCl₃): δ 7.77-7.86 (m, 2H), 7.36-7.52 (m, 4H), 7.32-7.33 (m, 3H), 5.72-5.75 (d, J=10.88 Hz, 1H), 5.54-5.56 (br, 1H), 5.44-5.66 (br, 2H), 4.56-4.61 (m, 2H), 3.71 (s, 6H), 3.36-3.46 (m, 2H), 3.01-3.03 (m, 4H), 2.54-2.57 (m, 2H), 2.04-2.10 (m, 4H), 1.91-1.94 (m, 2H), 2.17-2.20 (br, 2H), 1.25-1.33 (br, 10H), 1.05-1.15 (br, 5H), 0.81-0.85 (m, 12H).

Example 55

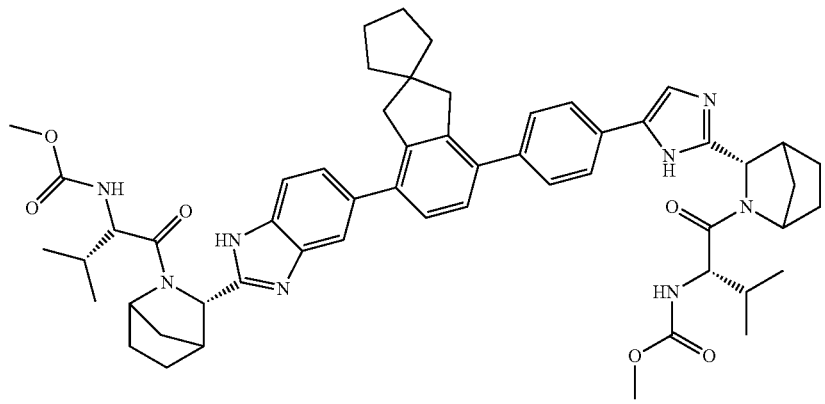

Synthetic Routes

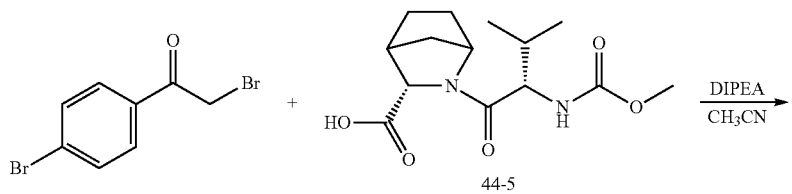

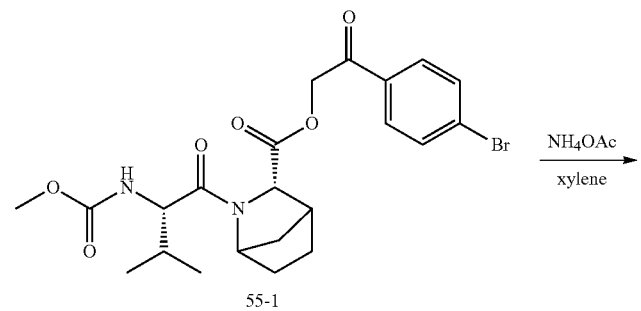

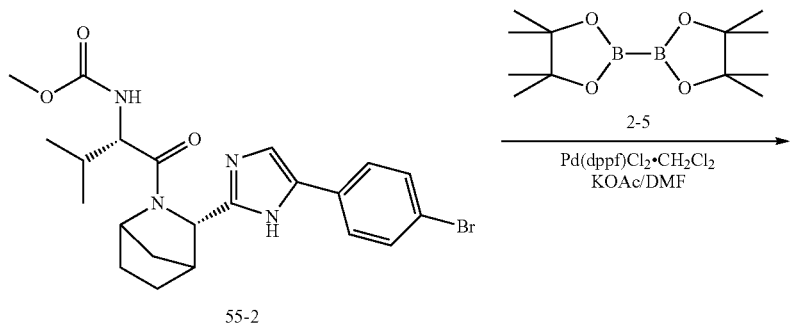

-continued
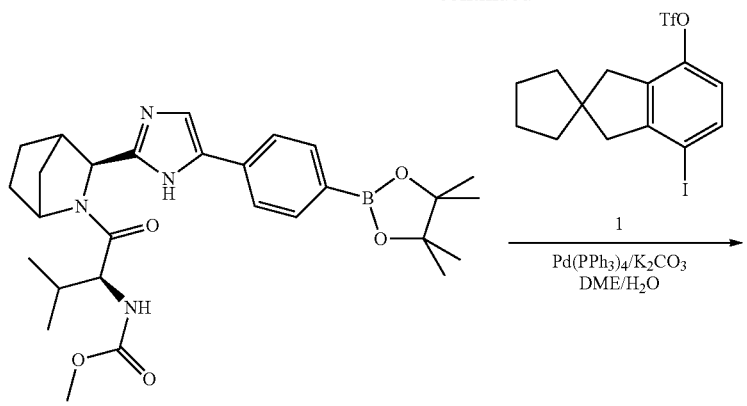
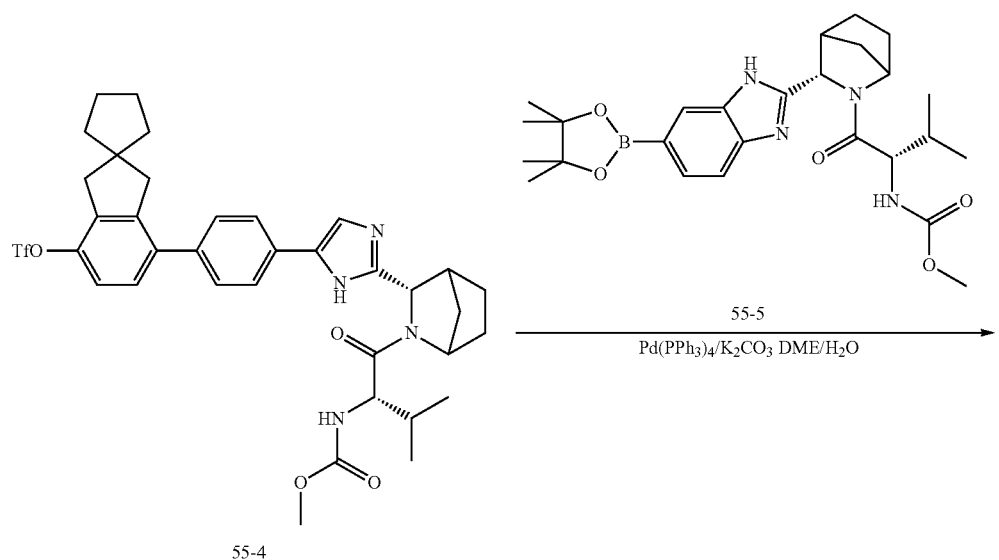
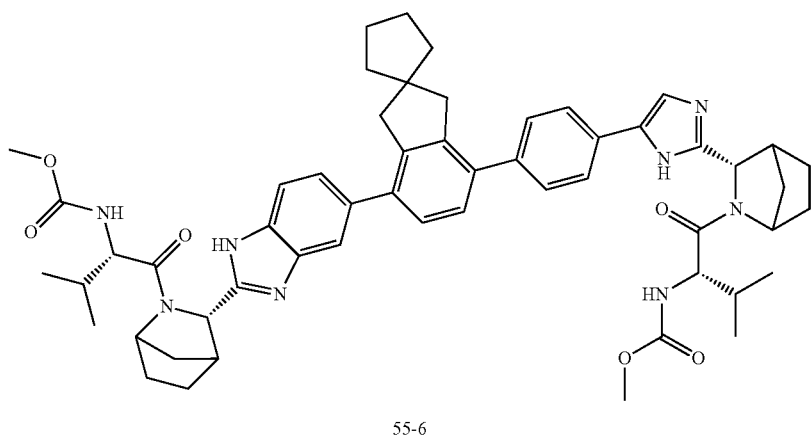
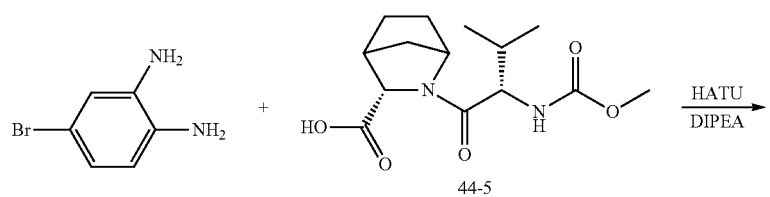

411

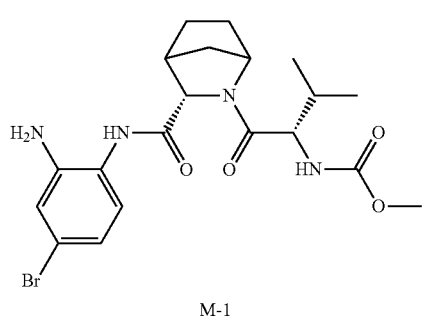

M-1

412

-continued

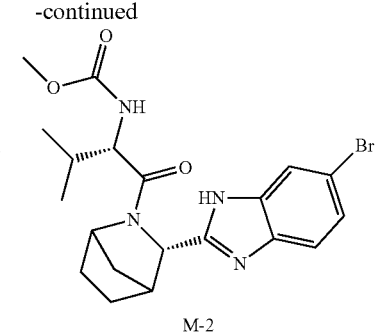

M-2

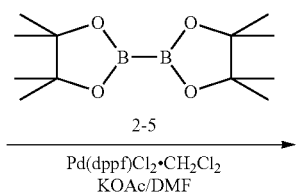

$\xrightarrow{\text{2-5}}$
Pd(dppf)Cl$_2$·CH$_2$Cl$_2$
KOAc/DMF

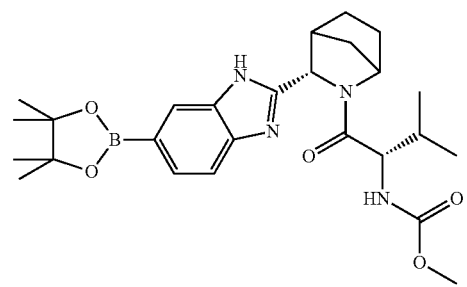

55-5

Step 1) The Preparation of Compound 55-1

A mixture of 2-bromo-1-(4-bromophenyl)ethanone (0.308 g, 1.1081 mmol), compound 44-5 (0.3 g, 1.0055 mmol) in CH$_3$CN (30.0 mL) was cooled to 0° C. in an ice bath under N$_2$. To the mixture was added DIPEA (0.21 mL, 1.2081 mmol) slowly. At the end of the addition, the ice bath was removed. The reaction mixture was stirred at rt for 4.0 hours and to the mixture was added H$_2$O (20 mL). The mixture was concentrated in vacuo. To the residue was added H$_2$O (20 mL). The mixture was extracted with EtOAc (50 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/2) to give the title compound 55-1 as a pale yellow solid (0.3326 g, 66.7%). The compound was characterized by the following spectroscopic data:

MS-ESI: m/z 496.3 [M+2H]$^{2+}$; and $^1$H NMR (400 MHz, CDCl$_3$): δ 7.75 (d, J=8.52 Hz, 2H), 7.68 (d, J=8.56 Hz, 2H), 5.45 (d, J=9.4 Hz, 1H), 5.24 (d, J=16.56 Hz, 1H), 4.55-4.59 (m, 1H), 3.67 (s, 3H), 3.57 (m, 1H), 2.65-2.73 (m, 2H), 2.19-2.27 (m, 1H), 2.04 (s, 1H), 1.77-1.84 (m, 2H), 1.46-1.49 (m, 1H), 1.24-1.27 (m, 1H), 1.07-1.08 (br, 1H), 1.03-1.05 (m, 1H), 0.91-0.89 (m, 6H).

Step 2) The Preparation of Compound 55-2

To a solution of compound 55-1 (0.3326 g, 0.6714 mmol) in xylene (15.0 mL) was added NH$_4$OAc (1.035 g, 13.43 mmol). The mixture was refluxed at 135° C. overnight, cooled down naturally and concentrated in vacuo. To the residue was added H$_2$O (20 mL). The mixture was extracted with EtOAc (50 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/2) to give the title compound 55-2 as a yellow solid (0.188 g, 58.94%). The compound was characterized by the following spectroscopic data:

MS-ESI: m/z 476.3 [M+H]$^+$; and $^1$H NMR (400 MHz, CDCl$_3$): δ 10.35 (s, 1H), 7.62-7.64 (d, J=8.52 Hz, 2H), 7.45-7.454 (d, J=1.84 Hz, 2H), 7.157 (s, 1H), 5.46-5.54 (br, 2H), 4.53-4.57 (m, 1H), 3.70 (s, 3H), 3.58 (m, 1H), 2.69 (m, 1H), 2.48-2.54 (m, 1H), 1.76-1.87 (m, 4H), 1.45-1.47 (m, 2H), 0.81-0.85 (m, 6H).

Step 3) The Preparation of Compound 55-3

To a mixture of compound 55-2 (0.1881 g, 0.3957 mmol), bis(pinacolato)diboron (150.75 mg, 0.596 mmol), Pd(dppf)Cl$_2$·CH$_2$Cl$_2$ (0.033 g, 0.04041 mmol) and KOAc (0.11645 g, 1.187 mmol) was added DMF (10.0 mL) via syringe under N$_2$. The reaction mixture was stirred at 90° C. overnight and cooled down naturally. To the resulting mixture was added H$_2$O (50.0 mL). The mixture was extracted with EtOAc (40.0 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=1/2) to give the title compound 55-3 as a beige solid (0.2 g, 96.75%). The compound was characterized by the following spectroscopic data:

MS-ESI: m/z 523.3 [M+H]$^+$; and $^1$H NMR (400 MHz, CDCl$_3$): δ 10.48 (s, 1H), 7.75-7.81 (m, 4H), 7.41-7.43 (d, J=8.0 Hz, 1H), 5.39-5.49 (m, 2H), 4.53-4.58 (m, 2H), 3.67 (s, 3H), 3.57 (m, 1H), 2.65 (m, 1H), 2.47-2.54 (m, 1H), 2.04-2.10 (m, 2H), 1.79-1.83 (m, 1H), 1.46-1.49 (m, 2H), 1.38 (s, 12H), 0.81-0.85 (m, 6H).

Step 4) The Preparation of Compound 55-4

To a mixture of compound 1 (0.09396 g, 0.2105 mmol), compound 55-3 (0.1 g, 0.1914 mmol), Pd(PPh$_3$)$_4$ (22.1 mg, 0.01914 mmol) and K$_2$CO$_3$ (79.82 mg, 0.574 mmol) were added DME (5.0 mL) and H$_2$O (1.0 mL) via syringe under N$_2$. The mixture was stirred at 90° C. overnight, cooled down naturally and concentrated in vacuo. To the residue was added H$_2$O (15.0 mL). The mixture was extracted with EtOAc (30.0 mL×3). The combined organic phases were washed with saturated brine, dried over anhydrous $Na_2SO_4$ and filtered. The filtrate was concentrated in vacuo and the residue was purified by silica gel column chromatography (PE/EtOAc (v/v)=1/2) to give the title compound 55-4 as a beige solid (0.109 g, 79.7%). The compound was characterized by the following spectroscopic data:

MS-ESI: m/z 701.7 [M+H]$^+$; and $^1$H NMR (400 MHz, CDCl$_3$): δ 7.84-7.82 (m, 1H), 7.69-7.66 (m, 2H), 7.57-7.55 (m, 1H), 7.48-7.44 (m, 2H), 7.40-7.36 (m, 1H), 5.41-5.39 (m, 1H), 5.29-5.27 (m, 1H), 4.59-4.57 (m, 1H), 4.34-4.30 (m, 1H), 3.75-3.70 (m, 2H), 3.70 (s, 3H), 3.64-3.62 (m, 1H), 3.20-3.01 (m, 1H), 2.99 (s, 2H), 2.95 (s, 2H), 2.65 (m, 1H), 2.25-2.20 (m, 1H), 2.20-2.13 (m, 2H), 1.96-1.94 (m, 1H), 1.87-1.79 (m, 4H), 1.78-1.52 (m, 4H), 0.88-0.86 (m, 6H).

Step 5) The Preparation of Compound 55-5

A mixture of compound 44-5 (0.583 g, 1.9542 mmol), HATU (0.782 g, 2.0566 mmol) in THF (20 mL) was cooled down in an ice bath under $N_2$. To the mixture was added DIPEA (0.41 mL, 2.481 mmol) slowly. At the end of the addition, the ice bath was removed. The reaction mixture was stirred at rt for 0.5 hour and cooled down in an ice bath. To the mixture was added a solution of 4-bromo-1,2-benzenediamine (0.4024 g, 2.152 mmol) in THF (10 mL) slowly. The mixture was stirred at rt for 2.0 hours. To the resulting mixture was added $H_2O$ (20 mL) and the mixture was concentrated in vacuo. To the residue was added $H_2O$ (20 mL). The mixture was extracted with EtOAc (50 mL×3). The combined organic phases were washed with brine, dried over anhydrous $Na_2SO_4$ and filtered. The filtrate was concentrated in vacuo and the residue was purified by silica gel column chromatography (PE/EtOAc (v/v)=4/1) to give compound M-1 as brown oil (1.34 g).

A solution of compound M-1 (1.34 g) in acetic acid glacial (40 mL) was stirred at 40° C. overnight and then cooled down in an ice bath. The mixture was quenched with $Na_2CO_3$ saturated solution (20 mL) until there was no more gas evolution. To the resulting mixture was added $H_2O$ (100 mL). The mixture was extracted with EtOAc (150 mL×3). The combined organic phases were washed with brine, dried over anhydrous $Na_2SO_4$ and filtered. The filtrate was concentrated in vacuo and the residue was purified by silica gel column chromatography (PE/EtOAc (v/v)=1/1) to give compound M-2 as a brown solid (0.5983 g, 68.06%). The compound was characterized by the following spectroscopic data:

MS-ESI: m/z 450.3 [M+H]$^+$; and $^1$H NMR (400 MHz, CDCl$_3$): δ 7.59-7.52 (m, 1H), 7.32-7.21 (m, 2H), 5.41-5.38 (m, 2H), 4.35-4.32 (m, 1H), 3.87-3.76 (m, 1H), 3.70 (s, 3H), 3.66-3.62 (m, 1H), 2.67-2.65 (m, 1H), 2.20-2.13 (m, 1H), 1.85-1.73 (m, 4H), 1.46-1.43 (m, 2H), 0.88-0.84 (m, 6H).

To a mixture of compound M-2 (0.147 g, 0.327 mmol), bis(pinacolato)diboron (0.125 g, 0.4922 mmol), Pd(dppf)Cl$_2$·CH$_2$Cl$_2$ (0.027 g, 0.0327 mmol) and KOAc (0.097 g, 0.9884 mmol) was added DMF (5.0 mL) via syringe under $N_2$. The reaction mixture was stirred at 90° C. overnight and cooled down naturally. To the resulting mixture was added $H_2O$ (20.0 mL). The mixture was extracted with EtOAc (30.0 mL×3). The combined organic phases were washed with brine, dried over anhydrous $Na_2SO_4$ and filtered. The filtrate was concentrated in vacuo and the residue was purified by silica gel column chromatography (PE/EtOAc (v/v)=1/2) to give compound 55-5 as a beige solid (0.09 g, 55.5%). The compound was characterized by the following spectroscopic data:

MS-ESI: m/z 497.3 [M+H]$^+$; and $^1$H NMR (400 MHz, CDCl$_3$): δ 7.85-7.80 (m, 1H), 7.72-7.68 (m, 2H), 5.45-5.41 (m, 2H), 4.56-4.48 (m, 1H), 4.33-4.30 (m, 1H), 3.86-3.84 (m, 1H), 3.70 (s, 3H), 3.64-3.62 (m, 1H), 3.04-2.98 (m, 1H), 2.25-2.20 (m, 1H), 2.20-2.13 (m, 2H), 1.87-1.76 (m, 1H), 1.46-1.49 (m, 2H), 1.35 (s, 12H), 0.88-0.84 (m, 6H).

6) The Preparation of Compound 55-6

To a mixture of compound 55-4 (0.05 g, 0.06995 mmol), compound 55-5 (0.039 g, 0.0786 mmol), Pd(PPh$_3$)$_4$ (0.008 g, 0.007 mmol) and K$_2$CO$_3$ (0.03 g, 0.21 mmol) were added DME (5.0 mL) and H$_2$O (1.0 mL) via syringe under N$_2$. The mixture was stirred at 90° C. overnight, cooled down naturally and concentrated in vacuo. To the residue was added H$_2$O (25.0 mL). The mixture was extracted with EtOAc (30.0 mL×3). The combined organic phases were washed with brine, dried over anhydrous Na$_2$SO$_4$ and filtered. The filtrate was concentrated in vacuo and the residue was purified by silica gel column chromatography (DCM/MeOH (v/v)=50/1) to give the title compound 55-6 as a beige solid (0.0265 g, 40.5%, HPLC: 93.88%). The compound was characterized by the following spectroscopic data:

MS-ESI: m/z 468.2 [M+2H]$^{2+}$; and $^1$H NMR (400 MHz, CDCl$_3$): δ 7.69-7.71 (m, 2H), 7.53-7.58 (m, 2H), 7.43-7.48 (m, 2H), 7.28-7.34 (m, 2H), 7.25-7.26 (m, 2H), 5.26-5.29 (m, 1H), 5.16-5.19 (m, 1H), 4.56-4.59 (m, 2H), 4.21-4.26 (m, 2H), 3.94-4.08 (m, 2H), 3.88-3.93 (m, 2H), 3.65 (s, 6H), 2.97 (s, 2H), 2.94 (s, 2H), 2.04-2.34 (m, 6H), 1.76-1.87 (m, 8H), 1.53-1.59 (m, 8H), 1.46-1.49 (m, 2H), 0.86-0.93 (m, 12H).

Example 56

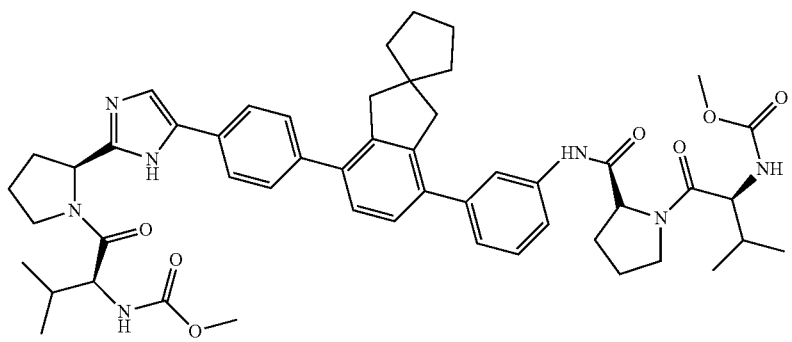

Synthetic Routes
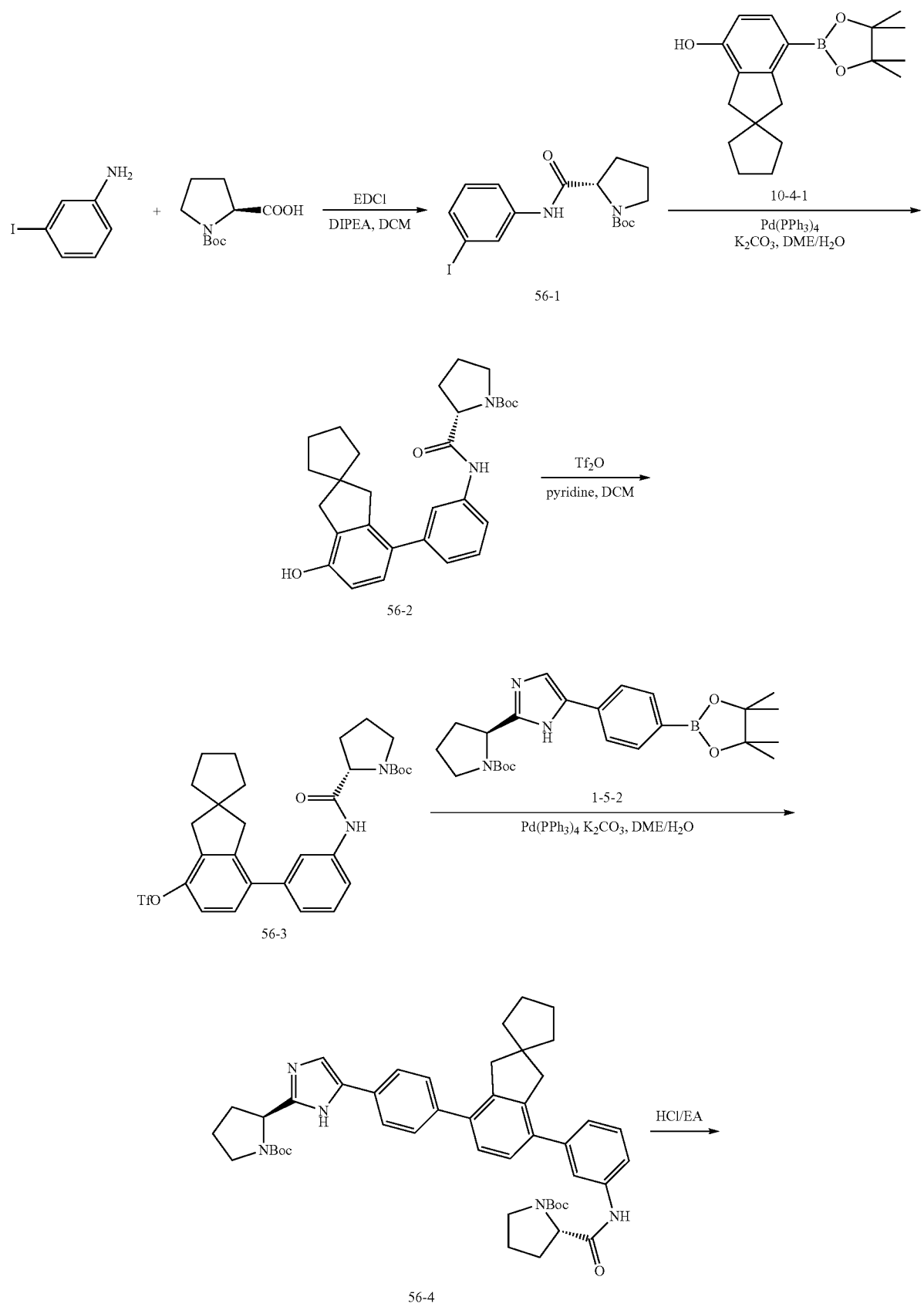

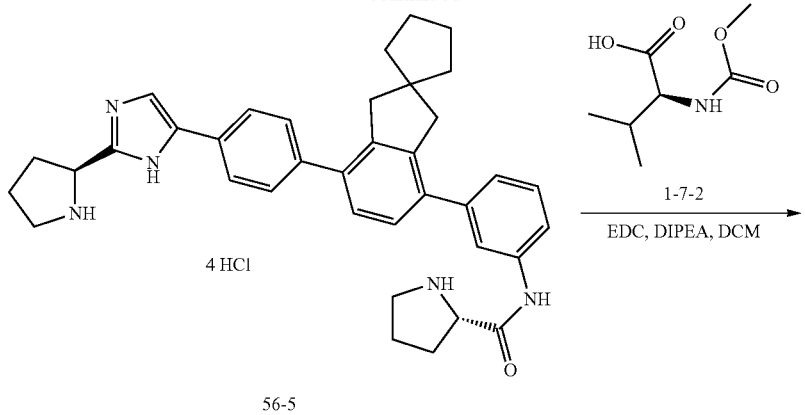

56-5

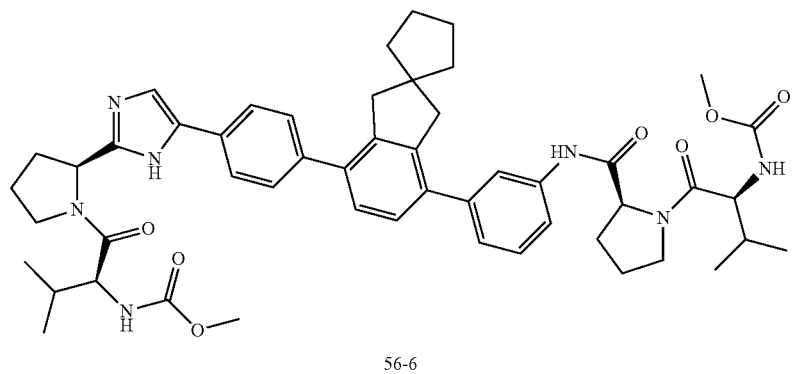

56-6

Step 1) The Preparation of Compound 56-1

A suspension of 3-iodoaniline (0.92 g, 4.2 mmol), EDCI (1.2 g, 6.3 mmol) and Boc-L-proline (1.08 g, 5 mmol) in $CH_2Cl_2$ (8 mL) was cooled to 0° C. in an ice bath. To the suspension was added DIPEA (3.0 mL) slowly. Then the mixture was stirred at rt for 10 hours. To the resulting mixture was added $H_2O$ (10 mL). The mixture was extracted with $CH_2Cl_2$ (10 mL×3). The combined organic phases were dried over anhydrous $Na_2SO_4$ and filtered. The filtrate was concentrated in vacuo and the residue was purified by silica gel column chromatography (hexane/DCM (v/v)=1/1) to give the title compound 56-1 (1.7 g, 97.3%). The compound was characterized by the following spectroscopic data:

MS-ESI: m/z 439.0 $[M+Na]^+$; and $^1$H NMR (400 MHz, $CDCl_3$): δ 9.62 (s, 1H), 7.99 (s, 1H), 7.40 (m, 2H), 6.98 (m, 1H), 4.44 (brs, 1H), 3.36 (m, 2H), 1.92 (m, 2H), 1.65 (m, 2H), 1.49 (s, 9H).

Step 2) The Preparation of Compound 56-2

To a mixture of compound 56-1 (0.8 g, 1.9 mmol), compound 10-4-1 (0.5 g, 1.6 mmol), $Pd(PPh_3)_4$ (0.18 g, 0.16 mmol) and $K_2CO_3$ (1.1 g, 8.0 mmol) were added DME (20 mL) and $H_2O$ (5 mL) via syringe under $N_2$. The mixture was refluxed at 90° C. for 3 hours, and cooled to rt. To the resulting mixture was added $H_2O$ (20 mL). The mixture was extracted with EtOAc (30 mL×3). The combined organic phases were dried over anhydrous $Na_2SO_4$ and filtered. The filtrate was concentrated in vacuo and the residue was purified by silica gel column chromatography (PE/EtOAc (v/v)=4/1) to give the title compound 56-2 (0.62 g, 81.3%). The compound was characterized by the following spectroscopic data:

$^1$H NMR (400 MHz, $CDCl_3$): δ 9.48 (s, 1H), 7.54 (s, 1H), 7.47 (d, J=7.44 Hz, 1H), 7.32 (m, 1H), 7.13 (s, 1H), 7.06 (d, J=8.2 Hz, 1H), 6.70 (d, J=8.3 Hz, 1H), 5.24 (s, 1H), 4.44 (brs, 1H), 3.42 (m, 2H), 2.90 (s, 2H), 2.80 (s, 2H), 1.93 (m, 2H), 1.59-1.66 (m, 10H), 1.49 (s, 9H).

Step 3) The Preparation of Compound 56-3

A solution of compound 56-2 (0.80 g, 1.7 mmol) in anhydrous $CH_2Cl_2$ (30 mL) was cooled to 0° C. To the solution were added dropwise pyridine (1.4 mL) and trifluoromethanesulfonic anhydride (1.76 mL) in turn. The reaction mixture was stirred at rt for 2 hours. To the resulting mixture was added $H_2O$ (10 mL). The mixture was extracted with $CH_2Cl_2$ (50 mL×3). The combined organic phases were dried over anhydrous $Na_2SO_4$ and filtered. The filtrate was concentrated in vacuo and the residue was purified by silica gel column chromatography to give the title compound 56-3 as colorless oil (0.87 g, 84.1%). The compound was characterized by the following spectroscopic data:

$^1$H NMR (400 MHz, $CDCl_3$): δ 9.62 (s, 1H), 7.63 (m, 1H), 7.47 (d, J=8.16 Hz, 1H), 7.36 (m, 1H), 7.22 (d, J=8.44 Hz, 2H), 7.09 (d, J=8.36 Hz, 1H), 6.70 (d, J=8.3 Hz, 1H), 4.48 (brs, 1H), 3.46 (m, 2H), 2.97 (s, 2H), 2.94 (s, 2H), 1.93 (m, 2H), 1.59-1.66 (m, 10H), 1.50 (s, 9H).

Step 4) The Preparation of Compound 56-4

To a mixture of compound 56-3 (0.87 g, 1.4 mmol), compound 1-5-2 (0.66 g, 1.5 mmol), $Pd(PPh_3)_4$ (0.18 g, 0.16 mmol) and $K_2CO_3$ (1.1 g, 8.0 mmol) were added DME (20 mL) and $H_2O$ (5 mL) via syringe under $N_2$. The mixture was refluxed at 90° C. for 3 hours, and cooled to rt. To the resulting mixture was added H₂O (20 mL). The mixture was extracted with EtOAc (30 mL×3). The combined organic phases were dried over anhydrous Na₂SO₄ and filtered. The filtrate was concentrated in vacuo and the residue was purified by silica gel column chromatography (PE/EtOAc (v/v)=1/2) to give the title compound 56-4 as a pale yellow solid (0.78 g, 70.7%). The compound was characterized by the following spectroscopic data:

¹H NMR (400 MHz, CDCl₃): δ 9.48 (s, 1H), 7.80-7.17 (m, 11H), 4.99 (m, 1H), 4.49 (brs, 1H), 3.42 (m, 4H), 2.98 (s, 4H), 2.18 (m, 2H), 1.99 (m, 4H), 1.59-1.66 (m, 10H), 1.51 (s, 18H).

Step 5) The Preparation of Compound 56-5

To a solution of compound 56-4 (0.7 g, 0.9 mmol) in EtOAc (10 mL) was added a solution of HCl in EtOAc (4 M, 11 mL). The mixture was stirred at rt overnight and filtered. The filter cake was washed with EtOAc (30 mL) to give the title compound 56-5 as a pale yellow solid (0.55 g, 84.6%). The product was used for the next step without further purification.

Step 6) The Preparation of Compound 56-6

A suspension of compound 56-5 (0.2 g, 0.28 mmol), EDCI (0.22 g, 1.15 mmol) and compound 1-7-2 (0.15 g, 0.86 mmol) in CH₂Cl₂ (5 mL) was cooled to 0° C. in an ice bath. To the suspension was added DIPEA (0.5 mL) slowly to get a pale yellow transparent solution. Then the solution was stirred at rt for 10 hours. To the resulting mixture was added H₂O (10 mL). The mixture was extracted with CH₂Cl₂ (10 mL×3). The combined organic phases were dried over anhydrous Na₂SO₄ and filtered. The filtrate was concentrated in vacuo and the residue was purified by silica gel column chromatography to give the title compound 56-6 as a pale yellow solid (0.09 g, 36.4%, HPLC: 95.3%). The compound was characterized by the following spectroscopic data:

MS-ESI: m/z 887.4 [M+H]⁺; and

¹H NMR (400 MHz, CDCl₃): δ 9.62 (s, 1H), 7.83 (m, 1H), 7.53-7.17 (m, 10H), 5.41 (m, 2H), 4.99 (m, 1H), 4.49 (brs, 1H), 3.70 (s, 3H), 3.69 (s, 3H), 3.42 (m, 4H), 2.98 (s, 4H), 2.63 (m, 2H), 2.18 (m, 2H), 1.99 (m, 4H), 1.59-1.66 (m, 10H), 0.89 (m, 12H).

Example 57

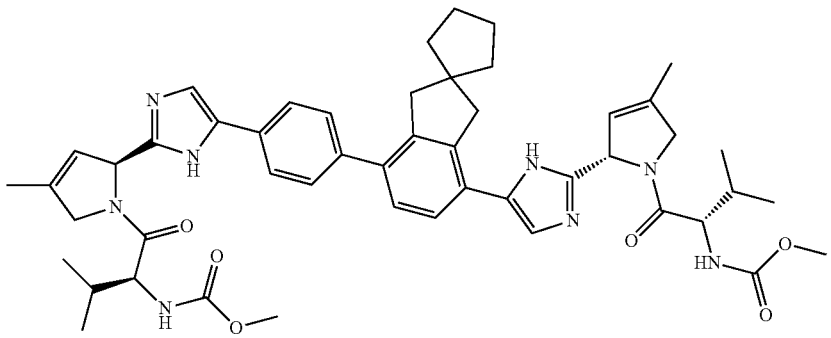

Synthetic Routes

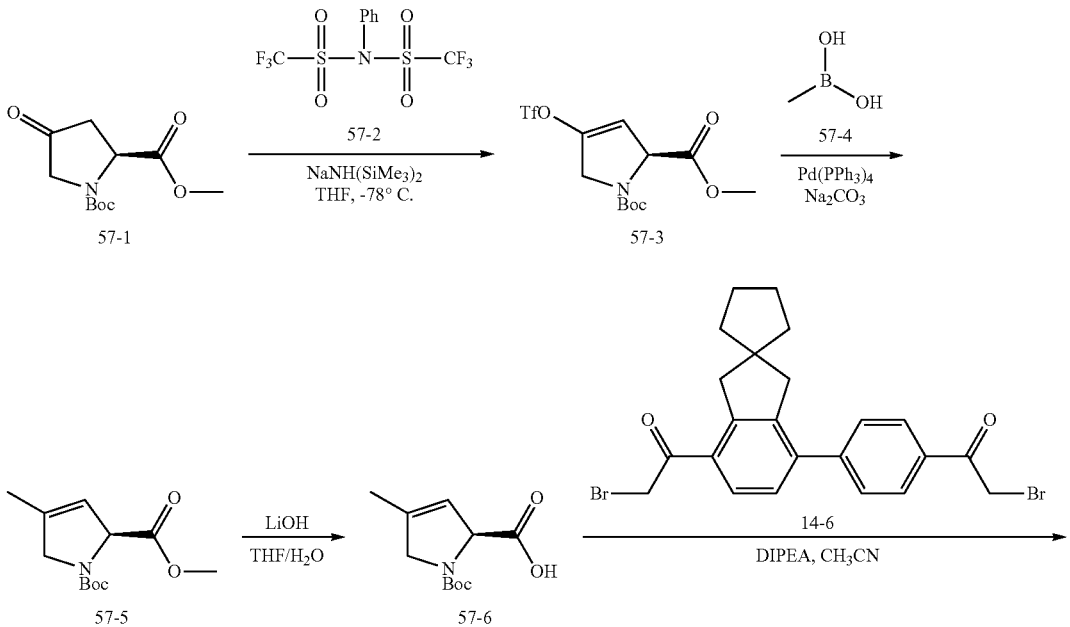

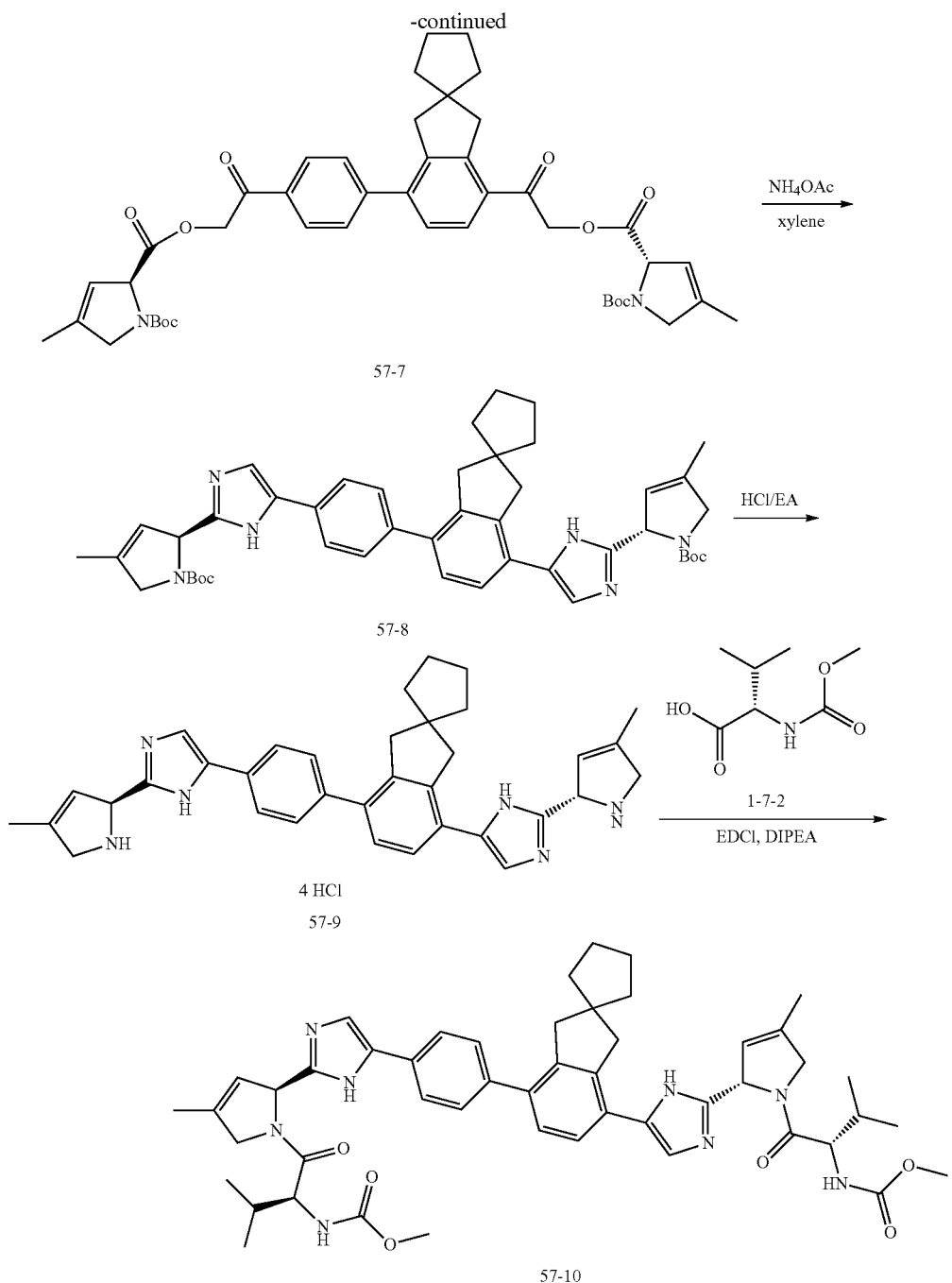

Step 1) The Preparation of Compound 57-3

To a solution of compound 57-1 (10 g, 41.1 mmol) in THF (50 mL) was added NaNH(SiMe$_3$)$_2$ (45.2 mL, 45.2 mmol, 1M in THF) dropwise at −78° C. under N$_2$. After the mixture was stirred for 20 minutes, compound 57-2 (15.4 g, 43.1 mmol) was added. The reaction mixture stirred at −78° C. for 3 hours, then quenched with NaHCO$_3$ (50 mL) saturated solution and extracted with EtOAc (100 mL×3). The combined organic phases were dried over anhydrous Na$_2$SO$_4$ and filtered. The filtrate was concentrated in vacuo and the residue was purified by silica gel column chromatography (PE/EtOAc (v/v)=4/1) to give compound 57-3 as colorless oil (14.8 g, 95.9%). The compound was characterized by the following spectroscopic data:

$^1$H NMR (400 MHz, CDCl$_3$): δ 5.72 (m, 1H), 5.02 (m, 1H), 4.28-4.42 (m, 2H), 3.77 (s, 3H), 1.42-1.47 (m, 9H).

Step 2) The Preparation of Compound 57-5

To a mixture of compound 57-3 (5.0 g, 13.3 mmol), compound 57-4 (1.0 g, 16.7 mmol), Pd(PPh$_3$)$_4$ (0.465 g, 0.402 mmol) and Na$_2$CO$_3$ aqueous solution (2M, 15 mL) was added DME (50 mL) via syringe under N$_2$. The reaction mixture was stirred at 90° C. for 3 hours, cooled down naturally and concentrated in vacuo. To the residue was added water (15 mL), and the mixture was extracted with EtOAc (30.0 mL×3). The combined organic phases were washed with brine, dried over anhydrous Na$_2$SO$_4$ and filtered. The filtrate was concentrated in vacuo and the residue was purified by silica gel column chromatography (PE/EtOAc (v/v)=3/1) to give the title compound 57-5 as colorless oil (2.25 g, 70.1%). The compound was characterized by the following spectroscopic data:

$^1$H NMR (400 MHz, CDCl$_3$): δ 5.36 (m, 1H), 4.90 (m, 1H), 4.04-4.16 (m, 2H), 3.72 (m, 3H), 1.79 (m, 3H), 1.42-1.47 (m, 9H).

Step 3) The Preparation of Compound 57-6

To a mixture of compound 57-5 (3.76 g, 15.6 mmol) and LiOH (1.3 g, 54.3 mmol) were added THF (15 mL) and H$_2$O (15 mL). The mixture was stirred at rt overnight, then concentrated in vacuo and to the residue was added H$_2$O (10 mL). The aqueous phase was washed with EtOAc (20 mL), adjusted to pH 3 and extracted with EtOAc (50 mL×3). The combined organic phases were washed with brine, dried over anhydrous Na$_2$SO$_4$ and filtered. The filtrate was concentrated in vacuo to give the title compound 57-6 as colorless oil (3.5 g, 98.7%). The compound was characterized by the following spectroscopic data:

MS-ESI: m/z 226 [M−H]$^−$.

Step 4) The Preparation of Compound 57-7

To a solution of compound 14-6 (1.08 g, 2.2 mmol) in anhydrous CH$_3$CN (22 mL) were added DIPEA (1.1 mL) and compound 57-6 (1.04 g, 4.6 mmol) in turn in an ice bath. The reaction mixture was stirred at rt for 1 hour, and concentrated in vacuo. The residue was purified by silica gel column chromatography (PE/EtOAc (v/v)=1/2) to give the title compound 57-7 as pale yellow slurry (1.4 g, 81.3%). The compound was characterized by the following spectroscopic data:

$^1$H NMR (400 MHz, CDCl$_3$): δ 7.79-7.80 (m, 2H), 7.67 (d, J=8.0 Hz, 1H), 7.53-7.56 (m, 2H), 7.28 (d, J=8.0 Hz, 1H), 5.11-5.59 (m, 8H), 3.58-3.60 (m, 2H), 3.40-3.49 (m, 2H), 2.91 (s, 2H), 2.86 (s, 2H), 1.95-1.98 (m, 6H), 1.50-1.54 (m, 8H), 1.45 (s, 9H), 1.47 (s, 9H).

Step 5) The Preparation of Compound 57-8

To a solution of compound 57-7 (1.4 g, 1.8 mmol) in xylene (20 mL) was added ammonium acetate (2.2 g, 28.5 mmol). The mixture was heated at 140° C. for 5 hours in a sealed tube, and cooled to rt. To the resulting mixture was added H$_2$O (50 mL). The mixture was extracted with EtOAc (50 mL×3). The combined organic phases were dried over anhydrous Na$_2$SO$_4$ and filtered. The filtrate was concentrated in vacuo and the residue was purified by silica gel column chromatography (PE/EtOAc (v/v)=1/4) to give the title compound 57-8 as a pale yellow solid (0.73 g, 54.6%). The compound was characterized by the following spectroscopic data:

$^1$H NMR (400 MHz, CDCl$_3$): δ 10.97 (brs, 1H), 10.49 (brs, 1H), 7.79-7.80 (m, 2H), 7.30-7.45 (m, 3H), 7.27 (d, J=8.0 Hz, 1H), 7.14 (s, 1H), 7.26 (s, 1H), 5.33-5.56 (m, 4H), 3.41-3.48 (m, 4H), 2.95-3.20 (m, 4H), 1.95-1.98 (m, 6H), 1.50-1.54 (m, 8H), 1.51 (s, 18H).

Step 6) The Preparation of Compound 57-9

To a solution of compound 57-8 (0.37 g, 0.5 mmol) in EtOAc (5 mL) was added a solution of HCl in EtOAc (4 M, 11 mL). Pale yellow solid precipitated out. The mixture was stirred at rt overnight and filtered. The filter cake was washed with EtOAc (20 mL) to give the title compound 57-9 as pale yellow solid (0.34 g, 98.7%).

Step 7) The Preparation of Compound 57-10

A suspension of compound 57-9 (0.147 g, 0.21 mmol), EDCI (0.22 g, 1.14 mmol) and compound 1-7-2 (0.15 g, 0.86 mmol) in CH$_2$Cl$_2$ (5 mL) was cooled to 0° C. in an ice bath. To the suspension was added DIPEA (0.5 mL) slowly to get a pale yellow transparent solution. Then the solution was stirred at rt for 10 hours. To the resulting mixture was added H$_2$O (10 mL). The mixture was extracted with CH$_2$Cl$_2$ (10 mL×3). The combined organic phases were dried over anhydrous Na$_2$SO$_4$ and filtered. The filtrate was concentrated in vacuo and the residue was purified by silica gel column chromatography (EtOAc) to give the title compound 57-10 as a pale yellow solid (0.05 g, 27.8%, HPLC: 99%). The compound was characterized by the following spectroscopic data:

$^1$H NMR (400 MHz, CDCl$_3$): δ 7.54-7.78 (m, 2H), 7.30-7.48 (m, 3H), 7.26 (m, 1H), 7.14 (m, 1H), 7.26 (m, 1H), 5.33-5.56 (m, 4H), 4.52 (m, 2H), 3.68 (s, 3H), 3.63 (s, 3H), 3.41-3.48 (m, 4H), 2.95-3.20 (m, 4H), 2.65 (m, 2H), 1.95-1.98 (m, 6H), 1.50-1.54 (m, 8H), 0.83-0.97 (m, 12H).

BIOLOGICAL ACTIVITY

An HCV Replicon assay was utilized in the present disclosure, and was prepared, developed and validated as described in *Science*, 1999, 285 (5424), 110-3 and *J. Virol.*, 2003, 77 (5), 3007-19.

HCV GT1a, GT1b and GT2a replicon cells were used to test the currently described compound series as well as wild-type cells HCV 1b and resistant cells Y93H, L31F, P32L and 1302V. GT1a, GT1b and GT2a are HCV Replicon System which is transfected HCV 1a, 1b, 2a genotype respectively. The system containing G418 resistance gene NEO and Luciferase Reporter Gene can be used to determine the level of HCV replication, and evaluate the effects of the compounds inhibiting HCV replication, by using a real-time quantitative polymerase chain reaction (qPCR) method to detect NEO, and chemiluminescence method to test Luciferase Reporter Gene.

Operating Procedure:

1. Testing EC$_{50}$ of the Compounds by Luciferase Assay

The GT1a cells and GT1b cells were seeded into 96-well plates (8,000 cells in 125 μl/well) respectively; each compound was diluted to desired concentration using 5-fold serial dilutions protocol, 10 dose in duplicate, and added to wells with POD™ 810 Plate Assembler. The final concentration of DMSO was 0.5%; the plates were incubated in a CO$_2$ incubator for 72 hours; after that, 40 μl of Luciferase assay substrate (Promega Bright-Glo) was added to each well, and detected by a chemiluminescence detection system (Topcount Microplate Scintillation and Luminescence Counter) 5 minutes later; data analysis.

2. Testing EC$_{50}$ of the Compounds by Detecting Antibiotic G418 Resistance Gene NEO Gene The GT1a cells and GT1b cells were seeded into 96-well plates (8,000 cells in 125 μl/well) respectively; each compound was diluted to desired concentration using 5-fold serial dilutions protocol, 10 dose in duplicate, and added to wells with POD™ 810 Plate Assembler, the final concentration of DMSO was 0.5%; the cells were incubated in a CO$_2$ incubator for 72 hours; quantitative PCR.

Sample preparation: the supernatant was removed, 100 μl of FCW buffer solution was added to each well, washed carefully and discarded the solution; 50 μl of lysate FCP was added to each well, the cells was lysed as PCR template and PCR template was diluted with DEPC water as sample template.

Quantitative PCR: preparation of reaction mixture according to PCR system; the reaction mixture was dispensed into a 384-well PCR reaction plate (specially for quantitative); and a standard template which was diluted in proportion was distributed into the plate; and the sample template was distributed into the plate; then the 384-well plate was sealed with closure plate membrane; the qualitative PCR machine was operated by procedures; data analysis.

3. Data processing: $EC_{50}$ values of compounds were analyzed by GRAPHPAD PRISM® software.

The compounds of the present disclosure can be effective against the HCV 1b genotype according to the experiment data. $EC_{50}$ ranges of compounds having different groups against HCV 1b are 1-999 pM and 1-99 nM. The compounds of the present disclosure can inhibit multiple genotypes of HCV (such as HCV 1a or HCV 2a). Table 2 shows the $EC_{50}$ values of representative compounds of the present disclosure against the HCV 1a and HCV 1b genotypes. In one embodiment compounds of the present disclosure are active against the 1a, 1b, 2a, 2b, 3a, 3b, 4a, and 5a genotypes. EC50 ranges against HCV 1a and HCV 1b are as follows: A=0.001-0.100 nM; B=0.101-1.000 nM; C=1.001-10.000 nM; and D>10 nM.

The experimental results of wild-type and resistance cells and the simulation results of molecular modeling and computer aided docking design show that compounds in the present disclosure play an excellent anti-HCV role, which suggest a novel anti-HCV mechanism by interfering with HCV NS5A protein.

TABLE 2

| example | range (1a) | range (1b) |
|---|---|---|
| 1 | A | C |
| 2 | B | D |
| 3 | A | A |
| 4 | A | A |
| 5 | A | B |
| 6 | A | A |
| 8 | A | C |
| 11 | A | A |
| 14 | A | D |
| 15 | A | D |
| 16 | A | D |
| 17 | B | D |
| 18 | A | D |
| 20 | A | B |
| 21 | A | C |
| 22 | A | A |
| 23 | A | A |
| 24 | A | A |
| 29 | A | A |
| 36 | A | A |
| 37 | C | C |
| 38 | B | D |
| 39 | A | B |
| 40 | A | C |
| 41 | C | D |
| 43 | A | D |
| 45 | A | D |
| 49 | A | C |
| 50 | A | C |
| 51 | A | D |
| 54 | A | B |
| 56 | A | C |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. The compounds of the present disclosure may inhibit multiple genotypes of HCV.

What is claimed is:

1. A compound of formula (I):

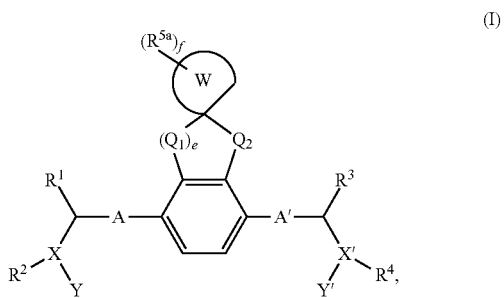

or a stereoisomer, a geometric isomer, a tautomer, an N-oxide, a hydrate, a solvate, or a pharmaceutically acceptable salt thereof, wherein:

each of A and A' is independently one of the following groups:

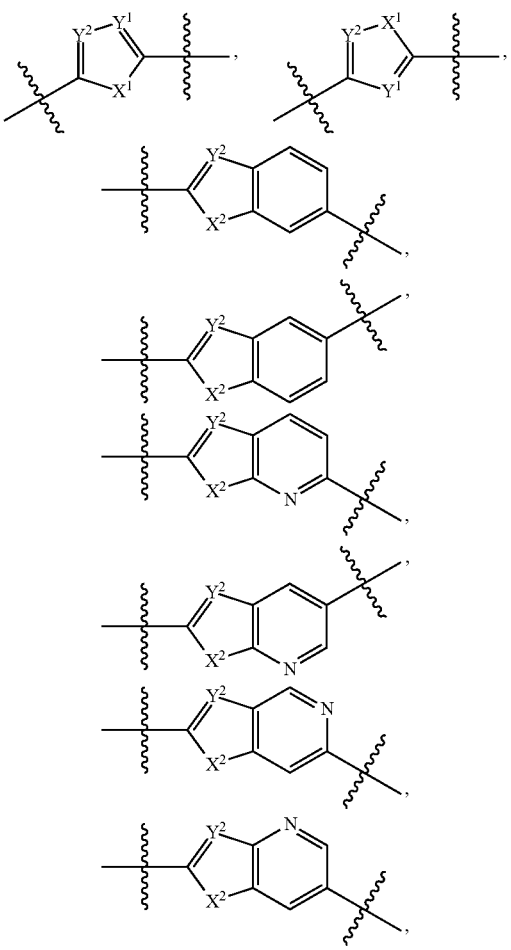

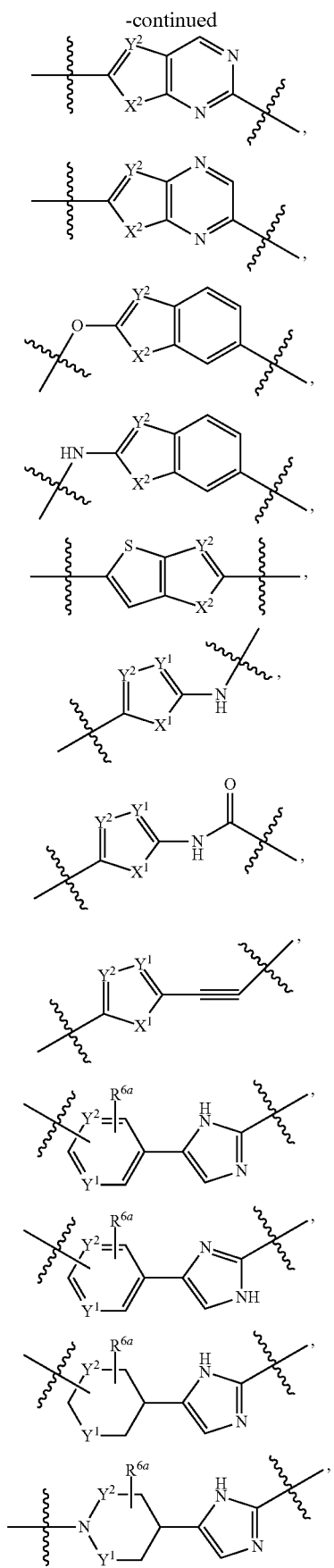
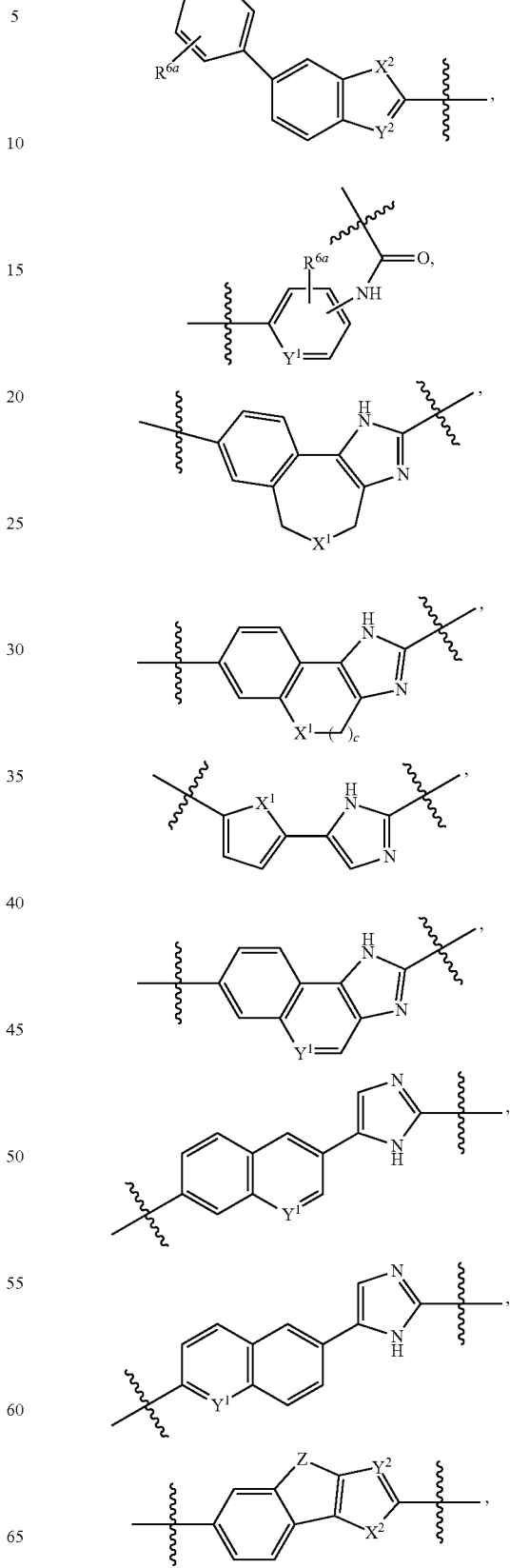

-continued

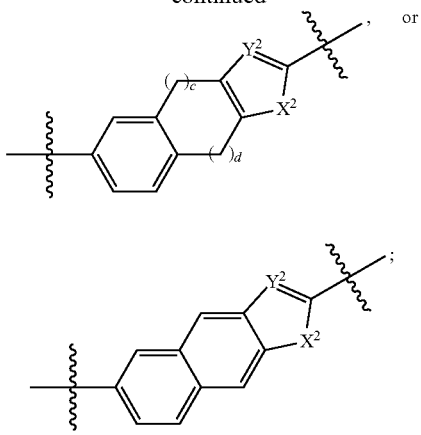

wherein each $X^1$ is independently O, S, $NR^6$ or $CR^7R^{7a}$;
each $Y^1$ and $Y^2$ is independently N or $CR^7$;
each $X^2$ is independently $NR^6$, O or S;
Z is —(CH$_2$)$_a$—, —CH=CH—, —N=CH—, —(CH$_2$)$_a$—N(R$^5$)—(CH$_2$)$_b$—, or —(CH$_2$)$_a$—O—(CH$_2$)$_b$—, wherein each a and b is independently 0, 1, 2 or 3;
each c is independently 1 or 2;
d is 1 or 2;
e is 1, 2, 3 or 4;
f is 0, 1, 2, 3 or 4;
each $Q_1$ and $Q_2$ is independently $NR^6$, O, S, C(=O) or $CR^7R^{7a}$, with the proviso that when $Q_1$ is $NR^6$, O, S or C(=O), e is 1;
W is $C_{3-8}$ carbocyclyl or $C_{2-10}$ heterocyclyl;
each of X and X' is independently N or $CR^7$;
each of Y and Y' is independently H, alkyl, heteroalkyl, cycloalkyl, heterocyclyl, aryl, heteroaryl, aralkyl, a group derived from a naturally occurring or commercially available α-amino acid or an optically isomer thereof, or each of Y and Y' is independently —[U—(CR$^9$R$^{9a}$)$_t$—N(R$^{10}$)—(CR$^9$R$^{9a}$)$_t$]$_k$—U—(CR$^9$R$^{9a}$)$_t$—N(R$^{11}$)—(CR$^9$R$^{9a}$)$_t$—R$^{12}$, —U—(R$^9$R$^{9a}$)$_t$—R$^{12}$ or —[U—(CR$^9$R$^{9a}$)$_t$—N(R$^{10}$)—(CR$^9$R$^{9a}$)$_t$]$_k$—U—(CR$^9$R$^{9a}$)$_t$—O—(CR$^9$R$^{9a}$)$_t$—R$^{12}$;
U is independently —C(=O)—, —C(=S)—, —S(=O)— or —S(=O)$_2$—;
each t is independently 0, 1, 2, 3 or 4;
each k is independently 0, 1 or 2;
each of $R^1$, $R^2$, $R^3$ and $R^4$ is independently H, alkyl, heteroalkyl, aralkyl, cycloalkyl, heterocyclyl, heteroaryl or aryl; or $R^1$ and $R^2$, together with X—CH, form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X'—CH, form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle;
$R^5$ is independently H, hydroxy, alkyl, heteroalkyl, cycloalkyl, heterocyclyl, aryl, heteroaryl, aralkyl, alkoxy, alkyl alkyl-OC(=O)—, alkyl-C(=O)—, carbamoyl, alkyl-OS(=O)$_r$—, alkyl-S(=O)$_r$O—, alkyl-S(=O)$_r$- or aminosulfonyl;
each $R^{5a}$ is independently H, oxo (=O), hydroxy, amino, F, Cl, Br, I, cyano, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N-alkyl, R$^7$S(=O)-alkyl, R$^7$R$^{7a}$N—C(=O)-alkyl, R$^{7a}$R$^7$N-alkoxy, R$^7$S(=O)-alkoxy, R$^7$R$^{7a}$N—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy;
each $R^6$ is independently H, R$^7$R$^{7a}$NC(=O)—, R$^7$OC(=O)—, R$^7$C(=O)—, R$^7$R$^{7a}$NS(=O)—, R$^7$OS(=O)—, R$^7$S(=O)—, R$^7$R$^{7a}$NS(=O)$_2$—, R$^7$OS(=O)$_2$—, R$^7$S(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;
each $R^{6a}$ is independently H, oxo, hydroxy, amino, F, Cl, Br, I, cyano, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N-alkyl, R$^7$S(=O)-alkyl, R$^7$R$^{7a}$N—C(=O)-alkyl, R$^{7a}$R$^7$N-alkoxy, R$^7$S(=O)-alkoxy, R$^7$R$^{7a}$N—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino, or aryloxy;
each $R^7$ and $R^{7a}$ is independently H, F, Cl, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring;
each $R^9$, $R^{9a}$, $R^{10}$ and $R^{11}$ is independently H, alkyl, heteroalkyl, cycloalkyl, heterocyclyl, aryl, heteroaryl, aralkyl, haloalkyl, hydroxyalkyl, heteroarylalkyl, heterocyclylalkyl, or cycloalkylalkyl;
each $R^{12}$ is independently R$^{13a}$R$^{13}$N—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13}$OS(=O)$_2$—, alkyl, heteroalkyl, cycloalkyl, heterocyclyl, aryl, heteroaryl or aralkyl; and
or $R^{11}$ and $R^{12}$, together with the nitrogen atom they are attached to, form a 4-7 membered ring;
each $R^{13}$ and $R^{13a}$ is independently H, alkyl, heteroalkyl, cycloalkyl, heterocyclyl, aryl, heteroaryl, or aralkyl;
wherein each of the following groups —[U—(CR$^9$R$^{9a}$)$_t$—N(R$^{10}$)—(CR$^9$R$^{9a}$)$_t$]$_k$—U—(CR$^9$R$^{9a}$)$_t$—N(R$^{11}$)—(CR$^9$R$^{9a}$)$_t$—R$^{12}$, —U—(R$^9$R$^{9a}$)$_t$—R$^{12}$, —[U—(CR$^9$R$^{9a}$)$_t$—N(R$^{10}$)—(CR$^9$R$^{9a}$)$_t$]$_k$—U—(CR$^9$R$^{9a}$)$_t$—

O—(CR$^9$R$^{9a}$)$_t$—R$^{12}$, NR$^6$, CR$^7$R$^{7a}$, CR$^7$, —(CH$_2$)$_a$—, —CH═CH—, —N═CH—, —(CH$_2$)$_a$—N(R$^5$)—(CH$_2$)$_b$—, —(CH$_2$)$_a$—O—(CH$_2$)$_b$—, R$^{13a}$R$^{13}$N—, —C(═O)R$^{13}$, —C(═S)R$^{13}$, —C(═O)—O—R$^{13}$, —C(═O)NR$^{13}$R$^{13a}$, —OC(═O)NR$^{13}$R$^{13a}$, —OC(═O)OR$^{13}$, —N(R$^{13}$)C(═O)NR$^{13}$R$^{13a}$, —N(R$^{13}$)C(═O)OR$^{13a}$, —N(R$^{13}$)C(═O)—R$^{13a}$, R$^{13}$R$^{13a}$N—S(═O)$_2$—, R$^{13}$S(═O)$_2$—, R$^{13}$S(═O)$_2$N(R$^{13a}$)—, R$^{13}$OS(═O)$_2$—, R$^{7a}$R$^7$N—, —C(═O)NR$^7$R$^{7a}$, —OC(═O)NR$^7$R$^{7a}$, —OC(═O)OR$^7$, —N(R$^7$)C(═O)NR$^7$R$^{7a}$, —N(R$^7$)C(═O)OR$^{7a}$, —N(R$^7$)C(═O)—R$^{7a}$, R$^7$R$^{7a}$N—S(═O)$_2$—, R$^7$S(═O)$_2$—, R$^7$S(═O)$_2$N(R$^{7a}$)—, alkyl-OC(═O)—, alkyl-C(═O)—, alkyl-OS(═O)$_r$, alkyl-S(═O)$_r$O—, alkyl-S(═O)$_r$—, R$^7$R$^{7a}$NC(═O)—, R$^7$OC(═O)—, R$^7$C(═O)—, R$^7$R$^{7a}$NS(═O)—, R$^7$OS(═O)—, R$^7$S(═O)—, R$^7$R$^{7a}$NS(═O)$_2$—, R$^7$OS(═O)$_2$—, R$^7$S(═O)$_2$—, R$^{7a}$R$^7$N-alkyl, R$^7$S(═O)-alkyl, R$^7$R$^{7a}$N—C(═O)-alkyl, R$^{7a}$R$^7$N-alkoxy, R$^7$S(═O)-alkoxy, R$^7$R$^{7a}$N—C(═O)-alkylamino, alkyl, heteroalkyl, carbocyclyl, cycloalkyl, heterocyclyl, aryl, heteroaryl, aralkyl, α-amino acid, C$_{5-12}$ fused bicycle, C$_{5-12}$ fused heterobicycle, C$_{5-12}$ spiro bicycle or C$_{5-12}$ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted or unsubstituted substituents.

2. The compound according to claim 1, wherein the structural unit of

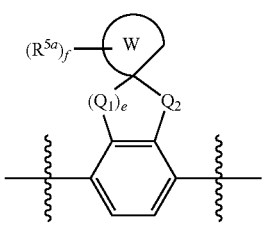

has one of the following structures:

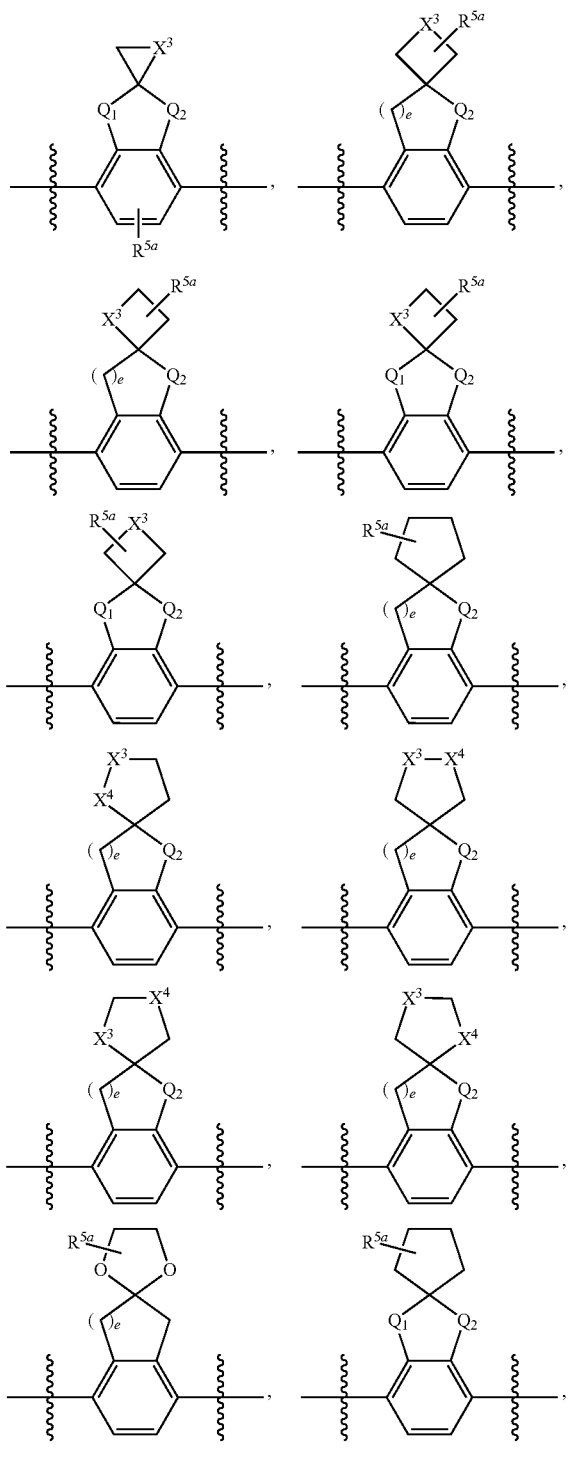

433

-continued

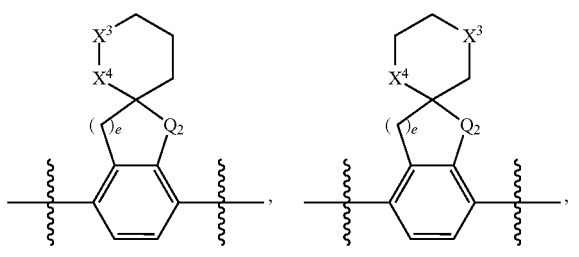

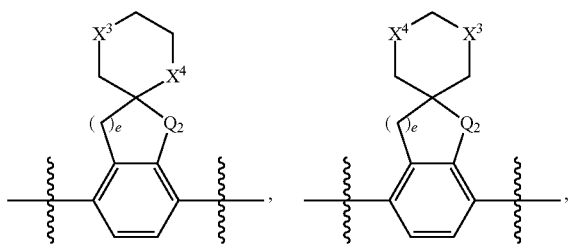

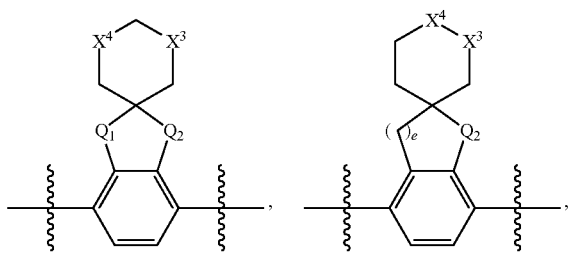

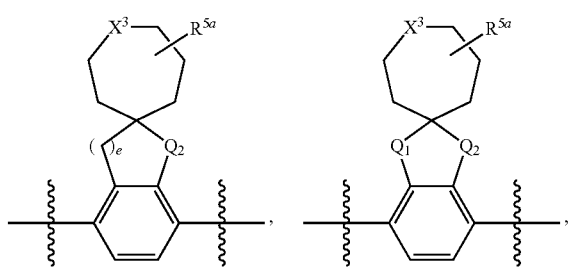

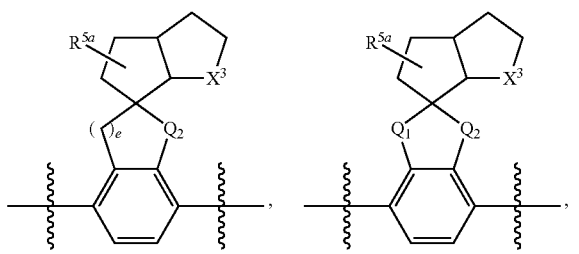

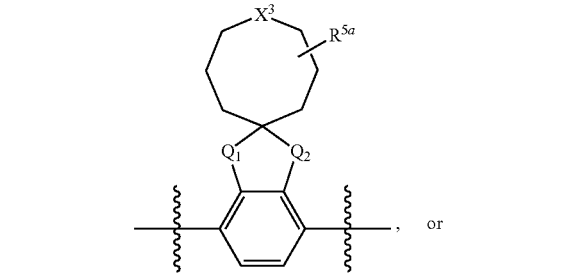

434

-continued

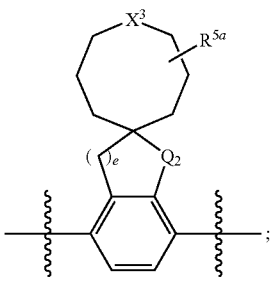

wherein each $X^3$ and $X^4$ is independently O, S, $NR^6$, or $CR^7R^7a$;

each e is 1, 2, 3 or 4;

f is 0, 1, 2, 3 or 4;

each $Q_1$ and $Q_2$ is independently $NR^6$, O, S, C(=O), or $CR^7R^{7a}$, with the proviso that when $Q_1$ is $NR^6$, O, S or C(=O), e is 1; and each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy.

3. The compound according to claim 1, wherein the structural unit of

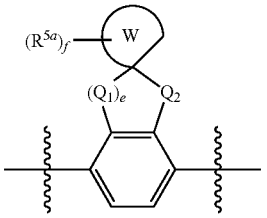

has one of the following structures:

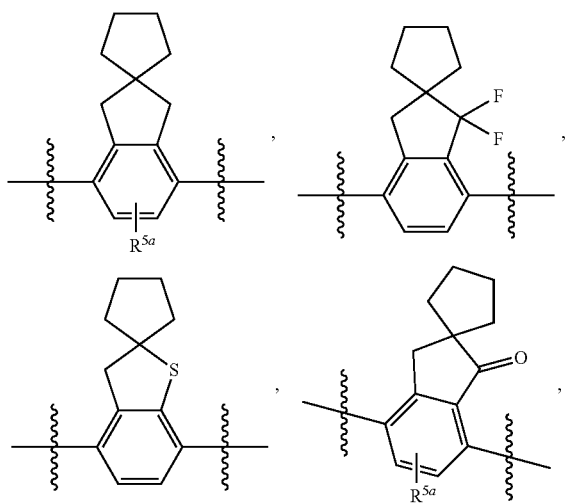

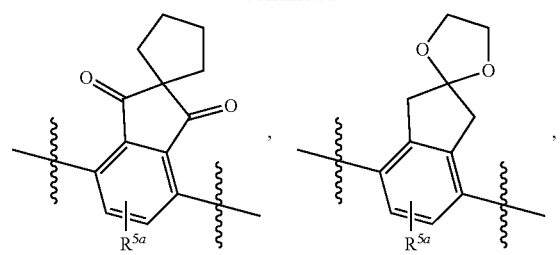
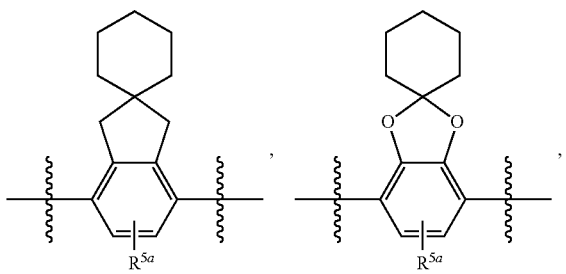
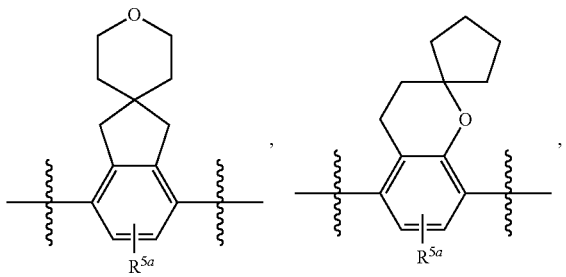
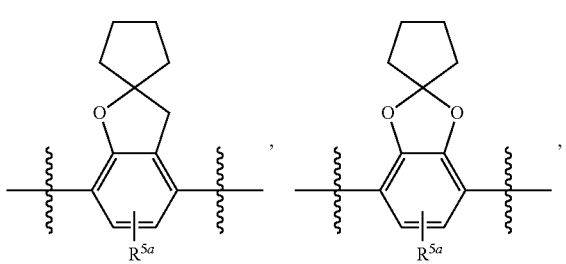
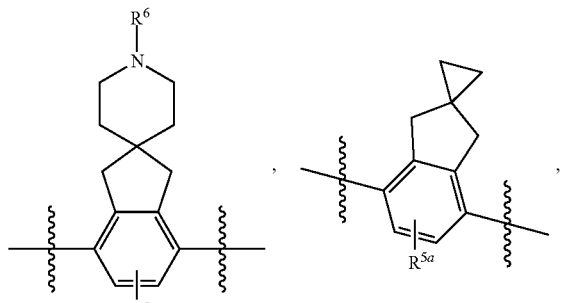
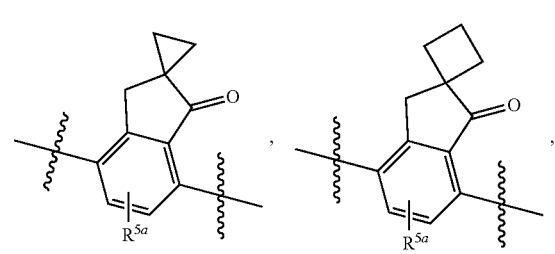

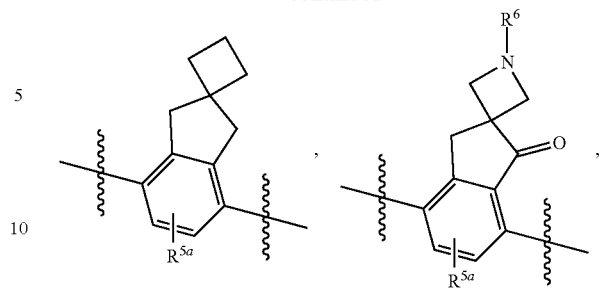
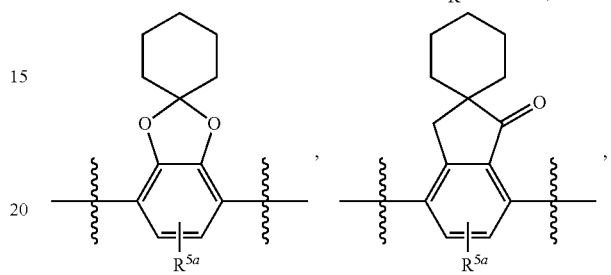
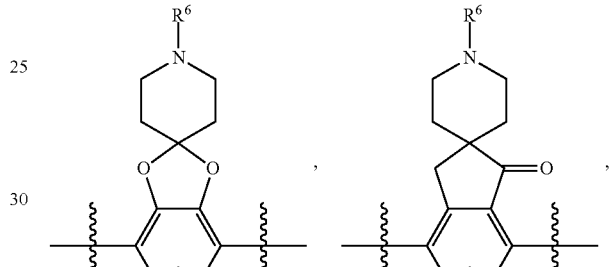
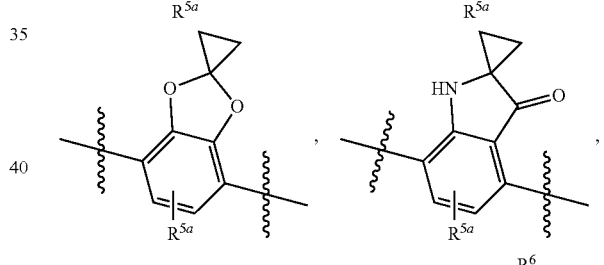
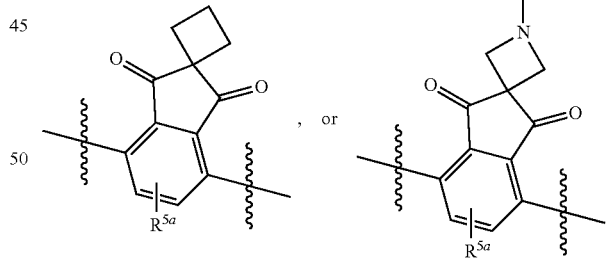

wherein each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, or $C_{1-6}$ alkylamino; and each $R^6$ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic or $C_{3-8}$ cycloalkyl-$C_{1-6}$-aliphatic.
4. The compound according to claim 1, wherein each of A and A' is independently one of the following groups:
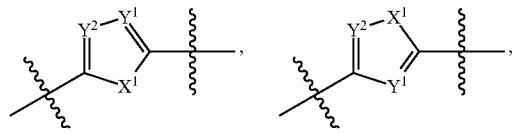
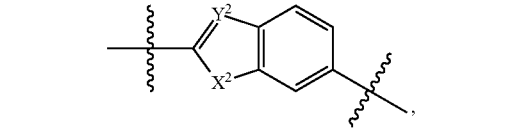
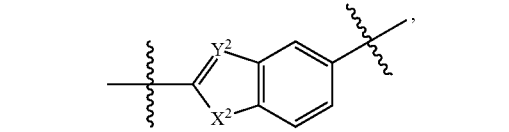
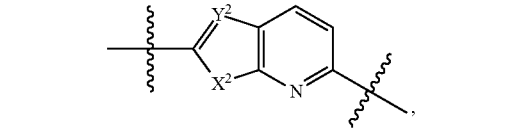
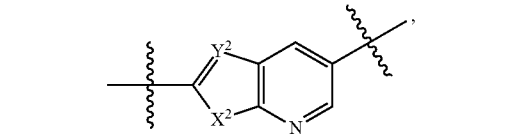
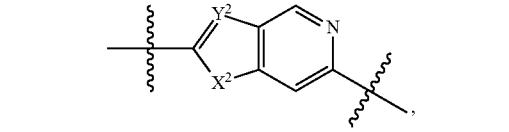
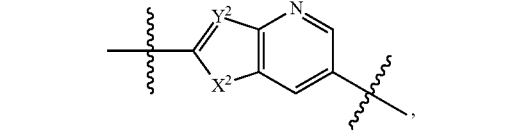
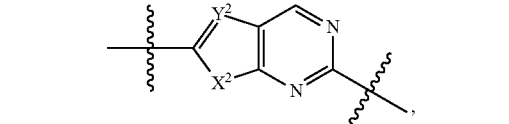
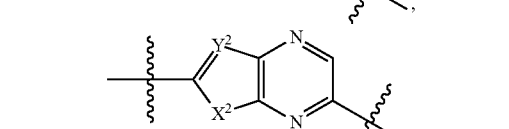
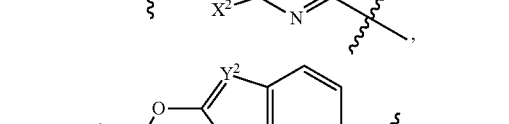
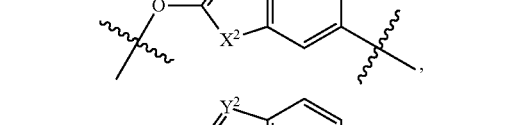
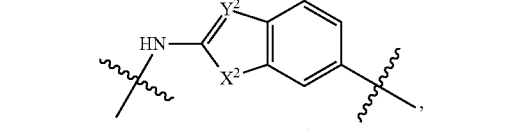
-continued
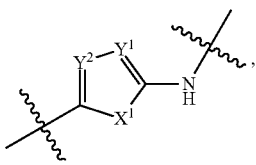
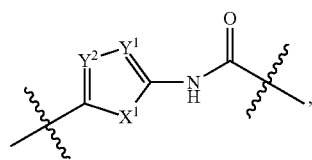
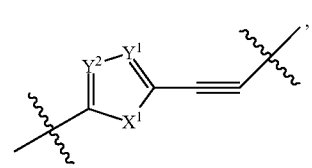
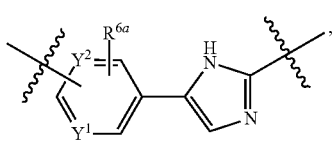
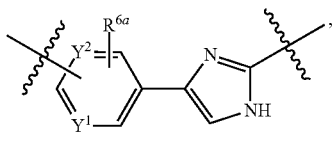
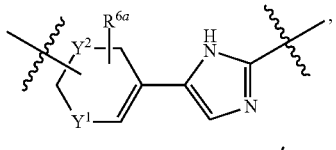
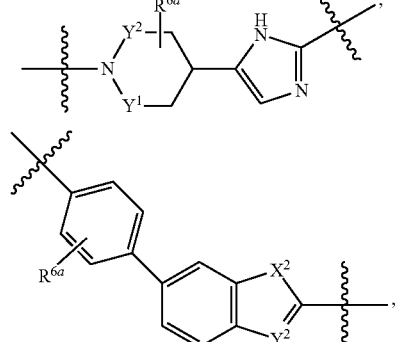
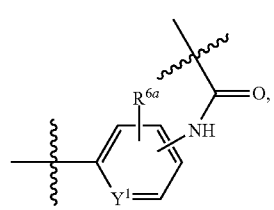
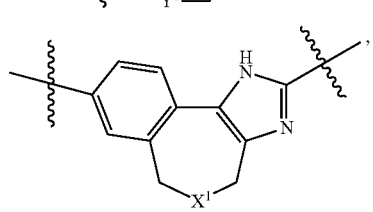

-continued

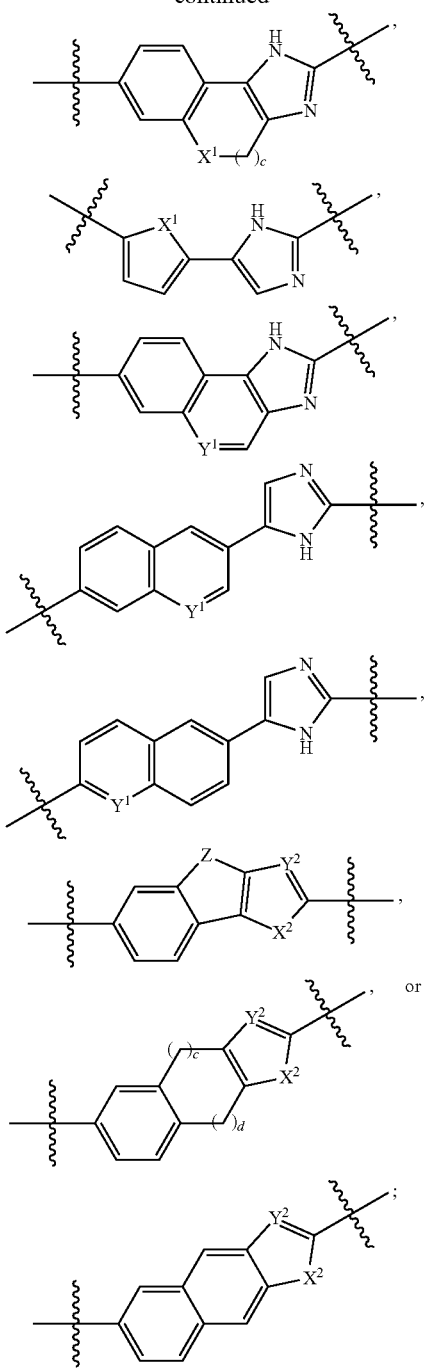

wherein each $R^5$ is independently H, hydroxy, $C_{1-6}$ alkyl, $C_{1-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;
each $R^{6a}$ is independently H, oxo, hydroxy, amino, F, Cl, Br, I, cyano, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2$N($R^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^7R^{7a}N$—$C_{1-6}$ alkoxy, $R^7S$(=O)—$C_{1-6}$ alkoxy, $R^7R^{7a}N$—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-9}$ heteroarylamino, or $C_{6-10}$ aryloxy; and each $R^7$ and $R^{7a}$ is independently H, F, Cl, $C_{1-6}$ aliphatic, $C_{1-6}$ heteroalkyl, $C_{1-6}$ haloaliphatic, hydroxy $C_{1-6}$ aliphatic, amino $C_{1-6}$ aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heterocyclyl-$C_{1-6}$-aliphatic, $C_{3-8}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-8}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-8}$ cycloalkylamino-$C_{1-6}$-aliphatic, $C_{6-10}$ aryl, $C_{1-9}$ heteroaryl, $C_{2-10}$ heterocyclyl or $C_{3-8}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring.

5. The compound according to claim 1, wherein each of A and A' is independently one of the following groups:

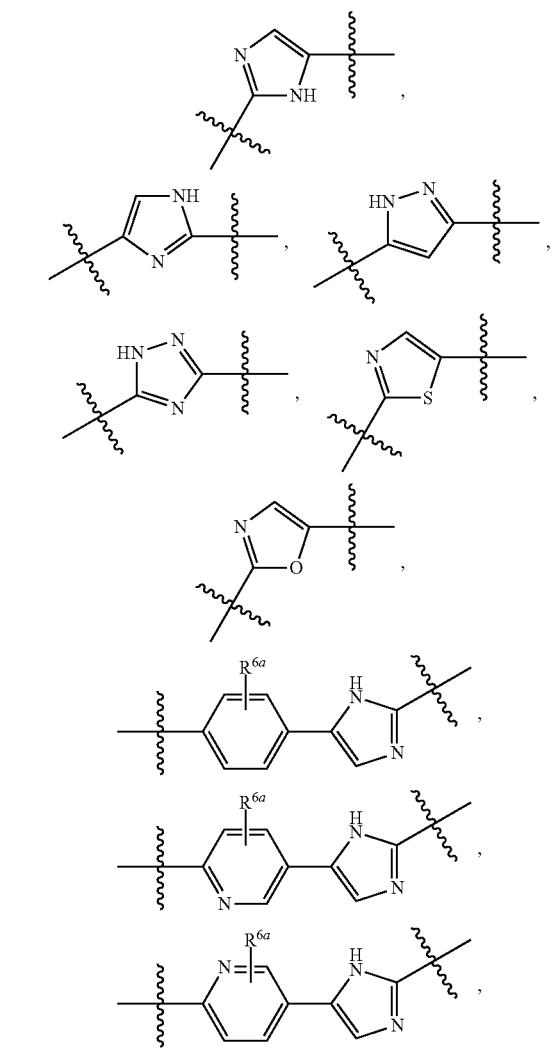

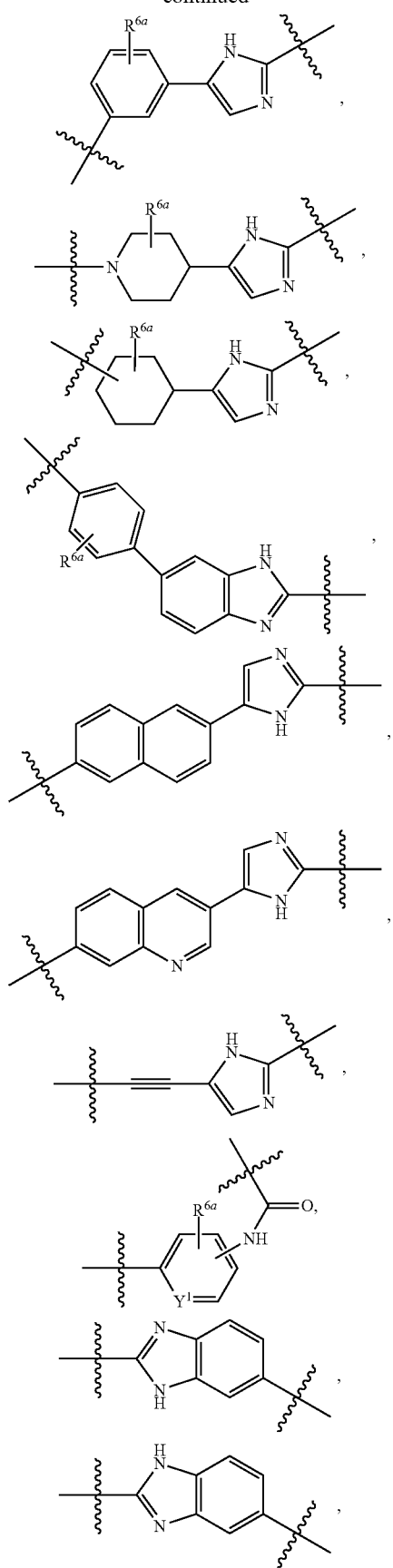
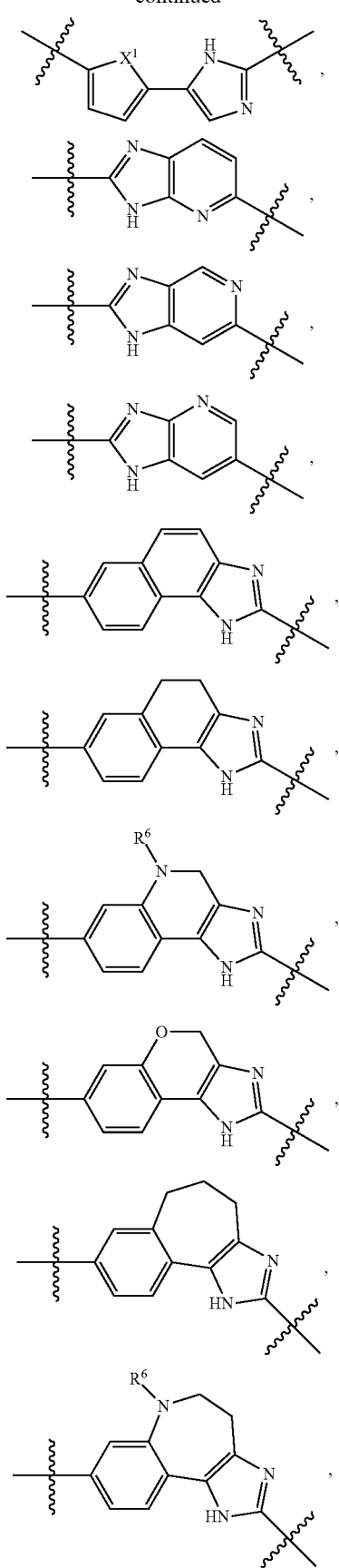

-continued

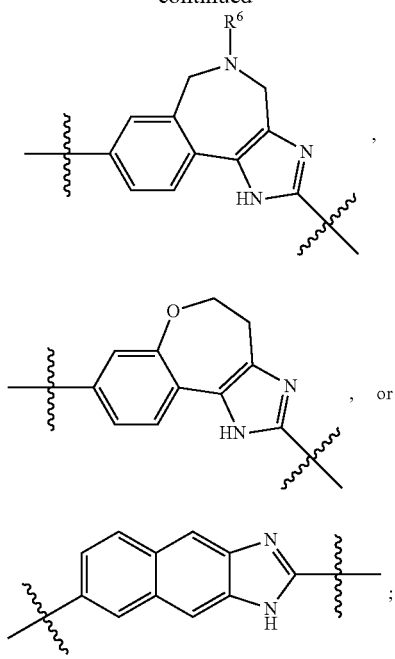

wherein $X^1$ is O or S;

each $R^6$ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic or $C_{3-8}$ cycloalkyl-$C_{1-6}$-aliphatic;

each $R^{6a}$ is independently H, hydroxy, amino, F, Cl, Br, I, cyano, oxo, $R^{7a}R^7N-$, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, mercapto or nitro; and each of $R^7$ and $R^{7a}$ is independently H, F, Cl, $C_{1-6}$ aliphatic, $C_{1-6}$ heteroalkyl, $C_{1-6}$ haloaliphatic, hydroxy $C_{1-6}$ aliphatic, amino $C_{1-6}$ aliphatic, $C_{1-6}$ alkoxy-$C_{1-6}$-aliphatic, $C_{1-6}$ alkylamino-$C_{1-6}$-aliphatic or $C_{1-6}$ alkylthio-$C_{1-6}$-aliphatic.

6. The compound according to claim 1, wherein each of $R^1$, $R^2$, $R^3$ and $R^4$ is independently H, $C_{1-8}$ alkyl, $C_{1-8}$ heteroalkyl, $C_{6-10}$ aryl-$C_{1-6}$-alkyl, $C_{3-10}$ cycloalkyl, $C_{2-10}$ heterocyclyl, $C_{1-9}$ heteroaryl or $C_{6-10}$ aryl, or $R^1$ and $R^2$, together with X—CH, form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X'—CH, form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle.

7. The compound according to claim 6, wherein $R^1$ and $R^2$, together with X—CH, or $R^3$ and $R^4$, together with X'—CH, form a 3-8 membered heterocycle, $C_{5-12}$ fused bicycle, $C_{5-12}$ fused heterobicycle, $C_{5-12}$ spiro bicycle or $C_{5-12}$ spiro heterobicycle.

8. The compound according to claim 6, wherein $R^1$, $R^2$ and X—CH together form one of the following monovalent groups:

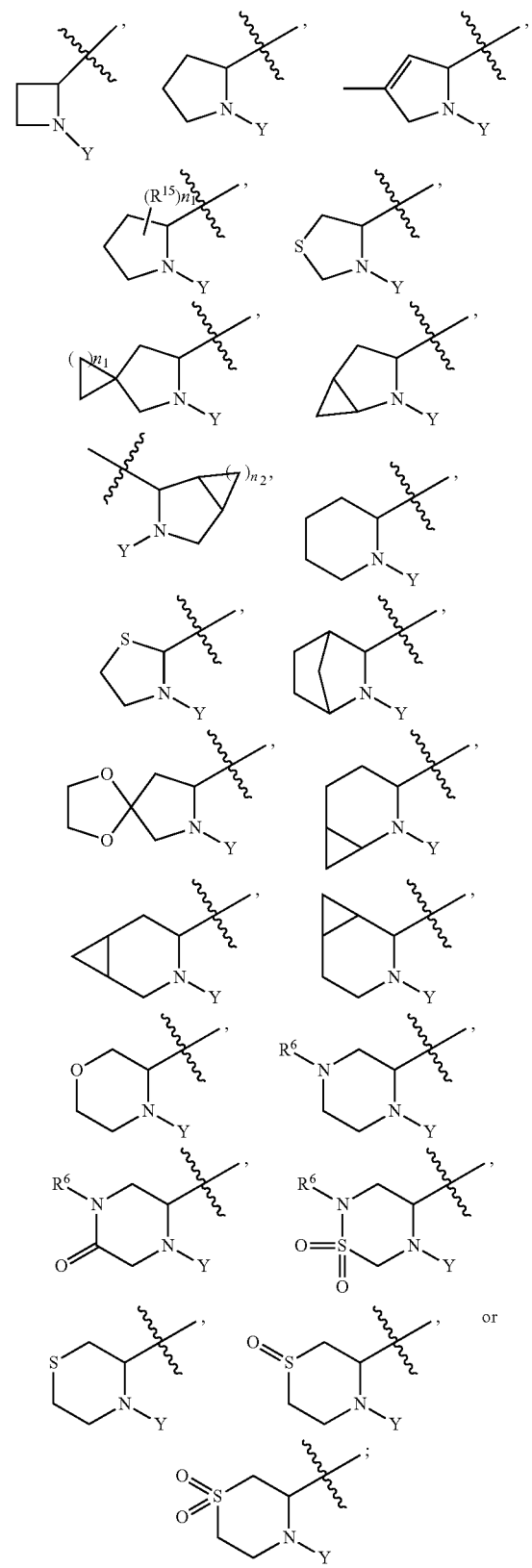

wherein each $R^{15}$ is independently H, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl; and each $n_1$ and $n_2$ is independently 1, 2, 3 or 4.

9. The compound according to claim 6, wherein $R^3$, $R^4$ and X'—CH together form one of the following monovalent groups:

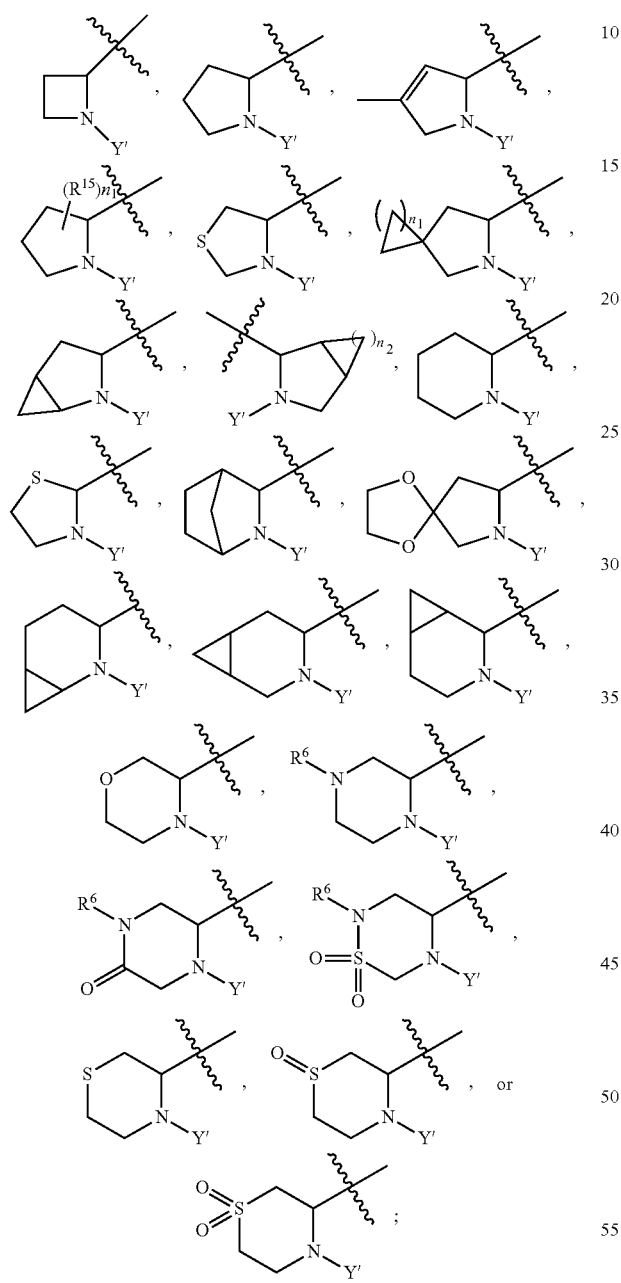

wherein each $R^{15}$ is independently H, F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl, or $C_{2-10}$ heterocyclyl; and each $n_1$ and $n_2$ is independently 1, 2, 3 or 4.

10. The compound according to claim 1 having the structure of formula (II):

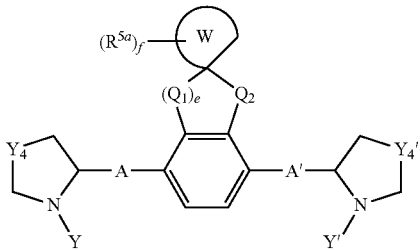

wherein the structural unit of

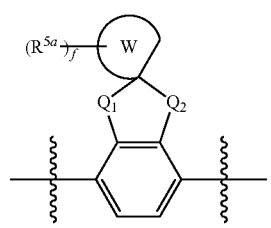

has one of the following structures:

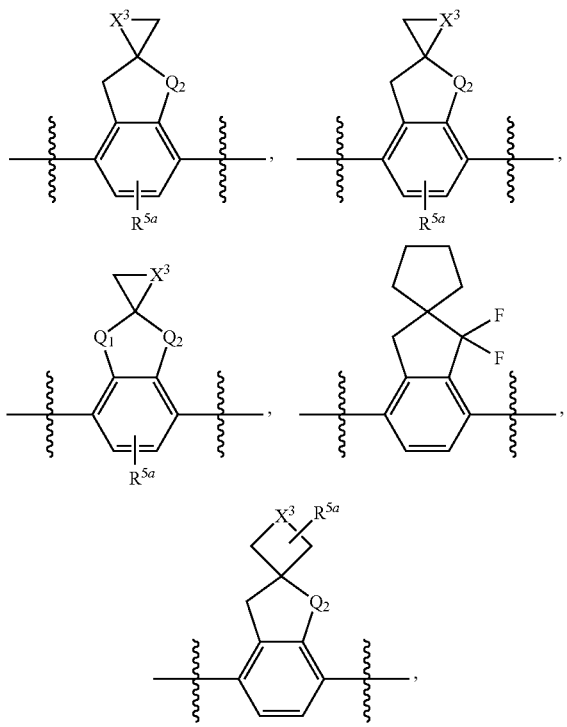

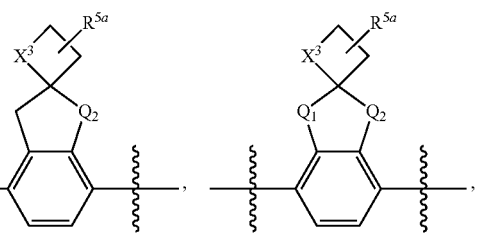

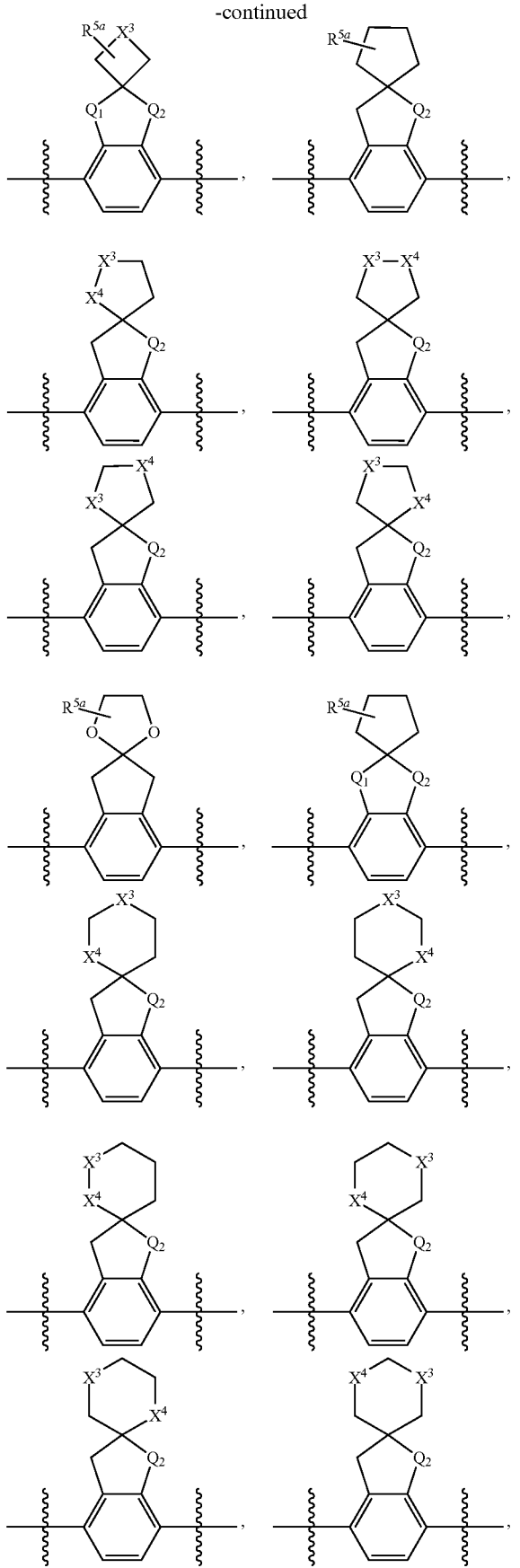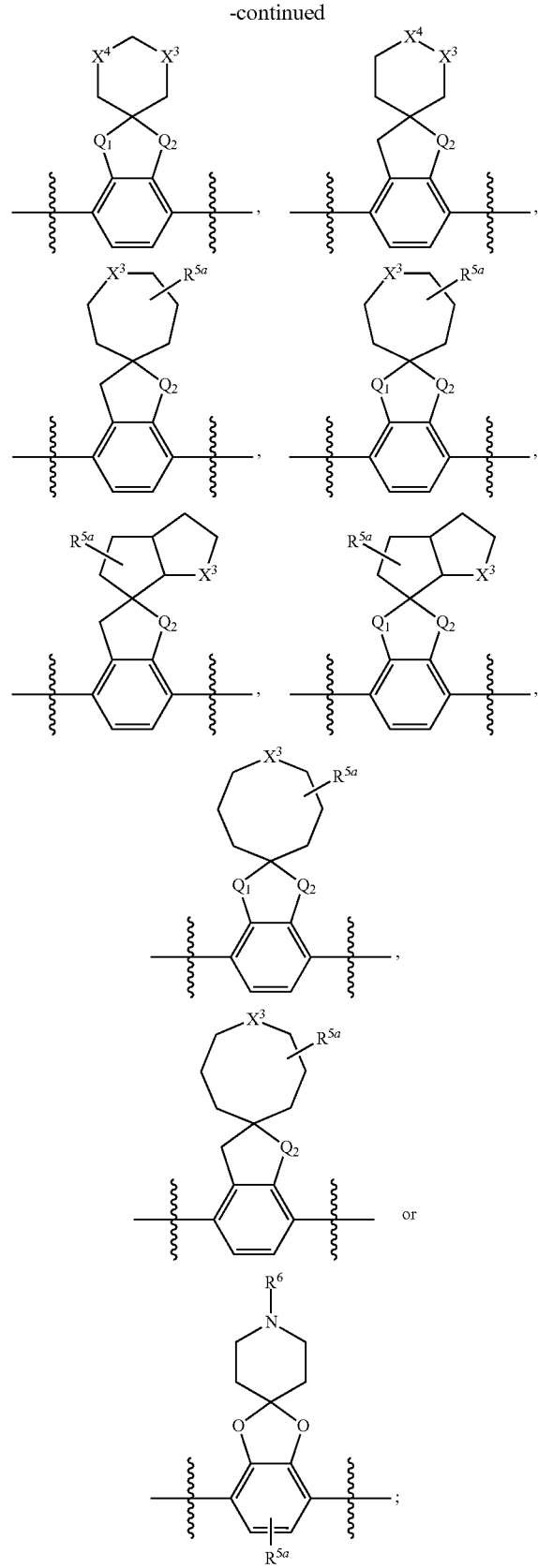
wherein each $Q_1$ and $Q_2$ is independently $NR^6$, O, S, C(=O) or $CH_2$;

each $X^3$ and $X^4$ is independently O, S, $NR^6$, or $CR^7R^{7a}$;
each of A and A' is independently one of the following groups:
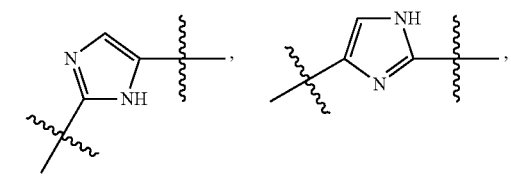
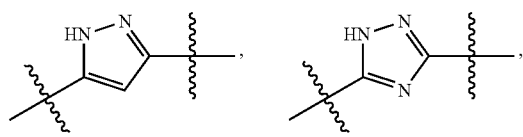
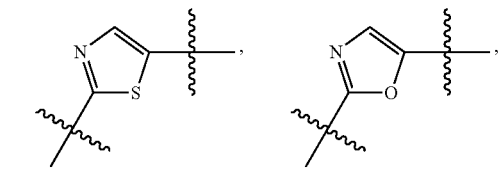
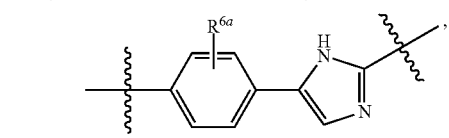
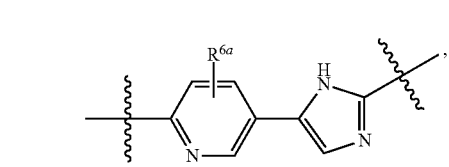
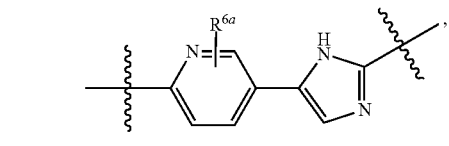
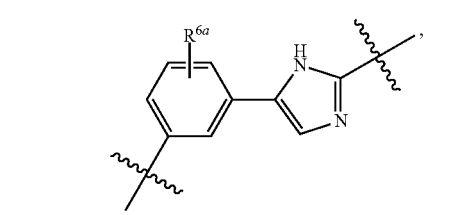
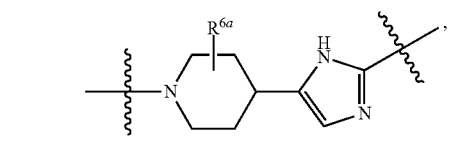
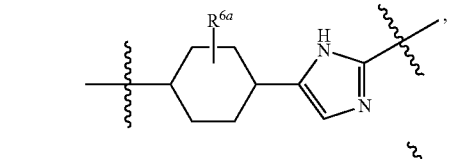
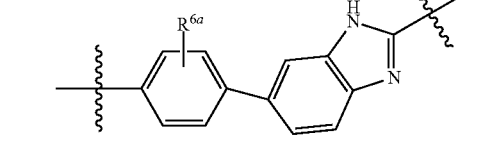
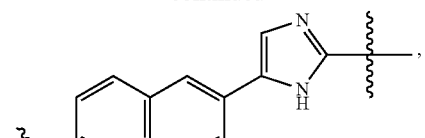
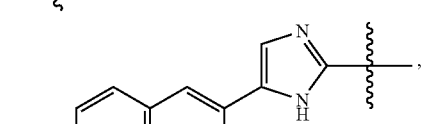
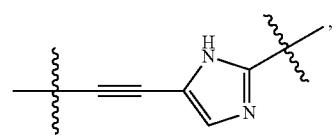
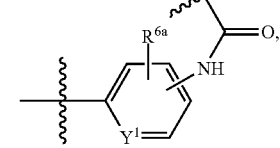
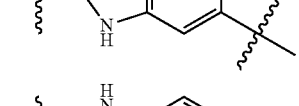
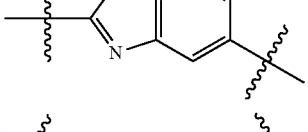
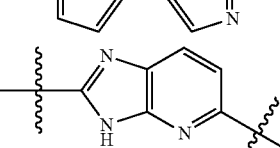
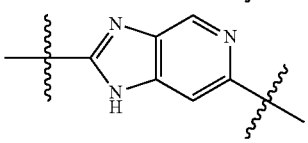
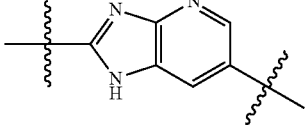
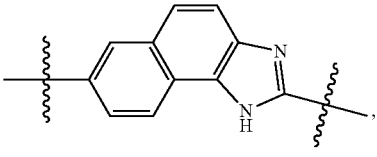

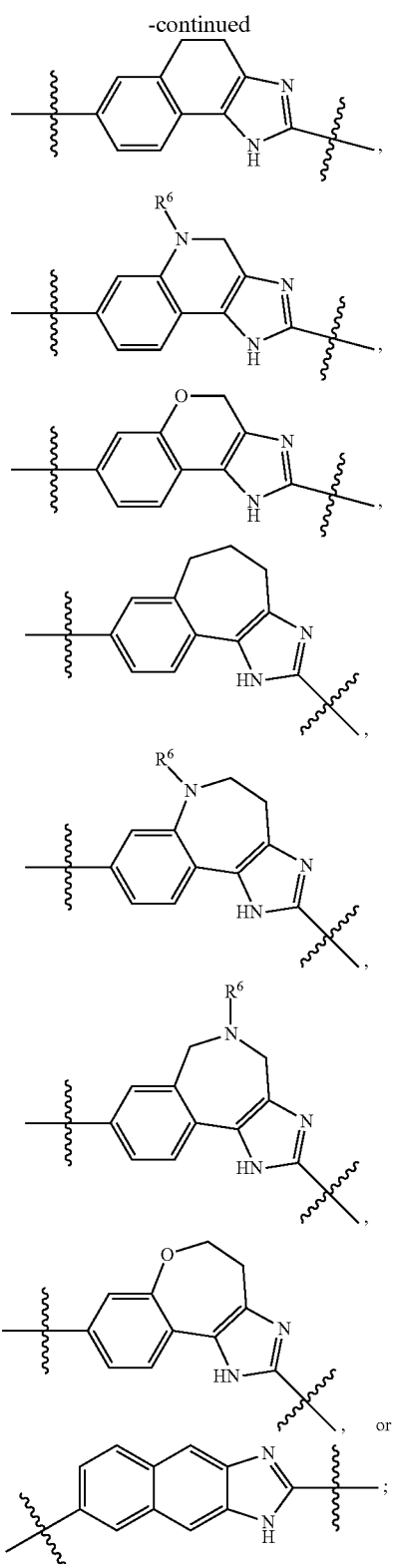

each R[5] is independently H, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, alkyl-S(=O)$_r$— or aminosulfonyl;

each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^6$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{6a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^7$ and $R^{7a}$ is independently H, $C_{1-6}$ aliphatic, $C_{1-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring;

each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, or —CH$_2$N(R$^6$)—;

each n is independently 0, 1, 2 or 3; and each r is independently 0, 1 or 2.

11. The compound according to claim 1 having the structure of formula (III):

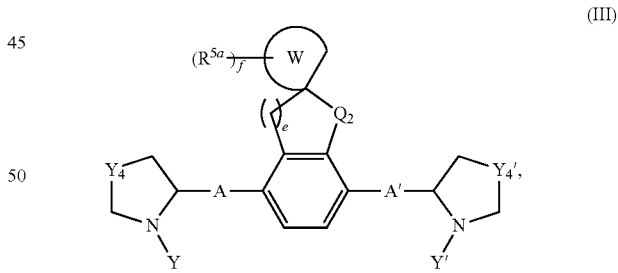

(III)

wherein the structural unit of

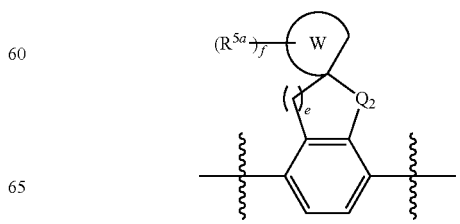

has one of the following structures:
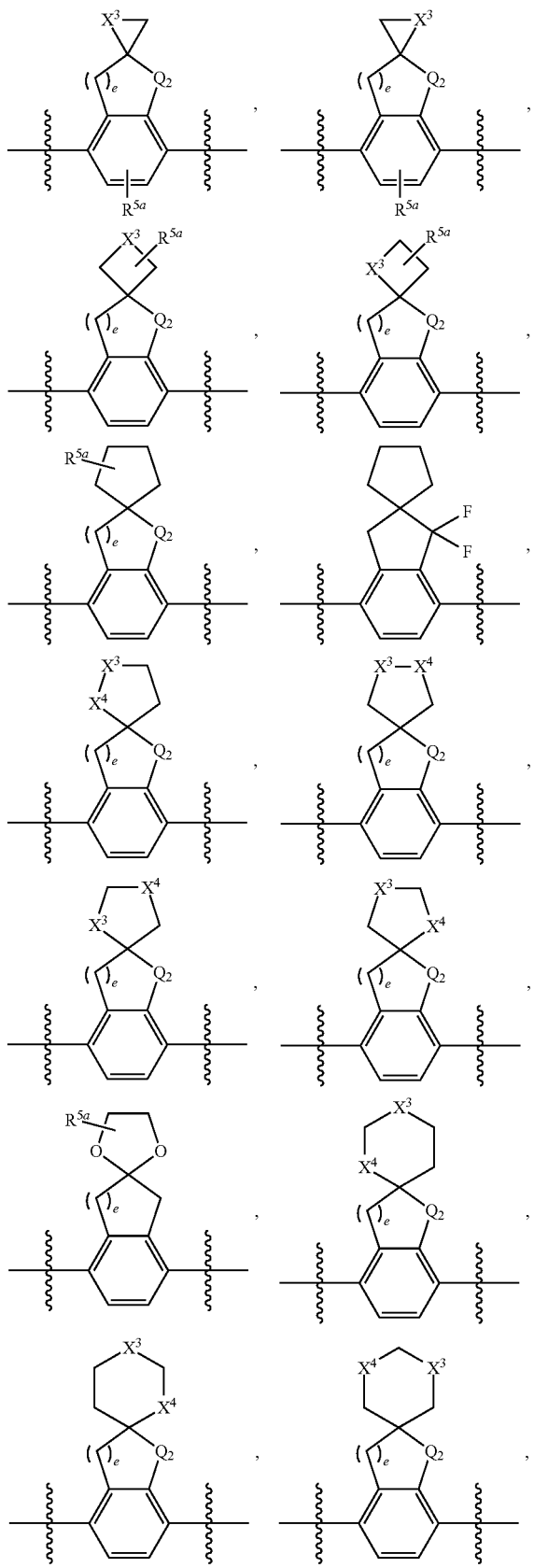
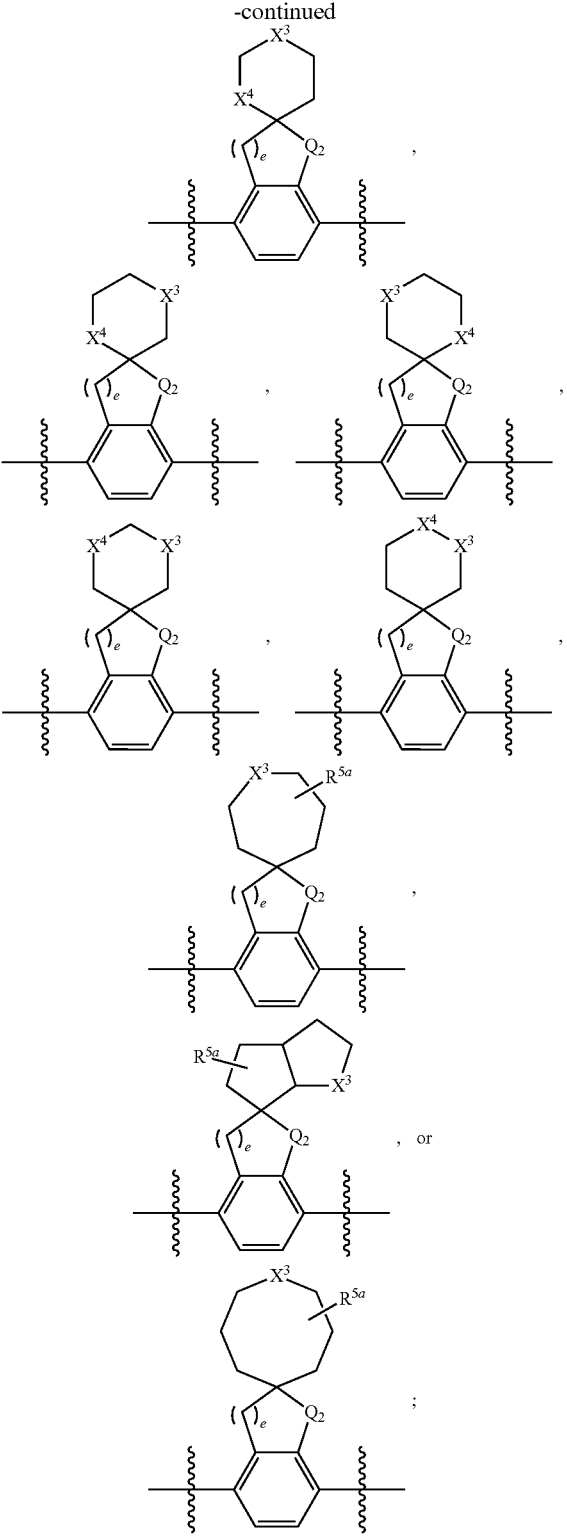
wherein each $Q_2$ is independently O, S, C(=O) or $CH_2$;
each $X^3$ and $X^4$ is independently O, S, $NR^6$, or $CR^7R^{7a}$;
each e is independently 1, 2, 3 or 4;
f is 0, 1, 2, 3 or 4;
each of A and A' is independently one of the following groups:

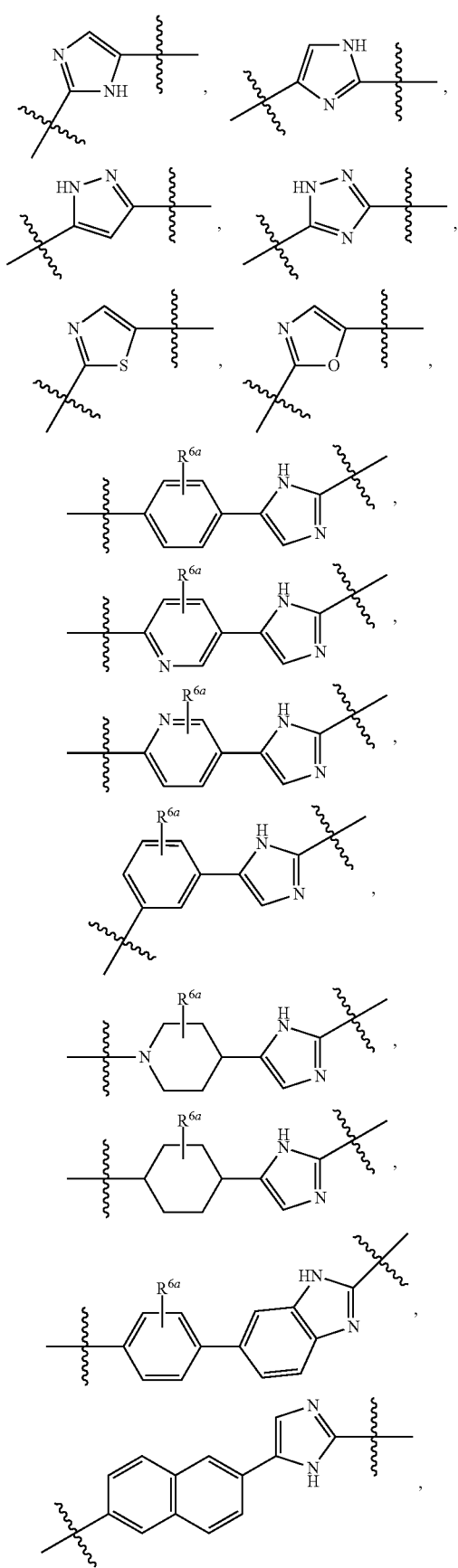
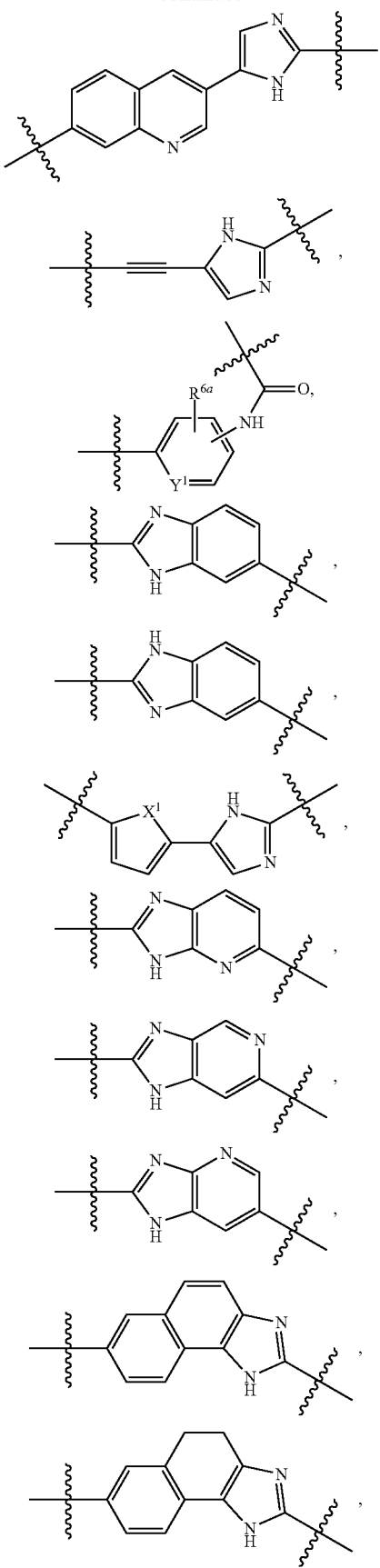
-continued

-continued

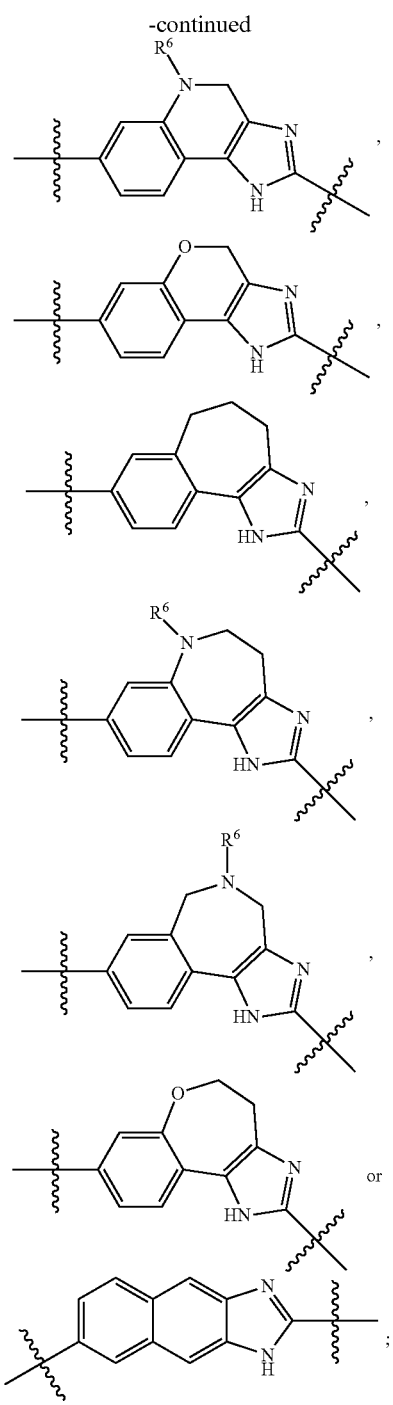

each $R^5$ is independently H, hydroxy, $C_{1-6}$ alkyl, $C_{1-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, alkyl-S(=O)$_r$— or aminosulfonyl;

each $R^{5a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^6$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{6a}$ is independently H, oxo (=O), hydroxy, amino, F, Cl, Br, I, cyano, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^7$ and $R^{7a}$ is independently H, $C_{1-6}$ aliphatic, $C_{1-6}$ heteroalkyl, $C_{1-6}$ alkoxy-$C_{1-6}$-aliphatic, $C_{1-6}$ alkylamine-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom, form a substituted or unsubstituted 3-8 membered ring;

each of $Y_4$ and $Y_4'$ is independently a bond, O, S, —(CH$_2$)$_n$—, —CH=CH—, —S(=O)$_r$—, —CH$_2$O—, —CH$_2$S—, —CH$_2$S(=O)$_r$—, or —CH$_2$N(R$^6$)—;

each n is independently 0, 1, 2 or 3; and each r is independently 0, 1 or 2.

12. The compound according to claim 11 having the structure of formula (IV):

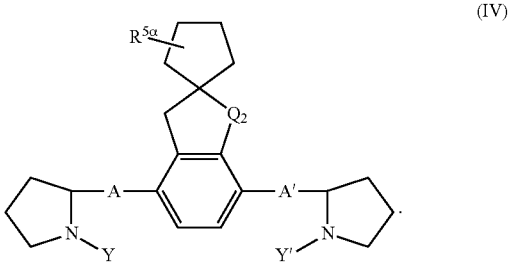

(IV)

13. The compound according to claim 11 having the structure of formula (V):

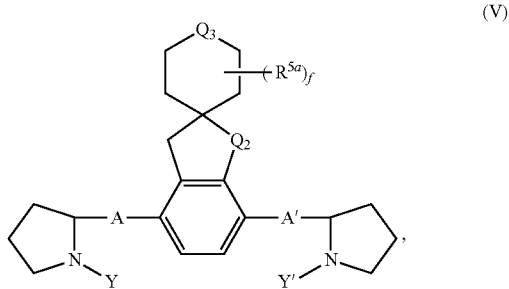

(V)

wherein each of Q$_2$ and Q$_3$ is independently O, S, C(=O), NR$^6$, or CH$_2$.

14. The compound according to claim 11 having formula (VI):

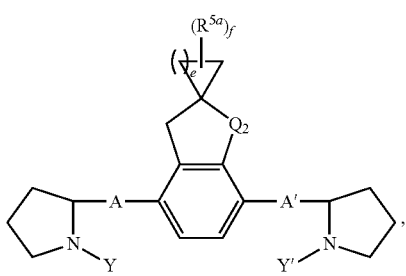

wherein e is 1, 2, 3 or 4.

15. The compound according to claim 1, wherein each of Y and Y' is independently a group derived from an α-amino acid.

16. The compound according to claim 15, wherein the α-amino acid is isoleucine, leucine, lysine, methionine, phenylalanine, threonine, tryptophane, valine, alanine, asparagine, aspartic acid, glutamic acid, glutamine, proline, serine, p-tyrosine, arginine, histidine, cysteine, glycine, sarcosine, N,N-dimethylglycine, homoserine, norvaline, norleucine, ornithine, homocysteine, homophenylalanine, phenylglycine, o-tyrosine, m-tyrosine or hydroxyproline.

17. The compound according to claim 16, wherein the α-amino acid is in the D configuration.

18. The compound according to claim 1, wherein each of Y and Y' is independently —[U—(CR$^9$R$^{9a}$)$_t$—N(R$^{10}$)—(CR$^9$R$^{9a}$)$_t$]$_k$—U—(CR$^9$R$^{9a}$)$_t$—N(R$^{11}$)—(CR$^9$R$^{9a}$)$_t$—R$^{12}$, —U—(R$^9$R$^{9a}$)$_t$—R$^{12}$ or —[U—(CR$^9$R$^{9a}$)$_t$—N(R$^{10}$)—(CR$^9$R$^{9a}$)$_t$]$_k$—U—(CR$^9$R$^{9a}$)$_t$—O—(CR$^9$R$^{9a}$)$_t$—R$^{12}$, —U—(CR$^9$R$^{9a}$)$_t$—N(R$^{10}$)—(CR$^9$R$^{9a}$)$_t$—U—(CR$^9$R$^{9a}$)$_t$—N(R$^{11}$)—(CR$^9$R$^{9a}$)$_t$—R$^{12}$, —U—(CR$^9$R$^{9a}$)$_t$—N(R$^{11}$)—(CR$^9$R$^{9a}$)$_t$—R$^{12}$, —[C(=O)—(CR$^9$R$^{9a}$)$_t$—N(R$^{10}$)—(CR$^9$R$^{9a}$)$_t$]$_k$—U—(CR$^9$R$^{9a}$)—N(R$^{11}$)—(CR$^9$R$^{9a}$)$_t$—R$^{12}$, —C(=O)—(CR$^9$R$^{9a}$)$_t$—N(R$^{10}$)—(CR$^9$R$^{9a}$)$_t$—U—(CR$^9$R$^{9a}$)$_t$—N(R$^{11}$)—(CR$^9$R$^{9a}$)$_t$—R$^{12}$, —[C(=O)—(CR$^9$R$^{9a}$)$_t$—N(R$^{10}$)—(CR$^9$R$^{9a}$)$_t$]$_k$—C(=O)—(CR$^9$R$^{9a}$)$_t$—N(R$^{11}$)—(CR$^9$R$^{9a}$)$_t$—R$^{12}$, —C(=O)—(CR$^9$R$^{9a}$)$_t$—N(R$^{10}$)—(CR$^9$R$^{9a}$)$_t$C(=O)—(CR$^9$R$^{9a}$)$_t$—N(R$^{11}$)—(CR$^9$R$^{9a}$)$_t$—R$^{12}$, —C(=O)—(CR$^9$R$^{9a}$)$_t$—N(R$^{10}$)—(CR$^9$R$^{9a}$)$_t$—C(=O)—(CR$^9$R$^{9a}$)$_t$—N(R$^{11}$)—(CR$^9$R$^{9a}$)$_t$—R$^{12}$, —C(=O)—(CR$^9$R$^{9a}$)$_t$—N(R$^{11}$)—(CR$^9$R$^{9a}$)$_t$—R$^{12}$, —C(=O)—(CR$^9$R$^{9a}$)$_n$—N(R$^{11}$)—(CR$^9$R$^{9a}$)$_n$—C(=O)—R$^{13}$, —C(=O)—(CR$^9$R$^{9a}$)$_n$—N(R$^{11}$)—C(=O)—R$^{13}$, —C(=O)—(CR$^9$R$^{9a}$)$_n$—N(R$^{11}$)—(CR$^9$R$^{9a}$)$_n$—C(=O)—O—R$^{13}$, —C(=O)—(CR$^9$R$^{9a}$)$_n$—N(R$^{11}$)—C(=O)—O—R$^{13}$, —C(=O)—(R$^9$R$^{9a}$)$_t$—R$^{12}$, —U—(CR$^9$R$^{9a}$)$_t$—N(R$^{10}$)—(CR$^9$R$^{9a}$)$_t$—U—(CR$^9$R$^{9a}$)$_t$—O—(CR$^9$R$^{9a}$)$_t$—R$^{12}$, —C(=O)—(CR$^9$R$^{9a}$)$_t$—N(R$^{10}$)—(CR$^9$R$^{9a}$)$_t$—C(=O)—(CR$^9$R$^{9a}$)$_t$—O—(CR$^9$R$^{9a}$)$_t$—R$^{12}$, —U—(CR$^9$R$^{9a}$)$_t$—O—(CR$^9$R$^{9a}$)$_t$—R$^{12}$, or —C(=O)—(CR$^9$R$^{9a}$)$_t$—O—(CR$^9$R$^{9a}$)$_t$—R$^{12}$, or —C(=O)—(CR$^9$R$^{9a}$)$_n$—NR$^{11}$—R$^{12}$, wherein R$^{11}$ and R$^{12}$, together with the nitrogen atom they are attached to, form a 4-7 membered ring.

19. The compound according to claim 18, wherein each R$^9$, R$^{9a}$, R$^{10}$ and R$^{11}$ is independently H, C$_{1-6}$ alkyl, C$_{1-6}$ heteroalkyl, C$_{3-10}$ cycloalkyl, C$_{2-10}$ heterocyclyl, C$_{6-10}$ aryl, C$_{1-9}$ heteroaryl, C$_{6-10}$ aryl-C$_{1-6}$-alkyl, C$_{1-6}$ haloalkyl, C$_{1-6}$ hydroxyalkyl, C$_{1-9}$ heteroaryl-C$_{1-6}$-alkyl, C$_{2-10}$ heterocyclyl-C$_{1-6}$-alkyl, or C$_{3-8}$ cycloalkyl-C$_{1-6}$-alkyl;

each R$^{12}$ is independently R$^{13a}$R$^{13}$N—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13}$OS(=O)$_2$—, C$_{1-6}$ alkyl, C$_{1-6}$ heteroalkyl, C$_{3-10}$ cycloalkyl, C$_{2-10}$ heterocyclyl, C$_{6-10}$ aryl, C$_{1-9}$ heteroaryl, or C$_{6-10}$ aryl-C$_{1-6}$-alkyl;

or R$^{11}$ and R$^{12}$, together with the nitrogen atom they are attached to, form a 4-7 membered ring; and each R$^{13}$ and R$^{13a}$ is independently H, C$_{1-6}$ alkyl, C$_{1-6}$ heteroalkyl, C$_{3-10}$ cycloalkyl, C$_{2-10}$ heterocyclyl, C$_{6-10}$ aryl, C$_{1-9}$ heteroaryl, or C$_{6-10}$ aryl-C$_{1-6}$-alkyl.

20. The compound according to claim 19, wherein each R$^9$, R$^{9a}$, R$^{10}$ and R$^{11}$ is independently H, methyl, ethyl, isopropyl, cyclohexyl, isobutyl or phenyl;

each R$^{12}$ is independently —C(=O)R$^{13}$, —C(=O)—O—R$^{13}$, —C(=O)NR$^{13}$R$^{13a}$, methyl, ethyl, propyl, phenyl, cyclohexyl, morpholinyl or piperidinyl;

or R$^{11}$ and R$^{12}$, together with the nitrogen atom they are attached to, form a 4-7 membered ring; and each R$^{13}$ and R$^{13a}$ is independently H, methyl, ethyl, propyl, phenyl, cyclohexyl, morpholinyl or piperidinyl.

21. The compound according to claim 10 having the structure of formula (VII):

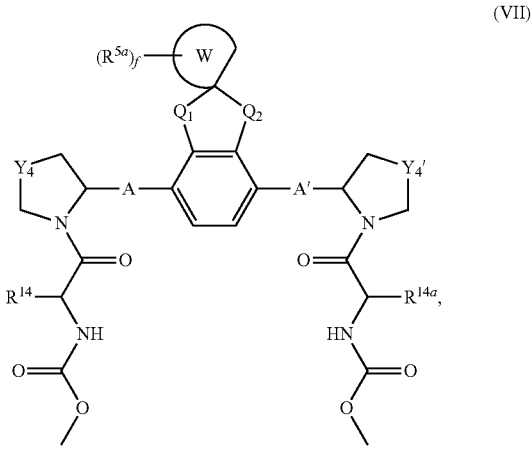

wherein each of R$^{14}$ and R$^{14a}$ is independently H, C$_{1-6}$ alkyl, C$_{1-6}$ haloalkyl, C$_{1-6}$ hydroxyalkyl, C$_{1-6}$ heteroalkyl, C$_{6-10}$ aryl, C$_{1-9}$ heteroaryl, C$_{2-10}$ heterocyclyl, C$_{3-8}$ cycloalkyl, C$_{6-10}$ aryl-C$_{1-6}$-alkyl, C$_{1-9}$ heteroaryl-C$_{1-6}$-alkyl, C$_{2-10}$ heterocyclyl-C$_{1-6}$-alkyl, or C$_{3-8}$ cycloalkyl-C$_{1-6}$-alkyl.

22. The compound according to claim 21 having the structure of formula (VIII):

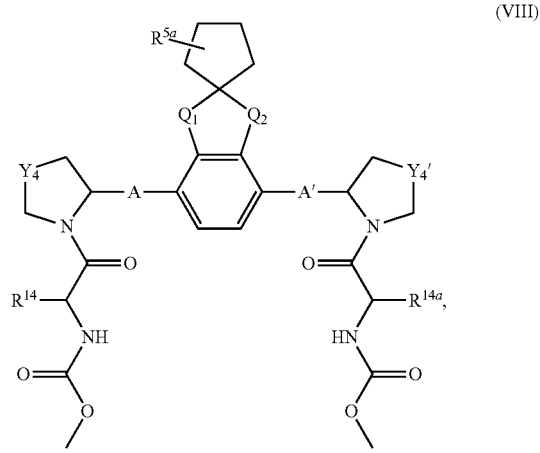

wherein each of $R^{14}$ and $R^{14a}$ is independently H, $C_{1-3}$ hydroxyalkyl, methyl, ethyl, isopropyl, isobutyl, tert-butyl, allyl, propargyl, trifluoroethyl, phenyl, pyranyl, morpholinyl, $-NR^7R^{7a}$, benzyl, piperazinyl, cyclopentyl, cyclopropyl, cyclohexyl, or $C_{1-9}$ heteroaryl.

23. The compound according to claim 1 having the structure of formula (IX):

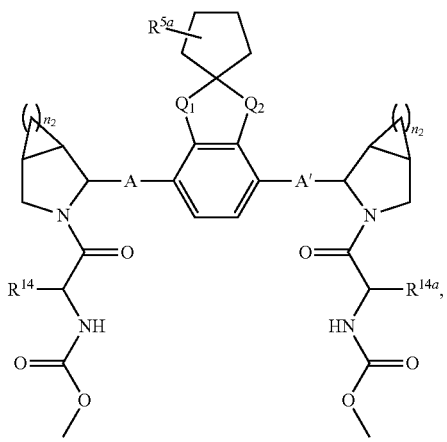

(IX)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_2$ is independently 1, 2, 3 or 4.

24. The compound according to claim 1 having the structure of formula (X):

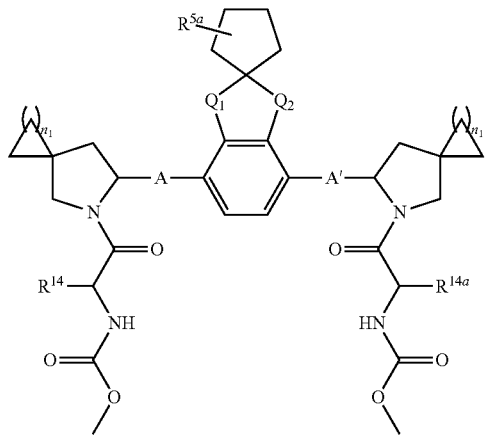

(X)

wherein each of $R^{14}$ and $R^{14a}$ is independently H, $C_{1-6}$ alkyl, $C_{1-6}$ haloalkyl, $C_{1-6}$ hydroxyalkyl, $C_{1-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; and each $n_1$ is independently 1, 2, 3 or 4.

25. The compound according to claim 1 having formula (XI):

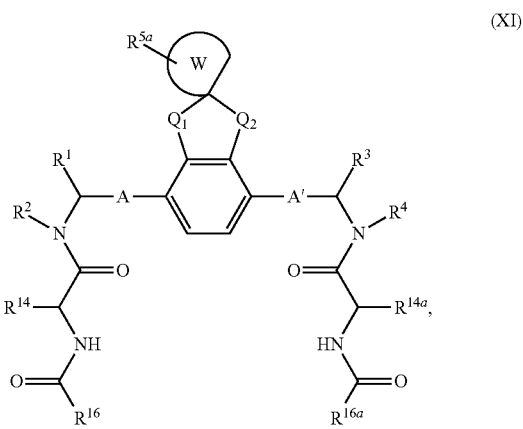

(XI)

wherein $R^{5a}$ is H, methyl, ethyl, F, Cl, Br or I;

$Q_1$ is $CH_2$, $C(=O)$, O, S, or NH;

$Q_2$ is $CH_2$, $C(=O)$, $CF_2$, O, or S;

each of $R^{14}$ and $R^{14a}$ is independently methyl, ethyl, phenyl, cyclohexyl, 1-methylpropyl, isopropyl or tert-butyl;

each of $R^{16}$ and $R^{16a}$ is independently hydroxy, methoxy, ethoxy, phenoxy,

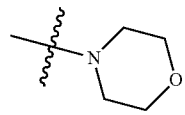 [SMILES: *N1CCOCC1]

or tert-butoxy;

wherein the structural unit of

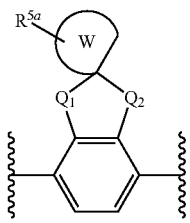

has one of the following structures:

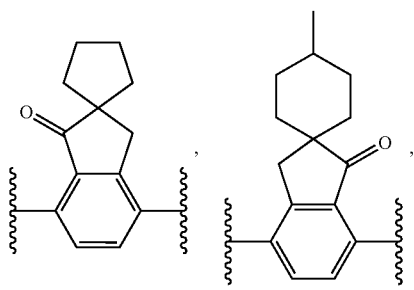

463
-continued
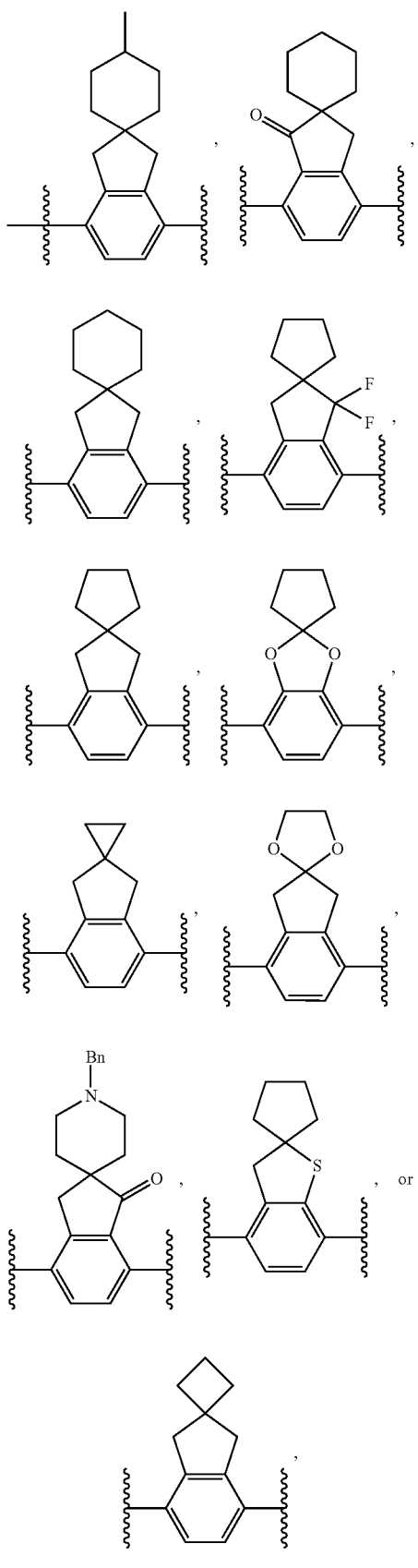
wherein Bn is benzyl; and
464
each of A and A' is independently
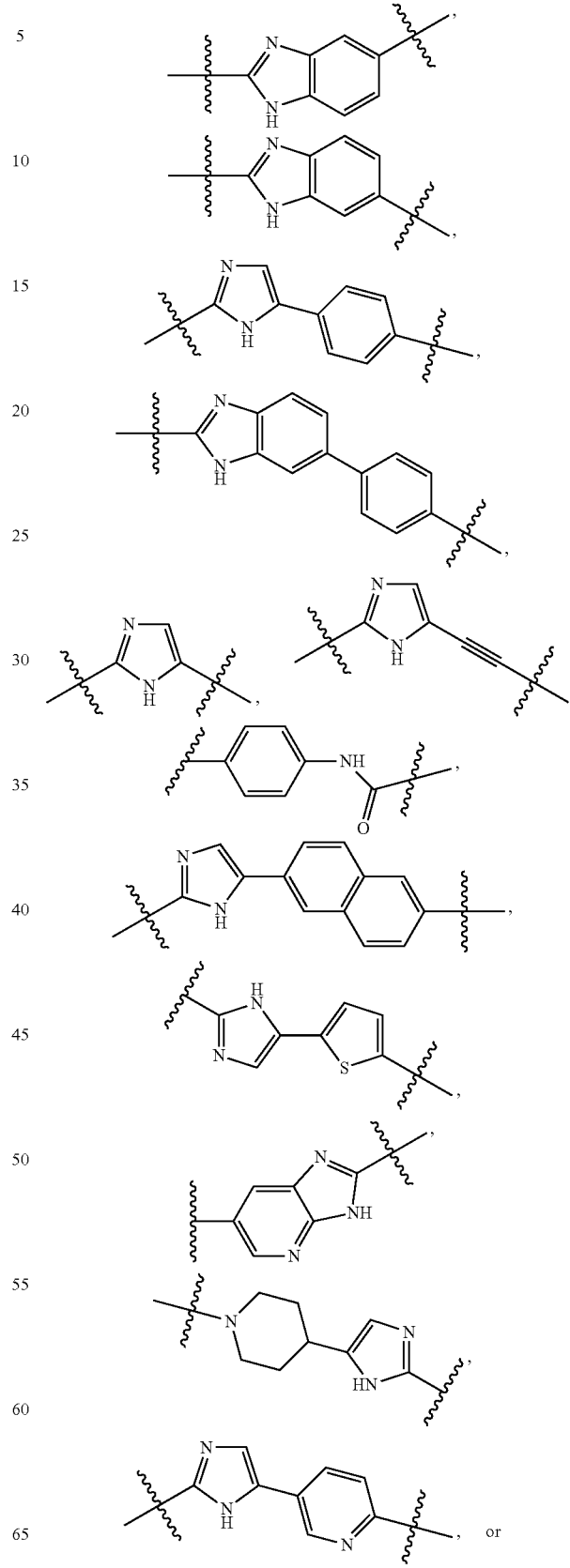

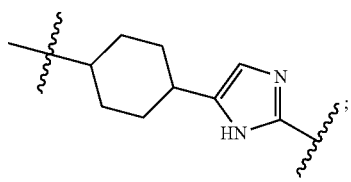

wherein R¹, R² and N—CH together form one of the following divalent groups:

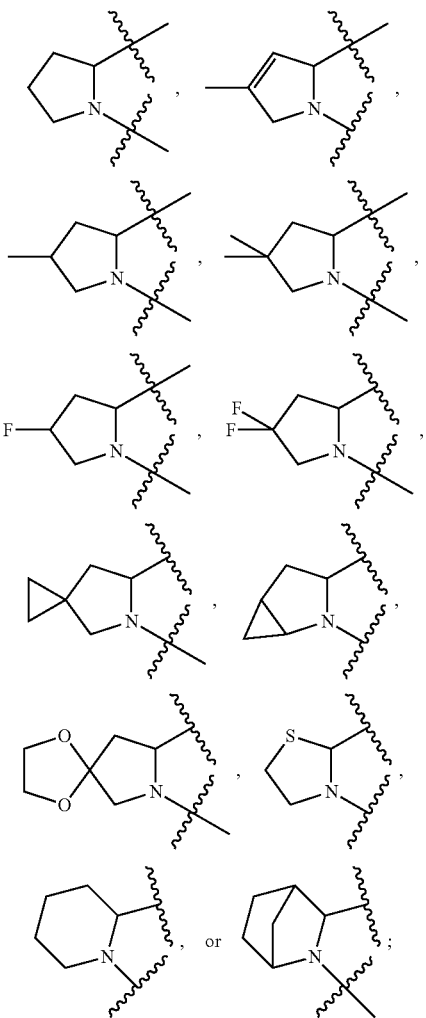

and wherein R³, R⁴ and N—CH together form one of the following divalent groups:

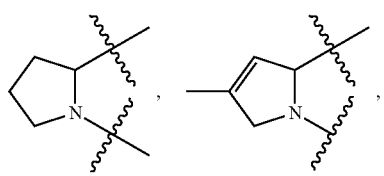

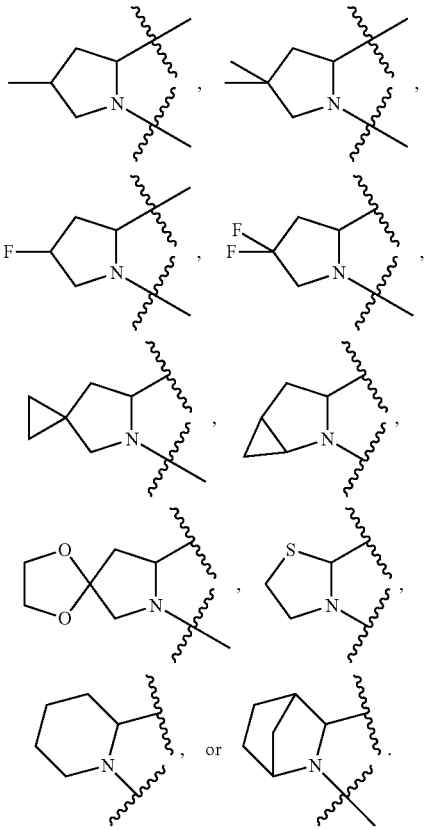

26. The compound according to claim 25 having formula (XII):

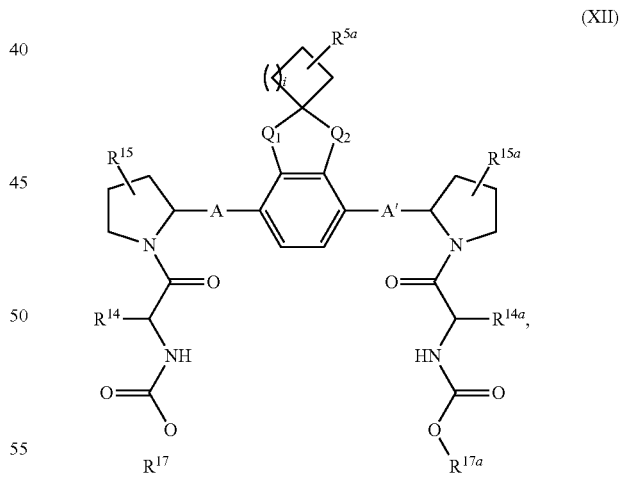

(XII)

wherein i is 1, 2, or 3;
$R^{5a}$ is H or methyl;
each of $Q_1$ and $Q_2$ is independently $CH_2$, $CF_2$, O or C(=O);
each of $R^{14}$ and $R^{14a}$ is independently methyl, ethyl, isobutyl, cyclohexyl, phenyl or isopropyl;
each of $R^{15}$ and $R^{15a}$ is independently H, F, Cl, Br, methyl, ethyl, isopropyl or tert-butyl;
each of $R^{17}$ and $R^{17a}$ is independently methyl, phenyl or ethyl; and each of A and A' is independently
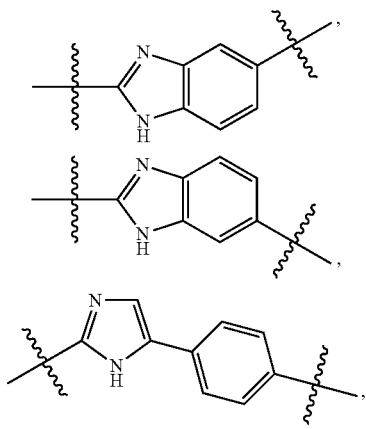
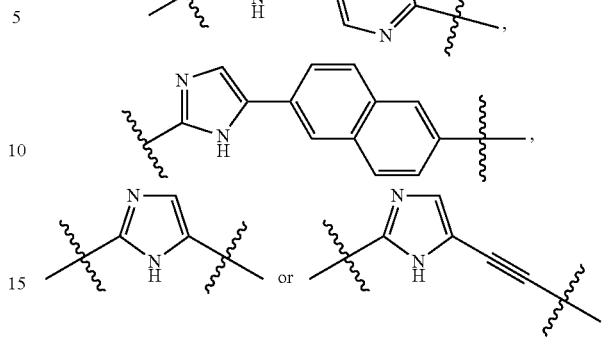
27. The compound of claim 1 having one of the following structures:
(1)
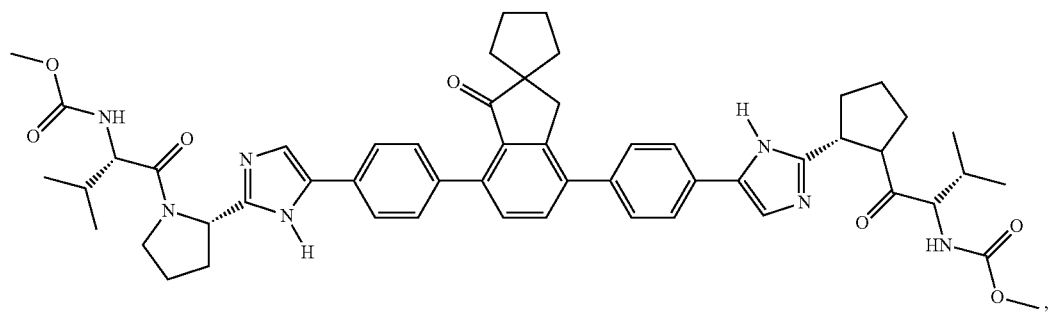
(2)
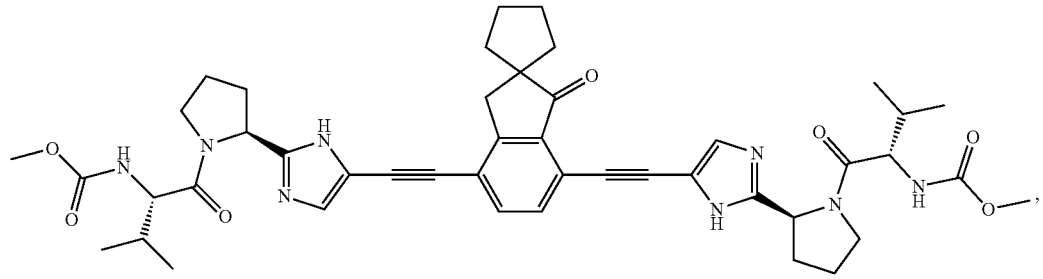
(3)
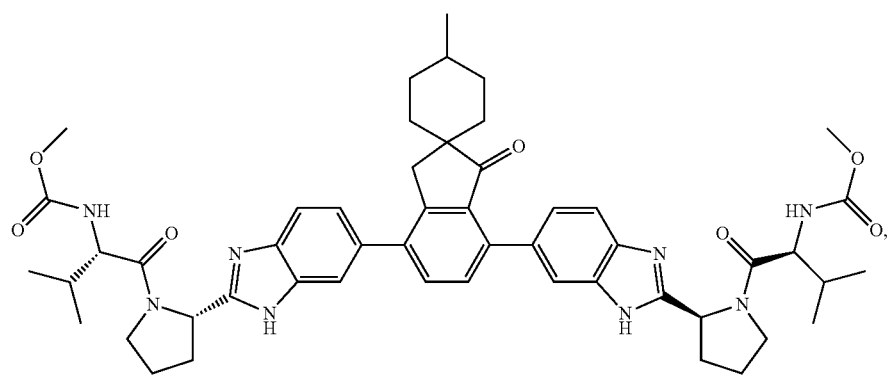

-continued
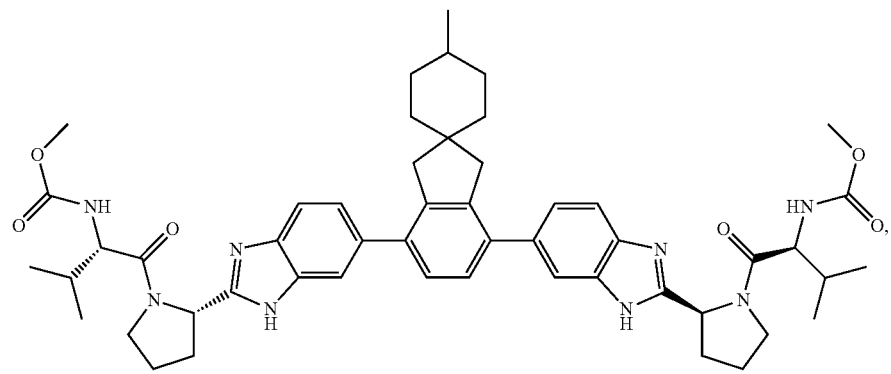
(4)
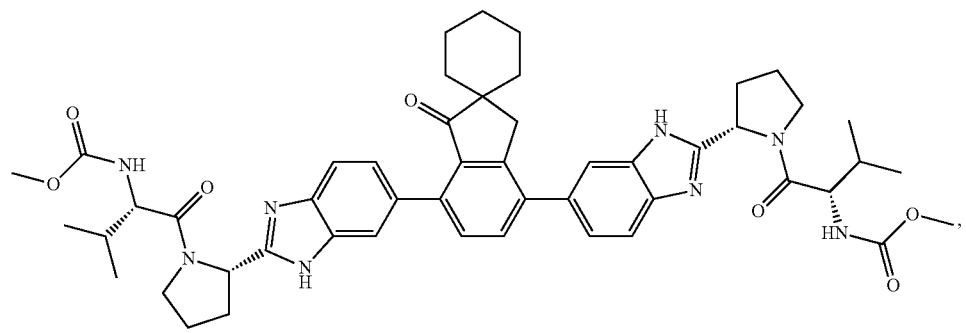
(5)
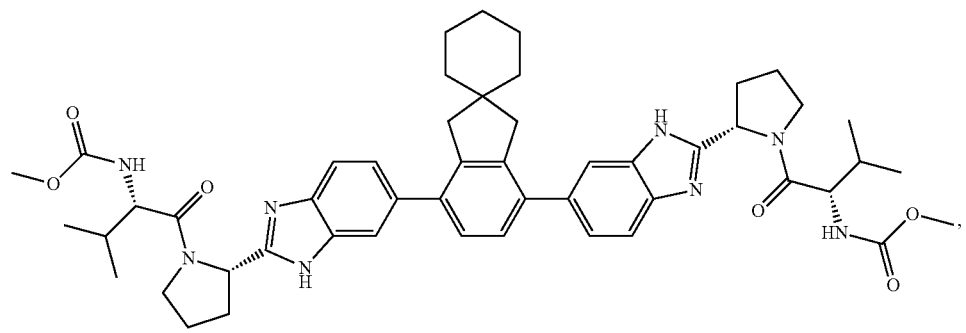
(6)
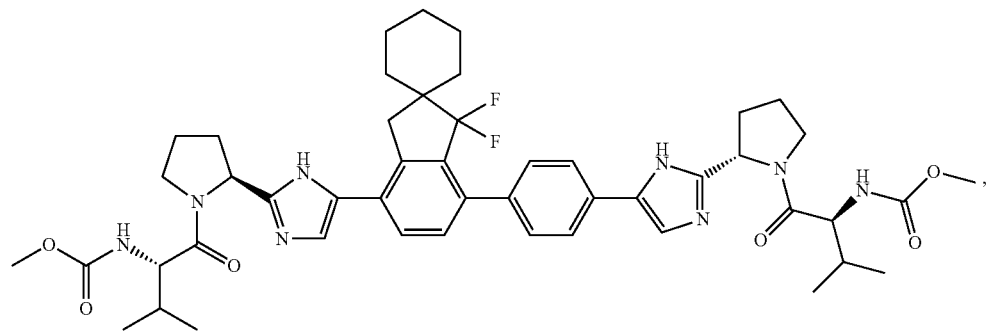
(7)

-continued
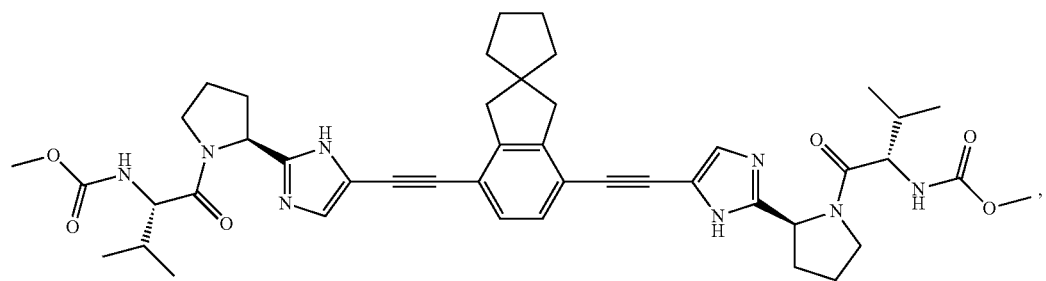
(8)
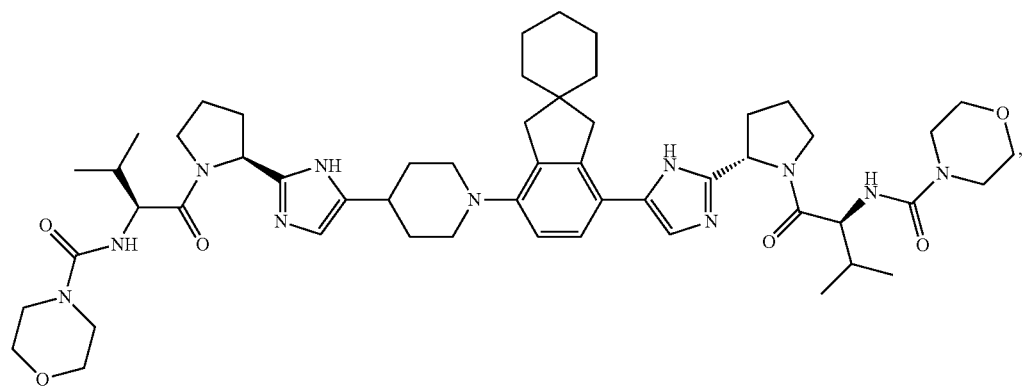
(9)
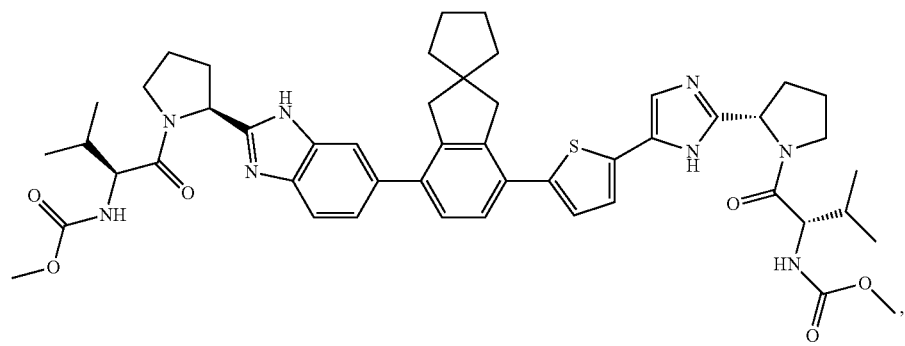
(10)
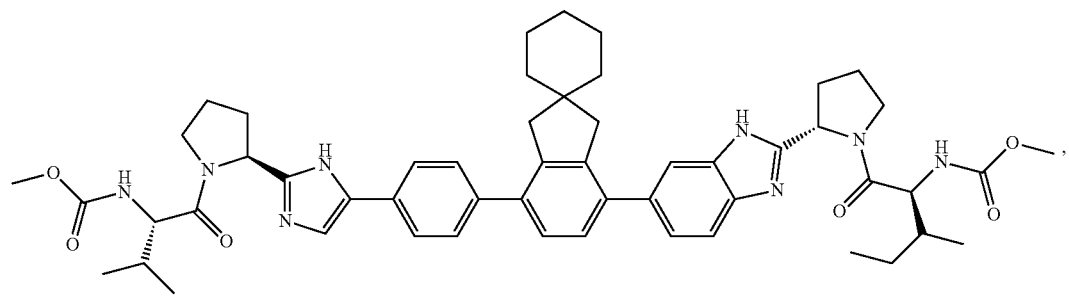
(11)

-continued
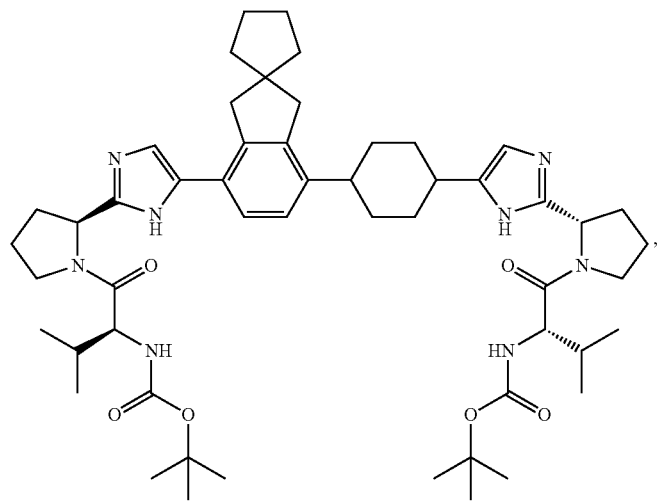
(12)
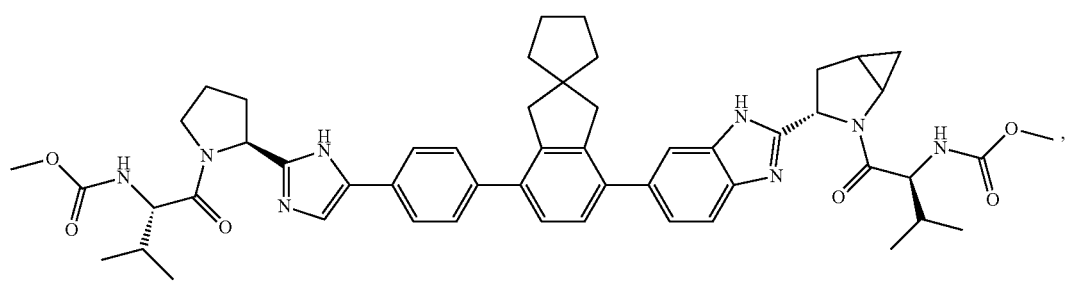
(13)
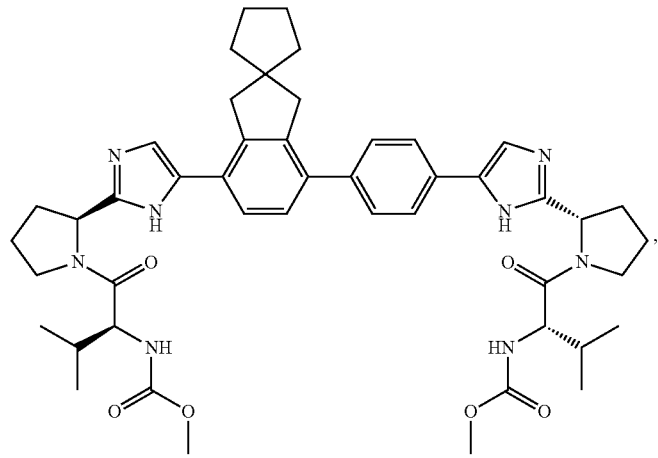
(14)
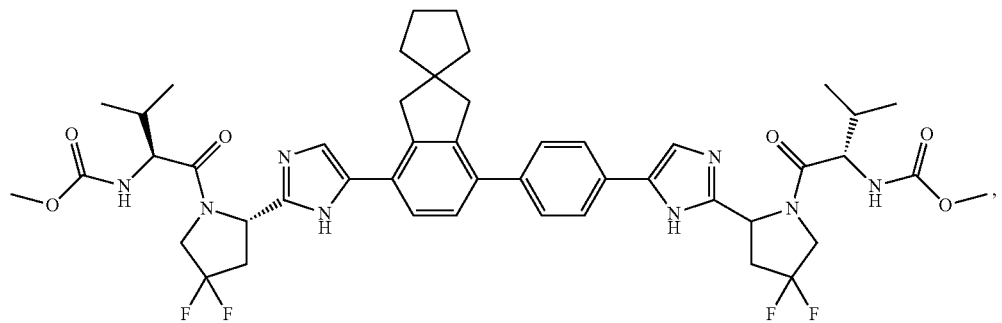
(15)

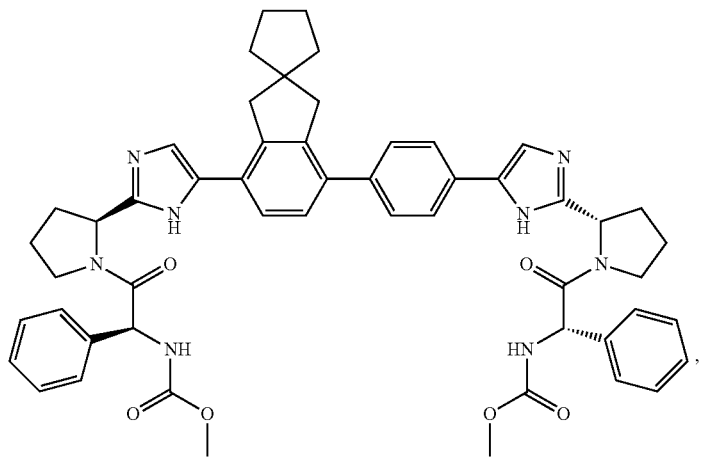
(16)
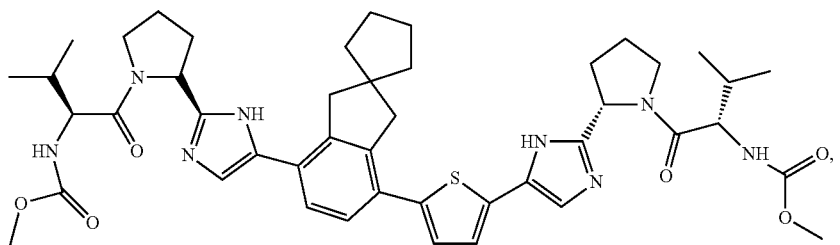
(17)
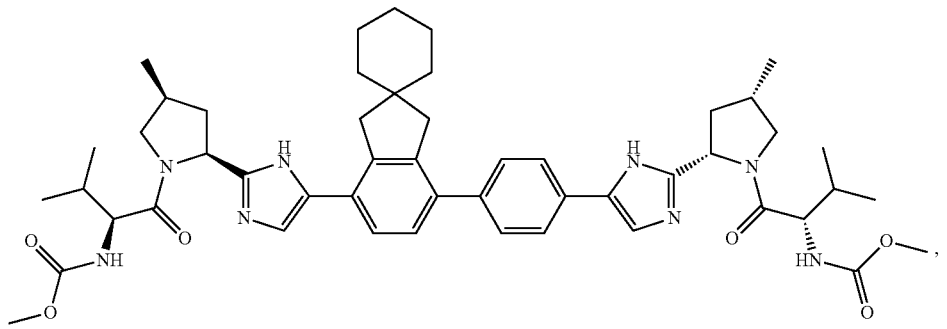
(18)
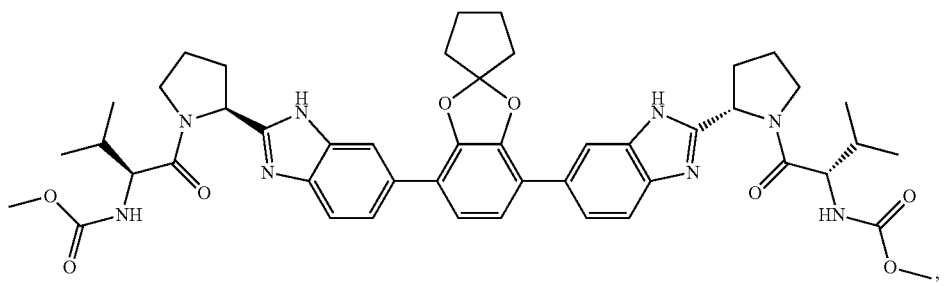
(19)

(20)
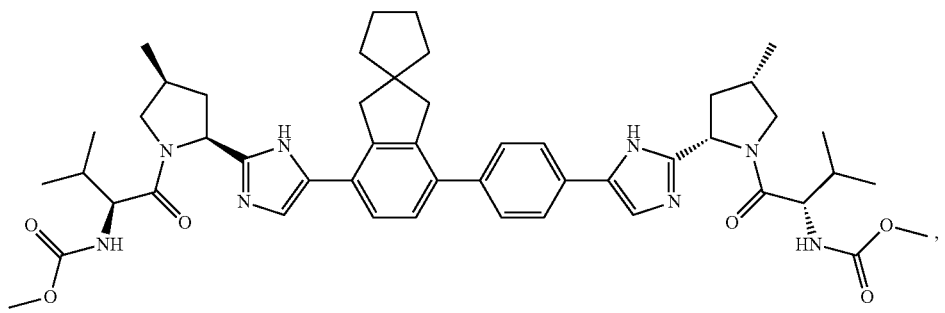
(21)
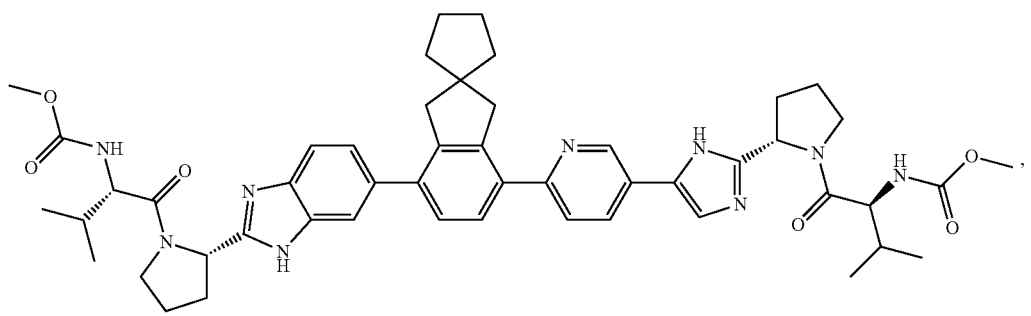
(22)
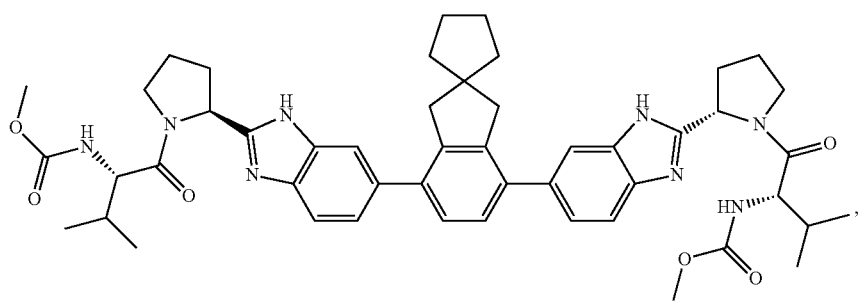
(23)
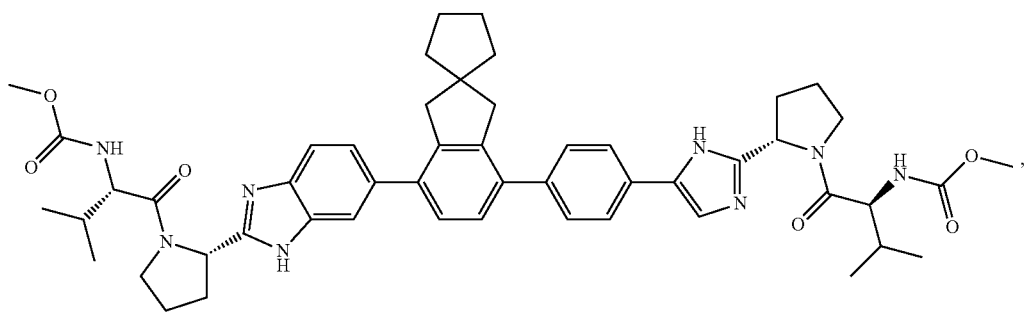

(24)
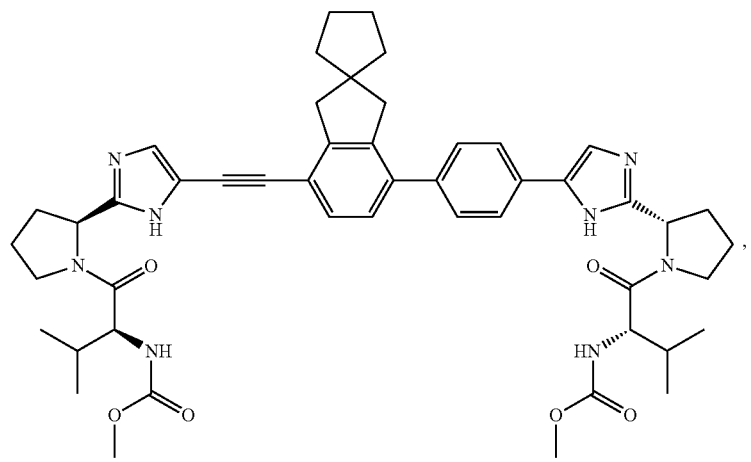
(25)
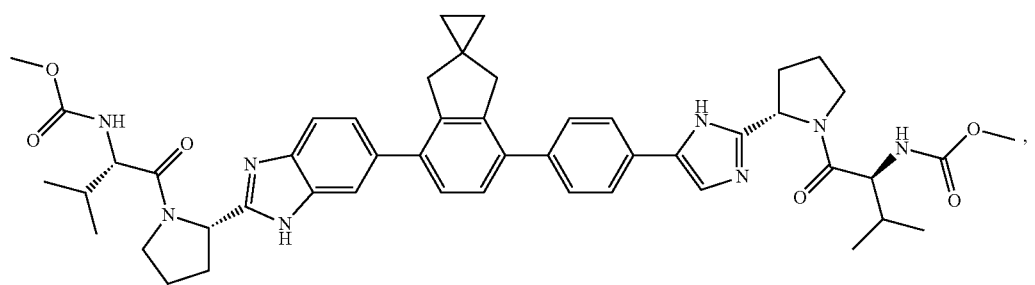
(26)
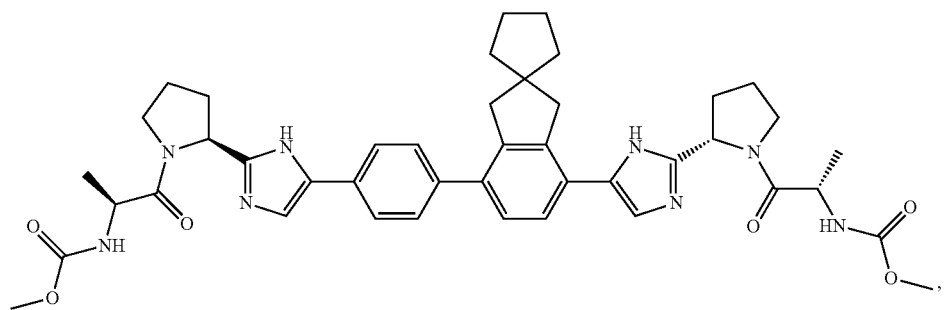
(27)
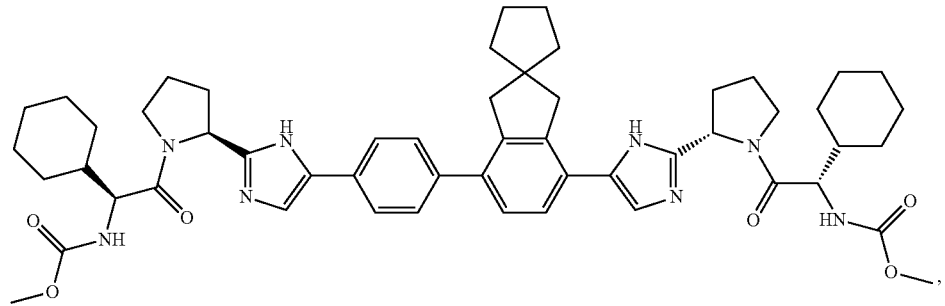

(28)
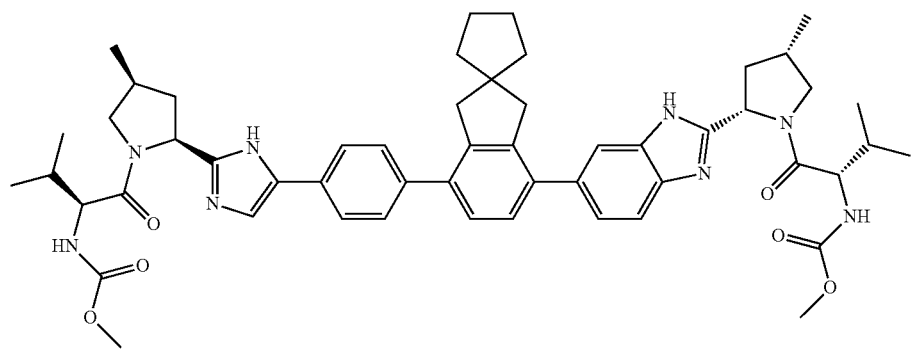
(29)
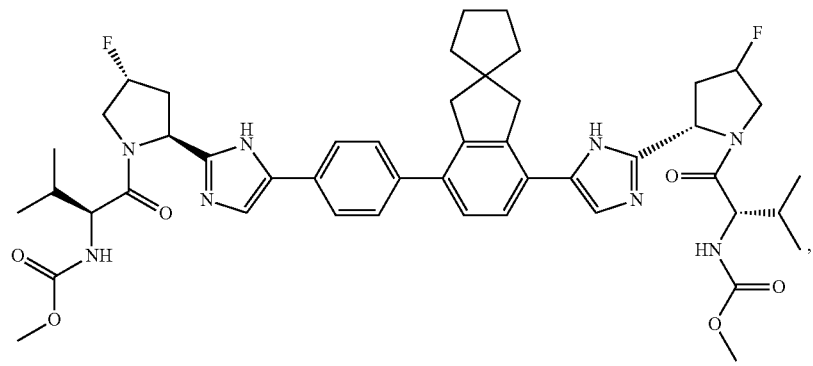
(30)
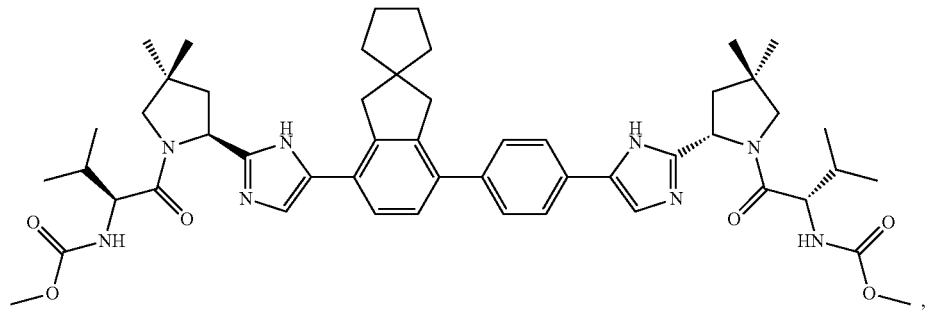
(31)
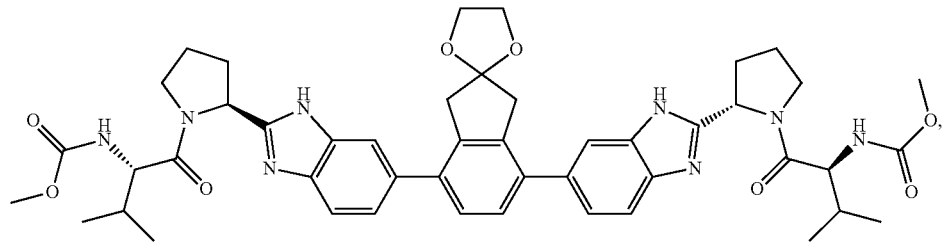
(32)
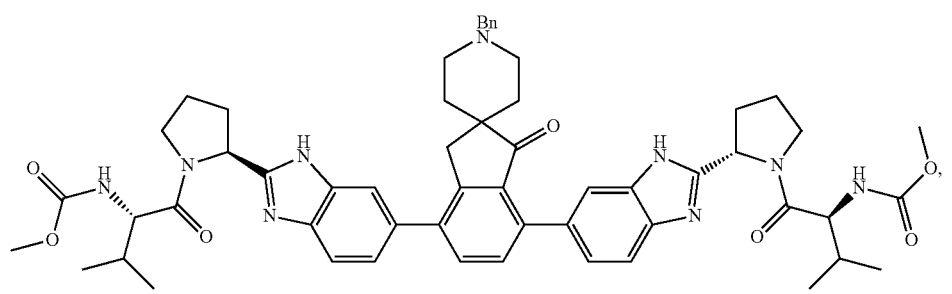

(33)
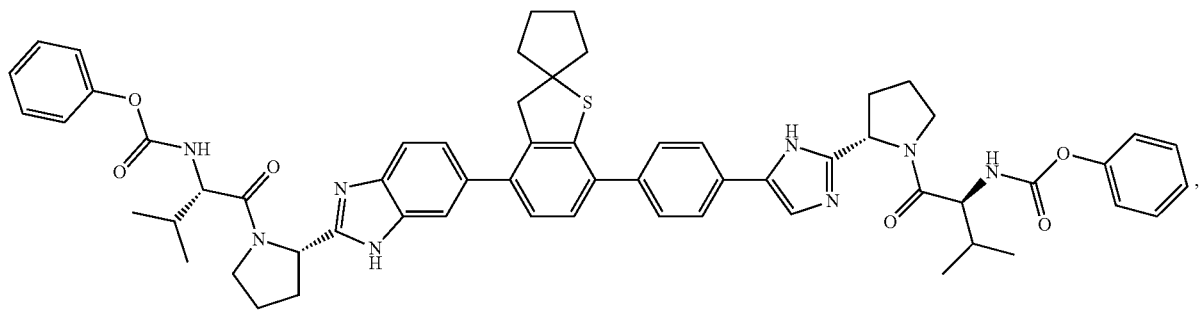
(34)
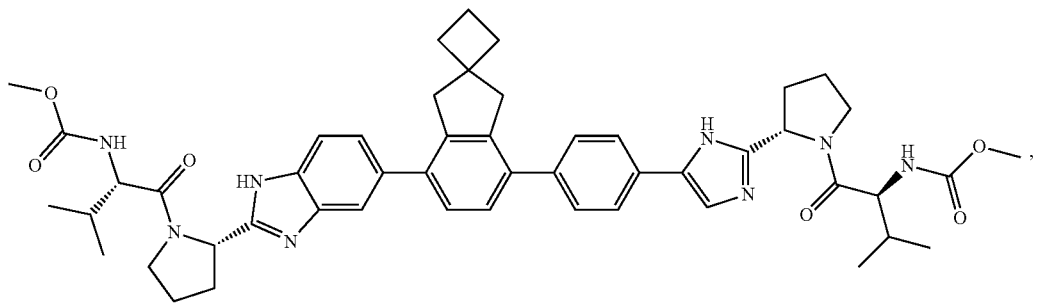
(35)
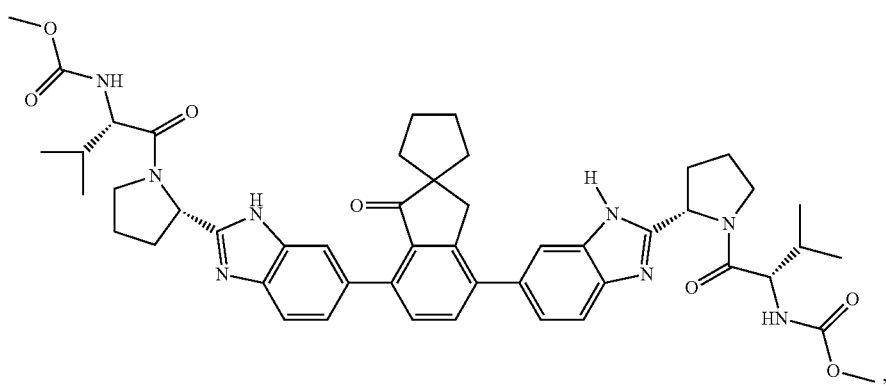
(36)
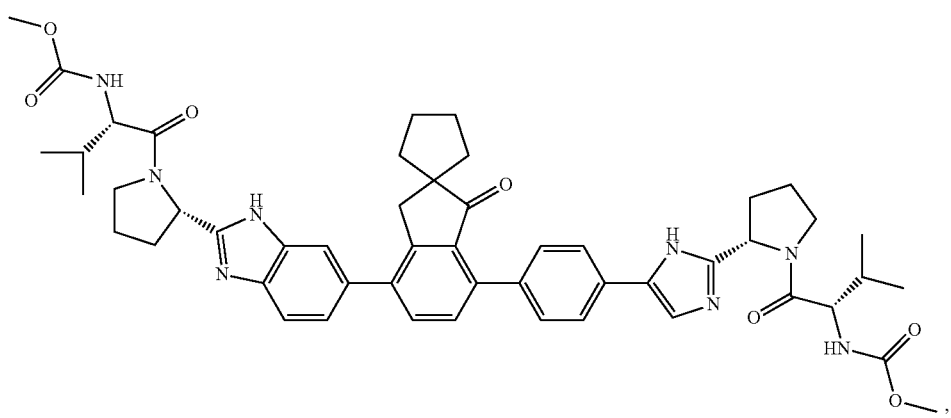

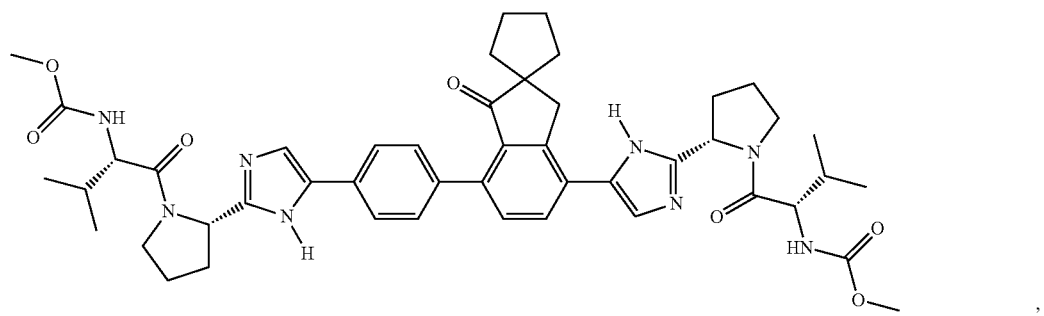
(37)
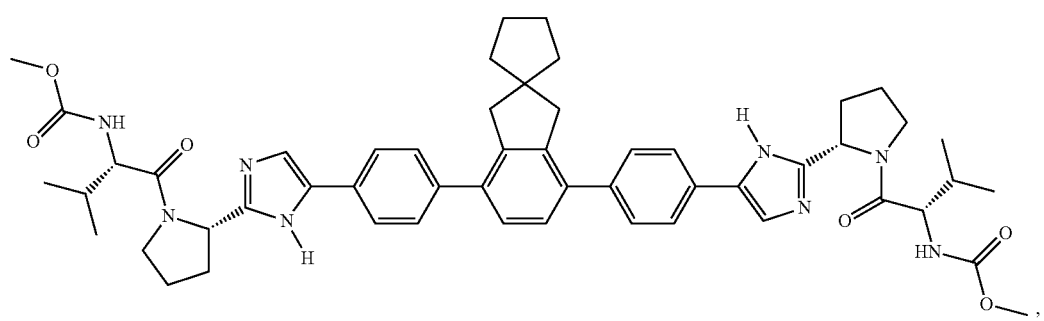
(38)
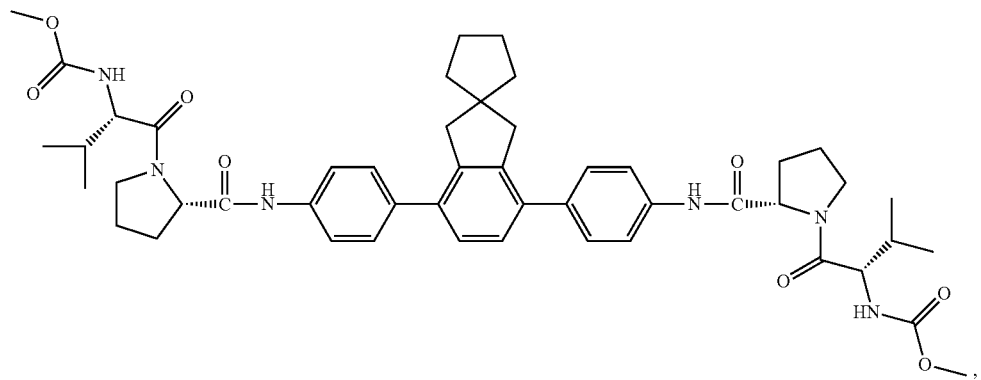
(39)
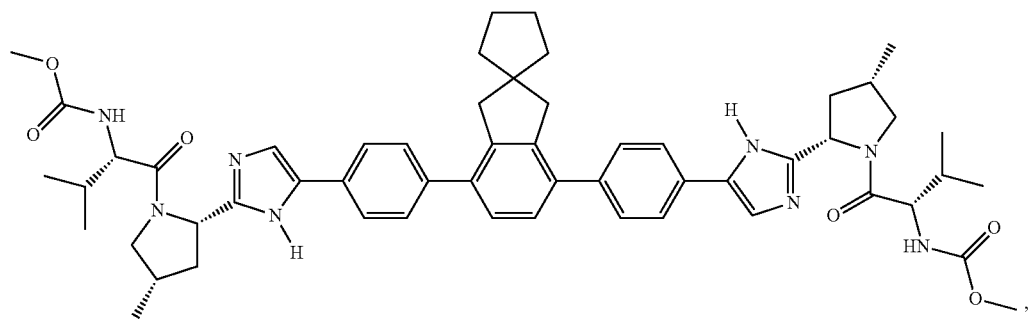
(40)

-continued
(41)
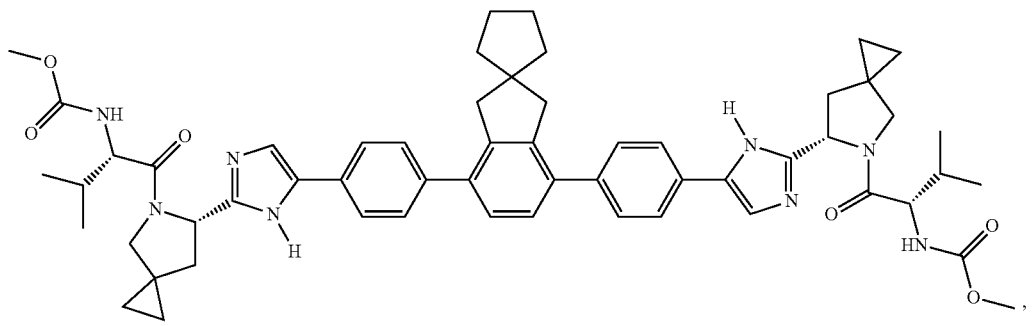
(42)
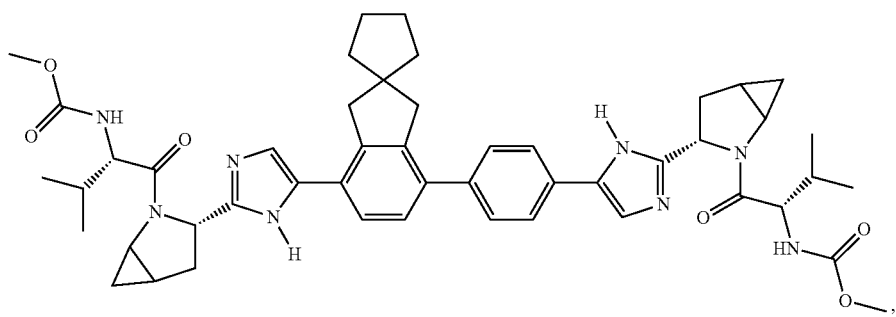
(43)
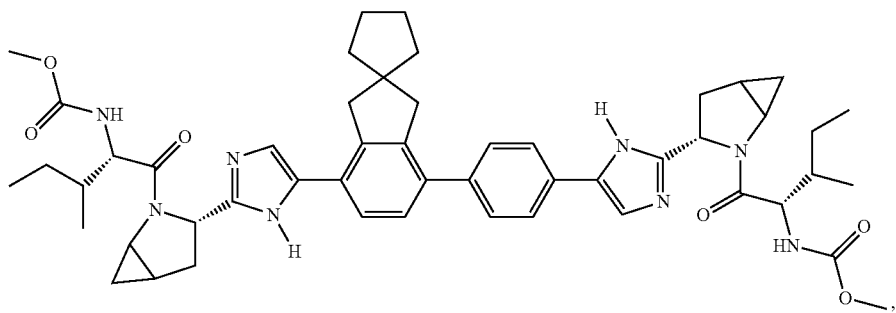
(44)
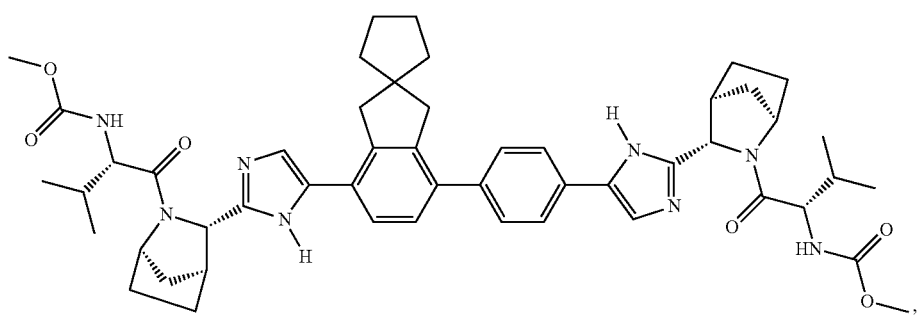
(45)
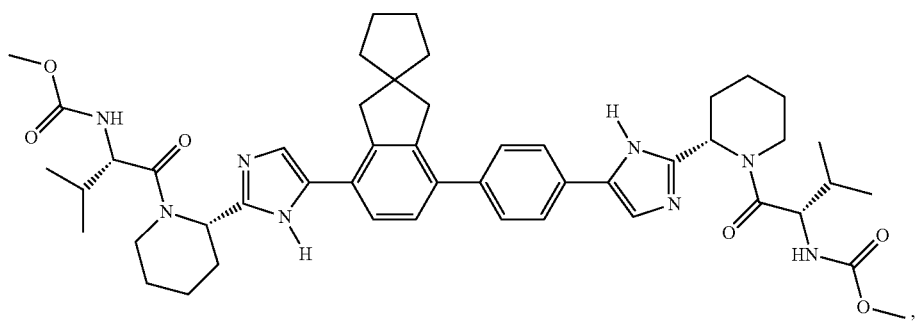

(46)
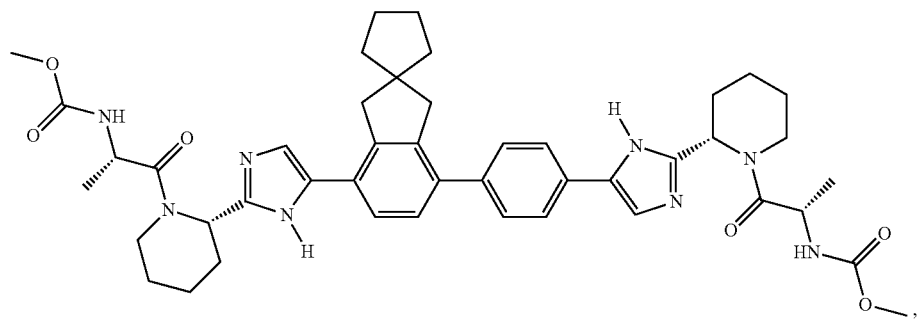
(47)
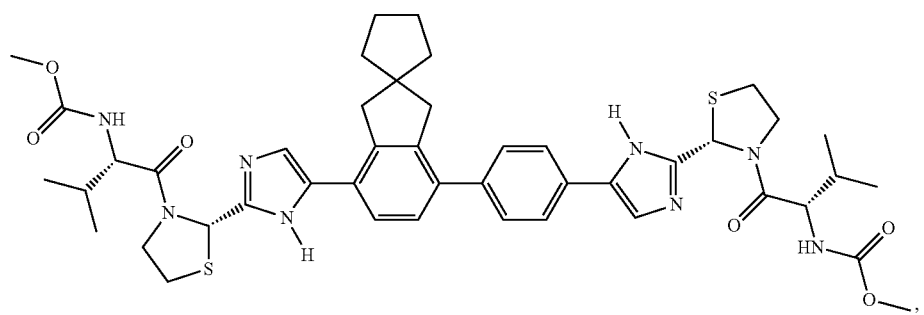
(48)
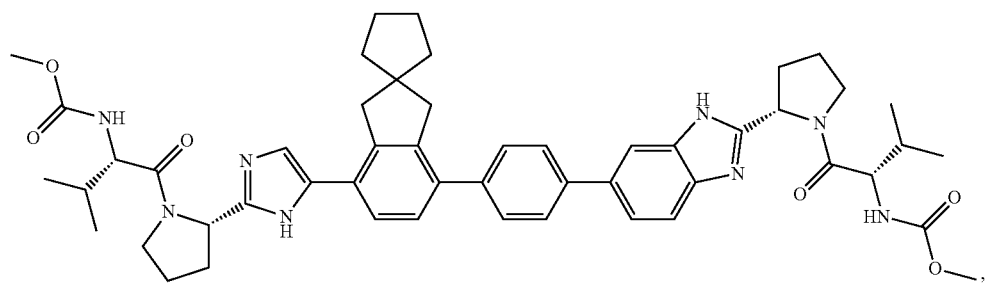
(49)
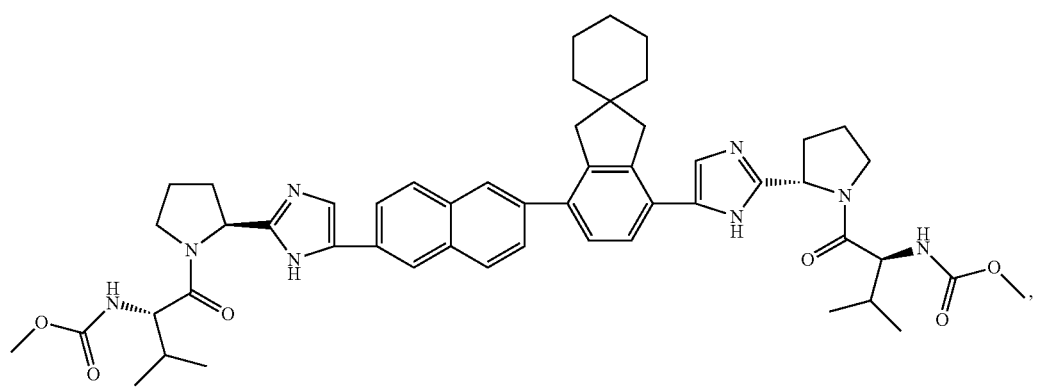
(50)
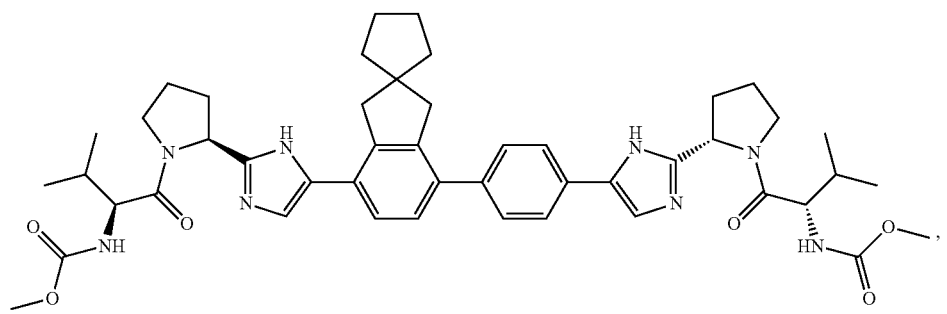

(51)
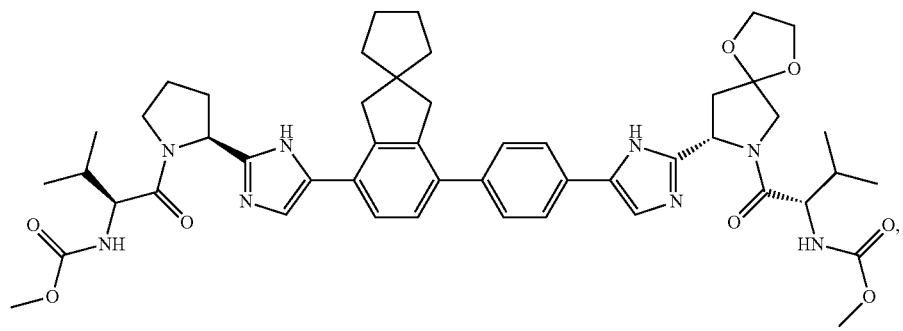
(52)
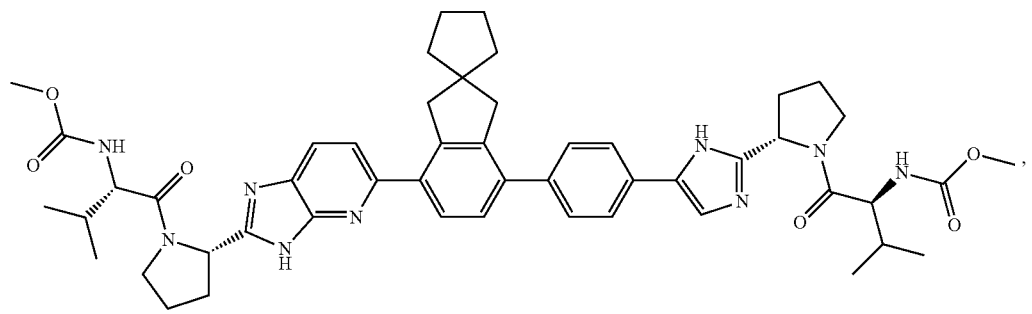
(53)
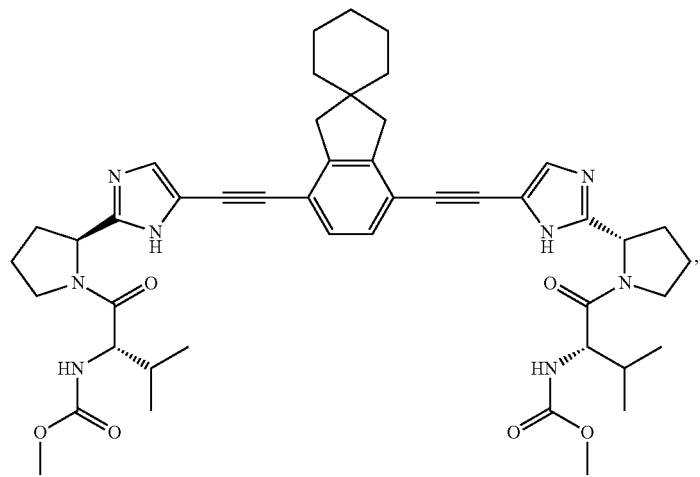
(54)
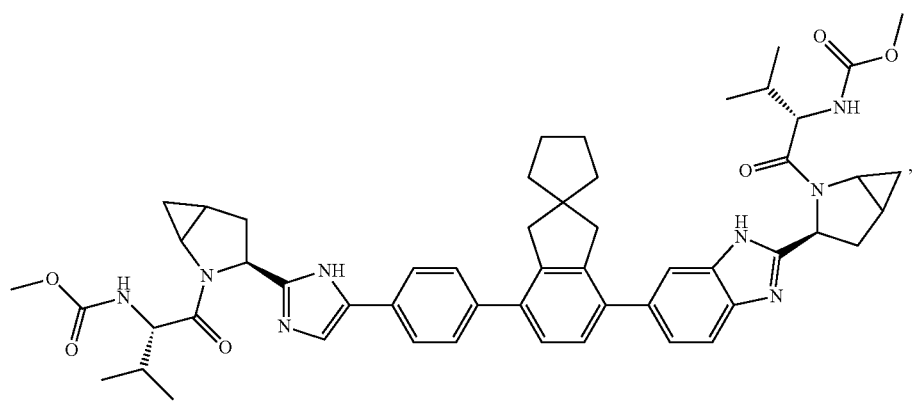

(55)

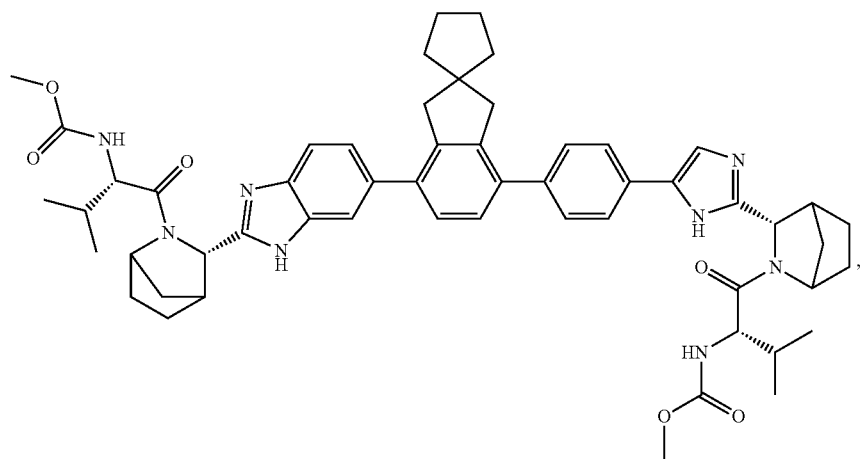

(56)

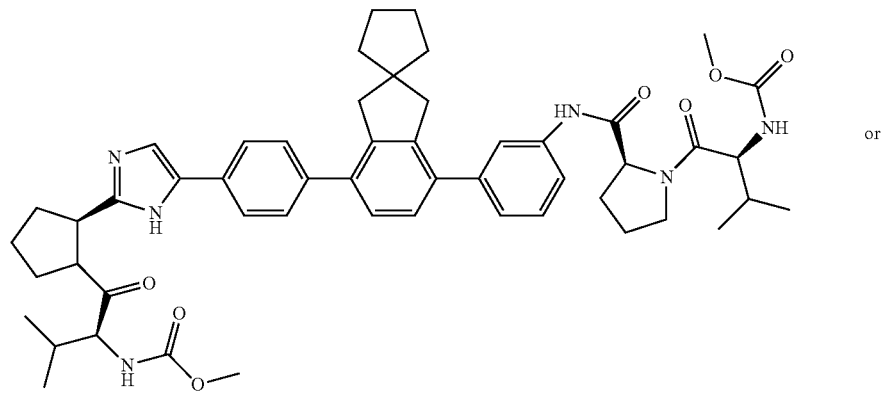

or (57)

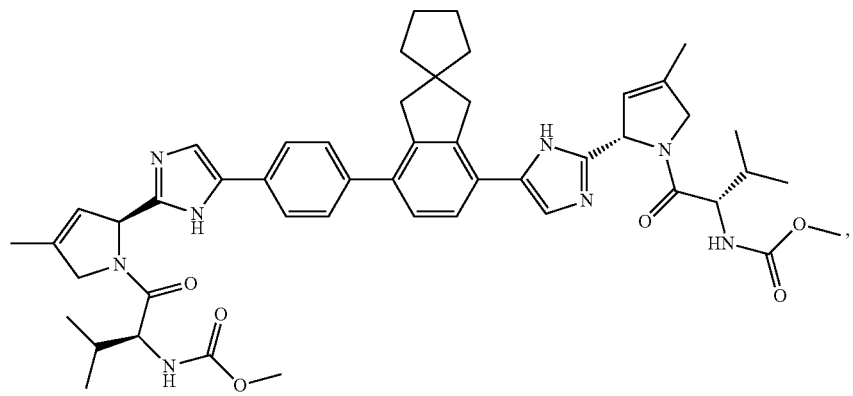

or a stereoisomer, a geometric isomer, a tautomer, an N-oxide, a hydrate, a solvate, or a pharmaceutically acceptable salt thereof.

28. A pharmaceutical composition comprising the compound according to claim 1 and a pharmaceutically acceptable carrier, excipient, diluent, adjuvant, vehicle or a combination thereof.

29. The pharmaceutical composition according to claim 28 further comprising an additional anti-HCV agent, wherein the anti-HCV agent is an interferon, ribavirin, IL-2, IL-6, IL-12, a compound that enhances the development of a type 1 helper T cell response, interfering RNA, anti-sense RNA, imiquimod, an inosine-5'-monophosphate dehydrogenase inhibitor, amantadine, rimantadine, boceprevir, telaprevir, daclatasvir, or a combination thereof, and wherein the interferon is interferon α-2b, pegylated interferon α, interferon α-2a, pegylated interferon α-2a, consensus interferon-α, or interferon γ.

30. The pharmaceutical composition according to claim 28 further comprising at least one additional compound which is effective to inhibit at least one target, wherein the target is selected from HCV metalloproteinase, HCV serine proteinase, HCV polymerase, HCV helicase, HCV NS4B protein, HCV entry, HCV assembly, HCV egress, HCV NS5A protein, and IMPDH.

31. The compound according to claim 1 for use in inhibiting at least one target wherein the target is selected from HCV metalloproteinase, HCV serine proteinase, HCV polymerase, HCV helicase, HCV NS4B protein, HCV entry, HCV assembly, HCV egress, HCV NS5A protein, and IMPDH.

32. The pharmaceutical composition according to claim 28 for use in inhibiting at least one target, wherein the target is selected from HCV metalloproteinase, HCV serine proteinase, HCV polymerase, HCV helicase, HCV NS4B protein, HCV entry, HCV assembly, HCV egress, HCV NS5A protein, and IMPDH.

* * * * *